US006133426A

United States Patent [19]
Gonzalez et al.

[11] Patent Number: 6,133,426
[45] Date of Patent: *Oct. 17, 2000

[54] HUMANIZED ANTI-IL-8 MONOCLONAL ANTIBODIES

[75] Inventors: Tania N. Gonzalez, Oakland; Steven R. Leong, Berkeley; Leonard G. Presta, San Francisco, all of Calif.

[73] Assignee: Genentech, Inc., South San Francisco, Calif.

[*] Notice: This patent is subject to a terminal disclaimer.

[21] Appl. No.: 09/026,985

[22] Filed: Feb. 20, 1998

Related U.S. Application Data

[60] Provisional application No. 60/038,664, Feb. 21, 1997, and provisional application No. 60/074,330, Jan. 22, 1998.

[51] Int. Cl.[7] .................................................. C07K 16/24
[52] U.S. Cl. .............................. 530/388.23; 530/387.1; 530/387.9; 530/388.1; 530/389.1; 530/389.2; 530/388.15; 424/130.1; 424/139.1; 424/145.1; 424/141.1; 424/142.1
[58] Field of Search ............................. 530/387.1, 387.9, 530/388.1, 388.23, 389.1, 389.2, 388.15; 424/130.1, 139.1, 145.1, 141.1, 142.1

[56] References Cited

U.S. PATENT DOCUMENTS

| | | | |
|---|---|---|---|
| 5,677,426 | 10/1997 | Fong et al. | 530/387.1 |
| 5,686,070 | 11/1997 | Doerschuk et al. | 424/145.1 |
| 5,698,196 | 12/1997 | Matsushima et al. | 424/139.1 |
| 5,702,946 | 12/1997 | Doerschuk et al. | 435/320.1 |
| 5,707,622 | 1/1998 | Fong et al. | 424/145.1 |

FOREIGN PATENT DOCUMENTS

| | | |
|---|---|---|
| 770628 | 5/1997 | European Pat. Off. . |
| WO 92/04372 | 3/1992 | WIPO . |
| WO 95/23813 | 9/1995 | WIPO . |
| WO 95/23865 | 9/1995 | WIPO . |
| WO 96/02576 | 2/1996 | WIPO . |

OTHER PUBLICATIONS

Deuel et al., "Amino acid sequence of human platelet factor 4" *Proc. Natl. Acad. Sci.* 74:2256–2258 (1977).

Gonzalez et al., "Humanization of Murine 6G425:An Anti–IL8 Monoclonal Antibody Which Blocks Binding of IL8 to Human Neutrophils" *1996 Keystone Symposia on Exploring and Exploiting Antibody and Ig Superfamily Combining Sites* (Poster) pp. 1–21 (Feb. 1996).

Hebert et al., "Endothelial and Leukocyte Forms of IL–8: Conversion by Thrombin and Interactions with Neutrophils" *J. Immunol.* 145(9):3033–3040 (Nov. 1, 1990).

Hebert et al., "Interleukin–8: A Review" *Cancer Investigation* 11(6):743–750 (1993).

Ko et al., "A sensitive enzyme–linked immunosorbent assay for human interleukin–8" *J. Immunol. Methods* 149:227–235 (1992).

Mulligan et al., "Inhibition of Lung Inflammatory Reactions in Rats by an Anti–Human IL–8 Antibody" *J. Immunol.* 150(12):5585–5595 (Jun. 15, 1993).

Sekido et al., "Prevention of lung reperfusion injury in rabbits by a monoclonal antibody against interleukin–8" *Nature* 365:654–657 (Oct. 14, 1993).

St. John et al., "Immunologic Therapy for ARDS, Septic Shock, and Multiple–Organ Failure" *Chest* 103:932–943 (1993).

Sticherling et al., "Immunohistochemical studies on NAP–1/IL–8 in contact eczema and atopic dermatitis" *Arch. Dermatol. Res.* 284:82–85 (1992).

Sticherling et al., "Production and Characterization of Monoclonal Antibodies Against the Novel Neutrophil Activating Peptide NAP/IL–8" *J. Immunol.* 143(5):1628–1634 (Sep. 1, 1989).

Tanaka et al., "Synthesis and biological characterization of monocyte–derived neutrophil chemotactic factor" *FEBS letters* 236(2):467–470 (Aug. 1988).

Van Damme et al., "Purification of granulocyte chemotactic peptide/interleukin–8 reveals N–terminal sequence heterogeneity similar to that of β–thromboglobulin" *European Journal of Biochemistry* 181:337–344 (1989).

Yoshimura et al., "Neutrophil attractant/activation protein–1 and monocyte chemoattractant protein–1 in rabbit. cDNA cloning and their expression in spleen cells" *J. Immunol.* 146:3483–3488 (1991).

*Primary Examiner*—Prema Mertz
*Attorney, Agent, or Firm*—Richard B. Love

[57] ABSTRACT

Humanized anti-IL-8 monoclonal antibodies and variants thereof are described for use in diagnostic applications and in the treatment of inflammatory disorders. Also described is a conjugate formed by an antibody fragment covalently attached to a non-proteinaceous polymer, wherein the apparent size of the conjugate is at least about 500 kD. The conjugate exhibits substantially improved half-life, mean residence time, and/or clearance rate in circulation as compared to the underivatized parental antibody fragment.

17 Claims, 136 Drawing Sheets

(1 of 136 Drawing Sheet(s) Filed in Color)

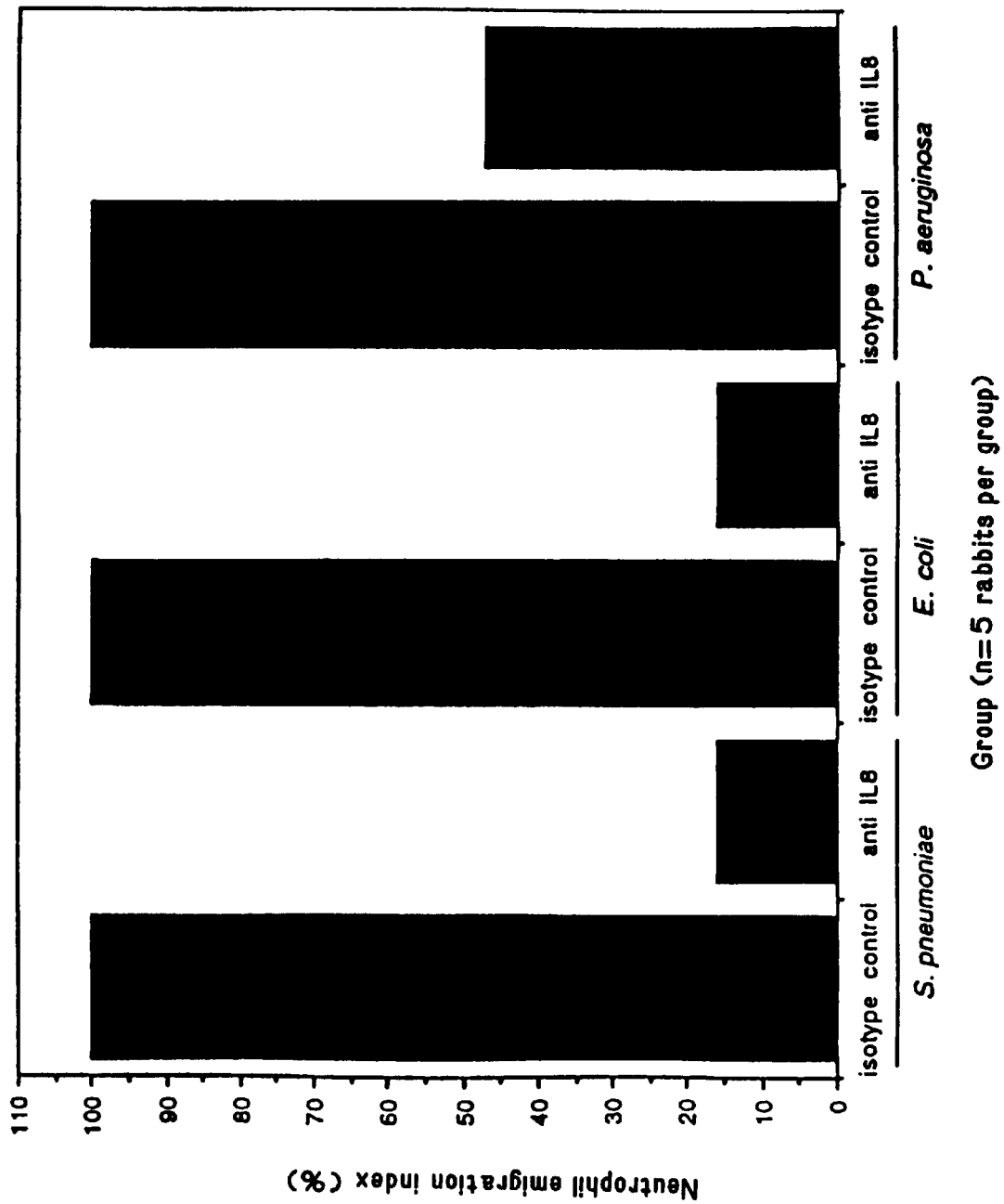

Light Chain Primers:

MKLC-1, 22mer    FIG. 13

5'    CAGTCCAACTGTTCAGGACGCC 3' (SEQ ID NO.1)

MKLC-2, 22mer

5'    GTGCTGCTCATGCTGTAGGTGC 3' (SEQ ID NO.2)

MKLC-3, 23mer

5'    GAAGTTGATGTCTTGTGAGTGGC    3' (SEQ ID NO.3)

Heavy Chain Primers:

IGG2AC-1, 24mer

5'    GCATCCTAGAGTCACCGAGGAGCC    3' (SEQ ID NO.4)

IGG2AC-2, 22mer

5'    CACTGGCTCAGGGAAATAACCC 3' (SEQ ID NO.5)

IGG2AC-3, 22mer

5'    GGAGAGCTGGGAAGGTGTGCAC 3' (SEQ ID NO.6)

FIG. 14

Light chain forward primer

SL001A-2  35 mer

```
5' ACAAACGCGTACGCT GACATCGTCATGACCCAGTC 3' (SEQ ID NO.7)
                       T T          T        (SEQ ID NO.8)
                                    A         (SEQ ID NO.9)
```

Light chain reverse primer

SL001B  37 mer

5' GCTCTTCGAATG GTGGGAAGATGGATACAGTTGGTGC 3' (SEQ ID NO.10)

FIG. 15

Heavy chain forward primer

SL002B  39 mer

```
5' CGATGGGCCCGG ATAGACCGATGGGGGCTGTGTTTTGGC 3' (SEQ ID NO.11)
                             T        C              (SEQ ID NO.12)
                             G                       (SEQ ID NO.13)
                             A                       (SEQ ID NO.14)
```

Heavy chain reverse primer

SL002B  39-MER

```
5' CGATGGGCCCGG ATAGACCGATGGGGGCTGTGTTTTGGC 3' (SEQ ID NO.11)
                             T                       (SEQ ID NO.15)
                             A                       (SEQ ID NO.14)
                             G                       (SEQ ID NO.13)
```

```
  1 GACATTGTCA TGACACAGTC TCAAAAATTC ATGTCCACAT CAGTAGGAGA CAGGGTCAGC
    CTGTAACAGT ACTGTGTCAG AGTTTTTAAG TACAGGTGTA GTCATCCTCT GTCCCAGTCG
  1 D   I   V   M   T   Q   S   Q   K   F   M   S   T   S   V   G   D   R   V   S

61 GTCACCTGCA AGGCCAGTCA GAATGTGGGT ACTAATGTAG CCTGGTATCA ACAGAAACCA
    CAGTGGACGT TCCGGTCAGT CTTACACCCA TGATTACATC GGACCATAGT TGTCTTTGGT
 21 V   T   C   K   A   S   Q   N   V   G   T   N   V   A   W   Y   Q   Q   K   P
                          *   *   *   *   *   *   *   *
                                        CDR #1

121 GGGCAATCTC CTAAAGCACT CTAAAGCACT GATTACTCG TCATCCTACC GGTACAGTGG AGTCCCTGAT
    CCCGTTAGAG GATTTCGTGA CTAAATGAGC AGTAGGATGG CCATGTCACC TCAGGGACTA
 41 G   Q   S   P   K   A   L   I   Y   S   S   S   Y   R   Y   S   G   V   P   D
                                      *   *   *   *   *   *   *
                                              CDR #2

181 CGCTTCACAG GCAGTGGATC TGGGACAGAT TTCACTCTCA CCATCAGCCA TGTGCAGTCT
    GCGAAGTGTC CGTCACCTAG ACCCTGTCTA AAGTGAGAGT GGTAGTCGGT ACACGTCAGA
 61 R   F   T   G   S   G   S   G   T   D   F   T   L   T   I   S   H   V   Q   S

241 GAAGACTTGG CAGACTATTT CTGTCAGCAA TATAACATCT ATCCTCTCAC GTTCGGTCCT
    CTTCTGAACC GTCTGATAAA GACAGTCGTT ATATTGTAGA TAGGAGAGTG CAAGCCAGGA
 81 E   D   L   A   D   Y   F   C   Q   Q   Y   N   I   Y   P   L   T   F   G   P
                                        *   *   *   *   *   *   *   *   *
                                                    CDR #3

301 GGGACCAAGC TGGAGTTGAA ACGGGCTGAT GCTGCACCAC CAACTGTATC CATCTTCCCA
    CCCTGGTTCG ACCTCAACTT TGCCCGACTA CGACGTGGTG GTTGACATAG GTAGAAGGGT
101 G   T   K   L   E   L   K   R   A   D   A   A   P   P   T   V   S   I   F   P

BstBI
361 CCATTCGAA        (SEQ ID NO.16)
    GGTAAGCTT
121 P   F   E        (SEQ ID NO.17)
```

FIG. 16

```
  1 TTCTATTGCT ACAAACGCGT ACGCTGAGGT GCAGCTGGTG GAGTCTGGGG GAGGCTTAGT
    AAGATAACGA TGTTTGCGCA TGCGACTCCA CGTCGACCAC CTCAGACCCC CTCCGAATCA
  1                                E   V   Q   L   V   E  S  G  G  L  V

61 GCCGCCTGGA GGGTCCCTGA AACTCTCCTG TGCAGCCTCT GGATTCATAT TCAGTAGTTA
    CGGCGGACCT CCCAGGGACT TTGAGAGGAC ACGTCGGAGA CCTAAGTATA AGTCATCAAT
 13  P   P   G   G   S   L   K   L   S   C   A   A   S   G   F   I   F   S   S   Y
                                                         ─────────────────────  * *
                                                                        CDR #1

121 TGGCATGTCT TGGGTTCGCC AGACTCCAGG CAAGAGCCTG GAGTTGGTCG CAACCATTAA
    ACCGTACAGA ACCCAAGCGG TCTGAGGTCC GTTCTCGGAC CTCAACCAGC GTTGGTAATT
 33  G   M   S   W   V   R   Q   T   P   G   K   S   L   E   L   V   A   T   I   N
     * * *                                                                   * * *

181 TAATAATGGT GATAGCACCT ATTATCCAGA CAGTGTGAAG GGCCGATTCA CCATCTCCCG
    ATTATTACCA CTATCGTGGA TAATAGGTCT GTCACACTTC CCGGCTAAGT GGTAGAGGGC
 53  N   N   G   D   S   T   Y   Y   P   D   S   V   K   G   R   F   T   I   S   R
     ─────────
     * * * * * * * * * * * * * * * * *
              CDR #2

241 AGACAATGCC AAGAACACCC TGTACCTGCA AATGAGCAGT CTGAAGTCTG AGGACACAGC
    TCTGTTACGG TTCTTGTGGG ACATGGACGT TTACTCGTCA GACTTCAGAC TCCTGTGTCG
 73  D   N   A   K   N   T   L   Y   L   Q   M   S   S   L   K   S   E   D   T   A

301 CATGTTTTAC TGTGCAAGAG CCCTCATTAG TTCGGCTACT TGGTTTGGTT ACTGGGGCCA
    GTACAAAATG ACACGTTCTC GGGAGTAATC AAGCCGATGA ACCAAACCAA TGACCCCGGT
 93  M   F   Y   C   A   R   A   L   I   S   S   A   T   W   F   G   Y   W   G   Q
                             ───────────────────────────────────
                             * * * * * * * * * * *
                                        CDR #3

361 AGGGACTCTG GTCACTGTCT CTGCAGCCAA AACAACAGCC CCATCTGTCT
    TCCCTGAGAC CAGTGACAGA GACGTCGGTT TTGTTGTCGG GGTAGACAGA
113  G   T   L   V   T   V   S   A   A   K   T   T   A   P   S   V   Y

ApaI
411 ATCCGGG (SEQ ID NO.18)
    TAGGCCC
130    P    (SEQ ID NO.19)
```

VL.front      31-MER

5' ACAAACGCGTACGCTGATATCGTCATGACAG   3' (SEQ ID NO.20)

VL.rear 31-MER

5' GCAGCATCAGCTCTTCGAAGCTCCAGCTTGG   3' (SEQ ID NO.21)

VH.front.SPE   21-MER

5' CCACTAGTACGCAAGTTCACG             3' (SEQ ID NO.22)

VH.rear 33-MER

5' GATGGGCCCTTGGTGGAGGCTGCAGAGACAGTG   3' (SEQ ID NO.23)

```
  1 ATGAAGAAGA ATATCGCATT TCTTCTTGCA TCTATGTTCG TTTTTTCTAT TGCTACAAAC
    TACTTCTTCT TATAGCGTAA AGAAGAACGT AGATACAAGC AAAAAAGATA ACGATGTTTG
-23 M   K   K   N    I   A   F   L   L   A    S   M   F   V    F   S   I   A   T   N

61 GCGTACGCTG ATATCGTCAT GACACAGTCT CAAAAATTCA TGTCCACATC AGTAGGAGAC
    CGCATGCGAC TATAGCAGTA CTGTGTCAGA GTTTTTAAGT ACAGGTGTAG TCATCCTCTG
 -3 A   Y   A   D    I   V   M    T   Q   S    Q   K   F   M    S   T   S   V   G   D

121 AGGGTCAGCG TCACCTGCAA GGCCAGTCAG AATGTGGGTA CTAATGTAGC CTGGTATCAA
    TCCCAGTCGC AGTGGACGTT CCGGTCAGTC TTACACCCAT GATTACATCG GACCATAGTT
 18 R   V   S    T   C   K    A   S   Q   N   V   G   T   N   V   A    W   Y   Q
                              *   *   *   *   *   *   *   *   *   *
                                              CDR #1

181 CAGAAACCAG GGCAATCTCC TAAAGCACTG ATTTACTCGT CATCCTACCG GTACAGTGGA
    GTCTTTGGTC CCGTTAGAGG ATTTCGTGAC TAAATGAGCA GTAGGATGGC CATGTCACCT
 38 Q   K   P   G    Q   S   P   K   A   L    I   Y   S   S   S   Y   R   Y   S   G
                                                      *   *   *   *   *   *   *
                                                          CDR #2

241 GTCCCTGATC GCTTCACAGG CAGTGGATCT GGGACAGATT TCACTCTCAC CATCAGCCAT
    CAGGGACTAG CGAAGTGTCC GTCACCTAGA CCCTGTCTAA AGTGAGAGTG GTAGTCGGTA
 58 V   P   D   R    F   T   G    S   G   S    G   T   D   F    T   L   T    I   S   H

301 GTGCAGTCTG AAGACTTGGC AGACTATTTC TGTCAGCAAT ATAACATCTA TCCTCTCACG
    CACGTCAGAC TTCTGAACCG TCTGATAAAG ACAGTCGTTA TATTGTAGAT AGGAGAGTGC
 78 V   Q   S   E    D   L   A    D   Y   F    C   Q   Q   Y   N   I   Y   P   L   T
                                                       *   *   *   *   *   *   *   *   *
                                                           CDR #3
                         BstBI
361 TTCGGTCCTG GGACCAAGCT GGAGCTTCGA AGAGCTGTGG CTGCACCATC TGTCTTCATC
    AAGCCAGGAC CCTGGTTCGA CCTCGAAGCT TCTCGACACC GACGTGGTAG ACAGAAGTAG
 98 F   G   P   G    T   K   L    E   L   R    R   A   V    A   P   S    V   F   I

421 TTCCCGCCAT CTGATGAGCA GTTGAAATCT GGAACTGCTT CTGTTGTGTG CCTGCTGAAT
    AAGGGCGGTA GACTACTCGT CAACTTTAGA CCTTGACGAA GACAACACAC GGACGACTTA
118 F   P   P   S    D   E   Q    L   K   S    G   T   A   S    V   V   C    L   L   N

481 AACTTCTATC CCAGAGAGGC CAAAGTACAG TGGAAGGTGG ATAACGCCCT CCAATCGGGT
    TTGAAGATAG GGTCTCTCCG GTTTCATGTC ACCTTCCACC TATTGCGGGA GGTTAGCCCA
138 N   F   Y   P    R   E   A    K   V   Q    W   K   V   D    N   A   L    Q   S   G

541 AACTCCCAGG AGAGTGTCAC AGAGCAGGAC AGCAAGGACA GCACCTACAG CCTCAGCAGC
    TTGAGGGTCC TCTCACAGTG TCTCGTCCTG TCGTTCCTGT CGTGGATGTC GGAGTCGTCG
158 N   S   Q   E    S   V   T    E   Q   D    S   K   D   S    T   Y   S    L   S   S

601 ACCCTGACGC TGAGCAAAGC AGACTACGAG AAACACAAAG TCTACGCCTG CGAAGTCACC
    TGGGACTGCG ACTCGTTTCG TCTGATGCTC TTTGTGTTTC AGATGCGGAC GCTTCAGTGG
178 T   L   T    S   K   A    D   Y   E    K   H   K   V    Y   A    C   E   V   T

661 CATCAGGGCC TGAGCTCGCC CGTCACAAAG AGCTTCAACA GGGGAGAGTG
    GTAGTCCCGG ACTCGAGCGG GCAGTGTTTC TCGAAGTTGT CCCCTCTCAC
198 H   Q   G   L    S   S   P    V   T   K    S   F   N    R   G   E   C (SEQ ID NO.25)

711    TTAA    (SEQ ID NO.24)
       AATT
216    O
```

FIG. 19

```
  1 ATGAAAAAGA ATATCGCATT TCTTCTTGCA TCTATGTTCG TTTTTTCTAT TGCTACAAAC
    TACTTTTTCT TATAGCGTAA AGAAGAACGT AGATACAAGC AAAAAAGATA ACGATGTTTG
-23  M  K  K    I  A  F    L  L  A    S  M  F    V  F  S    I  A  T  N

61 GCGTACGCTG AGGTGCAGCT GGTGGAGTCT GGGGGAGGCT TAGTGCCGCC TGGAGGGTCC
    CGCATGCGAC TCCACGTCGA CCACCTCAGA CCCCCTCCGA ATCACGGCGG ACCTCCCAGG
 -3  A  Y  A  E   V  Q  L    V  E  S    G  G  G    L  V  P  P    G  G  S

121 CTGAAACTCT CCTGTGCAGC CTCTGGATTC ATATTCAGTA GTTATGGCAT GTCTTGGGTT
    GACTTTGAGA GGACACGTCG GAGACCTAAG TATAAGTCAT CAATACCGTA CAGAACCCAA
 18  L  K  L  S   C  A  A    S  G  F    I  F  S    S  Y  G    M  S  W  V
                                      *   *  *  *   *
                                          CDR #1

181 CGCCAGACTC CAGGCAAGAG CCTGGAGTTG GTCGCAACCA TTAATAATAA TGGTGATAGC
    GCGGTCTGAG GTCCGTTCTC GGACCTCAAC CAGCGTTGGT AATTATTATT ACCACTATCG
 38  R  Q  T  P   G  K  S    L  E  L    V  A  T    I  N  N  N    G  D  S
                                                      *  *  *  *  *  *  *  *

241 ACCTATTATC CAGACAGTGT GAAGGGCCGA TTCACCATCT CCCGAGACAA TGCCAAGAAC
    TGGATAATAG GTCTGTCACA CTTCCCGGCT AAGTGGTAGA GGGCTCTGTT ACGGTTCTTG
 58  T  Y  Y  P   D  S  V    K  G  R    F  T  I    S  R  D    N  A  K  N
     *  *  *  *   *  *  *    *
        CDR #2

301 ACCCTGTACC TGCAAATGAG CAGTCTGAAG TCTGAGGACA CAGCCATGTT TTACTGTGCA
    TGGGACATGG ACGTTTACTC GTCAGACTTC AGACTCCTGT GTCGGTACAA AATGACACGT
 78  T  L  Y  L   Q  M  S    S  L  K    S  E  D    T  A  M    F  Y  C  A

361 AGAGCCCTCA TTAGTTCGGC TACTTGGTTT GGTTACTGGG GCCAAGGGAC TCTGGTCACT
    TCTCGGGAGT AATCAAGCCG ATGAACCAAA CCAATGACCC CGGTTCCCTG AGACCAGTGA
 98  R  A  L  I   S  S  A    T  W  F    G  Y  W    G  Q  G    T  L  V  T
        *  *  *  *  *  *  *  *  *  *  *
              CDR #3
              ApaI
421 GTCTCTGCAG CCTCCACCAA GGGCCCATCG GTCTTCCCCC TGGCACCCTC CTCCAAGAGC
    CAGAGACGTC GGAGGTGGTT CCCGGGTAGC CAGAAGGGGG ACCGTGGGAG GAGGTTCTCG
118  V  S  A  A   S  T  K    G  P  S    V  F  P    L  A  P    S  S  K  S

481 ACCTCTGGGG GCACAGCGGC CCTGGGCTGC CTGGTCAAGG ACTACTTCCC CGAACCGGTG
    TGGAGACCCC CGTGTCGCCG GGACCCGACG GACCAGTTCC TGATGAAGGG GCTTGGCCAC
138  T  S  G  G   T  A  A    L  G  C    L  V  K    D  Y  F    P  E  P  V

541 ACGGTGTCGT GGAACTCAGG CGCCCTGACC AGCGGCGTGC ACACCTTCCC GGCTGTCCTA
    TGCCACAGCA CCTTGAGTCC GCGGGACTGG TCGCCGCACG TGTGGAAGGG CCGACAGGAT
158  T  V  S  W   N  S  G    A  L  T    S  G  V    H  T  F    P  A  V  L

601 CAGTCCTCAG GACTCTACTC CCTCAGCAGC GTGGTGACCG TGCCCTCCAG CAGCTTGGGC
    GTCAGGAGTC CTGAGATGAG GGAGTCGTCG CACCACTGGC ACGGGAGGTC GTCGAACCCG
178  Q  S  S  G   L  Y  S    L  S  S    V  V  T    V  P  S    S  S  L  G
```

FIG. 20A

661 ACCCAGACCT ACATCTGCAA CGTGAATCAC AAGCCCAGCA ACACCAAGGT GGACAAGAAA
    TGGGTCTGGA TGTAGACGTT GCACTTAGTG TTCGGGTCGT TGTGGTTCCA CCTGTTCTTT
198  T  Q  T  Y  I  C  N  V  N  H  K  P  S  N  T  K  V  D  K  K    (SEQ ID NO.26)

721 GTTGAGCCCA AATCTTGTGA CAAAACTCAC ACATGA
    CAACTCGGGT TTAGAACACT GTTTTGAGTG TGTACT                          (SEQ ID NO.27)
218  V  E  P  K  S  C  D  K  T  H  T  O

FIG. 20B

Light Chain Primers:

MKLC-1, 22mer

5'    CAGTCCAACTGTTCAGGACGCC 3' (SEQ ID NO.1)

MKLC-2, 22mer

5'    GTGCTGCTCATGCTGTAGGTGC 3' (SEQ ID NO.2)

MKLC-3, 23mer

5'    GAAGTTGATGTCTTGTGAGTGGC    3' (SEQ ID NO.3)

Heavy Chain Primers:

IGG2AC-1, 24mer

5'    GCATCCTAGAGTCACCGAGGAGCC    3' (SEQ ID NO.4)

IGG2AC-2, 22mer

5'    CACTGGCTCAGGGAAATAACCC 3' (SEQ ID NO.5)

IGG2AC-3, 22mer

5'    GGAGAGCTGGGAAGGTGTGCAC 3' (SEQ ID NO.6)

FIG. 21

Light chain forward primer

6G4.light.Nsi  36-MER

```
5' CCAATGCATACGCT GAC ATC GTG ATG ACC CAG ACC CC 3'  (SEQ ID NO.28)
                      T   T           T   T          (SEQ ID NO.29)
                                  A       A          (SEQ ID NO.30)
```

Light chain reverse primer

6G4.light.Mun  35-MER

5' AGA TGT CAA TTG CTC ACT GGA TGG TGG GAA GAT GG 3' (SEQ ID NO.31)

FIG. 22

Heavy chain forward primer

6G4.heavy.Mlu 32-MER

5' CAAACGCGTACGCT GAG ATC CAG CAG CTG CAG CAG 3' (SEQ ID NO.32)
                        T           C              (SEQ ID NO.33)

Heavy chain reverse primer

SL002B 39-MER

5' CGATGGGCCCGG ATAGACCGATGGGGCTGTTGTTTGGC 3' (SEQ ID NO.11)
                        T                        (SEQ ID NO.15)
                        A                        (SEQ ID NO.14)
                        G                        (SEQ ID NO.13)

FIG. 23

```
 70 G ATATCGTGAT GACACAGACA CCACTCTCCC TGCCTGTCAG TCTTGGAGAT
    C TATAGCACTA CTGTGTCTGT GGTGAGAGGG ACGGACAGTC AGAACCTCTA
  1 D   I  V  M    T  Q  T    P  L  S    L  P  V    S  L  G  D

121 CAGGCCTCCA TCTCTTGCAG ATCTAGTCAG AGCCTTGTAC ACGGTATTGG AAACACCTAT
    GTCCGGAGGT AGAGAACGTC TAGATCAGTC TCGGAACATG TGCCATAACC TTTGTGGATA
 18 Q  A  S  I    S  C  R    S  S  Q    S  L  V  H   G  I  G   N  T  Y
                              *  *  *  *  *  *  *  *  *  *  *  *  *  *
                                            CDR #1

181 TTACATTGGT ACCTGCAGAA GCCAGGCCAG TCTCCAAAGC TCCTGATCTA CAAAGTTTCC
    AATGTAACCA TGGACGTCTT CGGTCCGGTC AGAGGTTTCG AGGACTAGAT GTTTCAAAGG
 38 L  H  W  Y    L  Q  K    P  G  Q    S  P  K    L  L  I  Y    K  V  S
    *  *                                                          *  *  *
                                                                 CDR #2

241 AACCGATTTT CTGGGGTCCC AGACAGGTTC AGTGGCAGTG GATCAGGGAC AGATTTCACA
    TTGGCTAAAA GACCCCAGGG TCTGTCCAAG TCACCGTCAC CTAGTCCCTG TCTAAAGTGT
 58 N  R  F  S    G  V  P    D  R  F    S  G  S    G  S  G  T    D  F  T
    *  *  *  *

301 CTCAGGATCA GCAGAGTGGA GGCTGAGGAT CTGGGACTTT ATTTCTGCTC TCAAAGTACA
    GAGTCCTAGT CGTCTCACCT CCGACTCCTA GACCCTGAAA TAAAGACGAG AGTTTCATGT
 78 L  R  I  S    R  V  E    A  E  D    L  G  L  Y    F  C  S    Q  S  T
                                                                  *  *  *
                                                                 CDR #3

MunI
361 CATGTTCCGC TCACGTTCGG TGCTGGGACC AAGCTGGAGC TGAAACGGGC TGATGCTGCA
    GTACAAGGCG AGTGCAAGCC ACGACCCTGG TTCGACCTCG ACTTTGCCCG ACTACGACGT
 98 H  V  P  L    T  F  G    A  G  T    K  L  E  L    K  R  A    D  A  A
    *  *  *  *   *

MunI
421 CCAACTGTAT CCATCTTCCC ACCATCCAGT GAGCAATTGA    (SEQ ID NO.34)
    GGTTGACATA GGTAGAAGGG TGGTAGGTCA CTCGTTAACT
118 P  T  V  S    I  F  P    P  S  S    E  Q  L  K   (SEQ ID NO.35)
```

FIG. 24

```
 70 G AGATTCAGCT GCAGCAGTCT GGACCTGAGC TGATGAAGCC TGGGGCTTCA
    C TCTAAGTCGA CGTCGTCAGA CCTGGACTCG ACTACTTCGG ACCCCGAAGT
  1 E   I   Q   L   Q   Q   S   G   P   E   L   M   K   P   G   A   S

121 GTGAAGATAT CCTGCAAGGC TTCTGGTTAT TCATTCAGTA GCCACTACAT GCACTGGGTG
    CACTTCTATA GGACGTTCCG AAGACCAATA AGTAAGTCAT CGGTGATGTA CGTGACCCAC
 18 V   K   I   S   C   K   A   S   G   Y   S   F   S   S   H   Y   M   H   W   V
                                        ─   ─   ─   ─   ─   ─   ─
                                                        *   *   *   *   *
                                            CDR #1

181 AAGCAGAGCC ATGGAAAGAG CCTTGAGTGG ATTGGCTACA TTGATCCTTC CAATGGTGAA
    TTCGTCTCGG TACCTTTCTC GGAACTCACC TAACCGATGT AACTAGGAAG GTTACCACTT
 38 K   Q   S   H   G   K   S   L   E   W   I   G   Y   I   D   P   S   N   G   E
                                                            *   ─   ─   ─   ─
                                                    *   *   *   *   *   *   *
                                                            CDR #2

241 ACTACTTACA ACCAGAAATT CAAGGGCAAG GCCACATTGA CTGTAGACAC ATCTTCCAGC
    TGATGAATGT TGGTCTTTAA GTTCCCGTTC CGGTGTAACT GACATCTGTG TAGAAGGTCG
 58 T   T   Y   N   Q   K   F   K   G   K   A   T   L   T   V   D   T   S   S   S
    *   *   *   *   *   *   *   *   *

301 ACAGCCAACG TGCATCTCAG CAGCCTGACA TCTGATGACT CTGCAGTCTA TTTCTGTGCA
    TGTCGGTTGC ACGTAGAGTC GTCGGACTGT AGACTACTGA GACGTCAGAT AAAGACACGT
 78 T   A   N   V   H   L   S   S   L   T   S   D   D   S   A   V   Y   F   C   A

361 AGAGGGGACT ATAGATACAA CGGCGACTGG TTTTTCGATG TCTGGGGCGC AGGGACCACG
    TCTCCCCTGA TATCTATGTT GCCGCTGACC AAAAAGCTAC AGACCCCGCG TCCCTGGTGC
 98 R   G   D   Y   R   Y   N   G   D   W   F   F   D   V   W   G   A   G   T   T
            ─   ─   ─   ─   ─   ─   ─   ─   ─   ─   ─
        *   *   *   *   *   *   *   *   *   *   *
                            CDR #3
    BstEII                                                          ApaI
421 GTCACCGTCT CCTCCGCCAA AACCGACAGC CCCATCGGTC TATCCGGGCC
    CAGTGGCAGA GGAGGCGGTT TTGGCTGTCG GGGTAGCCAG ATAGGCCCGG
118 V   T   V   S   S   A   K   T   D   S   P   I   G   L   S   G   P

471 CATC        (SEQ ID NO.36)
    GTAG
135 I           (SEQ ID NO.37)
```

FIG. 25

5' CTTGGTGGAGGCGGAGGAGACG 3' (SEQ ID NO.38)

Mutagenesis Primer for 6G425VL

DS/VF   38MER

5' GAAACGGGCTGTTGCTGCACCAACTGTATTCATCTTCC 3' (SEQ ID NO.39)

SYN.BstEII   31 MER

5' GTCACCGTCT CCTCCGCCTC CACCAAGGGC C 3' (SEQ ID NO.40)

SYN.Apa   22 MER

5' CTTGGTGGAGGCGGAGGAGACG   3' (SEQ ID NO.38)

FIG. 26

```
  1 ATGAAGAAGA ATATCGCATT TCTTCTTGCA TCTATGTTCG TTTTTTCTAT TGCTACAAAT
    TACTTCTTCT TATAGCGTAA AGAAGAACGT AGATACAAGC AAAAAAGATA ACGATGTTTA
-23 M  K  K   N  I  A  F   L  L  A   S  M  F  V   F  S  I   A  T  N

61 GCATACGCTG ATATCGTGAT GACACAGACA CCACTCTCCC TGCCTGTCAG TCTTGGAGAT
    CGTATGCGAC TATAGCACTA CTGTGTCTGT GGTGAGAGGG ACGGACAGTC AGAACCTCTA
 -3 A  Y  A  D   I  V  M   T  Q  T   P  L  S   L  P  V  S   L  G  D

121 CAGGCCTCCA TCTCTTGCAG ATCTAGTCAG AGCCTTGTAC ACGGTATTGG AAACACCTAT
    GTCCGGAGGT AGAGAACGTC TAGATCAGTC TCGGAACATG TGCCATAACC TTTGTGGATA
 18 Q  A  S   I  S  C  R   S  S  Q   S  L  V  H   G  I  G   N  T  Y
                           *  *  *   *  *  *  *  *  *  *   *  *  *
                                          CDR #1

181 TTACATTGGT ACCTGCAGAA GCCAGGCCAG TCTCCAAAGC TCCTGATCTA CAAAGTTTCC
    AATGTAACCA TGGACGTCTT CGGTCCGGTC AGAGGTTTCG AGGACTAGAT GTTTCAAAGG
 38 L  H  W   Y  L  Q  K   P  G  Q   S  P  K  L   L  I  Y   K  V  S
    *  *                                                    *  *  *
                                                              CDR #2

241 AACCGATTTT CTGGGGTCCC AGACAGGTTC AGTGGCAGTG GATCAGGGAC AGATTTCACA
    TTGGCTAAAA GACCCCAGGG TCTGTCCAAG TCACCGTCAC CTAGTCCCTG TCTAAAGTGT
 58 N  R  F   S  G  V  P   D  R  F   S  G  S  G   S  G  T   D  F  T
    *  *  *  *

301 CTCAGGATCA GCAGAGTGGA GGCTGAGGAT CTGGGACTTT ATTTCTGCTC TCAAAGTACA
    GAGTCCTAGT CGTCTCACCT CCGACTCCTA GACCCTGAAA TAAAGACGAG AGTTTCATGT
 78 L  R  I   S  R  V  E   A  E  D   L  G  L  Y   F  C  S   Q  S  T
                                                              *  *  *
                                                              CDR #3

361 CATGTTCCGC TCACGTTCGG TGCTGGGACC AAGCTGGAGC TGAAACGGGC TGTTGCTGCA
    GTACAAGGCG AGTGCAAGCC ACGACCCTGG TTCGACCTCG ACTTTGCCCG ACAACGACGT
 98 H  V  P  L   T  F  G   A  G  T   K  L  E  L   K  R  A   V  A  A
    *  *  *  *  *

421 CCAACTGTAT TCATCTTCCC ACCATCCAGT GAGCAATTGA AATCTGGAAC TGCCTCTGTT
    GGTTGACATA AGTAGAAGGG TGGTAGGTCA CTCGTTAACT TTAGACCTTG ACGGAGACAA
118 P  T  V  F   I  F  P   P  S  S   E  Q  L   K  S  G  T   A  S  V

481 GTGTGCCTGC TGAATAACTT CTATCCCAGA GAGGCCAAAG TACAGTGGAA GGTGGATAAC
    CACACGGACG ACTTATTGAA GATAGGGTCT CTCCGGTTTC ATGTCACCTT CCACCTATTG
138 V  C  L  L   N  N  F   Y  P  R   E  A  K  V   Q  W  K   V  D  N

541 GCCCTCCAAT CGGGTAACTC CCAGGAGAGT GTCACAGAGC AGGACAGCAA GGACAGCACC
    CGGGAGGTTA GCCCATTGAG GGTCCTCTCA CAGTGTCTCG TCCTGTCGTT CCTGTCGTGG
158 A  L  Q  S   G  N  S   Q  E  S   V  T  E  Q   D  S  K   D  S  T

601 TACAGCCTCA GCAGCACCCT GACGCTGAGC AAAGCAGACT ACGAGAAACA CAAAGTCTAC
    ATGTCGGAGT CGTCGTGGGA CTGCGACTCG TTTCGTCTGA TGCTCTTTGT GTTTCAGATG
178 Y  S  L  S   S  T  L   T  L  S   K  A  D  Y   E  K  H   K  V  Y
```

FIG. 27A

661 GCCTGCGAAG TCACCCATCA GGGCCTGAGC TCGCCCGTCA CAAAGAGCTT CAACAGGGGA
    CGGACGCTTC AGTGGGTAGT CCCGGACTCG AGCGGGCAGT GTTTCTCGAA GTTGTCCCCT
198  A   C  E   V   T   H   Q   G   L   S   S   P   V   T   K   S   F   N   R   G

721 GAGTGTTAA    (SEQ ID NO.41)
    CTCACAATT   (SEQ ID NO.42)
218  E   C   O

FIG. 27B

```
  1 ATGAAAAAGA ATATCGCATT TCTTCTTGCA TCTATGTTCG TTTTTTCTAT TGCTACAAAC
    TACTTTTTCT TATAGCGTAA AGAAGAACGT AGATACAAGC AAAAAAGATA ACGATGTTTG
-23 M  K  K   N  I  A  F  L  L  A   S  M  F  V   F  S  I  A  T  N

61 GCGTACGCTG AGATTCAGCT GCAGCAGTCT GGACCTGAGC TGATGAAGCC TGGGGCTTCA
    CGCATGCGAC TCTAAGTCGA CGTCGTCAGA CCTGGACTCG ACTACTTCGG ACCCCGAAGT
 -3 A  Y  A   E  I  Q  L  Q  Q  S   G  P  E  L   M  K  P  G  A  S

121 GTGAAGATAT CCTGCAAGGC TTCTGGTTAT TCATTCAGTA GCCACTACAT GCACTGGGTG
    CACTTCTATA GGACGTTCCG AAGACCAATA AGTAAGTCAT CGGTGATGTA CGTGACCCAC
 18 V  K  I   S  C  K  A  S  G  Y   S  F  S  S   H  Y  M  H  W  V
                              ‾  ‾  ‾  ‾  ‾  ‾   *  *  *  *
                                      CDR #1

181 AAGCAGAGCC ATGGAAAGAG CCTTGAGTGG ATTGGCTACA TTGATCCTTC CAATGGTGAA
    TTCGTCTCGG TACCTTTCTC GGAACTCACC TAACCGATGT AACTAGGAAG GTTACCACTT
 38 K  Q  S   H  G  K  S  L  E  W   I  G  Y  I   D  P  S  N  G  E
                                             *   *  ‾  ‾  ‾  ‾  *
                                                      CDR #2

241 ACTACTTACA ACCAGAAATT CAAGGGCAAG GCCACATTGA CTGTAGACAC ATCTTCCAGC
    TGATGAATGT TGGTCTTTAA GTTCCCGTTC CGGTGTAACT GACATCTGTG TAGAAGGTCG
 58 T  T  Y   N  Q  K  F  K  G  K   A  T  L  T   V  D  T  S  S  S
    *  *  *   *  *  *  *  *  *

301 ACAGCCAACG TGCATCTCAG CAGCCTGACA TCTGATGACT CTGCAGTCTA TTTCTGTGCA
    TGTCGGTTGC ACGTAGAGTC GTCGGACTGT AGACTACTGA GACGTCAGAT AAAGACACGT
 78 T  A  N   V  H  L  S  S  L  T   S  D  D  S   A  V  Y  F  C  A

361 AGAGGGGACT ATAGATACAA CGGCGACTGG TTTTTCGATG TCTGGGGCGC AGGGACCACG
    TCTCCCCTGA TATCTATGTT GCCGCTGACC AAAAAGCTAC AGACCCCGCG TCCCTGGTGC
 98 R  G  D   Y  R  Y  N  G  D  W   F  F  D  V   W  G  A  G  T  T
          ‾   ‾  ‾  ‾  ‾  ‾  ‾  ‾   ‾  ‾  ‾
          *   *  *  *  *  *  *  *   *  *  *
                     CDR #3

421 GTCACCGTCT CCTCCGCCTC CACCAAGGGC CCATCGGTCT TCCCCCTGGC ACCCTCCTCC
    CAGTGGCAGA GGAGGCGGAG GTGGTTCCCG GGTAGCCAGA AGGGGGACCG TGGGAGGAGG
118 V  T  V   S  S  A  S  T  K  G   P  S  V  F   P  L  A  P  S  S

481 AAGAGCACCT CTGGGGGCAC AGCGGCCCTG GGCTGCCTGG TCAAGGACTA CTTCCCCGAA
    TTCTCGTGGA GACCCCCGTG TCGCCGGGAC CCGACGGACC AGTTCCTGAT GAAGGGGCTT
138 K  S  T   S  G  G  T  A  A  L   G  C  L  V   K  D  Y  F  P  E

541 CCGGTGACGG TGTCGTGGAA CTCAGGCGCC CTGACCAGCG GCGTGCACAC CTTCCCGGCT
    GGCCACTGCC ACAGCACCTT GAGTCCGCGG GACTGGTCGC CGCACGTGTG GAAGGGCCGA
158 P  V  T   V  S  W  N  S  G  A   L  T  S  G   V  H  T  F  P  A

601 GTCCTACAGT CCTCAGGACT CTACTCCCTC AGCAGCGTGG TGACCGTGCC CTCCAGCAGC
    CAGGATGTCA GGAGTCCTGA GATGAGGGAG TCGTCGCACC ACTGGCACGG GAGGTCGTCG
178 V  L  Q   S  S  G  L  Y  S  L   S  S  V  V   T  V  P  S  S  S
```

FIG. 28A

```
661  TTGGGCACCC AGACCTACAT CTGCAACGTG AATCACAAGC CCAGCAACAC CAAGGTGGAC
     AACCCGTGGG TCTGGATGTA GACGTTGCAC TTAGTGTTCG GGTCGTTGTG GTTCCACCTG
198   L  G  T  Q   T  Y  I    C  N  V    N  H  K  P    S  N  T    K  V  D

721  AAGAAAGTTG AGCCCAAATC TTGTGACAAA ACTCACACAT GA   (SEQ ID NO.43)
     TTCTTTCAAC TCGGGTTTAG AACACTGTTT TGAGTGTGTA CT   (SEQ ID NO.44)
218   K  K  V  E   P  K  S    C  D  K    T  H  T  O
```

FIG. 28B

Variable Light Chain Domain

```
              10         20       abcde 30         40
6G425    DIVMTQTPLSLPVSLGDQASISCRSSQSLVHGIGNTYLHWYLQKPGQSPKLLIY
          #  # # ## #  ### #                    #    ##
F(ab)-1  DIQMTQSPSSLSASVGDRVTITCRSSQSLVHGIGNTYLHWYQQKPGKAPKLLIY
                             # ###########
humκI    DIQMTQSPSSLSASVGDRVTITCRASKTI-----SKYLAWYQQKPGKAPKLLIY
                             ============
                         +++++++++++++++
                                L1

50       60       70       80       90      100
6G425    YKVSNRFSGVPDRFSDSGSGTDFTLRISRVEAEDLGLYFCSQSTHVPLTFGAGTKLELKR  (SEQ ID NO.45)
           #  #        #  # ##### ### #             #  # #
F(ab)-1  YKVSNRFSGVPSRFSGSGSGTDFTLTISSLQPEDFATYYCSQSTHVPLTFGQGTKVEIKR  (SEQ ID NO.46)
         ## ###                                   #  ####
humκI    YSGSTLESGVPSRFSGSGSGTDFTLTISSLQPEDFATYYCQQHNEYPLTFGQGTKVEIKR  (SEQ ID NO.47)
         ===                                      ======
         +++++++                                 +++++++++
            L2                                       L3
```

Variable Heavy Chain Domain

```
              10         20         30        40
6G425    EIQLQQSGPELMKPGASVKISCKASGYSFSSHYMHWVKQSHGKSLEWI
          #  ## ## ##  # ### #                # ##  #  #
F(ab)-1  EVQLVESGGGLVQPGGSLRLSCAASGYSFSSHYMHWVRQAPGKGLEWV
                                    #  ## #  #
humIII   EVQLVESGGGLVQPGGSLRLSCAASGFSPTGHWMNWVRQAPGKGLEWV
                                  =======
                                      +++++
                                       H1

50     a        70        80    abc      90       100      110
6G425    GYIDPSNGETTYNQKFKGKATLTVDTSSSTANVHLSSLTSDDSAVYFCAARGDYRYNGDWFFDVWGAGT  (SEQ ID NO.48)
                        ## ### # ## ###### ### #   #                          #
F(ab)-1  GYIDPSNGETTYNQKFKGRFTISRDNSKNTLYLQMNSLRAEDTAVYYCAARGDYRYNGDWFFDVWGQGT  (SEQ ID NO.49)
         # #  ## # ####                                 # # ###  #
humIII   GMIHPSDSETRYADSVKGRFTISRDNSKNTLYLQMNSLRAEDTAVYYCAARGIYFY-GTTYFDYWGQGT  (SEQ ID NO.50)
         ====                                           ===========
         +++++++++++++++++                             +++++++++++++
                 H2                                          H3
```

Amino Acid Sequence of the humanized anti-IL-8 6G4.2.5V11 Light Chain

MKKNIAFLLASMFVFSIATNAYADIQMTQSPSSLSASVGDRVTITCRSSQSLVHGIGNTY
LHWYQQKPGKAPKLLIYKVSNRFSGVPSRFSGSGSGTDFTLTISSLQPEDFATYYCSQST
HVPLTFGQGTKVEIKRTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSFNRG
EC (SEQ ID NO.51)

Amino Acid Sequence of the humanized anti-IL-8 6G4.2.5V11 Heavy Chain

MKKNIAFLLASMFVFSIATNAYAEVQLVQSGGGLVQPGGSLRLSCAASGYSFSSHYMH
WVRQAPGKGLEWVGYIDPSNGETTYNQKFKGRFTLSRDNSKNTAYLQMNSLRAEDTAVYY
CARGDYRYNGDWFFDVWGQGTLVTVSSASTKGPSVFPLAPSSKSTSGGTAALGCLVKDYF
PEPVTVSWNSGALTSGVHTFPAVLQSSGLYSLSSVVTVPSSSLGTQTYICNVNHKPSNTK
VDKKVEPKSCDKTHT (SEQ ID NO.52)

Amino Acid Sequence of the peptide linker and M13 Phage Coat (gene-III)

SGGGSGSGDFDYEKMANANKGAMTENADENALQSDAKGKLDSVATDYGAAIDGFIGDVS
GLANGNGATGDFAGSSNSQMAVQGDGNSPLMNFRQYLPSLPQSVECRPFVFSAGKPY
EFSIDCDKINLFRGVFAFLLYVATFMYVFSTFANILRNKES (SEQ ID NO.53)

FIG. 31A

```
  1 ATGAAAAAGA ATATCGCATT TCTTCTTGCA TCTATGTTCG TTTTTTCTAT TGCTACAAAC
    TACTTTTTCT TATAGCGTAA AGAAGAACGT AGATACAAGC AAAAAAGATA ACGATGTTTG
-23 M  K  K    I  A  F    L  L  A    S  M  F    V  F  S  I   A  T  N

61 GCATACGCTG ATATCCAGAT GACCCAGTCC CCGAGCTCCC TGTCCGCCTC TGTGGGCGAT
    CGTATGCGAC TATAGGTCTA CTGGGTCAGG GGCTCGAGGG ACAGGCGGAG ACACCCGCTA
 -3 A  Y  A   D  I  Q  M  T  Q  S    P  S  S    L  S  A    S  V  G  D

121 AGGGTCACCA TCACCTGCAG GTCAAGTCAA AGCTTAGTAC ATGGTATAGG TAACACGTAT
    TCCCAGTGGT AGTGGACGTC CAGTTCAGTT TCGAATCATG TACCATATCC ACGATGCATA
 18 R  V  T  I   T  C  R  S  S  Q    S  L  V    H  G  I    G  N  T  Y

181 TTACACTGGT ATCAACAGAA ACCAGGAAAA GCTCCGAAAC TACTGATTTA CAAAGTATCC
    AATGTGACCA TAGTTGTCTT TGGTCCTTTT CGAGGCTTTG ATGACTAAAT GTTTCATAGG
 38 L  H  W  Y   Q  Q  K  P  G  K    A  P  K    L  L  I    Y  K  V  S

241 AATCGATTCT CTGGAGTCCC TTCTCGCTTC TCTGGATCCG GTTCTGGGAC GGATTTCACT
    TTAGCTAAGA GACCTCAGGG AAGAGCGAAG AGACCTAGGC CAAGACCCTG CCTAAAGTGA
 58 N  R  F  S   G  V  P  S  R  F    S  G  S    G  S  G  T   D  F  T

301 CTGACCATCA GCAGTCTGCA GCCAGAAGAC TTCGCAACTT ATTACTGTTC ACAGAGTACT
    GACTGGTAGT CGTCAGACGT CGGTCTTCTG AAGCGTTGAA TAATGACAAG TGTCTCATGA
 78 L  T  I  S   S  L  Q  P  E  D    F  A  T    Y  Y  C    S  Q  S  T

361 CATGTCCCGC TCACGTTTGG ACAGGGTACC AAGGTGGAGA TCAAACGAAC TGTGGCTGCA
    GTACAGGGCG AGTGCAAACC TGTCCCATGG TTCCACCTCT AGTTTGCTTG ACACCGACGT
 98 H  V  P  L   T  F  G  Q  G  T    K  V  E    I  K  R  T   V  A  A

421 CCATCTGTCT TCATCTTCCC GCCATCTGAT GAGCAGTTGA AATCTGGAAC TGCTTCTGTT
    GGTAGACAGA AGTAGAAGGG CGGTAGACTA CTCGTCAACT TTAGACCTTG ACGAAGACAA
118 P  S  V  F   I  F  P  P  S  D    E  Q  L    K  S  G    T  A  S  V

481 GTGTGCCTGC TGAATAACTT CTATCCCAGA GAGGCCAAAG TACAGTGGAA GGTGGATAAC
    CACACGGACG ACTTATTGAA GATAGGGTCT CTCCGGTTTC ATGTCACCTT CCACCTATTG
138 V  C  L  L   N  N  F  Y  P  R    E  A  K    V  Q  W    K  V  D  N

541 GCCCTCCAAT CGGGTAACTC CCAGGAGAGT GTCACAGAGC AGGACAGCAA GGACAGCACC
    CGGGAGGTTA GCCCATTGAG GGTCCTCTCA CAGTGTCTCG TCCTGTCGTT CCTGTCGTGG
158 A  L  Q  S   G  N  S  Q  E  S    V  T  E    Q  D  S    K  D  S  T

601 TACAGCCTCA GCAGCACCCT GACGCTGAGC AAAGCAGACT ACGAGAAACA CAAAGTCTAC
    ATGTCGGAGT CGTCGTGGGA CTGCGACTCG TTTCGTCTGA TGCTCTTTGT GTTTCAGATG
178 Y  S  L  S   S  T  L  T  L  S    K  A  D    Y  E  K  H   K  V  Y

661 GCCTGCGAAG TCACCCATCA GGGCCTGAGC TCGCCCGTCA CAAAGAGCTT CAACAGGGGA
    CGGACGCTTC AGTGGGTAGT CCCGGACTCG AGCGGGCAGT GTTTCTCGAA GTTGTCCCCT
198 A  C  E  V   T  H  Q  G  L  S    S  P  V    T  K  S    F  N  R  G
                                                                (SEQ ID NO.54)
721 GAGTGTTAAG CTGATCCTCT ACGCCGGACG CATCGTGGCC CTAGTACGCA ACTAGTCGTA
    CTCACAATTC GACTAGGAGA TGCGGCCTGC GTAGCACCGG GATCATGCGT TGATCAGCAT
218 E  C  O (SEQ ID NO.51)
```

FIG. 31B

Amino Acid Sequence of the humanized anti-IL-8 6G4.2.5V19 Light Chain

MKKNIAFLLASMFVFSIATNAYADIQMTQSPSSLSASVGDRVTITCRSSQSLVHGIGNTY
LHWYQQKPGKAPKLLIYKVSNRFSGVPSRFSGSGSGTDFTLTISSLQPEDFATYYCSQST
HVPLTFGQGTKVEIKRTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSFNRG
EC (SEQ ID NO.51)

Amino Acid Sequence of the humanized anti-IL-8 6G4.2.5V19 Heavy Chain

MKKNIAFLLASMFVFSIATNAYAEVQLVESGGGLVQPGGSLRLSCAASGYSFSSHYMH
WVKQAPGKGLEWVGYIDPSNGETTYNQKFKGRFTLSRDNSKNTAYLQMNSLRAEDTAVYY
CARGDYRYNGDWFFDVWGQGTLVTVSSASTKGPSVFPLAPSSKSTSGGTAALGCLVKDYF
PEPVTVSWNSGALTSGVHTFPAVLQSSGLYSLSSVVTVPSSSLGTQTYICNVNHKPSNTK
VDKKVEPKSCDKTHT (SEQ ID NO.55)

FIG. 31C

Amino Acid Sequence of the humanized anti-IL-8 6G4.2.5V11N35A Light Chain

MKKNIAFLLASMFVFSIATNAYADIQMTQSPSSLSASVGDRVTITCRSSQSLVHGIGATY
LHWYQQKPGKAPKLLIYKVSNRFSGVPSRFSGSGSGTDFTLTISSLQPEDFATYCSQST
HVPLTFGQGTKVEIKRTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSFNRG
EC (SEQ ID NO.56)

Amino Acid Sequence of the humanized anti-IL-8 6G4.2.5V11N35A Heavy Chain

MKKNIAFLLASMFVFSIATNAYAEVQLVQSGGGLVQPGGSLRLSCAASGYSFSSHYMH
WVRQAPGKGLEWVGYIDPSNGETTYNQKFKGRFTLSRDNSKNTAYLQMNSLRAEDTAVYY
CARGDYRYNGDWFFDVWGQGTLVTVSSASTKGPSVFPLAPSSKSTSGGTAALGCLVKDYF
PEPVTVSWNSGALTSGVHTFPAVLQSSGLYSLSSVVTVPSSSLGTQTYICNVNHKPSNTK
VDKKVEPKSCDKTHT (SEQ ID NO.52)

Amino Acid Sequence of the putative Pepsin Cleavage Site and GCN4 Leucine Zipper

CPPCPAPELLGGRMKQLEDKVEELLSKNYHLENEVARLKKLVGER (SEQ ID NO.57)

FIG. 35

```
  1 ATGAAAAAGA ATATCGCATT TCTTCTTGCA TCTATGTTCG TTTTTTCTAT TGCTACAAAC
    TACTTTTTCT TATAGCGTAA AGAAGAACGT AGATACAAGC AAAAAAGATA ACGATGTTTG
-23 M  K  K    I  A  F    L  L  A    S  M  F    V  F  S  I   A  T  N

61 GCATACGCTG ATATCCAGAT GACCCAGTCC CCGAGCTCCC TGTCCGCCTC TGTGGGCGAT
    CGTATGCGAC TATAGGTCTA CTGGGTCAGG GGCTCGAGGG ACAGGCGGAG ACACCCGCTA
 -3 A  Y  A   D  I  Q    M  T  Q  S  P  S  S   L  S  A  S  V  G  D

121 AGGGTCACCA TCACCTGCAG GTCAAGTCAA AGCTTAGTAC ATGGTATAGG TGCTACGTAT
    TCCCAGTGGT AGTGGACGTC CAGTTCAGTT TCGAATCATG TACCATATCC ACGATGCATA
 18 R  V  T  I   T  C   R  S  S  Q   S  L  V  H   G  I  G   A  T  Y

181 TTACACTGGT ATCAACAGAA ACCAGGAAAA GCTCCGAAAC TACTGATTTA CAAAGTATCC
    AATGTGACCA TAGTTGTCTT TGGTCCTTTT CGAGGCTTTG ATGACTAAAT GTTTCATAGG
 38 L  H  W  Y   Q  Q  K  P  G  K   A  P  K  L   L  I  Y   K  V  S

241 AATCGATTCT CTGGAGTCCC TTCTCGCTTC TCTGGATCCG GTTCTGGGAC GGATTTCACT
    TTAGCTAAGA GACCTCAGGG AAGAGCGAAG AGACCTAGGC CAAGACCCTG CCTAAAGTGA
 58 N  R  F  S   G  V  P    S  R  F    S  G  S    G  T  D  F  T

301 CTGACCATCA GCAGTCTGCA GCCAGAAGAC TTCGCAACTT ATTACTGTTC ACAGAGTACT
    GACTGGTAGT CGTCAGACGT CGGTCTTCTG AAGCGTTGAA TAATGACAAG TGTCTCATGA
 78 L  T  I  S   L  Q     P  E  D    F  A  T  Y    Y  C   S  Q  S  T

361 CATGTCCCGC TCACGTTTGG ACAGGGTACC AAGGTGGAGA TCAAACGAAC TGTGGCTGCA
    GTACAGGGCG AGTGCAAACC TGTCCCATGG TTCCACCTCT AGTTTGCTTG ACACCGACGT
 98 H  V  P  L   T  F  G    Q  G  T    K  V  E  I    K  R  T    V  A  A

421 CCATCTGTCT TCATCTTCCC GCCATCTGAT GAGCAGTTGA AATCTGGAAC TGCTTCTGTT
    GGTAGACAGA AGTAGAAGGG CGGTAGACTA CTCGTCAACT TTAGACCTTG ACGAAGACAA
118 P  S  V  F    I  F  P    P  S  D    E  Q  L  K    S  G  T    A  S  V

481 GTGTGCCTGC TGAATAACTT CTATCCCAGA GAGGCCAAAG TACAGTGGAA GGTGGATAAC
    CACACGGACG ACTTATTGAA GATAGGGTCT CTCCGGTTTC ATGTCACCTT CCACCTATTG
138 V  C  L  L    N  N  F    Y  P  R    E  A  K  V    Q  W  K    V  D  N

541 GCCCTCCAAT CGGGTAACTC CCAGGAGAGT GTCACAGAGC AGGACAGCAA GGACAGCACC
    CGGGAGGTTA GCCCATTGAG GGTCCTCTCA CAGTGTCTCG TCCTGTCGTT CCTGTCGTGG
158 A  L  Q  S    G  N  S    Q  E  S    V  T  E  Q    D  S  K    D  S  T

601 TACAGCCTCA GCAGCACCCT GACGCTGAGC AAAGCAGACT ACGAGAAACA CAAAGTCTAC
    ATGTCGGAGT CGTCGTGGGA CTGCGACTCG TTTCGTCTGA TGCTCTTTGT GTTTCAGATG
178 Y  S  L  S    S  T  L    T  L  S    K  A  D  Y    E  K  H    K  V  Y

661 GCCTGCGAAG TCACCCATCA GGGCCTGAGC TCGCCCGTCA CAAAGAGCTT CAACAGGGGA
    CGGACGCTTC AGTGGGTAGT CCCGGACTCG AGCGGGCAGT GTTTCTCGAA GTTGTCCCCT
198 A  C  E  V    T  H  Q    G  L  S    S  P  V  T    K  S  F    N  R  G
                                                          (SEQ ID NO.58)
721 GAGTGTTAAG CTGATCCTCT ACGCCGGACG CATCGTGGCC CTAGTACGCA ACTAGTCGTA
    CTCACAATTC GACTAGGAGA TGCGGCCTGC GTAGCACCGG GATCATGCGT TGATCAGCAT
218 E  C  O  (SEQ ID NO.56)
```

FIG. 36

```
 781 AAAAGGGTAT CTAGAGGTTG AGGTGATTTT ATGAAAAAGA ATATCGCATT TCTTCTTGCA
     TTTTCCCATA GATCTCCAAC TCCACTAAAA TACTTTTTCT TATAGCGTAA AGAAGAACGT
  -1                                  M  K  K   N  I  A  F  L  L  A

841 TCTATGTTCG TTTTTTCTAT TGCTACAAAC GCGTACGCTG AGGTTCAGCT AGTGCAGTCT
     AGATACAAGC AAAAAAGATA ACGATGTTTG CGCATGCGAC TCCAAGTCGA TCACGTCAGA
 -11 S  M  F   V  F  S  I  A  T  N   A  Y  A  E  V  Q  L   V  Q  S

901 GGCGGTGGCC TGGTGCAGCC AGGGGGCTCA CTCCGTTTGT CCTGTGCAGC TTCTGGCTAC
     CCGCCACCGG ACCACGTCGG TCCCCCGAGT GAGGCAAACA GGACACGTCG AAGACCGATG
   8 G  G  G   L  V  Q  P  G  G  S   L  R  L  S  C  A  A   S  G  Y

961 TCCTTCTCGA GTCACTATAT GCACTGGGTC CGTCAGGCCC CGGGTAAGGG CCTGGAATGG
     AGGAAGAGCT CAGTGATATA CGTGACCCAG GCAGTCCGGG GCCCATTCCC GGACCTTACC
  28 S  F  S   S  H  Y  M  H  W  V   R  Q  A  P  G  K  G   L  E  W

1021 GTTGGATATA TTGATCCTTC CAATGGTGAA ACTACGTATA ATCAAAAGTT CAAGGGCCGT
     CAACCTATAT AACTAGGAAG GTTACCACTT TGATGCATAT TAGTTTTCAA GTTCCCGGCA
  48 V  G  Y   I  D  P  S  N  G  E   T  T  Y  N  Q  K  F   K  G  R

1081 TTCACTTTAT CTCGCGACAA CTCCAAAAAC ACAGCATACC TGCAGATGAA CAGCCTGCGT
     AAGTGAAATA GAGCGCTGTT GAGGTTTTTG TGTCGTATGG ACGTCTACTT GTCGGACGCA
  68 F  T  L   S  R  D  N  S  K  N   T  A  Y  L  Q  M  N   S  L  R

1141 GCTGAGGACA CTGCCGTCTA TTACTGTGCA AGAGGGGATT ATCGCTACAA TGGTGACTGG
     CGACTCCTGT GACGGCAGAT AATGACACGT TCTCCCCTAA TAGCGATGTT ACCACTGACC
  88 A  E  D   T  A  V  Y  Y  C  A   R  G  D  Y  R  Y  N   G  D  W

1201 TTCTTCGACG TCTGGGGTCA AGGAACCCTG GTCACCGTCT CCTCGGCCTC CACCAAGGGC
     AAGAAGCTGC AGACCCCAGT TCCTTGGGAC CAGTGGCAGA GGAGCCGGAG GTGGTTCCCG
 108 F  F  D   V  W  G  Q  G  T  L   V  T  V  S  S  A  S   T  K  G

1261 CCATCGGTCT TCCCCCTGGC ACCCTCCTCC AAGAGCACCT CTGGGGGCAC AGCGGCCCTG
     GGTAGCCAGA AGGGGGACCG TGGGAGGAGG TTCTCGTGGA GACCCCCGTG TCGCCGGGAC
 128 P  S  V   F  P  L  A  P  S  S   K  S  T  S  G  G  T   A  A  L

1321 GGCTGCCTGG TCAAGGACTA CTTCCCCGAA CCGGTGACGG TGTCGTGGAA CTCAGGCGCC
     CCGACGGACC AGTTCCTGAT GAAGGGGCTT GGCCACTGCC ACAGCACCTT GAGTCCGCGG
 148 G  C  L   V  K  D  Y  F  P  E   P  V  T  V  S  W  N   S  G  A

1381 CTGACCAGCG GCGTGCACAC CTTCCCGGCT GTCCTACAGT CCTCAGGACT CTACTCCCTC
     GACTGGTCGC CGCACGTGTG GAAGGGCCGA CAGGATGTCA GGAGTCCTGA GATGAGGGAG
 168 L  T  S   G  V  H  T  F  P  A   V  L  Q  S  S  G  L   Y  S  L

1441 AGCAGCGTGG TGACCGTGCC CTCCAGCAGC TTGGGCACCC AGACCTACAT CTGCAACGTG
     TCGTCGCACC ACTGGCACGG GAGGTCGTCG AACCCGTGGG TCTGGATGTA GACGTTGCAC
 188 S  S  V   V  T  V  P  S  S  S   L  G  T  Q  T  Y  I   C  N  V

1501 AATCACAAGC CCAGCAACAC CAAGGTCGAC AAGAAAGTTG AGCCCAAATC TTGTGACAAA
     TTAGTGTTCG GGTCGTTGTG GTTCCAGCTG TTCTTTCAAC TCGGGTTTAG AACACTGTTT
 208 N  H  K   P  S  N  T  K  V  D   K  K  V  E  P  K  S   C  D  K

1561 ACTCACACAT GCCCGCCGTG CCCAGCACCA GAACTGCTGG GCGGCCGCAT GAAACAGCTA
     TGAGTGTGTA CGGGCGGCAC GGGTCGTGGT CTTGACGACC CGCCGGCGTA CTTTGTCGAT
 228 T  H  T   C  P  P  C  P  A  P   E  L  L  G  R  M  K   Q  L
```

FIG. 37A

```
1621 GAGGACAAGG TCGAAGAGCT ACTCTCCAAG AACTACCACC TAGAGAATGA AGTGGCAAGA
     CTCCTGTTCC AGCTTCTCGA TGAGAGGTTC TTGATGGTGG ATCTCTTACT TCACCGTTCT
 248 E   D   K   V   E   E   L   L   S   K   N   Y   H   L   E   N   E   V   A   R

1681 CTCAAAAAGC TTGTCGGGGA GCGCTAA      (SEQ ID NO.59)
     GAGTTTTTCG AACAGCCCCT CGCGATT
 268 L   K   K   L   V   G   E   R   O  (SEQ ID NO.60)
```

FIG. 37B

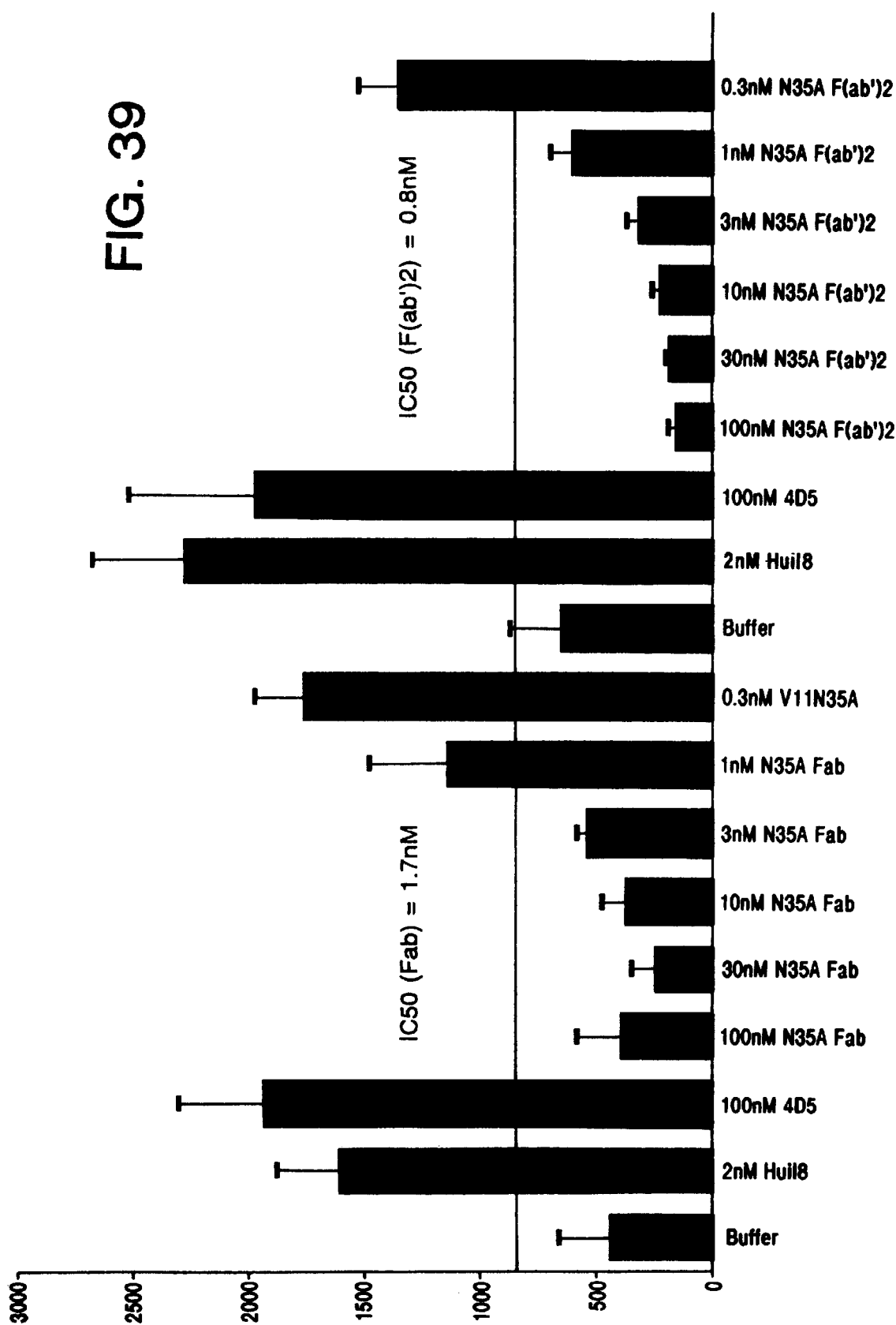

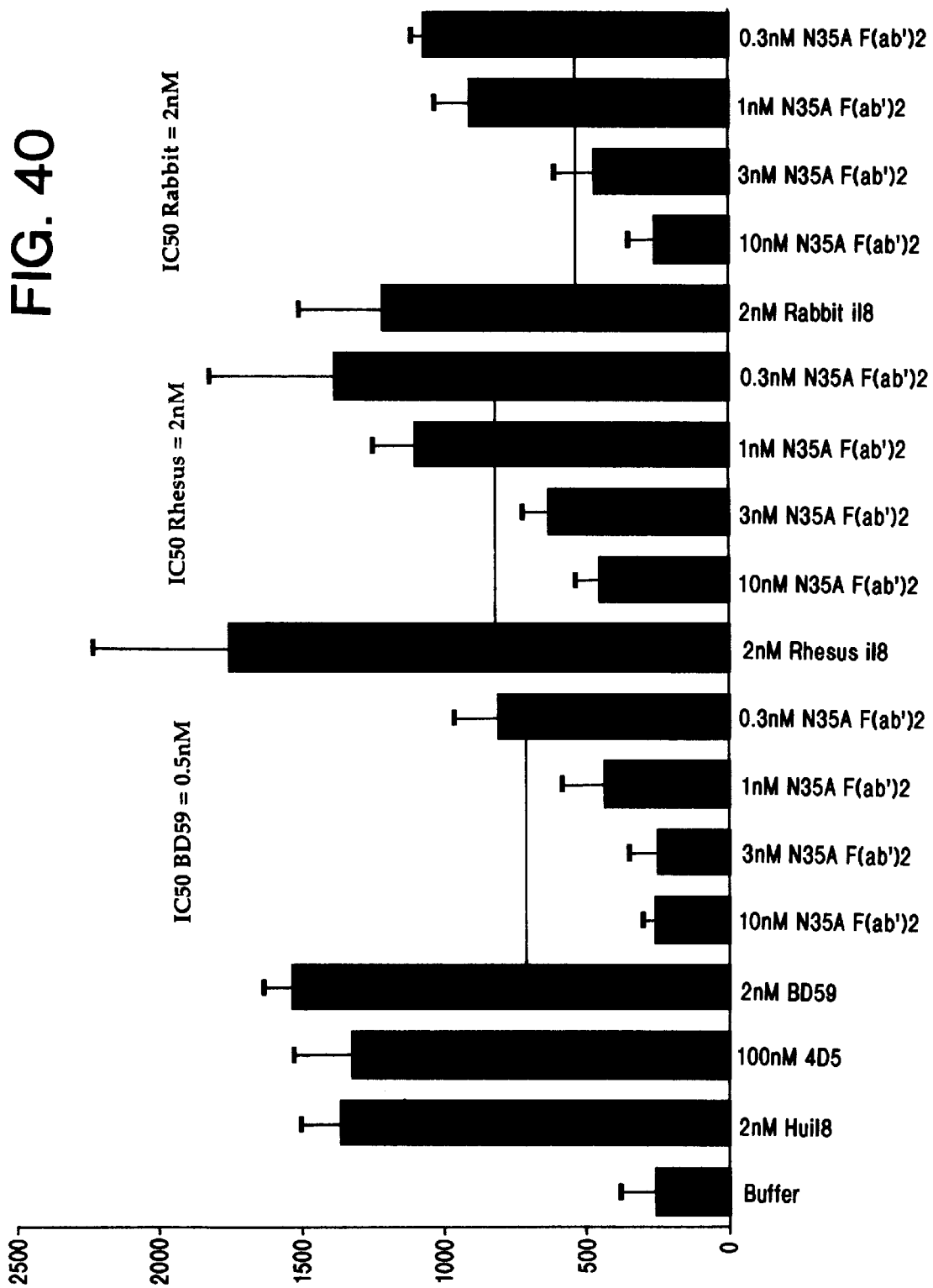

```
                              bsaJI        dsaV
                              avaI         bstNI
                              bsaJI        bslI
               sau96I         sau96I       apyI[dcm+]
        pleI   avaII          nlaIV        sau3AI                                                              maeII
        hinfI  asuI           asuI         mboI/ndeII[dam-]
   taqI        haeIII/palI    haeIII/palI  dpnI[dam+]
   xhoI                                                                                                hphI    bsaAI
   paeR7I                     ecoO109I/draII haeIII/palI  dpnII[dam-]  alwI[dam-]            snaBI
   avaI maeIII  bsrI
1401 CTTCTGAAGT CACTGTATATGC ACTGGGTCCG TCAGGCCCCG GGTAAGGGTC TGGAATGGGT TGGATATATT GATCCTTCCA ATGGTGAAAC TACGTATAAT
     GAAGAGCTCA GTGATATACG TGACCCAGGC AGTCCGGGGC CCATTCCCAG ACCTTACCCA ACCTATATAA CTAGGAAGGT TACCACTTTG ATGCATATTA
  29  F  S  S  H  Y  M  H  W  V  R   Q  A  P  G  K  G  L   E  W  V  G   Y  I  D  P  S  N   G  E  T  T  Y  N thaI                                                           scfI
                 fnuDII/mvnI                                                    pstI
       haeIII/palI   bstUI                                                      bsgI          cac8I      mnlI
       sau96I        bsh1236I                                                   bspMI         cac8I      ddeI    drdI
       asuI          nruI
1501 CAAAAGTTCA AGGGCCGTTT CACTTTATCT CGGACAACT CCAAAAACAC AGCATACCTG CAGATGAACA GCCTGCGTGC TGAGGACACT GCCGTCTATT
     GTTTTCAAGT TCCCGGCAAA GTGAAATAGA GCCGCTGTTGA GGTTTTTGTG TCGTATGGAC GTCTACTTGT CGGACGCACG ACTCCTGTGA CGGCAGATAA
  62  Q  K  F  K  G  R  F   T  L  S   R  D  N  S   K  N  T   A  Y  L   Q  M  N  S   L  R  A   E  D  T   A  V  Y  Y sau96I
                                                                                                            haeIII/palI
                                                                                                            sau96I
                                                                                                            nlaIV
                                                                                                            hgiJII
                                                                                                            bsp1286
                                                                                             bmyI           bsp120I
                                                             maeIII                                         banII
                                                             bstEII                  asuI
                                                    scrFI                            apaI
                                                    mvaI               mnlI          styI   asuI
                                             maeII    ecoRII  bsaJI                  bsaJI
                                             hinlI/acyI  dsaV  bseRI   esp3I
                             maeIII          ahaII/bsaHI  bstNI        bsaJI hphI bsmBI          mnlI    bsaJI
             mnlI        hphI bsrI mboII aatII  taqI             nlaIV apyI[dcm+] bsmAI    haeIII/palI ecoO109I/draII
1601 ACTGTGCAAG AGGGATTAT CGGTACAATG GTGACTGGTT CTTCGACGTC TGGGCTCAAG GAACCCTGGT CACCGTCTCC TCGGCCTCCA CCAAGGGCCC
     TGACACGTTC TCCCCTAATA GCCATGTTAC CACTGACCAA GAAGCTGCAG ACCCCAGTTC CTTGGGACCA GTGGCAGAGG AGCCGGAGGT GGTTCCCGGG
  96  C  A  R  G  D  Y   R  Y  N  G   D  W  F   F  D  V   W  G  Q  G   T  L  V  T  V  S   S  A  S  T   K  G  P
                                                                                   seq right is from p6G425chim2.fab2
```

```
                                                                                                                              mspI
                                                                                                                              hpaII
                                                                                                           haeIII/palI         bsaWI
                                    hinPI                                                    haeIII/palI   tgctcaacgg          bsrI aluI bsII
                                    hhaI/cfoI                                                hgiAI/aspHI   acgagttgcc          ctccttccgg
                                    nlaIV                                                    bsp1286                           gaggaagcc
                                    narI                                         hinPI       bsIHKAI                           accagtcag
                                    kasI                                         hhaI/cfoI   bmyI
                                    hinII/acyI                                   nlaIV       bsII aciI     gcggcgggg           bsrI aluI
        mspI                        hgiCI                                        narI        cac8I         cccgcccgcc          accagtcag
        hpaII                       haeII                                        kasI        ccttgcacgc    acgagtgcc
        naeI            mspI        hinII/acyI                                   hinII/acyI  ccttgcacgc    acgagtgcg
        cfr10I/bsrFI    banI        hgiCI          hphI                          hgiCI       aha1I/bsaHI   sfaNI
        cac8I           sgrAI       haeII          mboII[dam-]                   haeII       bsmFI
        haeIII/palI     hpaII       banI                                         banI
        eaeI hphI ahaII/bsaHI       ahaII/bsaHI    sau3AI cac8I                                                                 haeIII
        cfrI sfaNI cfr10I/bsrFI aciI cac8I         mboI/ndeII[dam-]                                                             bmyI bspHI hhaI/cfoI
                                                   dpnI[dam+]                                                                   banII nlaIII
                                                   dpnII[dam-]                                                                  rcaI hinPI
                                                                                                                                hgiJII haeII
                                                                                                                                bsp1286 eco47III
2601 GTGGCCGGCA TCACCGGCGC CACAGGTGCG GTTGCTGGCG CCTATATGCG CGACATCACC GATGGGGAAG ATCGGGCTCG CCACTTCGGG CTCATGAGCG
     CACCGGCCGT AGTGGCCGCG GTGTCCACGC CAACGACCGC GGATATAGCG CTGTAGTGG  CTACCCCTTC TAGCCCGAGC GGTGAAGCCC GAGTACTCGC
                                              scrFI
                                              nciI            hinPI
                                              mspI            hhaI/cfoI
                                              hpaII           nlaIV
                                    dsaI      dsaV            narI
                                    bslI      cauII           kasI
                                    sau96I    haeIII/palI                hinII/acyI
                                    nlaIV     eaeI                       hgiCI
                                    haeIII/palI                          hgiCI
                                    asuI bsaJI bsaJI                     haeII
                                    ecoO109I/draII                       banI
                  cac8I bslI cfrI  bsmFI      ahaII/bsaHI cac8I    bslI aciI aciI        haeIII/palI
2701 CTTGTTTCGG CGTGGGTATG GTGGCAGGCC CCGTGGCCGG GGGACTGTTG GGCGCCATCT CCTTGCACGC ACCATTCCTT GCGGCGGGGG TGCTCAACGG
     GAACAAAGCC GCACCCATAC CACCGTCCGG GGCACCGGCC CCCTGACAAC CCGCGGTAGA GGAACGTGCG TGGTAAGGAA CGCCGCCGCC ACGAGTTGCC fnu4HI                   pleI
        bsoFI    ecoNI               hinfI
    mnlI bslI   bsrI bbvI  bslI      hgaI        sfaNI                                                bsrI aluI bslI
2801 CCTCAACCTA CTACTGGGCT GCTTCCTAAT GCAGAGGGAG CATAAGGGAG AGCGTCGTTG GATGCCCTTG AGAGCCTTCA ACCAGTCAG CTCCTTCCGG
     GGAGTTGGAT GATGACCCGA CGAAGGATTA CGTCCTCCTC TCGCAGCAGG CTACGGGAAC TCTCGGAAGT TGGTCAGTC GAGGAAGCC

FIG. 41J
```

```
                                                                fnu4HI
                                                                mspI hinPI
                                                                naeI haeII
                                                                cfr10I/bsrFI
                                                                cac8I eco47III
                                                    nlaIV bsoFI               mnlI
                                                    hgiCI bbvI
                                                    banI hpaII hhaI/cfoI
              aciI                 mboII
              thaI                 bpuAI
              fnuDII/mvnI          bbsI           nlaIII
              bstUI nlaIII
     aciI     bsh1236I   aciI                                                                              sau96I
     thaI     hinPI      fnu4HI                                                                            nlaIV
     fnuDII/mvnI         bsoFI                                                                             avaII
     bstUI                                                                                                 asuI
     bsh1236I                                                                                        bsrI  aciI
     hinPI     bcgI                                                                                  maeIII bsmFI
     hhaI/cfoI
2901 TGGGCGCGGG GCATGACTAT CGTCGCCGCA CTTATGACTG TCTTCTTTAT CATGCAACTC GTAGGACAGG TGCCGGCAGC GCTCTGGGTC ATTTTCGGCG
     ACCCGCGCCC CGTACTGATA GCAGCGGCGT GAATACTGAC AGAAGAAATA GTACGTTGAG CATCCTGTCC ACGGCCGTCG CGAGACCCAG TAAAAGCCGC
              thaI
              fnuDII/mvnI
              bstUI         haeIII/palI
     aciI     bsh1236I      sau3AI
     sau96I   hinPI         mboI/ndeII[dam-]                                                thaI
     nlaIV    hhaI/cfoI     mboI/gsuI[dcm-] dpnI[dam+]                aciI          tfiI    hgaI
     avaII    bpmI/gsuI[dcm-] dpnII[dam-]  cac8I                      cac8I  hinfI  cac8I mnlI       thaI fnuDII/mvnI
     asuI                                                                                           fnuDII/mvnI
3001 AGGACCGCTT TCGCTGGAGC GCGACGATGA TCGGCCTGTC GCTTGCGGTA TTCGGAATCT TGCACGCCCT CGCTCAAGCC TTCGTCACTG GTCCCGCCAC
     TCCTGGCGAA AGCCGACCTC CGCTGCTACT AGCCGGACAG CGAACGCCAT AAGCCTTAGA ACGTGCGGGA GCGAGTTCGG AAGCAGTGAC CAGGGCGGTG
                                             mcrI                                                           bstUI bstUI
                                             eagI/xmaIII/eclXI                                              bsh1236I mnlI   haeI
                                             eaeI hinPI                                                     nruI  bsh1236I fokI haeIII/palI
                                             cfrI  hhaI/cfoI
                                      mspI   bsiEI  thaI
                                      naeI   fnu4HI fnuDII/mvnI
                                      cfr10I/bsrFI hpaII bstUI
     maeII                            bsoFI  aciI  hgaI  bsh1236I
     psp1406I          haeIII/palI    haeI   cac8I
              maeII    haeI    cac8I  bglI nlaIII haeIII/palI maeII cac8I
3101 CAAACGTTTC GGCGAGAAGC AGGCCATTAT CGCCGGCATG GGGCCGACG CGTCGGCTA CGTCTTGCTG GCGTTCGCGA CGGAGGCCTG GATGGCCTTC
     GTTTGCAAAG CCGCTCTTCG TCCGGTAATA GCGGCCGTAC CGCCGGCTGC GCAGCCGAT GCAGAACGAC GCAAGCGCT GCGCTCCGAC CTACCGGAAG
```

```
                                                                              hinPI                                    hgaI
                                                                              hhaI/cfoI                                thaI aclI
                                                                              mstI      pflMI                         fnuDII/mvnI
                 hphI                                                         aviII/fspI styI                         bstUI
       tfII      pflMI                                              aclI             bsmI    bsII bsaJI              bsh1236I
       hinfI     bsII      nlaIV
3501 CTAACGGATT CACCACTCCA AGAATTGGAG ACTGTGAATG CCAATCAATT CTTGCGGAGA CGCAAACCAA CCCTTGGCAG AACATATCCA TCGGGTCCGC
     GATTGCCTAA GTGGTGAGGT TCTTAACCTC TGACACTTAC GGTTAGTTAA GAACGCCTCT GCGTTTGGTT GGGAACCGTC TTGTATAGGT AGCGCAGGCG
                                                        haeIII/palI
                                                        mscI/balI
                                                        haeI
                                                        scrFI                                                          mspI
                                                        mvaI dsaI
                                                        ecoRII                                              hpaII
                                                        dsaV                                                scrFI
                                                        bstNI                                                          nciI
                                                        bsII bsaJI                          sau3AI                    dsaV
                                                        apyI[dcm+]                          mboI/ndeII[dam-]           sau96I
                                                 sau96I       dpnI[dam+]          nlaIV
                                                 avaII         dpnII[dam-]        avaII      cac8I
                                                 asuI eaeI    hinPI  hhaI/cfoI hgIAI/aspHI   asuI          rmaI
                                 fnu4HI          ppuMI        msII nlaIII bsp1286            ppuMI         maeI
               fnu4HI            bsoFI           nlaIV cfrI   aviII/fspI bsIHKAI                           ecoO109I/draII
               bsoFI fnu4HI/mvnI bbvI            ecoO109I/draII  msII    bmyI          mnII cauII-bfaI     aclI
               bsoFI bstUI                       bpmI[gsuI[dcm-] aclI sfaNI
       fnu4HI  bstUI
       bsoFI   cac8I    hhaI/cfoI   fnu4HI
       bbvI    aclI bsh1236I   avaI bsoFI                                                                  fnu4HI
                                    bbvI                                                                   bsoFI
3601 CATCTCCAGC AGCCGCAGC GGCGCATCTC GGGTCCTGGC CACGGGTGCG CATGATCGTG CTCCTGTCGT TGAGGACCCG GCTAGGCTGG
     GTAGAGGTCG TCGGCGTCG CCGCGTAGAG CCCAGGACCG GTGCCCACGC GTACTAGCAC GAGGACAGCA ACTCCTGGGC CGATCCGACC
                                            cac8I
                                            thaI                                                           fnu4HI
                                            fnuDII/mvnI                                                    bsoFI
                             hphI           bstUI                                                          bbvI
                 tfII        hinfI          bsh1236I maeII                                  bbvI           maeII
3701 CGGGGTTGCC TTACTGGTTA GCAGAATGAA TCACCGATAC GCGAGCGAAC GTGAAGCGAC TGCTGCTGCA AAACGTCTGC GACCTGAGCA ACAACATGAA
     GCCCCAACGG AATGACCAAT CGTCTTACTT AGTGGCTATG CGCTCGCTTG CACTTCGCTG ACGACGACGT TTTGCAGACG CTGGACTCGT TGTTGTACTT
                bsrI                                                                                                   ddeI          nlaIII
```

```
                                                                                              sau3AI
                                                                                              mboI/ndeII[dam-]
                                                                                              mamI[dam-]
                                                                                              dpnI[dam+]
                                                                                              dpnII[dam-]
                                                                                              bstYI/xhoII
                                                                                              alwI[dam-]
                                                                                         mspI
                                                                                         hpaII
                                                                                         mroI bsaBI[dam-]                fnu4HI
                                                                                         bspMII                          bsoFI
                                                                                         bspEI[dam-]                     bbvI
                                                         aciI                            bsaWI    sfaNI
                                                         thaI                            accIII[dam-]          fokI       cac8I
                                                         fnuDII/mvnI hinPI
                                                         bstUI       hhaI/cfoI
                                                         bsh1236I    haeII   msII
      mboII
      bpuAI
      bbsI
3801  TGGTCTTCGG TTTCCGTGTT TCGTAAAGTC TGGAAACGCG GAAGTCAGCG CCCTGCACCA TTATGTTCCG GATCTGCATC GCAGGATGCT GCTGGCTACC
      ACCAGAAGCC AAAGGCACAA AGCATTTCAG ACCTTTGCGC CTTCAGTCGC GGGACGTGGT AATACAAGGC CTAGACGTAG CGTCCTACGA CGACCGATGG aciI
                                                               cac8I              bsmFI    fokI
                                                               hinPI              sau96I   sfaNI
                                                               hhaI/cfoI          nlaIV  aciI
                                            tru9I haeII                           avaII fnu4HI           bsrI
                                            mseI  eco47III                 ddeI   asuI bsoFI             aciI                     mnlI
3901  CTGTGAACA CCTACATCTG TATTAACGAA GCGCTGGCAT TGACCCTGAG TGATTTTTCT CTGGTCCCGC CGGATCCATA CCGCCAGTTG TTTACCCTCA
      GACACCTTGT GGATGTAGAC ATAATTGCTT CGCGACCGTA ACTGGGACTC ACTAAAAAGA GACCAGGGCG GCCTAGTAT GGCGGTCAAC AAATGGGAGT nspI
                         scrFI
                         ncII
                         mspI                                   mnlI
                bsrI     hpaII                                  fokI
                bslI     dsaV nlaIII                            sfaNI
      maeII            cauII                                                              nlaIII        apoI       bslI
      psp1406I maeIII nspHI          maeIII
4001  CAACGTTCCA GTAACCGGGC ATGTTCATCA TCAGTAACCC GTTTCATCG CATCCTCTCT CGTATCGTGAG CATCCTCTCT CCCATGAAC AGAATTCCC
      GTTGCAAGGT CATTGGCCCG TACAAGTAGT AGTCATTGGG GCAAAGTAGC CATAGTAATG                    GGGTACTTG TCTTTAAGGG
```

```
                fnu4HI                                                                                      hglAI/aspHI
                bsoFI                       maeIII                                                          bsp1286
                bbvI    nlaIII bsrI bsaAI                                          sfaNI                    bsiHKAI
                hinPI   hhaI/cfoI tthlllI/aspI                                     fnu4HI         ddeI      bmyI ndeI
                hhaI/cfoI                    aciI         bstll07I tru9I           bsoFI          rsaI      apaLI/snoI
                                                          accI bsrI mseI           aciI          csp6I     alw44I/snoI
4401 CGGGTGTCGG GGCGCAGCCA TGACCCAGTC ACGTAGCGAT AGCGGAGTGT ATACTGGCTT AACTATGCGG CATCAGAGCA GATTGTACTG AGAGTGCACC
     GCCCACAGCC CCGCGTCGGT ACTGGGTCAG TGCATCGCTA TCGCCTCACA TATGACCGAA TTGATACGCC GTAGTCTCGT CTAACATGAC TCTCACGTGG mboII
                                                                      earI/ksp632I                       hinPI
                                                                      sapI                               hhaI/cfoI
                                                           sfaNI      hinPI                              fnu4HI
        aciI       aciI    sfaNI                           aciI       hhaI/cfoI         aciI  mnlI       pleI bsoFI           mcrI
4501 ATATGCGGTG TGAAATACCG CACAGATGCG TAAGGAGAAA ATACCGCATC AGGCGCTCTT CCGCTTCCTC GCTCACTGAC TCGCTGCGCT CGGTCGTTCG
     TATACGCCAC ACTTTATGGC GTGTCTACGC ATTCCTCTTT TATGGCGTAG TCCGCGAGAA GGCGAAGGAG CGAGTGACTG AGCGACGCGA GCCAGCAAGC fnu4HI
     bsoFI                                                                                                         bslI
     aciI                                                                                 nlaIII                   cac8I
     fnu4HI   aciI                                               tfiI                     nspI                     haeIII/palI
     bsoFI    bsrBI                                              hinfI                    nspHI                    haeI
     bbvI  cac8I            aluI                                                          aflIII
4601 GCTGCGGCGA GCGGTATCAG CTCACTCAAA GGCGGTAATA CGGTTATCCA CAGAATCAGG GGATAACGCA GGAAAGAACA TGTGAGCAAA AGGCCAGCAA
     CGACGCCGCT CGCCATAGTC GAGTGAGTTT CCGCCATTAT GCCAATAGGT GTCTTAGTCC CCTATTGCGT CCTTTCTTGT ACACTCGTTT TCCGGTCGTT scrFI          thaI
     mvaI           bstUI
     ecoRII         bsh1236I
     dsaV                                     aciI
     bstNI  bslI                              fnu4HI                                      hgaI
     apyI[dcm+]                               bsoFI  cac8I                                drdI
     haeIII/palI                              haeIII/palI                       sfaNI     taqI                     mnlI
     haeI  nlaIV                              nlaIV                              aciI
4701 AAGGCCAGGA ACCGTAAAAA GGCCGCGTTG CTGGCGTTTT TCCATAGGCT CCGCCCCCCT GACGAGCATC ACAAAAATCG ACGCTCAAGT CAGAGGTGGC
     TTCCGGTCCT TGGCATTTTT CCGGCGCAAC GACCGCAAAA AGGTATCCGA GGCGGGGGGA CTGCTCGTAG TGTTTTTAGC TGCGAGTTCA GTCTCCACCG
```

```
                                                    hinPI
                                                    thaI
                                                    fnuDII/mvnI
                                                    bstUI
                                                    bshl236I                            maeII
                                                    aciI                                hinlI/acyI
                                                                                        ahaII/bsaHI
                                              nlaIV hhaI/cfoI                           aatII ddeI
           nlaIII
           rcaI
           bspHI aciI
           bsmAI bsrBI
6401 TTGTCTCATG AGCGGATACA TATTGAAATG TATTTAGAAA AATAAACAAA TAGGGGTTCC GCGCACATTT CCCCGAAAAG TGCCACCTGA CGTCTAAGAA
     AACAGAGTAC TCGCCTATGT ATAAACTTTAC ATAAATCTTT TTATTTGTTT ATCCCCAAGG CGCGTGTAAA GGGGCTTTTC ACGGTGGACT GCAGATTCTT sau96I
                                           haeIII/palI
                                           asuI       mboII
                                           eco0109I/draII
                     nlaIII                   mnlI    bpuAI
                     rcaI tru9I                       bbsI
                     bspHI mseI         bssSI
6501 ACCATTATTA TCATGACATT AACCTATAAA AATAGGCGTA TCACGAGGCC CTTTCGTCTT CAA  (SEQ ID NO.61)
     TGGTAATAAT AGTACTGTAA TTGGATATTT TTATCCGCAT AGTGCTCCGG GAAAGCAGAA GTT
```

FIG. 41U

```
>length: 6563
aatII(GACGTC):        1645 6489
acc65I(GGTACC):       403 823
accI(GTMKAC):         1093 1963 4449
accIII(TCCGGA):       3867[dam-]
aciI(CCGC):           178 542 805 877 1340 1750 1826 2011 2039 2043 2182 2242 2384 2492 2501 2504
                      2628 2781 2784 2787 2906 2926 3005 3045 3094 3141 3226 3241 3309 3342 3367 3412
                      3436 3448 3490 3544 3597 3613 3619 3700 3838 3967 3970 3981 4139 4155 4210 4266
                      4351 4390 4400 4442 4467 4505 4518 4544 4561 4604 4611 4632 4723 4751 4878 4897
                      5018 5128 5263 5272 5634 5725 5916 5962 6083 6127 6204 6313 6412 6459
acyI                  see hinlI
aflIII(ACRYGT):       1307 4678
ageI(ACCGGT):         1788
ahaII/bsaHI(GRCGYC):  1645 1813 2616 2637 2751 3408 6107 6489
ahaIII/draI(TTTAAA):  5435 5454 6146
ahdI/eam1105I(GACNNNNNGTC): 346 5566
aluI(AGCT):           72 121 252 320 398 532 589 648 1126 1144 1167 1325 1386 1906 2054 2075 2126
                      2218 2233 2889 3292 4202 4259 4270 4319 4338 4619 4845 4935 4981 5238 5759 5859
                      5922
alw44I/snoI(GTGCAC):  1831 4494 4992 6238
alwI[dam-](GGATC):    412 413 712 713 1171 1471 2578 2579 3300 3870 5245 5319 5331 5416 5429 5893
                      6196 6214
alwNI[dcm-](CAGNNNCTG): 1117 1385 5089
apaI(GGGCCC):         1695
apaLI/snoI(GTGCAC):   1831 4494 4992 6238
apoI(RAATTY):         1 391 4093
apyI[dcm+](CCWGG):    640 999 1347 1357 1449 1665 1713 1755 1764 2333 3262 3645 4705 4826 4839
aseI/asnI/vspI(ATTAAT): 5742
asnI                  see aseI
asp700(GAANNNNTTC):   905 930 4234 6166
asp718(GGTACC):       403 823
aspHI                 see hgiAI
aspI                  see tth111I
asuI(GGNCC):          1119 1195 1425 1434 1446 1512 1695 1696 1752 2155 2375 2727 3002 3090 3339 3463
```

FIG. 41V

Stop Template Primer

SL.97.2    5' CAT GGT ATA GGT TAA ACT TAT TTA CAC 3'  (SEQ ID NO.63)

NNS Randomization Primer

SL.97.3    5' CAT GGT ATA GGT NNS ACT TAT TTA CAC 3'  (SEQ ID NO.64)

FIG. 42

Randomization of Position N35 of Variable Light Chain CDR-1 Amino Acid Frequency

Phage Display (NNS Codon Library) Sort #3

| Amino Acid | Frequency | % Total | IC50 (nM) |
|---|---|---|---|
| Asparagine (wt) | 1 | 5.6 | 4.9 |
| Glycine | 6 | 16.6 | 3.1 |
| Aspartic Acid | 3 | 16.6 | 3.1 |
| Glutamic Acid | 4 | 22.2 | 0.1 |
| Alanine | 2 | 5.6 | 0.2 |
| Lysine | 1 | 5.6 | ND |
| Serine | 1 | 1.9 | ND |

FIG. 43A

Representative Conc versus Time Plot. Shown is the kinetic data for 6G4V11N35A.F(ab')2

| SAMPLE | ka | kd | Kd |
|---|---|---|---|
| 6G4V11N35A-Fab | ND | ND | 114pM |
| 6G4V11N35A-F(ab')$_2$ | $2.0 \times 10^6$ | $2.1 \times 10^{-4}$ | 109pM |
| 6G4V11N35E-Fab | $4.7 \times 10^6$ | $2.6 \times 10^{-4}$ | 54pM |

```
  1 ATGAAAAAGA ATATCGCATT TCTTCTTGCA TCTATGTTCG TTTTTTCTAT TGCTACAAAC
    TACTTTTTCT TATAGCGTAA AGAAGAACGT AGATACAAGC AAAAAAGATA ACGATGTTTG
-23 M  K  K    N  I  A  F   L  L  A    S  M  F  V   F  S  I    A  T  N

61 GCATACGCTG ATATCCAGAT GACCCAGTCC CCGAGCTCCC TGTCCGCCTC TGTGGGCGAT
    CGTATGCGAC TATAGGTCTA CTGGGTCAGG GGCTCGAGGG ACAGGCGGAG ACACCCGCTA
 -3 A  Y  A    D  I  Q  M   T  Q  S    P  S  S    L  S  A  S   V  G  D

121 AGGGTCACCA TCACCTGCAG GTCAAGTCAA AGCTTAGTAC ATGGTATAGG TGAGACGTAT
    TCCCAGTGGT AGTGGACGTC CAGTTCAGTT TCGAATCATG TACCATATCC ACTCTGCATA
 18 R  V  T    I  T  C  R   S  S  Q    S  L  V  H   G  I  G    E  T  Y

181 TTACACTGGT ATCAACAGAA ACCAGGAAAA GCTCCGAAAC TACTGATTTA CAAAGTATCC
    AATGTGACCA TAGTTGTCTT TGGTCCTTTT CGAGGCTTTG ATGACTAAAT GTTTCATAGG
 38 L  H  W    Y  Q  Q  K   P  G  K    A  P  K  L   L  I  Y    K  V  S

241 AATCGATTCT CTGGAGTCCC TTCTCGCTTC TCTGGATCCG GTTCTGGGAC GGATTTCACT
    TTAGCTAAGA GACCTCAGGG AAGAGCGAAG AGACCTAGGC CAAGACCCTG CCTAAAGTGA
 58 N  R  F    S  G  V  P   S  R  F    S  G  S    G  S  G  T   D  F  T

301 CTGACCATCA GCAGTCTGCA GCCAGAAGAC TTCGCAACTT ATTACTGTTC ACAGAGTACT
    GACTGGTAGT CGTCAGACGT CGGTCTTCTG AAGCGTTGAA TAATGACAAG TGTCTCATGA
 78 L  T  I    S  L  Q    P  E  D    F  A  T  Y   Y  C  S    Q  S  T

361 CATGTCCCGC TCACGTTTGG ACAGGGTACC AAGGTGGAGA TCAAACGAAC TGTGGCTGCA
    GTACAGGGCG AGTGCAAACC TGTCCCATGG TTCCACCTCT AGTTTGCTTG ACACCGACGT
 98 H  V  P    L  T  F  G   Q  G  T    K  V  E  I   K  R  T    V  A  A

421 CCATCTGTCT TCATCTTCCC GCCATCTGAT GAGCAGTTGA AATCTGGAAC TGCTTCTGTT
    GGTAGACAGA AGTAGAAGGG CGGTAGACTA CTCGTCAACT TTAGACCTTG ACGAAGACAA
118 P  S  V    F  I  F  P   P  S  D    E  Q  L    K  S  G  T   A  S  V

481 GTGTGCCTGC TGAATAACTT CTATCCCAGA GAGGCCAAAG TACAGTGGAA GGTGGATAAC
    CACACGGACG ACTTATTGAA GATAGGGTCT CTCCGGTTTC ATGTCACCTT CCACCTATTG
138 V  C  L    L  N  N  F   Y  P  R    E  A  K    V  Q  W  K   V  D  N

541 GCCCTCCAAT CGGGTAACTC CCAGGAGAGT GTCACAGAGC AGGACAGCAA GGACAGCACC
    CGGGAGGTTA GCCCATTGAG GGTCCTCTCA CAGTGTCTCG TCCTGTCGTT CCTGTCGTGG
158 A  L  Q    S  G  N  S   Q  E  S    V  T  E    Q  D  S  K   D  S  T

601 TACAGCCTCA GCAGCACCCT GACGCTGAGC AAAGCAGACT ACGAGAAACA CAAAGTCTAC
    ATGTCGGAGT CGTCGTGGGA CTGCGACTCG TTTCGTCTGA TGCTCTTTGT GTTTCAGATG
178 Y  S  L    S  S  T  L   T  L  S    K  A  D    Y  E  K  H   K  V  Y

661 GCCTGCGAAG TCACCCATCA GGGCCTGAGC TCGCCCGTCA CAAAGAGCTT CAACAGGGGA
    CGGACGCTTC AGTGGGTAGT CCCGGACTCG AGCGGGCAGT GTTTCTCGAA GTTGTCCCCT
198 A  C  E    V  T  H  Q   G  L  S    S  P  V    T  K  S  F   N  R  G
                                                              (SEQ ID NO.65)
721 GAGTGTTAAG CTGATCCTCT ACGCCGGACG CATCGTGGCC CTAGTACGCA ACTAGTCGTA
    CTCACAATTC GACTAGGAGA TGCGGCCTGC GTAGCACCGG GATCATGCGT TGATCAGCAT
218 E  C  Q  (SEQ ID NO.62)
```

FIG. 45

N35AH1upr
5'-CTAGTGCAGTCTGGCGGTGGCCTGGTGCAGCCAGGGGCTCACTCCGTTTGTCCTGTGCAGCTTCTGGCTACTCCTTC-3'
(SEQ ID NO.66)

N35AH1lwr
5'-TCGAGAAGGAGTAGCCAGAAGCTGCACAGGACAAACGGAGTGAGCCCCCTGGCTGCACCAGGCCACCGCCAGACTGCACT
AG-3'
(SEQ ID NO.67)

Bold indicates nucleotide change destroying PvuII site.

FIG. 47

```
> length: 8120 (circular)
>This has the pSVI backbone with the pRK7 cloning linker (pSVI7) and the intron DHFR(ID)
>made from pSVI.WTSD.D by adding a linearization linker(LL) into the HpaI site scrFI
       cac8I                                                                                                            mvaI
       aluI                                                                                                             ecoRII
       sstI                                                                                                             dsaV
       sacI                              sau3AI  aluI                                                                   bstNI
       hgiJII                            mboI/ndeII[dam-]                                                               apyI[dcm+]
       hgiAI/aspHI                       dpnI[dam+]                                                                     bsaJI
       ecl136II                          pvuI/bspCI                                                                     nlaIV
       bsp1286                           pleI dpnII[dam-]                                                   bsmFI       cac8I
       bsiHKAI                           hinfI  taqI[dam-]                                                  sfaNI
       bmyI              rmaI       mcrI  pvuII                                                             ppul0I
       banII             maeI       bslEI  nspBII                                                           nsiI/avaIII
       taqI              bfaI       taqI[dam-]                                      scrFI          nlaIII   sphI        nspI
  1  TTCGAGCTCG CCCGACATTG ATTATTGACT AGAGTCGATC AGTCGACTGTG GACAGCTGTG GAATGTGTGT CAGTTAGGGT GTGGAAAGTC CCCAGGCTCC CCAGCAGGCA   nspHI
     AAGCTCGAGC GGGCTGTAAC TAATAACTGA TCTCAGCTAG CAGCTGACAC CTGTCGACAC CTTACACACA GTCAATCCCA CACCTTTCAG GGGTCCGAGG GGTCGTCCGT   cac8I sfaNI
                  ppul0I                                        scrFI
                  nsiI/avaIII                                   mvaI
                  nlaIII                                        ecoRII
                  sphI                                          dsaV
                  nspI                                          bstNI                   apyI[dcm+]
                  nspHI                                         apyI[dcm+]              bsaJI
                  cac8I                                         bsaJI      sexAI        bsmFI       nlaIV       cac8I
 101 GAAGTATGCA AAGCATGCAT CTCAATTAGT CAGCAACCAG GTGTGGAAAG TCCCCAGGCT CCCCAGCAGG CAGAAGTATG CAAAGCATGC ATCTCAATTA
     CTTCATACGT TCCGTACGTA GAGTTAATCA GTCGTTGGTC CACACCTTTC AGGGGTCCGA GGGGTCGTCC GTCTTCATAC GTTTCGTACG TAGAGTTAAT nlaIII
                                                                                                    styI
                                                                  acII                              ncoI
                                          acII                                                      bslI dsaI
            acII                          bsmFI      aciI foki    aciI bsrI aciI                    aciI bsaJI
 201 GTCAGCAACC ATAGTCCCGC CCCTAACTCC GCCCATCCCG CCCCAGTTCT CCGCCCATTCT CGGCCCATTC CGCCCAGTTC CCGCCCCATG GCTGACTAAT
     CAGTCGTTGG TATCAGGGCG GGGATTGAGG CGGGTAGGGC GGGGTCAAG GCGGGTAAGA GCCGGGTAAG GGGGGTCAAG GGCGGGGTAC CGACTGATTA
```

```
                                                                    scrFI
                                                                    mvaI
                                                                    ecoRII
                                                                    dsaV
                                                                    bstNI                     tfII       tru9I
                                                                    apyI[dcm+]                hinfI      mseI
               eco57I                                               sexAI    ddeI mboII taqI  ahaIII/draI
               mboII              tfII
          earI/ksp632I           hinfI hphI
          mnlI                   alwNI[dcm-]
601 CAAAGAATGA CCACAACCTC TTCAGTGGAA GGTAAACAGA ATCTGGTGAT TATGGGTAGG AAAACCTGT TCTCCATTCC TGAGAAGAAT CGACCTTAA
    GTTCTTACT GGTGTTGGAG AAGTCACCTT CCATTTGTCT TAGACCACTA ATACCCATCC TTTTGGACCA AGAGGTAAGG ACTCTTCTTA GCTGGAAATT sstI
                                                              sacI
                                                              hglJII
                                                              hg1AI/aspHI
                                                              ecl136II
                                                              bsp1286
                                                              bsiHKAI
                                                              bmyI
                                                    mnlI aluI                                      tru9I
          tru9I                                     bssSI banII                                    afIII/bfrI
          mseI    ddeI                              bslI  bseRI                    bstXI          fokI sfaNI mseI
    aseI/asnI/vspI
701 AGGACAGAAT TAATATAGTT CTCAGTAGAG AACTCAAGA ACCACCACGA GGAGCTCATT TTCTTGCCAA AAGTTTGGAT GATGCCTAA GACTTATTGA
    TCCTGTCTTA ATTATATCAA GAGTCATCTC TTGAGTTCT TGGTGGTGCT CCTCGAGTAA AAGAACGGTT TCAAACCTA CTACGGAATT CTGAATAACT haeII/palI
                                                                                                haeI
                                                     scrFI                scrFI
                                                     mvaI                 mvaI
                                                     ecoRII               ecoRII
                                                     dsaV  tfII nlaIII    dsaV
                                                     bstNI                bstNI          ddeI pleI
    mspI                                             apyI[dcm+] hinfI apyI[dcm+]         hinfI
    hpaII                                                                       bstNI
    bsaWI    accI nlaIII                   mnlI
801 ACAACCGGAA TTGCAAGTA AAGTAGACAT GGTTTGGATA GTCGGAGGCA GTTCTGTTTA CCAGGAAGCC ATGAATCAAC CAGGCCACCT TAGACTCTTT
    TGTTGGCCTT AACCGTTCAT TTCATCTGTA CCAAACCTAT CAGCCTCCGT CAAGACAAAT GGTCCTTCGG TACTTAGTTG GTCCGGTGGA ATCTGAGAAA
```

```
                                                                    scrFI
                                                                    ncII
                                                                    mspI
                                                                    hpaII
                                                                    dsaV
                                                                    cauII
                                                                    xmaI/pspAI
                                                                    smaI
                                                                    scrFI                          scrFI
                                                                    ncII                           mvaI
                                                                    dsaV                           ecoRII
                                                                    cauII                          dsaV
                                                                                                   bstNI
                                             rsaI         fokI                                     apyI[dcm+]                                           scrFI
                                             csp6I   bslI bsaJI mboII                              sexAI                                                 mvaI         mnlI         scfI cac8I
                          avaI               bsp1407I/bsrGI bslI avaI earI/ksp632I  GGGAAGAGAT GACCAAGAAC CAGGTCAGCC TGACCTGCCT GGTCAAAGGC TTCTATCCCA    ecoRII       pleI         nlaIV mboII  TCCTCTACAG
2401 CAGCCCCGAG AACCACAGT  GTACACCCTG CCCCATCCC   GGGAAGAGAT GACCAAGAAC CAGGTCAGCC TGACCTGCCT GGTCAAAGGC TTCTATCCCA
     GTCGGGGCTC TTGGTGTCCA CATGTGGGAC GGGGGTAGG   CCCTTCTCTA CTGGTTCTTG GTCCAGTCGG ACTGGACGGA CCAGTTTCCG AAGATAGGGT
347  Q  P  R  E  P  Q  V    Y  T  L  P  P  S  R    E  E  M  T  K  N  Q  V  S  L   T  C  L  V  K  G  F  Y  P  S mspI
                                                                    hpaII
                          dsaI                                      fnu4HI
                          bslI                                      bsoFI
                          msII bsaJI                     bsrDI      bbvI                                                    mnlI
2501 GCGACATCGC CGTGGAGTGG GAGAGCAATG GCAGCCGGA GCAGGGAAC AAGACCACGC CTCCCGTGCT CTTGTTGATG AAGACCACGC GGCTCCTTCT CCGAGGAAGA AGGAGATGTC
     CGCTGTAGCG GCACCTCACC CTCTCGTTAC CGTCGGCCT CGTCCCTTG TTCTGGTGCG GAGGGCACGA CAAGAACTAC TTCTGGTGCG CCGAGGACTG CCTGAGGCTG GAGGCACGA TCTCTACAG
381  D  I  A  V  E  W  E    S  N  G  Q  P  E  N    N  Y  K  T  T  P  P  V  L    D  S  D  G  S  F  F  L  Y  S mboII
                                                                    bpuAI
                          dsaI                                      nlaIII
                          hphI                       fnu4HI         ppu10I                                                                sapI
                          aluI bsaJI                 bsoFI maeII    nsII/avaIII                                                            mboII mnlI
2601 CAAGCTCACC GTGGACAAGA  GCAGGTGGCA GCAGGGAAC GTCTTCTCAT GCTCCGTGAT GCATGAGGCT CTGCACAACC ACTACACGCA GAAGAGCCTC
     GTTCGAGTGG CACCTGTTCT  CGTCCACCGT CGTCCCCTTG CAGAAGAGTA CGAGGCACTA CGTACTCCGA GACGTGTTGG TGATGTGCGT CTTCTCGGAG
414  K  L  T  V  D  K  S    R  W  Q  Q  G  N    V  F  S  C  S  V  M  H  E  A    L  H  N  H  Y  T  Q  K  S  L

```
                                                                                          scrFI
                                                                                          mval
                                                                                          ecoRII
                                                                     sfaNI                dsaV
                                                                     ppulOI               bstNI
                                                           nsII/avaIII                    apyI[dcm+]
                                                           nlaIII          sphI           sexAI        bsmFI
                                                                           nspI           dsaV
                                                                           nspHI          bstNI
                                                                           cac8I          apyI[dcm+]
3001 GAATGTGTGT CAGTTAGGGT GTGGAAAGTC CAGTTAGGGT GTGGAAAGTC CAGTTAGGGT GTGGAAAGTC CAGTTAGGGT GTGGAAAGTC
```

FIG. 48K

```
                                                              scrFI
                                                              ncII
                                                              mspI
                                                              hpaII
                                                              dsaV
                                                              haeIII/palI
                          rmaI
                          maeI
                          styI                  alul         mcrI                                                       tfII
                          bsaJI                 rmaI         eagI/xmaIII/eclXI                                          hinfI
                          blnI                  maeI         eaeI                                                       acII
                          avrII[dam-]           bfaI         cfrI                                                       thaI
                          haeIII/palI           nheI         bslEI                                                      fnuDII/mvnI                   pleI
                          stuI                  cac8I        mspI cauII                                                 bstUI                         hinfI
             mnlI bfaI   heaI                   aluI         hpaII                                                      bsh1236I
      mnlI                                                                                                                                            sau3AI
                                                                                                                                                      mboI/ndeII[dam-]
 3301 AGGAGGCTTT TTTGGAGGCC TAGGCTTTTG CAAAAAGCTA GCTTATCCGG CCGGGAACGG TGCATTGGAA CGCGGATTCC CCGTGCCAAG AGTCAGTAA
      TCCTCCGAAA AAACCTCCGG ATCCGAAAAC GTTTTTCGAT CGAATAGGCC GGCCCTTGCC ACGTAACCTT GCGCCTAAGG GGCACGGTTC TCAGTCCATT
                       ^seq from pSVI6B5-6G4VL: AvrII - HindIII frag                              U1 matched splice donar^
                                                                                                                                                      dpnI[dam+]
                                                                                                                                                      dpnII[dam-]
                                                                                                                                                      alwI[dam-]
                                                                                                                                                      taqI[dam-]
                                                                                                                                                      claI/bsp106[dam-]
                                                                                                                                                      bspDI[dam-]
                                                             fnu4HI                                                                                   sau3AI
                                                             bsoFI                                                                                    mboI/ndeII[dam-]
                                                             acII                                                                                     dpnI[dam+]
                        bstXI                                thaI                                                                                     dpnII[dam-]
      acII       scfI    sau96I  styI                        fnuDII/mvnI  tru9I                                                                       alwI[dam-]       fokI
      rsaI       pleI    haeIII/palI                         bstUI        mseI
      csp6I scfI hinfI   asuI    bsaJI                       bsh1236I     aseI/asnI/vspI
 3401 GTACCGCCTA TAGAGTCTAT AGGCCCACCC CCTTGGCTTC GTTAGAACGC GGCTACAAATT AATACATAAC CTTTTGGATC GATCCTACTG ACACTGACAT
      CATGGCGGAT ATCTCAGATA TCCGGGTGGG GGAACCGAAG CAATCTTGCG CCGATGTTAA TTATGTATTG GAAAACCTAG CTAGGATGAC TGTGACTGTA
                                 ^sp6 promoter                                                             ^removed ATG
                                                                                                            ^U2 match
                                                                                                             lariat consensus^
                                                                                           IgG vH natural lariat restored^
```

FIG. 48L

```
                                                                                          nlaIII
                                                      sau96I                                  styI
                                                      avaII                             nlaIII
                                                      asuI                              pflMI
                                                      scrFI                      clal/bsp106  ncoI
                                                      mvaI          rmaI         sfaNI        ecoRI    dsaI
                                                      ecoRII     maeI                         fnu4HI   apol  bslI fokI
                                                      dsaV       bfaI     thaI  nheI          bsoFI taqI    bsaJI
                                                      bstNI              fnuDII/mvnI                 bbvI bspDI[dam-]
                                                      apyI[dcm+]         bstUI                       GGCTGCATC GATTGAATTC CACCATGGGA
                                                      bsaJI              bshl236I aluI                CCGACGTAG CTAACTTAAG GTGGTACCCT
                                 bslI                        mnlI nruI  aluI                            ^cloning linker
3501 CCACTTTTTC TTTTTCTCCA CAGGTGTCCA CTCCCAGTTC CAACTGCACC TCGGTTCGCG AAGTAGCTT
     GGTGAAAAAG AAAAAGAGGT GTCCACAGGT GAGGGTCCAG GTTGACGTGG AGCCAAGCGC TTCGATCGAA aluI
                                                                    sstI
                                                                    sacI
                                                                    hglJII
                                                                    hglAI/aspHI
                                                                    ecl136II
                                                                    bsp1286
                                                                    bslHKAI
                                                            bsmFI   bmyI
                                          rmaI              bsrI    avaI          mnlI
                                          maeI              bpmI/gsuI[dcm-]       aclI
                                 nlaIII   bfaI       bsrI   csp6I   ecoRV         tthIIII/aspI banII
                                 fokI                                                                                        scrFI
                                                                                                                             mvaI
                                                                                                                             ecoRII
                                                                                                                             dsaV
                                                                                                                             bstNI  aluI
                                                                                                           bsrI              apyI[dcm+]
3601 TGGTCATGTA TCATCCTTTT TCTAGTAGCA ACTGCAACTG GAGTACATTC AGATATCCAG ATGACCCAGT CCCCGAGCTC CCTGTCCGCC TCTGTGGGCG
     ACCAGTACAT AGTAGGAAAA AGATCATCGT TGACGTTGAC CTCATGTAAG TCTATAGGTC TACTGGGTCA GGGGCTCGAG GGACAGGCGG AGACACCCGC
  1    W   S   Y   H   H   L    L    R    *   Q   L   Q   L    E   Y   I   Q   I   P   D    I   Q   M   T   Q   S   P   S   S   L   S   A   S   V   G   D scfI                                            maeII
                           pstI                              ddeI          snaBI
                           bsgI                              aluI csp6I    bsaAI                     bsrI
                           sse8387I                          hindIII       nlaIII
          hphI             bspMI
          maeIII           hphI bspMI
          bstEII
3701 ATAGGGTCAC CATCACCTGC AGGTCAAGTC AAAGCTTAGT ACATGGTATA GGTGCTACGT ATTACACTG GTATCAACAG AAACCAGGAA AAGCTCCGAA
     TATCCCAGTG GTAGTGGACG TCCAGTTCAG TTTCGAATCA TGTACCATAT CCACGATGCA TAAATGTGAC CATAGTTGTC TTTGGTCCTT TTCGAGGCTT
 18    R   V   T   I   T   C   R   S   S   Q   S   L   V   H   G   I   G   A   T   Y   L   H   W   Y   Q   Q   K   P   G   K   A   P   K
```

FIG. 48M

```
                                                                              mspI
                                                                              hpaII
                                                                              bslI
                                                                              bsaWI
                                                                              sau3AI
                                                                              mboI/ndeII[dam-]                                          fnu4HI
                                                                              dpnI[dam+]                                                bsoFI
                                                                              dpnII[dam-]                                               bbvI
                                                                              alwI[dam-]                                                scfI
                                                                              nlaIV                                                     pstI
                                          tfiI                                bstYI/xhoII                                               bsgI
                                          hinfI         bsmFI                 bamHI
                                          taqI         bpmI/gsuI[dcm-]        alwI[dam-]       bsmFI
                                          claI/bsp106  pleI
                                          bspDI[dam-]  hinfI
3801 ACTACTGATT TACAAAGTAT CCAATCGATT CTCTGGAGTC CCTTCTCGCT TCTCTGGATC CGGTTCTGGG ACGGATTTCA CTCTGACCAT CAGCAGTCTG
     TGATGACTAA ATGTTTCATA GGTTAGCTAA GAGACCTCAG GGAAGAGCGA AGAGACCTAG GCCAAGACCC TGCCTAAAGT GAGACTGGTA GTCGTCAGAC
 51   L  L  I  Y  K  V  S  N  R  F  S   G  V  P  S  R  F  S  G  S  G  S  G  T  D  F  T  L  T  I  S  S  L rsaI
                                                                                   csp6I
                                                                                   nlaIV
                                                                bsrBI               kpnI styI
                                                                acII                hgICI        sau3AI
                                                 rsaI           bsmFI               banI bsaJI   mboI/ndeII[dam-]  fnu4HI
                                                 csp6I          nlaIII              asp718       dpnI[dam+]        bsoFI
                                                 scaI           maeII   acc65I                   dpnII[dam-]       bbvI
3901 CAGCCAGAAG ACTTCGCAAC TTATTACTGT TCACAGAGTA CTCATGTCCC GCTCACGTTT GGACAGGGTA CCAAGGTGGA GATCAAACGA ACTGTGGCTG
     GTCGGTCTTC TGAAGCGTTG AATAATGACA AGTGTCTCAT GAGTACAGGG CGAGTGCAAA CCTGTCCCAT GGTTCCACCT CTAGTTTGCT TGACACCGAC
 84   Q  P  E  D  F  A  T  Y  Y  C  S  Q  Q  S  T  H  V  P  L  T  F  G  Q  G  T  K  V  E  I  K  R  T  V  A  A haeIII/palI
         mboII                                                                                            haeI
         bpuAI                                   xmnI                              xmnI                   mnlI
         bbsI    mboII acII                      asp700                            cac8I    asp700
4001 CACCATCTGT CTTCATCTTC CCGCCATCTG ATGAGCAGTT GAAATCTGGA ACTGCTTCTG TTGTGTGCCT GCTGAATAAC TTCTATCCCA GAGAGGCCAA
     GTGGTAGACA GAAGTAGAAG GGCGGTAGAC TACTCGTCAA CTTTAGACCT TGACGAAGAC AACACACGGA CGACTTATTG AAGATAGGGT CTCTCCGGTT
118   P  S  V  F  I  F  P  P  S  D  E  Q  L  K  S  G  T  A  S  V  V  C  L  L  N  N  F  Y  P  R  E  A  K
```

FIG. 48N

```
                                                      scrFI
                                                      nvaI
                                                      ecoRII
                                                      dsaV
                                                      bstNI
              rsaI              mnlI                  apyI[dcm+]
              csp6I    bslI     maeIII bsaJI  maeIII                                                           scfI   fnu4HI
                                                                                                                      ddeI bsoFI
                                                                                                                   mnlI bbvI
     4101 AGTACAGTGG AAGGTGGATA ACGCCCTCCA ATCGGGTAAC TCCCAGGAGA GTGTCACAGA GCAGGACAGC AAGGACAGCA CCTACAGCCT CAGCAGCACC
          TCATGTCACC TTCCACCTAT TGCGGGAGGT TAGCCCATTG AGGGTCCTCT CACAGTGTCT CGTCCTGTCG TTCCTGTCGT GGATGTCGGA GTCGTCGTGG
      151  V  Q  W   K  V  D  N   A  L  Q    S  G  N   S  Q  E  S   V  T  E    Q  D  S   K  D  S  T   Y  S  L   S  S  T sstI
                                                                       sacI
                                                                       hgiJII
                                                                       hgiAI/aspHI
                                                                       ecll36II
                                                                       bsp1286
                                                                       bslHKAI
                                                                       bmyI
                                                                       ddeI cac8I
                                                                       haeIII/palI
                                                                       sau96I alu1
                                                                       asuI banII
                                                            hphI       ecoO109I/draII
                         accI   cac8I        maeIII    alwNI[dcm-]              maeIII    aluI
     4201 CTGACGCTGA GCAAAGCAGA CTACGAGAAA CACAAAGTCT ACGCCTGCGA AGTCACCCAT CAGGGCCTGA GCTCGCCCGT CACAAAGAGC TTCAACAGGG
          GACTGCGACT CGTTTCGTCT GATGCTCTTT GTGTTTCAGA TGCGGACGCT TCAGTGGGTA GTCCCGGACT CGAGCGGGCA GTGTTTCTCG AAGTTGTCCC
      184  L  T  L  S   K  A  D   Y  E  K   H  K  V  Y   A  C  E    V  T  H    Q  G  L  S   S  P  V   T  K  S   F  N  R  G sau96I
                         haeIII/palI                            aluI
                   aclI  asuI                                   fnu4HI
                   fnu4HI nlaIII                                bsoFI
                   bsoFI                                        bbvI
                   sfil styI                                            maeIII                 sfaNI
              aluI haeIII/palI
              hindIII bglI ncoI
              tru9I eaeI dsaI
              mseI  cfrI bsaJI
     4301 GAGAGTGTTA AGCTTGGCCG CCATGGCCCA ACTTGTTTAT TGCAGCTTAT AATGGTTACA AATAAAGCAA TAGCATCACA AATTTCACAA ATAAAGCATT
          CTCTCACAAT TCGAACCGGC GGTACCGGGT TGAACAAATA ACGTCGAATA TTACCAATGT TTATTTCGTT ATCGTAGTGT TTAAAGTGTT TATTTCGTAA
      218  E  C  O
```

FIG. 48O

```
                                                                sau3AI
                                                                mboI/ndeII[dam-]
                                                                dpnI[dam+]
                                                                dpnII[dam-]
                                                                pvuI/bspCI
                                                                mcrI
                                                                bslEI
                                                                taqI[dam-]
                                                                claI/bsp106[dam-]
                                                                bspDI[dam-]  tru9I          fnu4HI    haeI
                                                                sau3AI       mseI           bsoFI    styI
                                                                mboI/ndeII[dam-]             bbvI    ncoI
                                                                dpnI[dam+]  xmnI           hinPI   dsaI haeIII/palI
                                                                dpnII[dam-] aseI/asnI/vspI         bsaJI
                                      rmaI                                   asp700      hhaI/cfoI nlaIII
                                      maeI                    nlaIII alwI[dam-]  GAATTAATTC  GGCGAGCAC CATGGCCTGA
                                      bfaI                    ATCATGTCTG GATCGATCGG CTTAATTAAG CCGCGTCGTG GTACCGGACT
           bsmI                                                                  ^sv40
4401 TTTTTCACTG CATTCTAGTT GTGGTTTGTC CAAACTCATC AATGTATCTT ATCATGTCTG GATCGATCGG GAATTAATTC GGCGAGCAC CATGGCCTGA
     AAAAAGTGAC GTAAGATCAA CACCAAACAG GTTTGAGTAG TTACATAGAA TAGTACAGAC CTAGCTAGCC CTTAATTAAG CCGCGTCGTG GTACCGGACT rsaI                                                                         scrFI
                            csp6I                                                                        mvaI
                            nlaIv                                                                        ecoRII
                            kpnI                                                     aluI                dsaV
                            hgiCI                                                    pvuII               bstNI
                            banI                                                     nspBII              apyI[dcm+]
                            asp718    mnlI                                                               bsaJI
                    mnlI    acc65I   ddeI aclI             scrFI       mvaI                   bsmFI     nlaIv
4501 AATAACCTCT GAAAGAGGAA CTTGGTTAGG TACCTTCTGA GGCGGAAAGA ACCAGCTGTG GAATGTGTGT CAGTTAGGGT GTGGAAAGTC CCCAGGCTCC
     TTATTGGAGA CTTTCTCCTT GAACCAATCC ATGGAAGACT CCGCCTTTCT TGGTCGACAC CTTACACACA GTCAATCCCA CACCTTTCAG GGGTCCGAGG sfaNI
                    ppu10I                       scrFI     mvaI                                          sfaNI
                    nsiI/avaIII                  mvaI      dsaV                                          ppu10I
                    nlaIII                       ecoRII    bstNI                                         nsiI/avaIII
                    sphI                         dsaV                                          nlaIII
                    nspI                         bstNI                                                       sphI          nspI
                    nspHI                        apyI[dcm+]                                                                nspHI
           cac8I                                 sexAI           bsmFI    nlaIv       cac8I                                cac8I
4601 CCAGCAGGCA GAAGTATGCA AGCATGCAT CTCAATTAGT CAGCAACCAG GTGTGAAAG TCCCCAGGCT CCCCAGCAGG CAGAAGATATG CAAAGCATGC
     GGTCGTCCGT CTTCATACGT TTCGTACGTA GAGTTAATCA GTCGTTGGTC CACACTTTC AGGGGTCCGA GGGGTCGTCC GTCTTCATAC GTTTCGTACG
```

FIG. 48P

```
                                                                                                                    nlaIII
                                                                                                                    styI
                                                                                                                    ncoI
                                                                                                           bslI dsaI
                                     acII                                                        acII bsrI acII     acII bsaJI
                       bsmFI      acII fokI              CCCTAACTCC GCCCATCCCG CCCTAACTCC CGCCCAGTTC CGCCCCATTCT CCGCCCCATG GCTGACTAAT
4701 ATCTCAATTA GTCAGCAACC ATAGTCCCGC
     TAGAGTTAAT CAGTCGTTGG TATCAGGGCG GGGATTGAGG CGGGTAGGGC CGGGTCAAG GCGGGTAAGA GCGGGGGTAC CGACTGATTA rmaI
                                                                                         maeI
                                                                                         styI
                       fnu4HI                                                            bsaJI
                       bsoFI                                                             blnI
                       bglI                                                              avrII[dam-]
                       sfiI                                                              haeIII/palI
                       haeIII/palI                                                       stuI
                 mnlI  mnlI      ddeI                                                    haeI               maeIII
                 haeIII/palI bsaJI  mnlI      aluI                         mnlI          mnlI bfaI          aluI
                 mnlI bsaJI acII      haeIII/palI                          bseRI
4801 TTTTTTTATT TATGCAGAGG CCGAGGCCGC CTCGGCCTCT GAGCTATTCC AGAAGTAGTG AGGAGGCTTT TTTGGAGGCC TAGGCTTTTG CAAAAAGCTG
     AAAAAAATAA ATACGTCTCC GGCTCCGGCG GAGCCGGAGA CTCGATAAGG TCTTCATCAC TCCTCCGAAA AAACCTCCGG ATCCGAAAAC GTTTTTCGAC
                                                                                                            start pUC118^ scrFI
                                                                                                                    mvaI
                                                                                            haeIII/palI             ecoRII
                                          bspMI                                             eaeI                    dsaV
                                             scfI                                           cfrI          bsrI      bstNI
             fnu4HI                          pstI                                                         maeIII    apyI[dcm+]
             haeIII/palI    hinPI                                             bsgI maeIII                           bsaJI
             mcrI           hhaI/cfoI                                         ase8387I aluI  bsrI
             eagI/xmaIII/eclXI thaI
             eaeI           fnuDII/mvnI
             notI           bstUI
         bsrBI bsoFI        hinPI
         taqI cfrI          hhaI/cfoI    tru9I pstI
         xhoI fnu4HI  tru9I cac8I        ahaIII/draI
         paeR7I bsiEI paeI ascI          msel
         avaI bsoFI  meeI tru9I bshl236I msel
         mnlI aciI aciI    msel bssHII swaI
4901 TTACCTCGAG CGGCCGCTTA ATTAAGGCGC GCCATTTAAA TCCTGCAGGT AACAGCTTGG CACTGGCCGT CGTTTTACAA CGTCGTGACT GGGAAAACCC
     AATGGAGCTC GCCGGCGAAT TAATTCCGCG CGGTAAATTT AGGACGTCCA TTGTCGAACC GTGACCGGCA GCAAAATGTT GCAGCACTGA CCCTTTTGGG
     ^linearization linker inserted into HpaI site
```

```
                                                                                  nlaIV
                                                                                  hgiCI   taqI
                                                                                  banI    mnlI
                                       nlaIV
                                       hgiJII
                                       bsp1286
                                       bmyI
            mspI                       banII                                                       tru9I       pleI
            hpaII                                             nlaIV                                msel        hinfI
            naeI                                                                    maeII pleI              tru9I
            cfr10I/bsrFI      alul                           maeII haeIII/palI      drdI hinfI maeII        msel
     maeII cacBI                       draIII sau96I                                                                   tru9I
                 hphI    bsaAI asuI                          bsll                                                      msel     alul        tru9I
                                                             bsll  aval                                    haeIII/palI          fnu4HI      msel
       bsrI                                                                                                             bsoFI   tru9I
                    thaI                                                                                                sfaNI   msel       aclI
                    fnuDII/mvnI                              maeII                           hgiAI/aspHI
           tru9I    apol tru9I                               psp1406I                        bsp1286                             sfaNI
           msel bstUI msel                                   tru9I                           bslHKAI                                                sfaNI
     apol bsh1236I             sspI msel                                                     bmyI ddeI                                   mspI
                                                                                             apaLI/snoI rsal                             hpaII
                                                                                             alw44I/snol csp6I                           scrFI
                                                                 hinPI                                                                   nclI
                                                                 fnu4HI                                hhaI/cfoI                         dsaV fokI
                                                                 bsoFI                                 thaI                              cauII    aclI
            maeIII                                               nlaIII hhaI/cfoI                      fnuDII/mvnI
            maeII bsrI                                           aspI bbvI                             bstUI
     bsaAI tth111I/aspI                                          aclI                                  nspBII bsh1236I      drdI
                                                                                                       aclI hgaI
5301 TTTCTCGCCA CGTTCGCCGG CTTTCCCCGT CAAGCTCTAA ATCGGGGGCT CCCTTTAGGG TTCCGATTTA GTGCTTTACG GGACCTCGAC CCCAAAAAAC
     AAAGAGCGGT GCAAGCGGCC GAAAGGGGCA GTTCGAGATT TAGCCCCCGA GGGAAATCCC AAGGCTAAAT CACGAAATGC CGTGGAGCTG GGGTTTTTG 5401 TTGATTTGGG TGATGGTTCA CGTAGTGGGC CATCGCCCTG ATAGACGGTT TTTCGCCCTT TGACGTTGGA GTCCACGTTC TTTAATAGTG GACTCTTGTT
     AACTAAACCC ACTACCAAGT GCATCACCCG GTAGCGGGAC TATCTGCCAA AAAGCGGGAA ACTGCAACCT CAGGTGCAAG AAATTATCAC CTGAGAACAA 5501 CCAAACTGGA ACAACACTCA ACCCTATCTC GGGCTATTCT TTTGATTTAT AAGGGATTTT GCCGATTTCG GCCTATTGGT TAAAAAATGA GCTGATTAAA
     GGTTTGACCT TGTTGTGAGT TGGGATAGAG CCCGATAAGA AAACTAAATA TTCCCTAAAA CGGCTAAAGC CGGATAACCA ATTTTTTACT CGACTAAATT 5601 CAAAATTTA ACGGAATTT TAACAAATA TTAACGTTTA CAATTTTATG GTGCACTCTC AGTACAATCT GCTCTGATGC CGATAGTTA AGCCAACTCC
     GTTTTTAAAT TGCGCTTAAA ATTGTTTTAT AATTGCAAAT GTTAAAATAC CACGTGAGAG TCATGTTAGA CGAGACTACG GCGTATCAAT TCGGTTGAGG 5701 GCTATCGCTA CGTGACTGGG TCATGGCTGC GCCCCGACAC CCGCTGACGC GCCCTGACGG GCTTGTCTGC TCCCGGCATC CGCTTACAGA
     CGATAGCGAT GCACTGACCC AGTACCGACG CGGGGCTGTG GGCGACTGCG CGGGACTGCC CGAACAGACG CGGGACTGCC AGGGCCGTAG GCGAATGTCT
```

```
                              sau3AI    sau3AI
                              mboI/ndeII[dam-]  mboI/ndeII[dam-]                                            maeII
                              dpnI[dam+]        dpnI[dam+]                                                  psp1406I       hgiAI/aspHI
                              bstYI/xhoI        dpnII[dam-]                                                 xmnI           bsp1286  tru9I
                   bsrI  dpnII[dam-]            alwI[dam-]                                                  asp700         bsiHKAI  mseI
      bssSI  maeIII  taqI  alwI[dam-]  aciI  bstYI/xhoI                                                     mboI           bmyI  ahaIII/draI
6201  CACGAGTGGG TTACATCGAA CTGGATCTCA ACAGCGGTAA GATCCTTGAG AGTTTTCGCC CCGAAGAACG TTTTCCAATG ATGAGCACTT TTAAAGTTCT
      GTGCTCACCC AATGTAGCTT GACCTAGAGT TGTCGCCATT CTAGGAACTC TCAAAAGCGG GGCTTCTTGC AAAAGGTTAC TACTCGTGAA AATTTCAAGA scrFI
                              nciI
                aciI          mspI
                thaI          hpaII
                fnuDII/mvnI   dsaV
                bstUI
                bshl236I              hinlI/acyI                        aciI
                hinPI                 hgaI  cauII       mcrI  fnu4HI                                                rsaI
      hhaI/cfoI                       ahaII/bsaHI  bcgI bsiEI bsoFI             ddeI                     scaI  hphI  csp6I  bsrI  maeIII
6301  GCTATGTGGC GCGGTATTAT CCCGTGATGA CGCCGGGCAA GAGCAACTCG GTCGCCCGAT ACACTATTCT CAGAATGACT TGGTTGAGTA CTCACCAGTC
      CGATACACCG CGCCATAATA GGGCACTACT GCGGCCCGTT CTCGTTGAGC CAGCGGGCTA TGTGATAAGA GTCTTACTGA ACCAACTCAT GAGTGGTCAG sau3AI
                                                                                                                    mboI/ndeII[dam-]
                                                                                            haeIII/paII              dpnI[dam+]
                                                                                            eaeI                     dpnII[dam-]
                                                                                            cfrI                     pvuI/bspCI
                                                                   fnu4HI                   fnu4HI                   mcrI
                                                                   bsoFI                    bsoFI                    bsIEI
            sfaNI   fokI  nlaIII                                   bbvI  msII nlaIII        aciI
6401  ACAGAAAAGC ATCTTACGGA TGGCATGACA GTAAGAGAAT TATGCAGTGC TGCCATAACC ATGAGTGATA ACACTGCGGC CAACTTACTT CTGACAACGA
      TGTCTTTTCG TAGAATGCCT ACCGTACTGT CATTCTCTTA ATACGTCACG ACGGTATTGG TACTCACTAT TGTGACGCCG GTTGAATGAA GACTGTTGCT nlaIII
                                                         sau3AI  maeIII                      mspI
                                                         mboI/ndeII[dam-]         sau3AI     nlaIV
      sau96I                                             dpnI[dam+]               mboI/ndeII[dam-]  aluI
      avaII                                              dpnII[dam-]              dpnI[dam+]       hpaII
      asuI                         aluI  aciI            nlaIII  alwI[dam-]       dpnII[dam-]      bsaWI
      mnII                                                                                                          
6501  TCGGAGACC GAAGGAGCTA ACCGCTTTTT TGCACAACAT GGGGGATCAT GTAACTCGCC TTGATCGTTG GAACCGGAG CTGAATGAAG CCATACCAAA
      AGCCTCCTGG CTTCCTCGAT TGGCGAAAAA ACGTGTTGTA CCCCCTAGTA CATTGAGCGG AACTAGCAA CCTTGGCCTC GACTTACTTC GGTATGGTTT
```

FIG. 48U

```
                                                                       hinPI
                                                                       hhaI/cfoI
                                                                       mstI                                               mspI
                                                                       avIII/fspI                                         hpaII
                                            fnu4HI                                   bsrI                     aluI        scrFI
                                            bsoFI                   maeII            tru9I                    rmaI        ncII         tru9I
                        msII        cac8I   bsrDI                   psp1406I         msel                     maeI        dsaV         msel
            maeIII      sfaNI       bbvI                                                                      bfaI        cauII        aseI/asnI/vspI
6601 CGACGAGCGT GACACCACGA TGCCAGCAGC AATGGCAACA ACGTTGCGCA AACTATTAAC TGGCGAACTA CTTACTCTAG CTTCCCGGCA ACAATTAATA
     GCTGCTCGCA CTGTGGTGCT ACGGTCGTCG TTACCGTTGT TGCAAGCGCT TTGATAATTG ACCGCTTGAT GAATGAGATC GAAGGGCCGT TGTTAATTAT bglI
                                                       sau96I         cac8I                                             mspI
                                      sau96I           haeIII/palI                                                      hpaII
     foxI        acII        avaII    hinPI    asuI    mspI                                                             cfr10I/bsrFI
     bsrI        mnII        asuI     hhaI/cfoI        hpaII                                              nlaIV  hphI                  bsmAI
6701 GACTGGATGG AGGCGGATAA AGTTGCAGGA CCACTTCTGC GCTCGGCCCT TCCGGCTGGC TGGTTTATTG CTGATAAATC TGGAGCCGGT GAGCGTGGGT
     CTGACCTACC TCCGCCTATT TCAACGTCCT GGTGAAGACG CGAGCCGGGA AGGCCGACCG ACCAAATAAC GACTATTTAG ACCTCGGCCA CTCGCACCCA
                                                                                                         bpmI/gsuI[dcm-]         bsaI acII
             thaI       fnu4HI     haeIII/palI
             fnuDII/mvnI bsoFI     sau96I                                                       pleI
             bstUI      bbvI       nlaIV                                                        hinfI                  foxI
             bsh1236I   bsrDI      bsrI   asuI            mnII                    ahdI/eam1105I
6801 CTCGCGGTAT CATTGCAGCA CTGGGCCAG ATGGTAAGCC CTCCCGTATC GTAGTTATCT ACACGACGGG GAGTCAGGCA ACTATGGATG AACGAAATAG
     GAGCGCCATA GTAACGTCGT GACCCCGGTC TACCATTCGG GAGGGCATAG CATCAATAGA TGTGCTGCCC CTCAGTCCGT TGATACCTAC TTGCTTTATC ddeI
         sau3AI        nlaIV
         mboI/ndeII[dam-]                                                                                         tru9I
         dpnI[dam+]         hgiCI        tru9I                                                                    msel        tru9I
         dpnII[dam-]        banI  mnII   msel       maeIII                                                        ahaIII/draI msel
6901 ACAGATCGCT GAGATAGGTG CCTCACTGAT TAAGCATTGG TAACTGTCAG ACCAAGTTTA CTCATATATA CTTTAGATTG ATTTAAAACT TCATTTTAA
     TGTCTAGCGA CTCTATCCAC GGAGTGACTA ATTCGTAACC ATTGACAGTC TGGTTCAAAT GAGTATATAT GAAATCTAAC TAAATTTTGA AGTAAAATT rmaI
                     maeI              sau3AI
                     sau3AI hphI       mboI/ndeII[dam-]                                     maeII
                     mboI/ndeII[dam-]                                                       tru9I                                sau3AI
                     dpnI[dam+]        dpnI[dam+]                                           msel                                 mboI/ndeII[dam-]
                     dpnII[dam-]       dpnII[dam-]                         nlaIII                                                dpnI[dam+]
     tru9I bstYI/xhoII alwI[dam-]                                          rcaI                           hgaI                   dpnII[dam-]
     msel  alwI[dam-] bstYI/xhoII                                          bspHI                          ddeI
     ahaIII/draI bfaI mboII[dam-]
7001 TTTAAAGGA TCTAGGTGAA GATCCTTTT GATAATCTCA TGACCAAAAT CCCTTAACGT GAGTTTTCGT TCCACTGAGC GTCAGACCCC GTAGAAAGA
     AAATTTCCT AGATCCACTT CTAGGAAAA CTATTAGAGT ACTGGTTTTA GGGAATTGCA CTCAAAAGCA AGGTGACTCG CAGTCTGGGG CATCTTTCT
```

FIG. 48V

```
                                                                                                                sau3AI
                                                                                                                mboI/ndeII[dam-]
                                                                                                                dpnI[dam+]
                                                                                                                dpnII[dam-]
                                                                                                                alwI[dam-]
                                                                                                                           aluI
                                                                                                           mspI
                                                                                                           hpaII
                                                                          aclI                                 haeIII/palI
                                                                          nspBII                               haeI
         sau3AI                                                                          rmaI
         mboI/ndeII[dam-]  thaI                                                          maeI
         mboI/ndeII[dam-]  fnuDII/mvnI                                                   bfaI          bslI
         dpnI[dam+]       bstUI         cac8I
         dpnII[dam-]      bsh1236I      fnu4HI
         dpnII[dam-]      hinPI         bsoFI
         alwI[dam-]       hhaI/cfoI     bbvI
    sau3AI
    mboI/ndeII[dam-]
    dpnI[dam+]                                                                                              fnu4HI
    dpnII[dam-]                                    bsrI                                                     bsoFI
    dpnII[dam-]                                    maeIII    eco57I                                         bbvI
    bstYI/xhoII                                                                                             fnu4HI[dcm-]
    alwI[dam-]       bstYI/xhoII                                                                            alwNI[dcm-]
                                                                                                            bsrI  bbvI  bsrI
                                                                                                maeIII      bsrI  bsoFI
7101 TCAAAGGATC TTCTTGAGAT CCTTTTTTTC TGCGCTGTAAT CTGCGCTGCTTG CAAACAAAAA AACCACCGCT ACCAGCGGTG GTTTGTTTGC CGGATCAAGA
     AGTTTCCTAG AAGAACTCTA GGAAAAAAAG ACGCGACATTA GACGACGAAC GTTTGTTTTT TTGGTGGCGA TGGTCGCCAC CAAACAAACG GCCTAGTTCT aclI                                                                          scrFI
                          nspBII                                                                        ncII
            scfI   aclI   fnu4HI           mnlI                                                         mspI            pleI
                          bsoFI                                                                         hpaII           hinfI
          mspI            bbvI  mcrI                                                                    dsaV
          hpaII           hinPI bsiEI                                                                   cauII
          bsaWI           hhaI/cfoI
          maeIII
7201 GCTACCAACT CTTTTTCCGA AGTAACTGGC CTTCAGCAGA GCGCAGATAC CAAATACTGT CCTTTCTAGTG TAGCCCGTAGT CTTCAAGAAC
     CGATGGTTGA GAAAAAGGCT TCATTGACC GAAGTCGTCT CGCGTCTATG GTTTATGACA GGAAGATCAC ATCGGCATCA GAAGTTCTTG aclI
               nspBII
         scfI  aclI    mnlI
7301 TCTGTAGCAC CGCCTACATA CCTCGCTCTG CTAATCCTGT TACCAGTGGC TGCTGCCAGT GGCGATAAGT CGGGTTGGAC TCAAGACGAT
     AGACATCGTG GCGGATGTAT GGAGCGAGAC GATTAGGACA ATGGTCACCG ACGACGGTCA CCGCTATTCA GCCCAACCTG AGTTCTGCTA hgIAI/aspHI
                           bsp1286
                           bslHKAI
           mspI            bmyI
           hpaII           apaLI/snoI
           bsaWI           alw44I/snoI   aluI                                                      ddeI    scfI
           maeIII
7401 AGTTACCGGA TAAGGCGCAG CGGTCGGGCT GAACGGGGGG TTCGTGCACA CAGCCCAGCT TGGAGCGAAC GACCTACACC GAACTGAGAT ACCTACAGCG
     TCAATGGCCT ATTCCGCGTC GCCAGCCCGA CTTGCCCCCC AAGCACGTGT GTCGGGTCGA ACCTCGCTTG CTGGATGTGG CTTGACTCTA TGGATGTCGC
```

FIG. 48W

```
                                                                                                                   scrFI
                                                                                                                   mvaI
                                                                                                                   ecoRII
                                                                                                                   dsaV
                                                                                                     bssSI          bstNI
                                                                                                     hinPI mnlI    bsaJI
                                                                          mspI                       hhaI/cfoI     aluI apyI[dcm+]
                                                                          hpaII fnu4HI
                                                                          bslI   bsoFI
                                              hinPI                acil   bsaWI aciI                                                   nlaIV
                                              hhaI/cfoI                                                                                aciI
                                              haeII                                 mnlI drdI     hgaI       sfaNI
7501 TGAGCATTGA CGCTTCCCGA AGGGAGAAAG CGCGGACAGT ATCCGGTAAG CGGCAGGGTC GGAACAGGAG GATGCTCGTC AGGGGGGGCGG AGCCTATGGA
     ACTCGTAACT CTTCGCGGCT GCGAAGGGCT TCCCTCTTTC CGCCTGTCCA TAGGCCATTC GCCGTCCCAG CCTTGTCCTC CTACGAGCAG TCCCCCCGCC TCGGATACCT scrFI
          mvaI
          ecoRII
          dsaV
          bstNI
          apyI[dcm+]                                                  haeIII/palI
7601 GGGGGAAACG CCTGGTATCT TTATAGTCCT GTCGGGTTTC GCCACCTCTG ACTTGAGCGT CGATTTTTGT GATGCTCGTC AGGGGGGCGG AGCCTATGGA
     CCCCCTTTGC GGACCATAGA AATATCAGGA CAGCCCAAAG CGGTGGAGAC TGAACTCGCA GCTAAAAACA CTACGAGCAG TCCCCCCGCC TCGGATACCT haeIII/palI
                          haeIII/palI
                fnu4HI                  scrFI
                bsoFI                   mvaI bslI
                aciI                    ecoRII
                thaI bslI               dsaV                                                              tfiI
                fnuDII/mvnI             bstNI                        nlaIII                               hinfI
                bstUI                   apyI[dcm+]          haeIII/palI nspI
       cac8I    bsh1236I       nlaIV    haeI      cac8I     haeI        aflIII
7701 AAAACGGCCAG CAACGGGCC TTTTTACGGT TCCTGGCCTT TTGCTGGCCT TTTGCTCACA TGTTCTTTCC TGCGTTATCC CCTGATTCTG TGGATAACCG
     TTTTGCGGGTC GTTGCGGCCG GTTGCCGCCG AAAAATGCCA AGGACCGGAA AACGACCGGA AAACGAGTGT ACAAGAAAGG ACGCAATAGG GGACTAAGAC ACCTATTGGC fnu4HI
                                bsoFI                              fnu4HI
                                bbvI                               bsoFI
                                cac8I aciI                         bbvI pleI                sapI hinPI
                                bsrBI fnu4HI               mcrI    hinPI hinfI              mboII hhaI/cfoI
         aciI     aluI          aciI    bsoFI              bsiEI   hhaI/cfoI                earI/ksp632I
7801 TATTACCGCC TTTGAGTGAG CTGATACCGC TCGCCGCAGC AGGCAGACCG CGAACGACCG AGGCCAGCGA GTCAGTGAGC AAGAGCGCCC AATACGCAAA
     ATAATGGCGG AAACTCACTC GACTATGGCG AGCGGCGTCG TCCGTCTGGC GCTTGCTGGC TCCGGTCGCT CAGTCACTCG CTCCGGCGGG TTATGCGTTT
                                                                                                       mnlI aciI haeII
```

FIG. 48X

```
                                                                                                                    tru9I
                                                                                                                    mseI       maeIII
                                                                                                    hinPI            aseI/asnI/vspI
                                                                                   cac8I            hhaI/cfoI  CAACGCAATT AATGTGAGTT
                                                                                   aciI
                                                              bsrI           TGGAAAGCGG GCAGTGAGCG CGTCACTCGC GTTGCGTTAA TTACACTCAA
                                              GGCACGACAG GTTTCCCGAC
                        CCGTGCTGTC CAAAGGGCTG ACCTTTCGCC
thaI
fnuDII/mvnI
bstUI
bsh1236I
hinPI
hhaI/cfoI                                                                                                     aciI
thaI                                                                                                          bsrBI
fnuDII/mvnI              cac8I                                                                          aluI
bstUI      haeIII/palI   aluI                                              mspI            CGGATAACAA TTTCACACAG GAAACAGCTA
bsh1236I   tru9I         pvuII                                             hpaII           GCCTATTGTT AAAGTGTGTC CTTTGTCGAT
         bslI  eaeI  tfiI aseI/asnI/vspI
mnlI     aciI  cfrI  hinfI mseI  nspBII
aciI   CCGCGGCGTTG GCCGATTCAT TAATCCAGCT
7901   GGCGCGCAAC CGGCTAAGTA ATTAGGTCGA
                     scrFI
                     mvaI
                     ecoRII
                     dsaV
                     nlaIV bstNI
                     hgiCI apyI[dcm+]
                     banI bsaJI
         mnlI  ACCTCACTCA TTAGGCACCC CAGGCTTTAC ACTTTATGCT TCCGGCTCGT ATGTTGTGTG GAATTGTGAG
8001     TGGAGTGAGT AATCCGTGGG GTCCGAAATG TGAAATACGA AGGCCGAGCA TACAACACAC CTTAACACTC
```

FIG. 48Y

```
                    tru9I
                     mseI
                      aseI/asnI/vspI
       nlaIII        xmnI
          asp700
 8101 TGACCATGAT TACGAATTAA  (SEQ ID NO.68)
      ACTGGTACTA ATGCTTAATT >length: 8120 aatII(GACGTC):    1690 5947
acc65I(GGTACC):   2969 3967 4529
accI(GTMKAC):      823 1039 2738 4237
aciI(CCGC):        217  229  238  250  260  271  317  422  454  485  574 1385 1795 1871 2248 2250 2758 2982
                  3167 3179 3188 3200 3210 3221 3267 3372 3404 3449 3686 3949 4021 4318 4542 4727
                  4739 4748 4760 4770 4781 4827 4910 4914 5070 5127 5153 5166 5203 5217 5220 5248
                  5275 5680 5699 5741 5751 5790 5979 6026 6125 6234 6311 6355 6476 6522 6713 6804
                  7166 7175 7310 7420 7541 7560 7687 7715 7806 7827 7834 7877 7901 7911 7967 8070
acyI              see hinlI
aflII/bfrI(CTTAAG):  786
aflIII(ACRYGT):    932 7758
ageI(ACCGGT):     1833
ahaII/BsaHI(GRCGYC): 988 1690 1858 5117 5947 6329
ahaIII/draI(TTTAAA): 696 4935 6290 6982 7001
ahdI/eam1105I(GACNNNNNGTC): 2087 6865
aluI(AGCT):          5   44  332  386  390  753 1097 1165 1370 1431 1951 2603 2751 2784 3282 3336 3340
                  3562 3566 3676 3733 3792 4270 4288 4311 4344 4554 4842 4896 4954 5047 5333 5590
                  5803 5822 6516 6579 6679 7200 7457 7593 7819 7937 8096
alw44I/snoI(GTGCAC): 1876 5651 6198 7444
```

FIG. 48Z

Representative Conc versus Time Plot. Shown is the kinetic data for 6G4V11N35A.IgG1

| SAMPLE | ka | kd | Kd |
|---|---|---|---|
| Murine 6G4.2.5 IgG2a | $8.3 \times 10^5$ | $2.9 \times 10^{-4}$ | 350pM |
| 6G4V11N35A-IgG1 | $8.7 \times 10^5$ | $7.7 \times 10^{-5}$ | 88pM |
| 6G4V11N35E-IgG1 | $3.0 \times 10^6$ | $1.4 \times 10^{-4}$ | 49pM |

```
 781 AAAAGGGTAT CTAGAGGTTG AGGTGATTTT ATGAAAAAGA ATATCGCATT TCTTCTTGCA
     TTTTCCCATA GATCTCCAAC TCCACTAAAA TACTTTTTCT TATAGCGTAA AGAAGAACGT
  -1                                   M  K  N   I  A  F    L  L  A

841 TCTATGTTCG TTTTTTCTAT TGCTACAAAC GCGTACGCTG AGGTTCAGCT AGTGCAGTCT
     AGATACAAGC AAAAAAGATA ACGATGTTTG CGCATGCGAC TCCAAGTCGA TCACGTCAGA
 -11 S  M  F   V  F  S  I A  T  N    A  Y  A    E  V  Q  L V  Q  S

901 GGCGGTGGCC TGGTGCAGCC AGGGGGCTCA CTCCGTTTGT CCTGTGCAGC TTCTGGCTAC
     CCGCCACCGG ACCACGTCGG TCCCCCGAGT GAGGCAAACA GGACACGTCG AAGACCGATG
   8 G  G  G  L V  Q  P   G  G  S    L  R  L    C  A  A  S G  Y

961 TCCTTCTCGA GTCACTATAT GCACTGGGTC CGTCAGGCCC CGGGTAAGGG CCTGGAATGG
     AGGAAGAGCT CAGTGATATA CGTGACCCAG GCAGTCCGGG GCCCATTCCC GGACCTTACC
  28 S  F  S  S H  Y  M   H  W  V    R  Q  A    P  K  G  L E  W

1021 GTTGGATATA TTGATCCTTC CAATGGTGAA ACTACGTATA ATCAAAAGTT CAAGGGCCGT
     CAACCTATAT AACTAGGAAG GTTACCACTT TGATGCATAT TAGTTTTCAA GTTCCCGGCA
  48 V  G  Y  I D  P  S   N  G  E    T  T  Y    N  Q  K  F K  G  R

1081 TTCACTTTAT CTCGCGACAA CTCCAAAAAC ACAGCATACC TGCAGATGAA CAGCCTGCGT
     AAGTGAAATA GAGCGCTGTT GAGGTTTTTG TGTCGTATGG ACGTCTACTT GTCGGACGCA
  68 F  T  L   S  R  D  N S  K  N    T  A  Y  L Q  M  N    S  L  R

1141 GCTGAGGACA CTGCCGTCTA TTACTGTGCA AGAGGGGATT ATCGCTACAA TGGTGACTGG
     CGACTCCTGT GACGGCAGAT AATGACACGT TCTCCCCTAA TAGCGATGTT ACCACTGACC
  88 A  E  D   T  A  V  Y Y  C  A    R  G  D  Y R  Y  N    G  D  W

1201 TTCTTCGACG TCTGGGGTCA AGGAACCCTG GTCACCGTCT CCTCGGCCTC CACCAAGGGC
     AAGAAGCTGC AGACCCCAGT TCCTTGGGAC CAGTGGCAGA GGAGCCGGAG GTGGTTCCCG
 108 F  F  D  V W  G  Q   G  T  L    V  T  V    S  S  A  S T  K  G

1261 CCATCGGTCT TCCCCCTGGC ACCCTCCTCC AAGAGCACCT CTGGGGGCAC AGCGGCCCTG
     GGTAGCCAGA AGGGGGACCG TGGGAGGAGG TTCTCGTGGA GACCCCCGTG TCGCCGGGAC
 128 P  S  V   F  P  L  A P  S  S    K  S  T  S G  G  T    A  A  L

1321 GGCTGCCTGG TCAAGGACTA CTTCCCCGAA CCGGTGACGG TGTCGTGGAA CTCAGGCGCC
     CCGACGGACC AGTTCCTGAT GAAGGGGCTT GGCCACTGCC ACAGCACCTT GAGTCCGCGG
 148 G  C  L   V  K  D  Y F  P  E    P  V  T  V S  W  N    S  G  A

1381 CTGACCAGCG GCGTGCACAC CTTCCCGGCT GTCCTACAGT CCTCAGGACT CTACTCCCTC
     GACTGGTCGC CGCACGTGTG GAAGGGCCGA CAGGATGTCA GGAGTCCTGA GATGAGGGAG
 168 L  T  S   G  V  H  T F  P  A    V  L  Q  S S  G  L    Y  S  L

1441 AGCAGCGTGG TGACCGTGCC CTCCAGCAGC TTGGGCACCC AGACCTACAT CTGCAACGTG
     TCGTCGCACC ACTGGCACGG GAGGTCGTCG AACCCGTGGG TCTGGATGTA GACGTTGCAC
 188 S  S  V   V  T  V  P S  S  S    L  G  T  Q T  Y  I    C  N  V

1501 AATCACAAGC CCAGCAACAC CAAGGTCGAC AAGAAAGTTG AGCCCAAATC TTGTGACAAA
     TTAGTGTTCG GGTCGTTGTG GTTCCAGCTG TTCTTTCAAC TCGGGTTTAG AACACTGTTT
 208 N  H  K   P  S  N  T K  V  D    K  K  V  E P  K  S    C  D  K

1561 ACTCACACAT GCCCGCCGTGA  (SEQ ID NO.69)
     TGAGTGTGTA CGGGCGGCACT
 228 T  H  T   C  P  P  Q   (SEQ ID NO.70)
```

FIG. 53

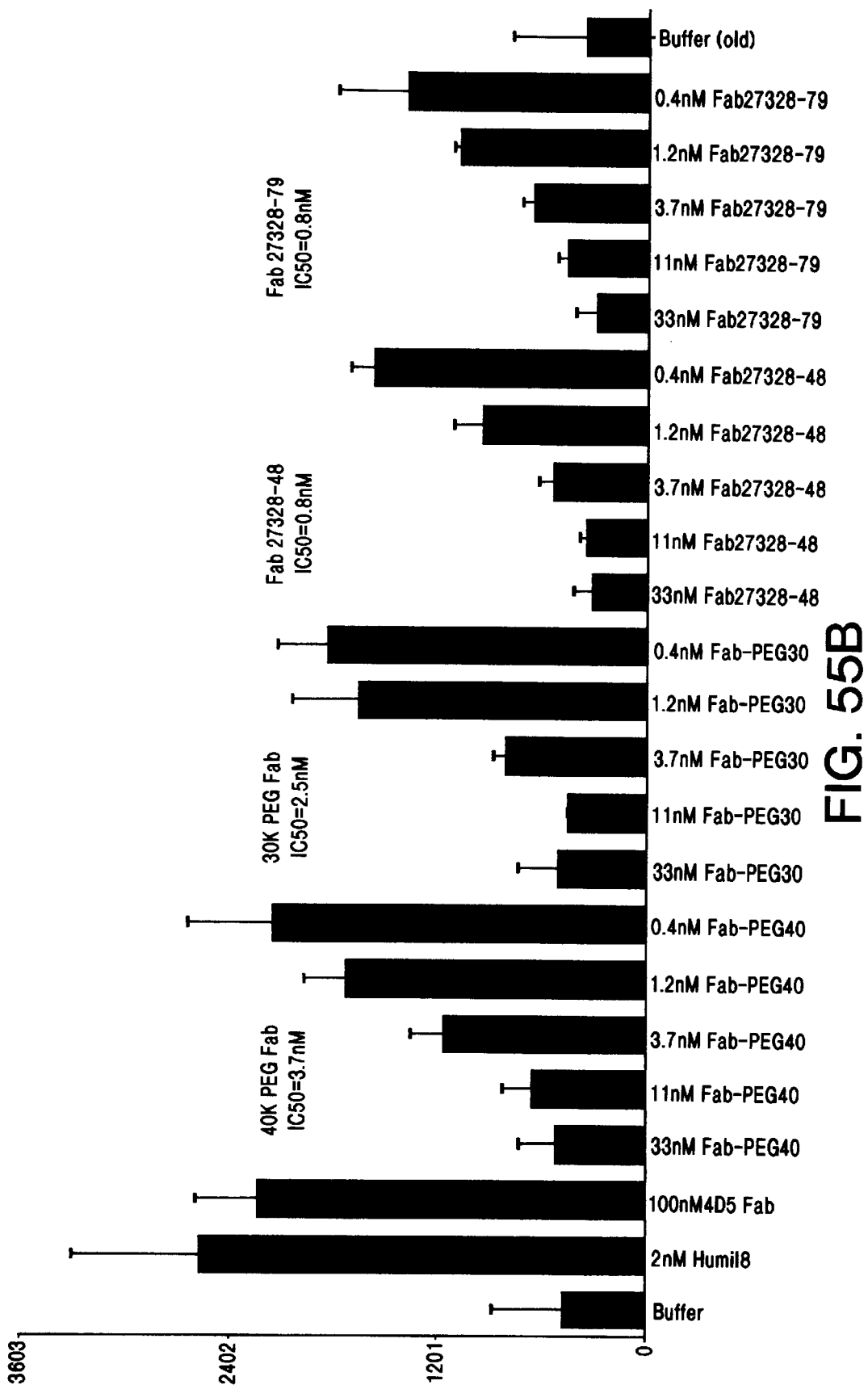

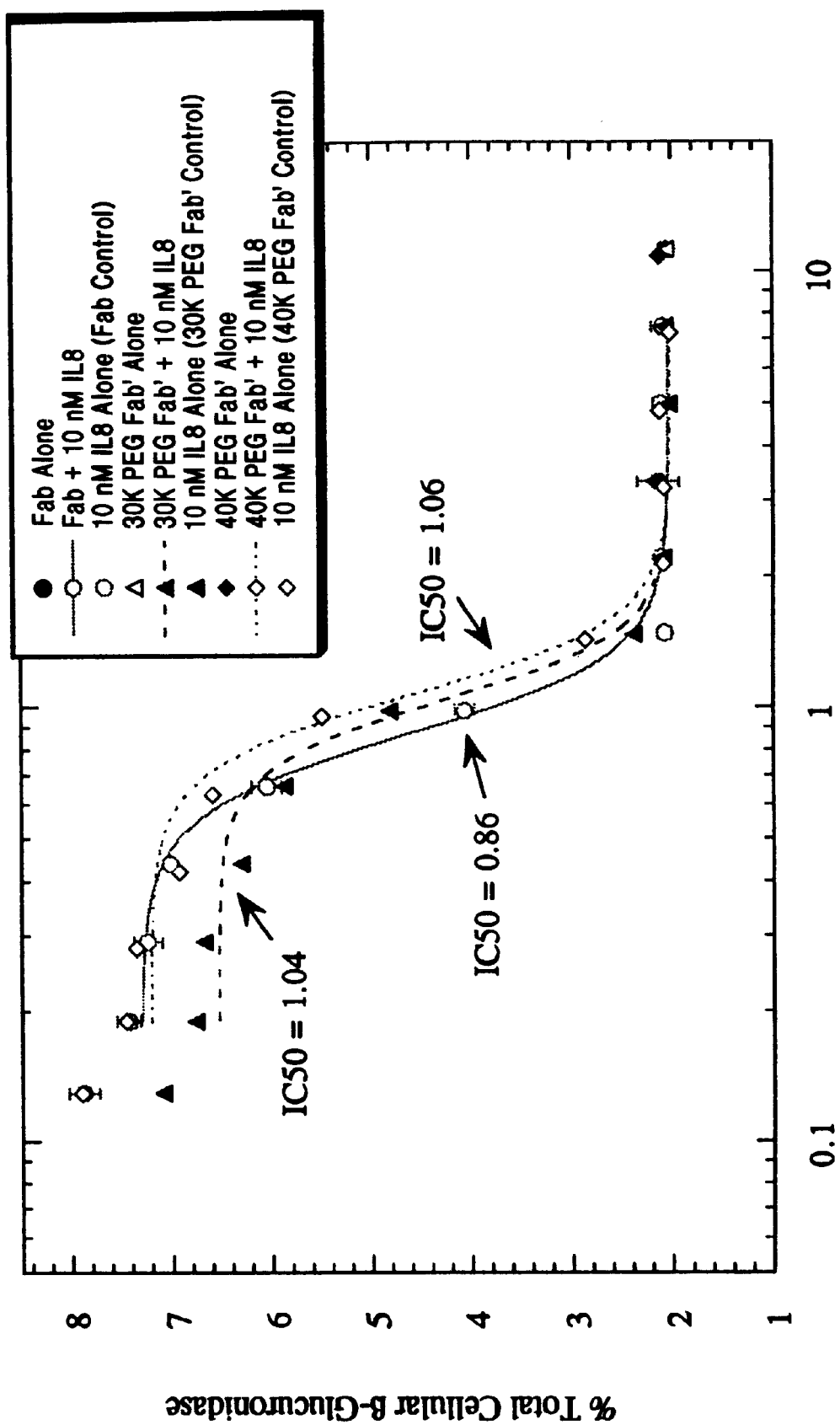

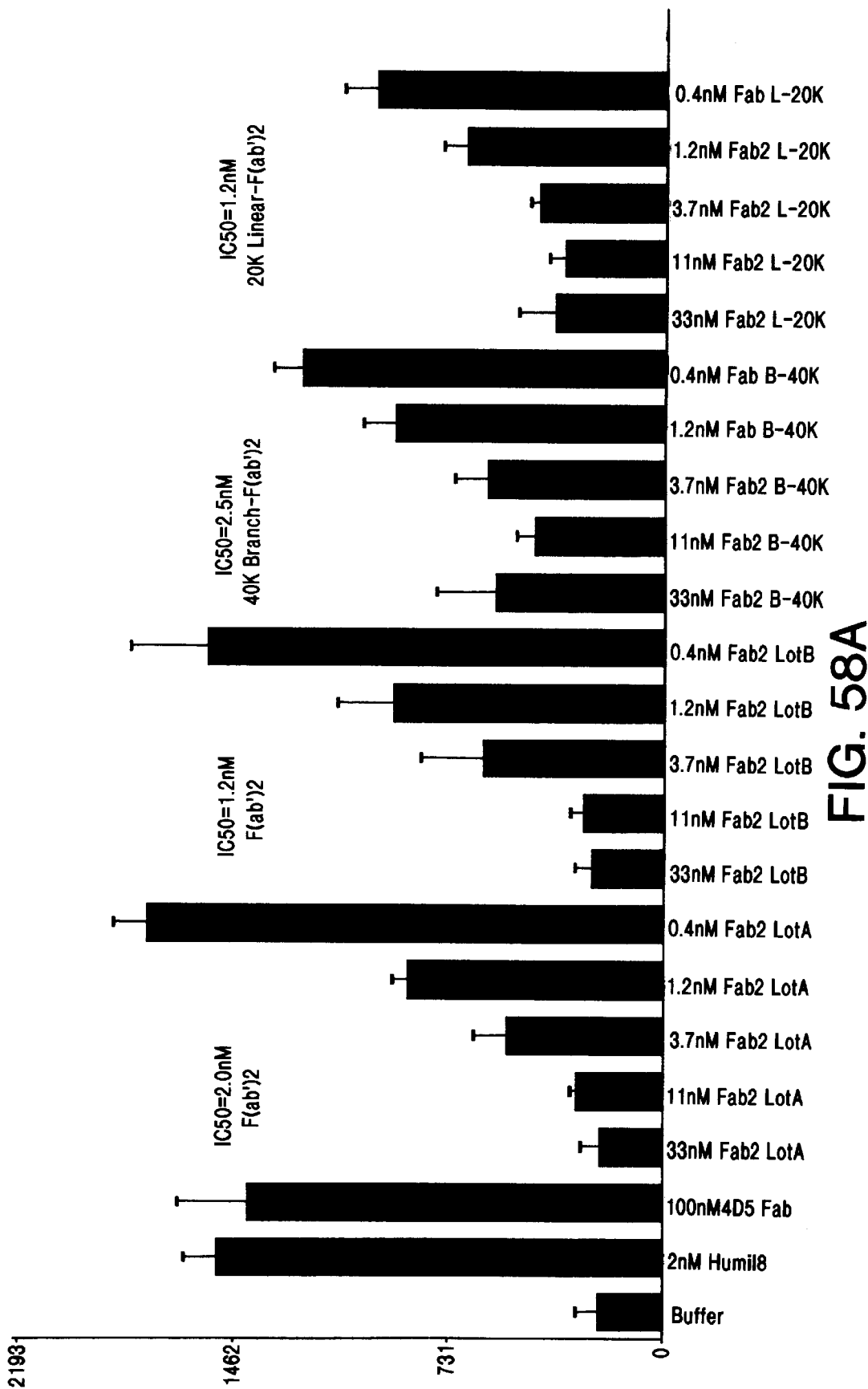

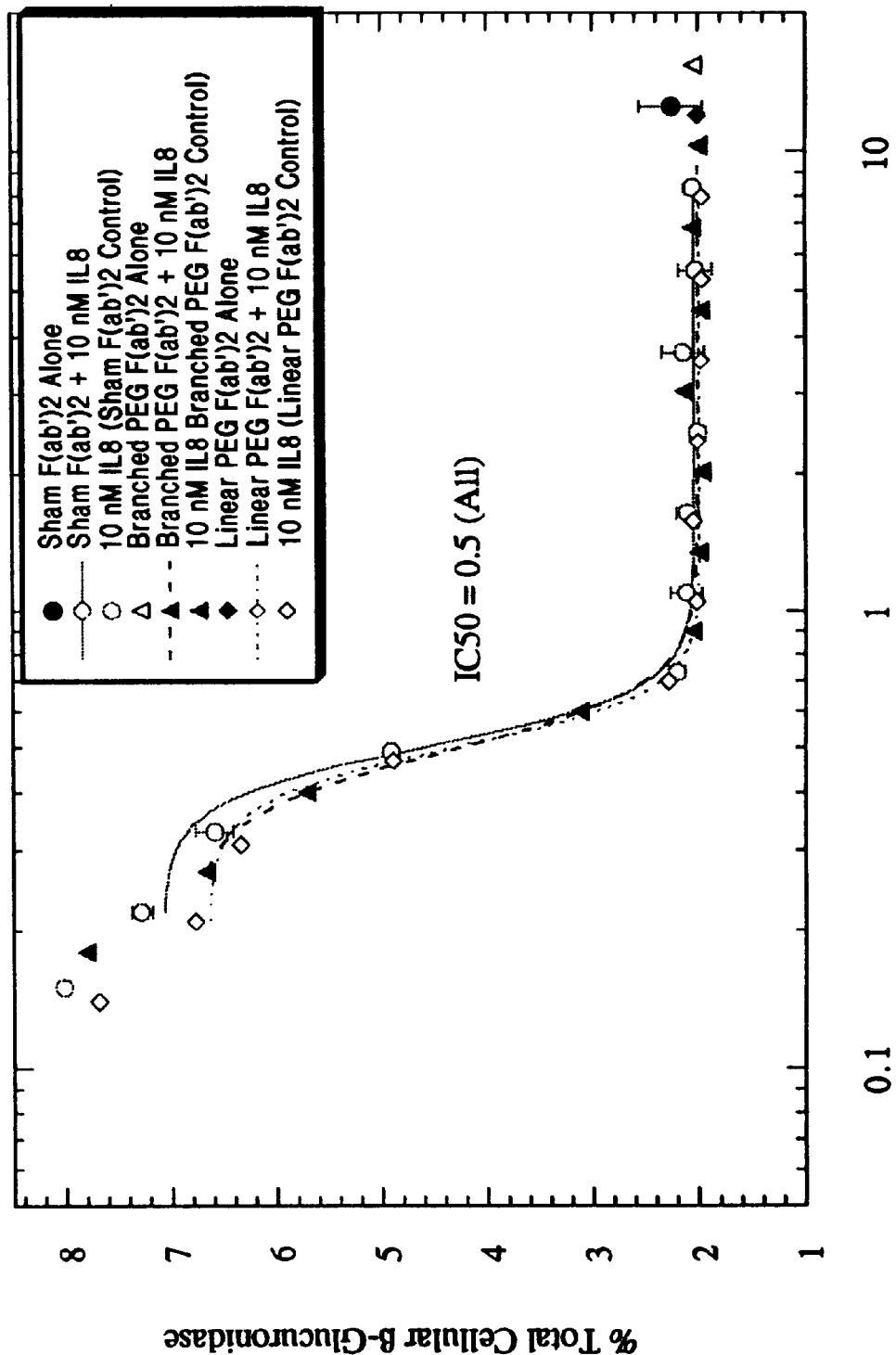

HUMANIZED ANTI-IL-8 MONOCLONAL ANTIBODIES

This is a non-provisional application claiming priority under 35 U.S.C. §119(e) to provisional application U.S. Ser. No. 60/038,664 filed Feb. 21, 1997, and to co-pending provisional application U.S. Ser. No. 60/074,330 filed Jan. 22, 1998, the entire disclosures of which provisional applications are incorporated herein by reference.

FIELD OF THE INVENTION

This application relates to the field of antibody fragments derivatized with polymers, and in particular to the use of such derivatization to increase the circulation half-lives of antibody fragment-polymer conjugates. This application also relates to humanized anti-interleukin-8 (IL-8) antibodies and to high affinity variants of such antibodies.

BACKGROUND

Modification of proteins with polyethylene glycol ("PEGylation") has the potential to increase residence time and reduce immunogenicity in vivo. For example, Knauf et al., *J. Biol. Chem.*, 263: 15064–15070 (1988) reported a study of the pharmacodynamic behavior in rats of various polyoxylated glycerol and polyethylene glycol modified species of interleukin-2. Despite the known advantage of PEGylation, PEGylated proteins have not been widely exploited for clinical applications. In the case of antibody fragments, PEGylation has not been shown to extend serum half-life to useful levels. Delgado et al., *Br. J. Cancer*, 73: 175–182 (1996), Kitamura et al., *Cancer Res.*, 51: 4310–4315 (1991), Kitamura et al., *Biochem. Biophys. Res. Comm.*, 171: 1387–1394 (1990), and Pedley et al., *Br. J. Cancer*, 70: 1126–1130 (1994) reported studies characterizing blood clearance and tissue uptake of certain anti-tumor antigen antibodies or antibody fragments derivatized with low molecular weight (5 kD) PEG. Zapata et al., *FASEB J.*, 9: A1479 (1995) reported that low molecular weight (5 or 10 kD) PEG attached to a sulfhydryl group in the hinge region of a Fab' fragment reduced clearance compared to the parental Fab' molecule.

Interleukin-8 (IL-8) is neutrophil chemotactic peptide secreted by a variety of cells in response to inflammatory mediators (for a review see Hebert et al. *Cancer Investigation* 11(6):743 (1993)). IL-8 can play an important role in the pathogenesis of inflammatory disorders, such as adult respiratory distress syndrome (ARDS), septic shock, and multiple organ failure. Immune therapy for such inflammatory disorders can include treatment of an affected patient with anti-IL-8 antibodies.

Sticherling et al. (*J. Immunol.* 143:1628 (1989)) disclose the production and characterization of four monoclonal antibodies against IL-8. WO 92/04372, published Mar. 19, 1992, discloses polyclonal antibodies which react with the receptor-interacting site of IL-8 and peptide analogs of IL-8, along with the use of such antibodies to prevent an inflammatory response in patients. St. John et al. (*Chest* 103:932 (1993)) review immune therapy for ARDS, septic shock, and multiple organ failure, including the potential therapeutic use of anti-IL-8 antibodies. Sekido et al. (*Nature* 365:654 (1993)) disclose the prevention of lung reperfusion injury in rabbits by a monoclonal antibody against IL-8. Mulligan et al. (*J. Immunol.* 150:5585 (1993)), disclose protective effects of a murine monoclonal antibody to human IL-8 in inflammatory lung injury in rats.

WO 95/23865 (International Application No. PCT/US95/02589 published Sep. 8, 1995) demonstrates that anti-IL-8 monoclonal antibodies can be used therapeutically in the treatment of other inflammatory disorders, such as bacterial pneumonias and inflammatory bowel disease.

Anti-IL-8 antibodies are additionally useful as reagents for assaying IL-8. For example, Sticherling et al. (*Arch. Dermatol. Res.* 284:82 (1992)), disclose the use of anti-IL-8 monoclonal antibodies as reagents in immunohistochemical studies. Ko et al. (*J. Immunol. Methods* 149:227 (1992)) disclose the use of anti-IL-8 monoclonal antibodies as reagents in an enzyme-linked immunoabsorbent assay (ELISA) for IL-8.

SUMMARY OF THE INVENTION

One aspect of the invention is a conjugate consisting essentially of one or more antibody fragments covalently attached to one or more polymer molecules, wherein the apparent size of the conjugate is at least about 500 kD.

Another aspect of the invention is an anti-IL-8 monoclonal antibody or antibody fragment comprising the complementarity determining regions of the 6G4.2.5LV11N35E light chain polypeptide amino acid sequence of FIG. 45 (SEQ ID NO:62).

Further aspects of the invention are a nucleic acid molecule comprising a nucleic acid sequence encoding the above-described anti-IL-8 monoclonal antibody or antibody fragment; an expression vector comprising the nucleic acid molecule operably linked to control sequences recognized by a host cell transfected with the vector; a host cell transfected with the vector; and a method of producing the antibody fragment comprising culturing the host cell under conditions wherein the nucleic acid encoding the antibody fragment is expressed, thereby producing the antibody fragment, and recovering the antibody fragment from the host cell.

BRIEF DESCRIPTION OF THE FIGURES

The file of this patent contains at least one drawing executed in color. Copies of this patent with color drawing(s) will be provided by the Patent and Trademark Office upon request and payment of the necessary fee.

FIG. 11A depicts myeloperoxidase levels in tissue; FIG. 11B depicts IL-8 levels in tissue; FIG. 11C depicts colon weight; FIG. 11D depicts gross inflammation; FIG. 11E depicts edema; FIG. 11F depicts extent of necrosis; FIG. 11G depicts severity of necrosis; FIG. 11H depicts neutrophil margination; FIG. 11I depicts neutrophil infiltration; and FIG. 11J depicts mononuclear infiltration.

FIG. 12 is a graph depicting the effect of anti-IL-8 monoclonal antibody treatment on the number of neutrophils in bronchoalveolar lavage (BAL) fluid in animals infected with *Streptococcus pneumoniae*, *Escherichia coli*, or *Pseudomonas aeruginosa*. Treatment with 6G4.2.5 significantly reduced the number of neutrophils present in the BAL fluid compared to animals treated with isotype control mouse IgG (FIG. 12).

FIG. 13 depicts the DNA sequences (SEQ ID NOS: 1–6) of three primers designed for each of the light and heavy chains. Multiple primers were designed in order to increase the chances of primer hybridization and efficiency of first strand cDNA synthesis for cloning the variable light and heavy regions of monoclonal antibody 5.12.14.

FIG. 14 depicts the DNA sequences (SEQ ID NOS: 7–10) of one forward primer and one reverse primer for the 5.12.14 light chain variable region amplification.

FIG. 15 depicts the DNA sequences (SEQ ID NOS: 11–15) of one forward primer and one reverse primer for the 5.12.14 heavy chain variable region amplification.

FIG. 16 depicts the DNA sequence (SEQ ID NO: 16) and the amino acid sequence (SEQ ID NO: 17) of the 5.12.14 light chain variable region and partial murine constant light region. CDRs are indicated by either X-ray crystallography (underlined amino acids) or by Kabat sequence comparison (amino acids denoted with asterisk). Important restriction sites are indicated in italics. The signal peptide of STII is amino acids −23 to −1. The murine variable light region is amino acids 1 to 109. The partial murine constant light region is amino acids 110 to 123 (in italics).

FIG. 17 depicts the DNA sequence (SEQ ID NO: 18) and the amino acid sequence (SEQ ID NO: 19) of the 5.12.14 heavy chain variable region and partial murine constant heavy region. CDRs are indicated by either X-ray crystallography (underlined amino acids) or by Kabat sequence comparison (amino acids denoted with asterisk). Important restriction sites are indicated in italics. The signal peptide of STII is amino acids −23 to −1. The murine variable heavy region is amino acids 1 to 120. The partial murine constant heavy region is amino acids 121 to 130.

FIG. 18 depicts the DNA sequences (SEQ ID NOS: 20–23) of amplification primers used to convert murine light and heavy chain constant region residues to their human equivalents.

FIG. 19 depicts the DNA sequence (SEQ ID NO: 24) and the amino acid sequence (SEQ ID NO: 25) for the 5.12.14 light chain variable region and the human IgG1 light chain constant region. CDRs are indicated by either X-ray crystallography (underlined amino acids) or by Kabat sequence comparison (amino acids denoted with asterisk). The human constant region is denoted in italics. The signal peptide of STII is amino acids −23 to −1. The murine variable light region is amino acids 1 to 109. The human constant light region is amino acids 110 to 215.

FIGS. 20A–20B depict the DNA sequence (SEQ ID NO: 26) and the amino acid sequence (SEQ ID NO: 27) for the 5.12.14 heavy chain variable region and the heavy chain constant region of human IgG1. CDRs are indicated by either X-ray crystallography (underlined amino acids) or by Kabat sequence comparison (amino acids denoted with asterisk). The human constant region is denoted in italics. The signal peptide of STII is amino acids −23 to −1. The murine variable heavy region is amino acids 1 to 120. The human constant heavy region is amino acids 121 to 229.

FIG. 21 depicts the DNA sequences (SEQ ID NOS: 1–6) of three primers designed for each of the light and heavy chains. Multiple primers were designed in order to increase the chances of primer hybridization and efficiency of first strand cDNA synthesis for cloning the variable light and heavy regions of monoclonal antibody 6G4.2.5.

FIG. 22 depicts the DNA sequences (SEQ ID NOS: 28–31) of one forward primer and one reverse primer for the 6G4.2.5 light chain variable region amplification.

FIG. 23 depicts the DNA sequences (SEQ ID NOS: 32,33,11,15,14, and 13) of one forward primer and one reverse primer for the 6G4.2.5 heavy chain variable region amplification.

FIG. 24 depicts the DNA sequence (SEQ ID NO: 34) and the amino acid sequence (SEQ ID NO: 35) of the 6G4.2.5 light chain variable region and partial murine constant light region. CDRs are indicated by either X-ray crystallography (underlined amino acids) or by Kabat sequence comparison (amino acids denoted with asterisk). Useful cloning sites are in italics. The signal peptide of STII is amino acids −23 to −1. The murine variable light region is amino acids 1 to 114. The partial murine constant light region is amino acids 115 to 131.

FIG. 25 depicts the DNA sequence (SEQ ID NO: 36) and the amino acid sequence SEQ ID NO: 37) of the 6G4.2.5 heavy chain variable region and partial murine constant heavy region. CDRs are indicated by either X-ray crystallography (underlined amino acids) or by Kabat sequence comparison (amino acids denoted with asterisk). Useful cloning sites are in italics. The signal peptide of STII is amino acids −23 to −1. The murine variable heavy region is amino acids 1 to 122. The partial murine constant heavy region is amino acids 123 to 135.

FIG. 26 depicts the DNA sequences (SEQ ID NOS: 38–40) of primers to convert the murine light chain and heavy chain constant regions to their human equivalents.

FIGS. 27A–27B depict the DNA sequence (SEQ ID NO: 41) and the amino acid sequence (SEQ ID NO: 42) for the chimeric 6G4.2.5 light chain. CDRs are indicated by either X-ray crystallography (underlined amino acids) or by Kabat sequence comparison (amino acids denoted with asterisk). The human constant region is denoted in italics. The signal peptide of STII is amino acids −23 to −1. The murine variable heavy region is amino acids 1 to 114. The human constant heavy region is amino acids 115 to 220.

FIGS. 28A–28B depict the DNA sequence (SEQ ID NO: 43) and the amino acid sequence (SEQ ID NO: 44) for the chimeric 6G4.2.5 heavy chain. CDRs are indicated by either X-ray crystallography (underlined amino acids) or by Kabat sequence comparison (amino acids denoted with asterisk). The human constant region is denoted in italics. The signal peptide of STII is amino acids −23 to −1. The murine variable heavy region is amino acids 1 to 122. The human constant heavy region is amino acids 123 to 231.

FIG. 29 depicts an amino acid sequence alignment of murine 6G425 light chain variable domain (SEQ ID NO: 45), humanized 6G425 F(ab)-1 light chain variable domain (SEQ ID NO: 46), and human light chain κI consensus framework (SEQ ID NO: 47) amino acid sequences, and an amino acid sequence alignment of murine 6G425 heavy chain variable domain (SEQ ID NO: 48), humanized 6G425 F(ab)-1 heavy chain variable domain (SEQ ID NO: 49), and human IgG1 subgroup III heavy chain variable domain (SEQ ID NO: 50) amino acid sequences, used in the humanization of 6G425. Light chain CDRs are labeled L1, L2, L3; heavy chain CDRs are labeled H1, H2, and H3. = and + indicate CDR sequences as defined by X-ray crystallographic contacts and sequence hypervariability, respectively. # indicates a difference between the aligned sequences. Residue numbering is according to Kabat et al. Lower case lettering denotes the insertion of an amino acid residue relative to the humIII consensus sequence numbering.

FIG. 30A presents inhibition data for F(ab)-9 samples at concentrations of 0.06 nM, 6.25 nM, 12.5 nM, 25 nM, 50 nM, and 100 nM, for an isotype control antibody (denoted "4D5") sample at a concentration of 100 nM, and for a no antibody control sample, in the presence of 2 nM human wild type IL-8. FIG. 30B presents inhibition data for F(ab)-9 samples at concentrations of 6.25 nM, 12.5 nM, 25 nM, and 50 nM, for an isotype control antibody (denoted "4D5") sample at a concentration of 100 nM, and for a no antibody control sample, in the presence of 4 nM human monomeric IL-8 (denoted as "BD59" and as "monomeric IL-8"). FIG. 30C presents inhibition data for F(ab)-9 samples at concentrations of 1 nM, 12.5 nM, 25 nM, and 50 nM, for an isotype control antibody (denoted "4D5") sample at a concentration of 100 riM, and for a no antibody control sample, in the presence of 2 nM rhesus IL-8. In addition, FIGS. 30A–30C each presents data for a no IL-8 buffer control sample (denoted as "Buffer") in the respective inhibition assay.

FIG. 31A depicts the amino acid sequences of the humanized anti-IL-8 6G4.2.5V11 light chain in an N-terminal fusion with the STII leader peptide (SEQ ID NO: 51), the humanized anti-IL-8 6G4.2.5V11 heavy chain in an N-terminal fusion with the STII leader peptide (SEQ ID NO: 52), and a peptide linker in a C-terminal fusion with M13 phage gene-III coat protein (SEQ ID NO: 53).

FIG. 31B depicts the nucleic acid sequence (SEQ ID NO: 54) and the translated amino acid sequence (SEQ ID NO: 51) of the humanized anti-IL-8 6G4.2.5V11 light chain in an N-terminal fusion with the STII leader peptide.

FIG. 31C depicts the amino acid sequences of the humanized anti-IL-8 6G4.2.5V19 light chain in an N-terminal fusion with the STII leader peptide (SEQ ID NO: 51), and the humanized anti-IL-8 6G4.2.5V19 heavy chain in an N-terminal fusion with the STII leader peptide (SEQ ID NO: 55).

FIG. 34A presents inhibition data for 6G4.2.5V11N35A Fab samples at concentrations of 0.5, 1, 2, 4, 8, 16, and 33 nM, for an isotype control antibody (denoted "4D5") sample at a concentration of 33 nM, and for a no antibody control (denoted "HuIL-8") sample, in the presence of 2 nM human wild type IL-8. FIG. 34C presents inhibition data for 6G4.2.5V11N35A Fab samples at concentrations of 0.5, 1, 2, 4, 8, 16, and 33 nM, for an intact 6G4.2.5 mAb sample at a concentration of 33 nM, for an isotype control antibody (denoted as "4D5") sample at a concentration of 33 nM, and for a no antibody control (denoted "BD59") sample, in the presence of 2 nM human monomeric IL-8. FIG. 34B presents inhibition data for 6G4.2.5V11N35A Fab samples at concentrations of 0.5, 1, 2, 4, 8, 16, and 33 nM, for an intact 6G4.2.5 mAb sample at a concentration of 33 nM, for an isotype control antibody (denoted "4D5") sample at a concentration of 33 nM, and for a no antibody control (denoted "Rab IL-8") sample, in the presence of 2 nM rabbit IL-8. FIG. 34D presents inhibition data for 6G4.2.5V11N35A Fab samples at concentrations of 0.5, 1, 2, 4, 8, 16, and 33 nM, for an intact 6G4.2.5 mAb sample at a concentration of 33 nM, for an isotype control antibody (denoted as "4D5") sample at a concentration of 33 nM, and for a no antibody control (denoted "Rhe IL-8") sample, in the presence of 2 nM rhesus IL-8. In addition, FIGS. 34B–34D each presents data for human wild type IL-8 control (denoted "HuIL-8") samples at a concentration of 2 nM in the respective assay, and FIGS. 34A–34D each presents data for a no IL-8 buffer control (denoted "Buffer") sample in the respective assay.

FIG. 35 depicts the amino acid sequences of the humanized anti-IL-8 6G4.2.5V11N35A light chain in an N-terminal fusion with the STII leader peptide (SEQ ID NO: 56), the humanized anti-IL-8 6G4.2.5V11N35A heavy chain in an N-terminal fusion with the STII leader peptide (SEQ ID NO: 52), and the GCN4 leucine zipper peptide (SEQ ID NO: 57). The Ala residue (substituted for the wild type Asn residue) at amino acid position 35 in the 6G4.2.5V11N35A light chain appears in bold case. A putative pepsin cleavage site in the GCN4 leucine zipper sequence is underlined.

FIG. 36 depicts the DNA sequence (SEQ ID NO: 58) and the amino acid sequence (SEQ ID NO: 56) of the humanized anti-IL-8 6G4.2.5V11N35A light chain in an N-terminal fusion with the STII leader peptide. Complementarity determining regions L1, L2, and L3 are underlined.

FIGS. 37A–37B depict the DNA sequence (SEQ ID NO: 59) and the amino acid sequence (SEQ ID NO: 60) of the humanized anti-IL-8 6G4.2.5V11N35A heavy chain in an N-terminal fusion with the STII leader peptide and in a C-terminal fusion with the GCN4 leucine zipper sequence. Complementarity determining regions H1, H2, and H3 are underlined.

FIG. 39 is a graph depicting a comparison of the wild type human IL-8 mediated neutrophil chemotaxis inhibition activities of the 6G4.2.5V11N35A F(ab')$_2$ and 6G4.2.5V11N35A Fab. Inhibition data are presented for 6G4.2.5V11N35A Fab samples (denoted "N35A Fab") and 6G4.2.5V11N35A F(ab')$_2$ samples (denoted N35A F(ab')$_2$) at concentrations of 0.3, 1, 3, 10, 30, and 100 nM, for an isotype control antibody (denoted as "4D5") sample at a concentration of 100 nM, and for a no antibody control sample, in the presence of 2 nM human wild type IL-8. In addition, inhibition data are presented for no IL-8 buffer control samples (denoted "Buffer").

FIG. 40 is a graph depicting the ability of 6G4.2.5V11N35A F(ab')$_2$ to inhibit human monomeric IL-8, rhesus IL-8, and rabbit IL-8 mediated neutrophil chemotaxis. Human monomeric IL-8 mediated neutrophil chemotaxis data are presented for 6G4.2.5V11N35A F(ab')$_2$ samples at concentrations of 0.3, 1, 3, and 10 nM, for an isotype control antibody (denoted as "4D5") sample at a concentration of 100 nM, and for a no antibody control sample (denoted as "BD59"), in the presence of human monomeric IL-8 (denoted as "BD59") at a concentration of 0.5 nM. Rhesus IL-8 mediated neutrophil chemotaxis data are presented for 6G4.2.5V11N35A F(ab')$_2$ samples at concentrations of 0.3, 1, 3, and 10 nM, and for a no antibody control sample, in the presence of rhesus IL-8 at a concentration of 2 nM. Rabbit IL-8 mediated neutrophil chemotaxis data are presented for 6G4.2.5V11N35A F(ab')$_2$ samples at concentrations of 0.3, 1, 3, and 10 nM, and for a no antibody control sample, in the presence of rabbit IL-8 at a concentration of 2 nM. In addition, inhibition data are presented for a no IL-8 buffer control sample (denoted as "Buffer") and for a 2 nM human wild type IL-8 (denoted as "HuIL-8").

FIGS. 41A–41V depict the nucleic acid sequence (SEQ ID NO: 61) of the p6G4V11N35A.F(ab')$_2$ vector.

FIG. 42 depicts the nucleic acid sequences of the stop template primer (SEQ ID NO: 63) and the NNS randomization primer (SEQ ID NO: 64) used for random mutagenesis of amino acid position 35 in variable light chain CDR-L1 of humanized antibody 6G4V11.

FIG. 43A is a table of data describing the frequencies of different phage display clones obtained from the randomization of amino acid position 35 in variable light chain CDR-L1 of humanized antibody 6G4V11.

FIG. 44 also contains a table of data providing the equilibrium constant for 6G4V11N35A Fab binding to IL-8 (rate constants were not determined "ND"), and the equilibrium and rate constants for 6G4V11N35A F(ab')$_2$ and 6G4V11N35E Fab binding to IL-8.

FIG. 45 depicts the DNA sequence (SEQ ID NO: 65) and amino acid sequence (SEQ ID NO: 62) of the 6G4V11N35E light chain in an N-terminal fusion with the STII leader peptide. Complementarity determining regions L1, L2 and L3 are underlined.

FIG. 47 depicts the DNA sequence of the sense (SEQ ID NO: 66) and anti-sense (SEQ ID NO: 67) strands of a PvuII-XhoI synthetic nucleotide encoding amino acids Leu4 to Phe29 of the 6G4V11N35A heavy chain.

FIGS. 48A–48Z depict the DNA sequence (SEQ ID NO: 68) of plasmid p6G4V11N35A.choSD9.

FIG. 51 also contains a table of data providing the equilibrium and rate constants for full length murine 6G4.2.5 IgG2a, 6G4V11N35A IgG1 and 6G4V11N35E IgG1 binding to IL-8.

FIG. 53 depicts the DNA sequence (SEQ ID NO: 69) and amino acid sequence (SEQ ID NO: 70) of the 6G4V11N35A Fab' heavy chain (6G4V11N35A Fab heavy chain modified to contain a cysteine residue in the hinge region).

FIGS. 55A–55C are graphs depicting the ability of PEG-maleimide modified 6G4V11N35A Fab' molecules to inhibit human IL-8 and rabbit IL-8 mediated neutrophil chemotaxis.

FIGS. 56A–56C are graphs depicting the ability of PEG-maleimide modified 6G4V11N35A Fab' molecules to inhibit IL-8 mediated release of β-glucuronidase from neutrophils.

FIGS. 58A–58B are graphs depicting the ability of PEG-succinimide modified 6G4V11N35A F(ab')$_2$ molecules to inhibit human IL-8 mediated neutrophil chemotaxis.

FIGS. 59A–59B are graphs depicting the ability of PEG-succinimide modified 6G4V11N35A F(ab')$_2$ molecules to inhibit human IL-8 mediated release of β-glucuronidase from neutrophils.

In FIG. 65A, "bran.(1)40K(s)Fab'" denotes 6G4V11N35A Fab' coupled to one 40 kD branched PEG-maleimide molecule, "lin.(1)40K(s)Fab'" denotes 6G4V11N35A Fab' coupled to one 40 kD linear PEG-maleimide molecule, "lin.(1)30K(s)Fab'" denotes 6G4V11N35A Fab' coupled to one 30 kD linear PEG-maleimide molecule, "lin.(1)20K(s)Fab'" denotes 6G4V11N35A Fab' coupled to one 20 kD linear PEG-maleimide molecule. In FIG. 65B, "bran.(2)40K(N)Fab'2" denotes 6G4V11N35A F(ab')$_2$ coupled to two 40 kD branched PEG-succinimide molecules, "bran.(1)40K(N) Fab'2" denotes 6G4V11N35A F(ab')$_2$ coupled to one 40 kD branched PEG-succinimide molecule, and "Fab'2" denotes unmodified 6G4V11N35A F(ab')$_2$. In both graphs, "IgG" denotes a full length IgG1 equivalent of the human-murine chimeric anti-rabbit IL-8 Fab described in Example F below.

DESCRIPTION OF THE PREFERRED EMBODIMENTS

I. DEFINITIONS

Figure 1:
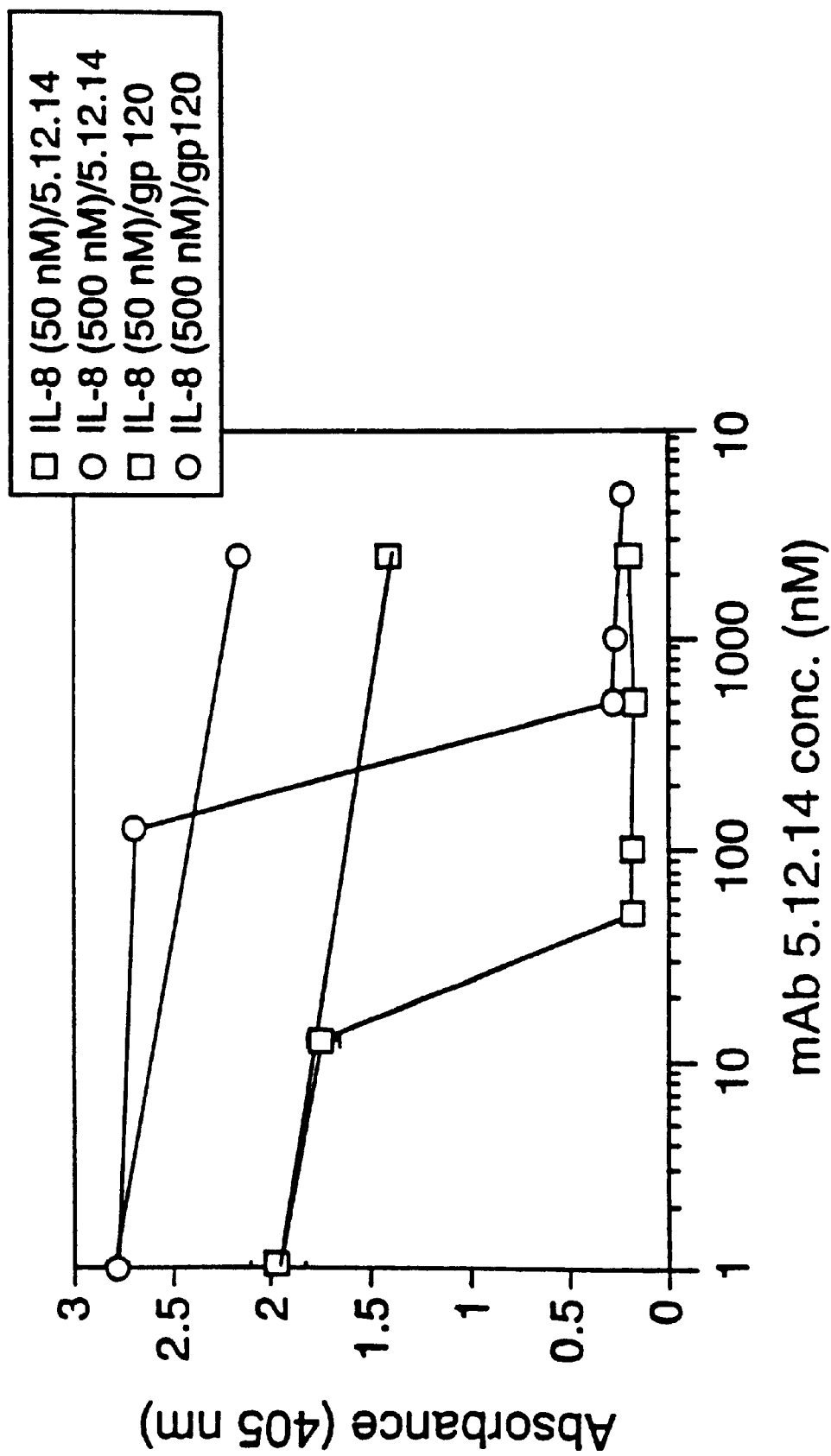
FIG. 1 is a graph depicting the blocking of IL-8 mediated elastase release from neutrophils by anti-IL-8 monoclonal antibody 5.12.14.

In general, the following words or phrases have the indicated definition when used in the description, examples, and claims.

"Polymerase chain reaction" or "PCR" refers to a procedure or technique in which minute amounts of a specific piece of nucleic acid, RNA and/or DNA, are amplified as described in U.S. Pat. No. 4,683,195 issued Jul. 28, 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers can coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.* 51:263 (1987); Erlich, ed., *PCR Technology* (Stockton Press, N.Y., 1989). As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

"Native antibodies and immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains (Clothia et al., *J. Mol. Biol.* 186:651 (1985); Novotny and Haber, *Proc. Natl. Acad. Sci. U.S.A.* 82:4592 (1985)).

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a $\beta$-sheet configuration, connected by three CDRs, 20 which form loops connecting, and in some cases forming part of, the $\beta$-sheet structure. The CDRs in each chain are held together in close proximity by the FR regions and, with the CDRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species (scFv), one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site. For a review of scFv see Pluckthun, in *The Pharmacology of Monoclonal Antibodies*, vol. 113, Rosenburg and Moore eds., Springer-Verlag, New York, pp. 269–315 (1994).

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (k) and lambda (l), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., IgG$_1$, IgG$_2$, IgG$_3$, IgG$_4$, IgA$_1$, and IgA$_2$. The heavy-chain constant domains that correspond to the different classes of immunoglobulins are called $\alpha$, $\delta$, $\epsilon$, $\downarrow$, and $\mu$, respectively. The subunit structures and three-dimensional configurations of different classes of immunoglobulins are well known.

The term "antibody" is used in the broadest sense and specifically covers single monoclonal antibodies (including agonist and antagonist antibodies) and antibody compositions with polyepitopic specificity.

"Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1)single-chain Fv (scFv) molecules (2)single chain polypeptides containing only one light chain variable domain, or a fragment thereof that contains the three CDRs of the light chain variable domain, without an associated heavy chain moiety and (3)single chain polypeptides containing only one heavy chain variable region, or a fragment thereof containing the three CDRs of the heavy chain variable region, without an associated light chain moiety; and multispecific or multivalent structures formed from antibody fragments. In an antibody fragment comprising one or more heavy chains, the heavy chain(s) can contain any constant domain sequence (e.g. CH1 in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s). Suitable leucine zipper sequences include the jun and fos leucine zippers taught by Kostelney et al., *J. Immunol.*, 148: 1547–1553 (1992) and the GCN4 leucine zipper described in the Examples below.

Unless specifically indicated to the contrary, the term "conjugate" as described and claimed herein is defined as a heterogeneous molecule formed by the covalent attachment of one or more antibody fragment(s) to one or more polymer molecule(s), wherein the heterogeneous molecule is water soluble, i.e. soluble in physiological fluids such as blood, and wherein the heterogeneous molecule is free of any structured aggregate. In the context of the foregoing definition, the term "structured aggregate" refers to (1) any aggregate of molecules in aqueous solution having a spheroid or spheroid shell structure, such that the heterogeneous molecule is not in a micelle or other emulsion structure, and is not anchored to a lipid bilayer, vesicle or liposome; and (2) any aggregate of molecules in solid or insolubilized form, such as a chromatography bead matrix, that does not release the heterogeneous molecule into solution upon contact with an aqueous phase. Accordingly, the term "conjugate" as defined herein encompasses the aforementioned heterogeneous molecule in a precipitate, sediment, bioerodible matrix or other solid capable of releasing the heterogeneous molecule into aqueous solution upon hydration of the solid.

Unless specifically indicated to the contrary, the terms "polymer", "polymer molecule", "nonproteinaceous polymer", and "nonproteinaceous polymer molecule" are used interchangeably and are defined as a molecule formed by covalent linkage of two or more monomers, wherein none of the monomers is contained in the group consisting of alanine (Ala), cysteine (Cys), aspartic acid (Asp), glutamic acid (Glu), phenylalanine (Phe), glycine (Gly), histidine (His), isoleucine (Ile), lysine (Lys), leucine (Leu), methionine (Met), asparagine (Asn), proline (Pro), glutamine (Gln), arginine (Arg), serine (Ser), threonine (Thr), valine (Val), tryptophan (Trp), and tyrosine (Tyr) residues.

The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each mAb is directed against a single determinant on the antigen. In addition to their specificity, the monoclonal antibodies are advantageous in that they can be synthesized by hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256:495 (1975), or may be made by recombinant DNA methods (see, e.g., U.S. Pat. No. 4,816,567 to Cabilly et al.). The "monoclonal antibodies" also include clones of antigen-recognition and binding-site containing antibody fragments (Fv clones) isolated from phage antibody libraries using the techniques described in Clackson et al., *Nature*, 352:624–628 (1991) and Marks et al., *J. Mol. Biol.*, 222:581–597 (1991), for example.

The monoclonal antibodies herein include hybrid and recombinant antibodies produced by splicing a variable (including hypervariable) domain of an anti-IL-8 antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$, and Fv), so long as they exhibit the desired biological activity. (See, e.g., U.S. Pat. No. 4,816,567 to Cabilly et al.; Mage and Lamoyi, in *Monoclonal Antibody Production Techniques and Applications*, pp. 79–97 (Marcel Dekker, Inc., New York, 1987).)

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Cabilly et al., supra; Morrison et al., *Proc. Natl. Acad. Sci. U.S.A.* 81:6851 (1984)).

"Humanized" forms of non-human (e.g., murine) antibodies are specific chimeric immunoglobulins, immunoglobulin chains or fragments thereof (such as Fv, Fab, Fab', F(ab')$_2$, or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat, or rabbit having the desired specificity, affinity, and capacity. In some instances, Fv framework residues of the human immunoglobulin are replaced by corresponding non-human residues. Furthermore, humanized antibodies can comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details see Jones el al., *Nature* 321:522 (1986); Reichmann et al., *Nature* 332:323 (1988); and Presta, *Curr. Op. Struct. Biol.* 2:593 (1992).

"Treatment" refers to both therapeutic treatment and prophylactic or preventative measures. Those in need of treatment include those already with the disorder as well as those prone to have the disorder or those in which the disorder is to be prevented.

"Mammal" for purposes of treatment refers to any animal classified as a mammal, including humans, domestic and farm animals, and zoo, sports, or pet animals, such as dogs, horses, cats, cows, etc. Preferably, the mammal herein is human.

As used herein, protein, peptide and polypeptide are used interchangeably to denote an amino acid polymer or a set of two or more interacting or bound amino acid polymers.

As used herein, the term "inflammatory disorders" refers to pathological states resulting in inflammation, typically caused by neutrophil chemotaxis. Examples of such disorders include inflammatory skin diseases including psoriasis; responses associated with inflammatory bowel disease (such as Crohn's disease and ulcerative colitis); ischemic reperfusion; adult respiratory distress syndrome; dermatitis; meningitis; encephalitis; uveitis; autoimmune diseases such as rheumatoid arthritis, Sjorgen's syndrome, vasculitis; diseases involving leukocyte diapedesis; central nervous system (CNS) inflammatory disorder, multiple organ injury syndrome secondary to septicaemia or trauma; alcoholic hepatitis, bacterial pneumonia, antigen-antibody complex mediated diseases; inflammations of the lung, including pleurisy, alveolitis, vasculitis, pneumonia, chronic bronchitis, bronchiectasis, and cystic fibrosis; etc. The preferred indications are bacterial pneumonia and inflammatory bowel disease such as ulcerative colitis.

The terms "hydrodynamic size", "apparent size", "apparent molecular weight", "effective size" and "effective molecular weight" of a molecule are used synonymously herein refer to the size of a molecule as determined by comparison to a standard curve produced with globular protein molecular weight standards in a size exclusion chromatography system, wherein the standard curve is created by mapping the actual molecular weight of each standard against its elution time observed in the size exclusion chromatography system. Thus, the apparent size of a test molecule is derived by using the molecule's elution time to extrapolate a putative molecular weight from the standard curve. Preferably, the molecular weight standards used to create the standard curve are selected such that the apparent size of the test molecule falls within the linear portion of the standard curve.

II. MODES FOR CARRYING OUT THE INVENTION

In one part, the invention arises from the surprising and unexpected discovery that antibody fragment-polymer conjugates having an effective or apparent size significantly greater than the antibody fragment-polymer conjugates described in the art confers an increase in serum half-life, an increase in mean residence time in circulation (MRT), and/or a decrease in serum clearance rate over underivatized antibody fragment which far exceed the modest changes in such biological property or properties obtained with the art-known antibody fragment-polymer conjugates. The present inventors have determined for the first time that increasing the effective size of an antibody fragment to at least about 500,000 D, or increasing the effective size of an antibody fragment by at least about 8 fold over the effective size of the parental antibody fragment, or derivatizing an antibody fragment with a polymer of at least about 20,000 D in molecular weight, yields a molecule with a commercially useful pharmacokinetic profile. The greatly extended serum half-life, extended MRT, and/or reduced serum clearance rate of the conjugates of the invention makes such conjugates viable alternatives to intact antibodies used for therapeutic treatment of many disease indications. Antibody fragments provide significant advantages over intact antibodies, notably the fact that recombinant antibody fragments can be made in bacterial cell expression systems. Bacterial cell expression systems provide several advantages over mammalian cell expression systems, including reduced time and cost at both the research and development and manufacturing stages of a product.

In another part, the present invention also arises from the humanization of the 6G4.2.5 murine anti-rabbit IL-8 monoclonal antibody ("6G4.2.5") described in WO 95/23865 (PCT/US95/02589 published Sep. 8, 1995), the entire disclosure of which is specifically incorporated herein by reference. The hybridoma producing antibody 6G4.2.5 was deposited on Sep. 28, 1994 with the American Type Culture Collection and assigned ATCC Accession No. HB 11722 as described in the Examples below. In one aspect, the invention provides a humanized derivative of the 6G4.2.5 antibody, variant 11 (referred to herein as "6G4.2.5v11"), in which the murine CDRs of 6G4.2.5 are grafted onto a consensus framework for human light chain κI (and human IgG1 heavy chain subgroup III, followed by importing three framework residues from the murine 6G4.2.5 parent heavy chain variable domain sequence into analogous sites in the heavy chain variable domain of the human template sequence, as described in the Examples below. In another aspect, the invention provides variants of the 6G4.2.5v11 antibody with certain amino acid substitution(s) yielding increased affinity for human IL-8 and/or promoting greater efficiency in recombinant manufacturing processes.

It will be understood that in the context of this Section (II) and all subsections thereof, every reference to "an antibody fragment" or "the antibody fragment" contained in a conjugate shall be a reference to one or more antibody fragment (s) in the conjugate (consistent with the definition of the term "conjugate" set forth in Section (I) above), except where the number of antibody fragment(s) in the conjugate is expressly indicated. It will be understood that in the context of this Section (II) and all subsections thereof, every reference to "a polymer", "a polymer molecule", "the polymer", or "the polymer molecule" contained in a conjugate shall be a reference to one or more polymer molecule(s) in the conjugate (consistent with the definition of the term "conjugate" set forth in Section (I) above), except where the number of polymer molecule(s) in the conjugate is expressly indicated.

1. Large Effective Size Antibody Fragment-Polymer Conjugates

In one aspect, the invention provides an antibody fragment covalently attached to a polymer to form a conjugate having an effective or apparent size of at least about 500,000 Daltons (D). In another aspect, the invention provides an antibody fragment covalently attached to a polymer to form a conjugate having an apparent size that is at least about 8 fold greater than the apparent size of the parental antibody fragment. In yet another aspect, the invention provides an antibody fragment covalently attached to a polymer of at least about 20,000 D in molecular weight (MW). It will be appreciated that the unexpectedly and surprisingly large increase in antibody fragment serum half-life, increase in MRT, and/or decrease in serum clearance rate can be achieved by using any type of polymer or number of polymer molecules which will provide the conjugate with an effective size of at least about 500,000 D, or by using any type of polymer or number of polymer molecules which will provide the conjugate with an effective size that is at least about 8 fold greater than the effective size of the parental antibody fragment, or by using any type or number of polymers wherein each polymer molecule is at least about 20,000 D in MW. Thus, the invention is not dependent on the use of any particular polymer or molar ratio of polymer to antibody fragment in the conjugate.

In addition, the beneficial aspects of the invention extend to antibody fragments without regard to antigen specificity. Although variations from antibody to antibody are to be expected, the antigen specificity of a given antibody will not substantially impair the extraordinary improvement in serum half-life, MRT, and/or serum clearance rate for antibody fragments thereof that can be obtained by derivatizing the antibody fragments as taught herein.

In one embodiment, the conjugate has an effective size of at least about 500,000 D, or at least about 800,000 D, or at least about 900,000 D, or at least about 1,000,000 D, or at least about 1,200,000 D, or at least about 1,400,000 D, or at least about 1,500,000 D, or at least about 1,800,000 D, or at least about 2,000,000 D, or at least about 2,500,000 D.

In another embodiment, the conjugate has an effective size of at or about 500,000 D to at or about 10,000,000 D, or an effective size of at or about 500,000 D to at or about 8,000,000 D, or an effective size of at or about 500,000 D to at or about 5,000,000 D, or an effective size of at or about 500,000 D to at or about 4,000,000 D, or an effective size of at or about 500,000 D to at or about 3,000,000 D, or an effective size of at or about 500,000 D to at or about 2,500,000 D, or an effective size of at or about 500,000 D to at or about 2,000,000 D, or an effective size of at or about 500,000 D to at or about 1,800,000 D, or an effective size of at or about 500,000 D to at or about 1,600,000 D, or an effective size of at or about 500,000 D to at or about 1,500,000 D, or an effective size of at or about 500,000 D to at or about 1,000,000 D.

In another embodiment, the conjugate has an effective size of at or about 800,000 D to at or about 10,000,000 D, or an effective size of at or about 800,000 D to at or about 8,000,000 D, or an effective size of at or about 800,000 D to at or about 5,000,000 D, or an effective size of at or about 800,000 D to at or about 4,000,000 D, or an effective size of at or about 800,000 D to at or about 3,000,000 D, or an effective size of at or about 800,000 D to at or about 2,500,000 D, or an effective size of at or about 800,000 D to at or about 2,000,000 D, or an effective size of at or about 800,000 D to at or about 1,800,000 D, or an effective size of at or about 800,000 D to at or about 1,600,000 D, or an effective size of at or about 800,000 D to at or about 1,500,000 D, or an effective size of at or about 800,000 D to at or about 1,000,000 D.

In another embodiment, the conjugate has an effective size of at or about 900,000 D to at or about 10,000,000 D, or an effective size of at or about 900,000 D to at or about 8,000,000 D, or an effective size of at or about 900,000 D to at or about 5,000,000 D, or an effective size of at or about 900,000 D to at or about 4,000,000 D, or an effective size of at or about 900,000 D to at or about 3,000,000 D, or an effective size of at or about 900,000 D to at or about 2,500,000 D, or an effective size of at or about 900,000 D to at or about 2,000,000 D, or an effective size of at or about 900,000 D to at or about 1,800,000 D, or an effective size of at or about 900,000 D to at or about 1,600,000 D, or an effective size of at or about 900,000 D to at or about 1,500,000 D.

In another embodiment, the conjugate has an effective size of at or about 1,000,000 D to at or about 10,000,000 D, or an effective size of at or about 1,000,000 D to at or about 8,000,000 D, or an effective size of at or about 1,000,000 D to at or about 5,000,000 D, or an effective size of at or about 1,000,000 D to at or about 4,000,000 D, or an effective size of at or about 1,000,000 D to at or about 3,000,000 D, or an effective size of at or about 1,000,000 D to at or about 2,500,000 D, or an effective size of at or about 1,000,000 D to at or about 2,000,000 D, or an effective size of at or about 1,000,000 D to at or about 1,800,000 D, or an effective size of at or about 1,000,000 D to at or about 1,600,000 D, or an effective size of at or about 1,000,000 D to at or about 1,500,000 D.

In a further embodiment, the conjugate has an effective size that is at least about 8 fold greater, or at least about 10 fold greater, or at least about 12 fold greater, or at least about 15 fold greater, or at least about 18 fold greater, or at least about 20 fold greater, or at least about 25 fold greater, or at least about 28 fold greater, or at least about 30 fold greater, or at least about 40 fold greater, than the effective size of the parental antibody fragment.

In another embodiment, the conjugate has an effective size that is about 8 fold to about 100 fold greater, or is about 8 fold to about 80 fold greater, or is about 8 fold to about 50 fold greater, or is about 8 fold to about 40 fold greater, or is about 8 fold to about 30 fold greater, or is about 8 fold to about 28 fold greater, or is about 8 fold to about 25 fold greater, or is about 8 fold to about 20 fold greater, or is about 8 fold to about 18 fold greater, or is about 8 fold to about 15 fold greater, than the effective size of the parental antibody fragment.

In another embodiment, the conjugate has an effective size that is about 12 fold to about 100 fold greater, or is about 12 fold to about 80 fold greater, or is about 12 fold to about 50 fold greater, or is about 12 fold to about 40 fold greater, or is about 12 fold to about 30 fold greater, or is about 12 fold to about 28 fold greater, or is about 12 fold to about 25 fold greater, or is about 12 fold to about 20 fold greater, or is about 12 fold to about 18 fold greater, or is about 12 fold to about 15 fold greater, than the effective size of the parental antibody fragment.

In another embodiment, the conjugate has an effective size that is about 15 fold to about 100 fold greater, or is about 15 fold to about 80 fold greater, or is about 15 fold to about 50 fold greater, or is about 15 fold to about 40 fold greater, or is about 15 fold to about 30 fold greater, or is about 15 fold to about 28 fold greater, or is about 15 fold to about 25 fold greater, or is about 15 fold to about 20 fold greater, or is about 15 fold to about 18 fold greater, than the effective size of the parental antibody fragment.

In another embodiment, the conjugate has an effective size that is about 18 fold to about 100 fold greater, or is about 18 fold to about 80 fold greater, or is about 18 fold to about 50 fold greater, or is about 18 fold to about 40 fold greater, or is about 18 fold to about 30 fold greater, or is about 18 fold to about 28 fold greater, or is about 18 fold to about 25 fold greater, or is about 18 fold to about 20 fold greater, than the effective size of the parental antibody fragment.

In another embodiment, the conjugate has an effective size that is about 20 fold to about 100 fold greater, or is about 20 fold to about 80 fold greater, or is about 20 fold to about 50 fold greater, or is about 20 fold to about 40 fold greater, or is about 20 fold to about 30 fold greater, or is about 20 fold to about 28 fold greater, or is about 20 fold to about 25 fold greater, than the effective size of the parental antibody fragment.

In another embodiment, the conjugate has an effective size that is about 25 fold to about 100 fold greater, or is about 25 fold to about 80 fold greater, or is about 25 fold to about 50 fold greater, or is about 25 fold to about 40 fold greater, or is about 25 fold to about 30 fold greater, or is about 25 fold to about 28 fold greater, than the effective size of the parental antibody fragment.

In another embodiment, the conjugate has an effective size that is about 28 fold to about 100 fold greater, or is about 28 fold to about 80 fold greater, or is about 28 fold to about 50 fold greater, or is about 28 fold to about 40 fold greater, or is about 28 fold to about 30 fold greater, than the effective size of the parental antibody fragment.

In another embodiment, the conjugate has an effective size that is about 30 fold to about 100 fold greater, or is about 30 fold to about 80 fold greater, or is about 30 fold to about 50 fold greater, or is about 30 fold to about 40 fold greater, than the effective size of the parental antibody fragment.

In another embodiment, the conjugate has an effective size that is about 40 fold to about 100 fold greater, or is about 40 fold to about 80 fold greater, or is about 40 fold to about 50 fold greater, than the effective size of the parental antibody fragment.

In still another embodiment, the conjugate is an antibody fragment covalently attached to at least one polymer having an actual MW of at least about 20,000 D.

In a further embodiment, the conjugate is an antibody fragment covalently attached to at least one polymer having an actual MW of at least about 30,000 D.

In yet another embodiment, the conjugate is an antibody fragment covalently attached to at least one polymer having an actual MW of at least about 40,000 D.

In another embodiment, the conjugate is an antibody fragment covalently attached to at least one polymer having an actual MW that is at or about 20,000 D to at or about 300,000 D, or is at or about 30,000 D to at or about 300,000 D, or is at or about 40,000 D to at or about 300,000 D.

In another embodiment, the conjugate is an antibody fragment covalently attached to at least one polymer having an actual MW that is at or about 20,000 D to at or about 100,000 D, or is at or about 30,000 D to at or about 100,000 D, or is at or about 40,000 D to at or about 100,000 D.

In another embodiment, the conjugate is an antibody fragment covalently attached to at least one polymer having an actual MW that is at or about 20,000 D to at or about 70,000 D, or is at or about 30,000 D to at or about 70,000 D, or is at or about 40,000 D to at or about 70,000 D.

In another embodiment, the conjugate is an antibody fragment covalently attached to at least one polymer having an actual MW that is at or about 20,000 D to at or about 50,000 D, or is at or about 30,000 D to at or about 50,000 D, or is at or about 40,000 D to at or about 50,000 D.

In another embodiment, the conjugate is an antibody fragment covalently attached to at least one polymer having an actual MW that is at or about 20,000 D to at or about 40,000 D, or is at or about 30,000 D to at or about 40,000 D.

The conjugates of the invention can be made using any suitable technique now known or hereafter developed for derivatizing antibody fragments with polymers. It will be appreciated that the invention is not limited to conjugates utilizing any particular type of linkage between an antibody fragment and a polymer.

The conjugates of the invention include species wherein a polymer is covalently attached to a non-specific site or non-specific sites on the parental antibody fragment, i.e. polymer attachment is not targeted to a particular region or a particular amino acid residue in the parental antibody fragment. In such embodiments, the coupling chemistry can, for example, utilize the free epsilon amino groups of lysine residues in the parental antibody as attachment sites for the polymer, wherein such lysine residue amino groups are randomly derivatized with polymer.

In addition, the conjugates of the invention include species wherein a polymer is covalently attached to a specific site or specific sites on the parental antibody fragment, i.e. polymer attachment is targeted to a particular region or a particular amino acid residue or residues in the parental antibody fragment. In such embodiments, the coupling chemistry can, for example, utilize the free sulfhydryl group of a cysteine residue not in a disulfide bridge in the parental antibody fragment. In one embodiment, one or more cysteine residue(s) is (are) engineered into a selected site or sites in the parental antibody fragment for the purpose of providing a specific attachment site or sites for polymer. The polymer can be activated with any functional group that is capable of reacting specifically with the free sulphydryl or thiol group(s) on the parental antibody, such as maleimide, sulfhydryl, thiol, triflate, tesylate, aziridine, exirane, and 5-pyridyl functional groups. The polymer can be coupled to the parental antibody fragment using any protocol suitable for the chemistry of the coupling system selected, such as the protocols and systems described in Section (II)(I)(b) or in Section (T) of the Examples below.

In another embodiment, polymer attachment is targeted to the hinge region of the parental antibody fragment. The location of the hinge region varies according to the isotype of the parental antibody. Typically, the hinge region of IgG, IgD and IgA isotype heavy chains is contained in a proline rich peptide sequence extending between the $C_H1$ and $C_H2$ domains. In a preferred embodiment, a cysteine residue or residues is (are) engineered into the hinge region of the parental antibody fragment in order to couple polymer specifically to a selected location in the hinge region.

In one aspect, the invention encompasses a conjugate having any molar ratio of polymer to antibody fragment that endows the conjugate with an apparent size in the desired range as taught herein. The apparent size of the conjugate will depend in part upon the size and shape of the polymer used, the size and shape of the antibody fragment used, the number of polymer molecules attached to the antibody fragment, and the location of such attachment site(s) on the antibody fragment. These parameters can easily be identified and maximized to obtain the a conjugate with the desired apparent size for any type of antibody fragment, polymer and linkage system.

In another aspect, the invention encompasses a conjugate with a polymer to antibody fragment molar ratio of no more than about 10:1, or no more than about 5:1, or no more than about 4:1, or no more than about 3:1, or no more than about 2:1, or no more than 1:1.

In yet another aspect, the invention encompasses a conjugate wherein the antibody fragment is attached to about 10 or fewer polymer molecules, each polymer molecule having a molecular weight of at least about 20,000 D, or at least about 30,000 D, or at least about 40,000 D. In another embodiment, the conjugate contains an antibody fragment attached to about 5 or fewer polymer molecules, each polymer molecule having a molecular weight of at least about 20,000 D, or at least about 30,000 D, or at least about 40,000 D. In still another embodiment, the conjugate contains an antibody fragment attached to about 4 or fewer polymer molecules, each polymer molecule having a molecular weight of at least about 20,000 D, or at least about 30,000 D, or at least about 40,000 D. In a further embodiment, the conjugate contains an antibody fragment attached to about 3 or fewer polymer molecules, each polymer molecule having a molecular weight of at least about 20,000 D, or at least about 30,000 D, or at least about 40,000 D. In an additional embodiment, the conjugate contains an antibody fragment attached to about 2 or fewer polymer molecules, each polymer molecule having a molecular weight of at least about 20,000 D, or at least about 30,000 D, or at least about 40,000 D. Also provided herein is a conjugate containing an antibody fragment attached to a single polymer molecule having a molecular weight of at least about 20,000 D, or at least about 30,000 D, or at least about 40,000 D.

In still another aspect, the invention encompasses a conjugate wherein every polymer molecule in the conjugate has a molecular weight that is at or about 20,000 D to at or about 300,000 D, or is at or about 30,000 D to at or about 300,000 D, or is at or about 40,000 D to at or about 300,000 D, and wherein the conjugate contains no more than about 10 polymer molecules, or no more than about 5 polymer molecules, or no more than about 4 polymer molecules, or no more than about 3 polymer molecules, or no more than about 2 polymer molecules, or no more than 1 polymer molecule.

In still another aspect, the invention encompasses a conjugate wherein every polymer molecule in the conjugate has a molecular weight that is at or about 20,000 D to at or about 100,000 D, or is at or about 30,000 D to at or about 100,000 D, or is at or about 40,000 D to at or about 100,000 D, and wherein the conjugate contains no more than about 10 polymer molecules, or no more than about 5 polymer molecules, or no more than about 4 polymer molecules, or no more than about 3 polymer molecules, or no more than about 2 polymer molecules, or no more than 1 polymer molecule.

In still another aspect, the invention encompasses a conjugate wherein every polymer molecule in the conjugate has a molecular weight that is at or about 20,000 D to at or about 70,000 D, or is at or about 30,000 D to at or about 70,000 D, or is at or about 40,000 D to at or about 70,000 D, and wherein the conjugate contains no more than about 10 polymer molecules, or no more than about 5 polymer molecules, or no more than about 4 polymer molecules, or no more than about 3 polymer molecules, or no more than about 2 polymer molecules, or no more than 1 polymer molecule.

In still another aspect, the invention encompasses a conjugate wherein every polymer molecule in the conjugate has a molecular weight that is at or about 20,000 D to at or about 50,000 D, or is at or about 30,000 D to at or about 50,000 D, or is at or about 40,000 D to at or about 50,000 D, and wherein the conjugate contains no more than about 10 polymer molecules, or no more than about 5 polymer molecules, or no more than about 4 polymer molecules, or no more than about 3 polymer molecules, or no more than about 2 polymer molecules, or no more than 1 polymer molecule.

In still another aspect, the invention encompasses a conjugate wherein every polymer molecule in the conjugate has a molecular weight that is at or about 20,000 D to at or about 40,000 D, or is at or about 30,000 D to at or about 40,000 D, and wherein the conjugate contains no more than about 10 polymer molecules, or no more than about 5 polymer molecules, or no more than about 4 polymer molecules, or no more than about 3 polymer molecules, or no more than about 2 polymer molecules, or no more than 1 polymer molecule.

It is believed that the serum half-life, MRT and/or serum clearance rate of any antibody fragment can be greatly improved by derivatizing the antibody fragment with polymer as taught herein. In one embodiment, the conjugate contains an antibody fragment selected from the group consisting of Fab, Fab', Fab'-SH, Fv, scFv and F(ab')$_2$.

In a preferred embodiment, the conjugate contains an antibody fragment selected from the group consisting of Fab, Fab', and Fab'-SH, wherein every polymer molecule in the conjugate is attached to the hinge region of the antibody fragment.

In another preferred embodiment, the conjugate contains an antibody fragment selected from the group consisting of Fab, Fab', and Fab'-SH, every polymer molecule in the conjugate molecule is attached to the hinge region of the antibody fragment, and the conjugate contains no more than about 10 polymer molecules, or no more than about 5 polymer molecules, or no more than about 4 polymer molecules, or no more than about 3 polymer molecules, or no more than about 2 polymer molecules, or no more than 1 polymer molecule.

In yet another preferred embodiment, the conjugate contains a F(ab')$_2$ antibody fragment attached to no more than about 2 polymer molecules, wherein every polymer molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In a further embodiment, the conjugate contains an antibody fragment selected from the group consisting of Fab, Fab', and Fab'-SH, wherein the antibody fragment is attached to no more than 1 polymer molecule and the polymer is coupled to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In an additional embodiment, the conjugate contains an antibody fragment selected from the group consisting of Fab, Fab', and Fab'-SH, every polymer molecule in the conjugate is at least about 20,000 D in molecular weight, or at least about 30,000 in molecular weight, or at least about 40,000 D in molecular weight, every polymer molecule in the conjugate is attached to the hinge region of the antibody fragment, and the conjugate contains no more than about 10 polymer molecules, or no more than about 5 polymer molecules, or no more than about 4 polymer molecules, or no more than about 3 polymer molecules, or no more than about 2 polymer molecules, or no more than 1 polymer molecule.

In another embodiment, the conjugate contains an antibody fragment selected from the group consisting of Fab, Fab', and Fab'-SH, every polymer molecule in the conjugate is at or about 20,000 D to at or about 300,000 D in molecular weight, or is at or about 30,000 D to at or about 300,000 D in molecular weight, or is at or about 40,000 D to at or about 300,000 D in molecular weight, every polymer molecule in the conjugate is attached to the hinge region of the antibody fragment, and the conjugate contains no more than about 10 polymer molecules, or no more than about 5 polymer molecules, or no more than about 4 polymer molecules, or no more than about 3 polymer molecules, or no more than about 2 polymer molecules, or no more than 1 polymer molecule.

In another embodiment, the conjugate contains an antibody fragment selected from the group consisting of Fab, Fab', and Fab'-SH, every polymer molecule in the conjugate is at or about 20,000 D to at or about 100,000 D in molecular weight, or is at or about 30,000 D to at or about 100,000 D in molecular weight, or is at or about 40,000 D to at or about 100,000 D in molecular weight, every polymer molecule in the conjugate is attached to the hinge region of the antibody fragment, and the conjugate contains no more than about 10 polymer molecules, or no more than about 5 polymer molecules, or no more than about 4 polymer molecules, or no more than about 3 polymer molecules, or no more than about 2 polymer molecules, or no more than 1 polymer molecule.

In another embodiment, the conjugate contains an antibody fragment selected from the group consisting of Fab, Fab', and Fab'-SH, every polymer molecule in the conjugate is at or about 20,000 D to at or about 70,000 D in molecular weight, or is at or about 30,000 D to at or about 70,000 D in molecular weight, or is at or about 40,000 D to at or about 70,000 D in molecular weight, every polymer molecule in the conjugate is attached to the hinge region of the antibody fragment, and the conjugate contains no more than about 10 polymer molecules, or no more than about 5 polymer molecules, or no more than about 4 polymer molecules, or no more than about 3 polymer molecules, or no more than about 2 polymer molecules, or no more than 1 polymer molecule.

In another embodiment, the conjugate contains an antibody fragment selected from the group consisting of Fab, Fab', and Fab'-SH, every polymer molecule in the conjugate is at or about 20,000 D to at or about 50,000 D in molecular weight, or is at or about 30,000 D to at or about 50,000 D in molecular weight, or is at or about 40,000 D to at or about 50,000 D in molecular weight, every polymer molecule in the conjugate is attached to the hinge region of the antibody fragment, and the conjugate contains no more than about 10 polymer molecules, or no more than about 5 polymer molecules, or no more than about 4 polymer molecules, or no more than about 3 polymer molecules, or no more than about 2 polymer molecules, or no more than 1 polymer molecule.

In another embodiment, the conjugate contains an antibody fragment selected from the group consisting of Fab, Fab', and Fab'-SH, every polymer molecule in the conjugate is at or about 20,000 D to at or about 40,000 D in molecular weight, or is at or about 30,000 D to at or about 40,000 D in molecular weight, every polymer molecule in the conjugate is attached to the hinge region of the antibody fragment, and the conjugate contains no more than about 10 polymer molecules, or no more than about 5 polymer molecules, or no more than about 4 polymer molecules, or no more than about 3 polymer molecules, or no more than about 2 polymer molecules, or no more than 1 polymer molecule.

In a further embodiment, the conjugate contains a F(ab')$_2$ antibody fragment attached to no more than about 2 polymer molecules, wherein every polymer molecule in the conjugate is at least about 20,000 D in molecular weight, or at least about 30,000 D in molecular weight, or at least about 40,000 D in molecular weight, and wherein every polymer molecule in the conjugate is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another embodiment, the conjugate contains a F(ab')$_2$ antibody fragment attached to no more than about 2 polymer molecules, wherein every polymer molecule in the conjugate is at or about 20,000 D to at or about 300,000 D in molecular weight, or is at or about 30,000 D to at or about 300,000 D in molecular weight, or is at or about 40,000 D to at or about 300,000 D in molecular weight, and wherein every polymer molecule in the conjugate is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another embodiment, the conjugate contains a F(ab')$_2$ antibody fragment attached to no more than about 2 polymer molecules, wherein every polymer molecule in the conjugate is at or about 20,000 D to at or about 100,000 D in molecular weight, or is at or about 30,000 D to at or about 100,000 D in molecular weight, or is at or about 40,000 D to at or about 100,000 D in molecular weight, and wherein every polymer molecule in the conjugate is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another embodiment, the conjugate contains a F(ab')$_2$ antibody fragment attached to no more than about 2 polymer molecules, wherein every polymer molecule in the conjugate is at or about 20,000 D to at or about 70,000 D in molecular weight, or is at or about 30,000 D to at or about 70,000 D in molecular weight, or is at or about 40,000 D to at or about 70,000 D in molecular weight, and wherein every polymer molecule in the conjugate is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another embodiment, the conjugate contains a F(ab')$_2$ antibody fragment attached to no more than about 2 polymer molecules, wherein every polymer molecule in the conjugate is at or about 20,000 D to at or about 50,000 D in molecular weight, or is at or about 30,000 D to at or about 50,000 D in molecular weight, or is at or about 40,000 D to at or about 50,000 D in molecular weight, and wherein every polymer molecule in the conjugate is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another embodiment, the conjugate contains a F(ab')$_2$ antibody fragment attached to no more than about 2 polymer molecules, wherein every polymer molecule in the conjugate is at or about 20,000 D to at or about 40,000 D in molecular weight, or is at or about 30,000 D to at or about 40,000 D in molecular weight, and wherein every polymer molecule in the conjugate is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In yet another embodiment, the conjugate contains an antibody fragment selected from the group consisting of Fab, Fab', and Fab'-SH, wherein the antibody fragment is attached to no more than 1 polymer molecule, wherein the polymer molecule is at least about 20,000 D in molecular weight, or at least about 30,000 D in molecular weight, or at least about 40,000 D in molecular weight, wherein the polymer molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another embodiment, the conjugate contains an antibody fragment selected from the group consisting of Fab, Fab', and Fab'-SH, wherein the antibody fragment is attached to no more than 1 polymer molecule, wherein the polymer molecule is at or about 20,000 D to at or about 300,000 D in molecular weight, or is at or about 30,000 D to at or about 300,000 D in molecular weight, or is at or about 40,000 D to at or about 300,000 D in molecular weight, wherein the polymer molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another embodiment, the conjugate contains an antibody fragment selected from the group consisting of Fab, Fab', and Fab'-SH, wherein the antibody fragment is attached to no more than 1 polymer molecule, wherein the polymer molecule is at or about 20,000 D to at or about 100,000 D in molecular weight, or is at or about 30,000 D to at or about 100,000 D in molecular weight, or is at or about 40,000 D to at or about 100,000 D in molecular weight, wherein the polymer molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another embodiment, the conjugate contains an antibody fragment selected from the group consisting of Fab, Fab', and Fab'-SH, wherein the antibody fragment is attached to no more than 1 polymer molecule, wherein the polymer molecule is at or about 20,000 D to at or about 70,000 D in molecular weight, or is at or about 30,000 D to at or about 70,000 D in molecular weight, or is at or about 40,000 D to at or about 70,000 D in molecular weight, wherein the polymer molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another embodiment, the conjugate contains an antibody fragment selected from the group consisting of Fab, Fab', and Fab'-SH, wherein the antibody fragment is attached to no more than 1 polymer molecule, wherein the polymer molecule is at or about 20,000 D to at or about 50,000 D in molecular weight, or is at or about 30,000 D to at or about 50,000 D in molecular weight, or is at or about 40,000 D to at or about 50,000 D in molecular weight, wherein the polymer molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another embodiment, the conjugate contains an antibody fragment selected from the group consisting of Fab, Fab', and Fab'-SH, wherein the antibody fragment is attached to no more than 1 polymer molecule, wherein the polymer molecule is at or about 20,000 D to at or about 40,000 D in molecular weight, or is at or about 30,000 D to at or about 40,000 D in molecular weight, wherein the polymer molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In still another embodiment, the conjugate contains an antibody fragment selected from the group consisting of Fab, Fab', and Fab'-SH, wherein the antibody fragment is attached to no more than 1 polymer molecule, wherein the polymer molecule is at least about 20,000 D in molecular weight, or at least about 30,000 D in molecular weight, or at least about 40,000 D in molecular weight, and wherein the polymer molecule is attached to the hinge region of the antibody fragment.

In another embodiment, the conjugate contains an antibody fragment selected from the group consisting of Fab, Fab', and Fab'-SH, wherein the antibody fragment is attached to no more than 1 polymer molecule, wherein the polymer molecule is at or about 20,000 D to at or about 300,000 D in molecular weight, or is at or about 30,000 D to at or about 300,000 D in molecular weight, or is at or about 40,000 D to at or about 300,000 D in molecular weight, and wherein the polymer molecule is attached to the hinge region of the antibody fragment.

In another embodiment, the conjugate contains an antibody fragment selected from the group consisting of Fab, Fab', and Fab'-SH, wherein the antibody fragment is attached to no more than 1 polymer molecule, wherein the polymer molecule is at or about 20,000 D to at or about 100,000 D in molecular weight, or is at or about 30,000 D to at or about 100,000 D in molecular weight, or is at or about 40,000 D to at or about 100,000 D in molecular weight, and wherein the polymer molecule is attached to the hinge region of the antibody fragment.

In another embodiment, the conjugate contains an antibody fragment selected from the group consisting of Fab, Fab', and Fab'-SH, wherein the antibody fragment is attached to no more than 1 polymer molecule, wherein the polymer molecule is at or about 20,000 D to at or about 70,000 D in molecular weight, or is at or about 30,000 D to at or about 70,000 D in molecular weight, or is at or about 40,000 D to at or about 70,000 D in molecular weight, and wherein the polymer molecule is attached to the hinge region of the antibody fragment.

In another embodiment, the conjugate contains an antibody fragment selected from the group consisting of Fab, Fab', and Fab'-SH, wherein the antibody fragment is attached to no more than 1 polymer molecule, wherein the polymer molecule is at or about 20,000 D to at or about 50,000 D in molecular weight, or is at or about 30,000 D to at or about 50,000 D in molecular weight, or is at or about 40,000 D to at or about 50,000 D in molecular weight, and wherein the polymer molecule is attached to the hinge region of the antibody fragment.

In another embodiment, the conjugate contains an antibody fragment selected from the group consisting of Fab, Fab', and Fab'-SH, wherein the antibody fragment is attached to no more than 1 polymer molecule, wherein the polymer molecule is at or about 20,000 D to at or about 40,000 D in molecular weight, or is at or about 30,000 D to at or about 40,000 D in molecular weight, and wherein the polymer molecule is attached to the hinge region of the antibody fragment.

Although any type of polymer is contemplated for use in constructing the conjugates of the invention, including the polymers and chemical linkage systems described in Section (II)(1)(b) below, polyethylene glycol (PEG) polymers are preferred for use herein.

In one embodiment, the conjugate is an antibody fragment covalently attached to at least one PEG having an actual MW of at least about 20,000 D.

In another embodiment, the conjugate is an antibody fragment covalently attached to at least one PEG having an actual MW of at least about 30,000 D.

In yet another embodiment, the conjugate is an antibody fragment covalently attached to at least one PEG having an actual MW of at least about 40,000 D.

In another embodiment, the conjugate is an antibody fragment covalently attached to at least one PEG having an actual MW that is at or about 20,000 D to at or about 300,000 D, or is at or about 30,000 D to at or about 300,000 D, or is at or about 40,000 D to at or about 300,000 D.

In another embodiment, the conjugate is an antibody fragment covalently attached to at least one PEG having an actual MW that is at or about 20,000 D to at or about 100,000 D, or is at or about 30,000 D to at or about 100,000 D, or is at or about 40,000 D to at or about 100,000 D.

In another embodiment, the conjugate is an antibody fragment covalently attached to at least one PEG having an actual MW that is at or about 20,000 D to at or about 70,000 D, or is at or about 30,000 D to at or about 70,000 D, or is at or about 40,000 D to at or about 70,000 D.

In another embodiment, the conjugate is an antibody fragment covalently attached to at least one PEG having an actual MW that is at or about 20,000 D to at or about 50,000 D, or is at or about 30,000 D to at or about 50,000 D, or is at or about 40,000 D to at or about 50,000 D.

In another embodiment, the conjugate is an antibody fragment covalently attached to at least one PEG having an actual MW that is at or about 20,000 D to at or about 40,000 D, or is at or about 30,000 D to at or about 40,000 D.

In another aspect, the invention encompasses a conjugate with a PEG to antibody fragment molar ratio of no more than about 10:1, or no more than about 5:1, or no more than about 4:1, or no more than about 3:1, or no more than about 2:1, or no more than 1:1.

In yet another aspect, the invention encompasses a conjugate wherein the antibody fragment is attached to about 10 or fewer PEG molecules, each PEG molecule having a molecular weight of at least about 20,000 D, or at least about 30,000 D, or at least about 40,000 D. In another embodiment, the conjugate contains an antibody fragment attached to about 5 or fewer PEG molecules, each PEG molecule having a molecular weight of at least about 20,000 D, or at least about 30,000 D, or at least about 40,000 D. In still another embodiment, the conjugate contains an antibody fragment attached to about 4 or fewer PEG molecules, each PEG molecule having a molecular weight of at least about 20,000 D, or at least about 30,000 D, or at least about 40,000 D. In a further embodiment, the conjugate contains an antibody fragment attached to about 3 or fewer PEG molecules, each PEG molecule having a molecular weight of at least about 20,000 D, or at least about 30,000 D, or at least about 40,000 D. In an additional embodiment, the conjugate contains an antibody fragment attached to about 2 or fewer PEG molecules, each PEG molecule having a molecular weight of at least about 20,000 D, or at least about 30,000 D, or at least about 40,000 D. Also provided herein is a conjugate containing an antibody fragment attached to a single PEG molecule having a molecular weight of at least about 20,000 D, or at least about 30,000 D, or at least about 40,000 D.

In another aspect, the invention encompasses a conjugate wherein the antibody fragment is derivatized with PEG, wherein every PEG molecule in the conjugate is at or about 20,000 D to at or about 300,000 D in molecular weight, or is at or about 30,000 D to at or about 300,000 D in molecular weight, or is at or about 40,000 D to at or about 300,000 D in molecular weight, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In another aspect, the invention encompasses a conjugate wherein the antibody fragment is derivatized with PEG, wherein every PEG molecule in the conjugate is at or about 20,000 D to at or about 100,000 D in molecular weight, or is at or about 30,000 D to at or about 100,000 D in molecular weight, or is at or about 40,000 D to at or about 100,000 D in molecular weight, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In another aspect, the invention encompasses a conjugate wherein the antibody fragment is derivatized with PEG, wherein every PEG molecule in the conjugate is at or about 20,000 D to at or about 70,000 D in molecular weight, or is at or about 30,000 D to at or about 70,000 D in molecular weight, or is at or about 40,000 D to at or about 70,000 D in molecular weight, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In another aspect, the invention encompasses a conjugate wherein the antibody fragment is derivatized with PEG, wherein every PEG molecule in the conjugate is at or about 20,000 D to at or about 50,000 D in molecular weight, or is at or about 30,000 D to at or about 50,000 D in molecular weight, or is at or about 40,000 D to at or about 50,000 D in molecular weight, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In another aspect, the invention encompasses a conjugate wherein the antibody fragment is derivatized with PEG, wherein every PEG molecule in the conjugate is at or about 20,000 D to at or about 40,000 D in molecular weight, or is at or about 30,000 D to at or about 40,000 D in molecular weight, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In still another aspect, the invention encompasses a conjugate containing an antibody fragment selected from the group consisting of Fab, Fab', Fab'-SH and F(ab')$_2$, wherein the antibody fragment is attached to about 10 or fewer PEG molecules, each PEG molecule having a molecular weight of at least about 20,000 D, or at least about 30,000 D, or at least about 40,000 D. In another embodiment, the foregoing conjugate contains an antibody fragment attached to about 5 or fewer PEG molecules, each PEG molecule having a molecular weight of at least about 20,000 D, or at least about 30,000 D, or at least about 40,000 D. In still another embodiment, the foregoing conjugate contains an antibody fragment attached to about 4 or fewer PEG molecules, each PEG molecule having a molecular weight of at least about 20,000 D, or at least about 30,000 D, or at least about 40,000 D. In a further embodiment, the foregoing conjugate contains an antibody fragment attached to about 3 or fewer PEG molecules, each PEG molecule having a molecular weight of at least about 20,000 D, or at least about 30,000 D, or at least about 40,000 D. In an additional embodiment, the foregoing conjugate contains an antibody fragment attached to about 2 or fewer PEG molecules, each PEG molecule having a molecular weight of at least about 20,000 D, or at least about 30,000 D, or at least about 40,000 D. Also provided herein is the foregoing conjugate that contains an antibody fragment attached to a single PEG molecule having a molecular weight of at least about 20,000 D, or at least about 30,000 D, or at least about 40,000 D.

In another aspect, the invention encompasses a conjugate containing an antibody fragment selected from the group consisting of Fab, Fab', Fab'-SH and F(ab')$_2$, wherein the antibody fragment is derivatized with PEG, wherein every PEG molecule in the conjugate is at or about 20,000 D to at or about 300,000 D in molecular weight, or is at or about 30,000 D to at or about 300,000 D in molecular weight, or is at or about 40,000 D to at or about 300,000 D in molecular weight, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In another aspect, the invention encompasses a conjugate containing an antibody fragment selected from the group consisting of Fab, Fab', Fab'-SH and F(ab')$_2$, wherein the antibody fragment is derivatized with PEG, wherein every PEG molecule in the conjugate is at or about 20,000 D to at or about 100,000 D in molecular weight, or is at or about 30,000 D to at or about 100,000 D in molecular weight, or is at or about 40,000 D to at or about 100,000 D in molecular weight, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In another aspect, the invention encompasses a conjugate containing an antibody fragment selected from the group consisting of Fab, Fab', Fab'-SH and F(ab')$_2$, wherein the antibody fragment is derivatized with PEG, wherein every PEG molecule in the conjugate is at or about 20,000 D to at or about 70,000 D in molecular weight, or is at or about 30,000 D to at or about 70,000 D in molecular weight, or is at or about 40,000 D to at or about 70,000 D in molecular weight, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In another aspect, the invention encompasses a conjugate containing an antibody fragment selected from the group consisting of Fab, Fab', Fab'-SH and F(ab')$_2$, wherein the antibody fragment is derivatized with PEG, wherein every PEG molecule in the conjugate is at or about 20,000 D to at or about 50,000 D in molecular weight, or is at or about 30,000 D to at or about 50,000 D in molecular weight, or is at or about 40,000 D to at or about 50,000 D in molecular weight, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In another aspect, the invention encompasses a conjugate containing an antibody fragment selected from the group consisting of Fab, Fab', Fab'-SH and F(ab')$_2$, wherein the antibody fragment is derivatized with PEG, wherein every PEG molecule in the conjugate is at or about 20,000 D to at or about 40,000 D in molecular weight, or is at or about 30,000 D to at or about 40,000 D in molecular weight, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In a preferred embodiment, the conjugate contains an antibody fragment selected from the group consisting of Fab, Fab', and Fab'-SH, wherein the antibody fragment is derivatized with PEG having a molecular weight of at least about 20,000 D, or at least about 30,000 D, or at least about 40,000 D, and wherein every PEG molecule in the conjugate is attached to the hinge region of the antibody fragment.

In another preferred embodiment, the conjugate contains an antibody fragment selected from the group consisting of Fab, Fab', and Fab'-SH, wherein the antibody fragment is derivatized with PEG having a molecular weight that is at or about 20,000 D to about 300,000 D, or is at or about 30,000 D to at or about 300,000 D, or is at or about 40,000 D to at or about 300,000 D, and wherein every PEG molecule in the conjugate is attached to the hinge region of the antibody fragment.

In another preferred embodiment, the conjugate contains an antibody fragment selected from the group consisting of Fab, Fab', and Fab'-SH, wherein the antibody fragment is derivatized with PEG having a molecular weight that is at or about 20,000 D to about 100,000 D, or is at or about 30,000 D to at or about 100,000 D, or is at or about 40,000 D to at or about 100,000 D, and wherein every PEG molecule in the conjugate is attached to the hinge region of the antibody fragment.

In another preferred embodiment, the conjugate contains an antibody fragment selected from the group consisting of Fab, Fab', and Fab'-SH, wherein the antibody fragment is derivatized with PEG having a molecular weight that is at or about 20,000 D to about 70,000 D, or is at or about 30,000 D to at or about 70,000 D, or is at or about 40,000 D to at or about 70,000 D, and wherein every PEG molecule in the conjugate is attached to the hinge region of the antibody fragment.

In another preferred embodiment, the conjugate contains an antibody fragment selected from the group consisting of Fab, Fab', and Fab'-SH, wherein the antibody fragment is derivatized with PEG having a molecular weight that is at or about 20,000 D to about 50,000 D, or is at or about 30,000 D to at or about 50,000 D, or is at or about 40,000 D to at or about 50,000 D, and wherein every PEG molecule in the conjugate is attached to the hinge region of the antibody fragment.

In another preferred embodiment, the conjugate contains an antibody fragment selected from the group consisting of Fab, Fab', and Fab'-SH, wherein the antibody fragment is derivatized with PEG having a molecular weight that is at or about 20,000 D to about 40,000 D, or is at or about 30,000 D to at or about 40,000 D, and wherein every PEG molecule in the conjugate is attached to the hinge region of the antibody fragment.

In another preferred embodiment, the conjugate contains an antibody fragment selected from the group consisting of Fab, Fab', and Fab'-SH, wherein the antibody fragment is derivatized with PEG, wherein every PEG molecule in the conjugate is at least about 20,000 D in molecular weight, or at least about 30,000 D in molecular weight, or at least about 40,000 D in molecular weight, wherein every PEG molecule in the conjugate molecule is attached to the hinge region of the antibody fragment, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In another preferred embodiment, the conjugate contains an antibody fragment selected from the group consisting of Fab, Fab', and Fab'-SH, wherein the antibody fragment is derivatized with PEG, wherein every PEG molecule in the conjugate is at or about 20,000 D to at or about 300,000 D in molecular weight, or is at or about 30,000 D to at or about 300,000 D in molecular weight, or is at or about 40,000 D to at or about 300,000 D in molecular weight, wherein every PEG molecule in the conjugate molecule is attached to the hinge region of the antibody fragment, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In another preferred embodiment, the conjugate contains an antibody fragment selected from the group consisting of Fab, Fab', and Fab'-SH, wherein the antibody fragment is derivatized with PEG, wherein every PEG molecule in the conjugate is at or about 20,000 D to at or about 100,000 D in molecular weight, or is at or about 30,000 D to at or about 100,000 D in molecular weight, or is at or about 40,000 D to at or about 100,000 D in molecular weight, wherein every PEG molecule in the conjugate molecule is attached to the hinge region of the antibody fragment, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In another preferred embodiment, the conjugate contains an antibody fragment selected from the group consisting of Fab, Fab', and Fab'-SH, wherein the antibody fragment is derivatized with PEG, wherein every PEG molecule in the conjugate is at or about 20,000 D to at or about 70,000 D in molecular weight, or is at or about 30,000 D to at or about 70,000 D in molecular weight, or is at or about 40,000 D to at or about 70,000 D in molecular weight, wherein every PEG molecule in the conjugate molecule is attached to the hinge region of the antibody fragment, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In another preferred embodiment, the conjugate contains an antibody fragment selected from the group consisting of Fab, Fab', and Fab'-SH, wherein the antibody fragment is derivatized with PEG, wherein every PEG molecule in the conjugate is at or about 20,000 D to at or about 50,000 D in molecular weight, or is at or about 30,000 D to at or about 50,000 D in molecular weight, or is at or about 40,000 D to at or about 50,000 D in molecular weight, wherein every PEG molecule in the conjugate molecule is attached to the hinge region of the antibody fragment, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In another preferred embodiment, the conjugate contains an antibody fragment selected from the group consisting of Fab, Fab', and Fab'-SH, wherein the antibody fragment is derivatized with PEG, wherein every PEG molecule in the conjugate is at or about 20,000 D to at or about 40,000 D in molecular weight, or is at or about 30,000 D to at or about 40,000 D in molecular weight, wherein every PEG molecule in the conjugate molecule is attached to the hinge region of the antibody fragment, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In yet another preferred embodiment, the conjugate contains a F(ab')$_2$ antibody fragment derivatized with PEG, wherein every PEG molecule in the conjugate is at least about 20,000 D in molecular weight, or at least about 30,000 D in molecular weight, or at least about 40,000 D in molecular weight, wherein the antibody fragment is attached to no more than about 2 PEG molecules, and wherein every PEG molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another preferred embodiment, the conjugate contains a F(ab')$_2$ antibody fragment derivatized with PEG, wherein every PEG molecule in the conjugate is at or about 20,000 D to at or about 300,000 D in molecular weight, or is at or about 30,000 D to at or about 300,000 D in molecular weight, or is at or about 40,000 D to at or about 300,000 D in molecular weight, wherein the antibody fragment is attached to no more than about 2 PEG molecules, and wherein every PEG molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another preferred embodiment, the conjugate contains a F(ab')$_2$ antibody fragment derivatized with PEG, wherein every PEG molecule in the conjugate is at or about 20,000 D to at or about 100,000 D in molecular weight, or is at or about 30,000 D to at or about 100,000 D in molecular weight, or is at or about 40,000 D to at or about 100,000 D in molecular weight, wherein the antibody fragment is attached to no more than about 2 PEG molecules, and wherein every PEG molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another preferred embodiment, the conjugate contains a F(ab')$_2$ antibody fragment derivatized with PEG, wherein every PEG molecule in the conjugate is at or about 20,000 D to at or about 70,000 D in molecular weight, or is at or about 30,000 D to at or about 70,000 D in molecular weight, or is at or about 40,000 D to at or about 70,000 D in molecular weight, wherein the antibody fragment is attached to no more than about 2 PEG molecules, and wherein every PEG molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another preferred embodiment, the conjugate contains a F(ab')$_2$ antibody fragment derivatized with PEG, wherein every PEG molecule in the conjugate is at or about 20,000 D to at or about 50,000 D in molecular weight, or is at or about 30,000 D to at or about 50,000 D in molecular weight, or is at or about 40,000 D to at or about 50,000 D in molecular weight, wherein the antibody fragment is attached to no more than about 2 PEG molecules, and wherein every PEG molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another preferred embodiment, the conjugate contains a F(ab')$_2$ antibody fragment derivatized with PEG, wherein every PEG molecule in the conjugate is at or about 20,000 D to at or about 40,000 D in molecular weight, or is at or about 30,000 D to at or about 40,000 D in molecular weight, wherein the antibody fragment is attached to no more than about 2 PEG molecules, and wherein every PEG molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In still another preferred embodiment, the conjugate contains an antibody fragment selected from the group consisting of Fab, Fab', and Fab'-SH, wherein the antibody fragment is derivatized with PEG, wherein every PEG molecule in the conjugate is at least about 20,000 D in molecular weight, or at least about 30,000 in molecular weight, or at least about 40,000 D in molecular weight, wherein the antibody fragment is attached to no more than 1 PEG molecule, and wherein the PEG molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another preferred embodiment, the conjugate contains an antibody fragment selected from the group consisting of Fab, Fab', and Fab'-SH, wherein the antibody fragment is derivatized with PEG, wherein every PEG molecule in the conjugate is at or about 20,000 D to at or about 300,000 D in molecular weight, or is at or about 30,000 D to at or about 300,000 D in molecular weight, or is at or about 40,000 D to at or about 300,000 D in molecular weight, wherein the antibody fragment is attached to no more than 1 PEG molecule, and wherein the PEG molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another preferred embodiment, the conjugate contains an antibody fragment selected from the group consisting of Fab, Fab', and Fab'-SH, wherein the antibody fragment is derivatized with PEG, wherein every PEG molecule in the conjugate is at or about 20,000 D to at or about 100,000 D in molecular weight, or is at or about 30,000 D to at or about 100,000 D in molecular weight, or is at or about 40,000 D to at or about 100,000 D in molecular weight, wherein the antibody fragment is attached to no more than 1 PEG molecule, and wherein the PEG molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another preferred embodiment, the conjugate contains an antibody fragment selected from the group consisting of Fab, Fab', and Fab'-SH, wherein the antibody fragment is derivatized with PEG, wherein every PEG molecule in the conjugate is at or about 20,000 D to at or about 70,000 D in molecular weight, or is at or about 30,000 D to at or about 70,000 D in molecular weight, or is at or about 40,000 D to at or about 70,000 D in molecular weight, wherein the antibody fragment is attached to no more than 1 PEG molecule, and wherein the PEG molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another preferred embodiment, the conjugate contains an antibody fragment selected from the group consisting of Fab, Fab', and Fab'-SH, wherein the antibody fragment is derivatized with PEG, wherein every PEG molecule in the conjugate is at or about 20,000 D to at or about 50,000 D in molecular weight, or is at or about 30,000 D to at or about 50,000 D in molecular weight, or is at or about 40,000 D to at or about 50,000 D in molecular weight, wherein the antibody fragment is attached to no more than 1 PEG molecule, and wherein the PEG molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another preferred embodiment, the conjugate contains an antibody fragment selected from the group consisting of Fab, Fab', and Fab'-SH, wherein the antibody fragment is derivatized with PEG, wherein every PEG molecule in the conjugate is at or about 20,000 D to at or about 40,000 D in molecular weight, or is at or about 30,000 D to at or about 40,000 D in molecular weight, wherein the antibody fragment is attached to no more than 1 PEG molecule, and wherein the PEG molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

It will be appreciated that all of the above-described embodiments of the invention utilizing PEG polymers include conjugates wherein the PEG polymer(s) is (are) linear or branched. In a preferred embodiment, the conjugate contains an antibody fragment selected from the group consisting of Fab, Fab', and Fab'-SH, wherein the antibody fragment is attached to no more than 1 PEG molecule, and wherein the PEG molecule is branched and at least about 40,000 D in molecular weight. In a particularly surprising and unexpected finding, the inventors discovered that the foregoing conjugate exhibits a serum half-life, MRT and serum clearance rate approaching that of full length antibody as shown in Example X below.

In another preferred embodiment, the conjugate contains an antibody fragment selected from the group consisting of Fab, Fab', and Fab'-SH, wherein the antibody fragment is attached to no more than 1 PEG molecule, and wherein the PEG molecule is branched and has a molecular weight that is at or about 40,000 D to at or about 300,000 D.

In another preferred embodiment, the conjugate contains an antibody fragment selected from the group consisting of Fab, Fab', and Fab'-SH, wherein the antibody fragment is attached to no more than 1 PEG molecule, and wherein the PEG molecule is branched and has a molecular weight that is at or about 40,000 D to at or about 100,000 D.

In another preferred embodiment, the conjugate contains an antibody fragment selected from the group consisting of Fab, Fab', and Fab'-SH, wherein the antibody fragment is attached to no more than 1 PEG molecule, and wherein the PEG molecule is branched and has a molecular weight that is at or about 40,000 D to at or about 70,000 D.

In another preferred embodiment, the conjugate contains an antibody fragment selected from the group consisting of Fab, Fab', and Fab'-SH, wherein the antibody fragment is attached to no more than 1 PEG molecule, and wherein the PEG molecule is branched and has a molecular weight that is at or about 40,000 D to at or about 50,000 D.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is branched and at least 40,000 D in molecular weight, and the PEG molecule is attached to the hinge region of the antibody fragment.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is branched and has a molecular weight that is at or about 40,000 D to at or about 300,000 D, and the PEG molecule is attached to the hinge region of the antibody fragment.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is branched and has a molecular weight that is at or about 40,000 D to at or about 100,000 D, and the PEG molecule is attached to the hinge region of the antibody fragment.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is branched and has a molecular weight that is at or about 40,000 D to at or about 70,000 D, and the PEG molecule is attached to the hinge region of the antibody fragment.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is branched and has a molecular weight that is at or about 40,000 D to at or about 50,000 D, and the PEG molecule is attached to the hinge region of the antibody fragment.

In one aspect, the invention provides any of the above-described conjugates wherein the conjugate contains no more than one antibody fragment. Additionally provided herein is any of the above-described conjugates wherein the conjugate contains one or more antibody fragment(s) covalently linked to one or more polymer molecule(s), such as conjugates containing two or more antibody fragments covalently linked together by polymer molecule(s). In one embodiment, a polymer molecule is used to link together two antibody fragments to form a dumbbell-shaped structure. Also encompassed herein are conjugates formed by more than two antibody fragments joined by polymer molecule(s) to form a rosette or other shapes. The antibody fragments in such structures can be of the same or different fragment type and can have the same antigen specificity or have different antigen specificities. Such structures can be made by using a polymer molecule derivatized with multiple functional groups permitting the direct attachment, or the attachment by means of bi- or multi-functional linkers, of two or more antibody fragments to the polymer backbone.

In another aspect, the invention encompasses any of the above-described conjugates utilizing an antibody fragment comprising an antigen recognition site that binds to rabbit IL-8 and/or human IL-8. In yet another aspect, the invention encompasses any of the above-described conjugates utilizing an antibody fragment comprising 6G4.2.5LV/L1N35A or 6G4.2.5LV/L1N35E as defined below. In still another aspect, the invention encompasses any of the above-described conjugates utilizing an antibody fragment comprising 6G4.5.2.5HV11 as defined below. In a further aspect, the invention encompasses any of the above-described conjugates utilizing an antibody fragment comprising hu6G4.2.5LV/L1N35A or hu6G4.2.5LV/L1N35E as defined below. In an additional aspect, the invention encompasses any of the above-described conjugates utilizing an antibody fragment comprising hu6G4.2.5HV. Further encompassed herein are any of the above-described conjugates utilizing an antibody fragment comprising 6G4.2.5LV/L1N35A or 6G4.2.5LV/L1N35E and further comprising the CDRs of 6G4.2.5HV as defined below. Also encompassed herein are any of the above described conjugates utilizing an antibody fragment comprising hu6G4.2.5LV/L1N35A or hu6G4.2.5LV/L1N35E and further comprising hu6G4.2.5HV as defined below. Additionally encompassed herein are any of the above-described conjugates utilizing an antibody fragment comprising 6G4.2.5LV11N35A or 6G4.2.5LV11N35E as defined below. Further provided herein are any of the above-described conjugates utilizing an antibody fragment comprising 6G4.2.5LV11N35A or 6G4.2.5LV11N35E and further comprising 6G4.2.5HV11 as defined below.

a. Production of Antibody Fragments

Antibody fragments can be produced by any method known in the art. Generally, an antibody fragment is derived from a parental intact antibody. The parental antibody can be generated by raising polyclonal sera against the desired antigen by multiple subcutaneous (sc) or intraperitoneal (ip) injections of antigen and an adjuvant, such as monophosphoryl lipid A (MPL)/trehalose dicrynomycolate (TDM) (Ribi Immunochem. Research, Inc., Hamilton, Mont.), at multiple sites. Two weeks later the animals are boosted. 7 to 14 days later animals are bled and the serum is assayed for anti-antigen titer. Animals are boosted until titer plateaus. Sera are harvested from animals, and polyclonal antibodies are isolated from sera by conventional immunoglobulin purification procedures, such as protein A-Sepharose chromatography, hydroxylapatite chromatography, gel filtration, dialysis, or antigen affinity chromatography. The desired antibody fragments can be generated from purified polyclonal antibody preparations by conventional enzymatic methods, e.g. F(ab')$_2$ fragments are produced by pepsin cleavage of intact antibody, and Fab fragments are produced by briefly digesting intact antibody with papain.

Alternatively, antibody fragments are derived from monoclonal antibodies generated against the desired antigen.

Monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp.59–103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOP-21 and M.C.-11 mouse tumors available from the Salk Institute Cell Distribution Center, San Diego, Calif. USA, and SP-2 or X63-Ag8-653 cells available from the American Type Culture Collection, Rockville, Maryland USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51–63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp.59–103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Review articles on recombinant expression in bacteria of antibody-encoding DNA include Skerra et al., *Curr. Opinion in Immunol.*, 5: 256 (1993) and Pluckthun, *Immunol. Revs.*, 130: 151 (1992).

In a preferred embodiment, the antibody fragment is derived from a humanized antibody. Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. It will be appreciated that variable domain sequences obtained from any non-human animal phage display library-derived Fv clone or from any non-human animal hybridoma-derived antibody clone provided as described herein can serve as the "import" variable domain used in the construction of the humanized antibodies of the invention. Humanization can be essentially performed following the method of Winter and co-workers (Jones et al., *Nature*, 321: 522 (1986); Riechmann et al., *Nature*, 332: 323 (1988); Verhoeyen et al., *Science*, 239: 1534 (1988)), by substituting non-human animal, e.g. rodent, CDRs or CDR sequences for the corresponding sequences of a human antibody. Accordingly, such "humanized" antibodies are chimeric antibodies (Cabilly et al., supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in non-human animal, e.g. rodent, antibodies.

The choice of human variable domains, both light and heavy, to be used in making the humanized antibodies is very important to reduce antigenicity. According to the so-called "best-fit" method, the sequence of the variable domain of a non-human animal, e.g. rodent, antibody is screened against the entire library of known human variable-domain sequences. The human sequence which is closest to that of the non-human animal is then accepted as the human framework (FR) for the humanized antibody (Sims et al., *J. Immunol.*, 151: 2296 (1993); Chothia and Lesk, *J. Mol. Biol.*, 196: 901 (1987)). Another method uses a particular framework derived from the consensus sequence of all human antibodies of a particular subgroup light or heavy chains. The same framework can be used for several different humanized antibodies (Carter et al., *Proc. Natl. Acad. Sci USA*, 89: 4285 (1992); Presta et al., *J. Immunol.*, 151: 2623 (1993)). It is also important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind to its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding.

In addition, antibody fragments for use herein can be derived from human monoclonal antibodies. Human monoclonal antibodies against the antigen of interest can be made by the hybridoma method. Human myeloma and mouse-human heteromyeloma cell lines for the production of human monoclonal antibodies have been described, for example, by Kozbor *J. Immunol.*, 133: 3001 (1984); Brodeur et al., *Monoclonal Antibody Production Techniques and Applications*, pp. 51–63 (Marcel Dekker, Inc., New York, 1987); and Boemer et al., *J. Immunol.*, 147: 86 (1991).

It is now possible to produce transgenic animals (e.g. mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci USA*, 90: 2551 (1993); Jakobovits et al., *Nature*, 362: 255 (1993); Bruggermann et al., *Year in Immunol.*, 7: 33 (1993).

Alternatively, phage display technology (McCafferty et al., *Nature* 348:552 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M 13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g., Johnson et al., *Current Opinion in Structural Biology* 3:564 (1993). Several sources of V-gene segments can be used for phage display. Clackson et al., *Nature* 352:624 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581 (1991), or Griffith et al., *EMBO J.* 12:725 (1993). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling" (Marks et al., *Bio/Technol.* 10:779 (1992)). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the nM range. A strategy for making very large phage antibody repertoires has been described by Waterhouse et al., *Nucl. Acids Res.* 21:2265 (1993).

Gene shuffling can also be used to derive human antibodies from non-human, e.g. rodent, antibodies, where the human antibody has similar affinities and specificities to the starting non-human antibody. According to this method, which is also called "epitope imprinting", either the heavy or light chain variable region of a non-human antibody fragment obtained by phage display techniques as described above is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e. the epitope governs (imprints) the choice of the human chain partner. When the process is repeated in order to replace the remaining non-human chain, a human antibody is obtained (see PCT WO 93/06213 published Apr. 1, 1993). Unlike traditional humanization of non-human antibodies by CDR grafting, this technique provides completely human antibodies, which have no FR or CDR residues of non-human origin.

The invention also encompasses the use of bispecific and heteroconjugate antibody fragments having specificities for at least two different antigens. Bispecific and heteroconjugate antibodies can be prepared as full length antibodies or as antibody fragments (e.g. $F(ab')_2$ bispecific antibody fragments). Antibody fragments having more than two valencies (e.g. trivalent or higher valency antibody fragments) are also contemplated for use herein. Bispecific antibodies, heteroconjugate antibodies, and multi-valent antibodies can be prepared as described in Section (II)(3)(C) below.

As described above, DNA encoding the monoclonal antibody or antibody fragment of interest can be isolated from its hybridoma or phage display clone of origin, and then manipulated to create humanized and/or affinity matured constructs. In addition, known techniques can be employed to introduce an amino acid residue or residues into any desired location on the polypeptide backbone of the antibody fragment, e.g. a cysteine residue placed in the hinge region of the heavy chain, thereby providing a site for specific attachment of polymer molecule(s). In one embodiment, the native cysteine residue in either the light or heavy chain of the antibody fragment that would ordinarily form the disulfide bridge linking the light and heavy chains is substituted with another amino acid, such as serine, in order to leave the partner cysteine residue in the opposite chain with a free suflhydryl for specific attachment of polymer molecule.

Upon construction of the desired antibody or antibody fragment-encoding clone, the clone can be used for recombinant production of the antibody fragment as described in Section (II)(4) below. Finally, the antibody or antibody fragment product can be recovered from host cell culture and purified as described in Section (II)(4)(F) below. In the case of embodiments utilizing an antibody fragment engineered to lack a cysteine residue that ordinarily forms the disulfide bridge between the light and heavy chains as described above, preferred recombinant production systems include bacterial expression and product recovery procedures utilizing the low pH osmotic shock method described in the "Alternative Fab'-SH Purification" section of Example T below. If a full length antibody is produced, the desired antibody fragment can be obtained therefrom by subjecting the intact antibody to enzymatic digestion according to known methods, e.g. as described in Section (II)(4)(G) below.

b. Construction of Antibody Fragment-Polymer Conjugates

The antibody fragment-polymer conjugates of the invention can be made by derivatizing the desired antibody fragment with an inert polymer. It will be appreciated that any inert polymer which provides the conjugate with the desired apparent size or which has the selected actual MW as taught herein is suitable for use in constructing the antibody fragment-polymer conjugates of the invention.

Many inert polymers are suitable for use in pharmaceuticals. See, e.g., Davis et al., *Biomedical Polymers: Polymeric Materials and Pharmaceuticals for Biomedical Use*, pp.441–451 (1980). In all embodiments of the invention, a non-proteinaceous polymer is used. The nonproteinaceous polymer ordinarily is a hydrophilic synthetic polymer, i.e., a polymer not otherwise found in nature. However, polymers which exist in nature and are produced by recombinant or in vitro methods are also useful, as are polymers which are isolated from native sources. Hydrophilic polyvinyl polymers fall within the scope of this invention, e.g. polyvinylalcohol and polyvinylpyrrolidone. Particularly useful are polyalkylene ethers such as polyethylene glycol (PEG); polyoxyalkylenes such as polyoxyethylene, polyoxypropylene, and block copolymers of polyoxyethylene and polyoxypropylene (Pluronics); polymethacrylates; carbomers; branched or unbranched polysaccharides which comprise the saccharide monomers D-mannose, D- and L-galactose, fucose, fructose, D-xylose, L-arabinose, D-glucuronic acid, sialic acid, D-galacturonic acid, D-mannuronic acid (e.g. polymannuronic acid, or alginic acid), D-glucosamine, D-galactosamine, D-glucose and neuraminic acid including homopolysaccharides and heteropolysaccharides such as lactose, amylopectin, starch, hydroxyethyl starch, amylose, dextrane sulfate, dextran, dextrins, glycogen, or the polysaccharide subunit of acid mucopolysaccharides, e.g. hyaluronic acid; polymers of sugar alcohols such as polysorbitol and polymannitol; heparin or heparon. The polymer prior to cross-linking need not be, but preferably is, water soluble, but the final conjugate must be water soluble. Preferably, the conjugate exhibits a water solubility of at least about 0.01 mg/ml, and more preferably at least about 0.1 mg/ml, and still more preferably at least about 1 mg/ml. In addition, the polymer should not be highly immunogenic in the conjugate form, nor should it possess viscosity that is incompatible with intravenous infusion or injection if the conjugate is intended to be administered by such routes.

In one embodiment, the polymer contains only a single group which is reactive. This helps to avoid cross-linking of protein molecules. However, it is within the scope herein to maximize reaction conditions to reduce cross-linking, or to purify the reaction products through gel filtration or ion exchange chromatography to recover substantially homogenous derivatives. In other embodiments, the polymer contains two or more reactive groups for the purpose of linking multiple antibody fragments to the polymer backbone. Again, gel filtration or ion exchange chromatography can be used to recover the desired derivative in substantially homogeneous form.

The molecular weight of the polymer can range up to about 500,000 D, and preferably is at least about 20,000 D, or at least about 30,000 D, or at least about 40,000 D. The molecular weight chosen can depend upon the effective size of the conjugate to be achieved, the nature (e.g. structure, such as linear or branched) of the polymer, and the degree of derivatization, i.e. the number of polymer molecules per antibody fragment, and the polymer attachment site or sites on the antibody fragment.

The polymer can be covalently linked to the antibody fragment through a multifunctional crosslinking agent which reacts with the polymer and one or more amino acid residues of the antibody fragment to be linked. However, it is also within the scope of the invention to directly crosslink the polymer by reacting a derivatized polymer with the antibody fragment, or vice versa.

The covalent crosslinking site on the antibody fragment includes the N-terminal amino group and epsilon amino groups found on lysine residues, as well as other amino, imino, carboxyl, sulfhydryl, hydroxyl or other hydrophilic groups. The polymer may be covalently bonded directly to the antibody fragment without the use of a multifunctional (ordinarily bifunctional) crosslinking agent. Covalent binding to amino groups is accomplished by known chemistries based upon cyanuric chloride, carbonyl diimidazole, aldehyde reactive groups (PEG alkoxide plus diethyl acetal of bromoacetaldehyde; PEG plus DMSO and acetic anhydride, or PEG chloride plus the phenoxide of 4-hydroxybenzaldehyde, activated succinimidyl esters, activated dithiocarbonate PEG, 2,4,5-trichlorophenylcloroformate or P-nitrophenylcloroformate activated PEG.) Carboxyl groups are derivatized by coupling PEG-amine using carbodiimide. Sulfhydryl groups are derivatized by coupling to maleimido-substituted PEG (e.g. alkoxy-PEG amine plus sulfosuccinimidyl 4-(N-maleimidomethyl)cyclohexane-1-carboxylate) as described in WO 97/10847 published Mar. 27, 1997, or PEG-maleimide commercially available from Shearwater Polymers, Inc., Huntsville, Ala.). Alternatively, free amino groups on the antibody fragment (e.g. epsilon amino groups on lysine residues) can be thiolated with 2-imino-thiolane (Traut's reagent) and then coupled to maleimide-containing derivatives of PEG as described in Pedley et al., *Br. J. Cancer*, 70: 1126–1130 (1994).

The polymer will bear a group which is directly reactive with an amino acid side chain, or the N- or C-terminus of the polypeptide linked, or which is reactive with the multifunctional cross-linking agent. In general, polymers bearing such reactive groups are known for the preparation of immobilized proteins. In order to use such chemistries here, one should employ a water soluble polymer otherwise derivatized in the same fashion as insoluble polymers heretofore employed for protein immobilization. Cyanogen bromide activation is a particularly useful procedure to employ in crosslinking polysaccharides.

"Water soluble" in reference to the starting polymer means that the polymer or its reactive intermediate used for conjugation is sufficiently water soluble to participate in a derivatization reaction.

The degree of substitution with such a polymer will vary depending upon the number of reactive sites on the antibody fragment, the molecular weight, hydrophilicity and other characteristics of the polymer, and the particular antibody fragment derivatization sites chosen. In general, the conjugate contains from 1 to about 10 polymer molecules, but greater numbers of polymer molecules attached to the antibody fragments of the invention are also contemplated. The desired amount of derivatization is easily achieved by using an experimental matrix in which the time, temperature and other reaction conditions are varied to change the degree of substitution, after which the level of polymer substitution of the conjugates is determined by size exclusion chromatography or other means known in the art.

The polymer, e.g. PEG, is cross-linked to the antibody fragment by a wide variety of methods known per se for the covalent modification of proteins with nonproteinaceous polymers such as PEG. Certain of these methods, however, are not preferred for the purposes herein. Cyanuronic chloride chemistry leads to many side reactions, including protein cross-linking. In addition, it may be particularly likely to lead to inactivation of proteins containing sulfhydryl groups. Carbonyl diimidazole chemistry (Beauchamp et al., *Anal Biochem.* 131, 25–33 [1983]) requires high pH (>8.5), which can inactivate proteins. Moreover, since the "activated PEG" intermediate can react with water, a very large molar excess of "activated PEG" over protein is required. The high concentrations of PEG required for the carbonyl diimidazole chemistry also led to problems in purification, as both gel filtration chromatography and hydrophilic interaction chromatography are adversely affected. In addition, the high concentrations of "activated PEG" may precipitate protein, a problem that per se has been noted previously (Davis, U.S. Pat. No. 4,179,337). On the other hand, aldehyde chemistry (Royer, U.S. Pat. No. 4,002,531) is more efficient since it requires only a 40-fold molar excess of PEG and a 1–2 hr incubation. However, the manganese dioxide suggested by Royer for preparation of the PEG aldehyde is problematic "because of the pronounced tendency of PEG to form complexes with metal-based oxidizing agents" (Harris et al., *J. Polym. Sci. Polym. Chem. Ed.* 22, 341–52 [1984]). The use of a Moffatt oxidation, utilizing DMSO and acetic anhydride, obviates this problem. In addition, the sodium borohydride suggested by Royer must be used at high pH and has a significant tendency to reduce disulfide bonds. In contrast, sodium cyanoborohydride, which is effective at neutral pH and has very little tendency to reduce disulfide bonds is preferred. In another preferred embodiment, maleimido-activated PEG is used for coupling to free thiols on the antibody fragment.

Functionalized PEG polymers to modify the antibody fragments of the invention are available from Shearwater Polymers, Inc. (Huntsville, AL). Such commercially available PEG derivatives include, but are not limited to, amino-PEG, PEG amino acid esters, PEG-hydrazide, PEG-thiol, PEG-succinate, carboxymethylated PEG, PEG-propionic acid, PEG amino acids, PEG succinimidyl succinate, PEG succinimidyl propionate, succinimidyl ester of carboxymethylated PEG, succinimidyl carbonate of PEG, succinimidyl esters of amino acid PEGs, PEG-oxycarbonylimidazole, PEG-nitrophenyl carbonate, PEG tresylate, PEG-glycidyl ether, PEG-aldehyde, PEG vinylsulfone, PEG-maleimide, PEG-orthopyridyl-disulfide, heterofunctional PEGs, PEG vinyl derivatives, PEG silanes, and PEG phospholides. The reaction conditions for coupling these PEG derivatives will vary depending on the protein, the desired degree of PEGylation, and the PEG derivative utilized. Some factors involved in the choice of PEG derivatives include: the desired point of attachment (such as lysine or cysteine R-groups), hydrolytic stability and reactivity of the derivatives, stability, toxicity and antigenicity of the linkage, suitability for analysis, etc. Specific instructions for the use of any particular derivative are available from the manufacturer.

The conjugates of this invention are separated from the unreacted starting materials by gel filtration or ion exchange HPLC. Heterologous species of the conjugates are purified from one another in the same fashion.

The conjugates may also be purified by ion-exchange chromatography. The chemistry of many of the electrophilically activated PEG's results in a reduction of amino group charge of the PEGylated product. Thus, high resolution ion exchange chromatography can be used to separate the free and conjugated proteins, and to resolve species with different levels of PEGylation. In fact, the resolution of different species (e.g. containing one or two PEG residues) is also possible due to the difference in the ionic properties of the unreacted amino acids. In one embodiment, species with difference levels of PEGylation are resolved according to the methods described in WO 96/34015 (International Application No. PCT/US96/05550 published Oct. 31, 1996).

In a preferred embodiment, the conjugate is generated by utilizing the derivatization and purification methods described in Section (T) of the Examples below.

In one aspect, the invention provides any of the above-described conjugates formed by its component parts, i.e. one or more antibody fragment(s) covalently attached to one or more polymer molecule(s), without any extraneous matter in the covalent molecular structure of the conjugate.

c. Other Derivatives of Large Effective Size Conjugates

In another aspect, any of the above-described conjugates can be modified to contain one or more component(s) in addition to the antibody fragment component(s) and polymer component(s) that form the conjugate, wherein the modification does not alter the essential functional property of the conjugate, namely, the substantially improved serum half-life, MRT and/or serum clearance rate as compared to that of the parental antibody fragment from which the conjugate is derived. In one embodiment, the invention provides any of the above-described conjugates modified to incorporate one or more nonproteinaceous functional group (s). For example, the conjugate can be modified to incorporate nonproteinaceous labels or reporter molecules, such as radiolabels, including any radioactive substance used in medical treatment or imaging or used as an effector function or tracer in an animal model, such as radioisotopic labels $^{99}Tc$, $^{90}Y$, $^{111}In$, $^{32}P$, $^{14}C$, $^{125}I$, $^{3}H$, $^{131}I$, $^{11}C$, $^{15}O$, $^{13}N$, $^{18}F$, $^{35}S$, $^{51}Cr$, $^{57}To$, $^{226}Ra$, $^{60}Co$, $^{59}Fe$, $^{57}Se$, $^{152}Eu$, $^{67}CU$, $^{217}Ci$, $^{211}At$, $^{212}Pb$, $^{47}Sc$, $^{109}Pd$, $^{234}Th$, $^{40}K$, and the like, non-radioisotopic labels such as $^{157}Gd$, $^{55}Mn$, $^{52}Tr$, $^{56}Fe$, etc., fluoescent or chemiluminescent labels, including fluorophores such as rare earth chelates, fluorescein and its derivatives, rhodamine and its derivatives, isothiocyanate, phycoerythrin, phycocyanin, allophycocyanin, o-phthaladehyde, fluorescamine, $^{152}Eu$, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels, stable free radicals, and the like.

Conventional methods are available to bind these labels covalently to the polypeptide antibody fragment or polymer component of the conjugate. In one aspect, any conjugate of the invention is modified by derivatizing the antibody fragment component with any of the above-described nonproteinaceous labels, wherein the label is directly or indirectly (through a coupling agent) attached to the antibody fragment, and wherein such derivatization of the antibody fragment does not contribute or introduce any polymer moiety into the molecular structure of the conjugate. For instance, coupling agents such as dialdehydes, carbodiimides, dimaleimides, bis-imidates, bis-diazotized benzidine, and the like can be used to tag the antibody fragment with the above-described fluorescent or chemiluminescent labels. See, for example, U.S. Pat. No. 3,940,475 (fluorimetry), Morrison, *Meth. Enzymol.*, 32b, 103 (1974), Svyanen et al., *J. Biol. Chem.*, 284, 3762 (1973), and Bolton and Hunter, *Biochem. J.*, 133, 529 (1973).

In the case of embodiments utilizing radiolabels, both direct and indirect labeling can be used to incorporate the selected radionuclide into the conjugate. As used herein in the context of radiolabeling, the phrases "indirect labeling" and "indirect labeling approach" both mean that a chelating agent is covalently attached to the antibody fragment moiety or polymer moiety of the conjugate and at least one raidonuclide is inserted into the chelating agent. Preferred chelating agents and radionuclides are set forth in Srivagtava, S. C. and Mease, R. C., "Progress in Research on Ligands, Nuclides and Techniques for Labeling Monoclonal Antibodies," *Nucl. Med. Bio.*, 18(6): 589–603 (1991). A particularly preferred chelating agent is 1-isothiocycmatobenzyl-3-methyldiothelene triaminepent acetic acid ("MX-DTPA"). As used herein in the context of radiolabeling, the phrases "direct labeling" and "direct labeling approach" both mean that a radionuclide is covalently attached directly to the antibody fragment moiety (typically via an amino acid residue) or to the polymer moiety of the conjugate. Preferred radionuclides for use in direct labeling of conjugate are provided in Srivagtava and Mease, supra. In one embodiment, the conjugate is directly labeled with $^{131}$I covalently attached to tyrosine residues. In another embodiment, the antibody fragment component of the conjugate is directly or indirectly labeled with any of the above-described radiolabels, wherein such labeling of the antibody fragment does not contribute or introduce any polymer moiety into the molecular structure of the conjugate.

d. Therapeutic Compositions and Administration of Large Effective Size Conjugates The conjugate of the invention is useful for treating the disease indications that are treated with the parent intact antibody. For example, a conjugate derived from an anti-IL-8 antibody or fragment is useful in the treatment of inflammatory disorders as described in Section (II)(5)(B) below. Therapeutic formulations of the conjugate of the invention can be prepared by utilizing the same procedures described for the formulation of the anti-IL-8 antibodies and fragments of the invention in Section (II)(5)(B) below. The conjugate of the invention can be administered in place of the parent antibody for a given disease indication by modifying the formulation, dosage, administration protocol, and other aspects of a therapeutic regimen as required by the different pharmacodynamic characteristics of the conjugate and as dictated by common medical knowledge and practice.

e. Reagent Uses for Large Effective Size Conjugates

The conjugate of the invention also finds application as a reagent in an animal model system for in vivo study of the biological functions of the antigen recognized by the conjugate. The conjugate would enable the practitioner to inactivate or detect the cognate antigen in circulation or in tissue for a far greater period of time than would be possible with art-known constructs while removing any Fc interaction (which could attend the use of an intact antibody) from the system. In addition, the increased half-life of the conjugate of the invention can be applied advantageously to the induction of tolerance for the underivatized antibody fragment in a test animal by employing the Wie et al., *Int. Archs. Allergy Appl. Immunol.*, 64: 84–99 (1981) method for allergen tolerization, which would permit the practitioner to repeatedly challenge the tolerized animal with the underivatized parental antibody fragment without generating an immune response against the parental fragment.

2. Humanized 6G4.2.5 Monoclonat Antibodies and Antibody Fragments

In one embodiment, the invention provides an antibody fragment or full length antibody comprising a heavy chain comprising the amino acid sequence of amino acids 1–230 (herein referred to as "6G4.2.5HV11") of the humanized anti-IL-8 6G4.2.5v11 heavy chain polypeptide amino acid sequence of FIGS. 37A–37B (SEQ ID NO: 60).

The invention encompasses a single chain antibody fragment comprising the 6G4.2.5HV11, with or without any additional amino acid sequence. In one embodiment, the invention provides a single chain antibody fragment comprising the 6G4.2.5HV11 without any associated light chain amino acid sequence, i.e. a single chain species that makes up one half of a Fab fragment.

Further provided herein are an antibody or antibody fragment comprising the 6G4.2.5HV11, and further comprising a light chain comprising the amino acid sequence of amino acids 1–219 (herein referred to as "6G4.2.5LV11") of the humanized anti-IL-8 6G4.2.5v11 light chain polypeptide amino acid sequence of FIG. 31B (SEQ ID NO: 51).

In one embodiment, the invention provides a single chain antibody fragment wherein the 6G4.2.5HV11 and the 6G4.2.5LV11 are contained in a single chain polypeptide species. In a preferred embodiment, the single chain antibody fragment comprises the 6G4.2.5HV11 joined to the 6G4.2.5LV11 by means of a flexible peptide linker sequence, wherein the heavy chain and light chain domains can associate in a "dimeric" structure analogous to that formed in a two-chain Fab species. In another embodiment, the single chain antibody fragment is a species comprising the 6G4.2.5HV11 joined to the 6G4.2.5LV11 by a linker that is too short to permit intramolecular pairing of complementary domains, i.e. a single chain polypeptide monomer that forms a diabody upon dimerization with another monomer.

In yet another embodiment, the invention provides an antibody fragment comprising a plurality of polypeptide chains, wherein one polypeptide chain comprises the 6G4.2.5HV11 and a second polypeptide chain comprises the 6G4.2.5LV11 and the two polypeptide chains are covalently linked by one or more interchain disulfide bonds. In a preferred embodiment, the foregoing two-chain antibody fragment is selected from the group consisting of Fab, Fab', Fab'-SH, and F(ab')$_2$.

The invention also provides an antibody or antibody fragment comprising a heavy chain containing the 6G4.2.5HV11 and optionally further comprising a light chain containing the 6G4.2.5LV11, wherein the heavy chain, and optionally the light chain, is (are) fused to an additional moiety, such as additional immunoglobulin constant domain sequence. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat et al. (supra).

In a preferred embodiment, the antibody or antibody fragment comprises the 6G4.2.5HV11 in a heavy chain that is fused to or contains a leucine zipper sequence. The leucine zipper can increase the affinity and/or production efficiency of the antibody or antibody fragment of interest. Suitable leucine zipper sequences include the jun and fos leucine zippers taught by Kostelney et al., *J. Immunol.*, 148: 1547–1553 (1992) and the GCN4 leucine zipper described in the Examples below. In a preferred embodiment, the antibody or antibody fragment comprises the 6G4.2.5HV11 fused at its C-terminus to the GCN4 leucine zipper to yield the amino acid sequence of amino acids 1–275 (herein referred to as "6G4.2.5HV11GCN4") of the heavy chain polypeptide amino acid sequence of FIGS. 37A–37B (SEQ ID NO: 60).

3. Variants or Humanized 6G4.2.5 Monoclonal Antibodies and Antibody Fragments The invention additionally encompasses humanized anti-IL-8 monoclonal antibody and antibody fragments comprising variants of the 6G4.2.5 complementarity determining regions (CDRs) or variants of the 6G4.2.5v11 variable domains which exhibit higher affinity for human IL-8 and/or possess properties that yield greater efficiency in recombinant production processes.

A. 6G4.2.5LV VARIANTS

In one aspect, the invention provides humanized anti-IL-8 monoclonal antibodies and antibody fragments comprising the complementarity determining regions (referred to herein as the "CDRs of 6G4.2.5LV") L1, L2, and L3 of the 6G4.2.5 light chain variable domain amino acid sequence of FIG. 24, wherein L1 corresponds to amino acids 24–39 of the amino acid sequence of FIG. 24, L2 corresponds to amino acids 55–61 of the amino acid sequence of FIG. 24 (SEQ ID NO: 35), and L3 corresponds to amino acids 94–102 of the amino acid sequence of FIG. 24 (SEQ ID NO: 35).

In addition, the invention provides a variant 6G4.2.5 humanized antibody or antibody fragment comprising a humanized light chain variable domain comprising a variant (hereinafter referred to a "6G4.2.5 LV CDRs variant") of the complementarity determining regions L1, L2, and L3 of the 6G4.2.5 variable light chain domain amino acid sequence of FIG. 24 (SEQ ID NO: 35). In one embodiment, the invention provides a variant 6G4.2.5 humanized antibody or antibody fragment comprising a 6G4.2.5LV CDRs variant (herein referred to as "6G4.2.5LV/L1N35$X_{35}$") wherein L1 corresponds to amino acids 24–39 of the amino acid sequence of FIG. 24 (SEQ ID NO: 35) with the proviso that any amino acid other than Asn (denoted as "$X_{35}$") is substituted for Asn at amino acid position 35, L2 corresponds to amino acids 55–61 of the amino acid sequence of FIG. 24 (SEQ ID NO: 35), and L3 corresponds to amino acids 94–102 of the amino acid sequence of FIG. 24 (SEQ ID NO: 35). In a preferred embodiment, the invention provides a variant 6G4.2.5 humanized antibody or antibody fragment comprising a 6G4.2.5LV CDRs variant (herein referred to as "6G4.2.5LV/L1N35A") wherein L1 corresponds to amino acids 24–39 of the amino acid sequence of FIG. 24 (SEQ ID NO: 35) with the proviso that Ala is substituted for Asn at amino acid position 35, L2 corresponds to amino acids 55–61 of the amino acid sequence of FIG. 24 (SEQ ID NO: 35), and L3 corresponds to amino acids 94–102 of the amino acid sequence of FIG. 24 (SEQ ID NO: 35). In another preferred embodiment, the invention provides a variant 6G4.2.5 humanized antibody or antibody fragment comprising a 6G4.2.5LV CDRs variant (herein referred to as "6G4.2.5LV/L1N35E") wherein L1 corresponds to amino acids 24–39 of the amino acid sequence of FIG. 24 (SEQ ID NO: 35) with the proviso that Glu is substituted for Asn at amino acid position 35, L2 corresponds to amino acids 55–61 of the amino acid sequence of FIG. 24 (SEQ ID NO: 35), and L3 corresponds to amino acids 94–102 of the amino acid sequence of FIG. 24 (SEQ ID NO: 35).

In a second aspect, the invention provides a variant 6G4.2.5 humanized antibody or antibody fragment comprising a 6G4.2.5LV CDRs variant (herein referred to as "6G4.2.5LV/L1S26$X_{26}$") wherein L1 corresponds to amino acids 24–39 of the amino acid sequence of FIG. 24 (SEQ ID NO: 35) with the proviso that any amino acid other than Ser (denoted as "$X_{26}$") is substituted for Ser at amino acid position 26, L2 corresponds to amino acids 55–61 of the amino acid sequence of FIG. 24 (SEQ ID NO: 35), and L3 corresponds to amino acids 94–102 of the amino acid sequence of FIG. 24 (SEQ ID NO: 35). In a preferred embodiment, the invention provides a variant 6G4.2.5 humanized antibody or antibody fragment comprising a 6G4.2.5LV CDRs variant (herein referred to as "6G4.2.5LV/L1S26A") wherein L1 corresponds to amino acids 24–39 of the amino acid sequence of FIG. 24 (SEQ ID NO: 35) with the proviso that Ala is substituted for Ser at amino acid position 26, L2 corresponds to amino acids 55–61 of the amino acid sequence of FIG. 24 (SEQ ID NO: 35), and L3 corresponds to amino acids 94–102 of the amino acid sequence of FIG. 24 (SEQ ID NO: 35).

In a third aspect, the invention provides a variant 6G4.2.5 humanized antibody or antibody fragment comprising a 6G4.2.5LV CDRs variant (herein referred to as "6G4.2.5LV/L3H98$X_{98}$") wherein L1 corresponds to amino acids 24–39 of the amino acid sequence of FIG. 24 (SEQ ID NO: 35), L2 corresponds to amino acids 55–61 of the amino acid sequence of FIG. 24 (SEQ ID NO: 35), and L3 corresponds to amino acids 94–102 of the amino acid sequence of FIG. 24 (SEQ ID NO: 35) with the proviso that any amino acid other than His (denoted as "$X_{98}$") is substituted for His at amino acid position 98. In a preferred embodiment, the invention provides a variant 6G4.2.5 humanized antibody or antibody fragment comprising a 6G4.2.5LV CDRs variant (herein referred to as "6G4.2.5LV/L3H98A") wherein L1 corresponds to amino acids 24–39 of the amino acid sequence of FIG. 24 (SEQ ID NO: 35), L2 corresponds to amino acids 55–61 of the amino acid sequence of FIG. 24 (SEQ ID NO: 35), and L3 corresponds to amino acids 94–102 of the amino acid sequence of FIG. 24 (SEQ ID NO: 35) with the proviso that Ala is substituted for His at amino acid position 98.

In a fourth aspect, the invention provides a variant 6G4.2.5 humanized antibody or antibody fragment comprising a 6G4.2.5LV CDRs variant (herein referred to as "6G4.2.5LV/L1S26$X_{26}$,N35$X_{35}$") wherein L1 corresponds to amino acids 24–39 of the amino acid sequence of FIG. 24 (SEQ ID NO: 35) with the proviso that any amino acid other than Ser (denoted as "$X_{26}$") is substituted for Ser at amino acid position 26 and any amino acid other than Asn (denoted as "$X_{35}$") is substituted for Asn at amino acid position 35, L2 corresponds to amino acids 55–61 of the amino acid sequence of FIG. 24 (SEQ ID NO:35), and L3 corresponds to amino acids 94–102 of the amino acid sequence of FIG. 24 (SEQ ID NO:35). In a preferred embodiment, the invention provides a variant 6G4.2.5 humanized antibody or antibody fragment comprising a 6G4.2.5LV CDRs variant (herein referred to as "6G4.2.5LV/L1S26A,N35A") wherein L1 corresponds to amino acids 24–39 of the amino acid sequence of FIG. 24 (SEQ ID NO:35) with the proviso that Ala is substituted for Ser at amino acid position 26 and Ala is substituted for Asn at amino acid position 35, L2 corresponds to amino acids 55–61 of the amino acid sequence of FIG. 24 (SEQ ID NO 35), and L3 corresponds to amino acids 94–102 of the amino acid sequence of FIG. 24 (SEQ ID NO 35).

In a fifth aspect, the invention provides a variant 6G4.2.5 humanized antibody or antibody fragment comprising a 6G4.2.5LV CDRs variant (herein referred to as "6G4.2.5LV/L1N35X$_{35}$/L3H98X$_{98}$") wherein L1 corresponds to amino acids 24–39 of the amino acid sequence of FIG. 24 (SEQ ID NO 35) with the proviso that any amino acid other than Asn (denoted as "X$_{35}$") is substituted for Asn at amino acid position 35, L2 corresponds to amino acids 55–61 of the amino acid sequence of FIG. 24 (SEQ ID NO 35), and L3 corresponds to amino acids 94–102 of the amino acid sequence of FIG. 24 (SEQ ID NO 35) with the proviso that any amino acid other than His (denoted as "X$_{98}$") is substituted for His at amino acid position 98. In a preferred embodiment, the invention provides a variant 6G4.2.5 humanized antibody or antibody fragment comprising a 6G4.2.5LV CDRs variant (herein referred to as "6G4.2.5LV/L1N35A/L3H98A") wherein L1 corresponds to amino acids 24–39 of the amino acid sequence of FIG. 24 (SEQ ID NO 35) with the proviso that Ala is substituted for Asn at amino acid position 35, L2 corresponds to amino acids 55–61 of the amino acid sequence of FIG. 24 (SEQ ID NO 35), and L3 corresponds to amino acids 94–102 of the amino acid sequence of FIG. 24 (SEQ ID NO 35) with the proviso that Ala is substituted for His at amino acid position 98.

In a sixth aspect, the invention provides a variant 6G4.2.5 humanized antibody or antibody fragment comprising a 6G4.2.5LV CDRs variant (herein referred to as "6G4.2.5LV/L1S26X$_{26}$/L3H98X$_{98}$") wherein L1 corresponds to amino acids 24–39 of the amino acid sequence of FIG. 24 (SEQ ID NO 35) with the proviso that any amino acid other than Ser (denoted as "X$_{26}$") is substituted for Ser at amino acid position 26, L2 corresponds to amino acids 55–61 of the amino acid sequence of FIG. 24 (SEQ ID NO 35), and L3 corresponds to amino acids 94–102 of the amino acid sequence of FIG. 24 (SEQ ID NO 35) with the proviso that any amino acid other than His (denoted as "X$_{98}$") is substituted for His at amino acid position 98. In a preferred embodiment, the invention provides a variant 6G4.2.5 humanized antibody or antibody fragment comprising a 6G4.2.5LV CDRs variant (herein referred to as "6G4.2.5LV/L1S26A/L3H98A") wherein L1 corresponds to amino acids 24–39 of the amino acid sequence of FIG. 24 (SEQ ID NO 35) with the proviso that Ala is substituted for Ser at amino acid position 26, L2 corresponds to amino acids 55–61 of the amino acid sequence of FIG. 24 SEQ ID NO 35), and L3 corresponds to amino acids 94–102 of the amino acid sequence of FIG. 24 (SEQ ID NO: 35) with the proviso that Ala is substituted for His at amino acid position 98.

In a seventh aspect, the invention provides a variant 6G4.2.5 humanized antibody or antibody fragment comprising a 6G4.2.5LV CDRs variant (here referred to as "6G4.2.5LV/L1S26X$_{26}$,N35X$_{35}$/L3H98X$_{98}$") wherein L1 corresponds to amino acids 24–39 of the amino acid sequence of FIG. 24 (SEQ ID NO: 35) with the proviso that any amino acid other than Ser (denoted as "X$_{26}$") is substituted for Ser at amino acid position 26 and any amino acid other than Asn (denoted as "X$_{35}$") is substituted for Asn at amino acid position 35, L2 corresponds to amino acids 55–61 of the amino acid sequence of FIG. 24 (SEQ ID NO: 35), and L3 corresponds to amino acids 94–102 of the amino acid sequence of FIG. 24 (SEQ ID NO: 35) with the proviso that any amino acid other than His (denoted as "X$_{98}$") is substituted for His at amino acid position 98. In a preferred embodiment, the invention provides a variant 6G4.2.5 humanized antibody or antibody fragment comprising a 6G4.2.5LV CDRs variant (here referred to as "6G4.2.5LV/L1S26A,N35A/L3H98A") wherein L1 corresponds to amino acids 24–39 of the amino acid sequence of FIG. 24 (SEQ ID NO: 35) with the proviso that Ala is substituted for Ser at amino acid position 26 and Ala is substituted for Asn at amino acid position 35, L2 corresponds to amino acids 55–61 of the amino acid sequence of FIG. 24 (SEQ ID NO: 35), and L3 corresponds to amino acids 94–102 of the amino acid sequence of FIG. 24 (SEQ ID NO: 35) with the proviso that Ala is substituted for His at amino acid position 98.

The humanized light chain variable domains of the invention can be constructed by using any of the techniques for antibody humanization known in the art. Humanization can be essentially performed following the method of Winter and co-workers (Jones et al., Nature 321:522(1986); Riechmann et al., Nature 332:323 (1988); Verhoeyen et al., Science 239:1534 (1988)), by substituting the CDRs of 6G4.2.5LV or the CDRs of a 6G4.2.5LV CDRs variant for the corresponding sequences of a human antibody light chain variable domain. Accordingly, such "humanzed" derivatives containing the CDRs of 6G4.2.5LV or the CDRs of a 6G4.2.5VL CDRs variant are chimeric (Cabilly et al., supra). The humanized light chain variable domain comprising the CDRs of 6G4.2.5LV or the CDRs of a 6G4.2.5LV CDRs variant can also contain some FR residues that are substituted by residues from analogous sites in the murine 6G4.2.5 antibody light chain variable domain ("6G4.2.5LV"). The complete amino acid sequence of 6G4.2.5LV is set out as amino acids 1–114 of the amino acid sequence of FIG. 24 (SEQ ID NO: 35).

The invention further provides a humanized antibody or antibody fragment comprising a humanized light chain variable domain comprising the CDRs of 6G4.2.5LV or the CDRs of a 6G4.2.5LV CDRs variant as described above, and further comprising a humanized heavy chain variable domain comprising the complementarity determining regions (CDRs) H1, H2, and H3 of the 6G4.2.5 (murine monoclonal antibody) variable heavy chain domain amino acid sequence of FIG. 25 (SEQ ID NO: 37), wherein H1 correspond to amino acids 26–35 of the amino acid sequence of FIG. 25 (SEQ ID NO: 37), wherein H2 corresponds to amino acids 50–66 of the amino acid sequence of FIG. 25 (SEQ ID NO: 37), and wherein H3 corresponds to amino acids 99–111 of the amino acid sequence of FIG. 25 (SEQ ID NO: 37). The above-described H1, H2, and H3CDRs of the 6G4.2.5 heavy chain variable domain ("6G4.2.5HV") are collectively referred to as the "CDRs of 6G4.2.5HV".

In another embodiment, the invention provides a humanized antibody or antibody fragment comprising a humanized light chain variable domain comprising the CDRs of 6G4.2.5LV or the CDRs of a 6G4.2.5LV CDRs variant as described above, and further comprising a humanized heavy chain variable domain comprising a variant (herein referred to as a "6G4.2.5HV CDRs variant") of the H1, H2, and H3 CDRs of the 6G4.2.5 (murine monoclonal antibody) variable heavy chain domain amino acid sequence of FIG. 25 (SEQ ID NO: 37). In one 6G4.2.5HV CDRs variant (referred to herein as "6G4.2.5HV/H1S31Z$_{31}$"), H1 correspond to amino acids 26–35 of the amino acid sequence of FIG. 25 (SEQ ID NO: 37) with the proviso that any amino acid other than Ser (denoted as "Z$_{31}$") is substituted for Ser at amino acid position 31, H2 corresponds to amino acids 50–66 of the amino acid sequence of FIG. 25 (SEQ ID NO: 37), and H3 corresponds to amino acids 99–111 of the amino acid sequence of FIG. 25 (SEQ ID NO: 37). In a preferred 6G4.2.5HV CDRs variant (referred to herein as "6G4.2.5HV/H1S31A"), H1 correspond to amino acids 26–35 of the amino acid sequence of FIG. 25 (SEQ ID NO: 37) with the proviso that Ala is substituted for Ser at amino acid position 31, H2 corresponds to amino acids 50–66 of the amino acid sequence of FIG. 25 (SEQ ID NO: 37), and H3 corresponds to amino acids 99–111 of the amino acid sequence of FIG. 25 (SEQ ID NO: 37).

In a second 6G4.2.5HV CDRs variant (referred to herein as "6G4.2.5HV/H2S54$Z_{54}$"), H1 corresponds to amino acids 26–35 of the amino acid sequence of FIG. 25 (SEQ ID NO: 37), H2 corresponds to amino acids 50–66 of the amino acid sequence of FIG. 25 (SEQ ID NO: 37) with the proviso that any amino acid other than Ser (denoted as "$Z_{54}$") is substituted for Ser at amino acid position 54, and H3 corresponds to amino acids 99–111 of the amino acid sequence of FIG. 25 (SEQ ID NO: 37). In a preferred 6G4.2.5HV CDRs variant (referred to herein as "6G4.2.5HV/H2S54A"), H1 corresponds to amino acids 26–35 of the amino acid sequence of FIG. 25 (SEQ ID NO: 37), H2 corresponds to amino acids 50–66 of the amino acid sequence of FIG. 25 (SEQ ID NO: 37) with the proviso that Ala is substituted for Ser at amino acid position 54, and H3 corresponds to amino acids 99–111 of the amino acid sequence of FIG. 25 (SEQ ID NO: 37).

In a third 6G4.2.5HV CDRs variant (referred to herein as "6G4.2.5HV/H3D100E"), wherein H1 correspond to amino acids 26–35 of the amino acid sequence of FIG. 25 (SEQ ID NO: 37), wherein H2 corresponds to amino acids 50–66 of the amino acid sequence of FIG. 25 (SEQ ID NO: 37), and wherein H3 corresponds to amino acids 99–111 of the amino acid sequence of FIG. 25 (SEQ ID NO: 37) with the proviso that Glu is substituted for Asp at amino acid position 100.

In a fourth 6G4.2.5HV CDRs variant (referred to herein as "6G4.2.5HV/H3R102K"), wherein H1 correspond to amino acids 26–35 of the amino acid sequence of FIG. 25 (SEQ ID NO: 37), wherein H2 corresponds to amino acids 50–66 of the amino acid sequence of FIG. 25 (SEQ ID NO: 37), and wherein H3 corresponds to amino acids 99–111 of the amino acid sequence of FIG. 25 (SEQ ID NO: 37) with the proviso that Lys is substituted for Arg at amino acid position 102.

In a fifth 6G4.2.5HV CDRs variant (referred to herein as "6G4.2.5HV/H3D106E"), wherein H1 correspond to amino acids 26–35 of the amino acid sequence of FIG. 25 (SEQ ID NO: 37), wherein H2 corresponds to amino acids 50–66 of the amino acid sequence of FIG. 25 (SEQ ID NO: 37), and wherein H3 corresponds to amino acids 99–111 of the amino acid sequence of FIG. 25 (SEQ ID NO: 37) with the proviso that Glu is substituted for Asp at amino acid position 106.

In a seventh 6G4.2.5HV CDRs variant (referred to herein as "6G4.2.5HV/H3D100E,R102K"), wherein H1 correspond to amino acids 26–35 of the amino acid sequence of FIG. 25 (SEQ ID NO: 37), wherein H2 corresponds to amino acids 50–66 of the amino acid sequence of FIG. 25 (SEQ ID NO: 37), and wherein H3 corresponds to amino acids 99–111 of the amino acid sequence of FIG. 25 (SEQ ID NO: 37) with the proviso that Glu is substituted for Asp at amino acid position 100 and Lys is substituted for Arg at amino acid position 102.

In an eighth 6G4.2.5HV CDRs variant (referred to herein as "6G4.2.5HV/H3R102K,D106E"), wherein H1 correspond to amino acids 26–35 of the amino acid sequence of FIG. 25 (SEQ ID NO: 37), wherein H2 corresponds to amino acids 50–66 of the amino acid sequence of FIG. 25 (SEQ ID NO: 37), and wherein H3 corresponds to amino acids 99–111 of the amino acid sequence of FIG. 25 (SEQ ID NO: 37) with the proviso that Lys is substituted for Arg at amino acid position 102 and Glu is substituted for Asp at amino acid position 106.

In a ninth 6G4.2.5HV CDRs variant (referred to herein as "6G4.2.5HV/H3D100E,D106E"), wherein H1 correspond to amino acids 26–35 of the amino acid sequence of FIG. 25 (SEQ ID NO: 37), wherein H2 corresponds to amino acids 50–66 of the amino acid sequence of FIG. 25 (SEQ ID NO: 37), and wherein H3 corresponds to amino acids 99–111 of the amino acid sequence of FIG. 25 (SEQ ID NO: 37) with the proviso that Glu is substituted for Asp at amino acid position 100 and Glu is substituted for Asp at amino acid position 106.

In a tenth 6G4.2.5HV CDRs variant (referred to herein as "6G4.2.5HV/H3D100E,R102K,D106E"), wherein H1 correspond to amino acids 26–35 of the amino acid sequence of FIG. 25 (SEQ ID NO: 37), wherein H2 corresponds to amino acids 50–66 of the amino acid sequence of FIG. 25 (SEQ ID NO: 37), and wherein H3 corresponds to amino acids 99–111 of the amino acid sequence of FIG. 25 (SEQ ID NO: 37) with the proviso that Glu is substituted for Asp at amino acid position 100, Lys is substituted for Arg at amino acid position 102, and Glu is substituted for Asp at amino acid position 106.

In an eleventh 6G4.2.5HV CDRs variant (referred to herein as "6G4.2.5HV/H1S31$Z_{31}$/H2S54$Z_{54}$"), H1 correspond to amino acids 26–35 of the amino acid sequence of FIG. 25 (SEQ ID NO: 37) with the proviso that any amino acid other than Ser (denoted as "$Z_{31}$") is substituted for Ser at amino acid position 31, H2 corresponds to amino acids 50–66 of the amino acid sequence of FIG. 25 (SEQ ID NO: 37) with the proviso that any amino acid other than Ser (denoted as "$Z_{54}$") is substituted for Ser at amino acid position 54, and H3 corresponds to amino acids 99–111 of the amino acid sequence of FIG. 25 (SEQ ID NO: 37). In a preferred 6G4.2.5HV CDRs variant (referred to herein as "6G4.2.5HV/H1S31A/H2S54A"), H1 correspond to amino acids 26–35 of the amino acid sequence of FIG. 25 (SEQ ID NO: 37) with the proviso that Ala is substituted for Ser at amino acid position 31, H2 corresponds to amino acids 50–66 of the amino acid sequence of FIG. 25 (SEQ ID NO: 37) with the proviso that Ala is substituted for Ser at amino acid position 54, and H3 corresponds to amino acids 99–111 of the amino acid sequence of FIG. 25 (SEQ ID NO: 37).

In a twelfth 6G4.2.5HV CDRs variant (referred to herein as "6G4.2.5HV/H1S31$Z_{31}$/H3D100E"), H1 correspond to amino acids 26–35 of the amino acid sequence of FIG. 25 (SEQ ID NO: 37) with the proviso that any amino acid other than Ser (denoted as "$Z_{31}$") is substituted for Ser at amino acid position 31, H2 corresponds to amino acids 50–66 of the amino acid sequence of FIG. 25 (SEQ ID NO: 37), and H3 corresponds to amino acids 99–111 of the amino acid sequence of FIG. 25 (SEQ ID NO: 37) with the proviso that Glu is substituted for Asp at amino acid position 100. In a preferred 6G4.2.5HV CDRs variant (referred to herein as "6G4.2.5HV/H1S31A/H3D100E"), H1 correspond to amino acids 26–35 of the amino acid sequence of FIG. 25 (SEQ ID NO: 37) with the proviso that Ala is substituted for Ser at amino acid position 31, H2 corresponds to amino acids 50–66 of the amino acid sequence of FIG. 25 (SEQ ID NO: 37), and H3 corresponds to amino acids 99–111 of the amino acid sequence of FIG. 25 (SEQ ID NO: 37) with the proviso that Glu is substituted for Asp at amino acid position 100.

In a thirteenth 6G4.2.5HV CDRs variant (referred to herein as "6G4.2.5HV/H1S31$Z_{31}$/H3R102K"), H1 correspond to amino acids 26–35 of the amino acid sequence of FIG. 25 (SEQ ID NO: 37) with the proviso that any amino acid other than Ser (denoted as "$Z_{31}$") is substituted for Ser at amino acid position 31, H2 corresponds to amino acids 50–66 of the amino acid sequence of FIG. 25 (SEQ ID NO: 37), and H3 corresponds to amino acids 99–111 of the amino acid sequence of FIG. 25 (SEQ ID NO: 37) with the proviso that Lys is substituted for Arg at amino acid position 102. In a preferred 6G4.2.5HV CDRs variant (referred to herein as "6G4.2.5HV/H1S31A/H3R102K"), H1 correspond to amino acids 26–35 of the amino acid sequence of FIG. 25 (SEQ ID NO: 37) with the proviso that Ala is substituted for Ser at amino acid position 31, H2 corresponds to amino acids 50–66 of the amino acid sequence of FIG. 25 (SEQ ID NO: 37), and H3 corresponds to amino acids 99–111 of the amino acid sequence of FIG. 25 (SEQ ID NO: 37) with the proviso that Lys is substituted for Arg at amino acid position 102.

A fourteenth 6G4.2.5HV CDRs variant (referred to herein as "6G4.2.5HV/H1S31Z$_{31}$/H3D106E"), H1 correspond to amino acids 26–35 of the amino acid sequence of FIG. 25 (SEQ ID NO: 37) with the proviso that any amino acid other than Ser (denoted as "Z$_3$") is substituted for Ser at amino acid position 31, H2 corresponds to amino acids 50–66 of the amino acid sequence of FIG. 25 (SEQ ID NO: 37), and H3 corresponds to amino acids 99–111 of the amino acid sequence of FIG. 25 (SEQ ID NO: 37) with the proviso that Glu is substituted for Asp at amino acid position 106. In a preferred 6G4.2.5HV CDRs variant (referred to herein as "6G4.2.5HV/H1S31A/H3D106E"), H1 correspond to amino acids 26–35 of the amino acid sequence of FIG. 25 (SEQ ID NO: 37) with the proviso that Ala is substituted for Ser at amino acid position 31, H2 corresponds to amino acids 50–66 of the amino acid sequence of FIG. 25 (SEQ ID NO: 37), and H3 corresponds to amino acids 99–111 of the amino acid sequence of FIG. 25 (SEQ ID NO: 37) with the proviso that Glu is substituted for Asp at amino acid position 106.

A fifteenth 6G4.2.5HV CDRs variant (referred to herein as "6G4.2.5HV/H1S31Z$_{31}$/H3D100E,R102K"), H1 correspond to amino acids 26–35 of the amino acid sequence of FIG. 25 (SEQ ID NO: 37) with the proviso that any amino acid other than Ser (denoted as "Z$_{31}$") is substituted for Ser at amino acid position 31, H2 corresponds to amino acids 50–66 of the amino acid sequence of FIG. 25 (SEQ ID NO: 37), and H3 corresponds to amino acids 99–111 of the amino acid sequence of FIG. 25 (SEQ ID NO: 37) with the proviso that Glu is substituted for Asp at amino acid position 100 and Lys is substituted for Arg at amino acid position 102. In a preferred 6G4.2.5HV CDRs variant (referred to herein as "6G4.2.5HV/H1S31A/H3D100E,R102K"), H1 correspond to amino acids 26–35 of the amino acid sequence of FIG. 25 (SEQ ID NO: 37) with the proviso that Ala is substituted for Ser at amino acid position 31, H2 corresponds to amino acids 50–66 of the amino acid sequence of FIG. 25 (SEQ ID NO: 37), and H3 corresponds to amino acids 99–111 of the amino acid sequence of FIG. 25 (SEQ ID NO: 37) with the proviso that Glu is substituted for Asp at amino acid position 100 and Lys is substituted for Arg at amino acid position 102.

In a sixteenth 6G4.2.5HV CDRs variant (referred to herein as "6G4.2.5HV/H1S31Z$_{31}$/H3R102K,D106E"), H1 correspond to amino acids 26–35 of the amino acid sequence of FIG. 25 (SEQ ID NO: 37) with the proviso that any amino acid other than Ser (denoted as "Z$_{31}$") is substituted for Ser at amino acid position 31, H2 corresponds to amino acids 50–66 of the amino acid sequence of FIG. 25 (SEQ ID NO: 37), and H3 corresponds to amino acids 99–111 of the amino acid sequence of FIG. 25 (SEQ ID NO: 37) with the proviso that Lys is substituted for Arg at amino acid position 102 and Glu is substituted for Asp at amino acid position 106. In a preferred 6G4.2.5HV CDRs variant (referred to herein as "6G4.2.5HV/H1S31A/H3R102K,D106E"), H1 correspond to amino acids 26–35 of the amino acid sequence of FIG. 25 (SEQ ID NO: 37) with the proviso that Ala is substituted for Ser at amino acid position 31, H2 corresponds to amino acids 50–66 of the amino acid sequence of FIG. 25 (SEQ ID NO: 37), and H3 corresponds to amino acids 99–111 of the amino acid sequence of FIG. 25 (SEQ ID NO: 37) with the proviso that Lys is substituted for Arg at amino acid position 102 and Glu is substituted for Asp at amino acid position 106.

In a seventeenth 6G4.2.5HV CDRs variant (referred to herein as "6G4.2.5HV/H1S31Z$_{31}$/H3D100E,D106E"), H1 correspond to amino acids 26–35 of the amino acid sequence of FIG. 25 (SEQ ID NO: 37) with the proviso that any amino acid other than Ser (denoted as "Z$_{31}$") is substituted for Ser at amino acid position 31, H2 corresponds to amino acids 50–66 of the amino acid sequence of FIG. 25 (SEQ ID NO: 37), and H3 corresponds to amino acids 99–111 of the amino acid sequence of FIG. 25 (SEQ ID NO: 37) with the proviso that Glu is substituted for Asp at amino acid position 100 and Glu is substituted for Asp at amino acid position 106. In a preferred 6G4.2.5HV CDRs variant (referred to herein as "6G4.2.5HV/H1S31A/H3D100E,D106E"), H1 correspond to amino acids 26–35 of the amino acid sequence of FIG. 25 (SEQ ID NO: 37) with the proviso that Ala is substituted for Ser at amino acid position 31, H2 corresponds to amino acids 50–66 of the amino acid sequence of FIG. 25 (SEQ ID NO: 37), and H3 corresponds to amino acids 99–111 of the amino acid sequence of FIG. 25 (SEQ ID NO: 37) with the proviso that Glu is substituted for Asp at amino acid position 100 and Glu is substituted for Asp at amino acid position 106.

In an eighteenth 6G4.2.5HV CDRs variant (referred to herein as "6G4.2.5HV/H1S31Z$_{31}$/H3D100E,R102K, D106E"), H1 correspond to amino acids 26–35 of the amino acid sequence of FIG. 25 (SEQ ID NO: 37) with the proviso that any amino acid other than Ser (denoted as "Z$_{31}$") is substituted for Ser at amino acid position 31, H2 corresponds to amino acids 50–66 of the amino acid sequence of FIG. 25 (SEQ ID NO: 37), and H3 corresponds to amino acids 99–111 of the amino acid sequence of FIG. 25 (SEQ ID NO: 37) with the proviso that Glu is substituted for Asp at amino acid position 100, Lys is substituted for Arg at amino acid position 102 and Glu is substituted for Asp at amino acid position 106. In a preferred 6G4.2.5HV CDRs variant (referred to herein as "6G4.2.5HV/H1S31A/ H3D100E,R102K,D106E"), H1 correspond to amino acids 26–35 of the amino acid sequence of FIG. 25 (SEQ ID NO: 37) with the proviso that Ala is substituted for Ser at amino acid position 31, H2 corresponds to amino acids 50–66 of the amino acid sequence of FIG. 25 (SEQ ID NO: 37), and H3 corresponds to amino acids 99–111 of the amino acid sequence of FIG. 25 (SEQ ID NO: 37) with the proviso that Glu is substituted for Asp at amino acid position 100, Lys is substituted for Arg at amino acid position 102 and Glu is substituted for Asp at amino acid position 106.

In a nineteenth 6G4.2.5HV CDRs variant (referred to herein as "6G4.2.5HV/H2S54Z$_{54}$/H3D100E"), H1 corresponds to amino acids 26–35 of the amino acid sequence of FIG. 25 (SEQ ID NO: 37), H2 corresponds to amino acids 50–66 of the amino acid sequence of FIG. 25 (SEQ ID NO: 37) with the proviso that any amino acid other than Ser (denoted as "Z$_{54}$") is substituted for Ser at amino acid position 54, and H3 corresponds to amino acids 99–111 of the amino acid sequence of FIG. 25 (SEQ ID NO: 37) with the proviso that Glu is substituted for Asp at amino acid position 100. In a preferred 6G4.2.5HV CDRs variant (referred to herein as "6G4.2.5HV/H2S54A/H3D100E"), H1 corresponds to amino acids 26–35 of the amino acid sequence of FIG. 25 (SEQ ID NO: 37), H2 corresponds to amino acids 50–66 of the amino acid sequence of FIG. 25 (SEQ ID NO: 37) with the proviso that Ala is substituted for Ser at amino acid position 54, and H3 corresponds to amino acids 99–111 of the amino acid sequence of FIG. 25 (SEQ ID NO: 37) with the proviso that Glu is substituted for Asp at amino acid position 100.

In a twentieth 6G4.2.5HV CDRs variant (referred to herein as "6G4.2.5HV/H2S54Z$_{54}$/H3R102K"), H1 corresponds to amino acids 26–35 of the amino acid sequence of FIG. 25 (SEQ ID NO: 37), H2 corresponds to amino acids 50–66 of the amino acid sequence of FIG. 25 (SEQ ID NO: 37) with the proviso that any amino acid other than Ser (denoted as "Z$_{54}$") is substituted for Ser at amino acid position 54, and H3 corresponds to amino acids 99–111 of the amino acid sequence of FIG. 25 (SEQ ID NO: 37) with the proviso that Lys is substituted for Arg at amino acid position 102. In a preferred 6G4.2.5HV CDRs variant (referred to herein as "6G4.2.5HV/H2S54A/H3R102K"), H1 corresponds to amino acids 26–35 of the amino acid sequence of FIG. 25 (SEQ ID NO: 37), H2 corresponds to amino acids 50–66 of the amino acid sequence of FIG. 25 (SEQ ID NO: 37) with the proviso that Ala is substituted for Ser at amino acid position 54, and H3 corresponds to amino acids 99–111 of the amino acid sequence of FIG. 25 (SEQ ID NO: 37) with the proviso that Lys is substituted for Arg at amino acid position 102.

In a twenty-first 6G4.2.5HV CDRs variant (referred to herein as "6G4.2.5HV/H2S54Z$_{54}$/H3D106E"), H1 corresponds to amino acids 26–35 of the amino acid sequence of FIG. 25 (SEQ ID NO: 37), H2 corresponds to amino acids 50–66 of the amino acid sequence of FIG. 25 (SEQ ID NO: 37) with the proviso that any amino acid other than Ser (denoted as "Z$_{54}$") is substituted for Ser at amino acid position 54, and H3 corresponds to amino acids 99–111 of the amino acid sequence of FIG. 25 (SEQ ID NO: 37) with the proviso that Glu is substituted for Asp at amino acid position 106. In a preferred 6G4.2.5HV CDRs variant (referred to herein as "6G4.2.5HV/H2S54A/H3D106E"), H1 corresponds to amino acids 26–35 of the amino acid sequence of FIG. 25 (SEQ ID NO: 37), H2 corresponds to amino acids 50–66 of the amino acid sequence of FIG. 25 (SEQ ID NO: 37) with the proviso that Ala is substituted for Ser at amino acid position 54, and H3 corresponds to amino acids 99–111 of the amino acid sequence of FIG. 25 (SEQ ID NO: 37) with the proviso that Glu is substituted for Asp at amino acid position 106.

In a twenty-second 6G4.2.5HV CDRs variant (referred to herein as "6G4.2.5HV/H2S54Z$_{54}$/H3D100E,R102K"), H1 corresponds to amino acids 26–35 of the amino acid sequence of FIG. 25 (SEQ ID NO: 37), H2 corresponds to amino acids 50–66 of the amino acid sequence of FIG. 25 (SEQ ID NO: 37) with the proviso that any amino acid other than Ser (denoted as "Z$_{54}$") is substituted for Ser at amino acid position 54, and H3 corresponds to amino acids 99–111 of the amino acid sequence of FIG. 25 (SEQ ID NO: 37) with the proviso that Glu is substituted for Asp at amino acid position 100 and Lys is substituted for Arg at amino acid position 102. In a preferred 6G4.2.5HV CDRs variant (referred to herein as "6G4.2.5HV/H2S54A/H3D100E,R102K"), H1 corresponds to amino acids 26–35 of the amino acid sequence of FIG. 25 (SEQ ID NO: 37), H2 corresponds to amino acids 50–66 of the amino acid sequence of FIG. 25 (SEQ ID NO: 37) with the proviso that Ala is substituted for Ser at amino acid position 54, and H3 corresponds to amino acids 99–111 of the amino acid sequence of FIG. 25 (SEQ ID NO: 37) with the proviso that Glu is substituted for Asp at amino acid position 100 and Lys is substituted for Arg at amino acid position 102.

In a twenty-third 6G4.2.5HV CDRs variant (referred to herein as "6G4.2.5HV/H2S54Z$_{54}$/H3R102K,D106E"), H1 corresponds to amino acids 26–35 of the amino acid sequence of FIG. 25 (SEQ ID NO: 37), H2 corresponds to amino acids 50–66 of the amino acid sequence of FIG. 25 (SEQ ID NO: 37) with the proviso that any amino acid other than Ser (denoted as "Z$_{54}$") is substituted for Ser at amino acid position 54, and H3 corresponds to amino acids 99–111 of the amino acid sequence of FIG. 25 (SEQ ID NO: 37) with the proviso that Lys is substituted for Arg at amino acid position 102 and Glu is substituted for Asp at amino acid position 106. In a preferred 6G4.2.5HV CDRs variant (referred to herein as "6G4.2.5HV/H2S54A/H3R102K,D106E"), H1 corresponds to amino acids 26–35 of the amino acid sequence of FIG. 25 (SEQ ID NO: 37), H2 corresponds to amino acids 50–66 of the amino acid sequence of FIG. 25 (SEQ ID NO: 37) with the proviso that Ala is substituted for Ser at amino acid position 54, and H3 corresponds to amino acids 99–111 of the amino acid sequence of FIG. 25 (SEQ ID NO: 37) with the proviso that Lys is substituted for Arg at amino acid position 102 and Glu is substituted for Asp at amino acid position 106.

In a twenty-fourth 6G4.2.5HV CDRs variant (referred to herein as "6G4.2.5HV/H2S54Z$_{54}$/H3D100E,D106E"), H1 corresponds to amino acids 26–35 of the amino acid sequence of FIG. 25 (SEQ ID NO: 37), H2 corresponds to amino acids 50–66 of the amino acid sequence of FIG. 25 (SEQ ID NO: 37) with the proviso that any amino acid other than Ser (denoted as "Z$_{54}$") is substituted for Ser at amino acid position 54, and H3 corresponds to amino acids 99–111 of the amino acid sequence of FIG. 25 (SEQ ID NO: 37) with the proviso that Glu is substituted for Asp at amino acid position 100 and Glu is substituted for Asp at amino acid position 106. In a preferred 6G4.2.5HV CDRs variant (referred to herein as "6G4.2.5HV/H2S54A/H3D100E, D106E"), H1 corresponds to amino acids 26–35 of the amino acid sequence of FIG. 25 (SEQ ID NO: 37), H2 corresponds to amino acids 50–66 of the amino acid sequence of FIG. 25 (SEQ ID NO: 37) with the proviso that Ala is substituted for Ser at amino acid position 54, and H3 corresponds to amino acids 99–111 of the amino acid sequence of FIG. 25 (SEQ ID NO: 37) with the proviso that Glu is substituted for Asp at amino acid position 100 and Glu is substituted for Asp at amino acid position 106.

In a twenty-fifth 6G4.2.5HV CDRs variant (referred to herein as "6G4.2.5HV/H2S54Z$_{54}$/H3D000E,R102K, D106E"), H1 corresponds to amino acids 26–35 of the amino acid sequence of FIG. 25 (SEQ ID NO: 37), H2 corresponds to amino acids 50–66 of the amino acid sequence of FIG. 25 (SEQ ID NO: 37) with the proviso that any amino acid other than Ser (denoted as "Z$_{54}$") is substituted for Ser at amino acid position 54, and H3 corresponds to amino acids 99–111 of the amino acid sequence of FIG. 25 (SEQ ID NO: 37) with the proviso that Glu is substituted for Asp at amino acid position 100, Lys is substituted for Arg at amino acid position 102 and Glu is substituted for Asp at amino acid position 106. In a preferred 6G4.2.5HV CDRs variant (referred to herein as "6G4.2.5HV/H2S54A/ H3D100E,R102K,D106E"), H1 corresponds to amino acids 26–35 of the amino acid sequence of FIG. 25 (SEQ ID NO: 37), H2 corresponds to amino acids 50–66 of the amino acid sequence of FIG. 25 (SEQ ID NO: 37) with the proviso that Ala is substituted for Ser at amino acid position 54, and H3 corresponds to amino acids 99–111 of the amino acid sequence of FIG. 25 (SEQ ID NO: 37) with the proviso that Glu is substituted for Asp at amino acid position 100, Lys is substituted for Arg at amino acid position 102 and Glu is substituted for Asp at amino acid position 106.

In a twenty-sixth 6G4.2.5HV CDRs variant (referred to herein as "6G4.2.5HV/H1S31Z$_{31}$/H2S54Z$_{54}$/H3D100E"), H1 correspond to amino acids 26–35 of the amino acid sequence of FIG. 25 (SEQ ID NO: 37) with the proviso that any amino acid other than Ser (denoted as "Z$_{31}$") is substituted for Ser at amino acid position 31, H2 corresponds to amino acids 50–66 of the amino acid sequence of FIG. 25 (SEQ ID NO: 37) with the proviso that any amino acid other than Ser (denoted as "Z$_{54}$") is substituted for Ser at amino acid position 54, and H3 corresponds to amino acids 99–111 of the amino acid sequence of FIG. 25 (SEQ ID NO: 37) with the proviso that Glu is substituted for Asp at amino acid position 100. In a preferred 6G4.2.5HV CDRs variant (referred to herein as "6G4.2.5HV/H1S31A/H2S54A/H3D100E"), H1 correspond to amino acids 26–35 of the amino acid sequence of FIG. 25 (SEQ ID NO: 37) with the proviso that Ala is substituted for Ser at amino acid position 31, H2 corresponds to amino acids 50–66 of the amino acid sequence of FIG. 25 (SEQ ID NO: 37) with the proviso that Ala is substituted for Ser at amino acid position 54, and H3 corresponds to amino acids 99–111 of the amino acid sequence of FIG. 25 (SEQ ID NO: 37) with the proviso that Glu is substituted for Asp at amino acid position 100.

In a twenty-seventh 6G4.2.5HV CDRs variant (referred to herein as "6G4.2.5HV/H1S31Z$_{31}$/H2S54Z$_{54}$/H3R102K"), H1 correspond to amino acids 26–35 of the amino acid sequence of FIG. 25 (SEQ ID NO: 37) with the proviso that any amino acid other than Ser (denoted as "Z$_{31}$") is substituted for Ser at amino acid position 31, H2 corresponds to amino acids 50–66 of the amino acid sequence of FIG. 25 (SEQ ID NO: 37) with the proviso that any amino acid other than Ser (denoted as "Z$_{54}$") is substituted for Ser at amino acid position 54, and H3 corresponds to amino acids 99–111 of the amino acid sequence of FIG. 25 (SEQ ID NO: 37) with the proviso that Lys is substituted for Arg at amino acid position 102. In a preferred 6G4.2.5HV CDRs variant (referred to herein as "6G4.2.5HV/H1S31A/H2S54A/H3R102K"), H1 correspond to amino acids 26–35 of the amino acid sequence of FIG. 25 (SEQ ID NO: 37) with the proviso that Ala is substituted for Ser at amino acid position 31, H2 corresponds to amino acids 50–66 of the amino acid sequence of FIG. 25 (SEQ ID NO: 37) with the proviso that Ala is substituted for Ser at amino acid position 54, and H3 corresponds to amino acids 99–111 of the amino acid sequence of FIG. 25 (SEQ ID NO: 37) with the proviso that Lys is substituted for Arg at amino acid position 102.

In a twenty-eighth 6G4.2.5HV CDRs variant (referred to herein as "6G4.2.5HV/H1S31Z$_{31}$/H2S54Z$_{54}$/H3D106E"), H1 correspond to amino acids 26–35 of the amino acid sequence of FIG. 25 (SEQ ID NO: 37) with the proviso that any amino acid other than Ser (denoted as "Z$_{31}$") is substituted for Ser at amino acid position 31, H2 corresponds to amino acids 50–66 of the amino acid sequence of FIG. 25 (SEQ ID NO: 37) with the proviso that any amino acid other than Ser (denoted as "Z$_{54}$") is substituted for Ser at amino acid position 54, and H3 corresponds to amino acids 99–111 of the amino acid sequence of FIG. 25 (SEQ ID NO: 37) with the proviso that Glu is substituted for Asp at amino acid position 106. In a preferred 6G4.2.5HV CDRs variant (referred to herein as "6G4.2.5HV/H1S31A/H2S54A/H3D106E"), H1 correspond to amino acids 26–35 of the amino acid sequence of FIG. 25 (SEQ ID NO: 37) with the proviso that Ala is substituted for Ser at amino acid position 31, H2 corresponds to amino acids 50–66 of the amino acid sequence of FIG. 25 (SEQ ID NO: 37) with the proviso that Ala is substituted for Ser at amino acid position 54, and H3 corresponds to amino acids 99–111 of the amino acid sequence of FIG. 25 (SEQ ID NO: 37) with the proviso that Glu is substituted for Asp at amino acid position 106.

In a twenty-ninth 6G4.2.5HV CDRs variant (referred to herein as "6G4.2.5HV/H1S31Z$_{31}$/H2S54Z$_{54}$/H3D100E, R102K"), H1 correspond to amino acids 26 . 35 of the amino acid sequence of FIG. 25 (SEQ ID NO: 37) with the proviso that any amino acid other than Ser (denoted as "Z$_{31}$") is substituted for Ser at amino acid position 31, H2 corresponds to amino acids 50–66 of the amino acid sequence of FIG. 25 (SEQ ID NO: 37) with the proviso that any amino acid other than Ser (denoted as "Z$_{54}$") is substituted for Ser at amino acid position 54, and H3 corresponds to amino acids 99–111 of the amino acid sequence of FIG. 25 (SEQ ID NO: 37) with the proviso that Glu is substituted for Asp at amino acid position 100 and Lys is substituted for Arg at amino acid position 102. In a preferred 6G4.2.5HV CDRs variant (referred to herein as "6G4.2.5HV/H1S31A/H2S54A/H3D100E,R102K"), H1 correspond to amino acids 26–35 of the amino acid sequence of FIG. 25 (SEQ ID NO: 37) with the proviso that Ala is substituted for Ser at amino acid position 31, H2 corresponds to amino acids 50–66 of the amino acid sequence of FIG. 25 (SEQ ID NO: 37) with the proviso that Ala is substituted for Ser at amino acid position 54, and H3 corresponds to amino acids 99–111 of the amino acid sequence of FIG. 25 (SEQ ID NO: 37) with the proviso that Glu is substituted for Asp at amino acid position 100 and Lys is substituted for Arg at amino acid position 102.

In a thirtieth 6G4.2.5HV CDRs variant (referred to herein as "6G4.2.5HV/H1S31Z$_{31}$/H2S54Z$_{54}$/H3R102K,D106E"), H1 correspond to amino acids 26–35 of the amino acid sequence of FIG. 25 (SEQ ID NO: 37) with the proviso that any amino acid other than Ser (denoted as "Z$_{31}$") is substituted for Ser at amino acid position 31, H2 corresponds to amino acids 50–66 of the amino acid sequence of FIG. 25 (SEQ ID NO: 37) with the proviso that any amino acid other than Ser (denoted as "Z$_{54}$") is substituted for Ser at amino acid position 54, and H3 corresponds to amino acids 99–111 of the amino acid sequence of FIG. 25 (SEQ ID NO: 37) with the proviso that Lys is substituted for Arg at amino acid position 102 and Glu is substituted for Asp at amino acid position 106. In a preferred 6G4.2.5HV CDRs variant (referred to herein as "6G4.2.5HV/H1S31A/H2S54A/H3R102K,D106E"), H1 correspond to amino acids 26–35 of the amino acid sequence of FIG. 25 (SEQ ID NO: 37) with the proviso that Ala is substituted for Ser at amino acid position 31, H2 corresponds to amino acids 50–66 of the amino acid sequence of FIG. 25 (SEQ ID NO: 37) with the proviso that Ala is substituted for Ser at amino acid position 54, and H3 corresponds to amino acids 99–111 of the amino acid sequence of FIG. 25 (SEQ ID NO: 37) with the proviso that Lys is substituted for Arg at amino acid position 102 and Glu is substituted for Asp at amino acid position 106.

In a thirty-first 6G4.2.5HV CDRs variant (referred to herein as "6G4.2.5HV/H1S31Z$_{31}$/H2S54Z$_{54}$/H3D100E, D106E"), H1 correspond to amino acids 26–35 of the amino acid sequence of FIG. 25 (SEQ ID NO: 37) with the proviso that any amino acid other than Ser (denoted as "Z$_{31}$") is substituted for Ser at amino acid position 31, H2 corresponds to amino acids 50–66 of the amino acid sequence of FIG. 25 (SEQ ID NO: 37) with the proviso that any amino acid other than Ser (denoted as "$Z_{54}$") is substituted for Ser at amino acid position 54, and H3 corresponds to amino acids 99–111 of the amino acid sequence of FIG. 25 (SEQ ID NO: 37) with the proviso that Glu is substituted for Asp at amino acid position 100 and Glu is substituted for Asp at amino acid position 106. In a preferred 6G4.2.5HV CDRs variant (referred to herein as "6G4.2.5HV/H1S31A/H2S54A/H3D100E,D106E"), H1 correspond to amino acids 26–35 of the amino acid sequence of FIG. 25 (SEQ ID NO: 37) with the proviso that Ala is substituted for Ser at amino acid position 31, H2 corresponds to amino acids 50–66 of the amino acid sequence of FIG. 25 (SEQ ID NO: 37) with the proviso that Ala is substituted for Ser at amino acid position 54, and H3 corresponds to amino acids 99–111 of the amino acid sequence of FIG. 25 (SEQ ID NO: 37) with the proviso that Glu is substituted for Asp at amino acid position 100 and Glu is substituted for Asp at amino acid position 106.

In a thirty-second 6G4.2.5HV CDRs variant (referred to herein as "6G4.2.5HV/H1S31$Z_{31}$/H2S54$Z_{54}$/H3D100E, R102K,D106E"), H1 correspond to amino acids 26–35 of the amino acid sequence of FIG. 25 (SEQ ID NO: 37) with the proviso that any amino acid other than Ser (denoted as "$Z_{31}$") is substituted for Ser at amino acid position 31, H2 corresponds to amino acids 50–66 of the amino acid sequence of FIG. 25 (SEQ ID NO: 37) with the proviso that any amino acid other than Ser (denoted as "$Z_{54}$") is substituted for Ser at amino acid position 54, and H3 corresponds to amino acids 99–111 of the amino acid sequence of FIG. 25 (SEQ ID NO: 37) with the proviso that Glu is substituted for Asp at amino acid position 100, Lys is substituted for Arg at amino acid position 102 and Glu is substituted for Asp at amino acid position 106. In a preferred 6G4.2.5HV CDRs variant (referred to herein as "6G4.2.5HV/H1S31A/H2S54A/H3D100E,R102K,D106E"), H1 correspond to amino acids 26–35 of the amino acid sequence of FIG. 25 (SEQ ID NO: 37) with the proviso that Ala is substituted for Ser at amino acid position 31, H2 corresponds to amino acids 50–66 of the amino acid sequence of FIG. 25 (SEQ ID NO: 37) with the proviso that Ala is substituted for Ser at amino acid position 54, and H3 corresponds to amino acids 99–111 of the amino acid sequence of FIG. 25 (SEQ ID NO: 37) with the proviso that Glu is substituted for Asp at amino acid position 100, Lys is substituted for Arg at amino acid position 102 and Glu is substituted for Asp at amino acid position 106.

As in the humanization of the light chain variable domain described above, a humanized heavy chain variable domain is constructed by substituting the CDRs of 6G4.2.5HV or the CDRs of a 6G4.2.5HV CDRs variant for the corresponding sequences in a human heavy chain variable domain. The humanized heavy chain variable domain comprising the CDRs of 6G4.2.5HV or the CDRs of a 6G4.2.5HV CDRs variant can also contain some FR residues that are substituted by residues from analogous sites in the murine 6G4.2.5 antibody heavy chain variable domain. The complete amino acid sequence of 6G4.2.5HV is set out as amino acids 1–122 of the amino acid sequence of FIG. 25 (SEQ ID NO: 37).

The choice of human variable domains, both light and heavy, to be used in making the humanized antibodies and antibody fragments is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.* 151: 2296 (1993); Chothia and Lesk, *J. Mol. Biol.* 196:901 (1987)). Another method uses a particular framework derived from the consensus sequence of all human antibodies of a particular subgroup of light or heavy chains. The same framework can be used for several different humanized antibodies (Carter et al., *Proc. Natl. Acad. Sci. U.S.A.* 89:4285 (1992); Presta et al., *J. Immunol.* 151:2623 (1993)).

It is also important that the antibodies and antibody fragments of the invention be humanized with retention of high affinity for human IL-8 and other favorable biological properties. To achieve this goal, according to a preferred method, the humanized antibodies and antibody fragments of the invention are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and parental sequences so that the desired antibody characteristic, such as increased affinity for the target antigen(s), is achieved.

Any and all humanized light chain variable domain amino acid sequences which comprise the CDRs of 6G4.2.5LV are collectively referred to herein as "hu6G4.2.5LV".

Any and all humanized light chain variable domain amino acid sequences which comprise the CDRs of 6G4.2.5LV/L1N35$X_{35}$ are collectively referred to herein as "hu6G4.2.5LV/L1N35$X_{35}$".

Any and all humanized light chain variable domain amino acid sequences which comprise the CDRs of 6G4.2.5LV/L1N35A are collectively referred to herein as "hu6G4.2.5LV/L1N35A".

Any and all humanized light chain variable domain amino acid sequences which comprise the CDRs of 6G4.2.5LV/L1N35E are collectively referred to herein as "hu6G4.2.5LV/L1N35E".

Any and all humanized light chain variable domain amino acid sequences which comprise the CDRs of 6G4.2.5LV/L1S26$X_{26}$ are collectively referred to herein as "hu6G4.2.5LV/L1S26$X_{26}$".

Any and all humanized light chain variable domain amino acid sequences which comprise the CDRs of 6G4.2.5LV/L1S26A are collectively referred to herein as "hu6G4.2.5LV/L1S26A".

Any and all humanized light chain variable domain amino acid sequences which comprise the CDRs of 6G4.2.5LV/L3H98$X_{98}$ are collectively referred to herein as "hu6G4.2.5LV/L3H98$X_{98}$".

Any and all humanized light chain variable domain amino acid sequences which comprise the CDRs of 6G4.2.5LV/L3H98A are collectively referred to herein as "hu6G4.2.5LV/L3H98A".

Any and all humanized light chain variable domain amino acid sequences which comprise the CDRs of 6G4.2.5LV/L1S26$X_{26}$,N35$X_{35}$ are collectively referred to herein as "hu6G4.2.5LV/L1S26$X_{26}$,N35$X_{35}$".

Any and all humanized light chain variable domain amino acid sequences which comprise the CDRs of 6G4.2.5LV/L1S26A,N35A are collectively referred to herein as "hu6G4.2.5LV/L1S26A,N35A".

Any and all humanized light chain variable domain amino acid sequences which comprise the CDRs of 6G4.2.5LV/L1N35$X_{35}$/L3H98$X_{98}$ are collectively referred to herein as "hu6G4.2.5LV/L1N35$X_{35}$/L3H98$X_{98}$".

Any and all humanized light chain variable domain amino acid sequences which comprise the CDRs of 6G4.2.5LV/L1N35A/L3H98A are collectively referred to herein as "hu6G4.2.5LV/L1N35A/L3H98A".

Any and all humanized light chain variable domain amino acid sequences which comprise the CDRs of 6G4.2.5LV/L1S26$X_{26}$/L3H98$X_{98}$ are collectively referred to herein as "hu6G4.2.5LV/L1S26$X_{26}$/L3H98$X_{98}$".

Any and all humanized light chain variable domain amino acid sequences which comprise the CDRs of 6G4.2.5LV/L1S26A/L3H98A are collectively referred to herein as "hu6G4.2.5LV/L1S26A/L3H98A".

Any and all humanized light chain variable domain amino acid sequences which comprise the CDRs of 6G4.2.5LV/L1S26$X_{26}$,N35$X_{35}$/L3H98$X_{98}$ are collectively refer herein as "hu6G4.2.5LV/L1S26$X_{26}$,N35$X_{35}$/L3H98$X_{98}$".

Any and all humanized light chain variable domain amino acid sequences which comprise the CDRs of 6G4.2.5LV/L1S26A,N35A/L3H98A are collectively referred to herein as "hu6G4.2.5LV/L1S26A,N35A/L3H98A".

The humanized light chain variable domain amino acid sequences of hu6G4.2.5LV/L1N35$X_{35}$, hu6G4.2.5LV/L1S26$X_{26}$, hu6G4.2.5LV/L1S26$X_{26}$/L3H98$X_{98}$, hu6G4.2.5LV/L1S26$X_{26}$,N35$X_{35}$, hu6G4.2.5LV/L1N35$X_{35}$/L3H98$X_{98}$, hu6G4.2.5LV/L1S26$X_{26}$/L3H98$X_{98}$, and hu6G4.2.5LV/L1S26$X_{26}$,N35$X_{35}$/L3H98$X_{98}$ are collectively referred to herein as "hu6G4.2.5LV/vL1-3X".

The humanized light chain variable domain amino acid sequences of hu6G4.2.5LV/L1N35A, hu6G4.2.5LV/L1S26A, hu6G4.2.5LV/L1S26A/L3H98A, hu6G4.2.5LV/L1S26A,N35A, hu6G4.2.5LV/L1N35A/L3H98A, hu6G4.2.5LV/L1S26A/L3H98A, hu6G4.2.5LV/L1S26A,N35A/L3H98A are collectively referred to herein as "hu6G4.2.5LV/vL1-3A".

Any and all humanized heavy chain variable domain amino acid sequences which comprise the CDRs of 6G4.2.5HV are collectively referred to herein as "hu6G4.2.5HV".

Any and all humanized heavy chain variable domain amino acid sequences which comprise the CDRs of 6G4.2.5HV/H1S31$Z_{31}$ are collectively referred to herein as "hu6G4.2.5HV/H1S31$Z_{31}$".

Any and all humanized heavy chain variable domain amino acid sequences which comprise the CDRs of 6G4.2.5HV/H1S31A are collectively referred to herein as "hu6G4.2.5HV/H1S31A".

Any and all humanized heavy chain variable domain amino acid sequences which comprise the CDRs of 6G4.2.5HV/H2S54$Z_{54}$ are collectively referred to herein as "hu6G4.2.5HV/H2S54$Z_{54}$".

Any and all humanized heavy chain variable domain amino acid sequences which comprise the CDRs of 6G4.2.5HV/H2S54A are collectively referred to herein as "hu6G4.2.5HV/H2S54A".

Any and all humanized heavy chain variable domain amino acid sequences which comprise the CDRs of 6G4.2.5HV/H3D100E are collectively referred to herein as "hu6G4.2.5HV/H3D100E".

Any and all humanized heavy chain variable domain amino acid sequences which comprise the CDRs of 6G4.2.5HV/H3R102K are collectively referred to herein as "hu6G4.2.5HV/H3R102K".

Any and all humanized heavy chain variable domain amino acid sequences which comprise the CDRs of 6G4.2.5HV/H3D106E are collectively referred to herein as "hu6G4.2.5HV/H3D106E".

Any and all humanized heavy chain variable domain amino acid sequences which comprise the CDRs of 6G4.2.5HV/H3D100E,R102K are collectively referred to herein as "hu6G4.2.5HV/H3D100E,R102K".

Any and all humanized heavy chain variable domain amino acid sequences which comprise the CDRs of 6G4.2.5HV/H3R102K,D106E are collectively referred to herein as "hu6G4.2.5HV/H3R102K,D106E".

Any and all humanized heavy chain variable domain amino acid sequences which comprise the CDRs of 6G4.2.5HV/H3D100E,D106E are collectively referred to herein as "hu6G4.2.5HV/H3D100E,D106E".

Any and all humanized heavy chain variable domain amino acid sequences which comprise the CDRs of 6G4.2.5HV/H3D100E,R102K,D106E are collectively referred to herein as "hu6G4.2.5HV/H3D100E,R102K,D106E".

Any and all humanized heavy chain variable domain amino acid sequences which comprise the CDRs of 6G4.2.5HV/H1S31$Z_{31}$/H2S54$Z_{54}$ are collectively referred to herein as "hu6G4.2.5HV/H1S31$Z_{31}$/H2S54$Z_{54}$".

Any and all humanized heavy chain variable domain amino acid sequences which comprise the CDRs of 6G4.2.5HV/H1S31$Z_{31}$/H3D100E are collectively referred to herein as "hu6G4.2.5HV/H1S31$Z_{31}$/H3D100E".

Any and all humanized heavy chain variable domain amino acid sequences which comprise the CDRs of 6G4.2.5HV/H1S31$Z_{31}$/H3R102K are collectively referred to herein as "hu6G4.2.5HV/H1S31$Z_{31}$/H3R102K".

Any and all humanized heavy chain variable domain amino acid sequences which comprise the CDRs of 6G4.2.5HV/H1S31$Z_{31}$/H3D106E are collectively referred to herein as "hu6G4.2.5HV/H1S31$Z_{31}$/H3D106E".

Any and all humanized heavy chain variable domain amino acid sequences which comprise the CDRs of 6G4.2.5HV/H1S31$Z_{31}$/H3D100E,R102K are collectively referred to herein as "hu6G4.2.5HV/H1S31$Z_{31}$/H3D100E,R102K".

Any and all humanized heavy chain variable domain amino acid sequences which comprise the CDRs of 6G4.2.5HV/H1S31$Z_{31}$/H3R102K,D106E are collectively referred to herein as "hu6G4.2.5HV/H1S31$Z_{31}$/H3R102K,D106E".

Any and all humanized heavy chain variable domain amino acid sequences which comprise the CDRs of 6G4.2.5HV/H1S31$Z_{31}$/H3D100E,D106E are collectively referred to herein as "hu6G4.2.5HV/H1S31$Z_{31}$/H3D100E,D106E".

Any and all humanized heavy chain variable domain amino acid sequences which comprise the CDRs of 6G4.2.5HV/H1S31$Z_{31}$/H3D100E,R102K,D106E are collectively referred to herein as "hu6G4.2.5HV/H1S31$Z_{31}$/H3D100E,R102K,D106E".

Any and all humanized heavy chain variable domain amino acid sequences which comprise the CDRs of 6G4.2.5HV/H2S54$Z_{54}$/H3D100E are collectively referred to herein as "hu6G4.2.5HV/H2S54$Z_{54}$/H3D100E".

Any and all humanized heavy chain variable domain amino acid sequences which comprise the CDRs of 6G4.2.5HV/H2S54$Z_{54}$/H3R102K are collectively referred to herein as "hu6G4.2.5HV/H2S54$Z_{54}$/H3R102K".

Any and all humanized heavy chain variable domain amino acid sequences which comprise the CDRs of 6G4.2.5HV/H2S54$Z_{54}$/H3D106E are collectively referred to herein as "hu6G4.2.5HV/H2S54$Z_{54}$/H3D106E".

Any and all humanized heavy chain variable domain amino acid sequences which comprise the CDRs of 6G4.2.5HV/H2S54$Z_{54}$/H3R102K,D106E are collectively referred to herein as "hu6G4.2.5HV/H2S54$Z_{54}$/H3R102K, D106E".

Any and all humanized heavy chain variable domain amino acid sequences which comprise the CDRs of 6G4.2.5HV/H2S54$Z_{54}$/H3D100E,D106E are collectively referred to herein as "hu6G4.2.5HV/H2S54$Z_{54}$/H3D100E, D106E".

Any and all humanized heavy chain variable domain amino acid sequences which comprise the CDRs of 6G4.2.5HV/H2S54$Z_{54}$/H3D100E,R102K,D106E are collectively referred to herein as "hu6G4.2.5HV/H2S54$Z_{54}$/H3D100E,R102K,D106E".

Any and all humanized heavy chain variable domain amino acid sequences which comprise the CDRs of 6G4.2.5HV/H1S31$Z_{31}$/H2S54$Z_{54}$/H3D100E are collectively referred to herein as "hu6G4.2.5HV/H1S31$Z_{31}$/H2S54$Z_{54}$/H3D100E".

Any and all humanized heavy chain variable domain amino acid sequences which comprise the CDRs of 6G4.2.5HV/H1S31$Z_{31}$/H2S54$Z_{54}$/H3R102K are collectively referred to herein as "hu6G4.2.5HV/H1S31$Z_{31}$/H2S54$Z_{54}$/H3R102K".

Any and all humanized heavy chain variable domain amino acid sequences which comprise the CDRs of 6G4.2.5HV/H1S31$Z_{31}$/H2S54$Z_{54}$/H3D106E are collectively referred to herein as "hu6G4.2.5HV/H1S31$Z_{31}$/H2S54$Z_{54}$/H3D106E".

Any and all humanized heavy chain variable domain amino acid sequences which comprise the CDRs of 6G4.2.5HV/H1S31$Z_{31}$/H2S54$Z_{54}$/H3D100E,R102K are collectively referred to herein as "hu6G4.2.5HV/H1S31$Z_{31}$/H2S54$Z_{54}$/H3D100E,R102K".

Any and all humanized heavy chain variable domain amino acid sequences which comprise the CDRs of 6G4.2.5HV/H1S31$Z_{31}$/H2S54$Z_{54}$/H3R102K,D106E are collectively referred to herein as "hu6G4.2.5HV/H1S31$Z_{31}$/H2S54$Z_{54}$/H3R102K,D106E".

Any and all humanized heavy chain variable domain amino acid sequences which comprise the CDRs of 6G4.2.5HV/H1S31$Z_{31}$/H2S54$Z_{54}$/H3D100E,D106E are collectivelly referred to herein as "hu6G4.2.5HV/H1S31$Z_{31}$/H2S54$Z_{54}$/H3D100E,D106E".

Any and all humanized heavy chain variable domain amino acid sequences which comprise the CDRs of 6G4.2.5HV/H1S31$Z_{31}$/H2S54$Z_{54}$/H3D100E,R102K, D106E are collectively referred to herein as "hu6G4.2.5HV/H1S31$Z_{31}$/H2S54$Z_{54}$/H3D100E,R102K,D106E".

Any and all humanized heavy chain variable domain amino acid sequences which comprise the CDRs of 6G4.2.5HV/H1S31A/H2S54A are collectively referred to herein as "hu6G4.2.5HV/H1S31A/H2S54A".

Any and all humanized heavy chain variable domain amino acid sequences which comprise the CDRs of 6G4.2.5HV/H1S31A/H3D100E are collectively referred to herein as "hu6G4.2.5HV/H1S31A/H3D100E".

Any and all humanized heavy chain variable domain amino acid sequences which comprise the CDRs of 6G4.2.5HV/H1S31A/H3R102K are collectively referred to herein as "hu6G4.2.5HV/H1S31A/H3R102K".

Any and all humanized heavy chain variable domain amino acid sequences which comprise the CDRs of 6G4.2.5HV/H1S31A/H3D106E are collectively referred to herein as "hu6G4.2.5HV/H1S3A/H3D106E".

Any and all humanized heavy chain variable domain amino acid sequences which comprise the CDRs of 6G4.2.5HV/H1S31A/H3D100E,R102K are collectively referred to herein as "hu6G4.2.5HV/H1S31A/H3D100E, R102K".

Any and all humanized heavy chain variable domain amino acid sequences which comprise the CDRs of 6G4.2.5HV/H1S31A/H3R102K,D106E are collectively referred to herein as "hu6G4.2.5HV/H1S31A/H3R102K, D106E".

Any and all humanized heavy chain variable domain amino acid sequences which comprise the CDRs of 6G4.2.5HV/H1S31A/H3D100E,D106E are collectively referred to herein as "hu6G4.2.5HV/H1S31A/H3D100E, D106E".

Any and all humanized heavy chain variable domain amino acid sequences which comprise the CDRs of 6G4.2.5HV/H1S31A/H3D100E,R102K,D106E are collectively referred to herein as "hu6G4.2.5HV/H1S31A/H3D100E,R102K,D106E".

Any and all humanized heavy chain variable domain amino acid sequences which comprise the CDRs of 6G4.2.5HV/H2S54A/H3D100E are collectively referred to herein as "hu6G4.2.5HV/H2S54A/H3D100E".

Any and all humanized heavy chain variable domain amino acid sequences which comprise the CDRs of 6G4.2.5HV/H2S54A/H3R102K are collectively referred to herein as "hu6G4.2.5HV/H2S54A/H3R102K".

Any and all humanized heavy chain variable domain amino acid sequences which comprise the CDRs of 6G4.2.5HV/H2S54A/H3D106E are collectively referred to herein as "hu6G4.2.5HV/H2S54A/H3D106E".

Any and all humanized heavy chain variable domain amino acid sequences which comprise the CDRs of 6G4.2.5HV/H2S54A/H3R102K,D106E are collectively referred to herein as "hu6G4.2.5HV/H2S54A/H3R102K, D106E".

Any and all humanized heavy chain variable domain amino acid sequences which comprise the CDRs of 6G4.2.5HV/H2S54A/H3D100E,D106E are collectively referred to herein as "hu6G4.2.5HV/H2S54A/H3D100E, D106E".

Any and all humanized heavy chain variable domain amino acid sequences which comprise the CDRs of 6G4.2.5HV/H2S54A/H3D100E,R102K,D106E are collectively referred to herein as "hu6G4.2.5HV/H2S54A/H3D100E,R102K,D106E".

Any and all humanized heavy chain variable domain amino acid sequences which comprise the CDRs of 6G4.2.5HV/H1S31A/H2S54A/H3D100E are collectively referred to herein as "hu6G4.2.5HV/H1S31A/H2S54A/H3D100E".

Any and all humanized heavy chain variable domain amino acid sequences which comprise the CDRs of 6G4.2.5HV/H1S31A/H2S54A/H3R102K are collectively referred to herein as "hu6G4.2.5HV/H1S31A/H2S54A/H3R102K".

Any and all humanized heavy chain variable domain amino acid sequences which comprise the CDRs of 6G4.2.5HV/H1S31A/H2S54A/H3D106E are collectively referred to herein as "hu6G4.2.5HV/H1S31A/H2S54A/H3D106E".

Any and all humanized heavy chain variable domain amino acid sequences which comprise the CDRs of 6G4.2.5HV/H1S31A/H2S54A/H3D100E,R102K are collectively referred to herein as "hu6G4.2.5HV/H1S31A/H2S54A/H3D100E,R102K".

Any and all humanized heavy chain variable domain amino acid sequences which comprise the CDRs of 6G4.2.5HV/H1S31A/H2S54A/H3R102K,D106E are collectively referred to herein as "hu6G4.2.5HV/H1S31A/H2S54A/H3R102K,D106E".

Any and all humanized heavy chain variable domain amino acid sequences which comprise the CDRs of 6G4.2.5HV/H1S31A/H2S54A/H3D100E,D106E are collectively referred to herein as "hu6G4.2.5HV/H1S31A/H2S54A/H3D100E,D106E".

Any and all humanized heavy chain variable domain amino acid sequences which comprise the CDRs of 6G4.2.5HV/H1S31A/H2S54A/H3D100E,R102K,D106E are collectively referred to herein as "hu6G4.2.5HV/H1S31A/H2S54A/H3D100E,R102K,D106E".

The humanized heavy chain variable domain amino acid sequences of hu6G4.2.5HV/H1S31$Z_{31}$, hu6G4.2.5HV/H2S54$Z_{54}$, hu6G4.2.5HV/H3D100E, hu6G4.2.5HV/H3R102K, hu6G4.2.5HV/H3D106E, hu6G4.2.5HV/H3D100E,R102K, hu6G4.2.5HV/H3R102K,D106E, hu6G4.2.5HV/H3D100E,D106E, hu6G4.2.5HV/H3D100E,R102K,D106E, hu6G4.2.5HV/H1S31$Z_{31}$/H2S54$Z_{54}$, hu6G4.2.5HV/H1S31$Z_{31}$/H3D100E, hu6G4.2.5HV/H1S31$Z_{31}$/H3R102K, hu6G4.2.5HV/H1S31$Z_{31}$/H3D106E, hu6G4.2.5HV/H1S31$Z_{31}$/H3D100E,R102K, hu6G4.2.5HV/H1S31$Z_{31}$/H3R102K,D106E, hu6G4.2.5HV/H1S31$Z_{31}$/H3D100E,D106E, hu6G4.2.5HV/H1S31$Z_{31}$/H3D100E,R102K,D106E, hu6G4.2.5HV/H2S54$Z_{54}$/H3D100E, hu6G4.2.5HV/H2S54$Z_{54}$/H3R102K, hu6G4.2.5HV/H2S54$Z_{54}$/H3D106E, hu6G4.2.5HV/H2S54$Z_{54}$/H3R102K,D106E, hu6G4.2.5HV/H2S54$Z_{54}$/H3D100E,D106E, hu6G4.2.5HV/H2S54$Z_{54}$/H3D00E,R102K,D106E, hu6G4.2.5HV/H1S31$Z_{31}$/H2S54$Z_{54}$/H3D100E, hu6G4.2.5HV/H1S31$Z_{31}$/H2S54$Z_{54}$/h3R102K, hu6G4.2.5HV/H1S31$Z_{31}$/H2S54$Z_{54}$/H3D106E, hu6G4.2.5HV/H1S31$Z_{31}$/H2S54$Z_{54}$/H3D100E,R102K, hu6G4.2.5HV/H1S31$Z_{31}$/H2S54$Z_{54}$/H3R102K,D106E, hu6G4.2.5HV/H1S31$Z_{31}$/H2S54$Z_{54}$/H3D100E,D106E, and hu6G4.2.5HV/H1S31$Z_{31}$/H2S54$Z_{54}$/H3D100E,R102K,D106E are collectively referred to herein as "hu6G4.2.5HV/vH1-3Z".

The humanized heavy chain variable domain amino acid sequences of hu6G4.2.5HV/H1S31A, hu6G4.2.5HV/H2S54A, hu6G4.2.5HV/H3D100E, hu6G4.2.5HV/H3R102K, hu6G4.2.5HV/H3D106E, hu6G4.2.5HV/H3D100E,R102K, hu6G4.2.5HV/H3R102K,D106E, hu6G4.2.5HV/H3D100E,D106E, hu6G4.2.5HV/H3D100E,R102K,D106E, hu6G4.2.5HV/H1S31A/H2S54A, hu6G4.2.5HV/H1S31A/H3D100E, hu6G4.2.5HV/H1S31A/H3R102K, hu6G4.2.5HV/H1S31A/H3D106E, hu6G4.2.5HV/H1S31A/H3D100E,R102K, hu6G4.2.5HV/H1S31A/H3R102K,D106E, hu6G4.2.5HV/H1S31A/H3D100E,D106E, hu6G4.2.5HV/H1S31A/H3D100E,R102K,D106E, hu6G4.2.5HV/H2S54A/H3D100E, hu6G4.2.5HV/H2S54A/H3R102K, hu6G4.2.5HV/H2S54A/H3D106E, hu6G4.2.5HV/H2S54A/H3R102K,D106E, hu6G4.2.5HV/H2S54A/H3D100E,D106E, hu6G4.2.5HV/H2S54A/H3D100E,R102K,D106E, hu6G4.2.5HV/H1S31A/H2S54A/H3D100E, hu6G4.2.5HV/H1S31A/H2S54A/H3R102K, hu6G4.2.5HV/H1S31A/H2S54A/H3D106E, hu6G4.2.5HV/H1S31A/H2S54A/H3D100E,R102K, hu6G4.2.5HV/H1S31A/H2S54A/H3R102K,D106E, hu6G4.2.5HV/H1S31A/H2S54A/H3D100E,D106E, and hu6G4.2.5HV/H1S31A/H2S54A/H3D100E,R102K,D106E are collectively referred to herein as "hu6G4.2.5HV/vH1-3A".

The invention provides a humanized antibody or antibody fragment that comprises a light chain variable domain comprising the hu6G4.2.5LV/vL1-3X. In another embodiment, the invention provides a humanized antibody or antibody fragment that comprises a light chain variable domain comprising the hu6G4.2.5LV/vL1-3A. In yet another embodiment, the invention provides a humanized antibody or antibody fragment that comprises a light chain variable domain comprising the hu6G4.2.5LV/L1N35$X_{35}$. In still another embodiment, the invention provides a humanized antibody or antibody fragment that comprises a light chain variable domain comprising the hu6G4.2.5LV/L1N35A. In a further embodiment, the invention provides a humanized antibody or antibody fragment that comprises a light chain variable domain comprising the hu6G4.2.5LV/L1N35E.

The invention additionally provides a humanized antibody or antibody fragment that comprises a light chain variable domain comprising the hu6G4.2.5LV/vL1-3X, and further comprises a heavy chain variable domain comprising the hu6G4.2.5HV or hu6G4.2.5HV/vH1-3Z. In another embodiment, the invention provides a humanized antibody or antibody fragment that comprises a light chain variable domain comprising the hu6G4.2.5LV/vL1-3A, and further comprises a heavy chain variable domain comprising the hu6G4.2.5HV or hu6G4.2.5HV/vH1-3Z. In yet another embodiment, the invention provides a humanized antibody or antibody fragment that comprises a light chain variable domain comprising the hu6G4.2.5LV/vL1-3A, and further comprises a heavy chain variable domain comprising the hu6G4.2.5HV/vH1-3A.

In a further embodiment, the invention provides a humanized antibody or antibody fragment that comprises a light chain variable domain comprising the hu6G4.2.5LV/L1N35$X_{35}$, and further comprises a heavy chain variable domain comprising the hu6G4.2.5HV or hu6G4.2.5HV/vH1-3Z. In another embodiment, the invention provides a humanized antibody or antibody fragment that comprises a light chain variable domain comprising the hu6G4.2.5LV/N35$X_{35}$, and further comprises a heavy chain variable domain comprising the hu6G4.2.5HV/vH1-3A. In a preferred embodiment, the antibody or antibody fragment comprises a light chain variable domain comprising the hu6G4.2.5LV/L1N35$X_{35}$ and further comprises a humanized heavy chain comprising the amino acid sequence of 6G4.2.5HV11.

In an additional embodiment, the invention provides a humanized antibody or antibody fragment that comprises a light chain variable domain comprising the hu6G4.2.5LV/L1N35A, and further comprises a heavy chain variable domain comprising the hu6G4.2.5HV or hu6G4.2.5HV/vH1-3Z. In another embodiment, the invention provides a humanized antibody or antibody fragment that comprises a light chain variable domain comprising the hu6G4.2.5LV/N35A, and further comprises a heavy chain variable domain comprising the hu6G4.2.5HV/vH1-3A. In still another embodiment, the humanized antibody or antibody fragment comprises a light chain variable domain comprising the hu6G4.2.5LV/L1N35A, and further comprises a heavy chain variable domain comprising the hu6G4.2.5HV. In a further embodiment, the humanized antibody or antibody fragment comprises a light chain variable domain comprising the hu6G4.2.5LV/L1N35E, and further comprises a heavy chain variable domain comprising the hu6G4.2.5HV. In a preferred embodiment, the antibody or antibody fragment comprises a light chain variable domain comprising the hu6G4.2.5LV/L1N35A and further comprises a humanized heavy chain comprising the amino acid sequence of 6G4.2.5HV11. In another preferred embodiment, the antibody or antibody fragment comprises a light chain variable domain comprising the hu6G4.2.5LV/L1N35E and further comprises a humanized heavy chain comprising the amino acid sequence of 6G4.2.5HV11.

The invention encompasses a single chain antibody fragment comprising the hu6G4.2.5LV/vL1-3X, with or without any additional amino acid sequence. In one embodiment, the invention provides a single chain antibody fragment comprising the hu6G4.2.5LV/vL1-3X without any associated heavy chain variable domain amino acid sequence, i.e. a single chain species that makes up one half of an Fv fragment. In another embodiment, the invention provides a single chain antibody fragment comprising the hu6G4.2.5LV/vL1-3A without any associated heavy chain variable domain amino acid sequence. In still another embodiment, the invention provides a single chain antibody fragment comprising the hu6G4.2.5LV/L1N35$X_{35}$ without any associated heavy chain variable domain amino acid sequence. In a preferred embodiment, the invention provides a single chain antibody fragment comprising the hu6G4.2.5LV/L1N35A without any associated heavy chain variable domain amino acid sequence. In another preferred embodiment, the invention provides a single chain antibody fragment comprising the hu6G4.2.5LV/L1N35E without any associated heavy chain variable domain amino acid sequence.

In one embodiment, the invention provides a single chain antibody fragment wherein the hu6G4.2.5LV/vL1-3X and the hu6G4.2.5HV or hu6G4.2.5HV/vH1-3Z are contained in a single chain polypeptide species. In a preferred embodiment, the single chain antibody fragment is a scFv species comprising the hu6G4.2.5LV/vL1-3X joined to the hu6G4.2.5HV or hu6G4.2.5HV/vH1-3Z by means of a flexible peptide linker sequence, wherein the heavy chain and light chain variable domains can associate in a "dimeric" structure analogous to that formed in a two-chain Fv species. In another embodiment, the single chain antibody fragment is a species comprising the hu6G4.2.5LV/vL1-3X joined to the hu6G4.2.5HV or hu6G4.2.5HV/vH1-3Z by a linker that is too short to permit intramolecular pairing of the two variable domains, i.e. a single chain polypeptide monomer that forms a diabody upon dimerization with another monomer.

In another embodiment, the invention provides a single chain antibody fragment wherein the hu6G4.2.5LV/vL1-3A and the hu6G4.2.5HV or hu6G4.2.5HV/vH1-3Z are contained in a single chain polypeptide species. In a preferred embodiment, the single chain antibody fragment is a scFv species comprising the hu6G4.2.5LV/vL1-3A joined to the hu6G4.2.5HV or hu6G4.2.5HV/vH1-3Z by means of a flexible peptide linker sequence, wherein the heavy chain and light chain variable domains can associate in a "dimeric" structure analogous to that formed in a two-chain Fv species. In another embodiment, the single chain antibody fragment is a species comprising the hu6G4.2.5LV/vL1-3A joined to the hu6G4.2.5HV or hu6G4.2.5HV/vH1-3Z by a linker that is too short to permit intramolecular pairing of the two variable domains, i.e. a single chain polypeptide monomer that forms a diabody upon dimerization with another monomer.

In yet another embodiment, the invention provides a single chain antibody fragment wherein the hu6G4.2.5LV/vL1-3A and the hu6G4.2.5HV/vH1-3A are contained in a single chain polypeptide species. In a preferred embodiment, the single chain antibody fragment is a scFv species comprising the hu6G4.2.5LV/vL1-3A joined to the hu6G4.2.5HV/vH1-3A by means of a flexible peptide linker sequence, wherein the heavy chain and light chain variable domains can associate in a "dimeric" structure analogous to that formed in a two-chain Fv species. In another embodiment, the single chain antibody fragment is a species comprising the hu6G4.2.5LV/vL1-3A joined to the hu6G4.2.5HV/vH1-3A by a linker that is too short to permit intramolecular pairing of the two variable domains, i.e. a single chain polypeptide monomer that forms a diabody upon dimerization with another monomer.

In still another embodiment, the invention provides a single chain antibody fragment wherein the hu6G4.2.5LV/L1N35$X_{35}$ and the hu6G4.2.5HV or hu6G4.2.5HV/vH1-3Z are contained in a single chain polypeptide species. In a preferred embodiment, the single chain antibody fragment is a scFv species comprising the hu6G4.2.5LV/L1N35$X_{35}$ joined to the hu6G4.2.5HV or hu6G4.2.5HV/vH1-3Z by means of a flexible peptide linker sequence, wherein the heavy chain and light chain variable domains can associate in a "dimeric" structure analogous to that formed in a two-chain Fv species. In another embodiment, the single chain antibody fragment is a species comprising the hu6G4.2.5LV/L1N35$X_{35}$ joined to the hu6G4.2.5HV or hu6G4.2.5HV/vH1-3Z by a linker that is too short to permit intramolecular pairing of the two variable domains, i.e. a single chain polypeptide monomer that forms a diabody upon dimerization with another monomer.

In a further embodiment, the invention provides a single chain antibody fragment wherein the hu6G4.2.5LV/L1N35$X_{35}$ and the hu6G4.2.5HV/vH1-3A are contained in a single chain polypeptide species. In a preferred embodiment, the single chain antibody fragment is a scFv species comprising the hu6G4.2.5LV/L1N35$X_{35}$ joined to the hu6G4.2.5HV/vH1-3A by means of a flexible peptide linker sequence, wherein the heavy chain and light chain variable domains can associate in a "dimeric" structure analogous to that formed in a two-chain Fv species. In another embodiment, the single chain antibody fragment is a species comprising the hu6G4.2.5LV/L1N35$X_{35}$ joined to the hu6G4.2.5HV/vH1-3A by a linker that is too short to permit intramolecular pairing of the two variable domains, i.e. a single chain polypeptide monomer that forms a diabody upon dimerization with another monomer.

In an additional embodiment, the invention provides a single chain antibody fragment wherein the hu6G4.2.5LV/L1N35A and the hu6G4.2.5HV or hu6G4.2.5HV/vH1-3Z are contained in a single chain polypeptide species. In a preferred embodiment, the single chain antibody fragment is a scFv species comprising the hu6G4.2.5LV/L1N35A joined to the hu6G4.2.5HV or hu6G4.2.5HV/vH1-3Z by means of a flexible peptide linker sequence, wherein the heavy chain and light chain variable domains can associate in a "dimeric" structure analogous to that formed in a two-chain Fv species. In another embodiment, the single chain antibody fragment is a species comprising the hu6G4.2.5LV/L1N35A joined to the hu6G4.2.5HV or hu6G4.2.5HV/vH1-3Z by a linker that is too short to permit intramolecular pairing of the two variable domains, i.e. a single chain polypeptide monomer that forms a diabody upon dimerization with another monomer.

Also provided herein is a single chain antibody fragment wherein the hu6G4.2.5LV/L1N35E and the hu6G4.2.5HV are contained in a single chain polypeptide species. In a preferred embodiment, the single chain antibody fragment is a scFv species comprising the hu6G4.2.5LV/L1N35E joined to the hu6G4.2.5HV by means of a flexible peptide linker sequence, wherein the heavy chain and light chain variable domains can associate in a "dimeric" structure analogous to that formed in a two-chain Fv species. In another embodiment, the single chain antibody fragment is a species comprising the hu6G4.2.5LV/L1N35E joined to the hu6G4.2.5HV by a linker that is too short to permit intramolecular pairing of the two variable domains, i.e. a single chain polypeptide monomer that forms a diabody upon dimerization with another monomer.

In still another embodiment, the invention provides a single chain antibody fragment wherein the hu6G4.2.5LV/L1N35A and the hu6G4.2.5HV/vH1-3A are contained in a single chain polypeptide species. In a preferred embodiment, the single chain antibody fragment is a scFv species comprising the hu6G4.2.5LV/L1N35A joined to the hu6G4.2.5HV/vH1-3A by means of a flexible peptide linker sequence, wherein the heavy chain and light chain variable domains can associate in a "dimeric" structure analogous to that formed in a two-chain Fv species. In another embodiment, the single chain antibody fragment is a species comprising the hu6G4.2.5LV/L1N35A joined to the hu6G4.2.5HV/vH1-3A by a linker that is too short to permit intramolecular pairing of the two variable domains, i.e. a single chain polypeptide monomer that forms a diabody upon dimerization with another monomer.

In yet another embodiment, the invention provides an antibody fragment comprising a plurality of polypeptide chains, wherein one polypeptide chain comprises the hu6G4.2.5LV/vL1-3X and a second polypeptide chain comprises the hu6G4.2.5HV or hu6G4.2.5HV/vH1-3Z and the two polypeptide chains are covalently linked by one or more interchain disulfide bonds.

In still another embodiment, the invention provides an antibody fragment comprising a plurality of polypeptide chains, wherein one polypeptide chain comprises the hu6G4.2.5LV/vL1-3X and a second polypeptide chain comprises the hu6G4.2.5HV/vH1-3A and the two polypeptide chains are covalently linked by one or more interchain disulfide bonds. In a preferred embodiment, the invention provides an antibody fragment comprising a plurality of polypeptide chains, wherein one polypeptide chain comprises the hu6G4.2.5LV/vL1-3X and a second polypeptide chain comprises the amino acid sequence of 6G4.2.5HV11 and the two polypeptide chains are covalently linked by one or more interchain disulfide bonds.

In a further embodiment, the invention provides an antibody fragment comprising a plurality of polypeptide chains, wherein one polypeptide chain comprises the hu6G4.2.5LV/vL1- 3A and a second polypeptide chain comprises the hu6G4.2.5HV or hu6G4.2.5HV/vH1-3Z and the two polypeptide chains are covalently linked by one or more interchain disulfide bonds.

In still another embodiment, the invention provides an antibody fragment comprising a plurality of polypeptide chains, wherein one polypeptide chain comprises the hu6G4.2.5LV/vL1-3A and a second polypeptide chain comprises the hu6G4.2.5HV/vH1-3A and the two polypeptide chains are covalently linked by one or more interchain disulfide bonds. In a preferred embodiment, the invention provides an antibody fragment comprising a plurality of polypeptide chains, wherein one polypeptide chain comprises the hu6G4.2.5LV/vL1-3A and a second polypeptide chain comprises the amino acid sequence of 6G4.2.5HV11 and the two polypeptide chains are covalently linked by one or more interchain disulfide bonds.

The invention also encompasses an antibody fragment comprising a plurality of polypeptide chains, wherein one polypeptide chain comprises the hu6G4.2.5LV/L1N35$X_{35}$ and a second polypeptide chain comprises the hu6G4.2.5HV or hu6G4.2.5HV/vH1-3Z and the two polypeptide chains are covalently linked by one or more interchain disulfide bonds.

In still another embodiment, the invention provides an antibody fragment comprising a plurality of polypeptide chains, wherein one polypeptide chain comprises the hu6G4.2.5LV/L1N35$X_{35}$ and a second polypeptide chain comprises the hu6G4.2.5HV/vH1-3A and the two polypeptide chains are covalently linked by one or more interchain disulfide bonds. In a preferred embodiment, the invention provides an antibody fragment comprising a plurality of polypeptide chains, wherein one polypeptide chain comprises the hu6G4.2.5LV/L1N35$X_{35}$ and a second polypeptide chain comprises the amino acid sequence of 6G4.2.5HV11 and the two polypeptide chains are covalently linked by one or more interchain disulfide bonds.

The invention further encompasses an antibody fragment comprising a plurality of polypeptide chains, wherein one polypeptide chain comprises the hu6G4.2.5LV/L1N35A and a second polypeptide chain comprises the hu6G4.2.5HV or hu6G4.2.5HV/vH1-3Z and the two polypeptide chains are covalently linked by one or more interchain disulfide bonds.

The invention also encompasses an antibody fragment comprising a plurality of polypeptide chains, wherein one polypeptide chain comprises the hu6G4.2.5LV/L1N35E and a second polypeptide chain comprises the hu6G4.2.5HV and the two polypeptide chains are covalently linked by one or more interchain disulfide bonds.

In still another embodiment, the invention provides an antibody fragment comprising a plurality of polypeptide chains, wherein one polypeptide chain comprises the hu6G4.2.5LV/L1N35A and a second polypeptide chain comprises the hu6G4.2.5HV/vH1-3A and the two polypeptide chains are covalently linked by one or more interchain disulfide bonds. In a preferred embodiment, the invention provides an antibody fragment comprising a plurality of polypeptide chains, wherein one polypeptide chain comprises the hu6G4.2.5LV/L1N35A and a second polypeptide chain comprises the amino acid sequence of 6G4.2.5HV11 and the two polypeptide chains are covalently linked by one or more interchain disulfide bonds. In another preferred embodiment, the invention provides an antibody fragment comprising a plurality of polypeptide chains, wherein one polypeptide chain comprises the hu6G4.2.5LV/L1N35E and a second polypeptide chain comprises the amino acid sequence of 6G4.2.5HV11 and the two polypeptide chains are covalently linked by one or more interchain disulfide bonds.

In a preferred embodiment, any of the foregoing two-chain antibody fragments are selected from the group consisting of Fab, Fab', Fab'-SH, Fv, and F(ab')$_2$. In another preferred embodiment, the antibody fragment is selected from the group consisting of Fab, Fab', Fab'-SH, Fv, and F(ab')$_2$, wherein the antibody fragment comprises one polypeptide chain comprising the hu6G4.2.5LV/L1N35$X_{35}$ and a second polypeptide chain comprising the hu6G4.2.5HV. In yet another preferred embodiment, the antibody fragment is selected from the group consisting of Fab, Fab', Fab'-SH, Fv, and F(ab')$_2$, wherein the antibody fragment comprises one polypeptide chain comprising the hu6G4.2.5LV/L1N35A and a second polypeptide chain comprising the hu6G4.2.5HV. In a further preferred embodiment, the antibody fragment is selected from the group consisting of Fab, Fab', Fab'-SH, Fv, and F(ab')$_2$, wherein the antibody fragment comprises one polypeptide chain comprising the hu6G4.2.5LV/L1N35E and a second polypeptide chain comprising the hu6G4.2.5HV. In still another preferred embodiment, the antibody fragment is a F(ab')$_2$ that comprises one polypeptide chain comprising the hu6G4.2.5LV/L1N35A and a second polypeptide chain comprising the amino acid sequence of 6G4.2.5HV11. In an additional preferred embodiment, the antibody fragment is a F(ab')$_2$ that comprises one polypeptide chain comprising the hu6G4.2.5LV/L1N35E and a second polypeptide chain comprising the amino acid sequence of 6G4.2.5HV11.

The invention also provides an antibody or antibody fragment comprising a light chain variable domain containing the hu6G4.2.5LV/vL1-3X and optionally further comprising a heavy chain variable domain containing the hu6G4.2.5HV or hu6G4.2.5HV/vH1-3Z, wherein the light chain variable domain, and optionally the heavy chain variable domain, is (are) fused to an additional moiety, such as a immunoglobulin constant domain. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat et al.

The invention additionally provides an antibody or antibody fragment comprising a light chain variable domain containing the hu6G4.2.5LV/vL1-3X and optionally further comprising a heavy chain variable domain containing the hu6G4.2.5HV/vH1-3A, wherein the light chain variable domain, and optionally the heavy chain variable domain, is (are) fused to an additional moiety, such as a immunoglobulin constant domain. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat et al.

The invention further provides an antibody or antibody fragment comprising a light chain variable domain containing the hu6G4.2.5LV/L1N35X$_{35}$ and optionally further comprising a heavy chain variable domain containing the hu6G4.2.5HV or hu6G4.2.5HV/vH1-3Z, wherein the light chain variable domain, and optionally the heavy chain variable domain, is (are) fused to an additional moiety, such as a immunoglobulin constant domain. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat et al.

The invention additionally provides an antibody or antibody fragment comprising a light chain variable domain containing the hu6G4.2.5LV/L1N35X$_{35}$ and optionally further comprising a heavy chain variable domain containing the hu6G4.2.5HV/vH1-3A, wherein the light chain variable domain, and optionally the heavy chain variable domain, is (are) fused to an additional moiety, such as a immunoglobulin constant domain. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat et al.

The invention also encompasses an antibody or antibody fragment comprising a light chain variable domain containing the hu6G4.2.5LV/L1N35A and optionally further comprising a heavy chain variable domain containing the hu6G4.2.5HV or hu6G4.2.5HV/vH1-3Z, wherein the light chain variable domain, and optionally the heavy chain variable domain, is (are) fused to an additional moiety, such as a immunoglobulin constant domain. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat et al.

The invention additionally provides an antibody or antibody fragment comprising a light chain variable domain containing the hu6G4.2.5LV/L1N35A and optionally further comprising a heavy chain variable domain containing the hu6G4.2.5HV/vH1-3A, wherein the light chain variable domain, and optionally the heavy chain variable domain, is (are) fused to an additional moiety, such as a immunoglobulin constant domain. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat et al.

The invention additionally encompasses an antibody or antibody fragment comprising a light chain variable domain containing the hu6G4.2.5LV/L1N35A and optionally further comprising a heavy chain containing the amino acid sequence of 6G4.2.5HV11, wherein the light chain variable domain, and optionally the heavy chain, is (are) fused to an additional moiety, such as immunoglobulin constant domain sequences. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat el al.

The invention further encompasses an antibody or antibody fragment comprising a light chain variable domain containing the hu6G4.2.5LV/L1N35E and optionally further comprising a heavy chain containing the amino acid sequence of 6G4.2.5HV11, wherein the light chain variable domain, and optionally the heavy chain, is (are) fused to an additional moiety, such as immunoglobulin constant domain sequences. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat et al.

In a preferred embodiment, the antibody or antibody fragment comprises a light chain variable domain containing the hu6G4.2.5LV/vL1-3X, and further comprises the hu6G4.2.5HV or hu6G4.2.5HV/vH1-3Z in a heavy chain that is fused to or contains a leucine zipper sequence. The leucine zipper can increase the affinity or production efficiency of the antibody or antibody fragment of interest. Suitable leucine zipper sequences include the jun and fos leucine zippers taught by Kostelney et al., J. Immunol., 148: 1547–1553 (1992) and the GCN4 leucine zipper described in the Examples below.

In particular, the invention provides an antibody or antibody fragment comprising a light chain comprising the amino acid sequence of amino acids 1–219 of the variant humanized anti-IL-8 6G4.2.5v11 light chain polypeptide amino acid sequence of FIG. 31B (SEQ ID NO: 51) with the proviso that any amino acid other than Asn (denoted as "$X_{35}$") is substituted for Asn at amino acid position 35 (herein referred to as "6G4.2.5LV11N35$X_{35}$").

In another embodiment, the invention provides an antibody or antibody fragment comprising a light chain comprising the amino acid sequence of amino acids 1–219 of the variant humanized anti-IL-8 6G4.2.5v11 light chain polypeptide amino acid sequence of FIG. 31B (SEQ ID NO: 51) with the proviso that any amino acid other than Ser (denoted as "$X_{26}$") is substituted for Ser at amino acid position 26 (herein referred to as "6G4.2.5LV11S26$X_{26}$").

In yet another embodiment, the invention provides an antibody or antibody fragment comprising a light chain comprising the amino acid sequence of amino acids 1–219 of the variant humanized anti-IL-8 6G4.2.5v11 light chain polypeptide amino acid sequence of FIG. 31B (SEQ ID NO: 51) with the proviso that any amino acid other than His (denoted as "$X_{98}$") is substituted for His at amino acid position 98 (herein referred to as "6G4.2.5LV11H98$X_{98}$").

In still another embodiment, the invention provides an antibody or antibody fragment comprising a light chain comprising the amino acid sequence of amino acids 1–219 of the variant humanized anti-IL-8 6G4.2.5v11 light chain polypeptide amino acid sequence of FIG. 31B (SEQ ID NO: 51) with the proviso that any amino acid other than Ser (denoted as "$X_{26}$") is substituted for Ser at amino acid position 26 and any amino acid other than Asn (denoted as "$X_{35}$") is substituted for Asn at amino acid position 35 (herein referred to as "6G4.2.5LV11S26$X_{26}$/N35$X_{35}$").

In a further embodiment, the invention provides an antibody or antibody fragment comprising a light chain comprising the amino acid sequence of amino acids 1–219 of the variant humanized anti-IL-8 6G4.2.5v11 light chain polypeptide amino acid sequence of FIG. 31B (SEQ ID NO: 51) with the proviso that any amino acid other than Asn (denoted as "$X_{35}$") is substituted for Asn at amino acid position 35 and any amino acid other than His (denoted as "$X_{98}$") is substituted for His at amino acid position 98 (herein referred to as "6G4.2.5LV11N35$X_{35}$/H98$X_{98}$").

In an additional embodiment, the invention provides an antibody or antibody fragment comprising a light chain comprising the amino acid sequence of amino acids 1–219 of the variant humanized anti-IL-8 6G4.2.5v11 light chain polypeptide amino acid sequence of FIG. 31B (SEQ ID NO: 51) with the proviso that any amino acid other than Ser (denoted as "$X_{26}$") is substituted for Ser at amino acid position 26 and any amino acid other than His (denoted as "$X_{98}$") is substituted for His at amino acid position 98 (herein referred to as "6G4.2.5LV11S26$X_{26}$/H98$X_{98}$").

The invention also encompasses an antibody or antibody fragment comprising a light chain comprising the amino acid sequence of amino acids 1–219 of the variant humanized anti-IL-8 6G4.2.5v11 light chain polypeptide amino acid sequence of FIG. 31B (SEQ ID NO: 51) with the proviso that any amino acid other than Ser (denoted as "$X_{26}$") is substituted for Ser at amino acid position 26, any amino acid other than Asn (denoted as "$X_{35}$") is substituted for Asn at amino acid position 35 and any amino acid other than His (denoted as "$X_{98}$") is substituted for His at amino acid position 98 (herein referred to as "6G4.2.5LV11S26$X_{26}$/N35$X_{35}$/H98$X_{98}$").

Additionally, the invention provides an antibody or antibody fragment comprising a light chain comprising the amino acid sequence of amino acids 1–219 of the variant humanized anti-IL-8 6G4.2.5v11 light chain polypeptide amino acid sequence (SEQ ID NO: 56) of FIG. 36 (herein referred to as "6G4.2.5LV11N35A").

Further provided herein is an antibody or antibody fragment comprising a light chain comprising the amino acid sequence of amino acids 1–219 of the variant humanized anti-IL-8 6G4.2.5v11 light chain polypeptide amino acid sequence (SEQ ID NO: 62) of FIG. 45 (herein referred to as "6G4.2.5LV11N35E").

In another embodiment, the invention provides an antibody or antibody fragment comprising a light chain comprising the amino acid sequence of amino acids 1–219 of the variant humanized anti-IL-8 6G4.2.5v11 light chain polypeptide amino acid sequence of FIG. 31B (SEQ ID NO: 51) with the proviso that Ala is substituted for Ser at amino acid position 26 (herein referred to as "6G4.2.5LV11S26A").

In yet another embodiment, the invention provides an antibody or antibody fragment comprising a light chain comprising the amino acid sequence of amino acids 1–219 of the variant humanized anti-IL-8 6G4.2.5v11 light chain polypeptide amino acid sequence of FIG. 31B (SEQ ID NO: 51) with the proviso that Ala is substituted for His at amino acid position 98 (herein referred to as "6G4.2.5LV11H98A").

In still another embodiment, the invention provides an antibody or antibody fragment comprising a light chain comprising the amino acid sequence of amino acids 1–219 of the variant humanized anti-IL-8 6G4.2.5v11 light chain polypeptide amino acid sequence of FIG. 31B (SEQ ID NO: 51) with the proviso that Ala is substituted for Ser at amino acid position 26 and Ala is substituted for Asn at amino acid position 35 (herein referred to as "6G4.2.5LV11S26A/N35A").

In a further embodiment, the invention provides an antibody or antibody fragment comprising a light chain comprising the amino acid sequence of amino acids 1–219 of the variant humanized anti-IL-8 6G4.2.5v11 light chain polypeptide amino acid sequence of FIG. 31B (SEQ ID NO: 51) with the proviso that Ala is substituted for Ser at amino acid position 26 and Ala is substituted for His at amino acid position 98 (herein referred to as "6G4.2.5LV11S26A/H98A").

The invention also encompasses an antibody or antibody fragment comprising a light chain comprising the amino acid sequence of amino acids 1–219 of the variant humanized anti-IL-8 6G4.2.5v11 light chain polypeptide amino acid sequence of FIG. 31B (SEQ ID NO: 51) with the proviso that Ala is substituted for Asn at amino acid position 35 and Ala is substituted for His at amino acid position 98 (herein referred to as "6G4.2.5LV11N35A/H98A").

The invention further encompasses an antibody or antibody fragment comprising a light chain comprising the amino acid sequence of amino acids 1–219 of the variant humanized anti-IL-8 6G4.2.5v11 light chain polypeptide amino acid sequence of FIG. 31B (SEQ ID NO: 51) with the proviso that Ala is substituted for Ser at amino acid position 26, Ala is substituted for Asn at amino acid position 35, and Ala is substituted for His at amino acid position 98 (herein referred to as "6G4.2.5LV11S26A/N35A/H98A").

The invention provides a single chain antibody fragment comprising a variant light chain selected from the group consisting of 6G4.2.5LV11N35$X_{35}$, 6G4.2.5LV11S26$X_{26}$, 6G4.2.5LV11H98$X_{98}$, 6G4.2.5LV11S26$X_{26}$N35$X_{35}$, 6G4.2.5LV11N35$X_{35}$/H98$X_{98}$, 6G4.2.5LV11S26$X_{26}$/H98$X_{98}$, and 6G4.2.5LV11S26$X_{26}$/N35$X_{35}$/H98$X_{98}$, with or without any additional amino acid sequence. It will be understood that the group consisting of 6G4.2.5LV11N35$X_{35}$, 6G4.2.5LV11S26$X_{26}$, 6G4.2.5LV11H98$X_{98}$, 6G4.2.5LV11S26$X_{26}$/N35$X_{35}$, 6G4.2.5LV11N35$X_{35}$/H98$X_{98}$, 6G4.2.5LV11S26$X_{26}$/H98$X_{98}$, and 6G4.2.5LV11S26$X_{26}$/N35$X_{35}$/H98$X_{98}$, is collectively referred to herein as the "group of 6G4.2.5LV11X variants", and that individual members of this group are generically referred to herein as a "6G4.2.5LV11X variant." In one embodiment, the invention provides a single chain antibody fragment comprising a 6G4.2.5LV11X variant without any associated heavy chain amino acid sequence, i.e. a single chain species that makes up one half of a Fab fragment. In a preferred embodiment, the invention provides a 6G4.2.5LV11N35$X_{35}$ variant without any associated heavy chain amino acid sequence.

The invention encompasses a single chain antibody fragment comprising a variant light chain selected from the group consisting of 6G4.2.5LV11N35A, 6G4.2.5LV11S26A, 6G4.2.5LV11H98A, 6G4.2.5LV11S26A/N35A, 6G4.2.5LV11N35A/H98A, 6G4.2.5LV11S26A/H98A, and 6G4.2.5LV11S26A/N35A/H98A, with or without any additional amino acid sequence. It will be understood that the group consisting of 6G4.2.5LV11N35A, 6G4.2.5LV11S26A, 6G4.2.5LV11H98A, 6G4.2.5LV11H26A/N35A, 6G4.2.5LV11N35A/H98A, 6G4.2.5LV11S26A/H98A, and 6G4.2.5LV11S26A/N35A/H98A is collectively referred to herein as the "group of 6G4.2.5LV11A variants", and that individual members of this group are generically referred to herein as a "6G4.2.5LV11A variant." In one embodiment, the invention provides a single chain antibody fragment comprising a 6G4.2.5LV11A variant without any associated heavy chain amino acid sequence, i.e. a single chain species that makes up one half of a Fab fragment. In a preferred embodiment, the invention provides the 6G4.2.5LV11N35A without any associated heavy chain amino acid sequence.

Further provided herein are an antibody or antibody fragment comprising a light chain comprising a 6G4.2.5LV11X variant, and further comprising a heavy chain comprising the 6G4.2.5HV11. In a preferred embodiment, the invention provides an antibody or antibody fragment comprising a 6G4.2.5LV11N35$X_{35}$ variant and further comprising the 6G4.2.5HV11. In a preferred embodiment, the invention provides an antibody or antibody fragment comprising the 6G4.2.5LV11N35A and further comprising the 6G4.2.5HV11. In another preferred embodiment, the invention provides an antibody or antibody fragment comprising the 6G4.2.5LV11N35E and further comprising the 6G4.2.5HV11.

In one embodiment, the invention provides a single chain antibody fragment wherein a 6G4.2.5LV11X variant and the 6G4.2.5HV11 are contained in a single chain polypeptide species. In a preferred embodiment, the single chain antibody fragment comprises a 6G4.2.5LV11X variant joined to the 6G4.2.5HV11 by means of a flexible peptide linker sequence, wherein the heavy chain and light chain domains can associate in a "dimeric" structure analogous to that formed in a two-chain Fab species. In another embodiment, the single chain antibody fragment is a species comprising a 6G4.2.5LV11X variant joined to the 6G4.2.5HV11 by a linker that is too short to permit intramolecular pairing of complementary domains, i.e. a single chain polypeptide monomer that forms a diabody upon dimerization with another monomer.

In still another embodiment, the invention provides a single chain antibody fragment wherein a 6G4.2.5LV11N35$X_{35}$ variant and the 6G4.2.5HV11 are contained in a single chain polypeptide species. In a preferred embodiment, the single chain antibody fragment comprises a 6G4.2.5LV11N35$X_{35}$ variant joined to the 6G4.2.5HV11 by means of a flexible peptide link sequence, wherein the heavy chain and light chain domains can associate in a "dimeric" structure analogous to that formed in a two-chain Fab species. In another embodiment, the single chain antibody fragment is a species comprising a 6G4.2.5LV11N35$X_{35}$ variant joined to the 6G4.2.5HV11 by a linker that is too short to permit intramolecular pairing of complementary domains, i.e. a single chain polypeptide monomer that forms a diabody upon dimerization with another monomer.

In a further embodiment, the invention provides a single chain antibody fragment wherein the 6G4.2.5LV11N35A and the 6G4.2.5HV11 are contained in a single chain polypeptide species. In a preferred embodiment, the single chain antibody fragment comprises the 6G4.2.5LV11N35A joined to the 6G4.2.5HV11 by means of a flexible peptide linker sequence, wherein the heavy chain and light chain domains can associate in a "dimeric" structure analogous to that formed in a two-chain Fab species. In another embodiment, the single chain antibody fragment is a species comprising the 6G4.2.5LV11N35A joined to the 6G4.2.5HV11 by a linker that is too short to permit intramolecular pairing of complementary domains, i.e. a single chain polypeptide monomer that forms a diabody upon dimerization with another monomer.

In an additional embodiment, the invention provides a single chain antibody fragment wherein the 6G4.2.5LV11N35E and the 6G4.2.5HV11 are contained in a single chain polypeptide species. In a preferred embodiment, the single chain antibody fragment comprises the 6G4.2.5LV11N35E joined to the 6G4.2.5HV11 by means of a flexible peptide linker sequence, wherein the heavy chain and light chain domains can associate in a "dimeric" structure analogous to that formed in a two-chain Fab species. In another embodiment, the single chain antibody fragment is a species comprising the 6G4.2.5LV11N35E joined to the 6G4.2.5HV11 by a linker that is too short to permit intramolecular pairing of complementary domains, i.e. a single chain polypeptide monomer that forms a diabody upon dimerization with another monomer.

In yet another embodiment, the invention provides an antibody fragment comprising a plurality of polypeptide chains, wherein one polypeptide chain comprises a 6G4.2.5LV11X variant and a second polypeptide chain comprises the 6G4.2.5HV11 and the two polypeptide chains are covalently linked by one or more interchain disulfide bonds. In still another embodiment, the invention provides an antibody fragment comprising a plurality of polypeptide chains, wherein one polypeptide chain comprises a 6G4.2.5LV11N35X$_{35}$ variant and a second polypeptide chain comprises the 6G4.2.5HV11 and the two polypeptide chains are covalently linked by one or more interchain disulfide bonds. In a preferred embodiment, any of the foregoing two-chain antibody fragments is selected from the group consisting of Fab, Fab', Fab'-SH, and F(ab')$_2$. In still another preferred embodiment, the two-chain antibody fragment is a F(ab')$_2$ wherein one polypeptide chain comprises the 6G4.2.5LV11N35A and the second polypeptide chain comprises the 6G4.2.5HV11. In a further preferred embodiment, the antibody fragment is a Fab, Fab', Fab'-SH, or F(ab')$_2$ wherein one polypeptide chain comprises the 6G4.2.5LV11N35E and the second polypeptide chain comprises the 6G4.2.5HV11. A particularly preferred embodiment, the antibody fragment is the 6G4V11N35A F(ab')$_2$ GCN4 leucine zipper species described in the Examples below. In another particularly preferred embodiment, the antibody fragment is the 6G4V11N35E F(ab')$_2$ GCN4 leucine zipper species described in the Examples below. In yet another particularly preferred embodiment, the antibody fragment is the 6G4V11N35E Fab described in the Examples below.

The invention also provides an antibody or antibody fragment comprising a light chain containing a 6G4.2.5LV11X variant and optionally further comprising a heavy chain containing the 6G4.2.5HV11, wherein the light chain, and optionally the heavy chain, is (are) fused to an additional moiety, such as additional immunoglobulin constant domain sequence. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat el al.

The invention additionally provides an antibody or antibody fragment comprising a light chain containing a 6G4.2.5LV11N35X$_{35}$ variant and optionally further comprising a heavy chain containing the 6G4.2.5HV11, wherein the light chain, and optionally the heavy chain, is (are) fused to an additional moiety, such as additional immunoglobulin constant domain sequence. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat et al.

The invention further provides an antibody or antibody fragment comprising a light chain containing the 6G4.2.5LV11N35A and optionally further comprising a heavy chain containing the 6G4.2.5HV11, wherein the light chain, and optionally the heavy chain, is (are) fused to an additional moiety, such as additional immunoglobulin constant domain sequence. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat et al.

The invention further provides an antibody or antibody fragment comprising a light chain containing the 6G4.2.5LV11N35E and optionally further comprising a heavy chain containing the 6G4.2.5HV11, wherein the light chain, and optionally the heavy chain, is (are) fused to an additional moiety, such as additional immunoglobulin constant domain sequence. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat et al.

In a preferred embodiment, the antibody or antibody fragment comprises a light chain containing a 6G4.2.5LV11X variant, and further comprises the 6G4.2.5HV11 in a heavy chain that is fused to or contains a leucine zipper sequence. The leucine zipper can increase the affinity or production efficiency of the antibody or antibody fragment of interest. Suitable leucine zipper sequences include the jun and fos leucine zippers taught by Kostelney et al., *J. Immunol.*, 148: 1547–1553 (1992) and the GCN4 leucine zipper described in the Examples below. In another preferred embodiment, the antibody or antibody fragment comprises a light chain containing the 6G4.2.5LV11N35A, and further comprises a heavy chain containing the 6G4.2.5HV11 fused to the GCN4 leucine zipper. In yet another preferred embodiment, the antibody or antibody fragment comprises a light chain containing the 6G4.2.5LV11N35E, and further comprises a heavy chain containing the 6G4.2.5HV11 fused to the GCN4 leucine zipper.

B. 6G4.2.5HV VARIANTS

The invention provides humanized antibodies and antibody fragments comprising the CDRs of a 6G4.2.5HV CDR variant. The use of a 6G4.2.5HV CDRs variant in the humanized antibodies and antibody fragments of the invention confer the advantages of higher affinity for human IL-8 and/or improved recombinant manufacturing economy.

A heavy chain variable domain comprising the CDRs of a 6G4.2.5HV CDRs variant can be humanized in conjunction with a light chain comprising the CDRs of 6G4.2.5LV or the CDRs of a 6G4.2.5LV CDRs variant, essentially as described in Section (II)(2)(A) above. In one embodiment, the invention provides a humanized antibody or antibody fragment comprising a 6G4.2.5HV CDRs variant selected from the group consisting of 6G4.2.5HV/H1S31Z$_{31}$, 6G4.2.5HV/H2S54Z$_{54}$, and 6G4.2.5HV/H1S31Z$_{31}$/H2S54Z$_{54}$. In addition, the invention provides a humanized antibody or antibody fragment comprising a 6G4.2.5HV CDRs variant selected from the group consisting of 6G4.2.5HV/H1S31A, 6G4.2.5HV/H2S54A, and 6G4.2.5HV/H1S31A/H2S54A. In particular, the 6G4.2.5HV CDRs variants can be used to construct a humanized antibody or antibody comprising the hu6G4.2.5HV/vH1-3Z as described in Section (II)(2)(A) above.

The invention additionally provides a humanized antibody or antibody fragment that comprises a heavy chain variable domain comprising the hu6G4.2.5HV/vH1-3Z, and further comprises a light chain variable domain comprising the hu6G4.2.5LV or hu6G4.2.5LV/vL1-3X.

The invention further encompasses a single chain humanized antibody fragment comprising the hu6G4.2.5HV/vH1-3Z, with or without any additional amino acid sequence. In one embodiment, the invention provides a single chain antibody fragment comprising the hu6G4.2.5HV/vH1-3Z without any associated heavy chain variable domain amino acid sequence, i.e. a single chain species that makes up one half of an Fv fragment.

In one embodiment, the invention provides a single chain humanized antibody fragment wherein the hu6G4.2.5HV/vH1-3Z and the hu6G4.2.5LV or hu6G4.2.5LV/vL1-3X are contained in a single chain polypeptide species. In a preferred embodiment, the single chain antibody fragment is a scFv species comprising the hu6G4.2.5HV/vH1-3Z joined to the hu6G4.2.5LV or hu6G4.2.5LV/vL1-3X by means of a flexible peptide linker sequence, wherein the heavy chain and light chain variable domains can associate in a "dimeric" structure analogous to that formed in a two-chain Fv species. In another embodiment, the single chain antibody fragment is a species comprising the hu6G4.2.5HV/vH1-3Z joined to the hu6G4.2.5LV or hu6G4.2.5LV/vL1-3X by a linker that is too short to permit intramolecular pairing of the two variable domains, i.e. a single chain polypeptide monomer that forms a diabody upon dimerization with another monomer.

In yet another embodiment, the invention provides a humanized antibody fragment comprising a plurality of polypeptide chains, wherein one polypeptide chain comprises the hu6G4.2.5HV/vH1-3Z and a second polypeptide chain comprises the hu6G4.2.5LV or hu6G4.2.5LV/vL1-3X and the two polypeptide chains are covalently linked by one or more interchain disulfide bonds. In a preferred embodiment, the foregoing two-chain antibody fragment is selected from the group consisting of Fab, Fab', Fab'-SH, Fv, and F(ab')$_2$.

The invention also provides a humanized antibody or antibody fragment comprising a heavy chain variable domain containing the hu6G4.2.5HV/vH1-3Z and optionally further comprising a light chain variable domain containing the hu6G4.2.5LV or hu6G4.2.5LV/vL1-3X, wherein the heavy chain variable domain, and optionally the light chain variable domain, is (are) fused to an additional moiety, such as an immunoglobulin constant domain. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat et al.

In a preferred embodiment, the humanized antibody or antibody fragment comprises the hu6G4.2.5HV/vH1-3Z in a heavy chain that is fused to or contains a leucine zipper sequence. The leucine zipper can increase the affinity or production efficiency of the antibody or antibody fragment of interest. Suitable leucine zipper sequences include the jun and fos leucine zippers taught by Kostelney et al., *J. Immunol.*, 148: 1547–1553 (1992) and the GCN4 leucine zipper described in the Examples below.

In addition, the invention provides a humanized antibody or antibody fragment comprising a heavy chain comprising the amino acid sequence of amino acids 1–230 of the 6G4.2.5HV11 polypeptide amino acid sequence of FIGS. 37A–37B (SEQ ID NO: 60) with the proviso that Ala is substituted for Ser at amino acid position 31 (hereinafter referred to as "6G4.2.5HV11S31A").

In another embodiment, the invention provides a humanized antibody or antibody fragment comprising a heavy chain comprising the amino acid sequence of amino acids 1–230 of the 6G4.2.5HV11 polypeptide amino acid sequence of FIGS. 37A–37B (SEQ ID NO: 60) with the proviso that Ala is substituted for Ser at amino acid position 54 (hereinafter referred to as "6G4.2.5HV11S54A").

In yet another embodiment, the invention provides a humanized antibody or antibody fragment comprising a heavy chain comprising the amino acid sequence of amino acids 1–230 of the 6G4.2.5HV11 polypeptide amino acid sequence of FIGS. 37A–37B (SEQ ID NO: 60) with the proviso that Ala is substituted for Ser at amino acid position 31 and Ala is substituted for Ser at amino acid position 54 (hereinafter referred to as "6G4.2.5HV11S31A/S54A").

Further provided herein is a humanized antibody or antibody fragment that comprises any of the light and heavy chain combinations listed in Tables 1–2 below.

TABLE 1

| Heavy Chain | Light Chain |
| --- | --- |
| 6G4.2.5HV11S31A | 6G4.2.5LV11 |
| 6G4.2.5HV11S31A | 6G4.2.5LV11N35A |
| 6G4.2.5HV11S31A | 6G4.2.5LV11S26A |
| 6G4.2.5HV11S31A | 6G4.2.5LV11H98A |
| 6G4.2.5HV11S31A | 6G4.2.5LV11S26A/N35A |
| 6G4.2.5HV11S31A | 6G4.2.5LV11S26A/H98A |
| 6G4.2.5HV11S31A | 6G4.2.5LV11N35A/H98A |
| 6G4.2.5HV11S31A | 6G4.2.5LV11S26A/N35A/H98A |
| 6G4.2.5HV11S54A | 6G4.2.5LV11 |
| 6G4.2.5HV11S54A | 6G4.2.5LV11N35A |
| 6G4.2.5HV11S54A | 6G4.2.5LV11S26A |
| 6G4.2.5HV11S54A | 6G4.2.5LV11H98A |
| 6G4.2.5HV11S54A | 6G4.2.5LV11S26A/N35A |
| 6G4.2.5HV11S54A | 6G4.2.5LV11S26A/H98A |
| 6G4.2.5HV11S54A | 6G4.2.5LV11N35A/H98A |
| 6G4.2.5HV11S54A | 6G4.2.5LV11S26A/N35A/H98A |
| 6G4.2.5HV11S31A/S54A | 6G4.2.5LV11 |
| 6G4.2.5HV11S31A/S54A | 6G4.2.5LV11N35A |
| 6G4.2.5HV11S31A/S54A | 6G4.2.5LV11S26A |
| 6G4.2.5HV11S31A/S54A | 6G4.2.5LV11H98A |
| 6G4.2.5HV11S31A/S54A | 6G4.2.5LV11S26A/N35A |
| 6G4.2.5HV11S31A/S54A | 6G4.2.5LV11S26A/H98A |
| 6G4.2.5HV11S31A/S54A | 6G4.2.5LV11N35A/H98A |
| 6G4.2.5HV11S31A/S54A | 6G4.2.5LV11S26A/N35A/H98A |

TABLE 2

| Heavy Chain | Light Chain |
| --- | --- |
| 6G4.2.5HV11S31A | 6G4.2.5LV11 |
| 6G4.2.5HV11S31A | 6G4.2.5LV11N35X$_{35}$ |
| 6G4.2.5HV11S31A | 6G4.2.5LV11S26X$_{26}$ |
| 6G4.2.5HV11S31A | 6G4.2.5LV11H98X$_{98}$ |
| 6G4.2.5HV11S31A | 6G4.2.5LV11S26X$_{26}$/N35X$_{35}$ |
| 6G4.2.5HV11S31A | 6G4.2.5LV11S26X$_{26}$/H98X$_{98}$ |
| 6G4.2.5HV11S31A | 6G4.2.5LV11N35X$_{35}$/H98X$_{98}$ |
| 6G4.2.5HV11S31A | 6G4.2.5LV11S26X$_{26}$/N35X$_{35}$/H98X$_{98}$ |
| 6G4.2.5HV11S54A | 6G4.2.5LV11 |
| 6G4.2.5HV11S54A | 6G4.2.5LV11N35X$_{35}$ |
| 6G4.2.5HV11S54A | 6G4.2.5LV11S26X$_{26}$ |
| 6G4.2.5HV11S54A | 6G4.2.5LV11H98X$_{98}$ |
| 6G4.2.5HV11S54A | 6G4.2.5LV11S26X$_{26}$/N35X$_{35}$ |
| 6G4.2.5HV11S54A | 6G4.2.5LV11S26X$_{26}$/H98X$_{98}$ |
| 6G4.2.5HV11S54A | 6G4.2.5LV11N35X$_{35}$/H98X$_{98}$ |
| 6G4.2.5HV11S54A | 6G4.2.5LV11S26X$_{26}$/N35X$_{35}$/H98X$_{98}$ |
| 6G4.2.5HV11S31A/S54A | 6G4.2.5LV11 |

TABLE 2-continued

| Heavy Chain | Light Chain |
|---|---|
| 6G4.2.5HV11S31A/S54A | 6G4.2.5LV11N35X$_{35}$ |
| 6G4.2.5HV11S31A/S54A | 6G4.2.5LV11S26X$_{26}$ |
| 6G4.2.5HV11S31A/S54A | 6G4.2.5LV11H98X$_{98}$ |
| 6G4.2.5HV11S31A/S54A | 6G4.2.5LV11S26X$_{26}$/N35X$_{35}$ |
| 6G4.2.5HV11S31A/S54A | 6G4.2.5LV11S26X$_{26}$/H98X$_{98}$ |
| 6G4.2.5HV11S31A/S54A | 6G4.2.5LV11N35X$_{35}$/H98X$_{98}$ |
| 6G4.2.5HV11S31A/S54A | 6G4.2.5LV11S26X$_{26}$/N35X$_{35}$/H98X$_{98}$ |

The invention encompasses a single chain humanized antibody fragment comprising a variant heavy chain selected from the group consisting of 6G4.2.5HV11S31A, 6G4.2.5HV11S54A, and 6G4.2.5HV11S31A/S54A, with or without any additional amino acid sequence. It will be understood that the group consisting of 6G4.2.5HV11S31A, 6G4.2.5HV11S54A, and 6G4.2.5HV11S31A/S54A is collectively referred to herein as the "group of 6G4.2.5HV11A variants", and that individual members of this group are generically referred to herein as a "6G4.2.5HV11A variant." In one embodiment, the invention provides a single chain humanized antibody fragment comprising a 6G4.2.5HV11A variant without any associated light chain amino acid sequence, i.e. a single chain species that makes up one half of a Fab fragment.

Further provided herein are a humanized antibody or antibody fragment comprising a heavy chain comprising a 6G4.2.5HV11A variant, and further comprising a light chain comprising a 6G4.2.5LV11A variant or a 6G4.2.5LV11X variant. In another embodiment, the humanized antibody or antibody fragment comprises any combination of light and heavy chains listed in Tables 1 and 2 above. In one embodiment, the invention provides a humanized antibody or antibody fragment comprising a 6G4.2.5HV11A variant and further comprising the 6G4.2.5LV11N35X$_{35}$. In a preferred embodiment, the invention provides a humanized antibody or antibody fragment comprising a 6G4.2.5HV11A variant and further comprising the 6G4.2.5LV11N35A.

In yet another embodiment, the invention provides a single chain humanized antibody fragment wherein a 6G4.2.5HV11A variant and the 6G4.2.5LV11 are contained in a single chain polypeptide species. In another embodiment, the invention provides a single chain humanized antibody fragment wherein any pair of light and heavy chains listed in Tables 1–2 above is contained in a single chain polypeptide species. In yet another embodiment, the invention provides a single chain humanized antibody fragment wherein a 6G4.2.5HV11A variant and a 6G4.2.5LV11X variant are contained in a single chain polypeptide species. In still another embodiment, the invention provides a single chain humanized antibody fragment wherein a 6G4.2.5HV11A variant and a 6G4.2.5LV11N35X$_{35}$ variant are contained in a single chain polypeptide species. In an additional embodiment, the invention provides a single chain humanized antibody fragment wherein a 6G4.2.5HV11A variant and the 6G4.2.5LV11N35A variant are contained in a single chain polypeptide species.

In a preferred embodiment, the single chain humanized antibody fragment comprises a 6G4.2.5HV11A variant joined to a 6G4.2.5LV11X variant, 6G4.2.5LV11N35X$_{35}$ variant, 6G4.2.5LV11N35A variant, or 6G4.2.5LV11 by means of a flexible peptide linker sequence, wherein the heavy chain and light chain domains can associate in a "dimeric" structure analogous to that formed in a two-chain Fab species. In a further embodiment, the single chain humanized antibody fragment is a species comprising a 6G4.2.5HV11A variant joined to a 6G4.2.5LV11X variant, 6G4.2.5LV11N35X$_{35}$ variant, 6G4.2.5LV11N35A variant, or 6G4.2.5LV11 by a linker that is too short to permit intramolecular pairing of complementary domains, i.e. a single chain polypeptide monomer that forms a diabody upon dimerization with another monomer.

In still another embodiment, the single chain humanized antibody fragment comprises any pair of light and heavy chains listed in Table 1 above joined by means of a flexible peptide linker sequence, wherein the heavy chain and light chain domains can associate in a "dimeric" structure analogous to that formed in a two-chain Fab species. In an additional embodiment, the single chain humanized antibody fragment comprises any pair of light and heavy chains listed in Tables 1–2 above joined by a linker that is too short to permit intramolecular pairing of complementary domains, i.e. a single chain polypeptide monomer that forms a diabody upon dimerization with another monomer.

In yet another embodiment, the invention provides a humanized antibody fragment comprising a plurality of polypeptide chains, wherein one polypeptide chain comprises a 6G4.2.5HV11A variant and a second polypeptide chain comprises a 6G4.2.5LV11X variant, 6G4.2.5LV11N35X$_{35}$ variant, 6G4.2.5LV11N35A variant, or 6G4.2.5LV11, and the two polypeptide chains are covalently linked by one or more interchain disulfide bonds. In a preferred embodiment, the foregoing two-chain antibody fragment is selected from the group consisting of Fab, Fab', Fab'-SH, and F(ab')$_2$.

In an additional embodiment, the invention provides a two-chain humanized antibody fragment comprising any pair of heavy and light chains listed in Tables 1–2 above, wherein each chain is contained on a separate molecule. In another embodiment, the two-chain antibody fragment comprising any pair of heavy and light chains listed in Tables 1–2 above is selected from the group consisting of Fab, Fab', Fab'-SH, and F(ab')$_2$. In a preferred embodiment, the two-chain humanized antibody fragment is a F(ab')$_2$ comprising any pair of heavy and light chains listed in Tables 1–2 above. In another preferred embodiment, the two-chain humanized antibody fragment is a F(ab')$_2$ wherein one polypeptide chain comprises a 6G4.2.5HV11A variant and the second polypeptide chain comprises the 6G4.2.5LV11N35A.

The invention also provides a humanized antibody or antibody fragment comprising a heavy chain containing a 6G4.2.5HV11A variant and optionally further comprising a light chain containing a 6G4.2.5LV11X variant, 6G4.2.5LV11N35X$_{35}$ variant, 6G4.2.5LV11N35A, or 6G4.2.5HV11, wherein the heavy chain, and optionally the light chain, is (are) fused to an additional moiety, such as additional immunoglobulin constant domain sequence. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat et al. (supra).

In a preferred embodiment, the humanized antibody or antibody fragment comprises a 6G4.2.5HV11A variant in a heavy chain that is fused to or contains a leucine zipper sequence. The leucine zipper can increase the affinity or production efficiency of the antibody or antibody fragment of interest. Suitable leucine zipper sequences include the jun and fos leucine zippers taught by Kostelney et al., *J. Immunol.*, 148:1547–1553 (1992) and the GCN4 leucine zipper described in the Examples below.

C. Bispecific Antibodies

Bispecific antibodies are monoclonal, preferably human or humanized, antibodies that have binding specificities for at least two different antigens. In the present case, one of the binding specificities is for IL-8, the other one is for any other antigen. For example, bispecific antibodies specifically binding a IL-8 and neurotrophic factor, or two different types of IL-8 polypeptides are within the scope of the present invention.

Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, *Nature* 305:537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in WO 93/08829 published May 13, 1993, and in Traunecker et al., *EMBO J.* 10:3655 (1991).

According to a different and more preferred approach, antibody-variable domains with the desired binding specificities (antibody-antigen combining sites) are fused to immunoglobulin constant-domain sequences. The fusion preferably is with an immunoglobulin heavy-chain constant domain, comprising at least part of the hinge, CH2, and CH3 regions. It is preferred to have the first heavy-chain constant region (CH1), containing the site necessary for light-chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the maximum yields. It is, however, possible to insert the coding sequences for two or all three polypeptide chains in one expression vector when the production of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation. For further details of generating bispecific antibodies, see, for example, Suresh et al., *Methods in Enzmology* 121:210 (1986).

According to another approach, the interface between a pair of antibody molecules can be engineered to maximize the percentage of heterodimers which are recovered from recombinant cell culture. The preferred interface comprises at least a part of the $C^H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/00373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J Exp. Med.*, 175: 217–225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.*, 148(5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad Sci. USA*, 90:6444–6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147: 60 (1991).

4. Production of Humanized Anti-IL-8 6G4.2.5 Monoclonal Antibody, Antibody Fragments, and Variants The antibodies and antibody fragments of the invention can be produced using any convenient antibody manufacturing process known in the art. Typically, the antibody or antibody fragment is made using recombinant expression systems. A multiple polypeptide chain antibody or antibody fragment species can be made in a single host cell expression system wherein the host cell produces each chain of the antibody or antibody fragment and assembles the polypeptide chains into a multimeric structure to form the antibody or antibody fragment in vivo, followed by recovery of the antibody or antibody fragment from the host cell. For example, suitable recombinant expression systems for the production of complete antibody or antibody fragment are described in Lucas et al., *Nucleic Acids Res.*, 24: 1774–1779 (1996). Alternatively, the separate polypeptide chains of the desired antibody or antibody fragment can be made in separate expression host cells, separately recovered from the respective host cells, and then mixed in vitro under conditions permitting the formation of the multi-subunit antibody or antibody fragment of interest. For example, U.S. Pat. No. 4,816,567 to Cabilly et al. and Carter et al., *Bio/Technology*, 10: 163–167 (1992) provide methods for recombinant production of antibody heavy and light chains in separate expression hosts followed by assembly of antibody from separate heavy and light chains in vitro.

The following discussion of recombinant expression methods applies equally to the production of single chain antibody polypeptide species and multi-subunit antibody and antibody fragment species. All recombinant procedures for the production of antibody or antibody fragment provided below shall be understood to describe: (1) manufacture of single chain antibody species as the desired end-product; (2) manufacture of multi-subunit antibody or antibody fragment species by production of all subunits in a single host cell, subunit assembly in the host cell, optionally followed by host cell secretion of the multi-subunit end-product into the culture medium, and recovery of the multi-subunit end-product from the host cell and/or culture medium; and (3) manufacture of multi-subunit antibody or antibody fragment by production of subunits in separate host cells (optionally followed by host cell secretion of subunits into the culture medium), recovery of subunits from the respective host cells and/or culture media, followed by in vitro subunit assembly to form the multi-subunit end-product. In the case of a multi-subunit antibody or antibody fragment produced in a single host cell, it will be appreciated that production of the various subunits can be effected by expression of multiple polypeptide-encoding nucleic acid sequences carried on a single vector or by expression of polypeptide-encoding nucleic acid sequences carried on multiple vectors contained in the host cell.

A. Construction of DNA Encoding Humanized 6G4.2.5 Monoclonal Antibodies, Antibody Fragments, and Variants Following the selection of the humanized antibody or antibody fragment of the invention according to the methods described above, the practitioner can use the genetic code to design DNAs encoding the desired antibody or antibody fragment. In one embodiment, codons preferred by the expression host cell are used in the design of a DNA encoding the antibody or antibody fragment of interest. DNA encoding the desired antibody or antibody fragment can be prepared by a variety of methods known in the art. These methods include, but are not limited to, chemical synthesis by any of the methods described in Engels et al., *Agnew. Chem. Int. Ed. Engl.*, 28: 716–734 (1989), the entire disclosure of which is incorporated herein by reference, such as the triester, phosphite, phosphoramidite and H-phosphonate methods.

A variation on the above procedures contemplates the use of gene fusions, wherein the gene(s) encoding the antibody or antibody fragment is associated, in the vector, with a gene encoding another protein or a fragment of another protein. This results in the antibody or antibody fragment being produced by the host cell as a fusion with another protein. The "other" protein is often a protein or peptide which can be secreted by the cell, making it possible to isolate and purify the desired protein from the culture medium and eliminating the necessity of destroying the host cells which arises when the desired protein remains inside the cell. Alternatively, the fusion protein can be expressed intracellularly. It is advantageous to use fusion proteins that are highly expressed.

The use of gene fusions, though not essential, can facilitate the expression of heterologous proteins in *E. coli* as well as the subsequent purification of those gene products (Harris, T. J. R. in *Genetic Engineering*, Williamson, R., Ed., Academic, London, Vol. 4, p. 127(1983); Uhlen, M. & Moks, T., *Methods Enzymol.* 185:129–143 (1990)). Protein A fusions are often used because the binding of protein A, or more specifically the Z domain of protein A, to IgG provides an "affinity handle" for the purification of the fused protein (Nilsson, B. & Abrahmsen, L. *Methods Enzymol.* 185:144–161 (1990)). It has also been shown that many heterologous proteins are degraded when expressed directly in *E. coli*, but are stable when expressed as fusion proteins (Marston, F. A. O., *Biochem J.* 240: 1 (1986)).

Fusion proteins can be cleaved using chemicals, such as cyanogen bromide, which cleaves at a methionine, or hydroxylamine, which cleaves between an Asn and Gly. Using standard recombinant DNA methodology, the nucleotide base pairs encoding these amino acids may be inserted just prior to the 5' end of the antibody or antibody fragment gene(s).

Alternatively, one can employ proteolytic cleavage of fusion proteins, which has been recently reviewed (Carter, P. (1990) in *Protein Purification: From Molecular Mechanisms to Large-Scale Processes*, Ladisch, M. R., Willson, R. C., Painton, C. C., and Builder, S. E., eds., American Chemical Society Symposium Series No. 427, Ch 13, 181–193).

Proteases such Factor Xa, thrombin, subtilisin and mutants thereof, have been successfully used to cleave fusion proteins. Typically, a peptide linker that is amenable to cleavage by the protease used is inserted between the "other" protein (e.g., the Z domain of protein A) and the protein of interest, such as humanized anti-IL-8 antibody or antibody fragment. Using recombinant DNA methodology, the nucleotide base pairs encoding the linker are inserted between the genes or gene fragments coding for the other proteins. Proteolytic cleavage of the partially purified fusion protein containing the correct linker can then be carried out on either the native fusion protein, or the reduced or denatured fusion protein.

Various techniques are also available which may now be employed to produce variant humanized antibodies or antibody fragments, which encodes for additions, deletions, or changes in amino acid sequence of the resultant protein(s) relative to the parent humanized antibody or antibody fragment.

By way of illustration, with expression vectors encoding humanized antibody or antibody fragment in hand, site specific mutagenesis (Kunkel et al., *Methods Enzymol.* 204:125–139 (1991); Carter, P., et al., *Nucl. Acids. Res.* 13:4331 (1986); Zoller, M. J. et al., *Nucl. Acids Res.* 10:6487 (1982)), cassette mutagenesis (Wells, J. A., et al., *Gene* 34:315 (1985)), restriction selection mutagenesis (Wells, J. A., et al., *Philos. Trans, R. Soc. London SerA* 317, 415 (1986)) or other known techniques may be performed on the antibody or antibody fragment DNA. The variant DNA can then be used in place of the parent DNA by insertion into the aforementioned expression vectors. Growth of host bacteria containing the expression vectors with the mutant DNA allows the production of variant humanized antibodies or antibody fragments, which can be isolated as described herein.

B. Insertion of DNA into a Cloning Vehicle

The DNA encoding the antibody or antibody fragment is inserted into a replicable vector for further cloning (amplification of the DNA) or for expression. Many vectors are available, and selection of the appropriate vector will depend on (1) whether it is to be used for DNA amplification or for DNA expression, (2) the size of the DNA to be inserted into the vector, and (3) the host cell to be transformed with the vector. Each vector contains various components depending on its function (amplification of DNA or expression of DNA) and the host cell for which it is compatible. The vector components generally include, but are not limited to, one or more of the following: a signal sequence, an origin of replication, one or more marker genes, an enhancer element, a promoter, and a transcription termination sequence.

(i) Signal Sequence Component

In general, a signal sequence may be a component of the vector, or it may be a part of the antibody or antibody fragment DNA that is inserted into the vector. Preferably, a heterologous signal sequence selected and fused to the antibody or antibody fragment DNA such that the signal sequence in the corresponding fusion protein is recognized, transported and processed (i.e., cleaved by a signal peptidase) in the host cell's protein secretion system. In the case of prokaryotic host cells, the signal sequence is selected, for example, from the group of the alkaline phosphatase, penicillinase, lpp, or heat-stable enterotoxin II leaders. In a preferred embodiment, the STII signal sequence is used as described in the Examples below. For yeast secretion the native signal sequence may be substituted by, e.g., the yeast invertase leader, α factor leader (including Saccharomyces and Kluyveromyces α-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2 $\mu$ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Most expression vectors are "shuttle" vectors, i.e. they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA may also be amplified by insertion into the host genome. This is readily accomplished using Bacillus species as hosts, for example, by including in the vector a DNA sequence that is homologous to a sequence found in Bacillus genomic DNA. Transfection of Bacillus with this vector results in homologous recombination with the genome and insertion of the antibody or antibody fragment DNA.

(iii) Selection Gene Component

Expression and cloning vectors should contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g. ampicillin, neomycin, methotrexate, or tetracycline, (b) complement auxotrophic deficiencies, or (c) supply critical nutrients not available from complex media, e.g. the gene encoding D-alanine racemase for Bacilli.

One example of a selection scheme utilizes a drug to arrest growth of a host cell. Those cells that are successfully transformed with a heterologous gene express a protein conferring drug resistance and thus survive the selection regimen. Examples of such dominant selection use the drugs neomycin (Southern et al., *J. Molec. Appl. Genet.*, 1: 327 (1982)), mycophenolic acid (Mulligan et al., *Science*, 209: 1422 (1980)) or hygromycin (Sugden et al., *Mol. Cell. Biol.*, 5: 410–413 (1985)). The three examples given above employ bacterial genes under eukaryotic control to convey resistance to the appropriate drug (G418 or neomycin (geneticin), xgpt (mycophenolic acid), and hygromycin, respectively.)

Another example of suitable selectable markers for mammalian cells are those that enable the identification of cells competent to take up the antibody or antibody fragment nucleic acid, such as dihydrofolate reductase (DHFR) or thymidine kinase. The mammalian cell transformants are placed under selection pressure which only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes the antibody or antibody fragment. Amplification is the process by which genes in greater demand for the production of a protein critical for growth are reiterated in tandem within the chromosomes of successive generations of recombinant cells. Increased quantities of the antibody or antibody fragment are synthesized from the amplified DNA.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub and Chasin, *Proc. Natl. Acad. Sci. USA*, 77: 4216 (1980). The transformed cells are then exposed to increased levels of methotrexate. This leads to the synthesis of multiple copies of the DHFR gene, and, concomitantly, multiple copies of other DNA comprising the expression vectors, such as the DNA encoding the antibody or antibody fragment. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060). Alternatively, host cells (particularly wild-type hosts that contain endogenous DHFR) transformed or co-transformed with DNA sequences encoding the antibody or antibody fragment, wild-type DHFR protein, and another selectable marker such as aminoglycoside 3' phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7. Stinchcomb et al., *Nature*, 282: 39 (1979); Kingsman et al., *Gene*, 7: 141 (1979); or Tschemper et al., *Gene*, 10: 157 (1980). The trp1 gene provides a selection marker for a mutant strain of yeast lacking the ability to grow in tryptophan, for example, ATCC No. 44076 or PEP4-1. Jones, *Genetics*, 85: 12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

(iv) Promoter Component

Expression vectors usually contain a promoter that is recognized by the host organism and is operably linked to the antibody or antibody fragment nucleic acid. Promoters are untranslated sequences located upstream (5') to the start codon of a structural gene (generally within about 100 to 1000 bp) that control the transcription and translation of a particular nucleic acid sequence, such as the antibody or antibody fragment encoding sequence, to which they are operably linked. Such promoters typically fall into two classes, inducible and constitutive. Inducible promoters are promoters that initiate increased levels of transcription from DNA under their control in response to some change in culture conditions, e.g. the presence or absence of a nutrient or a change in temperature. At this time a large number of promoters recognized by a variety of potential host cells are well known.

Promoters suitable for use with prokaryotic hosts include the β-lactamase and lactose promoter systems (Chang et al., *Nature*, 275: 615 (1978); and Goeddel et al., *Nature*, 281: 544 (1979)), alkaline phosphatase, a tryptophan (trp) promoter system (Goeddel, *Nucleic Acids Res.*, 8: 4057 (1980) and EP 36,776) and hybrid promoters such as the tac promoter (deBoer et al., *Proc. Natl. Acad. Sci. USA*, 80: 21–25 (1983)). However, other known bacterial promoters are suitable. Their nucleotide sequences have been published, thereby enabling a skilled worker to operably ligate them to DNA encoding the antibody or antibody fragment (Siebenlist et al., *Cell*, 20: 269 (1980)) using linkers or adaptors to supply any required restriction sites. Promoters for use in bacterial systems also generally will contain a Shine-Dalgarno (S.D.) sequence operably linked to the DNA encoding the antibody or antibody fragment.

Suitable promoting sequences for use with yeast hosts include the promoters for 3-phosphoglycerate kinase (Hitzeman et al., *J. Biol. Chem.*, 255: 2073 (1980)) or other glycolytic enzymes (Hess et al., *J. Adv. Enzvme Reg.*, 7: 149 (1968); and Holland, Biochemistry, 17: 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in Hitzeman et al., EP 73,657A. Yeast enhancers also are advantageously used with yeast promoters.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into mammalian expression vectors.

Vector driven transcription of antibody or antibody fragment encoding DNA in mammalian host cells can be controlled by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g. the actin promoter or an immunoglobulin promoter, and from heat-shock promoters, provided such promoters are compatible with the host cell systems.

The early and late promoters of the SV40 virus are conveniently obtained as an SV40 restriction fragment that also contains the SV40 viral origin of replication. Fiers et al., *Nature*, 273: 113 (1978); Mulligan and Berg, *Science*, 209: 1422–1427 (1980); Pavlakis et al., *Proc. Natl. Acad. Sci. USA*, 78: 7398–7402 (1981). The immediate early promoter of the human cytomegalovirus is conveniently obtained as a HindIII E restriction fragment. Greenaway et al., *Gene, 18: 355–360* (1982). A system for expressing DNA in mammalian hosts using the bovine papilloma virus as a vector is disclosed in U.S. Pat. No. 4,419,446. A modification of this system is described in U.S. Pat. No. 4,601,978. See also Gray et al., *Nature*, 295: 503–508 (1982) on expressing cDNA encoding immune interferon in monkey cells, Reyes et al., *Nature*, 297: 598–601 (1982) on expression of human -interferon cDNA in mouse cells under the control of a thymidine kinase promoter from herpes simplex virus, Canaani and Berg, *Proc. Natl. Acad. Sci. USA*, 79: 5166–5170 (1982) on expression of the human interferon I gene in cultured mouse and rabbit cells, and Gorman et al.,

*Proc. Natl. Acad. Sci. USA*, 79: 6777–6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

(v) Enhancer Element Component

Transcription of a DNA encoding antibody or antibody fragment by higher eukaryotic host cells is often increased by inserting an enhancer sequence into the vector. Enhancers are cis-acting elements of DNA, usually about from 10–300 bp, that act on a promoter to increase its transcription. Enhancers are relatively orientation and position independent having been found 5' (Laimins et al., *Proc. Natl. Acad. Sci. USA*, 78: 993 (1981)) and 3' (Lusky et al., *Mol. Cell Bio.*, 3: 1108 (1983)) to the transcription unit, within an intron (Banerji et al., *Cell*, 33: 729 (1983)) as well as within the coding sequence itself (Osborne et al., *Mol. Cell Bio.*, 4: 1293 (1984)). Many enhancer sequences are now known from mammalian genes (globin, elastase, albumin, -fetoprotein and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See also Yaniv, *Nature*, 297: 17–18 (1982) on enhancing elements for activation of eukaryotic promoters. The enhancer may be spliced into the vector at a position 5' or 3' to the antibody or antibody fragment DNA, but is preferably located at a site 5' from the promoter.

(vi) Transcription Termination Component

Expression vectors used in eukaryotic host cells (yeast, fungi, insect, plant, animal, human, or nucleated cells from other multicellular organisms) can also contain sequences necessary for the termination of transcription and for stabilizing the mRNA. Such sequences are commonly available from the 5' and, occasionally 3' untranslated regions of eukaryotic or viral DNAs or cDNAs. These regions contain nucleotide segments transcribed as polyadenylated fragments in the untranslated portion of the mRNA encoding the antibody or antibody fragment. The 3' untranslated regions also include transcription termination sites.

Suitable vectors containing one or more of the above listed components and the desired coding and control sequences are constructed by standard ligation techniques. Isolated plasmids or DNA fragments are cleaved, tailored, and religated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.*, 9: 309 (1981) or by the method of Maxam et al., *Methods in Enzymology*, 65: 499 (1980).

Particularly useful in the practice of this invention are expression vectors that provide for the transient expression in mammalian cells of DNA encoding the antibody or antibody fragment. In general, transient expression involves the use of an expression vector that is able to replicate efficiently in a host cell, such that the host cell accumulates many copies of the expression vector and, in turn, synthesizes high levels of a desired polypeptide encoded by the expression vector.

Other methods, vectors, and host cells suitable for adaptation to the synthesis of the antibody or antibody fragment in recombinant vertebrate cell culture are described in Gething et al., *Nature*, 293: 620–625 (1981); Mantei et al., *Nature*, 281: 40–46 (1979); Levinson et al., EP 117,060; and EP 117,058. A particularly useful plasmid for mammalian cell culture expression of the IgE peptide antagonist is pRK5 (EP pub. no. 307,247) or pSVI6B (PCT pub. no. WO 91/08291 published Jun. 13, 1991).

C. Selection and Transformation of Host Cells

Suitable host cells for cloning or expressing the vectors herein are the prokaryote, yeast, or higher eukaryote cells described above. Suitable prokaryotes include eubacteria, such as Gram-negative or Gram-positive organisms, for example, *E. coli*, *Bacilli* such as *B. subtilis*, *Pseudomonas* species such as *P. aeruginosa*, *Salmonella typhimurium*, or *Serratia marcescens*. One preferred *E. coli* cloning host is *E. coli* 294 (ATCC 31,446), although other strains such as *E. coli* B, *E. coli* 1776 (ATCC 31,537), and *E. coli* W3110 (ATCC 27,325) are suitable. These examples are illustrative rather than limiting. Preferably the host cell should secrete minimal amounts of proteolytic enzymes. In a preferred embodiment, the *E. coli* strain 49D6 is used as the expression host as described in the Examples below. Review articles describing the recombinant production of antibodies in bacterial host cells include Skerra et al., *Curr. Opinion in Immunol.*, 5: 256 (1993) and Pluckthun, *Immunol. Revs.*, 130: 151 (1992).

In addition to prokaryotes, eukaryotic microbes such as filamentous fungi or yeast are suitable hosts for vectors containing antibody or antibody fragment DNA. *Saccharomyces cerevisiae*, or common baker's yeast, is the most commonly used among lower eukaryotic host microorganisms. However, a number of other genera, species, and strains are commonly available and useful herein, such as *S. pombe* (Beach and Nurse, *Nature*, 290: 140 (1981)), *Kluyveromyces lactis* (Louvencourt et al., *J. Bacteriol.*, 737 (1983)), *yarrowia* (EP 402,226), *Pichia pastoris* (EP 183, 070), *Trichoderma reesia* (EP 244,234), *Neurospora crassa* (Case et al., *Proc. Natl. Acad. Sci. USA*, 76: 5259–5263 (1979)), and Aspergillus hosts such as *A. nidulans* (Ballance et al., *Biochem. Biophys. Res. Commun.*, 112: 284–289 (1983); Tilburn et al., *Gene*, 26: 205–221 (1983); Yelton et al., *Proc. Natl. Acad. Sci. USA*, 81: 1470–1474 (1984)) and *A. niger* (Kelly and Hynes, *EMBO J.*, 4: 475–479 (1985)).

Host cells derived from multicellular organisms can also be used in the recombinant production of antibody or antibody fragment. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* host cells have been identified. See, e.g., Luckow et al., *Bio/Technology*, 6: 47–55 (1988); Miller et al., in *Genetic Engineering*, Setlow, J. K. et al., 8: 277–279 (Plenum Publishing, 1986), and Maeda et al., *Nature*, 315: 592–594 (1985). A variety of such viral strains are publicly available, e.g., the L-1 variant of Autographa californica NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens*, which has been previously manipulated to contain the antibody or antibody fragment DNA. During incubation of the plant cell culture with *A. tumefaciens*, the DNA encoding antibody or antibody fragment is transferred to the plant cell host such that it is transfected, and will, under appropriate conditions, express the antibody or antibody fragment DNA. In addition, regulatory and signal sequences compatible with plant cells are available, such as the nopaline synthase promoter and polyadenylation signal sequences. Depicker et al, *J. Mol. Appl. Gen.*, 1: 561 (1982). In addition, DNA segments isolated from the upstream region of the T-DNA 780 gene are capable of activating or increasing transcription levels of plant-expressible genes in recombinant DNA-containing plant tissue. See EP 321,196 published Jun. 21, 1989.

Vertebrate cell culture is preferred for the recombinant production of full length antibodies. The propagation of vertebrate cells in culture (tissue culture) has become a routine procedure in recent years (*Tissue Culture*, Academic Press, Kruse and Patterson, editors (1973)). Examples of useful mammalian host cell lines are monkey kidney CV1 line transformed by SV40 (COS-7, ATCC CPL 1651); human embryonic kidney line (293 or 293 cells subcloned for growth in suspension culture, Graham et al., *J. Gen Virol.*, 36: 59 (1977)); baby hamster kidney cells (BHK, ATCC CCL 10); Chinese hamster ovary cells/-DHFR (CHO, Urlaub and Chasin, *Proc. Natl. Acad. Sci. USA*, 77: 4216 (1980)); mouse sertoli cells (TM4, Mather, *Biol. Reprod.*, 23: 243–251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.*, 383: 44–68 (1982)); MRC 5 cells; FS4 cells; and a human hepatoma cell line (Hep G2). Preferred host cells are human embryonic kidney 293 and Chinese hamster ovary cells. Myeloma cells that do not otherwise produce immunoglobulin protein are also useful host cells for the recombinant production of full length antibodies.

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ precipitation and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., supra, is generally used for prokaryotes or other cells that contain substantial cell-wall barriers. Infection with *Agrobacterium tumefaciens* is used for transformation of certain plant cells, as described by Shaw et al., *Gene*, 23: 315 (1983) and WO 89/05859 published Jun. 29, 1989. For mammalian cells without such cell walls, the calcium phosphate precipitation method described in sections 16.30–16.37 of Sambrook et al., supra, is preferred. General aspects of mammalian cell host system transformations have been described by Axel in U.S. Pat. No. 4,399,216 issued Aug. 16, 1983. Transformations into yeast are typically carried out according to the method of Van Solingen et al., *J. Bact.*, 130: 946 (1977) and Hsiao et al., *Proc. Natl. Acad. Sci.* (USA), 76: 3829 (1979). However, other methods for introducing DNA into cells such as by nuclear injection, electroporation, or by protoplast fusion may also be used.

D. Culturing the Host Cells

Prokaryotic cells used to produce the antibody or antibody fragment are cultured in suitable media as described generally in Sambrook et al., supra.

The mammalian host cells used to produce the antibody or antibody fragment can be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host cells. In addition, any of the media described in Ham and Wallace, *Meth. Enz.*, 58: 44 (1979), Barnes and Sato, *Anal. Biochem.*, 102: 255 (1980), U.S. Pat. Nos. 4,767,704; 4,657,866; 4,927,762; or U.S. Pat. No. 4,560,655; WO 90/03430; WO 87/00195; U.S. Pat. No. Re. 30,985; or U.S. Pat. No. 5,122,469, the disclosures of all of which are incorporated herein by reference, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

The host cells referred to in this disclosure encompass cells in in vitro culture as well as cells that are within a host animal.

E. Detecting Gene Amplification/Expression

Gene amplification and/or expression may be measured in a sample directly, for example, by conventional Southern blotting, northern blotting to quantitate the transcription of mRNA (Thomas, *Proc. Natl. Acad. Sci. USA*, 77: 5201–5205 (1980)), dot blotting (DNA analysis), or in situ hybridization, using an appropriately labeled probe, based on the sequences provided herein. Various labels may be employed, most commonly radioisotopes, particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product, where the labels are usually visually detectable, such as enzymatic labels, fluorescent labels, luminescent labels, and the like. A particularly sensitive staining technique suitable for use in the present invention is described by Hsu et al., *Am. J. Clin. Path.*, 75: 734–738 (1980).

F. Purification of the Antibody or Antibody Fragment

In the case of a host cell secretion system, the antibody or antibody fragment is recovered from the culture medium. Alternatively, the antibody can be produced intracellularly, or produced in the periplasmic space of a bacterial host cell. If the antibody is produced intracellularly, as a first step, the host cells are lysed, and the resulting particulate debris is removed, for example, by centrifugation or ultrafiltration. Carter et al., Bio/Technology 10:163–167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human $\gamma 1$, $\gamma 2$, or $\gamma 4$ heavy chains (Lindmark et al., *J. Immunol. Meth.* 62:1–13 (1983)). Protein G is recommended for all mouse isotypes and for human $\gamma 3$ (Guss et al, *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H 3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin Sepharose™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5–4.5, preferably performed at low salt concentrations (e.g. from about 0–0.25M salt).

G. Production of Antibody Fragments

Various techniques have been developed for the production of the humanized antibody fragments of the invention, including Fab, Fab', Fab'-SH, or F(ab')$_2$ fragments. Traditionally, these fragments were derived via proteolytic digestion of intact antibodies (see, e.g., Morimoto et al., *Journal of Biochemical and Biophysical Methods* 24:107–117 (1992) and Brennan et al., *Science*, 229:81 (1985)). However, these fragments can now be produced directly b y re combinant host cells. For example, Fab'-SH fragments can be directly recovered from *E. coli* and chemically coupled to form F(ab')$_2$ fragments (Carter et al., *Bio/Technology*, 10:163–167 (1992)). According to another approach, F(ab')$_2$ fragments can be isolated directly from recombinant host cell culture. Other techniques for the production of antibody fragments will l be apparent to the skilled practitioner.

5. Uses of Anti-IL-8 Antibodies

A. Diagnostic Uses

For diagnostic applications requiring the detection or quantitation of IL-8, the antibodies or antibody fragments of the invention typically will be labeled with a detectable moiety. The detectable moiety can be any one which is capable of producing, either directly or indirectly, a detectable signal. For example, the detectable moiety can be a radioisotope, such as $^3H$, $^{14}C$, $^{32}P$, $^{35}S$, or $^{125}I$; a fluorescent or chemiluminescent compound, such as fluorescein isothiocyanate, rhodamine, or luciferin; radioactive isotopic labels, such as, e.g., $^{125}I$, $^{32}P$, $^{14}C$, or $^3H$; or an enzyme, such as alkaline phosphatase, beta-galactosidase, or horseradish peroxidase.

Any method known in the art for separately conjugating the antibody or antibody fragment to the detectable moiety can be employed, including those methods described by Hunter et al, *Nature* 144:945 (1962); David et al., *Biochemistry* 13:1014 (1974); Pain et al., *J. Immunol. Meth.* 40:219 (1981); and Nygren, *J. Histochem. and Cytochem.* 30:407 (1982).

The antibodies and antibody fragments of the present invention can be employed in any known assay method, such as competitive binding assays, direct and indirect sandwich assays, and immunoprecipitation as says. For example, see Zola, *Monoclonal Antibodies: A Manual of Techniques*, pp. 147–158 (CRC Press, Inc., 1987).

Competitive binding assays rely on the ability of a labeled standard (which can be a IL-8 or an immunologically reactive portion thereof) to compete with the test sample analyte (IL-8) for binding with a limited amount of antibody or antibody fragment. The amount of IL-8 in the test sample is inversely proportional to the amount of standard that becomes bound to the antibodies. To facilitate determining the amount of standard that becomes bound, the antibodies or antibody fragments generally are insolubilized before or after the competition, so that the standard and analyte that are bound to the antibodies can conveniently be separated from the standard and analyte which remain unbound.

Sandwich assays involve the use of two antibodies, each capable of binding to a different antigenic portion, or epitope, of the protein (IL-8) to be detected. In a sandwich assay, the test sample analyte is bound by a first antibody which is immobilized on a solid support, and thereafter a second antibody binds to the analyte, thus forming an insoluble three-part complex (U.S. Pat. No. 4,376,110). The second antibody can itself be labeled with a detectable moiety (direct sandwich assays) or can be measured using an anti-immunoglobulin antibody that is labeled with a detectable moiety (indirect sandwich assay). For example, one type of sandwich assay is an ELISA assay, in which case the detectable moiety is an enzyme (e.g., horseradish peroxidase).

IL-8 antibodies and antibody fragments also are useful for the affinity purification of IL-8 from recombinant cell culture or natural sources. For example, these antibodies can be fixed to a solid support by techniques well known in the art so as to purify IL-8 from a source such as culture supernatant or tissue.

B. Therapeutic Compositions and Administration of Anti-IL-8 Antibody

The humanized anti-IL-8 antibodies and antibody fragments of the invention are useful in the treatment of inflammatory disorders, such as adult respiratory distress syndrome (ARDS), hypovolemic shock, ulcerative colitis, and rheumatoid arthritis.

Therapeutic formulations of the humanized anti-IL-8 antibodies and antibody fragments are prepared for storage by mixing the antibody or antibody fragment having the desired degree of purity with optional physiologically acceptable carriers, excipients, or stabilizers (*Remington's Pharmaceutical Sciences*, supra), in the form of lyophilized cake or aqueous solutions. Acceptable carriers, excipients or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

The humanized anti-IL-8 mAb or antibody fragment to be used for in vivo administration must be sterile. This is readily accomplished by filtration through sterile filtration membranes, prior to or following lyophilization and reconstitution. The humanized anti-IL-8 mAb or antibody fragment ordinarily will be stored in lyophilized form or in solution.

Therapeutic humanized anti-IL-8 mAb or antibody fragment compositions generally are placed into a container having a sterile access port, for example, an intravenous solution bag or vial having a stopper pierceable by a hypodermic injection needle.

The route of humanized anti-IL-8 mAb or antibody fragment administration is in accord with known methods, e.g., inhalation, injection or infusion by intravenous, intraperitoneal, intracerebral, intramuscular, intraocular, intraarterial, or intralesional routes, by enema or suppository, or by sustained release systems as noted below. Preferably the antibody is given systemically or at a site of inflammation.

Suitable examples of sustained-release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamate (Sidman et al., *Biopolymers* 22:547 (1983)), poly (2-hydroxyethyl-methacrylate) (Langer et al., *J. Biomed. Mater. Res.* 15:167 (1981) and Langer, *Chem. Tech.* 12:98 (1982)), ethylene vinyl acetate (Langer et al., supra) or poly-D-(-)-3-hydroxybutyric acid (EP 133,988). Sustained-release humanized anti-IL-8 antibody or antibody fragment compositions also include liposomally entrapped antibody or antibody fragment. Liposomes containing an antibody or antibody fragment are prepared by methods known per se: DE 3,218,121; Epstein et al., *Proc. Natl. Acad. Sci. U.S.A.* 82:3688 (1985); Hwang et al., *Proc. Natl. Acad. Sci. U.S.A.* 77:4030 (1980); EP 52,322; EP 36,676; EP 88,046; EP 143,949; EP 142,641; Japanese patent application 83–118008; U.S. Pat. Nos. 4,485,045 and 4,544,545; and EP 102,324. Ordinarily the liposomes are of the small (about 200–800 Angstroms) unilamelar type in which the lipid content is greater than about 30 mole percent cholesterol, the selected proportion being adjusted for the most efficacious antibody or antibody fragment therapy.

An "effective amount" of the humanized anti-IL-8 antibody or antibody fragment to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. Typically, the clinician will administer the humanized anti-IL-8 antibody or antibody fragment until a dosage is reached that achieves the desired effect. The progress of this therapy is easily monitored by conventional assays.

In the treatment and prevention of an inflammatory disorder with a humanized anti-IL-8 antibody or antibody fragment of the invention, the antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the antibody, the particular type of antibody, the method of administration, the scheduling of administration, and other factors known to medical practitioners. The "therapeutically effective amount" of antibody to be administered will be governed by such considerations, and is the minimum amount necessary to prevent, ameliorate, or treat the inflammatory disorder, including treating acute or chronic respiratory diseases and reducing inflammatory responses. Such amount is preferably below the amount that is toxic to the host or renders the host significantly more susceptible to infections.

As a general proposition, the initial pharmaceutically effective amount of the antibody or antibody fragment administered parenterally per dose will be in the range of about 0.1 to 50 mg/kg of patient body weight per day, with the typical initial range of antibody used being 0.3 to 20 mg/kg/day, more preferably 0.3 to 15 mg/kg/day.

As noted above, however, these suggested amounts of antibody or antibody fragment are subject to a great deal of therapeutic discretion. The key factor in selecting an appropriate dose and scheduling is the result obtained, as indicated above.

The antibody or antibody fragment need not be, but is optionally formulated with one or more agents currently used to prevent or treat the inflammatory disorder in question. For example, in rheumatoid arthritis, the antibody can be given in conjunction with a glucocorticosteroid. The effective amount of such other agents depends on the amount of antibody or antibody fragment present in the formulation, the type of disorder or treatment, and other factors discussed above. These are generally used in the same dosages and with administration routes as used hereinbefore or about from 1 to 99% of the heretofore employed dosages.

The following examples are offered by way of illustration and not by way of limitation. The disclosures of all references cited in the specification, and the disclosures of all citations in such references, are expressly incorporated herein by reference.

EXAMPLES

A. GENERATION AND CHARACTERIZATION OF MONOCLONAL ANTIBODIES AGAINST HUMAN IL-8

Balb/c mice were immunized in each hind footpad or intraperitoneally with 10 μg of recombinant human IL-8 (produced as a fusion of (ser-IL-8)$_{72}$ with ubiquitin (Hebert et al. *J. Immunology* 145:3033–3040 (1990)); IL-8 is available commercially from PeproTech, Inc., Rocky Hill, N.J.) resuspended in MPL/TDM (Ribi Immunochem. Research Inc., Hamilton, Mont.) and boosted twice with the same amount of IL-8. In these experiments, "IL-8" is intended to mean (ser-IL-8)$_{72}$ unless otherwise specified. A final boost of 10 μg of IL-8 was given 3 days before the fusion. Spleen cells or popliteal lymph node cells were fused with mouse myeloma P3X63Ag8U.1 (ATCC CRL 1597), a non-secreting clone of the myeloma P3X63Ag8, using 35% polyethylene glycol as described before. Ten days after the fusion, culture supernatant was screened for the presence of monoclonal antibodies to IL-8 by ELISA.

The ELISA was performed as follows. Nunc 96-well immunoplates (Flow Lab, McLean, Va.) were coated with 50 μl/well of 2 μg/ml IL-8 in phosphate-buffered saline (PBS) overnight at 4□C. The remaining steps were carried out at room temperature. Nonspecific binding sites were blocked with 0.5% bovine serum albumin (BSA) for 1 hour (hr). Plates were then incubated with 50 μl/well of hybridoma culture supernatants from 672 growing parental fusion wells for 1 hr, followed by the incubation with 50 μl/well of 1:1000 dilution of a 1 mg/ml stock solution of alkaline phosphatase-conjugated goat anti-mouse Ig (Tago Co., Foster City, Calif.) for 1 hr. The level of enzyme-linked antibody bound to the plate was determined by the addition of 100 μl/well of 0.5 mg/ml of r-nitrophenyl phosphate in sodium bicarbonate buffer, pH 9.6. The color reaction was measured at 405 nm with an ELISA plate reader (Titertrek Multiscan, Flow Lab, McLean, Va.). Between each step, plates were washed three times in PBS containing 0.05% Tween 20.

Culture supernatants which promoted 4-fold more binding of IL-8 than did control medium were selected as positives. According to this criterion, 16 of 672 growing parental fusion wells (2%) were positive. These positive hybridoma cell lines were cloned at least twice by using the limiting dilution technique.

Seven of the positive hybridomas were further characterized as follows. The isotypes of the monoclonal antibodies were determined by coating Nunc 96-well immunoplates (Flow Lab, McLean, Va.) with IL-8 overnight, blocking with BSA, incubating with culture supernatants followed by the addition of predetermined amount of isotype-specific alkaline phosphatase-conjugated goat anti-mouse Ig (Fisher Biotech, Pittsburgh, Pa.). The level of conjugated antibodies bound to the plate was determined by the addition of r-nitrophenyl phosphate as described above.

All the monoclonal antibodies tested belonged to either IgG$_1$ or IgG$_2$ immunoglobulin isotype. Ascites fluid containing these monoclonal antibodies had antibody titers in the range of 10,000 to 100,000 as determined by the reciprocal of the dilution factor which gave 50% of the maximum binding in the ELISA.

To assess whether these monoclonal antibodies bound to the same epitopes, a competitive binding ELISA was performed. At a ratio of biotinylated mAb to unlabeled mAb of 1:100, the binding of biotinylated mAb 5.12.14 was significantly inhibited by its homologous mAb but not by mAb 4.1.3, while the binding of biotinylated mAb 4.1.3 was inhibited by mAb 4.1.3 but not by mAb 5.12.14. Monoclonal antibody 5.2.3 behaved similarly to mAb 4.1.3, while monoclonal antibodies 4.8 and 12.3.9 were similar to mAb 5.12.14. Thus, mAb 4.1.3 and mAb 5.2.3 bind to a different epitope(s) than the epitope recognized by monoclonal antibodies 12.3.9, 4.8 and 5.12.14.

Immunodot blot analysis was performed to assess antibody reactivity to IL-8 immobilized on nitrocellulose paper. All seven antibodies recognized IL-8 immobilized on paper, whereas a control mouse IgG antibody did not.

The ability of these monoclonal antibodies to capture soluble $^{125}$I-IL-8 was assessed by a radioimmune precipitation test (RIP). Briefly, tracer $^{125}$I-IL-8 (4×10$^4$ cpm) was incubated with various dilutions of the monoclonal anti-IL-8 antibodies in 0.2 ml of PBS containing 0.5% BSA and 0.05% Tween 20 (assay buffer) for 1 hr at room temperature. One hundred microliters of a predetermined concentration of goat anti-mouse Ig antisera (Pel-Freez, Rogers, AR) were added and the mixture was incubated at room temperature for 1 hr. Immune complexes were precipitated by the addition of 0.5 ml of 6% polyethylene glycol (M.W. 8000) kept at 4□C. After centrifugation at 2,000×g for 20 min at 4□C, the supernatant was removed by aspiration and the radioactivity remaining in the pellet was counted in a gamma counter. Percent specific binding was calculated as (precipitated cpm—background cpm)/(total cpm—background cpm). Monoclonal antibodies 4.1.3, 5.2.3, 4.8, 5.12.14 and 12.3.9 captured $^{125}$I-IL-8 very efficiently, while antibodies 9.2.4 and 8.9.1 were not able to capture soluble $^{125}$I-IL-8 in the RIP even though they could bind to IL-8 coated onto ELISA plates (Table 1).

The dissociation constants of these monoclonal antibodies were determined using a competitive binding RIP assay. Briefly, competitive inhibition of the binding each antibody to $^{125}$I-IL-8 (20,000–40,000 cpm per assay) by various amounts of unlabeled IL-8 was determined by the RIP described above. The dissociation constant (affinity)of each mAb was determined by using Scatchard plot analysis (Munson, et al., *Anal. Biochem.* 107:220 (1980)) as provided in the VersaTerm-PRO computer program (Synergy Software, Reading, Pa.).The K$_d$'s of these monoclonal antibodies (with the exception of 9.2.4. and 8.9.1) were in the range from 2×10$^{-8}$ to 3×10$^{-10}$M. Monoclonal antibody 5.12.14 with a K$_d$ of 3×10$^{-10}$M showed the highest affinity among all the monoclonal antibodies tested (Table 3).

TABLE 3

Characterization of Anti-IL-8 Monoclonal Antibodies

| Antibody | % Specific Binding to IL-8 | K$_d$(M) | Isotype | pI |
|---|---|---|---|---|
| 4.1.3 | 58 | 2 × 10$^{-9}$ | IgG$_1$ | 4.3–6.1 |
| 5.2.3 | 34 | 2 × 10$^{-8}$ | IgG$_1$ | 5.2–5.6 |
| 9.2.4 | 1 | — | IgG$_1$ | 7.0–7.5 |
| 8.9.1 | 2 | — | IgG$_1$ | 6.8–7.6 |
| 4.8 | 62 | 3 × 10$^{-8}$ | IgG$_{2a}$ | 6.1–7.1 |
| 5.12.14 | 98 | 3 × 10$^{-10}$ | IgG$_{2a}$ | 6.2–7.4 |
| 12.3.9 | 86 | 2 × 10$^{-9}$ | IgG$_{2a}$ | 6.5–7.1 |

To assess the ability of these monoclonal antibodies to neutralize IL-8 activity, the amount of $^{125}$I-IL-8 bound to human neutrophils in the presence of various amounts of culture supernatants and purified monoclonal antibodies was measured. Neutrophils were prepared by using Mono-Poly Resolving Medium (M-PRM) (Flow Lab. Inc., McLean, Va.). Briefly fresh, heparinized human blood was loaded onto M-PRM at a ratio of blood to medium, 3.5:3.0, and centrifuged at 300×g for 30 min at room temperature. Neutrophils enriched at the middle layer were collected and washed once in PBS. Such a preparation routinely contained greater than 95% neutrophils according to the Wright's Giemsa staining. The receptor binding assay was done as follows. 50 µl of $^{125}$I-IL-8 (5 ng/ml) was incubated with 50 µl of unlabeled IL-8 (100 µg/ml) or monoclonal antibodies in PBS containing 0.1% BSA for 30 min at room temperature. The mixture was then incubated with 100 µl of neutrophils ($10^7$ cells/ml) for 15 min at 37□C. The $^{125}$I-IL-8 bound was separated from the unbound material by loading mixtures onto 0.4 ml of PBS containing 20% sucrose and 0.1% BSA and by centrifugation at 300×g for 15 min. The supernatant was removed by aspiration and the radioactivity associated with the pellet was counted in a gamma counter.

Monoclonal antibodies 4.1.3, 5.2.3, 4.8, 5.12.14, and 12.3.9 inhibited greater than 85% of the binding of IL-8 to human neutrophils at a 1:25 molar ratio of IL-8 to mAb. On the other hand, monoclonal antibodies 9.2.4 and 8.9.1 appeared to enhance the binding of IL-8 to its receptors on human neutrophils. Since a control mouse IgG also enhanced the binding of IL-8 on neutrophils, the enhancement of IL-8 binding to its receptors by mAb 9.2.4 and 8.9.1 appears to be nonspecific. Thus, monoclonal antibodies, 4.1.3, 5.1.3, 4.8, 5.12.14, and 12.3.9 are potential neutralizing monoclonal antibodies while monoclonal antibodies 8.9.1 and 9.2.4 are non-neutralizing monoclonal antibodies.

The ability of the anti-IL-8 antibodies to block neutrophil chemotaxis induced by IL-8 was tested as follows. Neutrophil chemotaxis induced by IL-8 was determined using a Boyden chamber method (Larsen, et al. Science 243:1464 (1989)). One hundred µl of human neutrophils ($10^6$ cells/ml) resuspended in RPMI containing 0.1% BSA were placed in the upper chamber and 29 µl of the IL-8 (20 nM) with or without monoclonal antibodies were placed in the lower chamber. Cells were incubated for 1 hr at 37□C. Neutrophils migrated into the lower chamber were stained with Wright's Giemsa stain and counted under the microscope (100× magnification). Approximately 10 different fields per experimental group were examined. Neutralizing monoclonal antibodies 5.12.14 and 4.1.3 blocked almost 70% of the neutrophil chemotactic activity of IL-8 at 1:10 ratio of IL-8 to mAb.

The isoelectric focusing (IEF) pattern of each mAb was determined by applying purified antibodies on an IEF polyacrylamide gel (pH 3–9, Pharmacia) using the Fast gel system (Pharmacia, Piscataway, N.J.). The IEF gel was pretreated with pharmalyte containing 1% Triton X100 (Sigma, St. Louis, Mo.) for 10 min before loading the samples. The IEF pattern was visualized by silver staining according to the instructions from the manufacturer. All of the monoclonal antibodies had different IEF patterns, confirming that they originated from different clones. The pI values for the antibodies are listed in Table 3.

All these monoclonal antibodies bound equally well to both (ala-IL-8)77 and (ser-IL-8)72 forms of IL-8. Because IL-8 has greater than 30% sequence homology with certain other members of the platelet factor 4 (PF4) family of inflammatory cytokines such as β-TG (Van Damme et al., Eur. J. Biochem. 181:337(1989); Tanaka et al., FEB 236(2):467 (1988)) and PF4 (Deuel et al., Proc. Natl. Acad. Sci. U.S.A. 74:2256 (1977)), they were tested for possible cross reactivity to β-TG and PF4, as well as to another neutrophil activating factor, C5a. No detectable binding to any of these proteins was observed, with the exception of mAb 4.1.3, which had a slight cross reactivity to β-TG.

One of the antibodies, mAb 5.12.14, was further studied to determine whether it could block the IL-8 mediated release of elastase by neutrophils. Briefly, human neutrophils were resuspended in Hanks balanced salt solution (Gibco, Grand Island, N.Y.) containing 1.0% BSA, Fraction V (Sigma, St. Louis, Mo.), 2 mg/ml alpha-D-glucose (Sigma), 4.2 mM sodium bicarbonate (Sigma) and 0.01 M HEPES, pH 7.1 (JRH Bioscience, Lenexa, Kans.). A stock of cytochalasin B (Sigma) was prepared (5 mg/ml in dimethylsulfoxide (Sigma) and stored at 2–8° C. Cytochalasin B was added to the neutrophil preparation to produce a final concentration of 5 µg/ml, and incubated for 15 min at 37° C. Human IL-8 was incubated with mAb 5.12.14 (20 µl), or a negative control antibody, in 1 ml polypropylene tubes (DBM Scientific, San Fernando, Calif.) for 30 min at 37° C. The final assay concentrations of IL-8 were 50 and 500 nM. The monoclonal antibodies were diluted to produce the following ratios (IL-8:Mab): 1:50, 1:10, 1:2, 1:1, and 1:0.25. Cytochalasin B-treated neutrophils were added (100 µl/tube) and incubated for 2 hours at 25° C. The tubes were centrifuged (210×g, 2–8° C.) for 10 min, and supernatants wer transferred to 96 well tissue culture plates (30 µl/well). Elastase substrate stock, 10 mM methoxysuccinyl-alanyl-alanyl-propyl-valyl-p-nitroanilide (Calbiochem, La Jolla, Calif.) in DMSO was prepared and stored at 2–8° C. Elastase substrate solution (1.2 mM substrate, 1.2 M NaCl (Mallinckrodt, Paris, Ky.), 0.12 M HEPES pH 7.2 in distilled water) was added (170 µl/well) to the supernatants and incubated for 0.5 to 2 hours at 37° C. (until control O.D. of 1.0 was reached). Absorbance was measured at 405 nm (SLT 340 ATTC plate reader, SLT Lab Instruments, Austria).

The results are shown in FIG. 1. At a 1:1 ratio of IL-8 to mAb 5.12.14, the antibody was able to effectively block the release of elastase from neutrophils.

The hybridoma producing antibody 5.12.14 was deposited on Feb. 15, 1993 with the American Type Culture Collection, 12301 Parklawn Drive, Rockville, Md., U.S.A. (ATCC) and assigned ATTC Accession No. HB 11553.

B. GENERATION AND CHARACTERIZATION OF MONOCLONAL ANTIBODIES AGAINST RABBIT IL-8

Antibodies against rabbit IL-8 were generated in essentially the same process as anti-human IL-8 antibodies using rabbit IL-8 as immunogen (kindly provided by C. Broaddus; see also Yoshimura et al. J. Immunol. 146:3483 (1991)). The antibody was characterized as described above for binding to other cytokines coated onto ELISA plates; no measurable binding was found to MGSA, FMLP, C5a, b-TG, TNF, PF4, or IL-1.

The hybridoma producing antibody 6G4.2.5 was deposited on Sep. 28, 1994, with the American Type Culture Collection, 12301 Parklawn Drive, Rockville, Md., U.S.A. (ATCC) and assigned ATTC Accession No. HB 11722.

Recombinant human-murine chimeric Fabs for 5.12.14 and 6G4.2.5 were constructed as described below. A chimeric 6G.4.25 Fab is compared with a chimeric 5.12.14 Fab in detail below.

1. INHIBITION OF IL-8 BINDING TO HUMAN NEUTROPHILS BY 5.12.14-FAB AND6G4 2.5-FAB

The ability of the two chimeric Fabs, 5.12.14-Fab and 6G4.2.5-Fab, to efficiently bind IL-8 and prevent IL-8 from binding to IL-8 receptors on human neutrophils was determined by performing a competition binding assay which allows the calculation of the $IC_{50}$—concentration required to achieve 50% inhibition of IL-8 binding.

Figure 2:
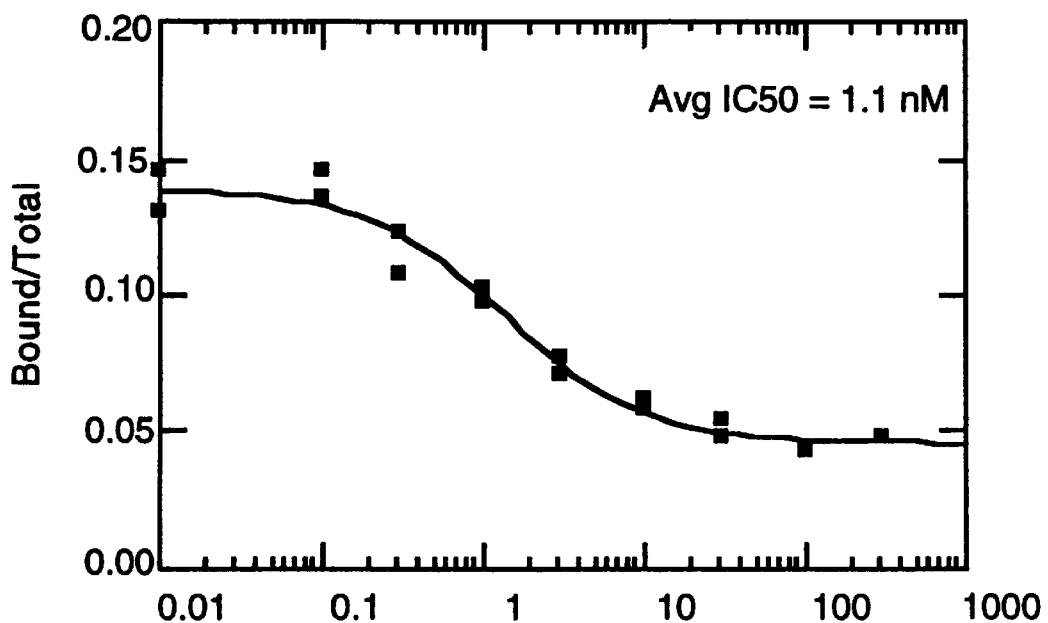
FIG. 2 is a graph depicting the inhibition of $^{125}$I-IL-8 binding to neutrophils by unlabeled IL-8.
Figure 3:
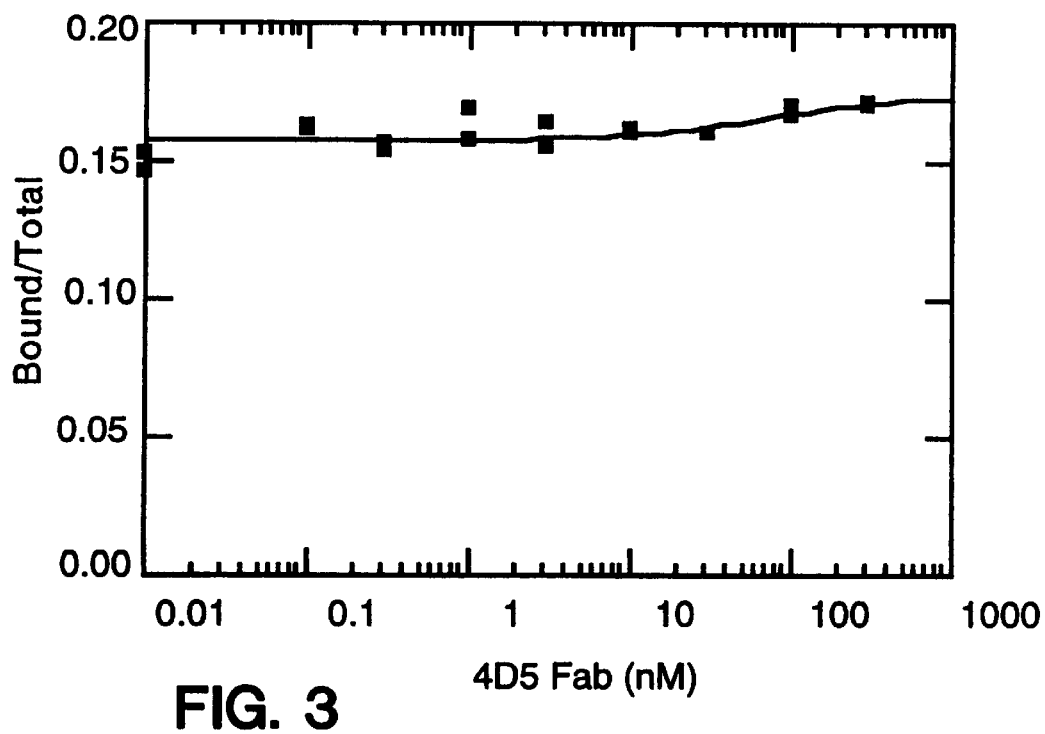
FIG. 3 demonstrates that a isotype matched negative control Fab (denoted as "4D5 Fab") does not inhibit the binding of $^{125}$I-IL-8 to human neutrophils.
Figure 4:
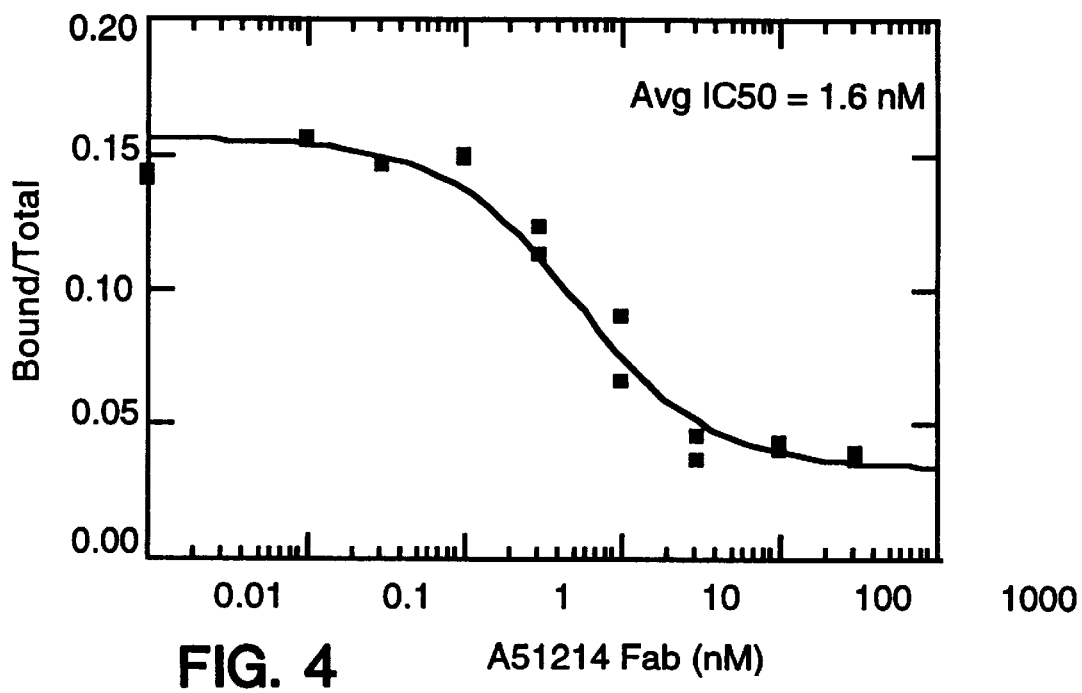
FIG. 4 is a graph depicting the inhibition of binding of $^{125}$I-IL-8 to human neutrophils by chimeric 5.12.14 Fab with an average IC$_{50}$ of 1.6 nM.
Figure 5:
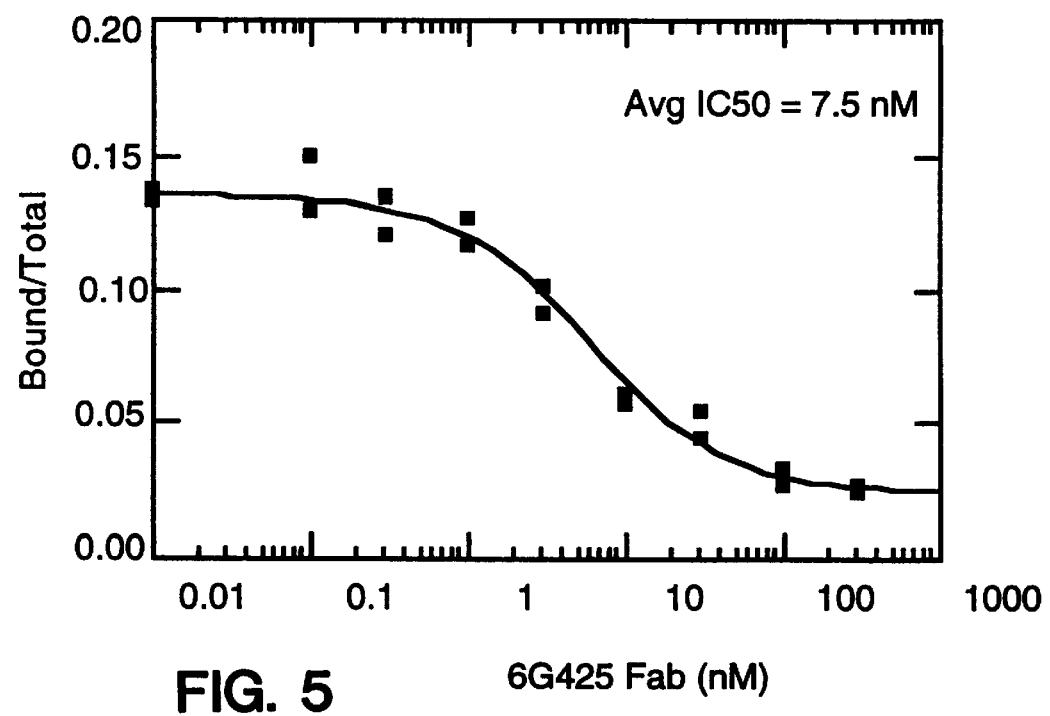
FIG. 5 is a graph depicting the inhibition of binding of $^{125}$I-IL-8 to human neutrophils by chimeric 6G.4.25 Fab with an average IC$_{50}$ of 7.5 nM.

Human neutrophils ($5\times10^5$) were incubated for 1 hour at 4° C. with 0.5 nM $^{125}$I-IL-8 in the presence of various concentrations (0 to 300 nM) of 5.12.14-Fab, 6G4.2.5-Fab, an isotype control (4D5-Fab) or unlabeled IL-8. After the incubation, the unbound $^{125}$I-IL-8 was removed by centrifugation through a solution of 20% sucrose and 0.1% bovine serum albumin in phosphate buffered saline and the amount of $^{125}$I-IL-8 bound to the cells was determined by counting the cell pellets in a gamma counter. FIG. 2 demonstrates the inhibition of $^{125}$I-IL-8 binding to neutrophils by unlabeled IL-8. FIG. 3 demonstrates that a negative isotype matched Fab does not inhibit the binding of $^{125}$I-IL-8 to human neutrophils. Both the anti-IL-8 Fabs, 5.12.14 Fab (FIG. 4) and 6G.4.25 Fab (FIG. 5) were able to inhibit the binding of $^{125}$I-IL-8 to human neutrophils with an average $IC_{50}$ of 1.6 nM and 7.5 nM, respectively.

2. INHIBITION OF IL-8-MEDIATED NEUTROPHIL CHEMOTAXIS BY 5.12.14-FAB AND 6G4.2.5-FAB

Human neutrophils were isolated, counted and resuspended at $5\times10^6$ cells/ml in Hank's balanced salt solution (abbreviated HBSS; without calcium and magnesium) with 0.1% bovine serum albumin. The neutrophils were labeled by adding calcein AM (Molecular Probe, Eugene, OR) at a final concentration of 2.0 $\mu$M. Following a 30 minute incubation at 37° C., cells were washed twice with HBSS-BSA and resuspended at $5\times10^6$ cells/ml.

Chemotaxis experiments were carried out in a Neuro Probe (Cabin John, Md.) 96-well chamber, model MBB96. Experimental samples (buffer only control, IL-8 alone or IL-8 +Fabs) were loaded in a Polyfiltronics 96-well View plate (Neuro Probe Inc.) placed in the lower chamber. 100 $\mu$l of the calcein AM-labeled neutrophils were added to the upper chambers and allowed to migrate through a 5 micrometer porosity PVP free polycarbonate framed filter (Neuro Probe Inc.) toward the bottom chamber sample. The chemotaxis apparatus was then incubated for 40 to 60 minutes at 37° C. with 5% $CO_2$. At the end of the incubation, neutrophils remaining in the upper chamber were aspirated and upper chambers were washed three times with PBS. Then the polycarbonate filter was removed, non-migrating cells were wiped off with a squeegee wetted with PBS, and the filter was air dried for 15 minutes.

The relative number of neutrophils migrating through the filter (Neutrophil migration index) was determined by measuring fluorescence intensity of the filter and the fluorescence intensity of the contents of the lower chamber and adding the two values together. Fluorescence intensity was measured with a CytoFluor 2300 fluorescent plate reader (Millipore Corp. Bedford, Mass.) configured to read a Corning 96-well plate using the 485–20 nm excitation filter and a 530–25 emission filter, with the sensitivity set at 3.

Figure 6:
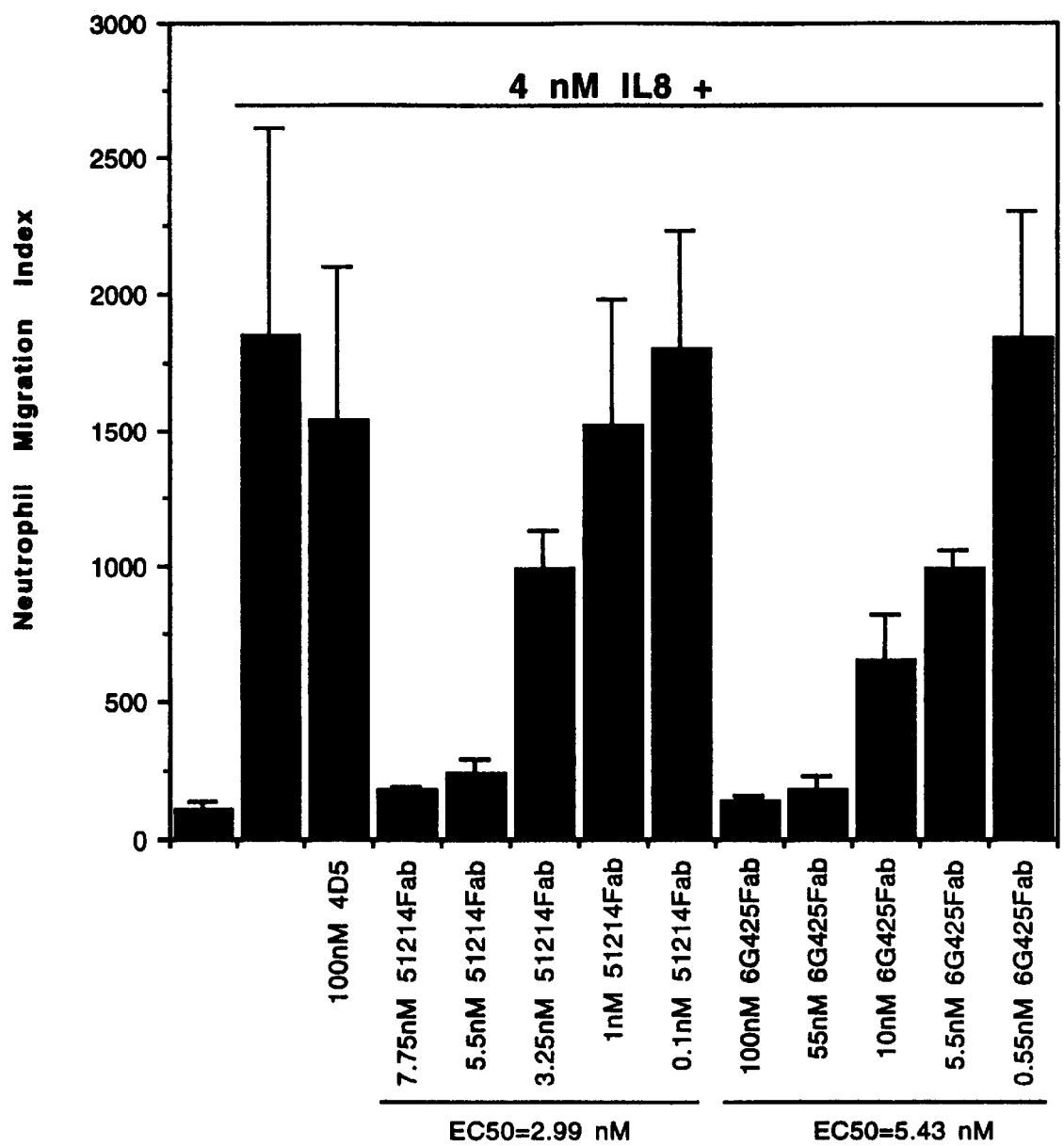
FIG. 6 demonstrates the inhibition of human IL-8 mediated neutrophil chemotaxis by chimeric 6G4.2.5 Fab and chimeric 5.12.14 Fab.
Figure 7:
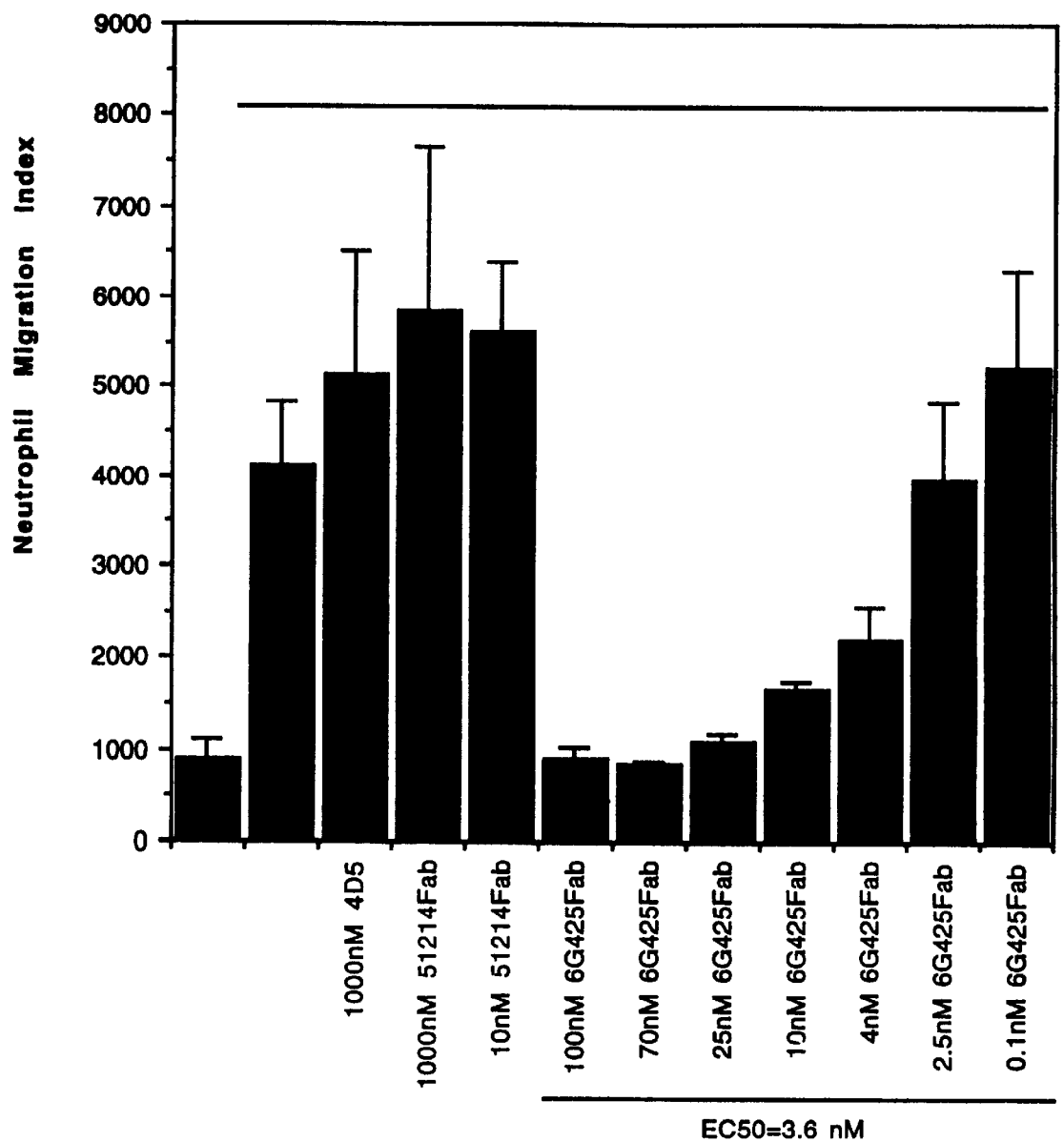
FIG. 7 demonstrates the relative abilities of chimeric 6G4.2.5 Fab and chimeric 5.12.14 Fab to inhibit rabbit IL-8 mediated neutrophil chemotaxis.

The results are shown in FIGS. 6 and 7. FIG. 6 demonstrates the inhibition of human IL-8 mediated neutrophil chemotaxis by chimeric 6G4.2.5 and 5.12.14 Fabs. FIG. 7 demonstrates the relative abilities of chimeric 6G4.2.5 and 5.12.14 Fabs to inhibit rabbit IL-8 mediated neutrophil chemotaxis.

3. INHIBITION OF IL-8-MEDIATED NEUTROPHIL ELASTASE RELEASE BY VARIOUS CONCENTRATIONS OF 6G4.2.5 AND 5.12.14 FABS

Blood was drawn from healthy male donors into heparinized syringes. Neutrophils were isolated by dextran sedimentation, centrifugation over Lymphocyte Separation Medium (Organon Teknika, Durham, N.C.), and hypotonic lysis of contaminating red blood cells as described by Berman et al. (*J. Cell Biochem.* 52:183 (1993)). The final neutrophil pellet was suspended at a concentration of $1\times10^7$ cells/ml in assay buffer, which consisted of Hanks Balanced Salt Solution (GIBCO, Grand Island, N.Y.) supplemented with 1.0% BSA (fraction V, Sigma, St. Louis, Mo.), 2 mg/ml glucose, 4.2 mM sodium bicarbonate, and 0.01 M HEPES, pH 7.2. The neutrophils were stored at 4□C for not longer than 1 hr.

Figure 8:
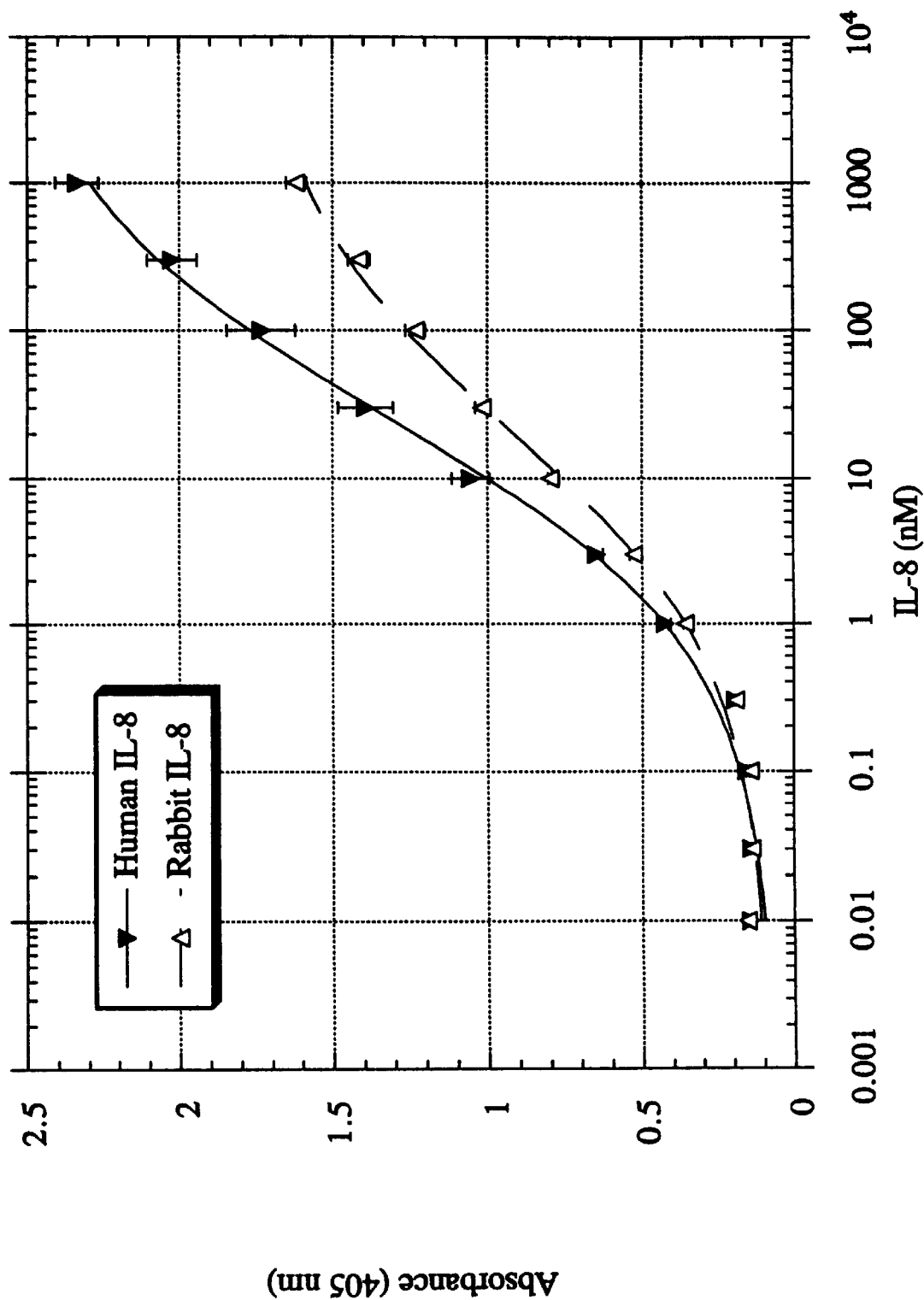
FIG. 8 depicts the stimulation of elastase release from human neutrophils by various concentrations of human and rabbit IL-8. The relative extent of elastase release was quantitated by measurement of absorbance at 405 nm. The data represent mean±SEM of triplicate samples.
Figure 9:
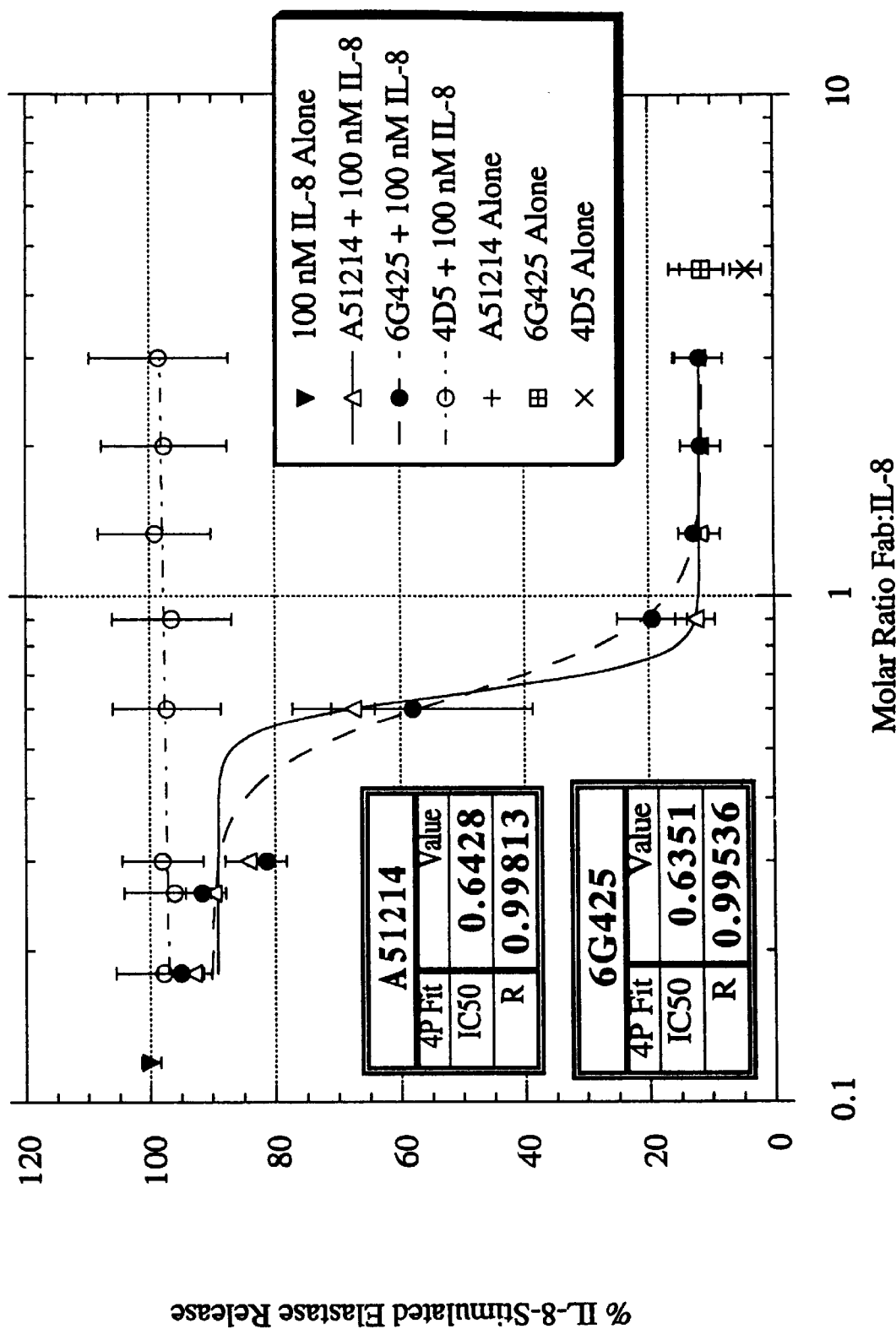
FIG. 9 is a graph depicting the ability of chimeric 6G4.2.5 Fab and chimeric 5.12.14 Fab to inhibit elastase release from human neutrophils stimulated by human IL-8. The results were normalized to reflect the percentage of elastase release elicited by 100 nM IL-8 alone. The data represent the mean±SEM of three separate experiments performed on different days with different blood donors. $IC_{50}$ values were calculated by four parameter fit.
Figure 10:
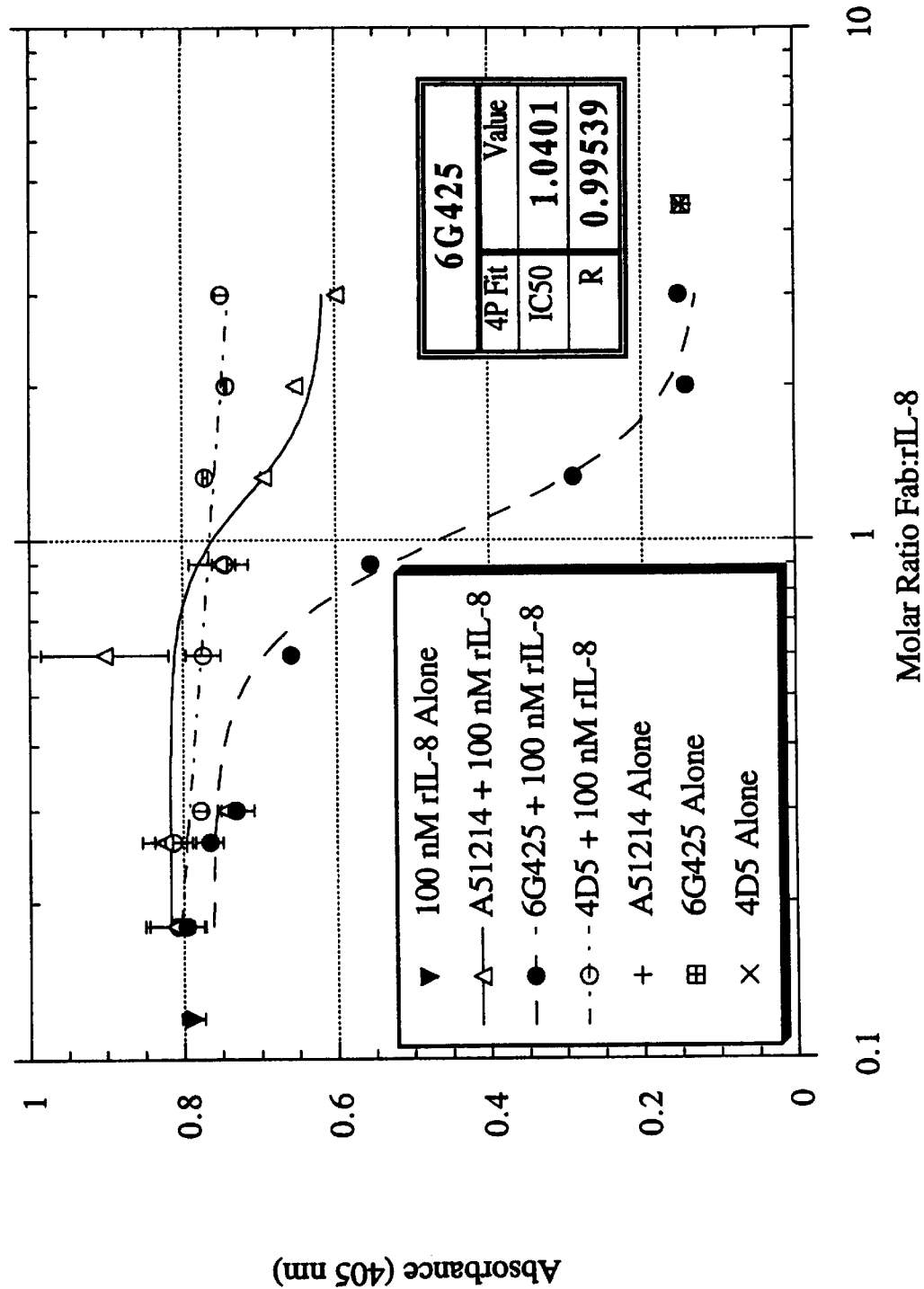
FIG. 10 is a graph depicting the relative abilities of chimeric 6G4.2.5 Fab and chimeric 5.12.14 Fab to inhibit elastase release from human neutrophils stimulated by rabbit IL-8. The results were normalized to reflect the percentage of elastase release elicited by 100 nM IL-8 alone. The data represent the mean±SEM of three separate experiments performed on different days with different blood donors. $IC_{50}$ values were calculated by four parameter fit.
Figure 11B:
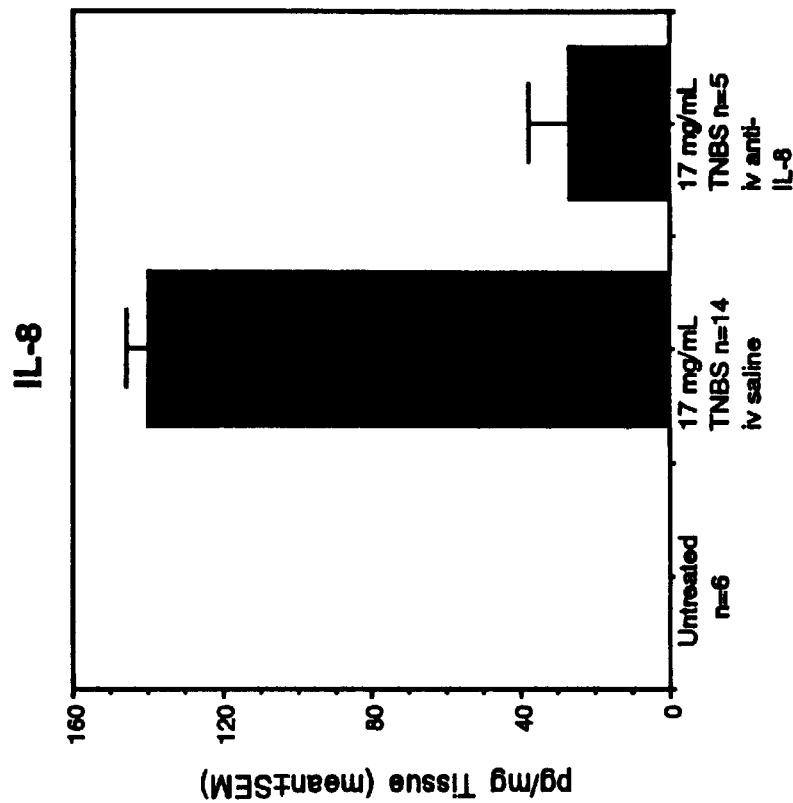
FIGS. 11A–11J are a set of graphs depicting the following parameters in a rabbit ulcerative colitis model.
Figure 11A:
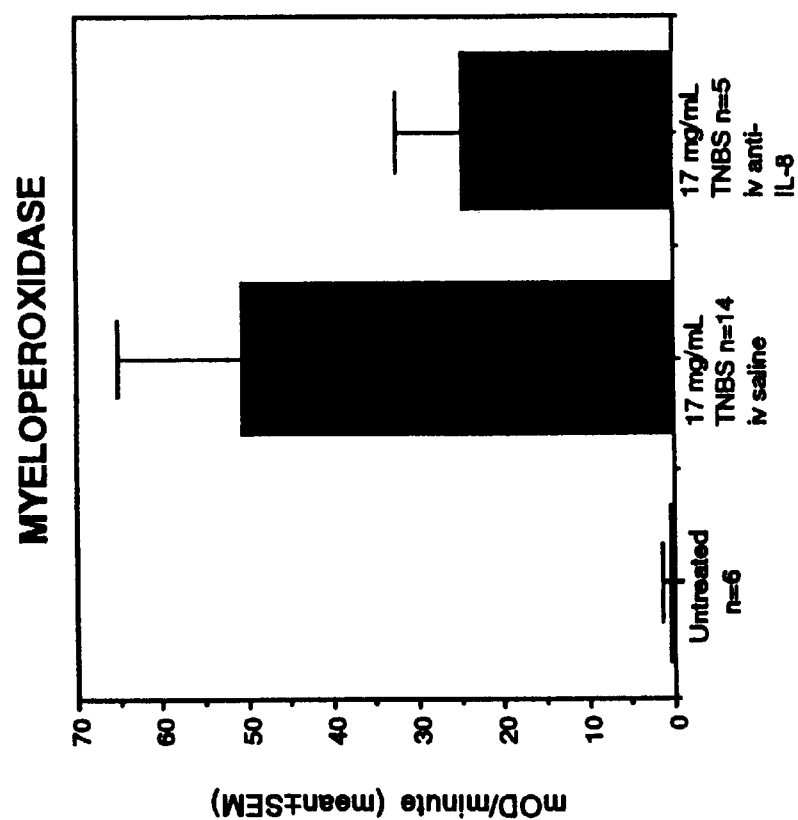
Figure 11D:
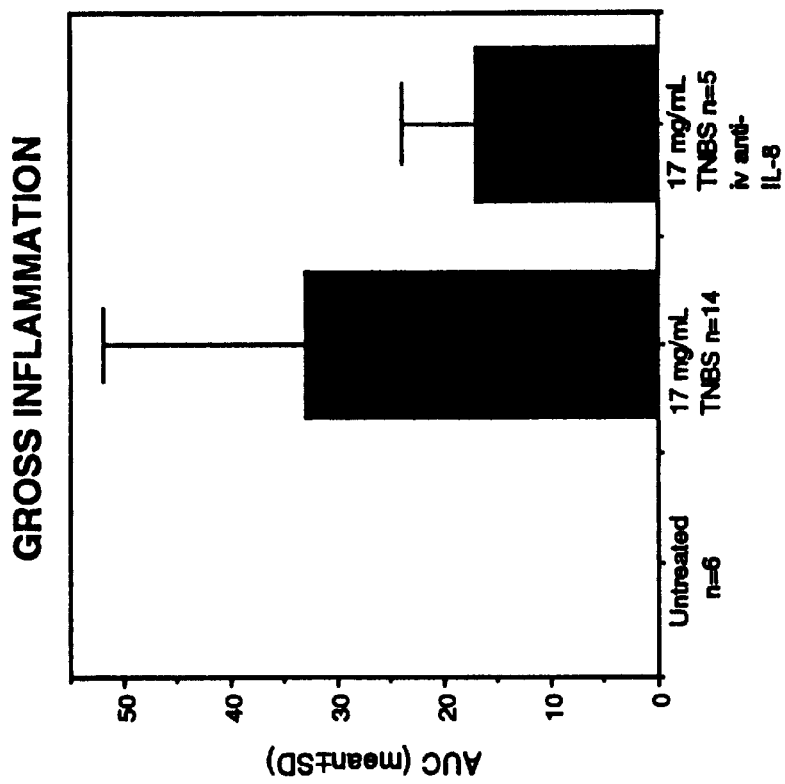
Figure 11C:
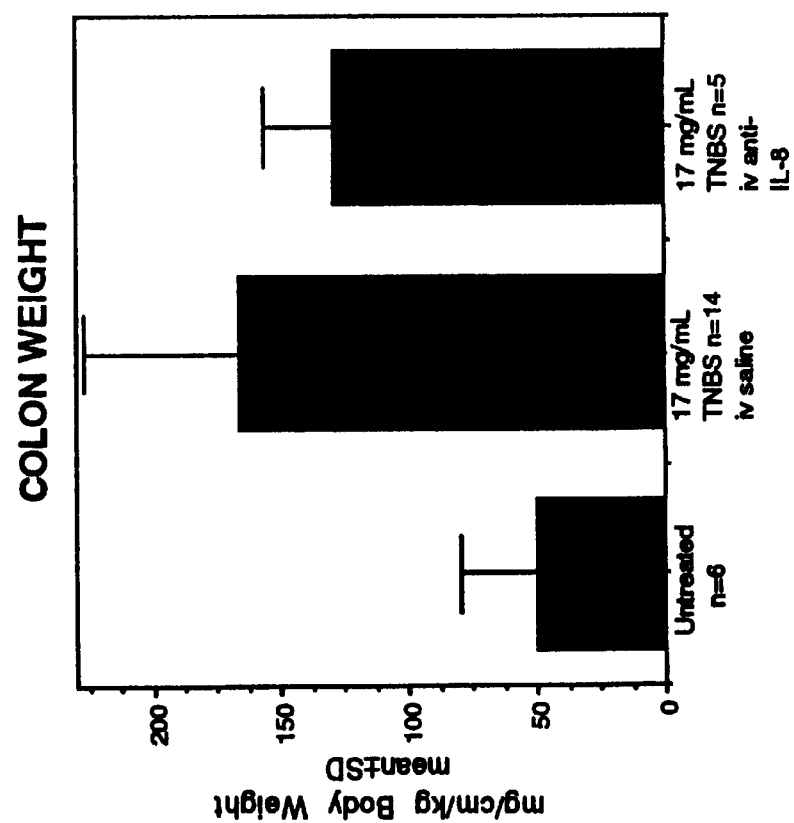
Figure 11F:
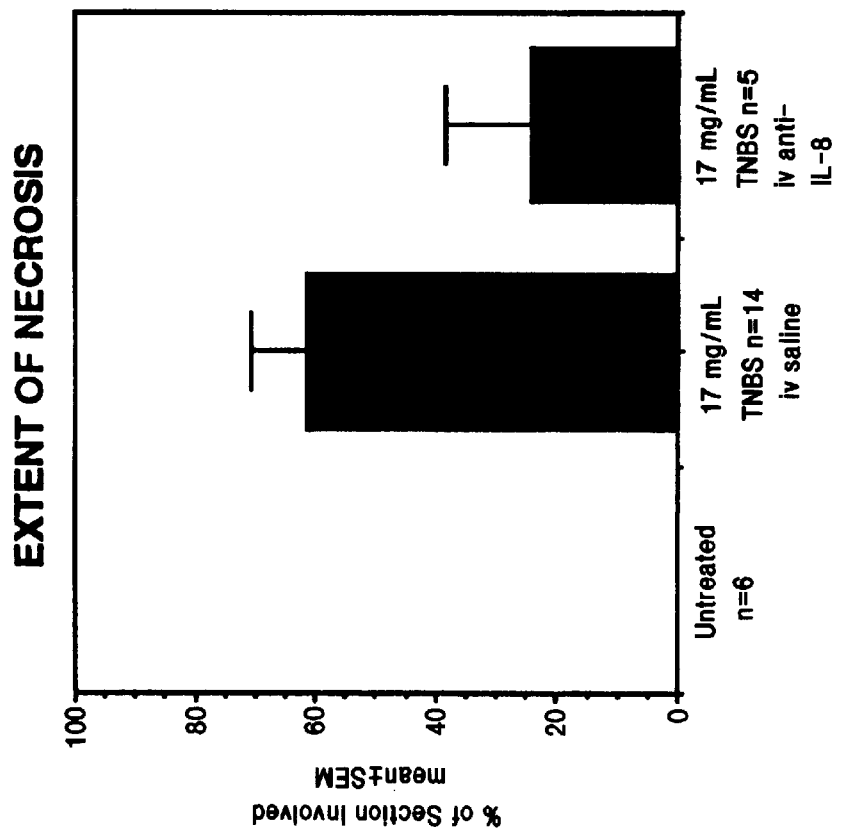
Figure 11E:
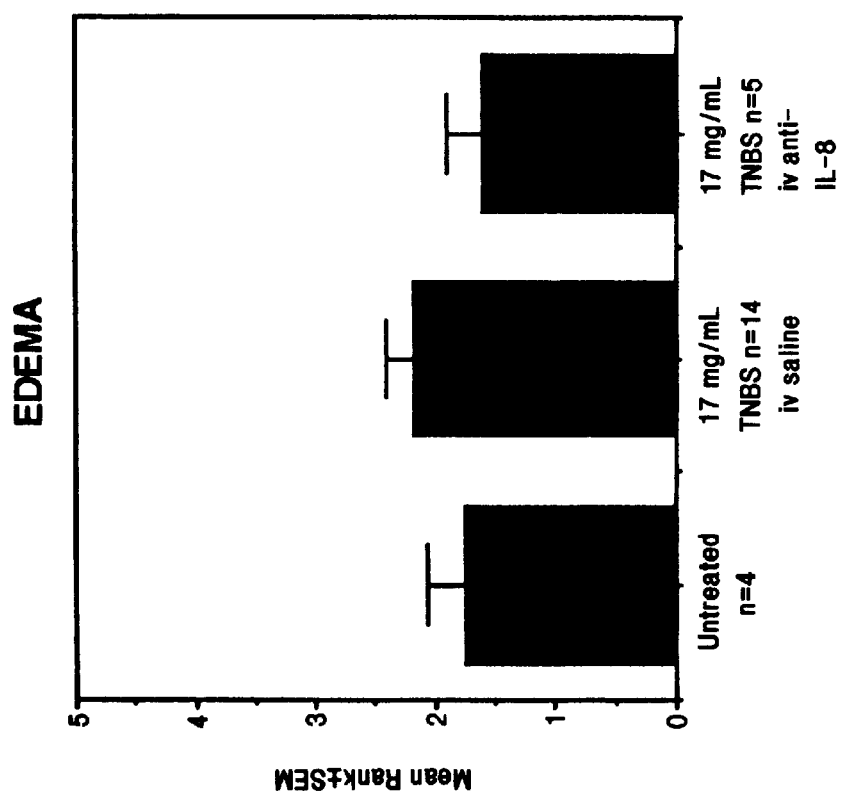
Figure 11H:
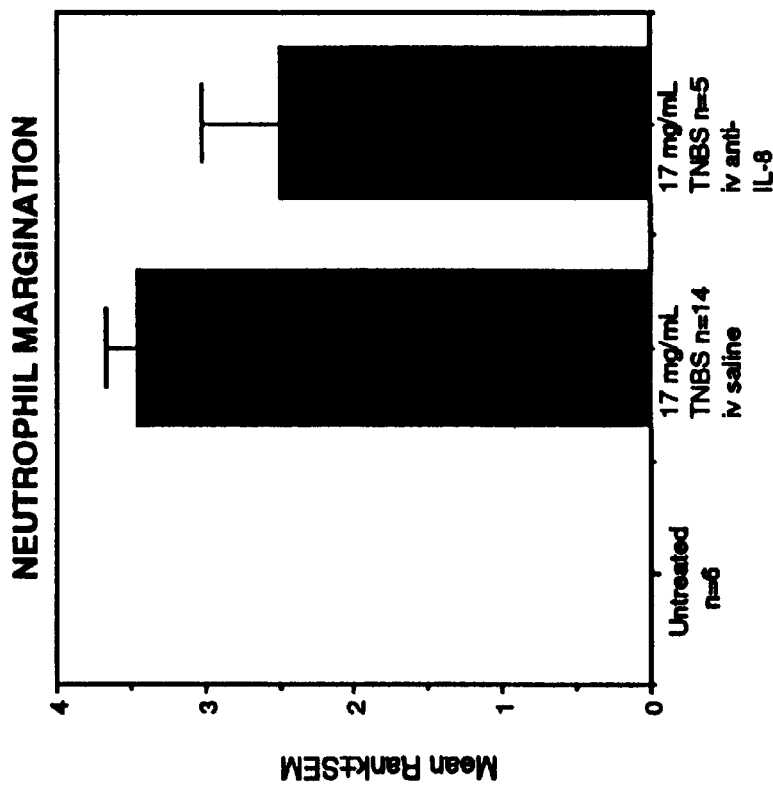
Figure 11G:
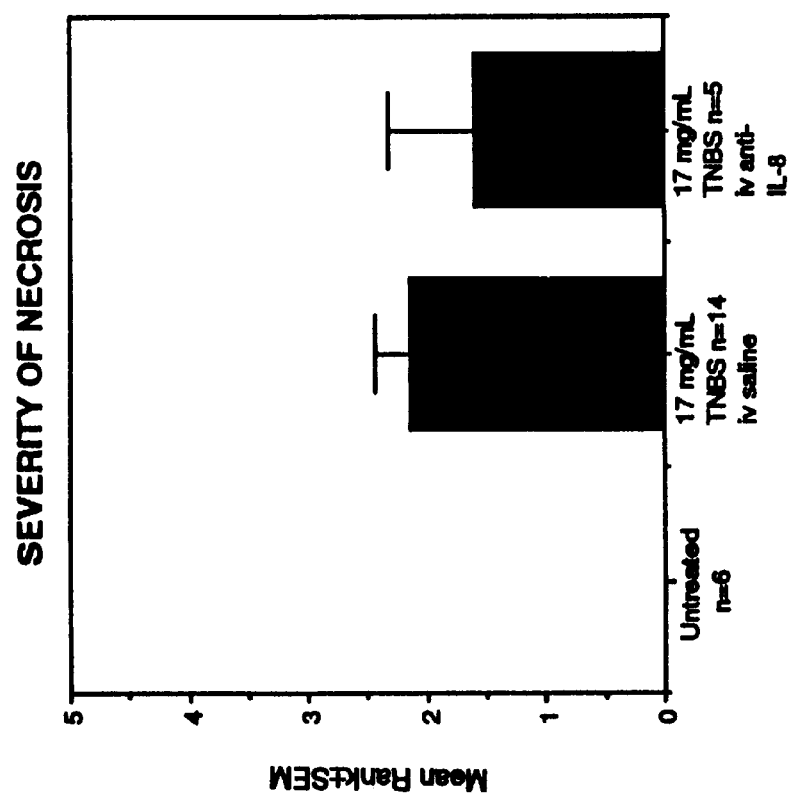
Figure 11J:
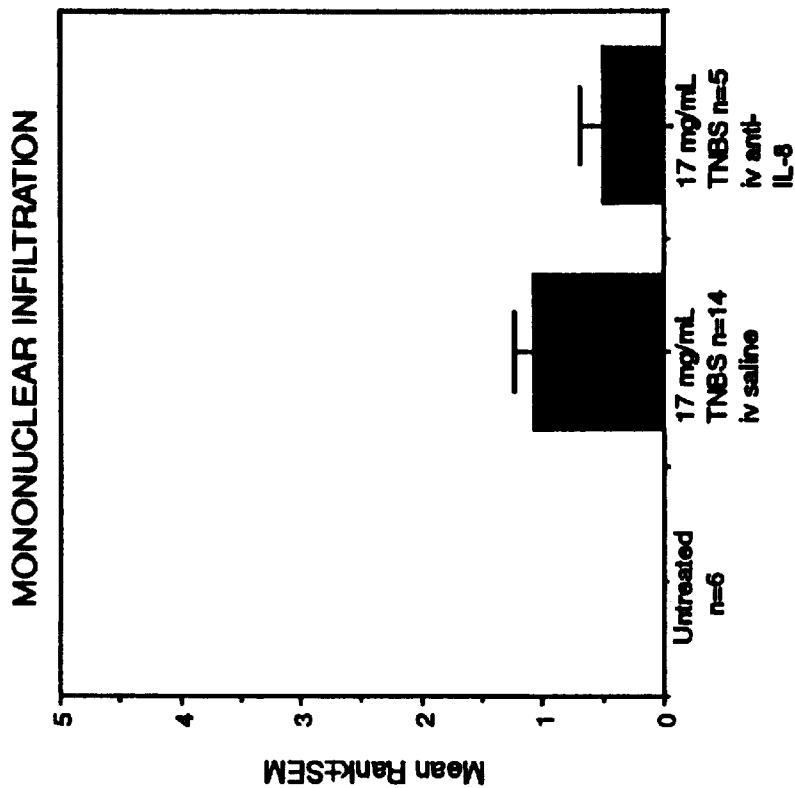
Figure 11I:
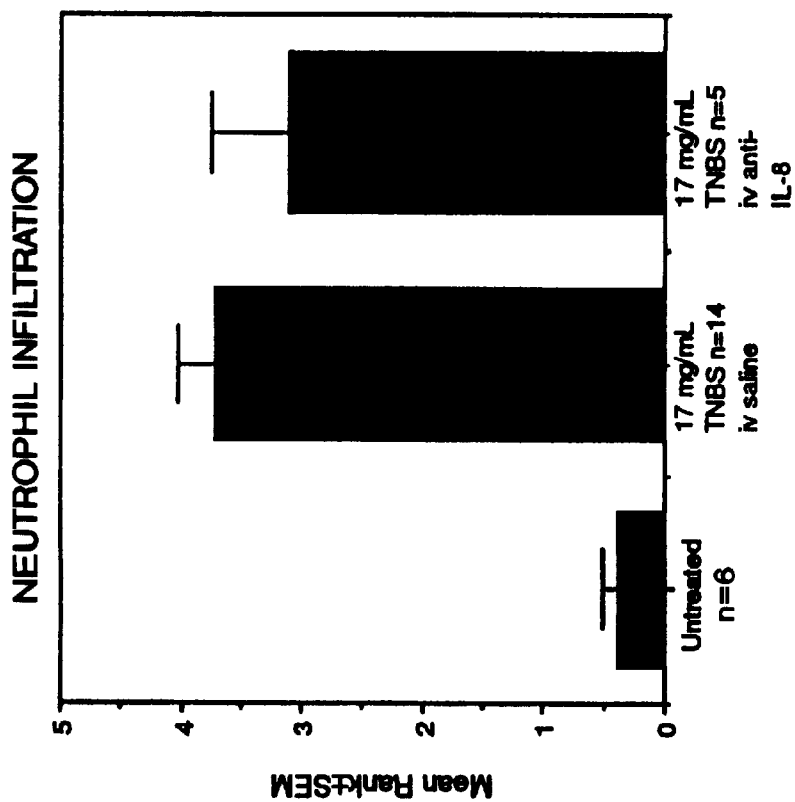

IL-8 (10 $\mu$l) was mixed with anti-IL-8 Fab, an isotype control Fab, or buffer (20 11) in 1 ml polypropylene tubes and incubated in a 37□C water bath for 30 min. IL-8 was used at final concentrations ranging from 0.01 to 1000 nM in dose response studies (FIG. 8) and at a final concentration of 100 nM in the experiments addressing the effects of the Fabs on elastase release (FIGS. 9 and 10). Fab concentrations ranged from approximately 20 nM to 300 nM, resulting in Fab:IL-8 molar ratios of 0.2:1 to 3:1. Cytochalasin B (Sigma) was added to the neutrophil suspension at a concentration of 5 $\mu$g/ml (using a 5 mg/ml stock solution made up in DMSO), and the cells were incubated for 15 min in a 37□C water bath. Cytochalasin B-treated neutrophils (100 $\mu$l) were then added to the IL-8/Fab mixtures. After a 3 hr incubation at room temperature, the neutrophils were pelleted by centrifugation (200×g for 5 min), and aliquots of the cell-free supernatants were transferred to 96 well plates (30 $\mu$l/well). The elastase substrate, methoxysuccinyl-alanyl-alanyl-prolyl-valyl-p-nitroanilide (Calbiochem, La Jolla, Calif.), was prepared as a 10 mM stock solution in DMSO and stored at 4□C. Elastase substrate working solution was prepared just prior to use (1.2 mM elastase substrate, 1.2 M NaCl, 0.12 M HEPES, pH 7.2), and 170 $\mu$l was added to each sample-containing well. The plates were placed in a 37□C tissue culture incubator for 30 min or until an optical density reading for the positive controls reached at least 1.0. Absorbance was measured at 405 nm using an SLT 340 plate reader (SLT Lab Instruments, Austria).

FIG. 9 demonstrates the ability of the chimeric anti-IL-8 Fabs to inhibit elastase release from human neutrophils stimulated by human IL-8; FIG. 10 demonstrates the relative abilities of the chimeric anti-IL-8 Fabs to inhibit elastase release from human neutrophils stimulated by rabbit IL-8.

C. MOLECULAR CLONING OF THE VARIABLE LIGHT AND HEAVY REGIONS OF THE MURINE 5.12.14 (ANTI-IL-8) MONOCLONAL ANTIBODY

Total RNA was isolated from $1\times10^8$ cells (hybridoma cell line ATCC HB-11722) using the procedure described by Chomczynski and Sacchi (*Anal. Biochem.* 162:156 (1987)). First strand cDNA was synthesized by specifically priming the mRNA with synthetic DNA oligonucleotides designed to hybridize with regions of the murine RNA encoding the constant region of the kappa light chain or the IgG2a heavy chain (the DNA sequence of these regions are published in *Sequences of Proteins of Immunological Interest*, Kabat, E. A. et al (1991) NIH Publication 91–3242, V 1–3.). Three primers (SEQ ID NOS: 1–6) were designed for each of the light and heavy chains to increase the chances of primer hybridization and efficiency of first strand cDNA synthesis (FIG. 13). Amplification of the first strand cDNA to double-stranded (ds) DNA was accomplished using two sets of synthetic DNA oligonucleotide primers: one forward primer (SEQ ID NOS: 7–9) and one reverse primer (SEQ ID NO: 10) for the light chain variable region amplification (FIG. 14) and one forward primer (SEQ ID NOS: 11–14) and one reverse primer (SEQ ID NOS: 11, 15, 14 and 13) for the heavy chain variable region amplification (FIG. 15). The N-terminal sequence of the first eight amino acids of either the light or heavy chains of 5.12.14 was used to generate a putative murine DNA sequence corresponding to this region. (A total of 29 amino acids was sequenced from the N-terminus of both the light chain and heavy chain variable regions using the Edman degradation protein sequencing technique.) This information was used to design the forward amplification primers which were made degenerate in the third position for some codons to increase the chances of primer hybridization to the natural murine DNA codons and also included the unique restriction site, MluI, for both the light chain variable region forward primer and the heavy chain variable region forward primer to facilitate ligation to the 3' end of the STII element in the cloning vector. The reverse amplification primers were designed to anneal with the murine DNA sequence corresponding to a portion of the constant region of the light or heavy chains near the variable/constant junction. The light chain variable region reverse primer contained a unique BstBI restriction site and the heavy chain variable region reverse primer contained a unique ApaI restriction site for ligation to the 5' end of either the human IgG1 constant light or IgG1 constant heavy regions in the vectors, pB13.1 (light chain) and pB14 (heavy chain). The polymerase chain reaction using these primer sets yielded DNA fragments of approximately 400 bp. The cDNA encoding the 5.12.14 light chain variable region was cloned into the vector pB13.1, to form pA51214VL and the 5.12.14 heavy chain variable region was cloned into the vector, pB14, to form pA51214VH. The cDNA inserts were characterized by DNA sequencing and are presented in the DNA sequence (SEQ ID NO: 16) and amino acid sequence (SEQ ID NO: 17) of FIG. 16 (murine light chain variable region) and in the DNA sequence (SEQ ID NO: 18) and amino acid (SEQ ID NO: 19) of FIG. 17 (murine heavy chain variable region).

D. CONSTRUCTION OF A 5.12.14 FAB VECTOR

In the initial construct, pA51214VL, the amino acids between the end of the 5.12.14 murine light chain variable sequence and the unique cloning site, BstBI, in the human IgG1 constant light sequence were of murine origin corresponding to the first 13 amino acids of the murine IgG1 constant region (FIG. 16). Therefore, this plasmid contained a superfluous portion of the murine constant region separating the 5.12.14 murine light chain variable region and the human light chain IgG1 constant region. This intervening sequence would alter the amino acid sequence of the chimera and most likely produce an incorrectly folded Fab. This problem was addressed by immediately truncating the cDNA clone after A109 and re-positioning the BstBI site to the variable/constant junction by the polymerase chain reaction. FIG. 18 shows the amplification primers used to make these modifications. The forward primer, VL.front (SEQ ID NO: 20), was designed to match the last five amino acids of the STII signal sequence, including the MluI cloning site, and the first 4 amino acids of the 5.12.14 murine light chain variable sequence. The sequence was altered from the original cDNA in the third position of the first two codons D1 (T to C) and 12 (C to T) to create a unique EcoRV cloning site which was used for later constructions. The reverse primer, VL.rear (SEQ ID NO: 21), was designed to match the first three amino acids of the human IgG1 constant light sequence and the last seven amino acids of the 5.12.14 light chain variable sequence which included a unique BstBI cloning site. In the process of adding the BstBI site, the nucleotide sequence encoding several amino acids were altered: L106 (TTG to CTT), K107 (AAA to CGA) resulting in a conservative amino acid substitution to arginine, and R108 (CGG to AGA). The PCR product encoding the modified 5.12.14 light chain variable sequence was then subcloned into pB13.1 in a two-part ligation. The MluI-BstBI digested 5.12.14 PCR product encoding the light chain variable region was ligated into MluI-BstBI digested vector to form the plasmid, pA51214VL'. The modified cDNA was characterized by DNA sequencing. The coding sequence for the 5.12.14 light chain is shown in FIG. 19.

Likewise, the DNA sequence between the end of the heavy chain variable region and the unique cloning site, ApaI, in the human IgG1 heavy chain constant domain of pA51214VH was reconstructed to change the amino acids in this area from murine to human. This was done by the polymerase chain reaction. Amplification of the murine 5.12.14 heavy chain variable sequence was accomplished using the primers shown in FIG. 18. The forward PCR primer (SEQ ID NO: 22) was designed to match nucleotides 867–887 in pA51214VH upstream of the STII signal sequence and the putative cDNA sequence encoding the heavy chain variable region and included the unique cloning site SpeI. The reverse PCR primer (SEQ ID NO: 23) was designed to match the last four amino acids of the 5.12.14 heavy chain variable sequence and the first six amino acids corresponding to the human IgG1 heavy constant sequence which also included the unique cloning site, ApaI. The PCR product encoding the modified 5.12.14 heavy chain variable sequence was then subcloned to the expression plasmid, pMHM24.2.28 in a two-part ligation. The vector was digested with SpeI-ApaI and the SpeI-ApaI digested 5.12.14 PCR product encoding the heavy chain variable region was ligated into it to form the plasmid, pA51214VH'. The modified cDNA was characterized by DNA sequencing. The coding sequence for the 5.12.14 heavy chain is shown in the DNA sequence (SEQ ID NO: 26) and amino acid sequence (SEQ ID NO: 27) of FIGS. 20A–20B.

The first expression plasmid, pantiIL-8.1, encoding the chimeric Fab of 5.12.14 was made by digesting pA51214VH' with EcoRV and Bpu 11021 to replace the EcoRV-Bpu1102I fragment with a EcoRV-Bpu1102I fragment encoding the murine 5.12.14 light chain variable region of pA51214VL'. The resultant plasmid thus contained the murine-human variable/constant regions of both the light and heavy chains of 5.12.14.

Preliminary analysis of Fab expression using pantiIL-8.1 showed that the light and heavy chains were produced intracellularly but very little was being secreted into the periplasmic space of E. coli. To correct this problem, a second expression plasmid was constructed.

The second expression plasmid, pantiIL-8.2, was constructed using the plasmid, pmy187, as the vector. Plasmid pantiIL-8.2 was made by digesting pmy187 with MluI and SphI and the MluI (partial)-SphI fragment encoding the murine 5.12.14 murine-human chimeric Fab of pantiIL-8.1 was ligated into it. The resultant plasmid thus contained the murine-human variable/constant regions of both the light and heavy chains of 5.12.14.

The plasmid pantiIL-8.2 was deposited on Feb. 10, 1995 with the American Type Culture Collection, 12301 Parklawn Drive, Rockville, Md., U.S.A. (ATCC) and assigned ATTC Accession No. ATCC 97056.

E. MOLECULAR CLONING OF THE VARIABLE LIGHT AND HEAVY REGIONS OF THE MURINE 6G4.2.5 MONOCLONAL ANTIBODY

Total RNA was isolated from $1 \times 10^8$ cells (hybridoma cell line 6G4.2.5) using the procedure described by Chomczynski and Sacchi (*Anal. Biochem.* 162:156 (1987)). First strand cDNA was synthesized by specifically priming the mRNA with synthetic DNA oligonucleotides designed to hybridize with regions of the murine RNA encoding the constant region of the kappa light chain or the IgG2a heavy chain (the DNA sequence of these regions are published in *Sequences of Proteins of Immunological Interest*, Kabat et al. (1991) NIH Publication 91–3242, V 1–3). Three primers (SEQ ID NOS: SEQ ID NOS: 1–6) were designed for each the light and heavy chains to increase the chances of primer hybridization and efficiency of first strand cDNA synthesis (FIG. 21). Amplification of the first strand cDNA to double-stranded (ds) DNA was accomplished using two sets of synthetic DNA oligonucleotide primers: one forward primer (SEQ ID NOS: 28–30) and one reverse primer (SEQ ID NO: 31) for the light chain variable region amplification (FIG. 22) and one forward primer (SEQ ID NOS: 32–33) and one reverse primer (SEQ ID NOS: 11,15,14 and 13) for the heavy chain variable region amplification (FIG. 23). The N-terminal sequence of the first eight amino acids of either the light or heavy chains of 6G4.2.5 was used to generate a putative murine DNA sequence corresponding to this region. (A total of 29 amino acids were sequenced from the N-terminus of both the light chain and heavy chain variable regions using the Edman degradation protein sequencing technique.) This information was used to design the forward amplification primers which were made degenerate in the third position for some codons to increase the chances of primer hybridization to the natural murine DNA codons and also included the unique restriction site, NsiI, for the light chain variable region forward primer and the unique restriction site, MluI, for the heavy chain variable region forward primer to facilitate ligation to the 3' end of the STII element in the vector, pchimFab. The reverse amplification primers were designed to anneal with the murine DNA sequence corresponding to a portion of the constant region of the light or heavy chains near the variable/constant junction. The light chain variable region reverse primer contained a unique MunI restriction site and the heavy chain variable region reverse primer contained a unique ApaI restriction site for ligation to the 5' end of either the human IgG1 constant light or IgG1 constant heavy regions in the vector, pchimFab. The polymerase chain reaction using these primer sets yielded DNA fragments of approximately 400 bp and were cloned individually into the vector, pchimFab, to form p6G425VL and p6G425VH. The cDNA inserts were characterized by DNA sequencing and are presented in the DNA sequence (SEQ ID NO: 34) and amino acid sequence (SEQ ID NO: 35) of FIG. 24 (murine light chain variable region) and the DNA sequence (SEQ ID NO: 36) and amino acid sequence (SEQ ID NO: 37) of FIG. 25 (murine heavy chain variable region).

F. CONSTRUCTION OF A 6G4.2.5 CHIMERIC FAB VECTOR

In the initial construct, p6G425VL, the amino acids between the end of the 6G4.2.5 murine light chain variable sequence and the unique cloning site, MunI, in the human IgG1 constant light sequence were of murine origin. These amino acids must match the human IgG1 amino acid sequence to allow proper folding of the chimeric Fab. Two murine amino acids, D115 and S121, differed dramatically from the amino acids found in the loops of the β-strands of the human IgG1 constant domain and were converted to the proper human amino acid residues, V115 and F121, by site-directed mutagenesis using the primers (SEQ ID NOS: 38,39,40) shown in FIG. 26. These specific mutations were confirmed by DNA sequencing and the modified plasmid named p6G425VL'. The coding sequence is shown in the DNA sequence (SEQ ID NO: 41) and amino acid sequence (SEQ ID NO: 42) of FIGS. 27A–27B.

Likewise, the DNA sequence between the end of the heavy chain variable region and the unique cloning site, ApaI, in the human IgG1 heavy chain constant domain of p6G425VH was reconstructed to change the amino acids in this area from murine to human. This process was facilitated by the discovery of a BstEII site near the end of the heavy chain variable region. This site and the ApaI site were used for the addition of a synthetic piece of DNA encoding the corresponding IgG human amino acid sequence. The synthetic oligo-nucleotides shown in FIG. 26 were designed as complements of one another to allow the formation of a 27 bp piece of ds DNA. The construction was performed as a three-part ligation because the plasmid, p6G425VH, contained an additional BstEII site within the vector sequence. A 5309 bp fragment of p6G425VH digested with MluI-ApaI was ligated to a 388 bp fragment carrying the 6G4.2.5 heavy chain variable region and a 27 bp synthetic DNA fragment encoding the first six amino acids of the human IgG1 constant region to form the plasmid, p6G425VH'. The insertion of the synthetic piece of DNA was confirmed by DNA sequencing. The coding sequence is shown in the DNA sequence (SEQ ID NO: 43) and amino acid sequence (SEQ ID NO: 44) of FIGS. 28A–28B.

The expression plasmid, p6G425chim2, encoding the chimeric Fab of 6G4.2.5 was made by digesting p6G425chimVL' with MluI and ApaI to remove the STII-murine HPC4 heavy chain variable region and replacing it with the MluI-ApaI fragment encoding the STII-murine 6G4.2.5 heavy chain variable region of p6G425chimVH'. The resultant plasmid thus contained the murine-human variable/constant regions of both the light and heavy chains of 6G4.2.5.

The plasmid p6G425chim2 was deposited on Feb. 10, 1995 with the American Type Culture Collection, 12301 Parklawn Drive, Rockville, Md., U.S.A. (ATCC) and assigned ATTC Accession No. 97055.

G. Construction or Humanized Versions of Anti-IL-8 Antibody 6G4.2.5

The murine cDNA sequence information obtained from the hybridoma cell line, 6G4.2.5, was used to construct recombinant humanized variants of the murine anti-IL-8 antibody. The first humanized variant, F(ab)-1, was made by grafting synthetic DNA oligonucleotide primers encoding the murine CDRs of the heavy and light chains onto a phagemid vector, pEMX1 (Werther et al., *J. Immunol*, 157: 4986–4995 (1996)), which contains a human 6-subgroup I light chain and a human IgG1 subgroup III heavy chain (FIG. 29). Amino acids comprising the framework of the antibody that were potentially important for maintaining the conformations necessary for high affinity binding to IL-8 by the complementarity-determining regions (CDR) were identified by comparing molecular models of the murine and humanized 6G4.2.5 (F(ab)-1) variable domains using methods described by Carter et al., PNAS 89:4285 (1992) and Eigenbrot, et. al., *J. Mol. Biol.* 229:969 (1993). Additional humanized framework variants (F(ab) 2–9) were constructed from the information obtained from these models and are presented in Table 2 below. In these variants, the site-directed mutagenesis methods of Kunkel, *Proc. Natl. Acad. Sci USA*), 82:488 (1985) were utilized to exchange specific human framework residues with their corresponding 6G4.2.5 murine counterparts. Subsequently, the entire coding sequence of each variant was confirmed by DNA sequencing. Expression and purification of each F(ab) variant was performed as previously described by Werther et. al., supra, with the exception that hen egg white lysozyme was omitted from the purification protocol. The variant antibodies were analyzed by SDS-PAGE, electrospray mass spectroscopy and amino acid analysis.

chimeric F(ab). In-vitro binding experiments revealed no change in affinity for F(ab)-7 (38.4 nM) but a significant improvement in affinity for F(ab)-8/9 of 14 nM and 19 nM, respectively. By analysis of a 3-D computer-generated model of the anti-IL-8 antibody, it was hypothesized that the substitution of murine Lys for Arg at H38 in F(ab)-8 influences CDR-H2 while a change at H6 of murine Gln for Glu in F(ab)-9 affects CDR-H3. Examination of the human

TABLE 4

Humanized 6G425 Variants

| Variant | Version | Template | Changes[a] | Purpose[b] | IC50[c] Mean | S.D. | N |
|---|---|---|---|---|---|---|---|
| F(ab)-1 | version 1 | | CDR Swap | | 63.0 | 12.3 | 4 |
| F(ab)-2 | version 2 | F(ab)-1 | PheH67*Ala* | packaging w/ CDR H2 | 106.0 | 17.0 | 2 |
| F(ab)-3 | version 3 | F(ab)-1 | ArgH71*Val* | packaging w/ CDRS H1, H2 | 79.8 | 42.2 | 4 |
| F(ab)-4 | version 6 | F(ab)-1 | IleH69*Leu* | packaging w/ CDR H2 | 44.7 | 9.0 | 3 |
| F(ab)-5 | version 7 | F(ab)-1 | LeuH78*Ala* | packaging w/ CDRs H1, H2 | 52.7 | 31.0 | 9 |
| F(ab)-6 | version 8 | F(ab)-1 | IleH69*Leu* LeuH78*Ala* | combine F(ab)-4 and -5 | 34.6 | 6.7 | 7 |
| F(ab)-7 | version 16 | F(ab)-6 | LeuH78*Ala* | packaging w/ CDR H1 | 38.4 | 9.1 | 2 |
| F(ab)-8 | version 19 | F(ab)-6 | ArgH38*Lys* | packaging w/ CDR H2 | 14.0 | 5.7 | 2 |
| F(ab)-9 | version 11 | F(ab)-6 | GluH6*Gln* | packaging w/ CDR H3 | 19.0 | 5.1 | 7 |
| Chimeric[d] F(ab) | | | | | 11.4 | 7.0 | 1 3 |
| rhu4D5[e] F(ab) | | | | | >200 µM | | 5 |

[a]Amino acid changes made relative to the template used. Murine residues are in bold italics and residue numbering is according to Kabat et al.
[b]Purpose for making changes based upon interactions observed in molecular models of the humanized and murine variable domains.
[c]nM concentration of variant necessary to inhibit binding of iodinated IL-8 to human neutrophils in the competitive binding assay.
[d]Chimeric F(ab) is a (F(ab)) which carries the murine heavy and light chain variable domains fused to the human light chain kI constant domain and the human heavy chain subgroup III constant domain I respectively.
[e]rhu4D5F(ab) is of the same isotype as the humanized 6G425 F(ab)s and is a humanized anti-HER2 F(ab) and therefore should not bind to IL8.

Figure 30A:
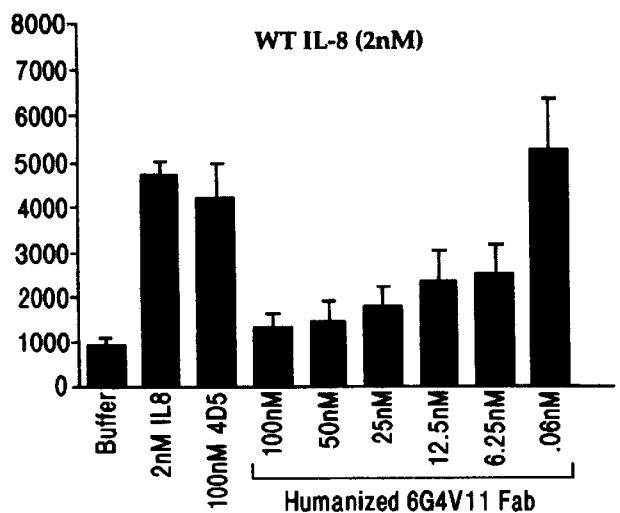
FIGS. 30A, 30B and 30C are graphs depicting the ability of F(ab)-9 (humanized 6G4V11 Fab) to inhibit human wild type IL-8, human monomeric IL-8, and rhesus IL-8 mediated neutrophil chemotaxis, respectively.
Figure 30B:
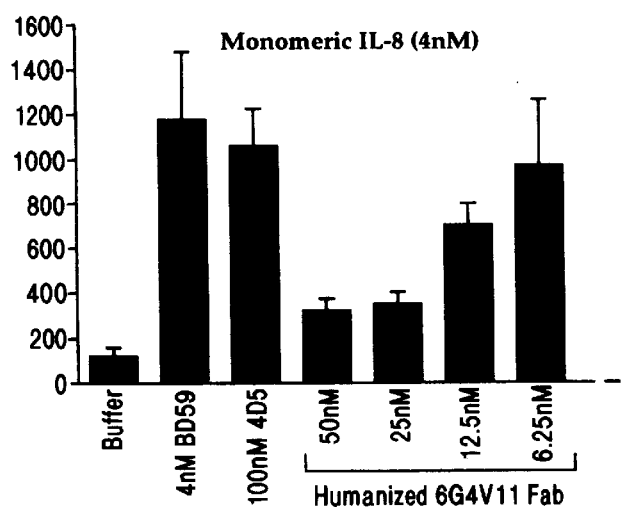
Figure 30C:
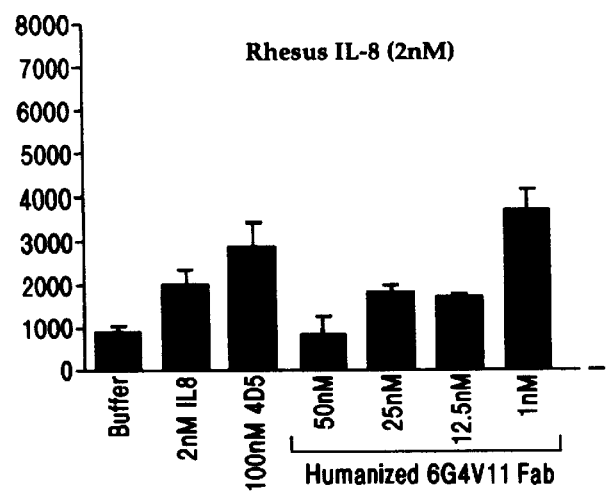

The first humanized variant, F(ab)-1, was an unaltered CDR swap in which all the murine CDR amino acids defined by both x-ray crystallography and sequence hypervariability were transferred to the human framework. When the purified F(ab) was tested for its ability to inhibit $^{125}$I-IL-8 binding to human neutrophils according to the methods described in Section (B)(1) above, a 5.5 fold reduction in binding affinity was evident as shown in Table 4 above. Subsequent versions of F(ab)-1 were engineered to fashion the 3-dimensional structure of the CDR loops into a more favorable conformation for binding IL-8. The relative affinities of the F(ab) variants determined from competition binding experiments using human neutrophils as described in Section (B)(1) above are presented in Table 4 above. A slight decrease in IL-8 binding (<2 fold) was observed for F(ab)-2–3 while only slight increases in IL-8 binding were noted for F(ab) 3–5. Variant F(ab)-6 had the highest increase in affinity for IL-8 (approximately 2 fold), exhibiting an IL-8 binding affinity of 34.6 nM compared to the F(ab)-1 IL-8 binding affinity of 63 nM. The substitutions of murine Leu for Ile at H69 and murine Ala for Leu at H78 are predicted to influence the packing of CDRs H1 and H2. Further framework substitutions using the F(ab)-6 variant as template were made to bring the binding affinity closer to that of the antibody sequences with respect to amino acid variability revealed that the frequency of Arg at residue H38 is >99% whereas residue H6 is either Gln ~20% or Glu ~80% (Kabat et. al., Sequences of Proteins of Immunological Interest 5th Ed. (1991)). Therefore, to reduce the likelihood of causing an immune response to the antibody, F(ab)-9 was chosen over F(ab)-8 for further affinity maturation studies. Variant F(ab)-9 was also tested for its ability to inhibit IL-8-mediated chemotaxis (FIG. 30). This antibody was able to block neutrophil migration induced by wild-type human IL-8, human monomeric IL-8 and Rhesus IL-8 with $IC_{50}$=s of approximately 12 nM, 15 nM, and 22 nM, respectively, in IL-8 mediated neutrophil chemotaxis inhibition assays performed as described in Section (B)(2) above. The amino acid sequence for variant F(ab)-8 is provided in FIG. 31c. The F(ab)-8 was found to block human and rhesus IL-8-mediated chemotaxis with $IC_{50}$=s of 12 nM and 10 nM, respectively, in IL-8 mediated neutrophil chemotaxis inhibition assays performed as described in Section (B)(2) above.

H. Construction of an Anti-IL-8-Gene III Fusion Protein for Phage Display and Alanine Scanning Mutagenesis An expression plasmid, pPh6G4.V11, encoding a fusion protein (heavy chain of the humanized 6G4.2.5 version 11 antibody and the M13 phage gene-III coat protein) and the light chain of the humanized 6G4.2.5 version 11 antibody was assembled to produce a monovalent display of the anti-IL-8 antibody on phage particles. The construct was made by digesting the plasmid, pFPHX, with EcoRV and ApaI to remove the existing irrelevant antibody coding sequence and replacing it with a 1305 bp EcoRV-ApaI fragment from the plasmid, p6G4.V11, encoding the humanized 6G4.2.5 version 11 anti-IL-8 antibody. The translated sequence of the humanized 6G4.2.5 version 11 heavy chain (SEQ ID NO: 52), peptide linker and gene III coat protein (SEQ ID NO: 53) is shown in FIG. 31A. The pFPHX plasmid is a derivative of phGHam-3 which contains an in-frame amber codon (TAG) between the human growth hormone and gene-III DNA coding sequences. When transformed into an amber suppressor strain of *E. coli*, the codon (TAG) is read as Glutamate producing a growth hormone (hGH)-gene III fusion protein. Likewise, in a normal strain of *E. coli*, the codon (TAG) is read as a stop preventing translational read-through into the gene-III sequence and thus allowing the production of soluble hGH. The pGHam-3 plasmid is described in *Methods: A Companion to Methods in Enzymology*, 3:205 (1991). The final product, pPh6G4.V11, was used as the template for the alanine scanning mutagenesis of the CDRs and for the construction of randomized CDR libraries of the humanized 6G4.V11 antibody.

I. Alanine Scanning Mutagenesis of Humanized Antibody 6G4.2.5 Version 11

The solvent exposed amino acid residues in the CDRs of the humanized anti-IL-8 6G4.2.5 version 11 antibody (h6G4V11) were identified by analysis of a 3-D computer-generated model of the anti-IL-8 antibody. In order to determine which solvent exposed amino acids in the CDRs affect binding to interleukin-8, each of the solvent exposed amino acids was individually changed to alanine, creating a panel of mutant antibodies wherein each mutant contained an alanine substitution at a single solvent exposed residue. The alanine scanning mutagenesis was performed as described by Leong et. al., *J. Biol. Chem.*, 269: 19343 (1994)).

The IC$_{50}$'s (relative affinities) of h6G4V11 wt and mutated antibodies were established using a Competition Phage ELISA Assay described by Cunningham et. al., (*EMBO J.* 13:2508 (1994)) and Lee et. al., (*Science* 270:1657 (1995)). The assay measures the ability of each antibody to bind IL-8 coated onto a 96-well plate in the presence of various concentrations of free IL-8 (0.2 to 1 uM) in solution. The first step of the assay requires that the concentrations of the phage carrying the wild type and mutated antibodies be normalized, allowing a comparison of the relative affinities of each antibody. The normalization was accomplished by titering the phage on the IL-8 coated plates and establishing their EC$_{50}$. Sulfhydryl coated 96-well binding plates (Corning-Costar; Wilmington, Mass.) were incubated with a 0.1 mg/ml solution of K64C IL-8 (Lysine 64 is substituted with Cysteine to allow the formation of a disulfide bond between the free thiol group of K64C IL-8 and the sulfhydryl coated plate, which results in the positioning of the IL-8 receptor binding domains towards the solution interface) in phosphate buffered saline (PBS) pH 6.5 containing 1 mM EDTA for 1 hour at 25EC followed by three washes with PBS and a final incubation with a solution of PBS containing 1.75 mg/ml of L-cysteine-HCl and 0.1M NaHCO$_3$ to block any free reactive sulfhydryl groups on the plate. The plates were washed once more and stored covered at 4EC with 200 ul of PBS/well. Phage displaying either the reference antibody, h6G4V11, or the mutant h6G4V11 antibodies were grown and harvested by PEG precipitation. The phage were resuspended in 500 ul 10 mM Tris-HCl pH 7.5, 1 mM EDTA and 100 mM NaCl and held at 4EC for no longer than 3 hours. An aliquot of each phage was diluted 4-fold in PBS containing 0.05% Tween-20 (BioRad, Richmond, Calif.) and 0.5% BSA RIA grade (Sigma, St. Louis, Mo.) (PBB) and added to IL-8 coated plates blocked for at least 2 hours at 25EC with 50 mg/ml skim milk powder in 25 mM Carbonate Buffer pH 9.6. The phage were next serially diluted in 3 fold steps down the plate from well A through H. The plates were incubated for 1 hour at 25EC followed by nine quick washes with PBS containing 0.05% Tween-20 (PBST). The plates were then incubated with a 1:3200 dilution of rabbit anti-phage antibody and a 1:1600 dilution of secondary goat-anti-rabbit Fc HRP-conjugated antibody for 15 minutes at 25EC followed by nine quick washes with PBST. The plates were developed with 80 ul/well of 1 mg/ml OPD (Sigma, St. Louis, Mo.) in Citrate Phosphate buffer pH 5.0 containing 0.015% H$_2$O$_2$ for 4 minutes at 25EC and the reaction stopped with the addition of 40 ul of 4.5M H$_2$SO$_4$. The plates were analyzed at wavelength 8$_{492}$ in a SLT model 340ATTC plate reader (SLT Lab Instruments). The individual EC$_{50}$=s were determined by analyzing the data using the program Kaleidagraph (Synergy Software, Reading, Pa.) and a 4-parameter fit equation. The phage held at 4EC were then immediately diluted in PBB to achieve a final concentration corresponding to their respective EC$_{50}$ or target OD$_{492}$ for the competition segment of the experiment, and dispensed into a 96 well plate containing 4-fold serial dilutions of soluble IL-8 ranging from 1 uM in well A and ending with 0.2 uM in well H. Using a 12-channel pipet, 100 ul of the phage/IL-8 mixture was transferred to an IL-8 coated 96-well plate and executed as described above. Each sample was done in triplicate—3 columns/sample.

TABLE 5

Relative Affinities (IC50) for Alanine-scan Anti-IL-8 6G4V11 CDR Mutants

| CDR | Amino Acid Residue | Avg IC50 (nM) | Std Dev |
|---|---|---|---|
| V11 | Reference | 11.5 | 6.4 |
| CDR-L1 | S26 | 6.3 | 2.9 |
|  | Q27 | 10.2 | 2.4 |
|  | S28 | 14.2 | 5.2 |
|  | V30 | 29.1 | 12.3 |
|  | H31 | 580.3 | 243.0 |
|  | I33 | 64.2 | 14.6 |
|  | N35 | 3.3 | 0.7 |
|  | T36 | 138.0 | nd |
|  | Y37 | NDB | nd |
| CDR-L2 | K55 | 24.2 | 14.9 |
|  | V56 | 15.5 | 3.8 |
|  | S57 | 12.4 | 4.0 |
|  | N58 | 17.6 | 3.7 |
|  | R59 | nd | nd |
| CDR-L3 | S96 | 10.8 | 4.4 |
|  | T97 | 70.6 | 55.2 |
|  | H98 | 8.0 | 1.2 |
|  | V99 | 19.6 | 1.9 |
| CDR-H1 | S28 | 8.6 | 3.1 |
|  | S30 | nd | nd |
|  | S31 | 7.8 | 2.5 |
|  | H32 | 13.3 | 5.8 |
|  | Y53 | 48.2 | 15.8 |
| CDR-H2 | Y50 | 35.6 | 13.0 |
|  | D52 | 13.3 | 7.5 |
|  | S53 | 6.0 | 3.4 |

TABLE 5-continued

Relative Affinities (IC50) for Alanine-scan Anti-IL-8 6G4V11 CDR Mutants

| CDR | Amino Acid Residue | Avg IC50 (nM) | Std Dev |
|---|---|---|---|
| CDR-H3 | N54 | 96.0 | 5.8 |
| | E56 | 15.8 | 4.5 |
| | T57 | 8.4 | 1.6 |
| | T58 | 11.3 | 1.8 |
| | Y59 | 9.1 | 3.7 |
| | Q61 | 12.6 | 6.4 |
| | K64 | 18.5 | 12.1 |
| | D96 | NDB | nd |
| | Y97 | NDB | nd |
| | R98 | 36.6 | 15.3 |
| | Y99 | 199.5 | nd |
| | N100 | 278.3 | 169.4 |
| | D102 | 159.2 | 44 |
| | W103 | NDB | nd |
| | F104 | NDB | nd |
| | F105 | 209.4 | 72.3 |
| | D106 | 25.3 | 21.7 |

Each sample performed in triplicate/experiment.
NDB = No Detectable Binding /nd = value not determined*
Residue numbering is according to Kabat et al.

Figure 32:
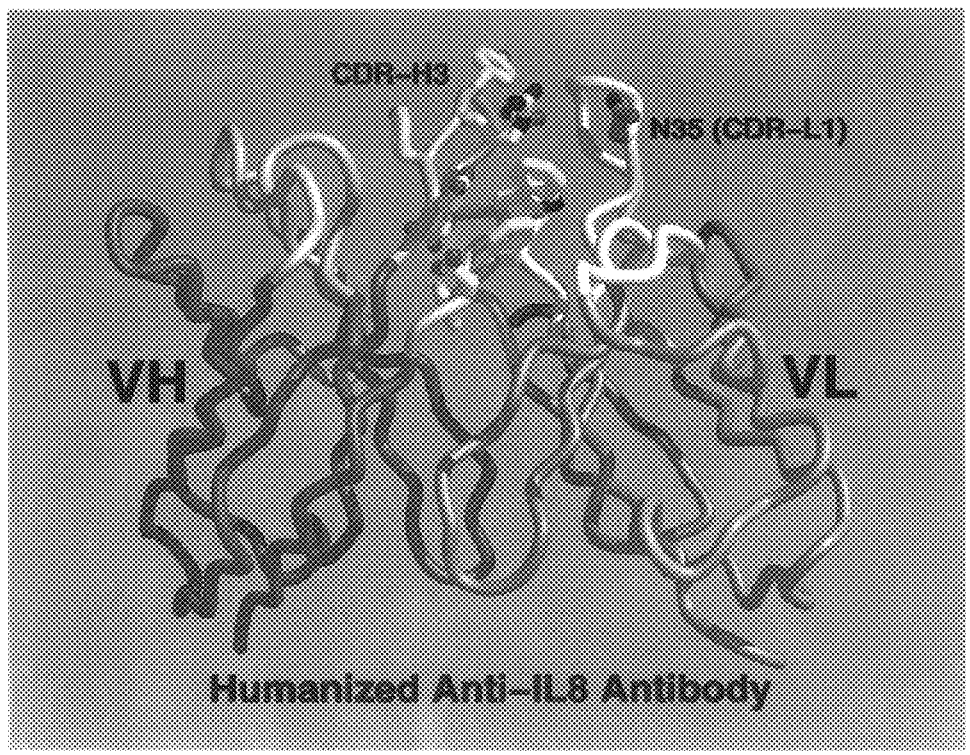
FIG. 32 is a three dimensional computer model of the humanized anti-IL-8 6G4.2.5V11 antibody. Heavy chain CDR loops and variable domain regions appear in purple, and CDR-H3 side chain residues appear in yellow. Heavy chain constant domain regions appear in red. Light chain CDR loops and variable domain regions appear in off-white, and the Asn residue at amino acid position 35 (N35) in CDR L1 appears in green. Light chain constant domain regions appear in amber.

The results of the alanine-scan are summarized in Table 5 above. The alanine substitutions in of many of the mutant antibodies had little or no adverse effects (<3 fold) on the binding affinity for IL-8. Mutants that were found to exhibit no detectable binding of IL-8 (NDB) presumably contained disruptions in the conformational structure of the antibody conferred by crucial structural or buried amino acids in the CDR. Based on the results of the scan, CDR-H3 (heavy chain, 3rd CDR) was identified as the dominant binding epitope for binding IL-8. Alanine substitutions in this CDR resulted in a 3 to >26 fold decrease in binding affinity. The amino acids, Y597, Y599 and D602 are of particular interest because it was determined from the computer generated model of the anti-IL-8 antibody that these residues are solvent exposed and that these residues might participate in hydrogen bonding or charge interactions with IL-8 or other amino acids of the antibody that influence either binding to IL-8 or the conformation of the CDR-H3 loop structure. (See the model depicted in FIG. 32). Unexpected increases in binding affinity (1.8>2.7 fold) were noted for S528 and S531 of CDR-H1 and S553 of CDR-H2.

Surprisingly, a significant increase in binding affinity was observed in the alanine mutant N35A located in CDR-L1 (light chain, 1st CDR). A 3–6 fold increase in affinity was observed compared to the wild-type h6G4V11 antibody. This augmentation of IL-8 binding could be the result of the close proximity of N35A to CDR-H3. The alanine substitution may have imparted a slight change in the conformation of CDR-L1 which alters the packing interaction of neighboring amino acid residues on CDR-H3, thereby tweaking the loop of CDR-H3 into a conformation that facilitates more appropriate contacts with IL-8. Similarly, N35A may also influence the orientation of amino acids in CDR-L1 or its interaction directly with IL-8. Unexpected increases in affinity (~2 fold) were also observed for S26 of CDR-L1 and H98 of CDR-L3.

J. Characterization of Humanized Anti-IL-8 Antibody 6G4V11N35A

Figure 33:
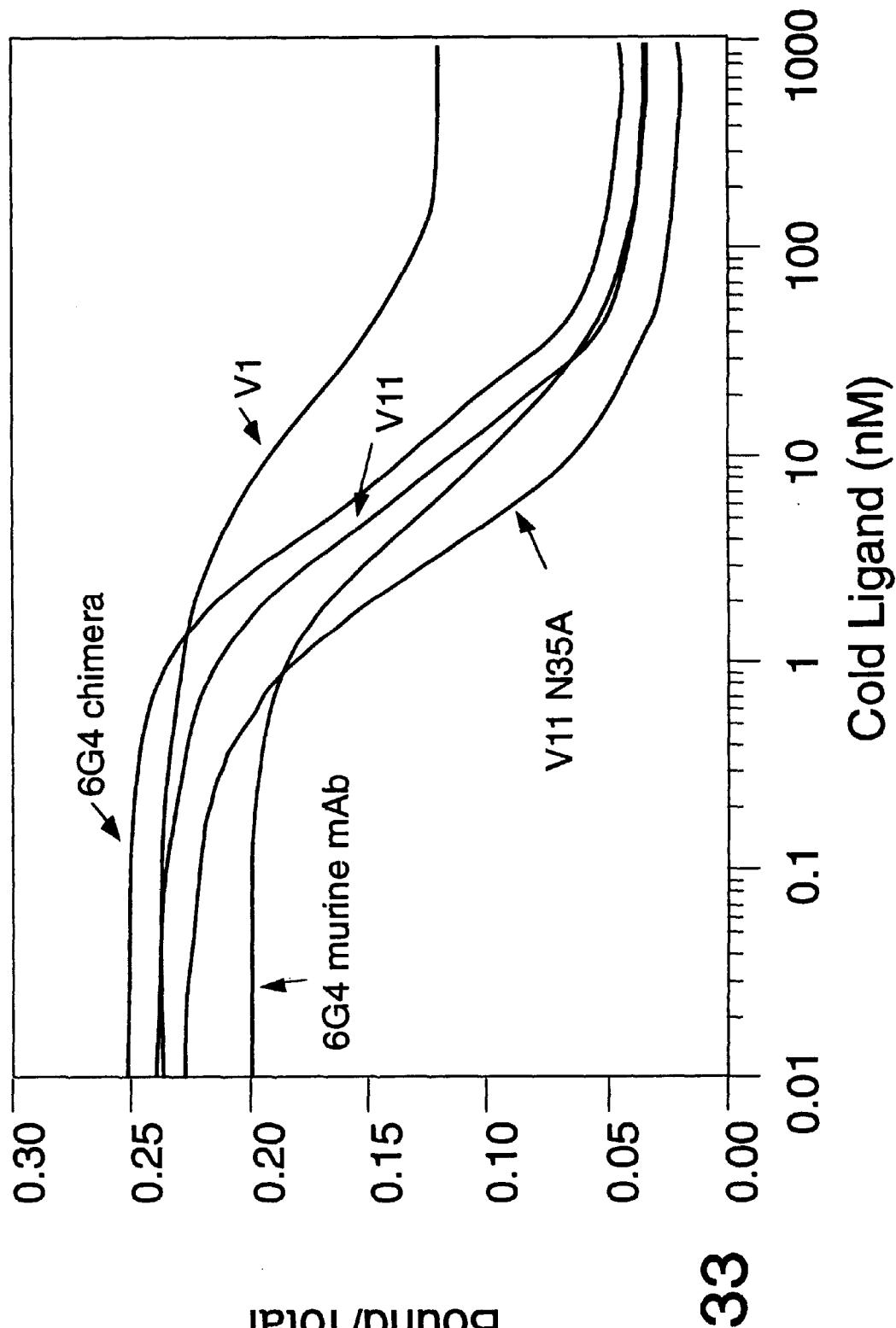
FIG. 33 is a Scatchard plot depicting the inhibition of $^{125}$I-IL-8 binding to human neutrophils exhibited by intact murine 6G4.2.5 antibody (denoted 6G4 murine mAb), 6G4.2.5 murine-human chimera Fab (denoted 6G4 chimera), humanized 6G4.2.5 Fab versions 1 and 11 (denoted V1 and V11), and variant 6G4.2.5V11N35A Fab (denoted V11N35A).
Figure 34A:
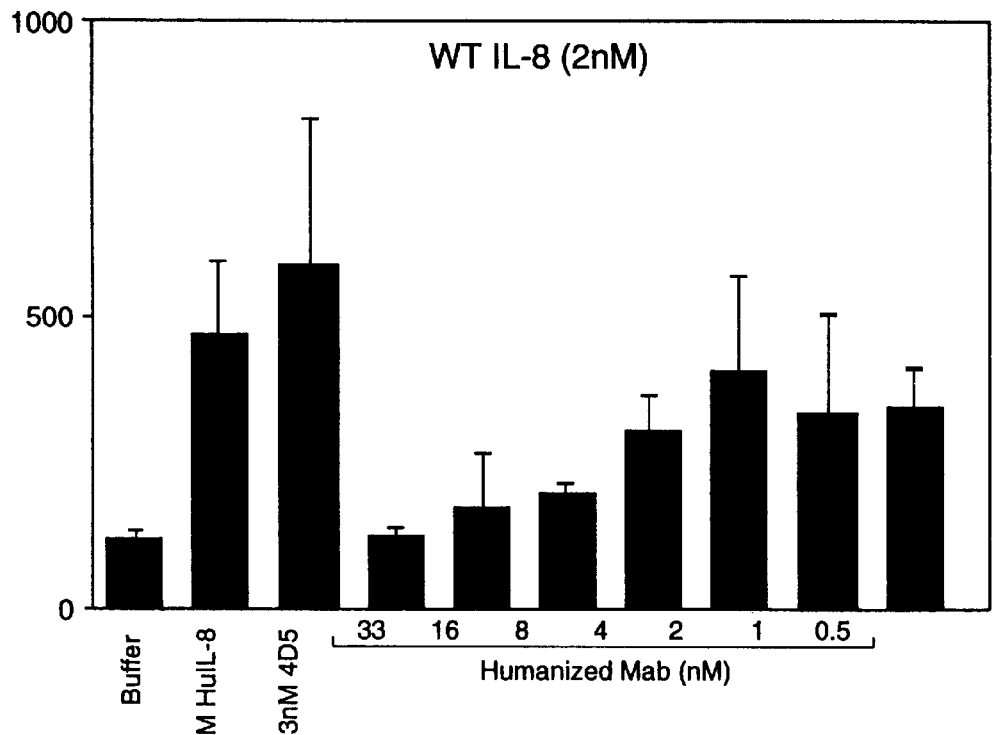
FIGS. 34A, 34C, 34B, and 34D are graphs depicting the ability of 6G4.2.5V11N35A Fab to inhibit human wild type IL-8, human monomeric IL-8, rabbit IL-8, and rhesus IL-8 mediated neutrophil chemotaxis, respectively.
Figure 34B:
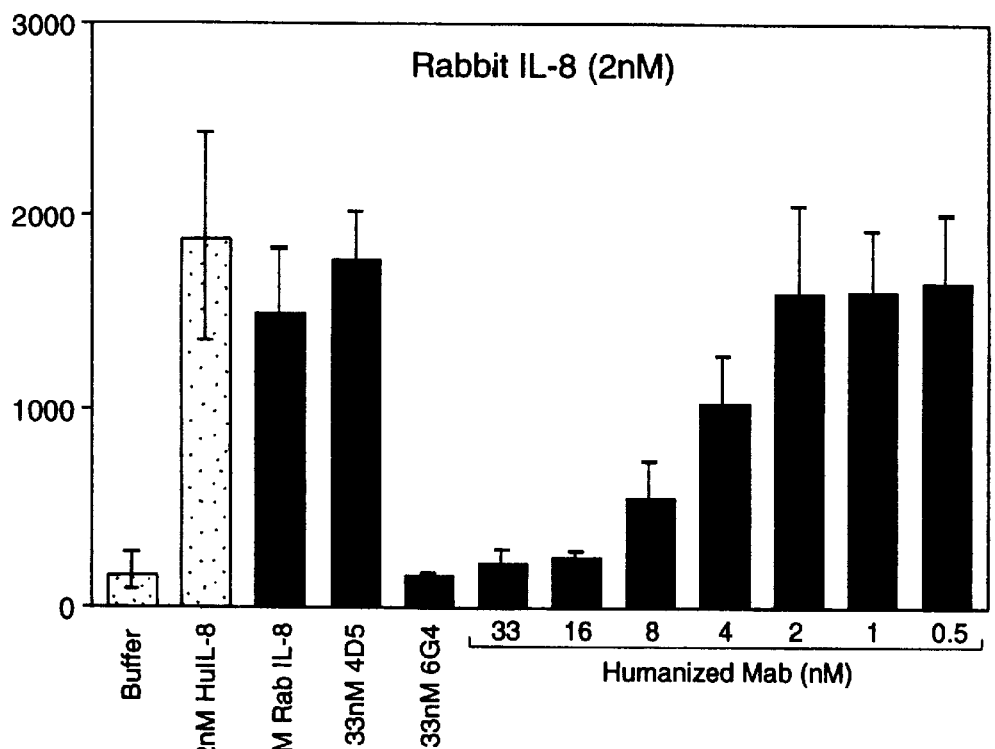
Figure 34C:
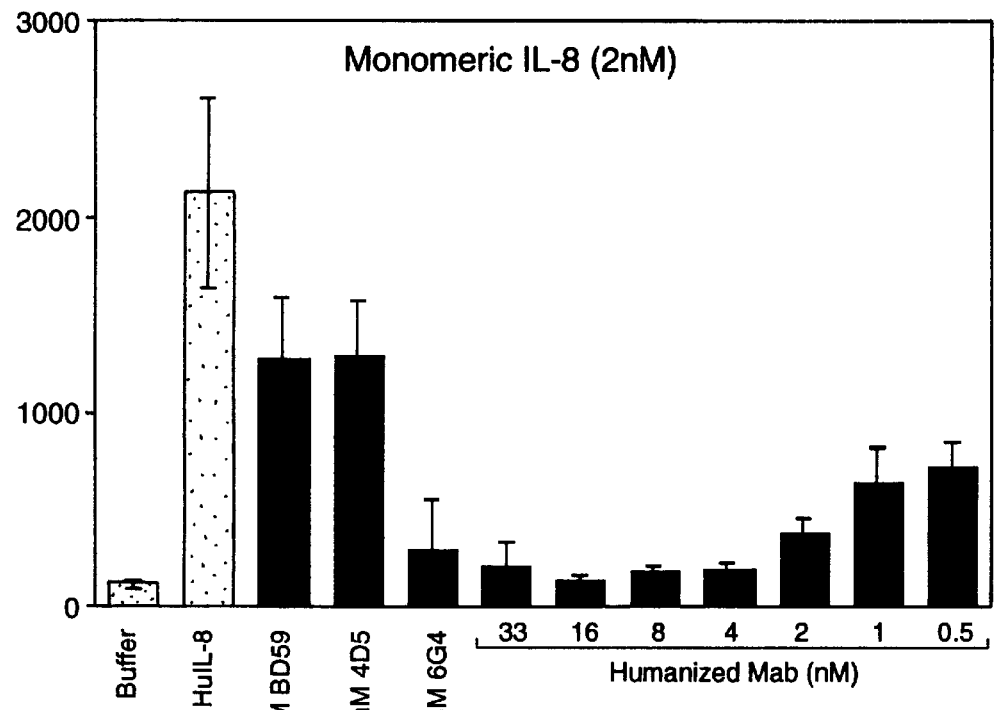
Figure 34D:
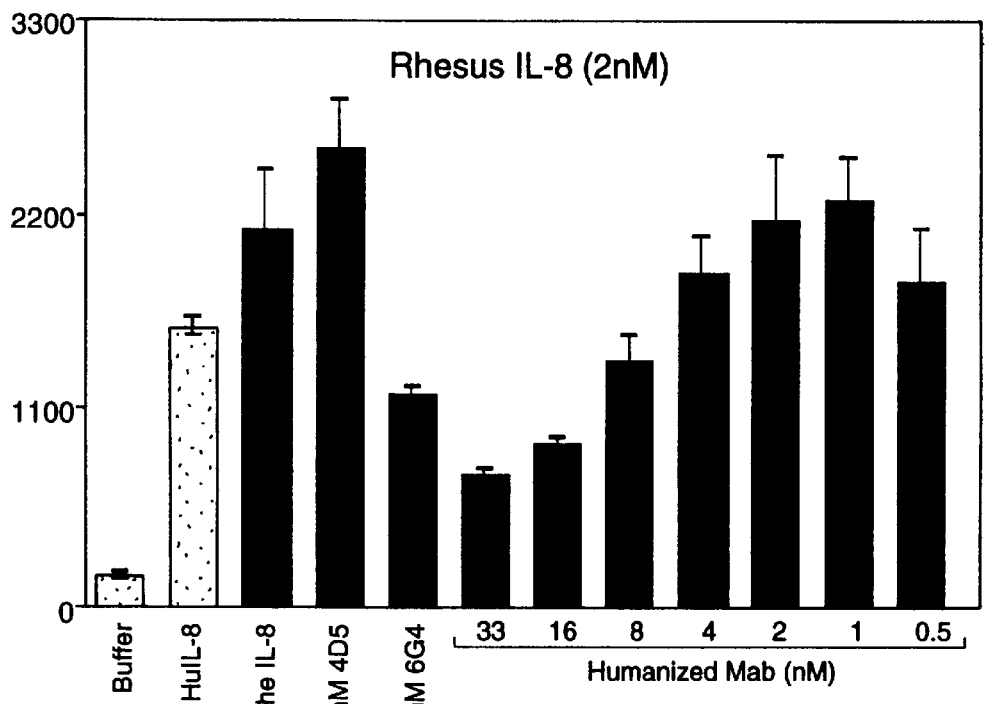

Soluble 6G4V11N3 5A Fab antibody was made by transforming an amber non-suppressor strain of E. coli, 34B8, with pPh6G4.V11 and growing the culture in low phosphate medium for 24 hours. The periplasmic fraction was collected and passed over a H1-Trap Protein-G column (Pharmacia, Piscataway, N.J.) followed by a desalting and concentration step. The protein was analyzed by SDS-PAGE, mass spectrometry and amino acid analysis. The protein had the correct size and amino acid composition (FIG. 35). The 6G4V11N35A Fab was tested for its ability to inhibit $^{125}$I-IL-8 binding to human neutrophils and to inhibit IL-8 mediated neutrophil chemotaxis as described in Section (B)(1) and (B)(2) above. As shown in FIG. 33, hybridoma-derived intact murine antibody (6G4 murine mAB), recombinant 6G4 murine-human chimera Fab, recombinant humanized Fab versions 1 and 11, and 6G4V11N35A Fab were found to inhibit $^{125}$I-IL-8 binding to human neutrophils with an average $IC_{50}$ of 5 nM, 8 nM, 40 nM, 10 nM and 3 nM, respectively. The 6G4V11N35A Fab had at least a 2-fold higher affinity than the 6G4.2.5 chimera Fab and a 3-fold higher affinity than 6G4V11. As shown in FIG. 34, the 6G4V11N35A Fab was found to inhibit IL-8 mediated neutrophil chemotaxis induced by both wild type and monomeric human IL-8, and by two different animal species of IL-8, namely, rabbit and rhesus. The irrelevant isotype control Fab (4D5) did not inhibit neutrophil migration. The average $IC_{50}$ values were 3 nM (wt IL-8), 1 nM (monomeric IL-8), 5 nM (Rabbit IL-8), and 10 nM (Rhesus IL-8).

K. Construction of A 6G4V11N35A F(ab')$_2$ Leucine Zipper

Production of a F(ab')$_2$ version of the humanized anti-IL-8 6G4V11N35A Fab was accomplished by constructing a fusion protein with the yeast GCN4 leucine zipper. The expression plasmid p6G4V11N35A.F(ab')$_2$ was made by digesting the plasmid p6G425chim2.fab2 with the restriction enzymes bsaI and apaI to remove the DNA sequence encoding the 6G4.2.5 murine-human chimeric Fab and replacing it with a 2620 bp bsaI-apaI fragment from pPh6G4.V11N35A. The plasmid p6G425chim2.fab2 is a derivative of pS1130 which encodes a fusion protein (the GCN4 leucine zipper fused to the heavy chain of anti-CD18) and the light chain of anti-CD18 antibody. The expression plasmid p6G4V11N35A.F(ab')$_2$ was deposited on Feb. 20, 1996 with the American Type Culture Collection, 12301 Parklawn Drive, Rockville, Md., U.S.A. (ATCC) and assigned ATCC Accession No. 97890. A pepsin cleavage site in the hinge region of the antibody facilitates the removal of the leucine zipper leaving the two immunoglobin monomers joined by the cysteines that generate the interchain disulfide bonds. The DNA and protein sequence of the h6G4V11N35A.F(ab')$_2$ are depicted in FIGS. 35–37.

An expression host cell was obtained by transforming E. coli strain 49D6 with p6G4V11N35A.F(ab')$_2$ essentially as described in Section (II)(3)(C) above. The transformed host E. coli 49D6 (p6G4V11N35A.F(ab')$_2$) was deposited on Feb. 20, 1997 at the ATCC and assigned ATCC Accession No. 98332. Transformed host cells were grown in culture, and the 6G4V11N35A F(ab')$_2$ product was harvested from the host cell periplasmic space essentially as described in Section (II)(3)(F) above.

L. Characterization of the Humanized6G4V11N35A F(ab')$_2$ Leucine Zipper

Figure 38:
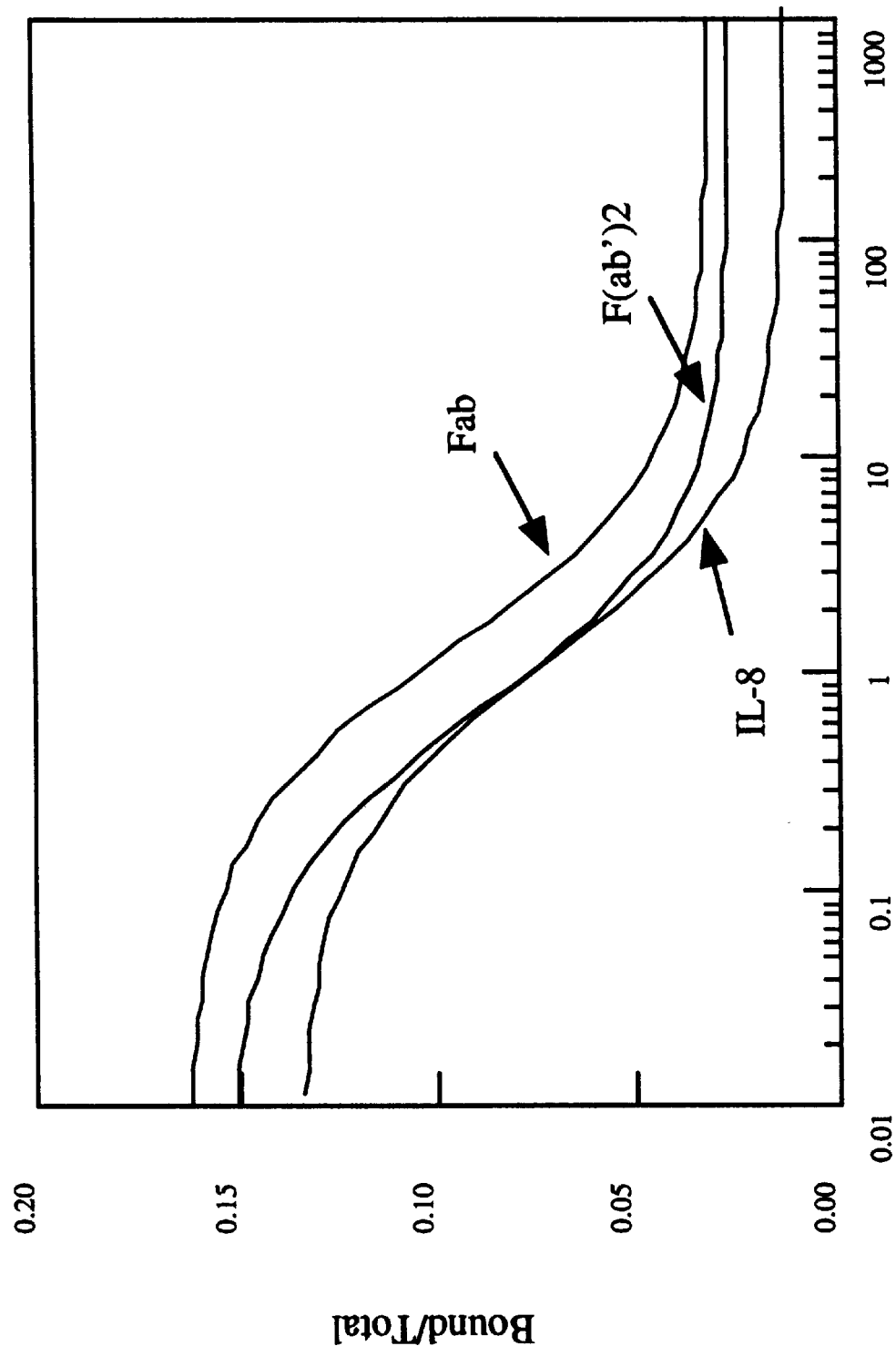
FIG. 38 is a Scatchard plot depicting the inhibition of $^{125}$I-IL-8 binding to human neutrophils exhibited by 6G4.2.5V11N35A Fab (denoted Fab), 6G4.2.5V11N35A F(ab')$_2$ (denoted F(ab')$_2$), and human wild type IL-8 control (denoted IL-8).

The 6G4V11N35A Fab and F(ab')$_2$ were tested for their ability to inhibit $^{125}$I-IL-8 binding to neutrophils according to the procedures described in Section (B)(1) above. The displacement curves from a representative binding experiment performed in duplicate is depicted in FIG. 38. Scatchard analysis of this data shows that 6G4V11N35A F(ab')$_2$ inhibited $^{125}$I-IL-8 binding to human neutrophils with an average IC$_{50}$ of 0.7 nM (+/−0.2). This is at least a 7 fold increase in affinity compared to the hybridoma-derived intact murine antibody (average IC$_{50}$ of 5 nM) and at least a 2.8 fold increase in affinity over the Fab version (average IC$_{50}$ of 2 nM).

The 6G4V11N35A F(ab')$_2$ was also tested for its ability to inhibit IL-8 mediated neutrophil chemotaxis according to the procedures described in Section (B)(2) above. The results of a representative chemotaxis experiment performed in quadruplicate are depicted in FIG. 39. As shown in FIG. 39, the 6G4V11N35A F(ab')$_2$ inhibited human IL-8 mediated neutrophil chemotaxis. The 6G4V11N35A F(ab')$_2$ exhibited an average IC$_{50}$ value of 1.5 nM versus 2.7 nM for the 6G4V11N35A Fab, which represents an approximately 2 fold improvement in the antibody's ability to neutralize the effects of IL-8. The irrelevant isotype control Fab (4D5) did not inhibit neutrophil migration. Furthermore, the 6G4V11N35A F(ab')$_2$ antibody retained its ability to inhibit IL-8 mediated neutrophil chemotaxis by monomeric IL-8 and by two different animal species of IL-8, namely rabbit and rhesus, in neutrophil chemotaxis experiments conducted as described above. An individual experiment is shown in FIG. 40. The average IC$_{50}$ values were 1 nM (monomeric IL-8), 4 nM (Rabbit IL-8), and 2.0 nM (Rhesus IL-8).

M. Random Mutagenesis of Lisghtchain Amino Acid (N35A) IN CDR-L1 of Humanized Antibody 6G4V11

A 3-fold improvement in the IC$_{50}$ for inhibiting $^{125}$I-IL-8 binding to human neutrophils was observed when alanine was substituted for asparagine at position 35 in CDR-L1 (light chain) of the humanized 6G4V11 mAb as described in Section (I) above. This result might be attributed to an improvement in the contact between the antigen-antibody binding interfaces as a consequence of the replacement of a less bulky nonpolar side chain (R-group) that may have altered the conformation of CDR-L1 or neighboring CDR-H3 (heavy chain) to become more accessible for antigen docking. The acceptance of alanine at position 35 of CDR-L1 suggested that this position contributed to improved affinity and that an assessment of the re-modeling of CDR loops/antigen-binding region(s) by other amino acids at this location was warranted. Selection of an affinity matured version of the humanized 6G4.V11 mAB (Kunkel, T. A., *Proc. Natl. Acad. Sci. USA*, 82:488 (1995)) was accomplished by randomly mutagenizing position 35 of CDR-L1 and constructing an antibody-phage library. The codon for Asparagine (N) at position 35 of CDR-L1, was targeted for randomization to any of the 20 known amino acids.

Initially, a stop template, pPh6G4.V11-stop, was made to eliminate contaminating wild-type N35 sequence from the library. This was accomplished by performing site-directed mutagenesis (Muta-Gene Kit, Biorad, Ricmond, Calif.) of pPH6G4V11 (described in Section (H) above) to replace the codon (AAC) for N35 with a stop codon (TAA) using the primer SL.97.2 (SEQ ID NO:63)(FIG. 42). The incorporation of the stop codon was confirmed by DNA sequencing. Subsequently, uracil containing single-stranded DNA derived from *E. coli* CJ236 transformed with the stop template was used to generate an antibody-phage library following the method described by Lowman (*Methods in Molecular Biology*, 87 Chapter 25: 1–15 (1997). The variants generated from this library were predicted to produce a collection of antibodies containing one of the 20 known amino acids at position N35 in CDR-L1. The amino acid substitutions were accomplished by site-directed mutagenesis using the degenerate oligonucleotide primer (SL.97.3) with the sequence NNS (N=A/G/T/C; S=G/C;) (SEQ ID NO: 64)(FIG. 42). This codon usage should allow for the expression of any of the 20 amino acids including the amber stop codon (TAG). The collection of antibody-phage variants was transfected into *E. coli* strain XL-1 blue (Stratagene, San Diego, Calif.) by electroporation and grown at 37° C. overnight to amplify the library. Selection of tight binding humanized 6G4V11 Fab's were accomplished by panning the library on IL-8 coated 96-well plates as described in Section (I) above. Prior to panning, the number of phage/library was normalized to $1.1 \times 10^{13}$ phage/ml (which produces a maximum OD$_{270}$ reading=1 OD unit) and IL-8 coated plates were incubated with blocking solution (25mN Carbonate buffer containing 50 mg/ml skim milk) for 2 hours before the addition of phage (each sort used eight IL-8 coated wells/library). After the blocking and washing steps, every sort began with the addition of 100 ul of antibody-phage (titered at $1.1 \times 10^{13}$ phage/ml) to each of eight IL-8 coated wells followed by an 1 hour incubation at 25° C. The non-specifically bound antibody-phage were removed by 10 quick washes with PBS-0.05% Tween 20 (PBS-Tween). For sort #1, a low stringency wash (100 ul PBS-Tween/well for 10 minutes at 25° C.) was employed to capture the small proportion of tight binding antibody-phage bound to the immobilized IL-8. The antibody-phage variants specifically bound to IL-8 were eluted with 100 ul/well of 200 mM Glycine pH 2.0 for 5 minutes at 25° C. The eluted antibody-phage variants from the 8 wells were then pooled and neutralized with 1M Tris-HCl pH 8.0 (⅓ the elution volume). The phage were titered and propagated as described in Section (I) above. The stringency of the washes were successively increased with each round of panning depending upon the percent recovery of phage at the end of a sort. The wash conditions were as follows: sort #2 (4×15 minute intervals; total time=60 minutes) and sort #3 (either #3a: 8×15 minute intervals or #3b: 12×10 minute intervals; total time=120 minutes). The total number of phage recovered was progressively reduced after each sort suggesting that non- or weak-binders were being selected against. The recovery of the negative control (the antibody-phage stop variant) was constant throughout the panning (approximately 0.0001 to 0.00001 percent).

Eighteen random variants from sort #3 were analyzed by DNA sequencing to look for an amino acid consensus at position 35 of CDR-L1. The data presented in FIG. 43A showed that Glycine occupied position 35 in 33% of the variants sequenced. However, after correcting for the number of NNS codon combinations/amino acid, the frequency of Glycine was reduced to 16.6%. Glutamic Acid was represented with the highest frequency (22%) followed by Aspartic Acid and Glycine (16.6%). The frequencies of recovery of the wild-type Asparagine and substituted Alanine were only 5.6%. Interestingly, the high frequency of Glycine may suggest that a much wider range of conformations might be allowed for the loop of CDR-L1 which may be attributed to the reduction in steric hindrance of bond angle (φ-ψ) pairing as a result of the single hydrogen atom as the side chain. Conversely, Glutarnic Acid at position 35 might restrict the flexibility of the loop by imposing less freedom of rotation imposed by the more rigid and bulky charged polar side chain.

Figure 43B:
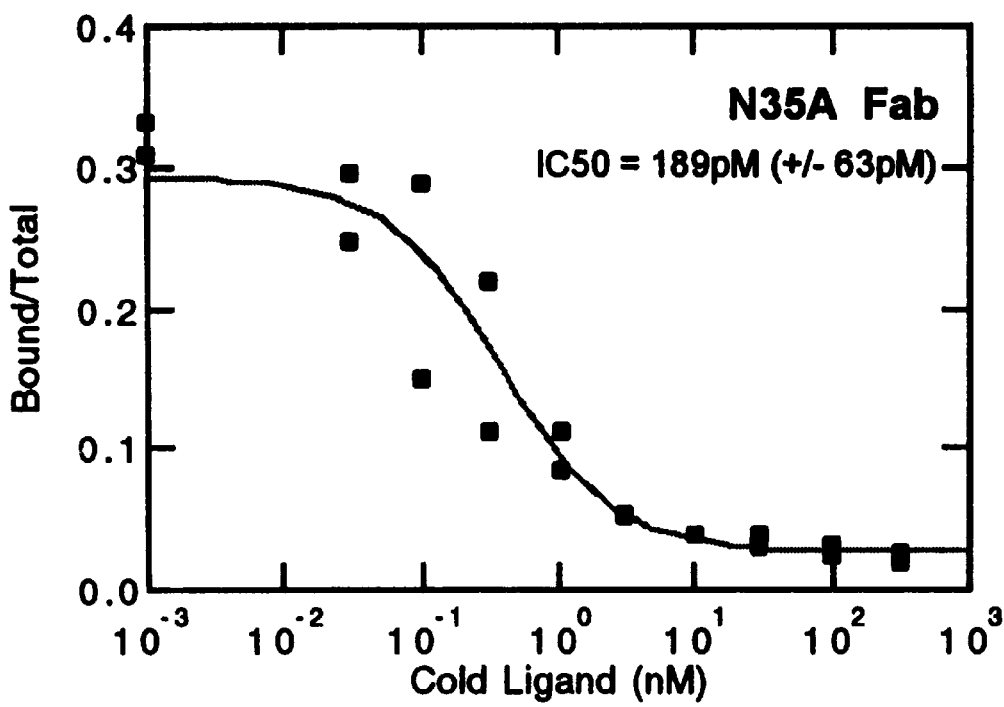
FIGS. 43B, 43C, 43D and 43E are graphs of displacement curves depicting the inhibition of $^{125}$I-IL-8 binding to neutrophils exhibited by the 6G4V11N35A, 6G4V11N35D, 6G4V11N35E and 6G4V11N35G Fab's.
Figure 43C:
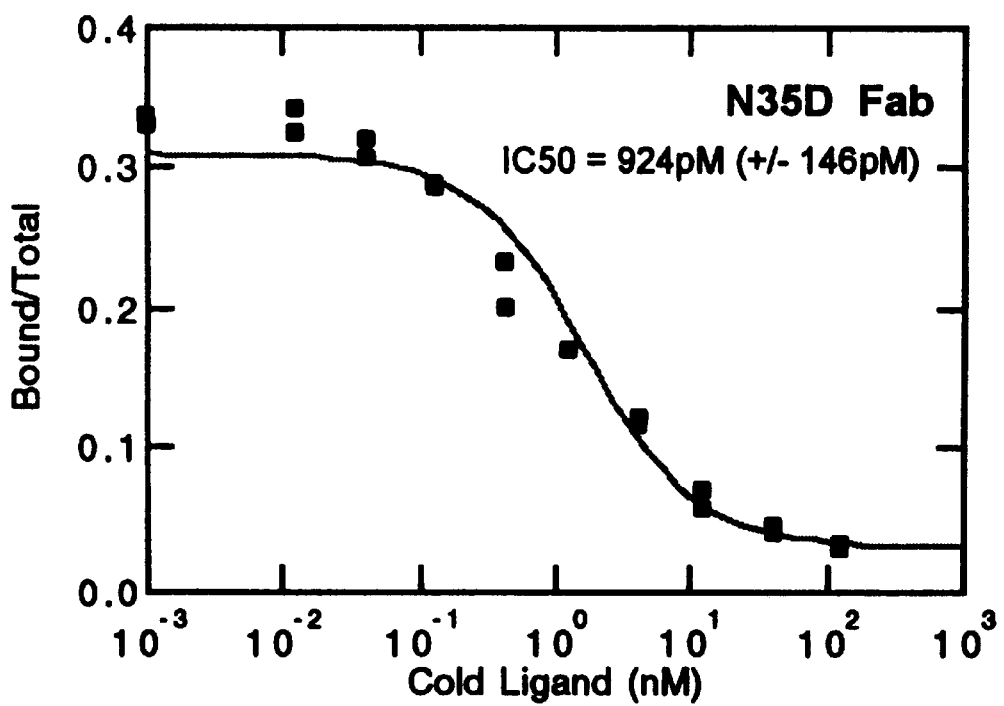
Figure 43D:
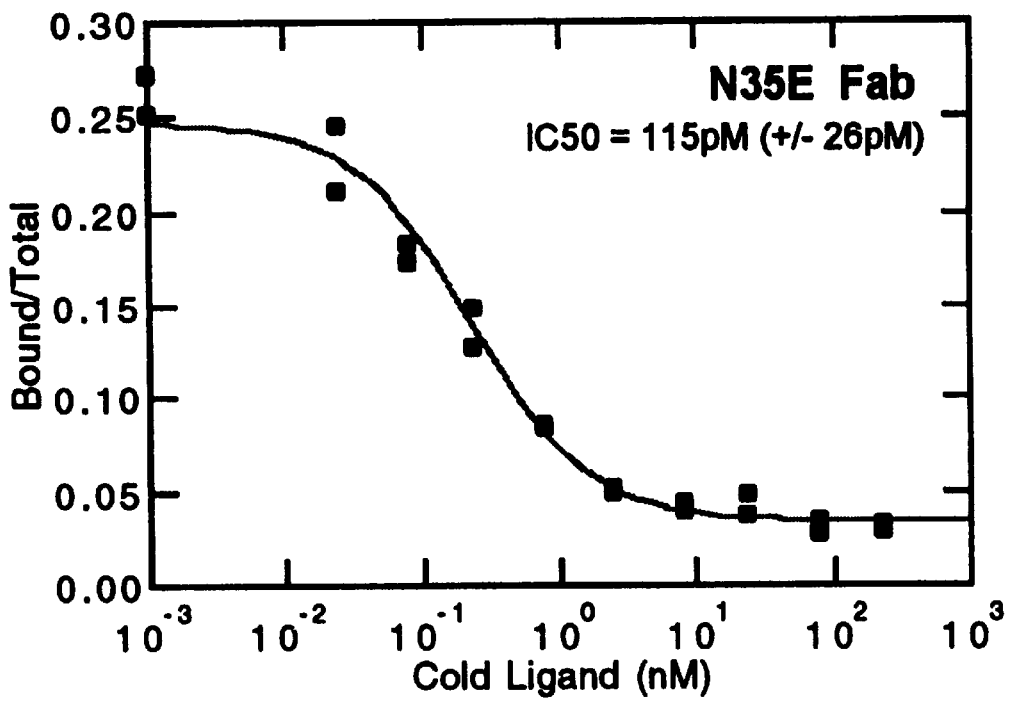
Figure 43E:
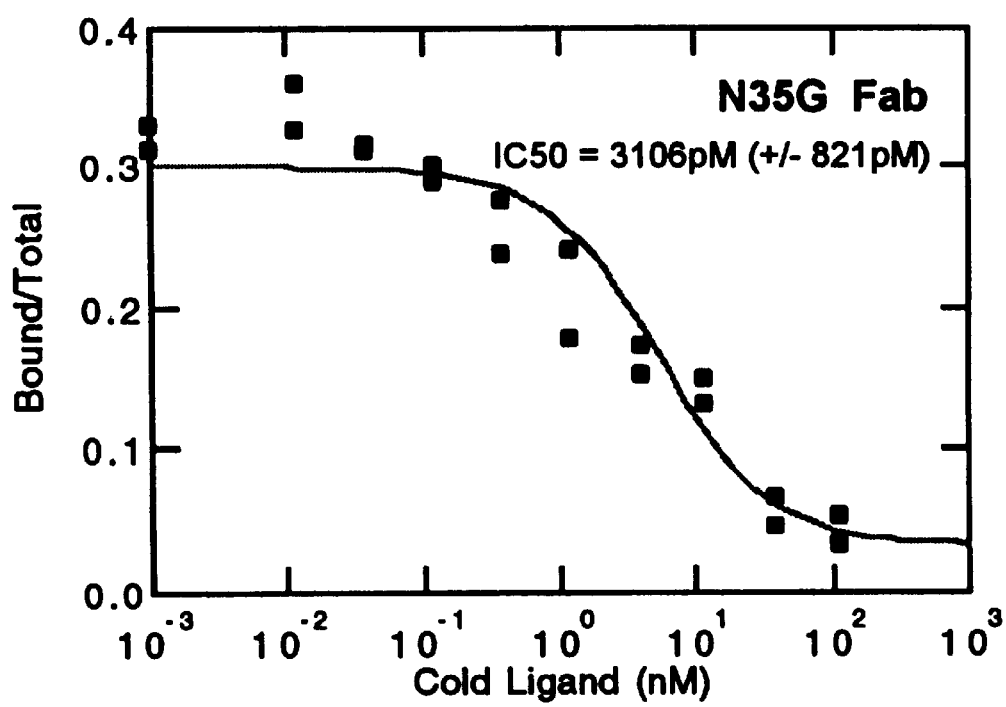

Soluble Fab's of the affinity matured variants (N35G, N35D, N35E and N35A) were made as described in Section (J) above for evaluating their ability to block IL-8 binding. As shown in FIG. 43B, variants N35A, N35D, N35E and N35G were found to inhibit $^{125}$I-IL-8 binding to human neutrophils with an approximate IC$_{50}$ of 0.2 nM, 0.9 nM, 0.1 nM and 3.0 nM, respectively. All of the affinity matured variants showed an improvement in binding IL-8 ranging from 3–100 fold compared to the humanized 6G4V11 mAb. The affinity-matured variant, 6G4V11N35E, was 2-fold more potent in blocking IL-8 binding to human neutrophils than the alanine-scan variant, 6G4V11N35A.

Equilibrium and kinetic measurements of variants 6G4V11N35A and 6G4V11N35E were determined using KinEXA™ automated immunoassay system (Sapidyne Instruments Inc., Idaho City, Id.) as described by Blake et al., *J. Biol. Chem.* 271: 27677 (1996). The procedure for preparing the antigen-coated particles was modified as follows: 1 ml of activated agarose beads (Reacti-Gel 6X; Pierce, Rockford, Ill.) were coated with antigen in 50 mM Carbonate buffer pH 9.6 containing 20 ug/ml of human IL-8 and incubated with gentle agitation on a rocker overnight at 25° C. The IL-8 coated beads were then washed twice with 1M Tris-HCl pH 7.5 to inactivate any unreactive groups on the beads and blocked with Superblock (Pierce, Rockford, Ill.) for 1 hour at 25C to reduce non-specific binding. The beads were resuspended in assay buffer (0.1% bovine serum albumin in PBS) to a final volume of 30 ml. A 550 ul aliquot of the IL-8 coated bead suspension was used each time to pack a fresh 4 mm high column in the KinEXA observation cell. The amount of unbound antibody from the antibody-antigen mixtures captured by the IL-8-coated beads in both the equilibrium and kinetic experiments was quantified using a fluorescently labeled secondary antibody. Murine 6G4.2.5 was detected with a R-PE AffiniPure F(ab')$_2$ goat anti-mouse IgG, Fc fragment specific 2° antibody (Jackson Immuno Research Laboratories, West Grove, Pa.) and humanized affinity matured N35A (Fab and F(ab')$_2$) and N35E Fab were detected with a R-PE AffiniPure F(ab')$_2$ donkey anti-human IgG (H+L) 2° antibody (Jackson Immunoresearch Laboratories, West Grove, Pa.); both at a 1:1000 dilution.

Equilibrium measurements were determined by incubating a constant amount of anti-IL-8 antibody (0.005 ug/ml) with various concentrations of human IL-8 (0, 0.009, 0.019, 0.039, 0.078, 0.156, 0.312, 0.625, 1.25, 2.5 nM). The antibody-antigen mixture was incubated for 2 hours at 25° C. to allow the molecules to reach equilibrium. Subsequently, each sample was passed over a naive IL-8 coated bead pack in the KinEXA observation cell at a flow rate of 0.5 ml/minute for a total of 9 minutes/sample. The equilibrium constant (Kd) was calculated using the software provided by Sapidyne Instruments Inc.

Rates of association (ka) and dissociation (kd) were determined by incubating together a constant amount of antibody and antigen, and measuring the amount of uncomplexed anti-IL-8 bound to the IL-8 coated beads over time. The concentration of antibody used in the kinetic experiments was identical to that used in the equilibrium experiment described above. Generally, the amount of human IL-8 used was the concentration derived from the binding curves of the equilibrium experiment that resulted in 70% inhibition of anti-IL-8 binding to the IL-8 coated beads. Measurements were made every 15 minutes to collect approximately nine data points. The ka was calculated using the software provided by Sapidyne Instruments, Inc. The off rate was determined using the equation: kd=Kd/ka.

Figure 44:
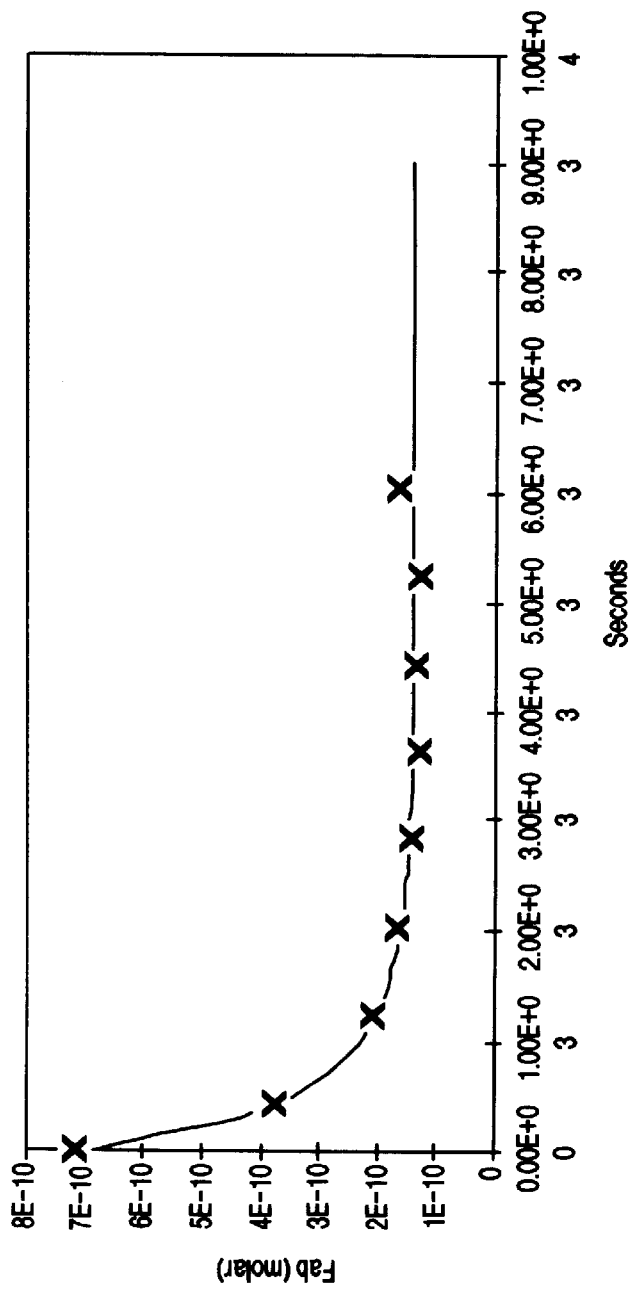
FIG. 44 contains a graph depicting the typical kinetics of an anti-IL-8 antibody fragment (6G4V11N35A F(ab')$_2$) binding to IL-8.

FIG. 44 shows the equilibrium constants (Kd) for the affinity matured variants 6G4V11N35E and 6G4V11N35A Fab's were approximately 54 pM and 114 pM, respectively. The improvement in affinity of 6G4V11N35E Fab for IL-8 can be attributed to a 2-fold faster rate of association (K$_{on}$) of 4.7×10$^6$ for 6G4V11N35E Fab versus 2.0×10$^6$ for 6G4V11N35A F(ab')$_2$. (The Kd of the 6G4V11N35A F(ab')2 and 6G4V11N35A Fab are similar.) The dissociation rates (K$_{off}$) were not significantly different. Molecular modeling suggests that substitution of Aspargine with Glutamic Acid might either affect the antibody's interaction with IL-8 directly or indirectly by neutralizing the charge of neighboring residues R98 (CDR-H3) or K50 (CDR-L2) in the CDR's to facilitate contact with IL-8. Another effect might be the formation of a more stable loop conformation for CDR-L1 that could have facilitated more appropriate contacts of other CDR-L1 loop residues with IL-8. The DNA (SEQ ID NO: 65) and amino acid (SEQ ID NO:62) sequences of p6G4V11N35E.Fab showing the Asparagine to Glutamic Acid substitution in the light chain are presented in FIG. 45.

N. Characterization of Humanized Anti-IL-8 Variant 6G4V11N35E Fab

Figure 46:
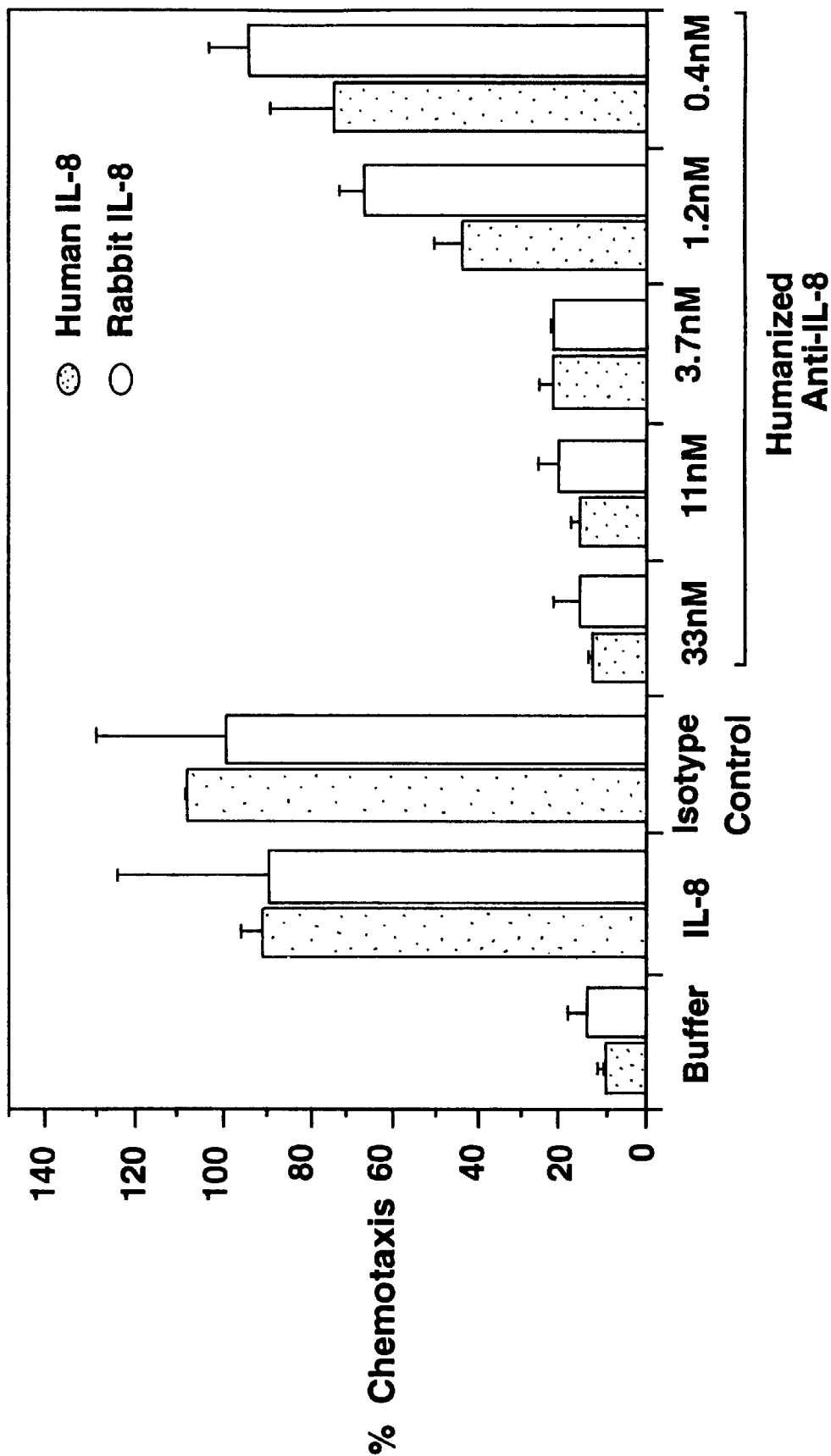
FIG. 46 is a graph depicting the ability of 6G4V11N35E Fab to inhibit human IL-8 (dark columns) and rabbit IL-8 (light columns) mediated neutrophil chemotaxis. Data are presented for 6G4V11N35E Fab samples at concentrations of 0.4, 1.2, 3.7, 11 and 33 nM, and for an isotype control antibody (4D5) sample at a concentration of 100 nM, in the presence of 2 nM human IL-8 or 2 nM rabbit IL-8. In addition, inhibition data are presented for a no IL-8 buffer control sample (denoted "Buffer") and for human and rabbit IL-8 control samples (denoted "IL-8").
Figure 49A:
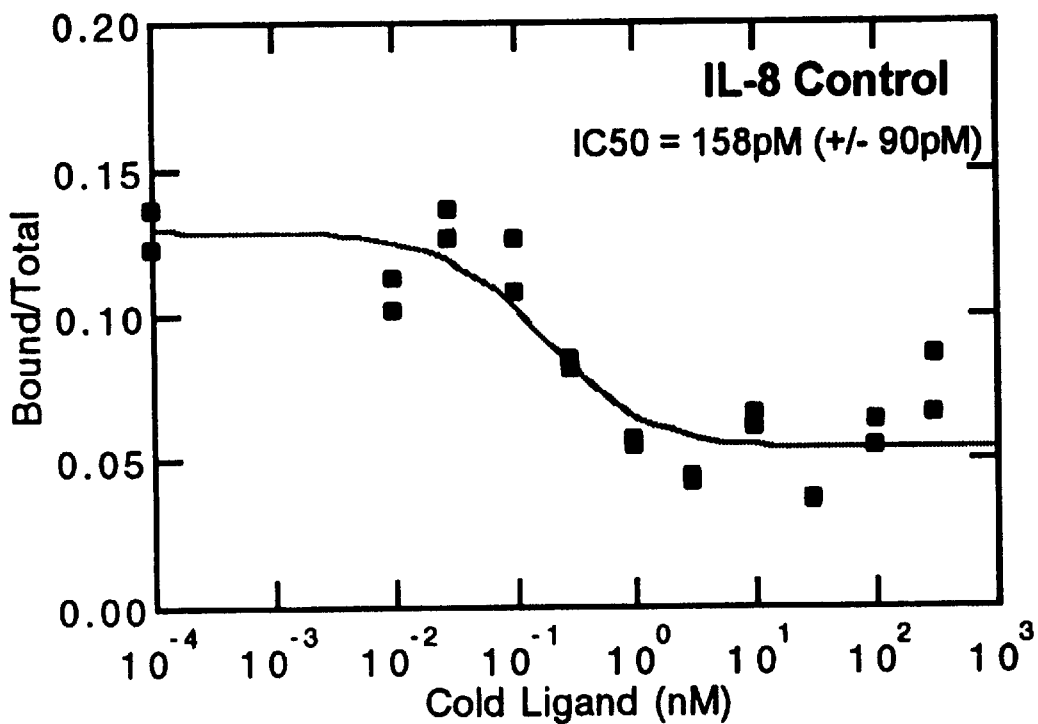
FIGS. 49A, 49B, 49C and 49D are graphs of displacement curves depicting the inhibition of $^{125}$I-IL-8 binding to neutrophils exhibited by IL-8 control, intact murine 6G4.2.5 antibody, the full length IgG1 form of variant 6G4V11N35A, and the full length IgG1 form of variant 6G4V11N35E, respectively.
Figure 49B:
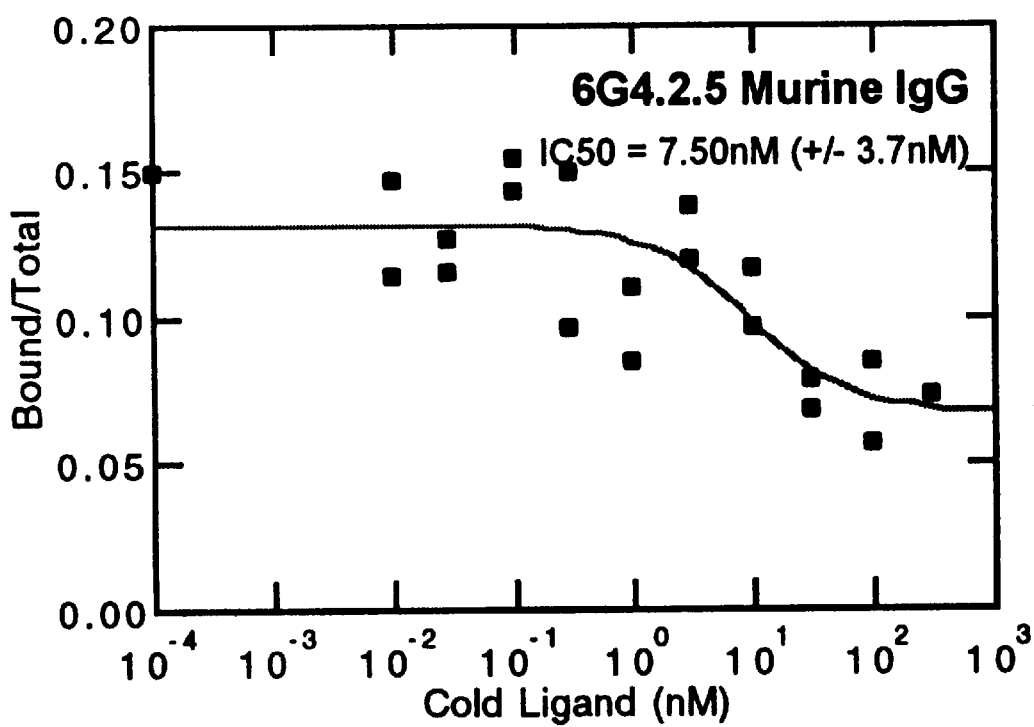
Figure 49C:
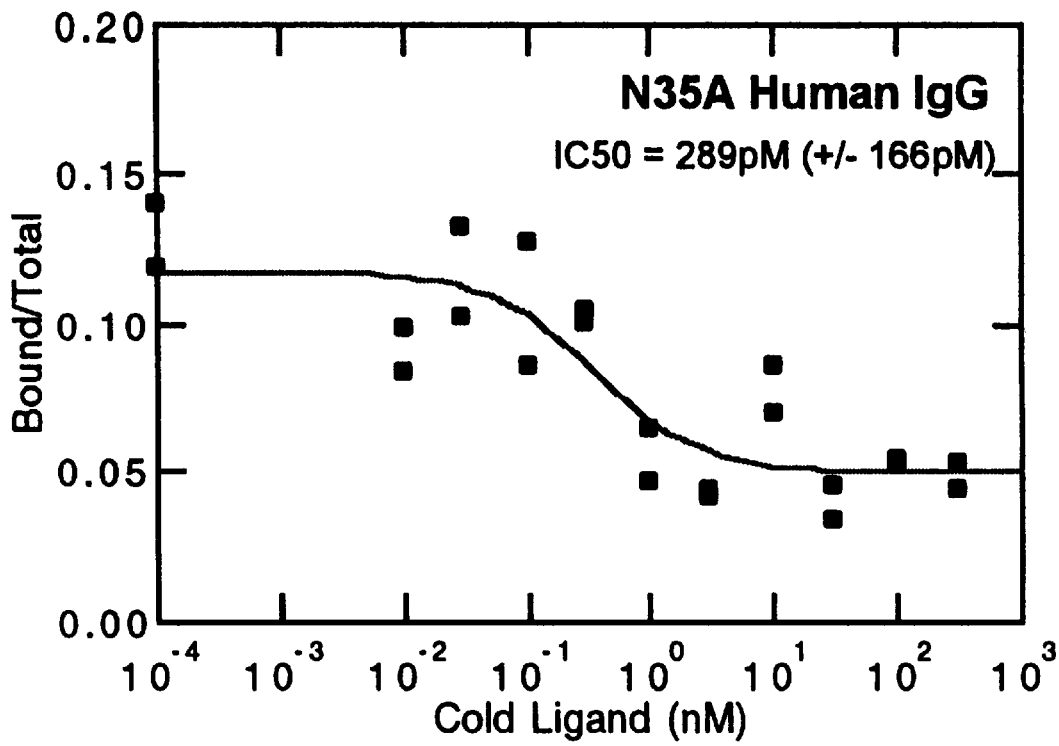
Figure 49D:
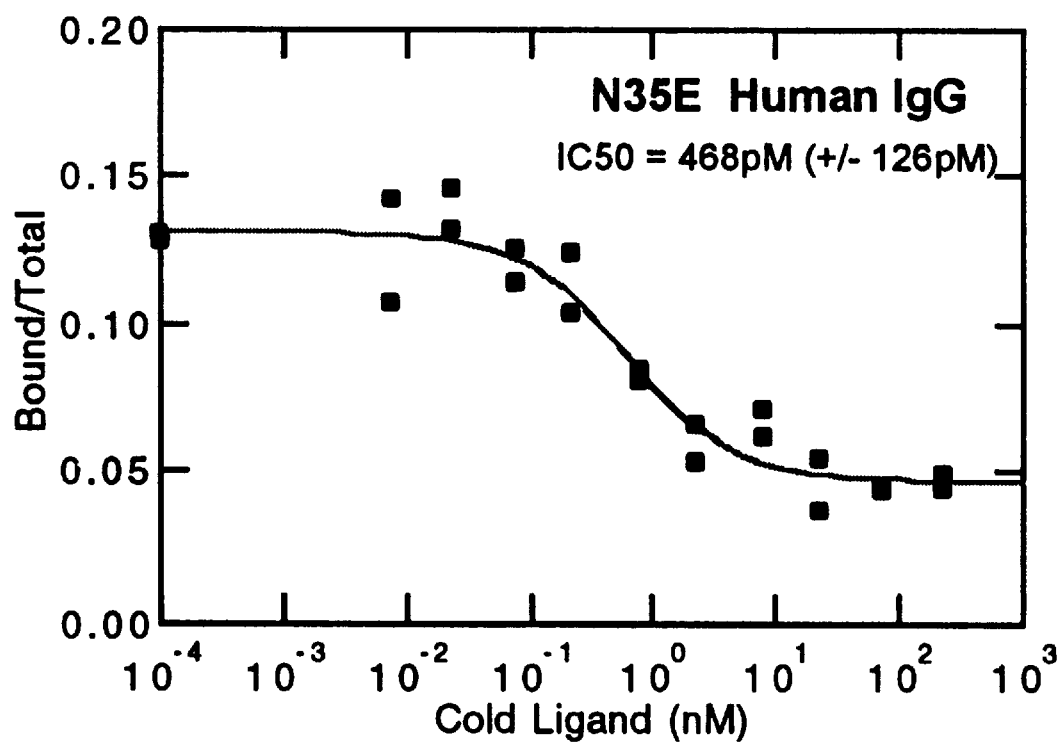

The affinity matured Fab variant, 6G4V11N35E, was tested for its ability to inhibit IL-8 mediated neutrophil chemotaxis as described in Section (B)(2) above. The reuseable 96-well chemotaxis chamber described in Section (B)(2) was replaced with endotoxin-free disposable chemotaxis chambers containing 5-micron PVP-free polycarbonate filters (ChemoTx101-5, Neuro Probe, Inc. Cabin John, Md.). As illustrated in FIG. 46, variant N35E effectively blocks IL-8 mediated neutrophil chemotaxis induced by a 2 nM stimulus of either rabbit or human IL-8. In fact, the level of inhibition at antibody concentrations between 3.7 nM–33 nM was not significantly different from the buffer control indicating variant N35E could completely inhibit this response. The IC$_{50}$'s for both rabbit and human IL-8 were approximately 2.8 nM and 1.2 nM, respectively. The irrelevant isotype control Fab (4D5) did not inhibit neutrophil migation indicating the results observed for the affinity matured variant, N35E, is IL-8 specific.

O. Construction of Humanized6G4V11N35E F(ab')$_2$ Leucine Zipper

A F(ab')$_2$ expression plasmid for 6G4V11N35E was constructed using methods similar to those described in Section (K) above. The expression plasmid, p6G4V11N35E.F(ab')$_2$, was made by digesting the plasmid p6G4V11N35A.F(ab')$_2$ (described in Section (K) above) with the restriction enzymes ApaI and NdeI to isolate a 2805 bp fragment encoding the heavy chain constant domain—GCN4 leucine zipper and ligating it to a 3758 bp ApaI-NdeI fragment of the pPH6G4V11N35E phage display clone (encoding 6G4V11N35E Fab) obtained as described in Section (M) above. The integrity of the entire coding sequence was confirmed by DNA sequencing.

P. Construction of the Full Length Humanized6G4V11N35A IgG Expression Plasmid

The full length IgG, version of the humanized anti-IL8 variant 6G4V11N35A was made using a dicistronic DHFR-Intron expression vector (Lucas et al., *Nucleic Acids Res.*, 24: 1774–1779 (1996)) which contained the full length recombinant murine-human chimera of the 6G4.2.5 anti-IL8 mAb. The expression plasmid encoding the humanized variant 6G4V11N35A was assembled as follows. First an intermediate plasmid (pSL-3) was made to shuttle the sequence encoding the variable heavy chain of humanized anti-IL-8 variant 6G4V11N35A to pRK56G4chim.2Vh— which contains the variable heavy region of the chimeric 6G4.5 anti-IL8 antibody. The vector pRK56G4chim.Vh was digested with PvuII and ApaI to remove the heavy chain variable region of the chimeric antibody and religated with an 80 bp PvuII-XhoI synthetic oligonucleotide (encoding Leu4 to Phe29 of 6G4V11N35A) (FIG. 47) and a 291 bp XhoI-ApaI fragment from p6G4V11N35A.7 carrying the remainder of the variable heavy chain sequence of 6G4V11N35A to create pSL-3. This intermediate plasmid was used in conjunction with 2 other plasmids, p6G4V11N35A.F(ab')$_2$ and p6G425chim2.choSD, to create the mammalian expression plasmid, p6G4V11N35AchoSD.9 (identified as p6G425V11N35A.choSD in a deposit made on Dec. 16, 1997 with the ATCC and assigned ATCC Accession No. 209552). This expression construct was assembled in a 4-part ligation using the following DNA fragments: a 5,203 bp ClaI-BlpI fragment encoding the regulatory elements of the mammalian expression plasmid (p6G425 chim2.choSD), a 451 bp ClaI-ApaI fragment containing the heavy chain variable region of the humanized 6G4V11N35A antibody (pSL-3), a 1,921 bp ApaI-EcoRV fragment carrying the heavy chain constant region of 6G4V11N35A (p6G425chim2.choSD) and a 554 bp EcoRV-BlpI fragment encoding the light chain variable and constant regions of 6G4V11N35A (p6G4V11N35A.F(ab')$_2$). The DNA sequence (SEQ ID NO: 68) of clone p6G4V11N35A.choSD.9 was confirmed by DNA sequencing and is presented in FIG. 48.

Q. Construction of the Full Length Humanized6G4V11N35E IgG Expression Plasmid A mammalian expression vector for the humanized 6G4V11N35E was made by swapping the light chain variable region of 6G4V11N35A with 6G4V11N35E as follows: a 7,566 bp EcoRV-BlpI fragment (void of the 554 bp fragment encoding the light chain variable region of 6G4V11N35A) from p6G4V11N35A.choSD.9 was ligated to a 554 bp EcoRV-BlpI fragment (encoding the light chain variable region of 6G4V11N35E) from pPH6G4V11N35E.7. The mutation at position N35 of the light chain of p6G4V11N35E.choSD.10 was confirmed by DNA sequencing.

R. Stable Cho Cell Lines for Variants N35A AND N35E

For stable expression of the final humanized IgG1 variants (6G4V11N35A and 6G4V11N35E), Chinese hamster ovary (CHO) DP-12 cells were transfected with the above-described dicistronic vectors (p6G4V11N35A.choSD.9 and p6G4V11N35E.choSD.10, respectively) designed to coexpress both heavy and light chains (Lucas et al., *Nucleic Acid Res.* 24:1774–79 (1996)). Plasmids were introduced into CHO DP12 cells via lipofection and selected for growth in GHT-free medium (Chisholm, V. High efficiency gene transfer in mammalian cells. In: Glover, D M, Hames, B D. *DNA Cloning* 4. *Mammalian systems*. Oxford Univ. Press, Oxford pp 1–41 (1996)). Approximately 20 unamplified clones were randomly chosen and reseeded into 96 well plates. Relative specific productivity of each colony was monitored using an ELISA to quantitate the full length human IgG accumulated in each well after 3 days and a fluorescent dye, Calcien AM, as a surrogate marker of viable cell number per well. Based on these data, several unamplified clones were chosen for further amplification in the presence of increasing concentrations of methotrexate. Individual clones surviving at 10, 50, and 100 nM methotrexate were chosen and transferred to 96 well plates for productivity screening. One clone for each antibody (clone#1933 aIL8.92NB 28605/12 for 6G4V11N35A; clone#1934 aIL8.42NB 28605/14 for 6G4V11N35E), which reproducibly exhibited high specific productivity, was expanded in T-flasks and used to inoculate a spinner culture. After several passages, the suspension-adapted cells were used to inoculate production cultures in GHT-containing, serum-free media supplemented with various hormones and protein hydrolysates. Harvested cell culture fluid containing recombinant humanized anti-IL8 was purified using protein A-Sepharose CL-4B. The purity after this step was approximately 99%. Subsequent purification to homogeneity was carried out using an ion exchange chromatography step. Production titer of the humanized 6G4V11N35E IgG1 antibody after the first round of amplification and 6G4V11N35A IgG1 after the second round of amplification were 250 mg/L and 150 mg/L, respectively.

S. Characterization of the Humanized6G4V11N35A/E IgG Variants

Figure 50A:
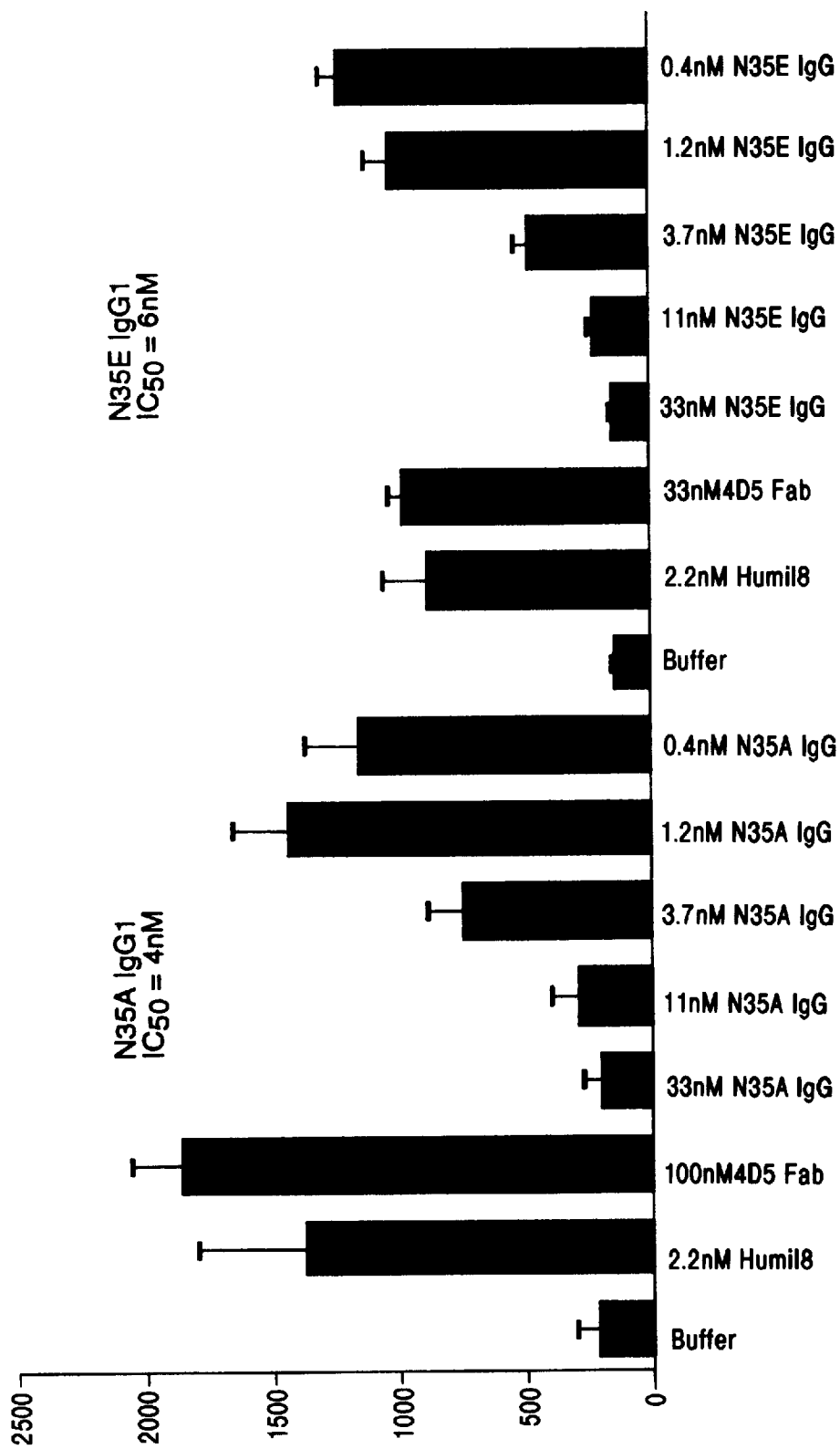
FIGS. 50A–50B are graphs depicting the ability of full length 6G4V11N35A IgG1 and 6G4V11N35E IgG1 to inhibit human IL-8 (FIG. 50A) and rabbit IL-8 (FIG. 50B) mediated neutrophil chemotaxis.
Figure 50B:
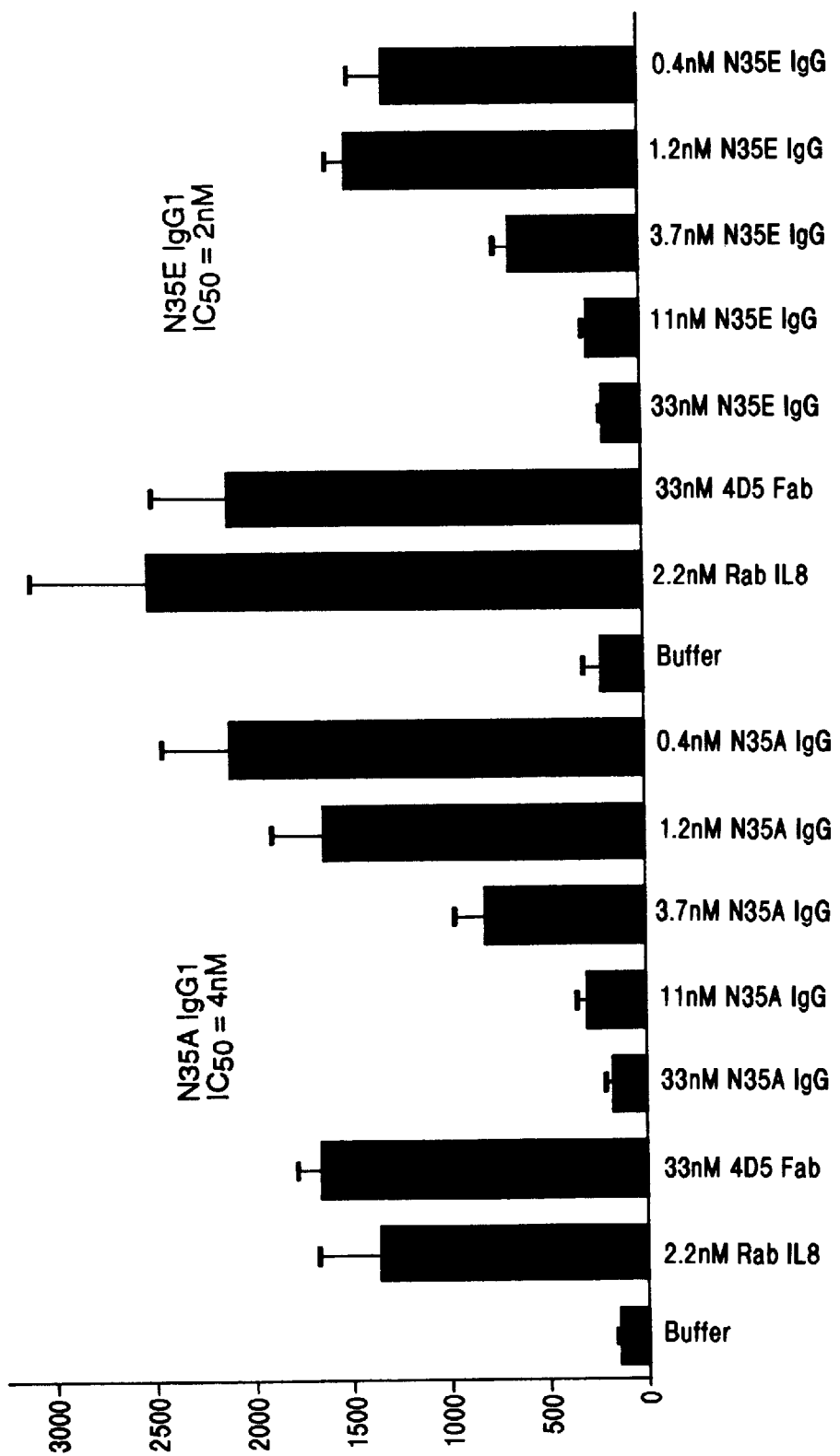

The humanized full length IgG variants of 6G4.2.5 were tested for their ability to inhibit $^{125}$I-IL-8 binding and to neutralize activation of human neutrophils; the procedures are described in Sections (B)(1) and (B)(2) above. As shown in FIG. 49, the full length IgG1 forms of variants 6G4V11N35A and 6G4V11N35E equally inhibited $^{125}$I-IL-8 binding to human neutrophils with approximate IC$_{50}$'s of 0.3 nM and 0.5 nM, respectively. This represents a 15–25 fold improvement in blocking binding of IL-8 compared to the full length murine mAb (IC$_{50}$=7.5 nM). Similarly, the two anti-IL-8 variants showed equivalent neutralizing capabilities with respect to inhibiting IL-8 mediated human neutrophil chemotaxis (FIGS. 50A–50B). The IC$_{50}$'s of 6G4V11N35A IgG1 and 6G4V11N35E IgG1 for human IL-8 were 4.0 nM and 6.0 nM, respectively, and for rabbit IL-8 were 4.0 nM and 2.0 nM, respectively. The irrelevant isotype control Fab (4D5) did not inhibit neutrophil migration.

Figure 51:
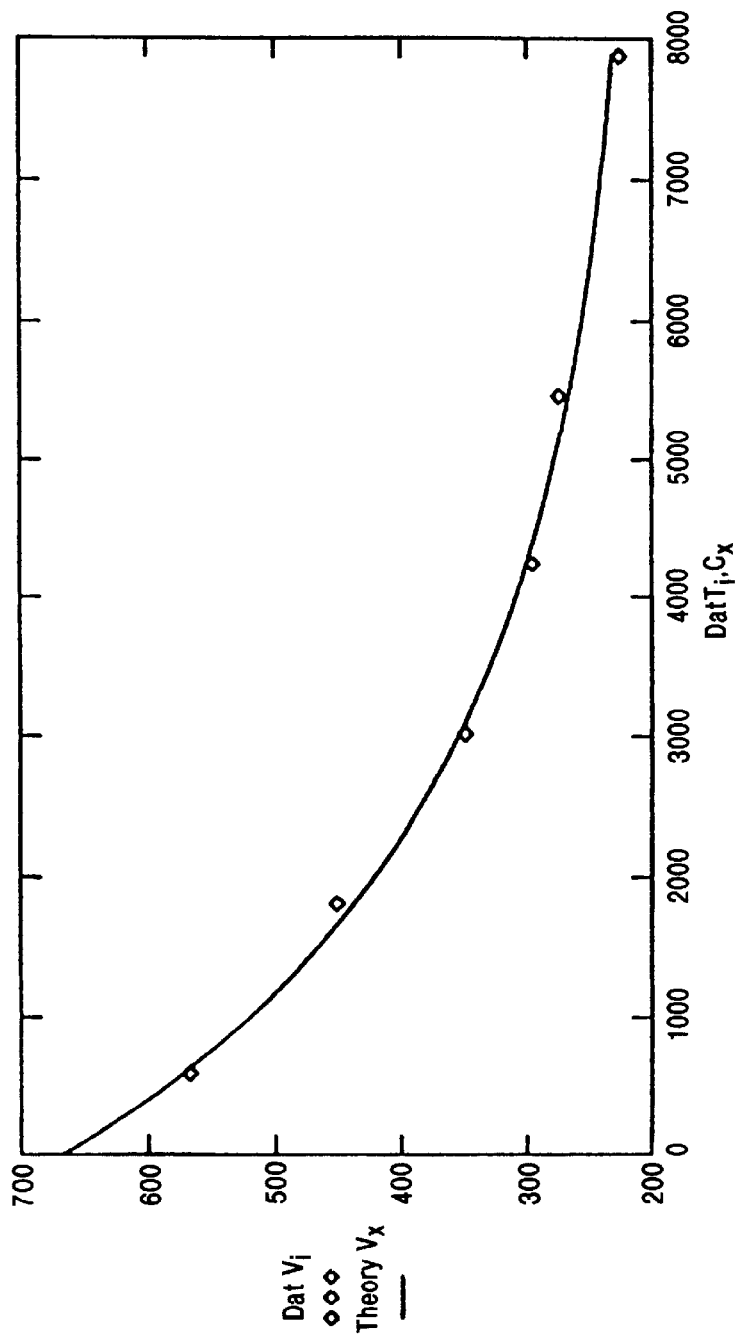
FIGS. 51 contains a graph depicting the typical kinetics of a full length anti-IL8 antibody (6G4V11N35A IgG1) binding to IL-8.
Figure 52A:
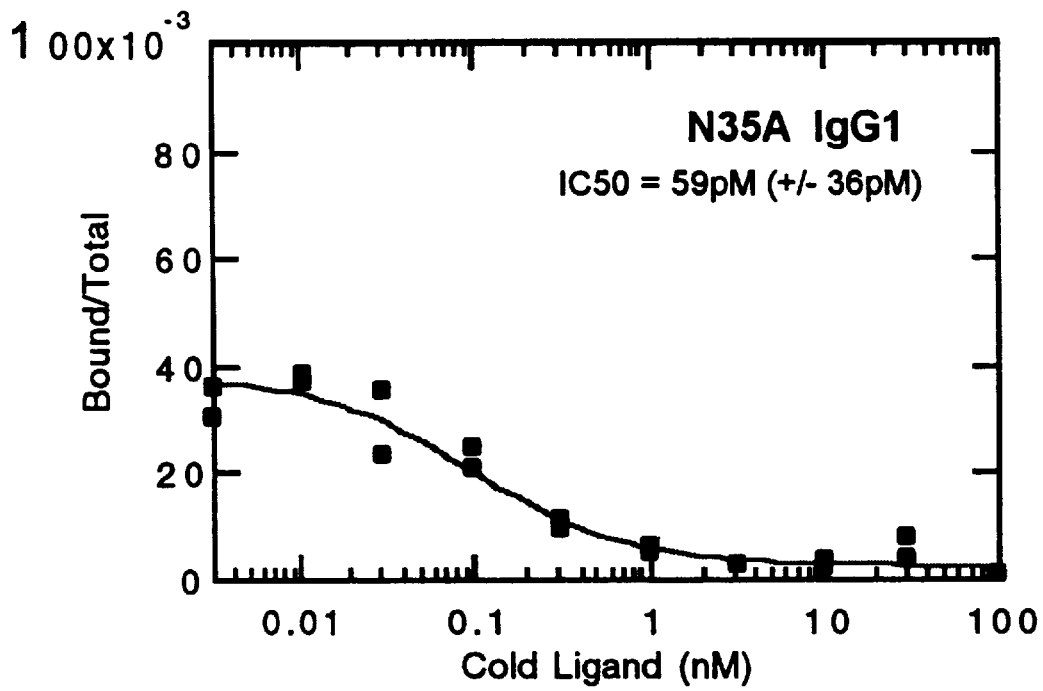
FIGS. 52A and 52B are graphs of displacement curves depicting the results of an unlabeled IL-8/$^{125}$I-IL-8 competition radioimmunoassay performed with full length 6G4V11N35A IgG1 and 6G4V11N35E IgG1, respectively.
Figure 52B:
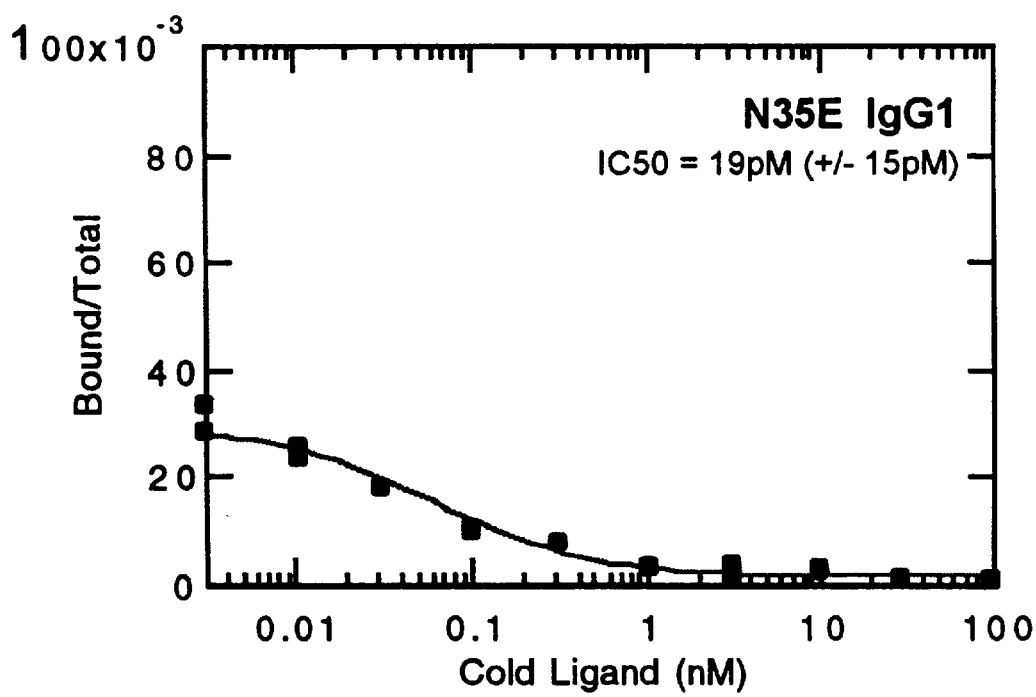

The affinity for IL-8 of these variants relative to the murine 6G4.2.5 mAb was determined using KinExA as described in Section (M). FIG. 51 shows the equilibrium constant (Kd) for the full length affinity matured variants 6G4V11N35E IgG1 and 6G4V11N35A IgG1 were approximately 49 pM and 88 pM, respectively. The Kd for 6G4V11N35A IgG1 was determined directly from the kinetic experiment. As reported with their respective Fabs, this improvement in affinity might be attributed to an approximate 2-fold increase in the on-rate of 6G4V11N35E IgG1 (ka=3.0×10$^6$) compared to that 6G4V11N35A IgG1 (ka=8.7×10$^5$). In addition, these results were confirmed by a competition radio-immune assay using iodinated human IL-8. 50 pM of 6G4V11N35A IgG1 or 6G4V11N35E IgG1 was incubated for 2 hours at 25° C. with 30–50 pM of $^{125}$I-IL-8 and varying concentrations (0 to 100 nM) of unlabeled IL-8. The antibody-antigen mixture was then incubated for 1 hour at 4C with 10 ul of a 70% slurry of Protein-A beads (pre-blocked with 0.1% BSA). The beads were briefly spun in a microcentrifuge and the supernatant discarded to remove the unbound $^{125}$I-IL-8. The amount of $^{125}$I-IL-8 specifically bound to the anti-IL-8 antibodies was determined by counting the protein-A pellets in a gamma counter. The approximate Kd values were similar to those determined by KinEXA. The average Kd for 6G4V11N35A IgG1 and 6G4V11N35E IgG1 were 54 pM (18–90 pM) and 19 pM (5–34 pM), respectively (FIG. 52).

T. Construction of Humanized 6G4V11N35A/E Fab's for Modification by Polyethylene Glycol A Fab' expression vector for 6G4V11N35A was constructed by digesting p6G4V11N35A.F(ab')$_2$ with the restriction enzymes ApaI and NdeI to remove the 2805 bp fragment encoding the human IgG$_1$ constant domain fused with the yeast GCN4 leucine zipper and replacing it with the 2683 bp ApaI-NdeI fragment from the plasmid pcDNA.18 described in Eigenbrot et al., *Proteins: Struct. Funct. Genet.*, 18: 49–62 (1994). The pcDNA.18 ApaI-NdeI fragment carries the coding sequence for the human constant IgG1 heavy domain, including the free cysteine in the hinge region that was used to attach the PEG molecule. The 3758 bp ApaI-NdeI fragment (encodes the light chain and heavy variable domain of 6G4V11N35A) isolated from p6G4V11N35A.F(ab')$_2$ was ligate to the 2683 bp ApaI-NdeI fragment of pcDNA.18 to create p6G4V11N35A.PEG-1. The integrity of the entire coding sequence was confirmed by DNA sequencing. The nucleotide and translated amino acid sequences of heavy chain constant domain with the cysteine in the hinge are presented in FIG. 53.

A Fab' expression plasmid for 6G4V11N35E was made similarly by digesting pPH6G4V11N35E (from Section (O) above) with the restriction enzymes ApaI and NdeI to isolate the 3758 bp ApaI-NdeI DNA fragment carrying the intact light chain and heavy variable domain of 6G4V11N35E and ligating it to the 2683 bp ApaI-NdeI DNA fragment from p6G4V11N35A.PEG-1 to create p6G4V11N35E.PEG-3. The integrity of the entire coding sequence was confirmed by DNA sequencing.

Anti-IL-8 6G4V11N35A Fab' variant was modified with 20 kD linear methoxy-PEG-maleimide, 30 kD linear methoxy-PEG-maleimide, 40 kD linear methoxy-PEG-maleimide, or 40 kD branched methoxy-PEG-maleimide as described below. All PEG's used were obtained commercially from Shearwater Polymers, Inc.

a. Materials and Methods

Fab'-SH Purification

A Fab'-SH antibody fragment of the affinity matured antibody 6G4V11N35A was expressed in *E. coli* grown to high cell density in the fermentor as described by Carter et al., *Bio/Technology* 10, 163–167 (1992). Preparation of Fab'-SH fragments was accomplished by protecting the Fab'-SH fragments with 4',4'-dithiodipyridine (PDS), partially purifying the protected Fab'-PDS fragments, deprotect the Fab'-PDS with dithiothreitol (DTT) and finally isolate the free Fab'-SH by using gel permeation chromatography.

Protection of Fab'-SH with PDS

Fermentation paste samples were dissolved in 3 volumes of 20 mM MES, 5 mM EDTA, pH 6.0 containing 10.7 mg of 4',4'-dithiodipyridine per gram fermentation paste, resulting in a suspension with a pH close to 6.0 The suspension was passed through a homogenizer followed by addition of 5% PEI (w/v), pH 6 to the homogenate to a final concentration of 0.25%. The mixture was then centrifuged to remove solids and the clear supernatant was conditioned to a conductivity of less than 3 mS by the addition of cold water.

Partial Purification of the Fab'-SH Molecule Using Ion Exchange Chromatography

The conditioned supernatant was loaded onto an ABX (Baker) column equilibrated in 20 mM MES, pH 6.0. The column was washed with the equilibration buffer followed by elution of the Fab'-SH with a 15 column volume linear gradient from 20 mM MES, pH 6.0 to 20 mM MES, 350 mM sodium chloride. The column was monitored by absorbance at 280 nm, and the eluate was collected in fractions.

Deprotection of the Fab'-SH Antibody Fragments with DTT

The pH of the ABX pool was adjusted to 4.0 by the addition of dilute HCl. The pH adjusted solution was then deprotected by adding DTT to a final concentration of 0.2 mM. The solution was incubated for about 30 minutes and then applied to a gel filtration Sephadex G25 column, equilibrated with 15 mM sodium phosphate, 25 mM MES, pH 4.0. After elution, the pH of the pool was raised to pH 5.5 and immediately flash frozen at −70° C. for storage or derivatized with PEG-MAL as described below.

Alternative Fab'-SH Purification

Alternatively Fab'-SH fragments can be purified using the following procedure. 100 g fermentation paste is thawed in the presence of 200 ml 50 mM acetic acid, pH 2.8, 2 mM EDTA, 1 mM PMSF. After mixing vigorously for 30 min at room temperature, the extract is incubated with 100 mg hen egg white lysozyme. DEAE fast flow resin (approximately 100 mL) is equilibrated with 10 mM MES, pH 5.5, 1 mM EDTA on a sintered glass funnel. The osmotic shock extract containing the Fab'-SH fragment is then filtered through the resin.

A protein G Sepharose column is equilibrated with 10 mM MES, pH 5.5, 1 mM EDTA and then loaded with the DEAE flow-through sample. The column is washed followed by three 4 column volume washes with 10 mM MES, pH 5.5, 1 mM EDTA. The Fab'-SH antibody fragment containing a free thiol is eluted from the column with 100 mM acetic acid, pH 2.8, 1 mM EDTA. After elution, the pH of the pool is raised to pH 5.5 and immediately flash frozen at −70° C. for storage or derivatized with PEG-MAL as described below.

Preparation of Fab'-S-PEG

The free thiol content of the Fab'-SH preparation obtained as described above was determined by reaction with 5,5'-dithiobis(2-nitrobenzoic acid) (DTNB) analysis according to the method of Creighton in *Protein Structure: A Practical Aipproach*, Creighton, T. E., ed, IRL Press (Oxford, UK: 1990), pp. 155–167. The concentration of free thiol was calculated from the increase on absorbance at 412 nm, using $e_{412}$=14,150 cm$^{-1}$ M$^{-1}$ for the thionitrobenzoate anion and a $M_r$=48,690 and $e_{280}$=1.5 for the Fab'-SH antibody. To the Fab'-SH protein G Sepharose pool, or the deprotected Fab'-SH gel permeation pool, 5 molar equivalents of PEG-MAL were added and the pH was immediately adjusted to pH 6.5 with 10% NaOH.

The Fab'-S-PEG was purified using a 2.5×20 cm cation exchange column (Poros 50-HS). The column was equilibrated with a buffer containing 20 mM MES, pH 5.5. The coupling reaction containing the PEGylated antibody fragment was diluted with deionized water to a conductivity of approximately 2.0 mS. The conditioned coupling reaction was then loaded onto the equilibrated Poros 50 HS column. Unreacted PEG-MAL was washed from the column with 2 column volumes of 20 mM MES, pH 5.5. The Fab'-S-PEG was eluted from the column using a linear gradient from 0 to 400 mM NaCl, in 20 mM MES pH 5.5, over 15 column volumes.

Alternatively a Bakerbond ABX column can be used to purify the Fab'-S-PEG molecule. The column is equilibrated with 20 mM MES, pH 6.0 (Buffer A). The coupling reaction is diluted with deionized water until the conductivity equaled that of the Buffer A (approximately 2.0 mS) and loaded onto the column. Unreacted PEG-MAL is washed from the column with 2 column volumes of 20 mM MES, pH 6.0. The Fab'-S-PEG is eluted from the column using a linear gradient from 0 to 100 mM (NH$_4$)$_2$SO$_4$, in 20 mM MES pH 6.0, over 15 column volumes.

Size Exclusion Chromatography

The hydrodynamic or effective size of each molecule was determined using a Pharmacia Superose-6 HR 10/30 column (10×300 mm). The mobile phase was 200 mM NaCl, 50 mM sodium phosphate pH 6.0. Flow rate was at 0.5 ml/min and the column was kept at ambient temperature. Absorbance at 280 nm was monitored where PEG contributed little signal. Biorad MW standards containing cyanocobalamin, myoglobin, ovalbumin, IgG, Thyroglobulin monomer and dimer were used to generate a standard curve from which the effective size of the pegylated species was estimated.

b. RESULTS

Size Exclusion Chromatography

Figure 60:
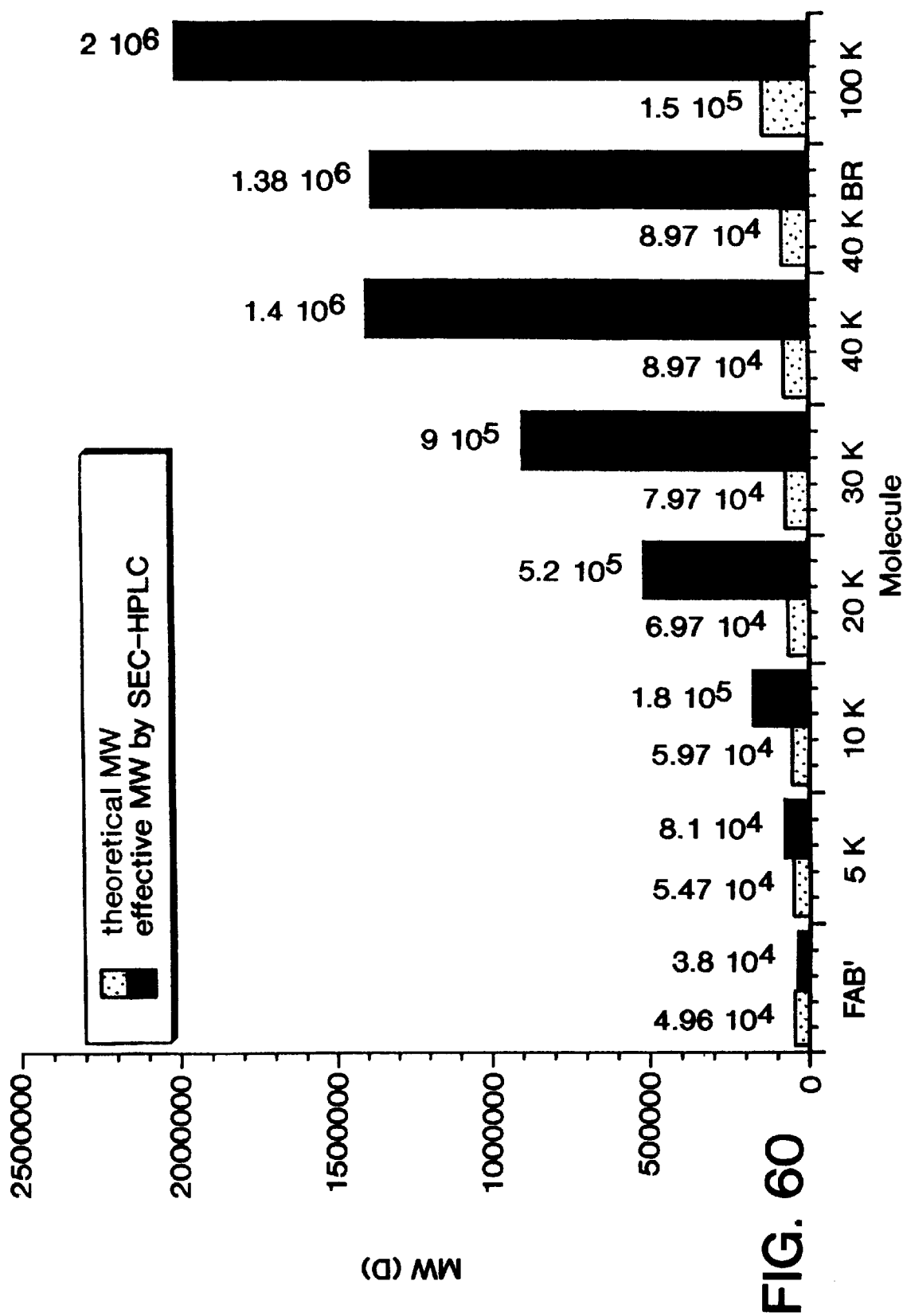
FIG. 60 is a graph depicting the theoretical molecular weight (dotted bars) and effective size (solid bars) of PEG-maleimide modified 6G4V11N35A Fab' molecules as determined by SEC-HPLC.

The effective size of each modified species was characterized using size exclusion chromatography. The results are shown in FIG. 60 below. The theoretical molecular weight of the anti-IL8 Fab fragments modified with PEG 5 kD, 10 kD, 20 kD, 30 kD, 40 kD (linear), 40 kD (branched) or 100000 kD is shown along with the apparent molecular weight of the PEGylated fragments obtained by HPLC size exclusion chromatography. When compared to the theoretical molecular weight of the Fab'-S-PEG fragments, the apparent molecular weight (calculated by size exclusion HPLC) increases dramatically by increasing the size of the PEG attached to the fragments. Attachment of a small molecular weight PEG, for example PEG 10,000 D only increases the theoretical molecular weight of the PEGylated antibody fragment (59,700 D) by 3 fold to an apparent molecular weight of 180,000 D. In contrast attachment of a larger molecular weight PEG for example 100,000 D PEG to the antibody fragment increases the theoretical molecular weight of the PEGylated antibody fragment (158,700 D) by 12 fold to an apparent molecular weight of 2,000,000 D.

SDS-PAGE

Figure 61A:
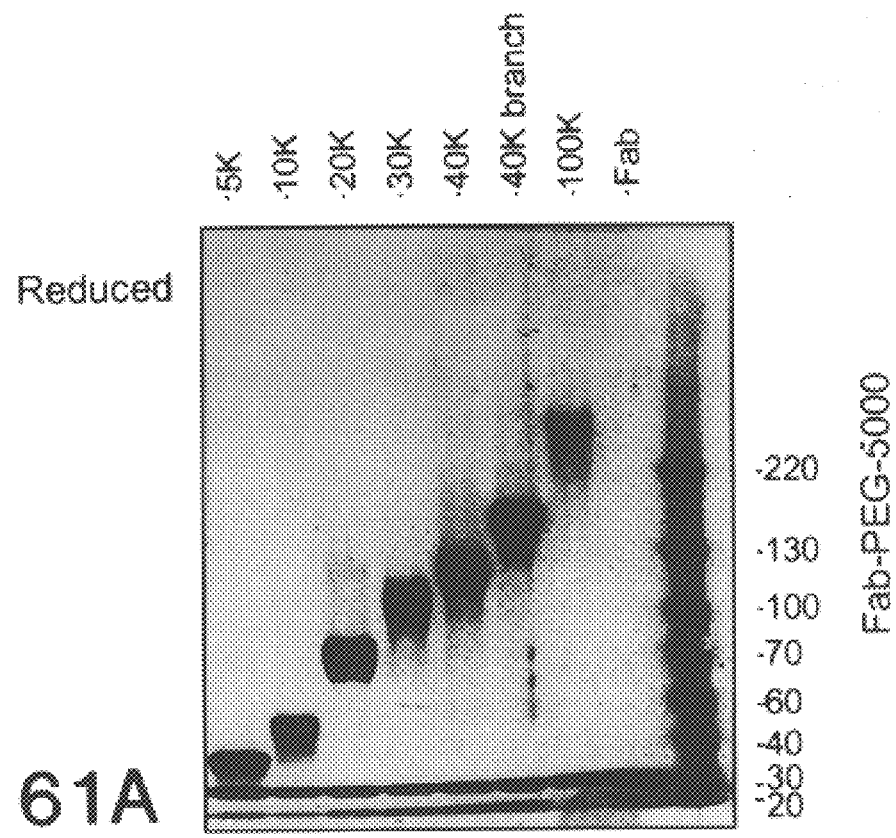
FIGS. 61A and 61B are SDS-PAGE gels depicting the electrophoretic mobility of various PEG-maleimide modified 6G4V11N35A Fab' molecules under reducing and non-reducing conditions, respectively.
Figure 61B:
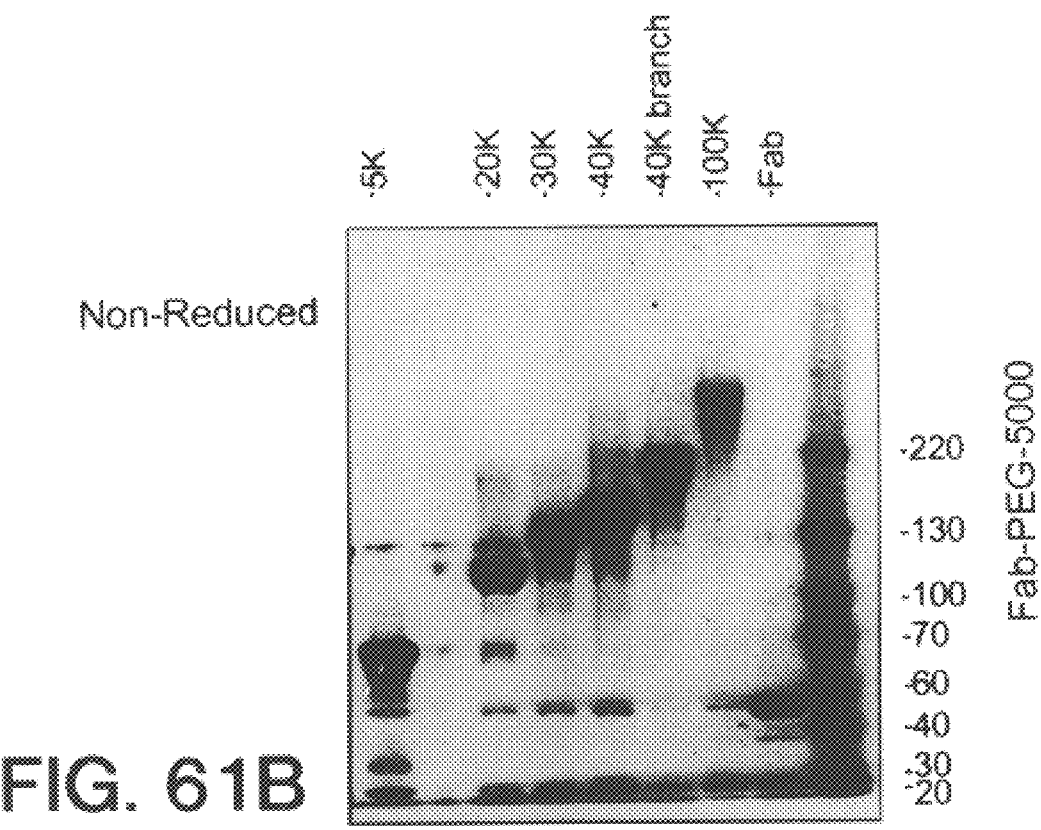

In FIG. 61, the upper panel shows the size of the anti-IL-8 Fab fragments modified with PEG of molecular weight 5 kD (linear), 10 kD (linear), 20 kD (linear), 30 kD (linear), 40 kD (linear), 40 kD (branched) or 100 kD (linear) under reduced conditions. The unmodified Fab is shown in lane 2 from right to left. Both the heavy and light chains of the Fab had a molecular weight of approximately 30 kD as determined by PAGE. Each PEGylated fragment sample produced two bands: (1) a first band (attributed to the light chain) exhibiting a molecular weight of 30 kD; and (2) a second band (attributed to the heavy chain to which the PEG is attached specifically at the hinge SH) exhibiting increasing molecular weights of 40, 45, 70, 110, 125, 150 and 300 kD. This result suggested that PEGylation was specifically restricted to the heavy chain of the Fab's whereas the light chain remained unmodified.

The lower panel is non-reduced PAGE showing the size of the anti-IL-8 Fab fragments modified with PEG of molecular weight 5 kD (linear), 20 kD (linear), 30 kD (linear), 40 kD (linear), 40 kD (branched), or 100 kD (linear). The PEGylated fragments exhibited molecular weights of approximately 70 kD, 115 kD, 120 kD, 140 kD, 200 kD and 300 kD.

The SDS PAGE gels confirm that all Fab'-S-PEG molecules were purified to homogeneity and that the molecules differed only with respect to the size of the PEG molecule attached to them.

U. Amine Specific Pegylation of Anti-IL-8 F(ab')$_2$ Fragments

Pegylated F(ab')$_2$ species were generated by using large MW or branched PEGs in order to achieve a large effective size with minimal protein modification which might affect activity. Modification involved N-hydroxysuccinamide chemistry which reacts with primary amines (lysines and the N-terminus). To decrease the probability of modifying the N-terminus, which is in close proximity to the CDR region, a reaction pH of 8, rather than the commonly used pH of 7, was employed. At pH 8.0, the amount of the reactive species (charged $NH_3^+$) would be considerably more for the $\epsilon$-NH2 group of lysines ($pK_a$=10.3) than for the $\alpha$-NH2 group ($pK_a$ of approximately 7) of the amino-terminus. For the linear PEGs, a methoxy-succinimidyl derivative of an NHS-PEG was used because of the significantly longer half-life in solution (17 minutes at 25° C. at pH 8.0) compared to the NHS esters of PEGs (which have 5–7 minute half life under the above conditions). By using a PEG that is less prone to hydrolysis, a greater extent of modification is achieved with less PEG. Branched PEGs were used to induce a large increase in effective size of the antibody fragments.

a. Materials

All PEG reagents were purchased from Shearwater Polymers and stored at −70° C. in a desiccator: branched N-hydroxysuccinamide-PEG (PEG2-NHS-40 KDa) has a 20 kDa PEG on each of the two branches, methoxy-succinimidyl-propionic acid-PEG (M-SPA-20000) is a linear PEG molecule with 20 kDa PEG. Protein was recombinantly produced in *E. coli* and purified as a (Fab)'$_2$ as described in Sections (K) and (O) above.

b. Methods

IEX method: A J. T. Baker Wide-Pore Carboxy-sulfone (CSX), 5 micron, 7.75×100 mm HPLC column was used for fractionation of the different pegylated products, taking advantage of the difference in charge as the lysines are modified. The column was heated at 40° C. A gradient as shown in Table 7 below was used where Buffer A was 25 mM sodium Borate/25 mM sodium phosphate pH 6.0, and Buffer B was 1 M ammonium sulfate, and Buffer C was 50 mM sodium acetate pH 5.0.

TABLE 7

| Time (min) | % B | % C | flow mL/min |
| --- | --- | --- | --- |
| 0 | 10 | 10 | 1.5 |
| 20 | 18 | 7.5 | 1.5 |
| 25 | 25 | 7.5 | 1.5 |
| 27 | 70 | 3.0 | 2.5 |
| 29 | 70 | 3.0 | 2.5 |
| 30 | 10 | 10 | 2.5 |
| 33 | 10 | 10 | 2.5 |

SEC-HPLC: The hydrodynamic or effective size of each molecule was determined using a Pharmacia Superose-6 HR 10/30 column (10×300 mm). The mobile phase was 200 mM NaCl, 50 mM sodium phosphate pH 6.0. Flow rate was at 0.5 ml/min and the column was kept at ambient temperature. Absorbance at 280 nm was monitored where PEG contributed little signal. Biorad MW standards containing cyanocobalamin, myoglobin, ovalbumin, IgG, Thyroglobulin monomer and dimer were used to generate a standard curve from which the effective size of the pegylated species was estimated.

SEC-HPLC-Light Scattering: For determination of the exact molecular weight, this column was connected to an on-line light scattering detector (Wyatt Minidawn) equipped with three detection angles of 50°, 90°, and 135° C. A refractive index detector (Wyatt) was also placed on-line to determine concentration. All buffers were filtered with Millipore 0.1 µ filters; in addition al 0.02 µ Whatman Anodisc 47 was placed on-line prior to the column.

The intensity of scattered light is directly proportional to the molecular weight (M) of the scattering species, independent of shape, according to:

$$M = R_0/K.c$$

where $R_0$ is the Rayleigh ratio, K is an optical constant relating to the refractive index of the solvent, the wavelength of the incident light, and dn/dc, the differential refractive index between the solvent and the solute with respect to the change in solute concentration, c. The system was calibrated with toluene ($R_0$ of $1.406 \times 10^{-5}$ at 632.8 nm); a dn/dc of 0.18, and an extinction coefficient of 1.2 was used. The system had a mass accuracy of ~5%.

SDS-PAGE: 4–12% Tris-Glycine Novex minigels were used along with the Novex supplied Tris-Glycine running buffers. 10–20 ug of protein was applied in each well and the gels were run in a cold box at 150 mV/gel for 45 minutes. Gels were then stained with colloidal Coomassie Blue (Novex) and then washed with water for a few hours and then preserved and dried in drying buffer (Novex).

Preparation of a linear(1)20 KDa-(N)-(Fab')2: A 4 mg/ml solution of anti-IL8 formulated initially in a pH 5.5 buffer was dialyzed overnight against a pH 8.0 sodium phosphate buffer. 5 mL protein was mixed at a molar ratio of 3:1. The reaction was carried out in a 15 mL polypropylene Falcon tube and the PEG was added while vortexing the sample at low speed for 5 seconds. It was then placed on a nutator for 30 minutes. The extent of modification was evaluated by SDS-PAGE. The whole 5 ml reaction mixture was injected on the IEX for removal of any unreacted PEG and purification of singly or doubly pegylated species. The above reaction generated a mixture of 50% singly-labeled anti-IL8. The other 50% unreacted anti-IL8 was recycled through the pegylation/purification steps. The pooled pegylated product was dialyzed against a pH 5.5 buffer for in vitro assays and animal PK studies. Endotoxin levels were measured before administration to animals or for the cell based assays. Levels were below 0.5 eu/ml. The fractions were also run on SDS-PAGE to confirm homogeneity. Concentration of the final product was assessed by absorbance at 280 nm using an extinction coefficient of 1.34, as well as by amino acid analysis.

Preparation of a branched(1)40KDa-(N)-(Fab')2: A 4 mg/mL solution of anti-IL8 (Fab')$_2$ formulated in a pH 5.5 buffer was dialyzed overnight against a pH 8.0 phosphate buffer. Solid PEG powder was added to 5 mL protein in two aliquots to give a final PEG:protein molar ratio of 6:1. Each solid PEG aliquot was added to the protein in a 15 mL polypropylene Falcon tube while vortexing at low speed for 5 sec, and then placing the sample on a nutator for 15 minutes. The extent of modification was evaluated by SDS-PAGE using a 4–12% Tris-Glycine (Novex) gel and stained with colloidal Coomasie blue (Novex). The 5 mL PEG-protein mixture was injected on the ion exchange column for removal of any unreacted PEG. The above reaction generated a mixture of unreacted (37%), singly-labelled (45%), doubly and triply-labeled (18%) species. These were the optimal conditions for obtaining the greatest recovery of the protein with only 1 PEG per antibody rather than the higher molecular weight adducts. The unmodified anti-IL8 was recycled. The pegylated products were separated and fractionated in falcon tubes and then dialyzed against a pH 5.5 buffer for assays and animal PK studies. Endotoxin levels were below 0.5 eu/ml. The fractions were also run on SDS-PAGE to confirm homogeneity. The concentration of the final product was assessed by absorbance at 280 nm using an extinction coefficient of 1.34, as well as by amino acid analysis.

Preparation of branched(2)-40 KDa-(N)(Fab')2: This molecule was most efficiently made by adding three times in 15 minute intervals a 3:1 molar ratio of PEG to the already modified branched(1)-40 KDa-(N)-(Fab')2. The molecule was purified on IEX as 50% branched(2)-40 KDa-(N)-(Fab') 2. The unmodified molecule was recycled until ~20 mg protein was isolated for animal PK studies. The product was characterized by SEC-light scattering and SDS-PAGE.

c. Results

Figure 62:
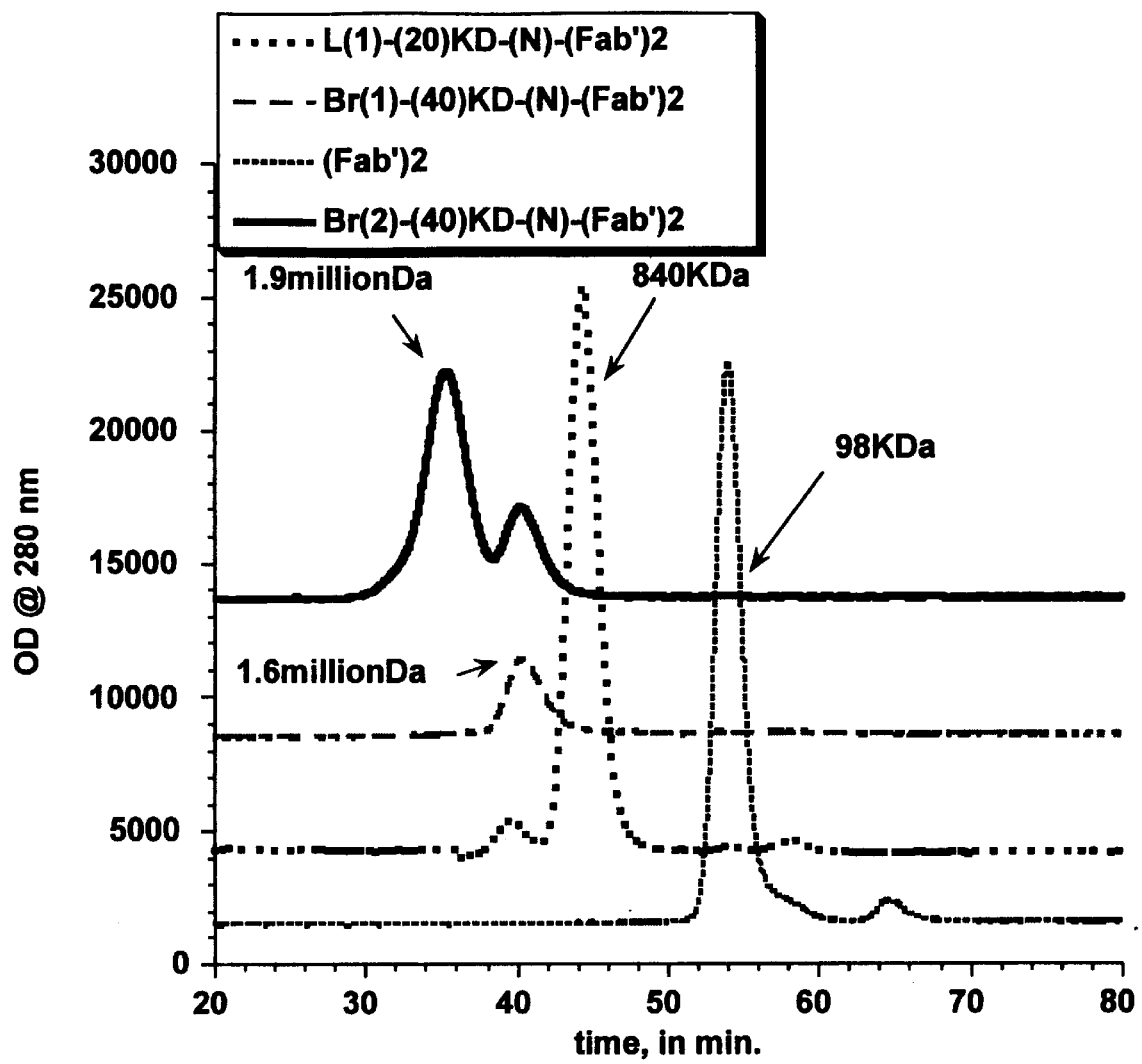
FIG. 62 contains size exclusion chromatograms (SEC-HPLC) depicting the retention times and effective (hydrodynamic) sizes of various PEG-succinimide modified 6G4V11N35A F(ab')$_2$ molecules.

PEGs increased the hydrodynamic or effective size of the product significantly as determined by gel filtration (SEC-HPLC). FIG. 62 shows the SEC profile of the pegylated F(ab')$_2$ species with UV detection at 280 nm. The hydrodynamic size of each molecule was estimated by reference to the standard MW calibrators. As summarized in FIG. 62, the increase in the effective size of (Fab')$_2$ was about 7-fold by adding one linear 20 kDa PEG molecule and about 11-fold by adding one branched ("Br(1)") 40 kDa PEG molecule, and somewhat more with addition of two branched ("Br(2)") PEG molecules.

Figure 63:
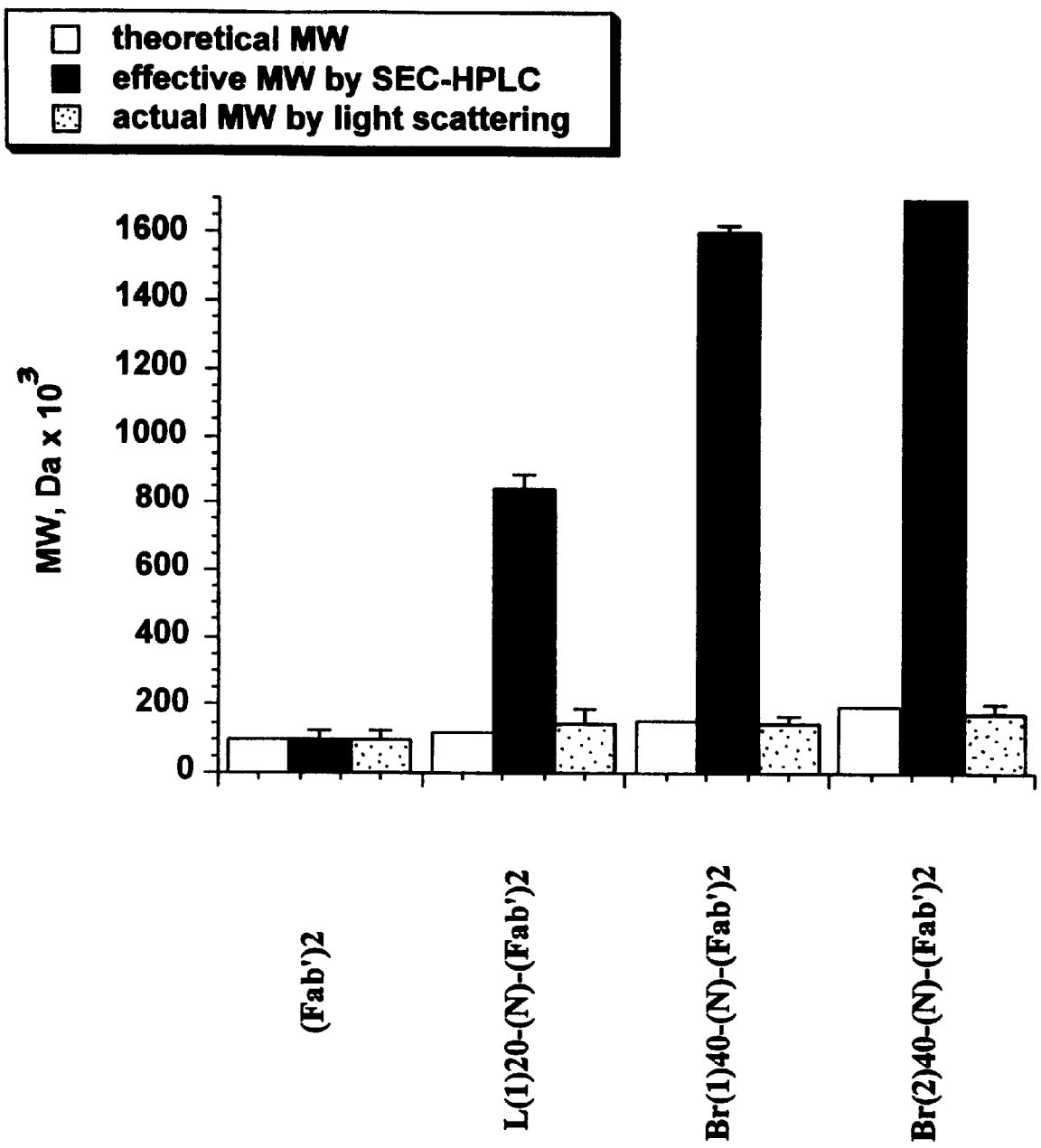
FIG. 63 is a graph depicting the theoretical molecular weight (open columns), effective size determined by SEC-HPLC (solid columns), and the actual molecular weight determined by SEC-light scattering (shaded columns) for various PEG-succinimide modified 6G4V11N35A F(ab')$_2$ molecules.
Figure 64:
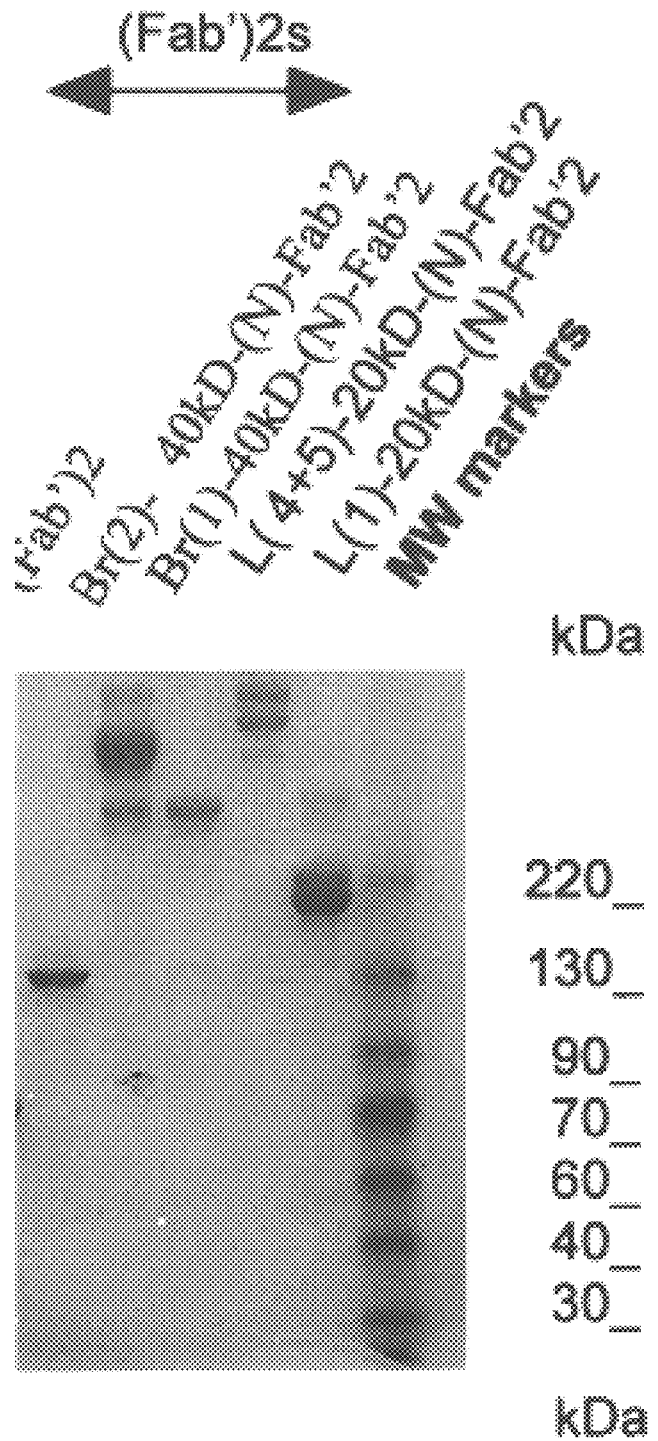
FIG. 64 is an SDS-PAGE gel depicting the electrophoretic mobility of various PEG-succinimide modified 6G4V11N35A F(ab')$_2$ molecules. From left to right, lane 1 contains unmodified F(ab')$_2$, lane 2 contains F(ab')$_2$ coupled to two 40 kD branched PEG-succinimide molecules (denoted "Br(2)-40 kD(N)-F(ab')2"), lane 3 contains F(ab')$_2$ coupled to one 40 kD branched PEG-succinimide molecule (denoted "Br(1)-40 kD-(N)-Fab'2"), lane 4 contains a mixture of F(ab')$_2$ coupled to four 20 kD linear PEG-succinimide molecules and F(ab')$_2$ coupled to five 20 kD linear PEG-succinimide molecules (denoted "L(4+5)-20 kD-(N)-Fab'2"), lane 5 contains F(ab')$_2$ coupled to one 20 kD linear PEG-succinimide molecule (denoted "L(1)-20 kD-(N)-Fab'2"), and lane 6 contains molecular weight standards.

Light scattering detection gave the exact molecular weight of the products and confirmed the extent of modification (FIG. 63). The homogeneity of the purified material was shown by SDS-PAGE (FIG. 64). Underivatized F(ab')$_2$ migrated as a 120 kDa species, the linear(1)20 KD-(N)-F(ab')$_2$ migrated as a band at 220 kDa, the Br(1)-40 KD(N)-F(ab')$_2$ migrated as one major band at 400 kDa, and the Br(2)-40 KD-(N)-F(ab')$_2$ migrated as a major band at around 500 kDa. The proteins appeared somewhat larger than their absolute MW due to the steric effect of PEG.

V. In Vitro Activity Characterization of Peg Modified Fab' Fragments of 6G4V11N35A (Maleimide Chemical Coupling Method)

Figure 54A:
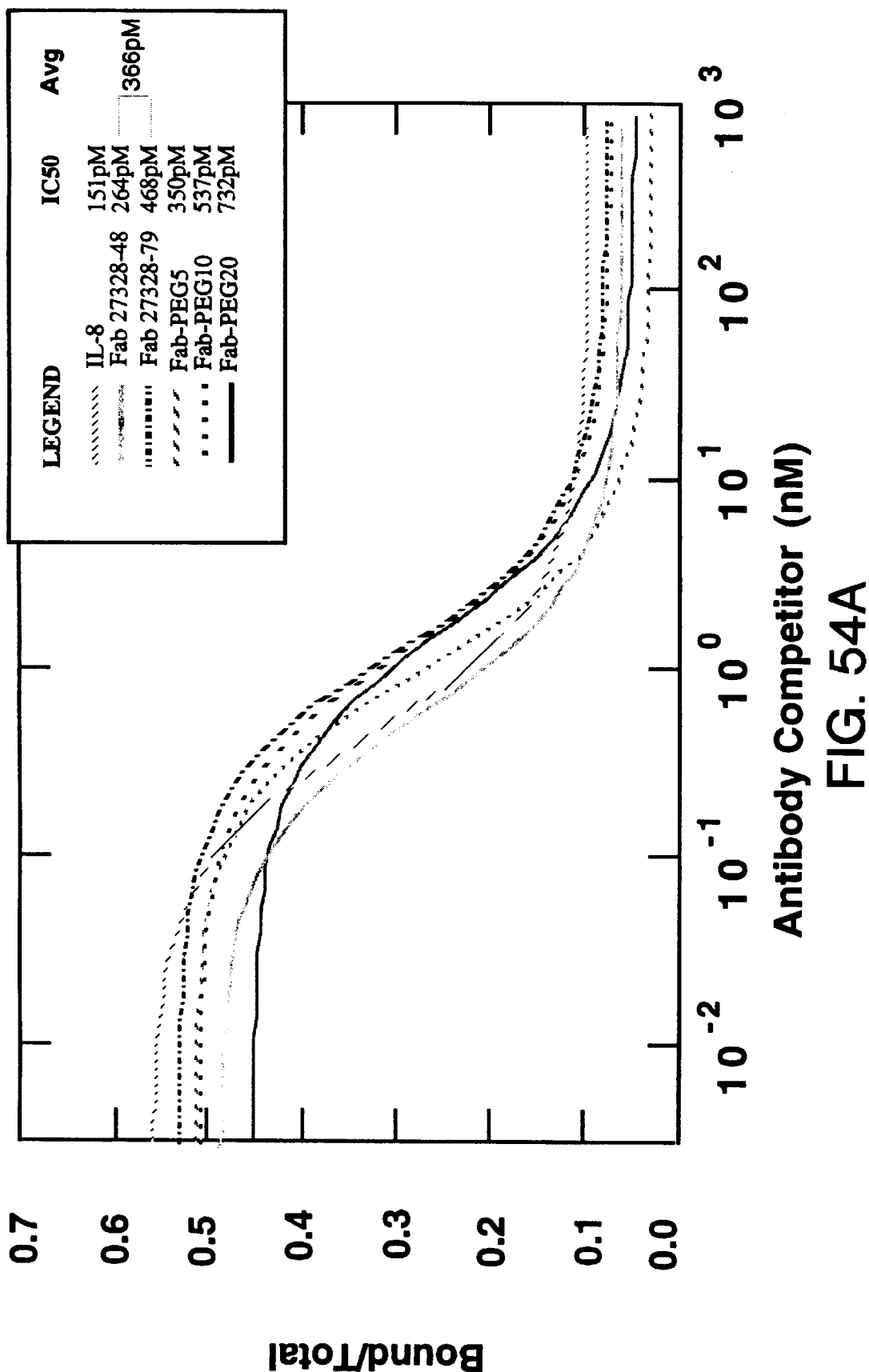
FIGS. 54A–54C contain graphs of displacement curves depicting the IL-8 binding and IC$_{50}$'s for PEG-maleimide modified 6G4V11N35A Fab' molecules.
Figure 54B:
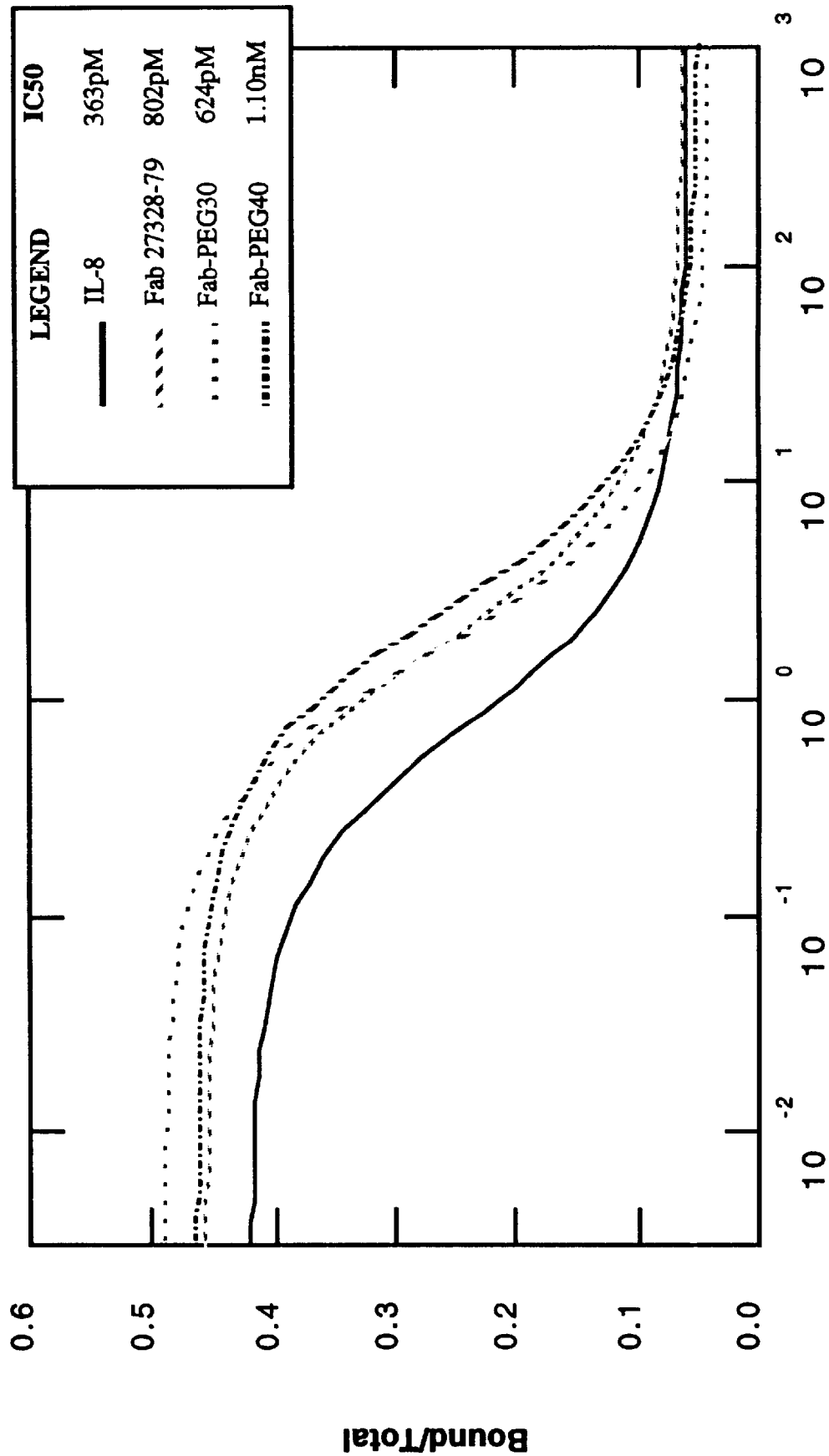
Figure 54C:
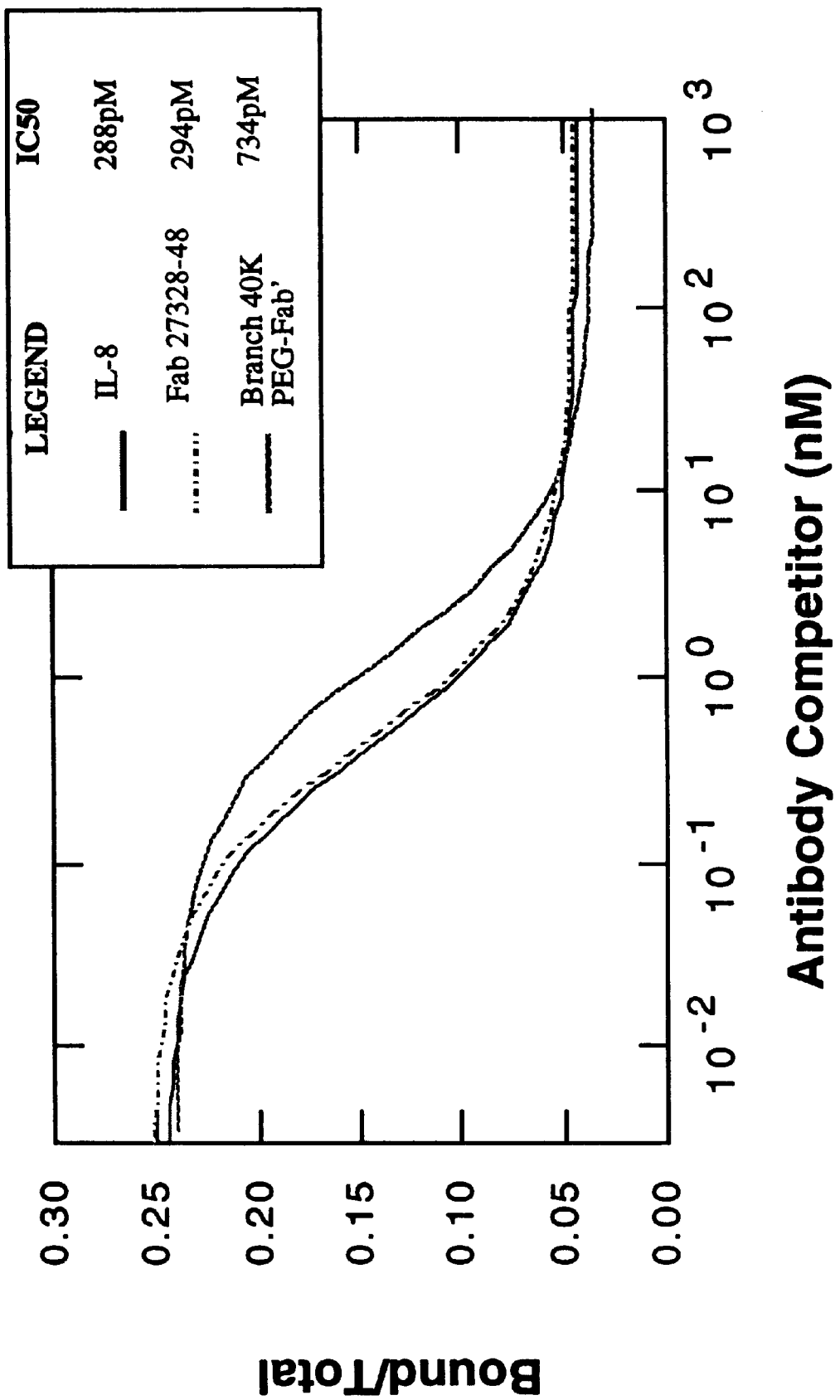

Anti-IL-8 6G4V11N35A Fab' variants modified with 5–40 kD linear PEG molecules and a 40 kD branched PEG molecule were tested for their ability to inhibit both IL-8 binding and activation of human neutrophils; the procedures were described in Sections (B)(1), (B)(2) and (B)(3) above. The binding curves and $IC_{50}$'s for PEG-maleimide modified 6G4V11N35A Fab' molecules are presented in FIGS. 54A–54C. The $IC_{50}$ of the 5 kD pegylated Fab' (350 pM) and the average $IC_{50}$ of the Fab control (366 pM) were not significantly different, suggesting that the addition of a 5 kD MW PEG did not affect the binding of IL-8 to the modified Fab' (FIG. 54A). However, a decrease in the binding of IL-8 to the 10 kD and 20 kD pegylated Fab' molecules was observed as depicted by the progressively higher $IC_{50}$'s (537 pM and 732 pM, respectively) compared to the average $IC_{50}$ of the native Fab. These values represent only a minimal loss of binding activity (between 1.5- and 2.0-fold). A less pronounced difference in IL-8 binding was observed for the 30 kD and 40 kD linear PEG antibodies (FIG. 54B). The $IC_{50}$'s were 624 pM and 1.1 nM, respectively, compared to the 802 pM value of the Fab control. The 40 kD branched PEG Fab' showed the largest decrease in IL-8 binding (2.5 fold) relative to the native Fab (FIG. 54C). Nevertheless, the reduction in binding of IL-8 by these pegylated Fab's is minimal.

Figure 55A:
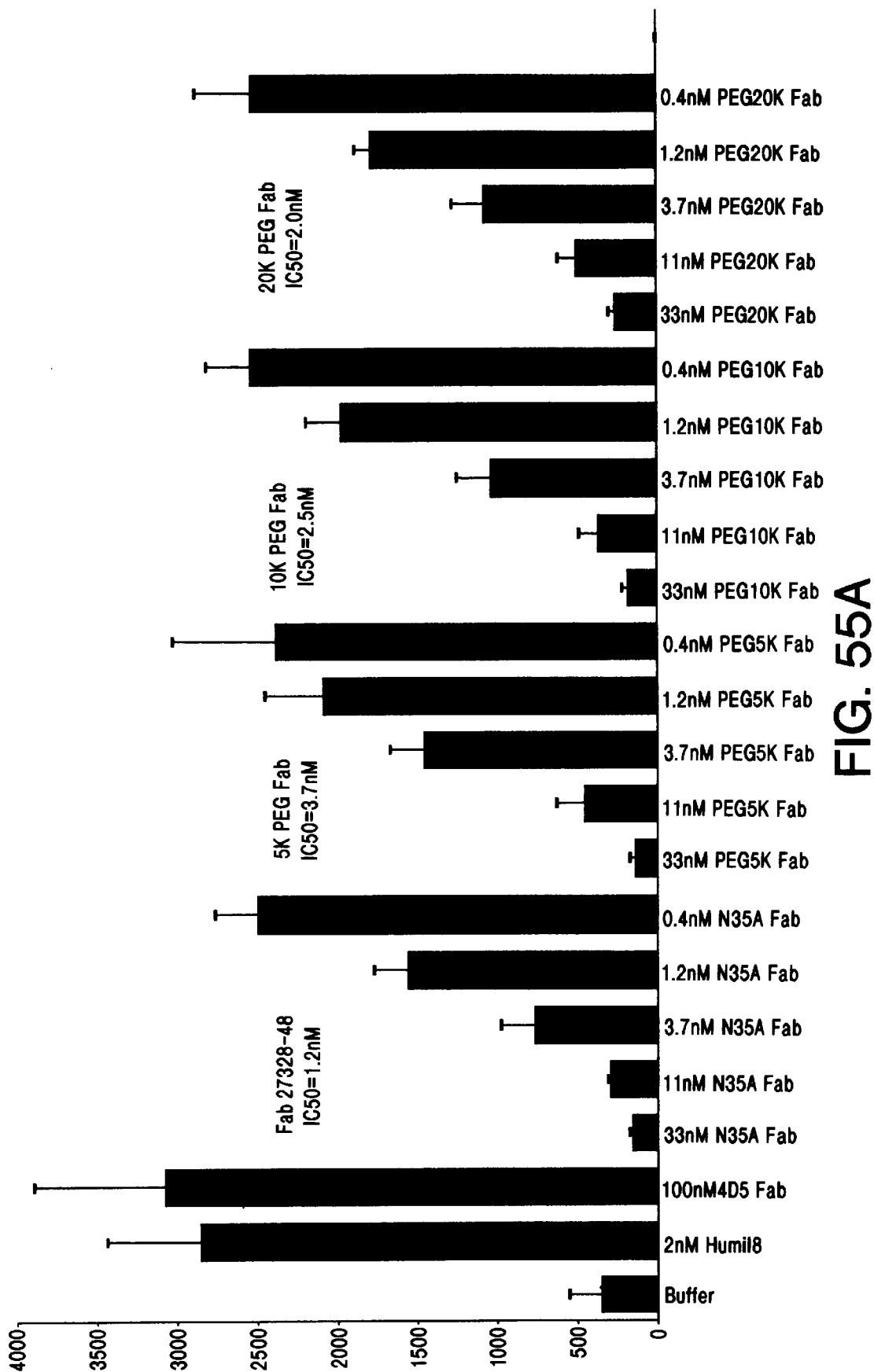
Figure 55C:
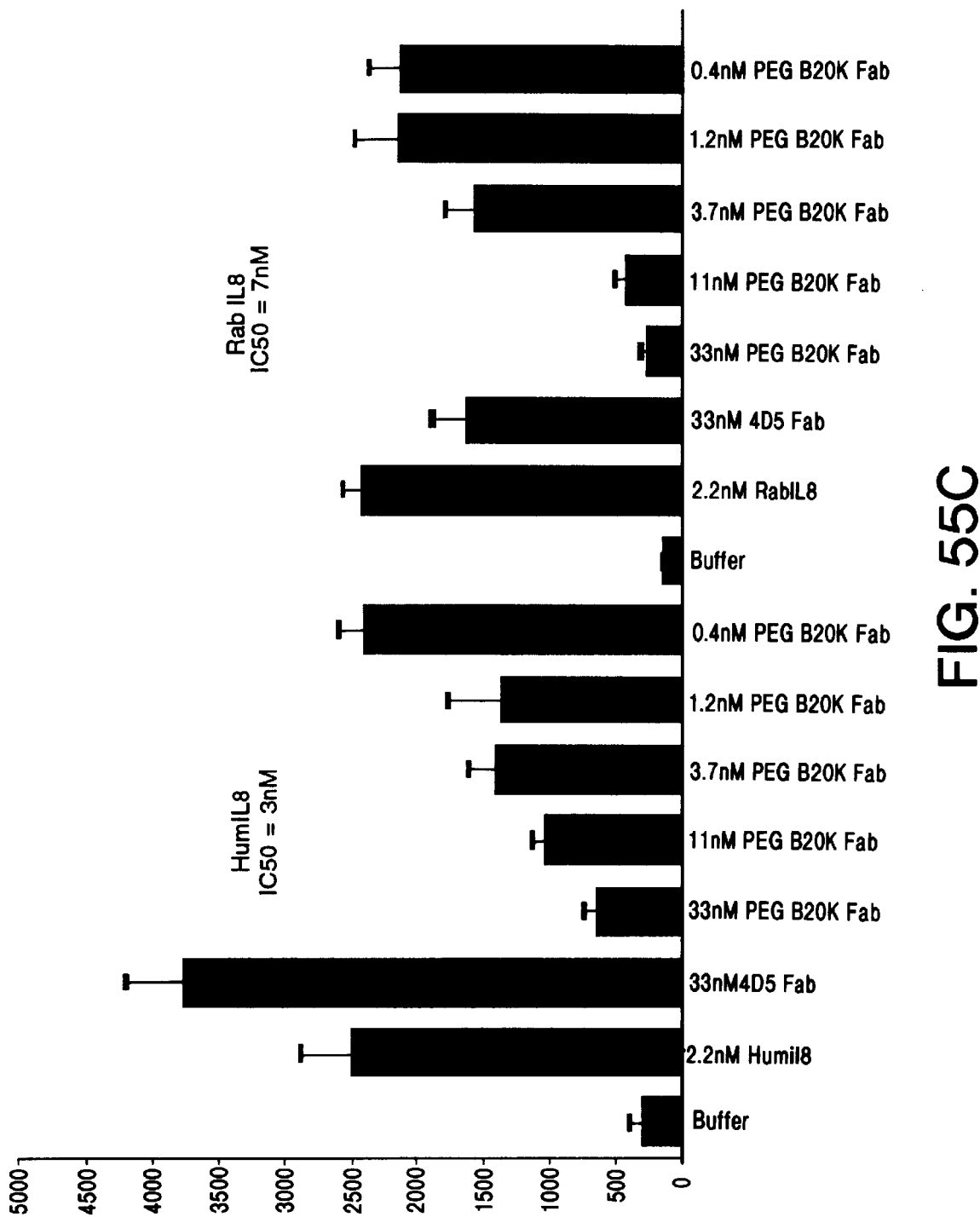
Figure 56A:
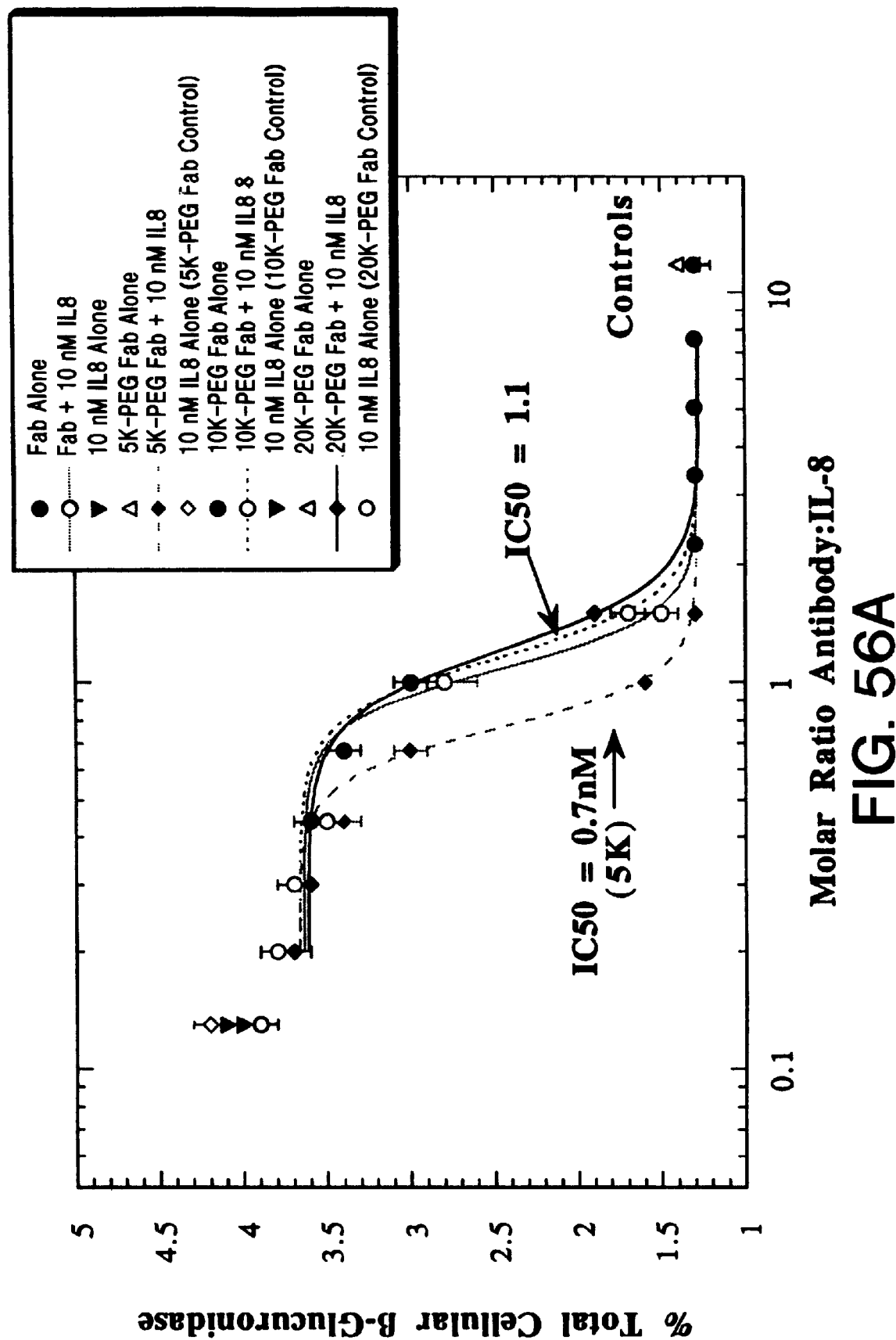
Figure 56C:
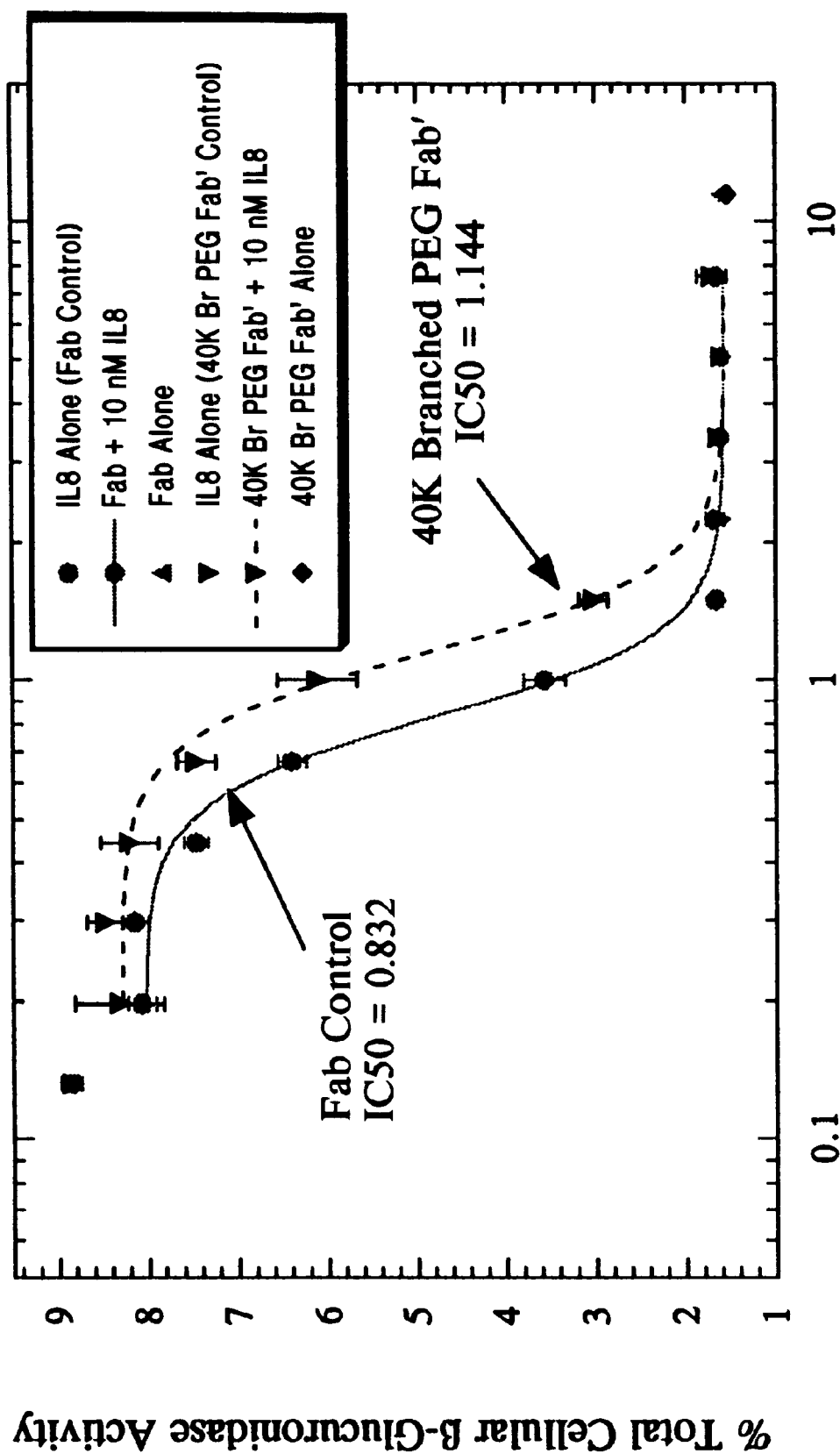

The ability of the pegylated antibodies to block IL-8 mediated activation of human neutrophils was demonstrated using the PMN chemotaxis (according to the method described in Section B(2) above) and β-glucuronidase release (according to the method described in Lowman et al., *J. Biol. Chem.*, 271: 14344 (1996)) assays. The $IC_{50}$'s for blocking IL-8 mediated chemotaxis are shown in FIGS. 55A–55C. The 5–20 kD linear pegylated Fab' antibodies were able to block IL-8 mediated chemotaxis within 2–3 fold of the unpegylated Fab control (FIG. 55A). This difference is not significant because the inherent variation can be up to 2 fold for this type of assay. However, a significant difference was detected for the 30 kD and 40 kD linear pegylated Fab' antibodies as illustrated by the higher $IC_{50}$'s of the 30 kD linear PEG-Fab' (2.5 nM) and 40 kD linear PEG-Fab' (3.7 nM) compared to the Fab control (0.8 nM) (FIG. 55B). The ability of the 40 kD branched PEG Fab' molecule to block IL-8 mediated chemotaxis was similar to that of the 40 kD linear PEG Fab' (FIG. 55C). At most, the ability of the pegylated Fab' antibodies to block IL-8 mediated chemotaxis was only reduced 2–3 fold. Furthermore, release of β-glucuronidase from the granules of neutrophils was used as another criteria for assessing IL-8 mediated activation of human PMNs. FIG. 56A (depicting results obtained with 5 kD, 10 kD and 20 kD linear PEGs), FIG. 56B (depicting results obtained with 30 kD and 40 kD linear PEGs), and FIG. 56C (depicting results obtained with 40 kD branched PEG) show that all the pegylated Fab' antibodies were able to inhibit IL-8 mediated release of β-glucuronidase as well as or better than the unpegylated Fab control. The data collectively shows that the pegylated Fab' variants are biological active and are capable of inhibiting high amounts of exogenous IL-8 in in-vitro assays using human neutrophils.

W. In Vitro Activity Characterization of Peg Modified F(ab')$_2$ Fragments OF 6G4V11N35A (Succinimidyl Chemical Coupling Method)

Figure 57A:
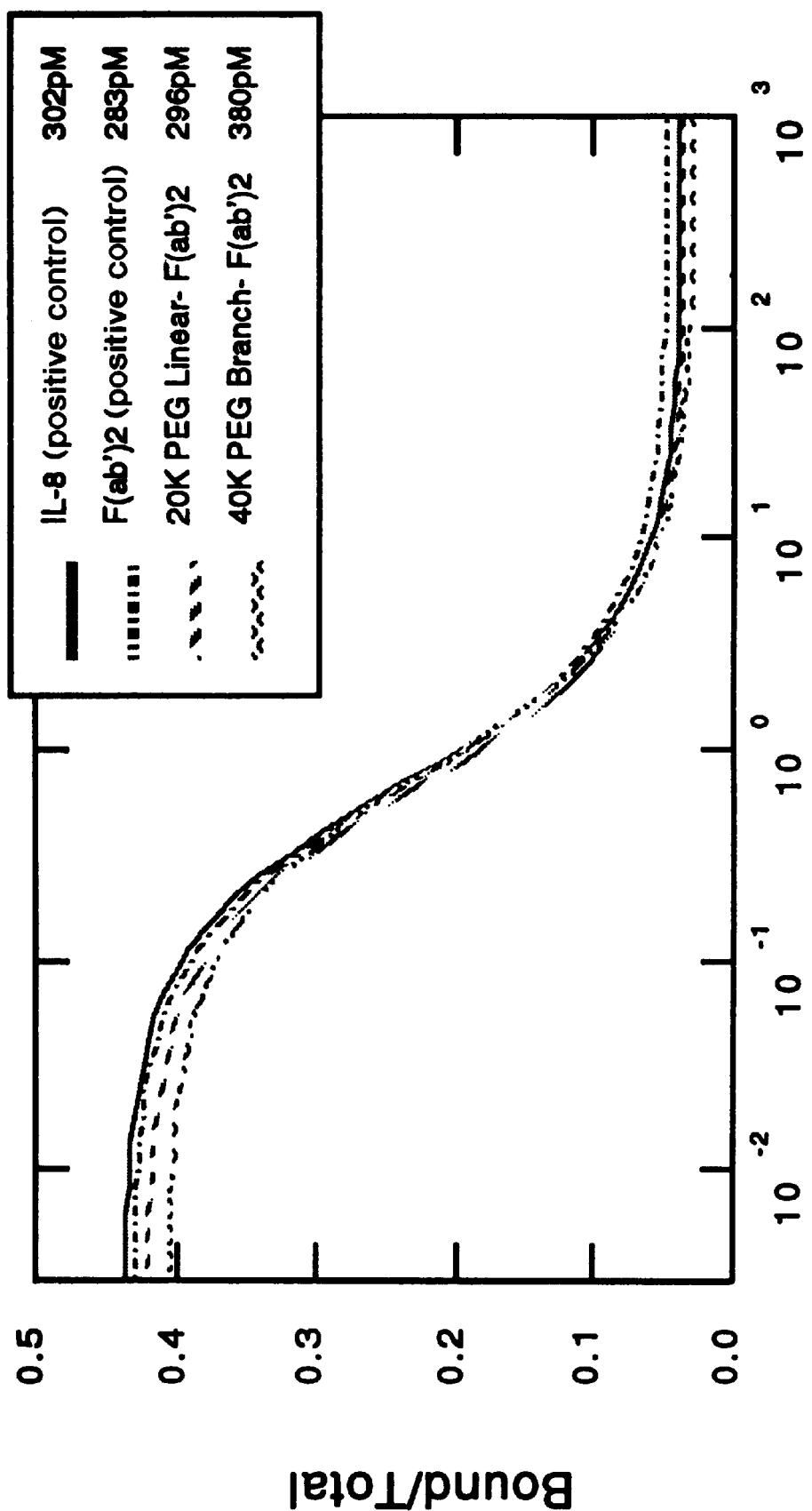
FIGS. 57A–57B contain graphs of displacement curves depicting the inhibition of $^{125}$I-IL-8 binding to neutrophils exhibited by PEG-succinimide modified 6G4V11N35A Fab'$_2$ molecules.
Figure 57B:
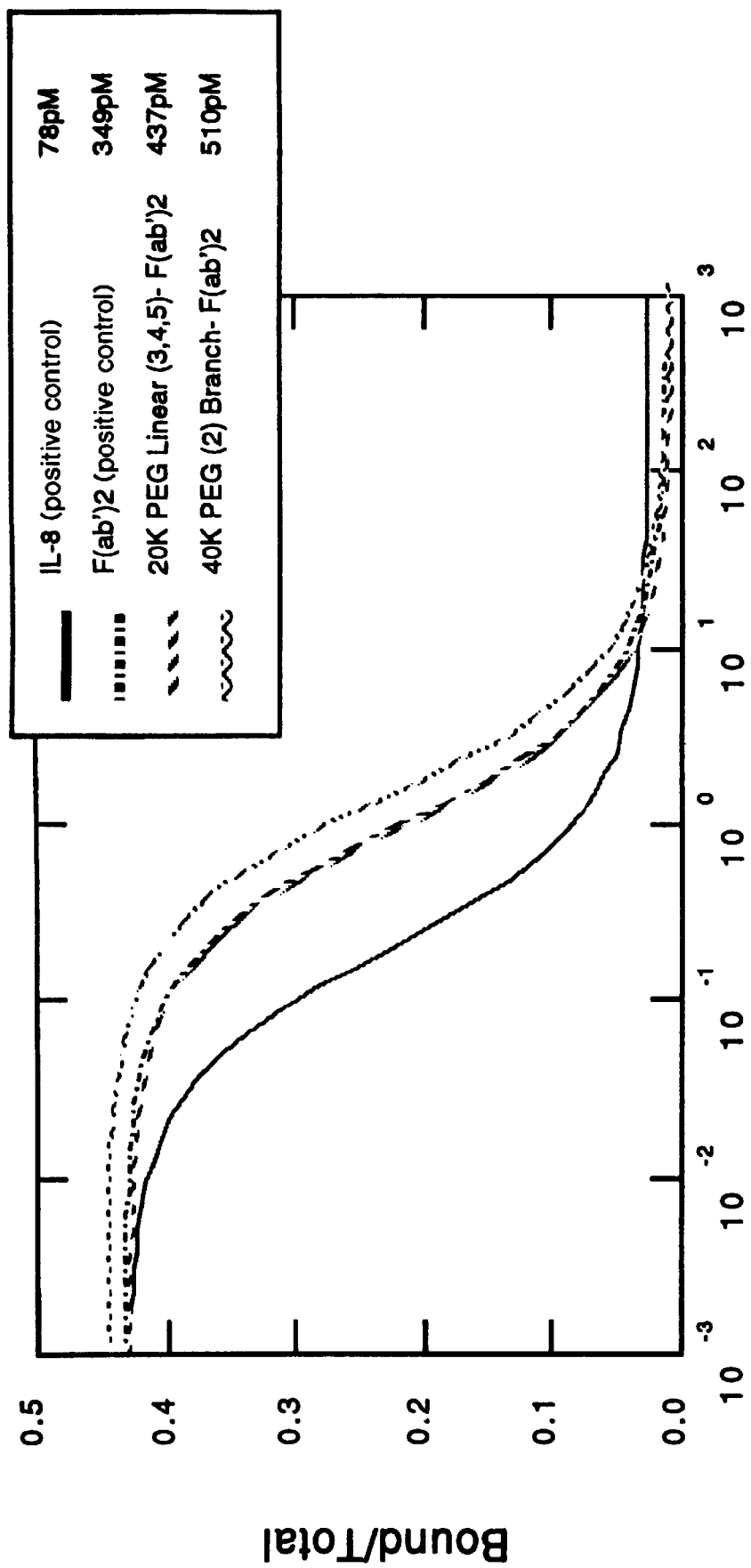

The anti-IL-8 variant 6G4V11N35A F(ab')$_2$ modified with (a) a single 20 kD linear PEG molecule per F(ab')$_2$, (b) a single 40 kD branched PEG molecule per F(ab')$_2$, (c) with three, four, or five 20 kD linear PEG molecules per F(ab')$_2$ (a mixture of: (1) species having three 20 kD linear PEG molecules per F(ab')$_2$; (2) species having four 20 kD linear PEG molecules per F(ab')$_2$; and (3) species having five 20 kD linear PEG molecules per F(ab')$_2$; denoted as "20 kD linear PEG (3,4,5) F(ab')$_2$"), or (d) with two 40 kD branched PEG molecules per F(ab')$_2$ (denoted as "40 kD branch PEG (2) F(ab')$_2$"), were tested for their ability to inhibit $^{125}$I-IL-8 binding and to neutralize activation of human neutrophils. The procedures used are described in Sections (B)(1), (B)(2) and (B)(3) above. The binding curves for pegylated F(ab')$_2$ variants are shown in FIGS. 57A–57B. No significant differences were observed amongst the F(ab')$_2$ control, the single 20 kD linear PEG-modified F(ab')$_2$, and the single 40 kD branched PEG-modified F(ab')$_2$ (FIG. 57A). However, the F(ab')$_2$ variants containing multiple PEG molecules showed a slight reduction (less than 2-fold) in their ability to bind IL-8. The $IC_{50}$'s of the 20 kD linear PEG (3,4,5) F(ab')$_2$ and 40 kD branch PEG (2) F(ab')$_2$ variants were 437 pM and 510 pM, respectively, compared to 349 pM of the F(ab')$_2$ control (FIG. 57B).

Figure 58B:
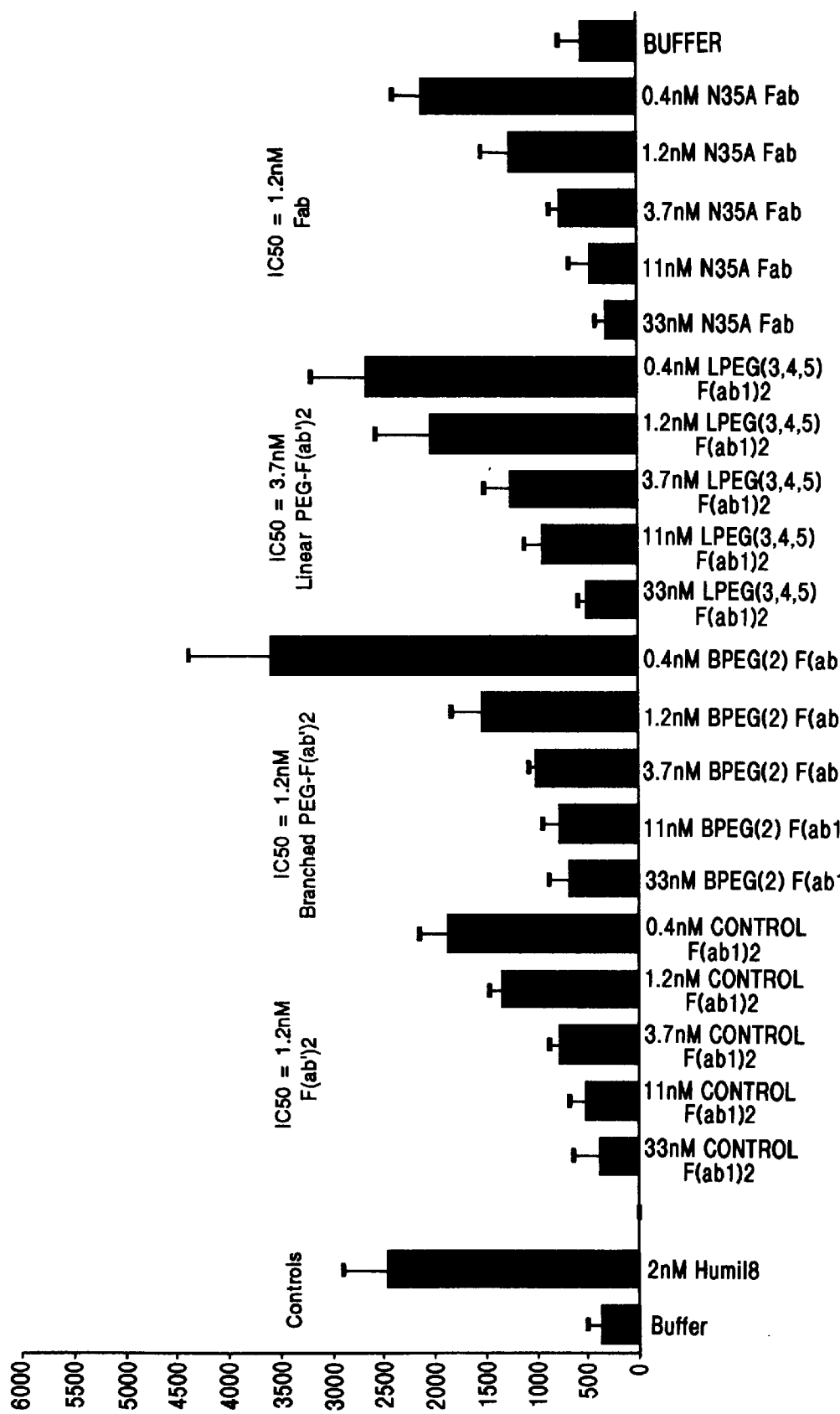

The ability of these pegylated F(ab')$_2$ variants to block IL-8 mediated neutrophil chemotaxis is presented in FIGS. 58A–58B. Consistent with the PMN binding data, the single linear and branched PEG F(ab')$_2$ variants were able to block IL-8 mediated chemotaxis similar to the unpegylated F(ab')$_2$ control (FIG. 58A). The ability of the 40 kD branch PEG (2) F(ab')$_2$ variant to inhibit PMN chemotaxis was identical to the control F(ab')$_2$ while the 20 kD linear PEG (3,4,5) F(ab')$_2$ mixture was able to inhibit within 3-fold of the control antibody (FIG. 58B).

Figure 59B:
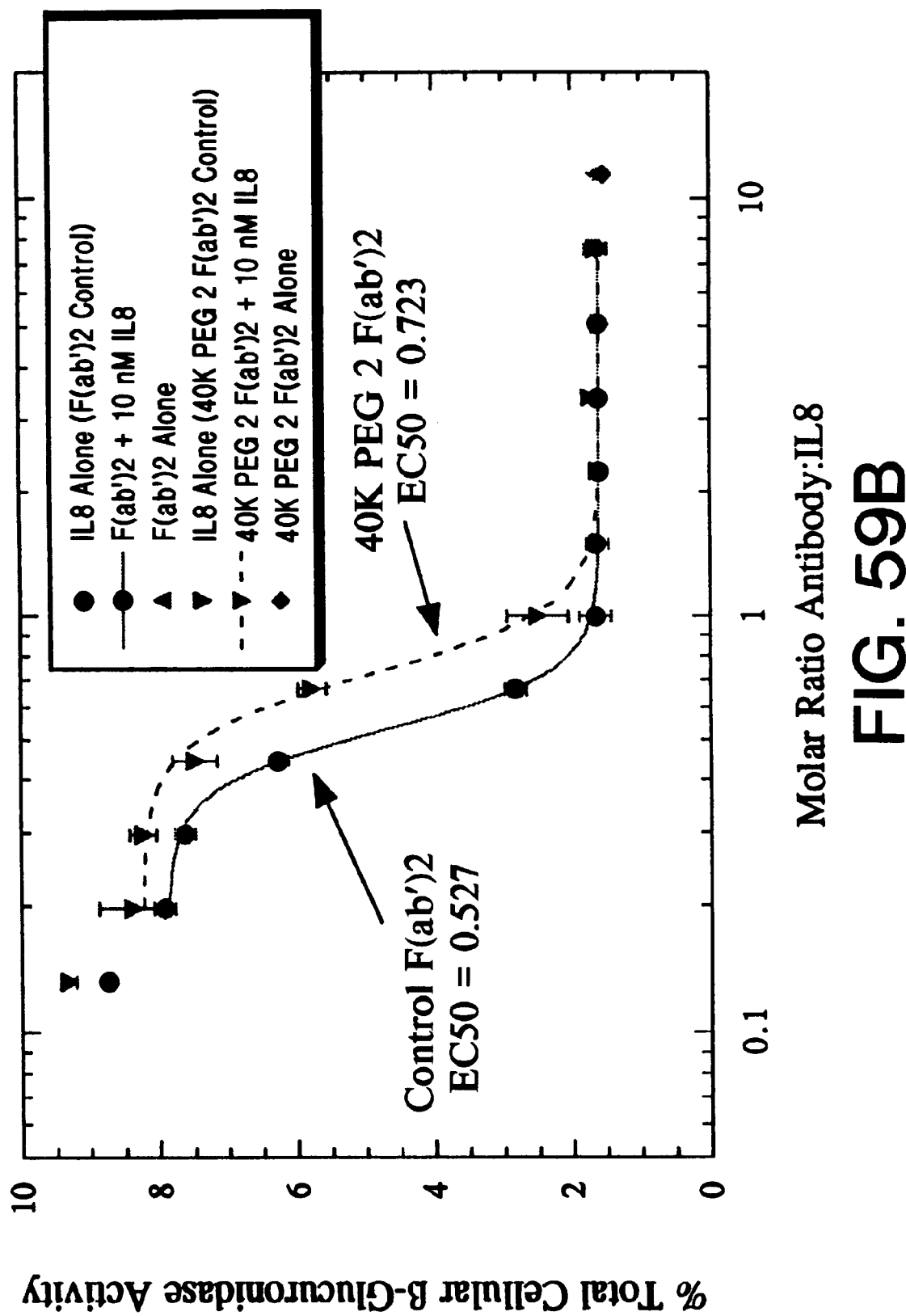

Shown in FIGS. 59A and 59B are the results of the β-glucuronidase release assay which is a measure of degranulation by IL-8 stimulated human neutrophils. The single 20 kD linear PEG-modified F(ab')$_2$ and the single 40 kD branched PEG-modified F(ab')$_2$ variants were able to inhibit release of β-glucuronidase as well as the F(ab')$_2$ control (FIG. 59A). The 40 kD branch PEG (2) F(ab')$_2$ inhibited this response within 2-fold of the F(ab')$_2$ control (FIG. 59B). The 20 kD linear PEG (3,4,5) molecule was not tested. Overall, the F(ab')$_2$ pegylated anti-IL-8 antibodies were biologically active and effectively prevented IL-8 binding to human neutrophils and the signaling events leading to cellular activation.

X. Pharmacokinetic and Safety Study of Eight Constructs of Pegylated Anti-IL-8 (Humanized) F(ab')2 and Fab' Fragments in Normal Rabbits Following Intravenous Administration The objective of this study was to evaluate the effect of pegylation on the pharmacokinetics and safety of six pegylated humanized anti-IL-8 constructs (pegylated 6G4V11N35A.Fab' and pegylated 6G4V11N35A.F(ab')$_2$ obtained as described in Sections (T) and (U) above) relative to the non-pegylated fragments in normal rabbits. Eight groups of two/three male rabbits received equivalent protein amounts of pegylated 6G4V11N35A.Fab' or pegylated 6G4V11N35A.F(ab')$_2$ constructs (2 mg/kg) via a single intravenous (IV) bolus dose of one anti-IL8 construct. Serum samples were collected according to the schedule shown in Table 8 below and analyzed for anti-IL8 protein concentrations and antibody formation against anti-IL8 constructs by ELISA.

TABLE 8

| Group No. | Dose level/ Route | Material | Blood Collection |
|---|---|---|---|
| 1 | 2 mg/kg (protein conc.) IV bolus | Fab' control | 0,5,30 min; 1,2,3,4,6,8, 10,14,20,24,360 hr |
| 2 | | linear(1)20K(s)Fab' | 0,5,30 min; 1,2,4,6,8,10, 12,24,28,32,48,72,96, 168,216,264,336,360 hr |
| 3 | | linear(1)40K(s)Fab' | |
| 4 | | branched(1)40K(N)F(ab')$_2$ | |
| 5 | | F(ab')$_2$ control | 0,5,30 min; 1,2,4,6,8,10, 12,24,28,32,48,52,56, 336 hr |
| 6 | | branched (2)40K(s)Fab' | 0,5,30 min; 1,2,4,6,8,10, 12,24,28,32,48,72,96, 168,216,264,336 hr; Day 17,21,25 |
| 7 | | branched(2)40K(N)F(ab')$_2$ | 0,5,30 min; 1,2,4,6,8,10, 12,24,28,32,48,72,144, 192,240 hr; Day 13,16, 20,23 |
| 8 | | linear(1)30K(s)Fab' | 0,5,30 min; 1,2,4,6,8,10, 12,24,28,32,48,72,96, 168,216,264,336 hr; Day 17,21,25 | a. Methods

Three male New Zealand White (NZW) rabbits per group (with exception to Group 7, n=2) received an equivalent amount of 6G4V11N35A protein (Fab' or F(ab')$_2$) construct at 2 mg/kg via an IV bolus dose in a marginal ear vein. Amino acid composition analysis and absorbance at 280 nm using extinction coefficients of 1.26 for 6G4V11N35A Fab' constructs and 1.34 for 6G4V11N35A F(ab')$_2$ constructs were performed to determine the protein concentration. Whole blood samples were collected via an ear artery cannulation (ear opposing dosing ear) at the above time points. Samples were harvested for serum and assayed for free 6G4V11N35A Fab' or F(ab')$_2$ constructs using an IL-8 Binding ELISA. Assays were conducted throughout the study as samples became available. All animals were sacrificed following the last blood draw, and necropsies were performed on all animals in Groups 1, 4–8. Due to the development of antibodies against the 6G4V11N35A constructs, non-compartmental pharmacokinetic analysis was conducted on concentration versus time data only up to 168 hours.

b. Results

In four animals (Animals B, P, Q, V), interference to rabbit serum in the ELISA assay was detected (i.e. measurable concentrations of anti-IL8 antibodies at pre-dose). However, because these values were at insignificant levels and did not effect the pharmacokinetic analysis, the data were not corrected for this interference.

One animal (Animal G; Group 3) was exsanguinated before the termination of the study and was excluded from the pharmacokinetic analysis. At 4 hours, the animal showed signs of a stroke that was not believed to be drug related, as this can occur in rabbits following blood draws via ear artery cannulation.

Figure 65A:
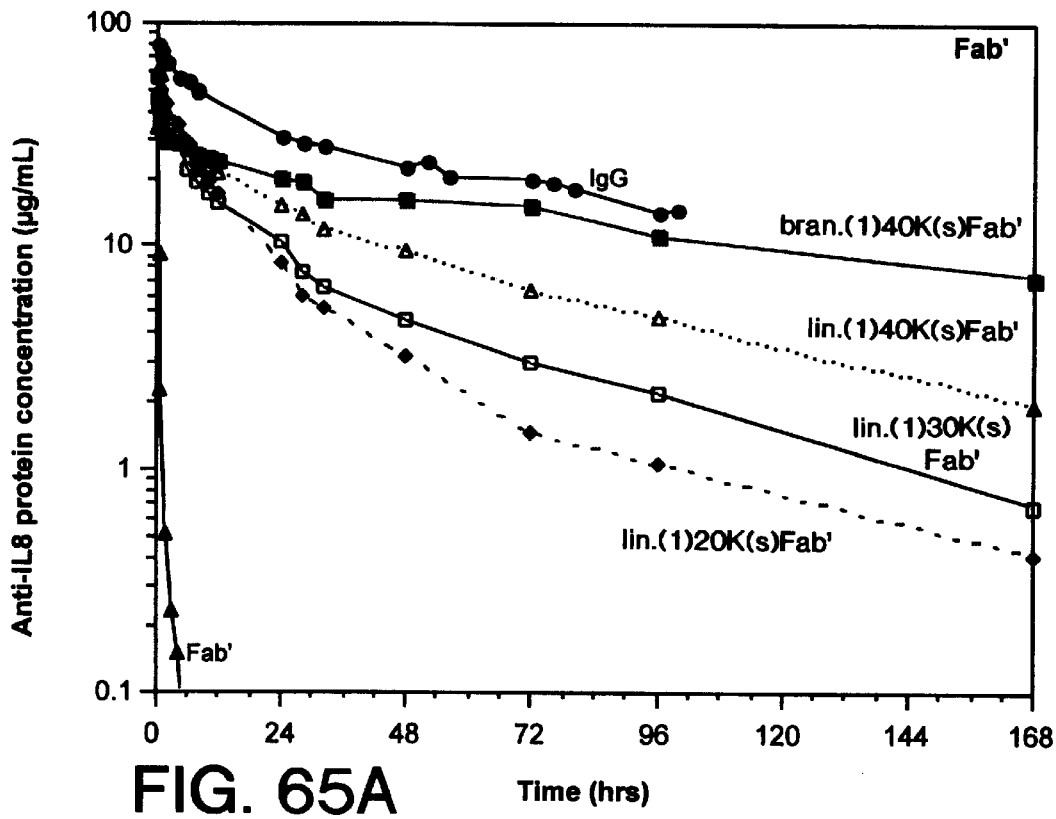
FIGS. 65A and 65B are graphs comparing the serum concentration vs. time profiles of various PEG-maleimide modified 6G4V11N35A Fab' molecules (FIG. 65A) and various PEG-succinimide modified 6G4V11N35A F(ab')$_2$ molecules (FIG. 65B) in rabbits.
Figure 65B:
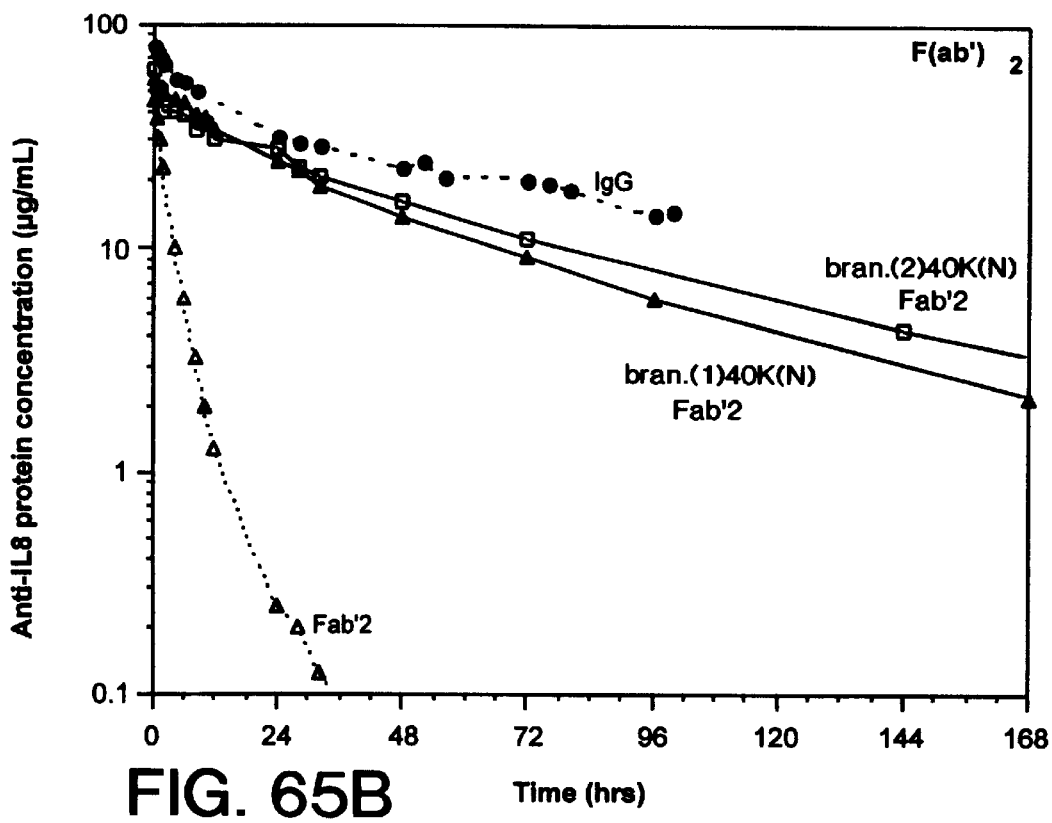

The mean concentration-time profiles of the eight anti-IL8 constructs in normal rabbits are depicted in FIG. 65, and the pharmacokinetic parameters for the eight constructs are summarized in Table 9 below. Significant antibodies to the anti-IL-8 constructs were present at Day 13/14 in all dose groups except Group 1 (Fab' control).

TABLE 9

Pharmacokinetic parameters.

| Molecule | Fab' | | | | | F(ab')$_2$ | | |
| --- | --- | --- | --- | --- | --- | --- | --- | --- |
| Group No. | 1 | 2 | 8 | 3 | 6 | 5 | 4 | 7 |
| PEG structure | — | linear | linear | linear | branched | — | branched | branched |
| Number of PEGs | — | 1 | 1 | 1 | 1 | — | 1 | 2 |
| PEG MW | — | 20K | 30K | 40K | 40K | — | 40K | 40K |
| Dose (mg/kg) | 2 | 2 | 2 | 2 | 2 | 2 | 2 | 2 |
| $V_c$ (mL/kg)[a] | 58 ± 3 | 36 ± 3 | 35 ± 1 | 34 | 44 ± 1 | 45 ± 5 | 36 ± 1 | 32 |
| $V_{ss}$ (mL/kg)[b] | 68 ± 8 | 80 ± 8 | 110 ± 15 | 79 | 88 ± 21 | 59 ± 4 | 50 ± 3 | 52 |
| Cmax(μg/mL)[c] | 35 ± 1 | 58 ± 3 | 57 ± 1 | 60 | 45 ± 1 | 45 ± 6 | 56 ± 2 | 62 |
| Tmax(min)[d] | 5 | 5 | 5 | 5 | 5 | 5 | 5 | 5 |
| t½ term (hr)[e] | 3.0 ± 0.9 | 44 ± 2 | 43 ± 7 | 50 | 105 ± 11 | 8.5 ± 2.1 | 45 ± 3 | 48 |
| AUC$_{0-\infty}$ (hr·μg/mL)[f] | 18 ± 3 | 80 ± 74 | 910 ± 140 | 1600 | 3400 ± 1300 | 140 ± 3 | 2200 ± 77 | 2500 |
| CL (mL/hr/kg)[g] | 110 ± 17 | 2.5 ± 0.2 | 2.2 ± 0.4 | 1.3 | 0.63 ± 0.20 | 14 ± 0 | 0.92 ± 0.03 | 0.83 |
| MRT(hr)[h] | 0.61 ± 0.15 | 32 ± 2 | 45 ± 9 | 63 | 140 ± 18 | 4.2 ± 0.3 | 55 ± 3 | 64 |
| No. of Animals | 3 | 3 | 3 | 2 | 3 | 3 | 3 | 2 |

[a]Initial volume of distribution.
[b]Volume of distribution at steady state.
[c]Observed maximum concentration.
[d]Observed time to Cmax.
[e]t½ term = half-life associated with the terminal phase of the concentration vs. time profile.
[f]Area under the concentration versus time curve (extrapolated to infinity).
[g]CL = serum clearance.
[h]MRT = Mean residence time.

The initial volume of distribution approximated the plasma volume for both the Fab' and F(ab')$_2$. Pegylation decreased serum CL of anti-IL8 fragments and extended both the terminal half-life and MRT as shown in Table 10 below.

TABLE 10

Fold decrease/increase in clearance, terminal half-life & MRT of pegylated anti-IL8 fragments.

| anti-IL8 fragment | Fab' | | | | | F(ab')$_2$ | | |
| --- | --- | --- | --- | --- | --- | --- | --- | --- |
| Group No. | 1 | 2 | 8 | 3 | 6 | 5 | 4 | 7 |
| PEG structure | — | linear | linear | linear | bran. | — | bran. | bran. |
| No. of PEGs | — | 1 | 1 | 1 | 1 | — | 1 | 2 |
| PEG MW | — | 20K | 30K | 40K | 40K | — | 40K | 40K |
| CL: | | | | | | | | |
| mean (mL/hr/kg) | 110 | 2.5 | 2.2 | 1.3 | 0.63 | 14 | 0.92 | 0.83 |
| fold decrease | 1 | 46 | 51 | 90 | 180 | 1 | 15 | 17 |
| t½ term: | | | | | | | | |
| mean (hr) | 3.0 | 44 | 43 | 50 | 110 | 8.5 | 45 | 48 |
| fold increase | 1 | 14 | 14 | 17 | 35 | 1 | 5.3 | 5.7 |
| MRT: | | | | | | | | |
| mean (hr) | 0.61 | 32 | 45 | 63 | 140 | 4.2 | 55 | 64 |
| fold increase | 1 | 53 | 73 | 100 | 240 | 1 | 13 | 15 |

Figure 66:
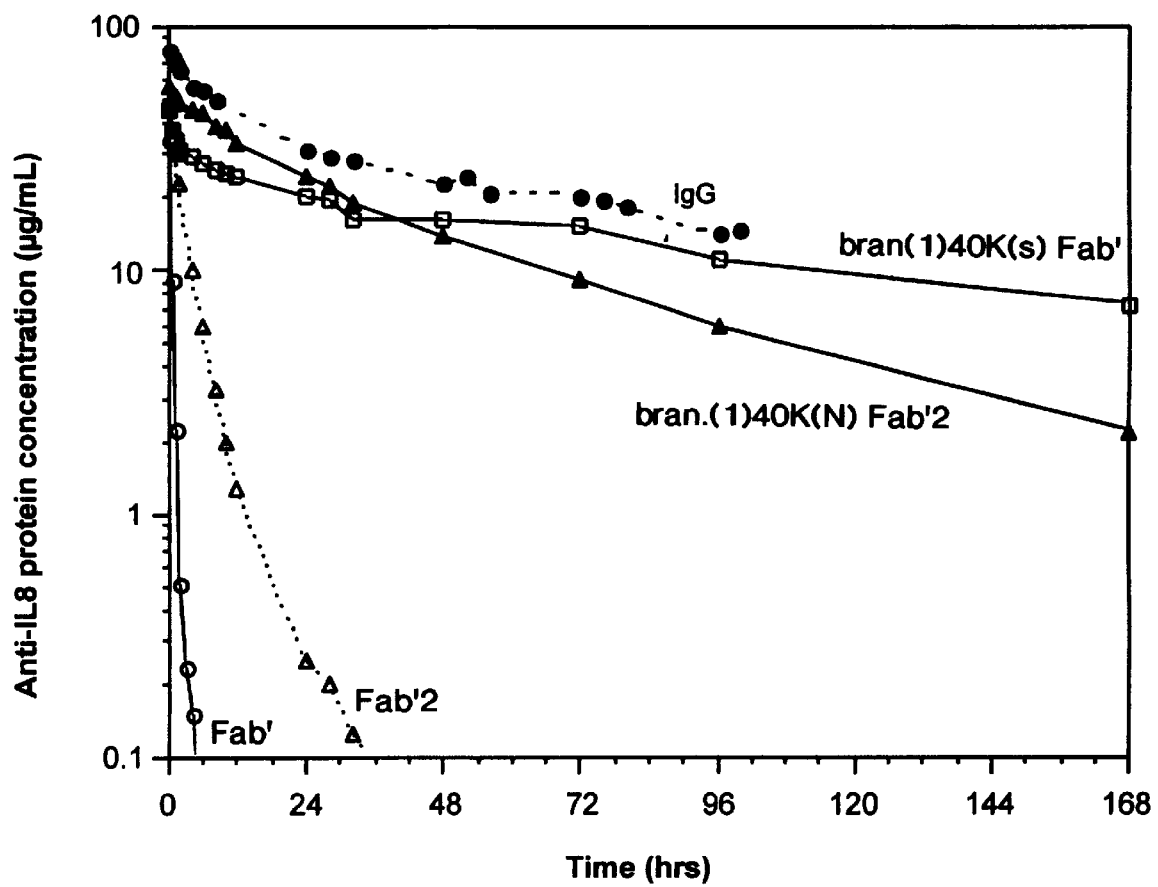
FIG. 66 contains graphs comparing the serum concentration vs. time profiles of 6G4V11N35A Fab' coupled to one 40 kD branched PEG-maleimide molecule (denoted as "bran.(1)40K(s)Fab'"), 6G4V11N35A F(ab')$_2$ coupled to one 40 kD branched PEG-succinimide molecule (denoted as "bran.(1)40K(N)Fab'2"), unmodified 6G4V11N35A F(ab')$_2$ (denoted as "Fab'2"), unmodified 6G4V11N35A Fab' (denoted as "Fab'"), and a full length IgG1 (denoted as "IgG") equivalent of the human-murine chimeric anti-rabbit IL-8 Fab described in Example F below.

For the pegylated anti-IL8 Fab' fragments, CL decreased by 46 to 180-fold. Terminal half-life and MRT increased 14 to 35-fold and 53 to 240-fold, respectively. For pegylated anti-IL8 F(ab')$_2$ molecules, CL decreased 15 to 17-fold with pegylation, and terminal half-life and MRT increased by greater than 5-fold and 13-fold, respectively. The changes in these parameters increased for both pegylated Fab' and F(ab')$_2$ molecules with increasing PEG molecular weight and approached the values of the full-length anti-IL8 (terminal half-life of 74 hours, MRT of 99 hours and CL of 0.47 mL/hr/kg). In comparing the branched(1)40K Fab' (Group 6) and branched(1)40K F(ab')$_2$ (Group 4), unexpected pharmacokinetics were observed. The pegylated Fab' molecule appeared to remain in the serum longer than the pegylated F(ab')$_2$ (see FIG. 66). The mean CL of branched (1)40K Fab' was 0.63 mL/hr/kg, but a higher CL was observed for branched(1)40 kD F(ab')$_2$ (CL 0.92 mL/hr/kg).

The terminal half-life, likewise, was longer for the Fab' than the F(ab')$_2$ pegylated molecule (110 vs 45 hours).

The pharmacokinetic data demonstrated that pegylation decreased CL and increased terminal tl/2 and MRT of anti-IL8 fragments (Fab' and F(ab')$_2$) to approach that of the full-length anti-IL8. Clearance was decreased with pegylation 46 to 180-fold for the Fab' and approximately 16-fold for the F(ab')$_2$. The terminal half-life of the Fab' anti-IL8 fragment was increased by 14 to 35-fold and approximately 5-fold for the F(ab')$_2$ anti-IL8. MRT, likewise, were extended by 53 to 240-fold for the Fab' and approximately 14-fold for the F(ab')$_2$. The branched(1) 40 kD Fab' had a longer terminal half-life and lower clearance compared to the branched(1) 40 kD F(ab')$_2$.

Y. In Vivo Efficacy Testing of Anti-IL-8 Antibody Reagents in Rabbit Model of Ischemis/Reperfusion and Acid Aspiration-Induced Acute Respiratory Distress Syndrome (ARDS)

Full length murine anti-rabbit IL-8 monoclonal antibody 6G4.2.5, 40 kD branched PEG-6G4V11N35A Fab', and control antibody (anti-HIV gp120 monoclonal antibody 9E3.1F10) were tested in a rabbit ARDS model. The animals were weighed and anaesthetized by intramuscular injection of ketamine (50 mg/kg body weight), xylazine (5 mg/kg body weight), and acepromazine (0.75 mg/kg body weight). A second dose (20% of the first dosage) was given IM 15 minutes before removal of vascular clip, and third dose (60% of the first dosage) was given at tracheotomy. Intra-arterial catheter (22G, 1 in. Angiocath) and intra-venous catheter (24G, 1 in. angiocath) were be placed in the ear central artery and posterior marginal ear vein for blood samplings (arterial blood gases and CBC) and anti-IL-8 and fluid administration, respectively. The anaesthetized animals were transferred in a supine position to an operating tray; the abdominal area was shaved and prepared for surgery. Via a midline laparotomy, the superior mesenteric artery (SMA) was isolated and a microvascular arterial clip applied at the aortic origin. Before the temporary closure of the abdomen using 9 mm wound clip (Autoclip, Baxter), 15 ml of normal saline was given intraperitoneally as fluid supplement. After 110 minutes of intestinal ischemia, the abdominal incision was reopened and the arterial clip was released to allow reperfusion. Before closure, 5 ml of normal saline was given intraperitoneally for fluid replacement. The laparotomy incision was closed in two layers and the animals allowed to awaken.

After surgery, the animals were placed on a heating pad (38° C.) and continuously monitored for up to 6 hours post reperfusion and lactated Ringer's 8–12 ml/kg/hr IV was given as fluid supplement.

At 22–24 hr post-reperfusion, a tracheotomy was performed under anesthesia. Normal physiologic saline was diluted 1:3 with water and adjusted to pH 1.5 (adjusted by using 1N HCL); 3 ml/kg body weight was then instilled intra-tracheally. Rectal temperature was maintained at 37 +/−1 degree C using a homeothermic heat therapy pad (K-Mod II, Baxter). Fluid supplements (LRS) at a rate of 5 ml/kg/hour IV were given. Blood gases were monitored every hour. The rabbits were returned to the cage after 6 hr of continuous monitoring.

Just prior to aspiration, animals were treated with saline, the control monoclonal antibody (anti-HIV gp-120 IgG9E3.1F10), the full length murine anti-rabbit IL8 (6 g4.2.5 murine IgG2a anti-rabbit IL8) or the pegylated 6G4V11N35A Fab' (6G4V11N35A Fab' modified with 40 kD branched PEG-maleimide as described in Section T above, denoted as "40 kD branched PEG-6G4V11N35A Fab' "). Data from saline or control antibody treated animals was combined and presented as "Control". Arterial blood gases and A-a PO2 gradient measurements were taken daily, and IV fluid supplementation was performed daily. A-a PO2 gradient was measured at 96 hr of reperfusion. The A-a PO2 gradient was calculated as:

$$\text{A-a PO2} = [\text{FIO2}(\text{PB}-\text{PH2O}) - (\text{PaCO2}/\text{RQ})] - \text{PaO2}.$$

PaO2/FiO2 ratios were measured at 24 hr and 48 hr in room air and 100% oxygen.

After the final A-a PO2 gradient measurement, the animals were anesthetized with Nembutal 100 mg/kg i.v. and the animals were euthanized by transecting the abdominal aorta in order to reduce red blood cell contamination of bronchoalveolar lavage fluid (BAL). The lungs were removed en bloc. The entire lung was weighed and then lavaged with an intratracheal tube (Hi-Lo tracheal tube, 3 mm) using 30 ml of HBSS and lidocain. Total and differential leukocyte counts in the BAL were determined. Lesions/changes were verified by histological examination of each lobe of the right lung of each animal.

Figure 67:
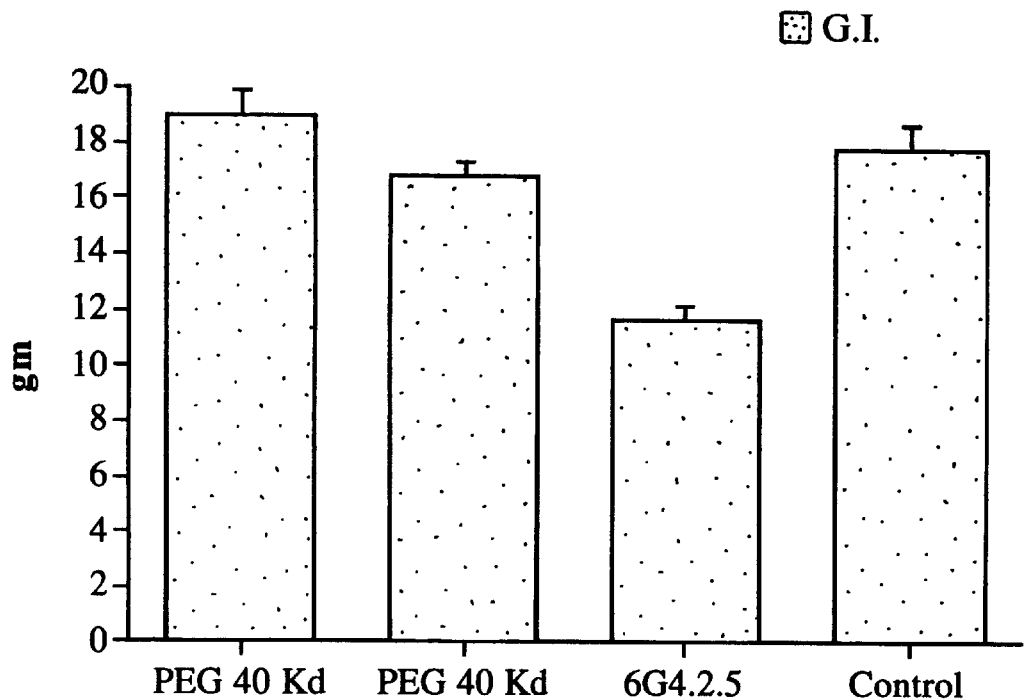
FIG. 67 is a graph depicting the effect of 6G4V11N3 5A Fab' coupled to one 40 kD branched PEG-maleimide molecule (denoted as "PEG 40 Kd") and murine anti-rabbit IL-8 monoclonal antibody 6G4.2.5 (full length IgG2a) (denoted as "6G4.2.5") on gross weight of entire lung in an ARDS rabbit model.
Figure 68:
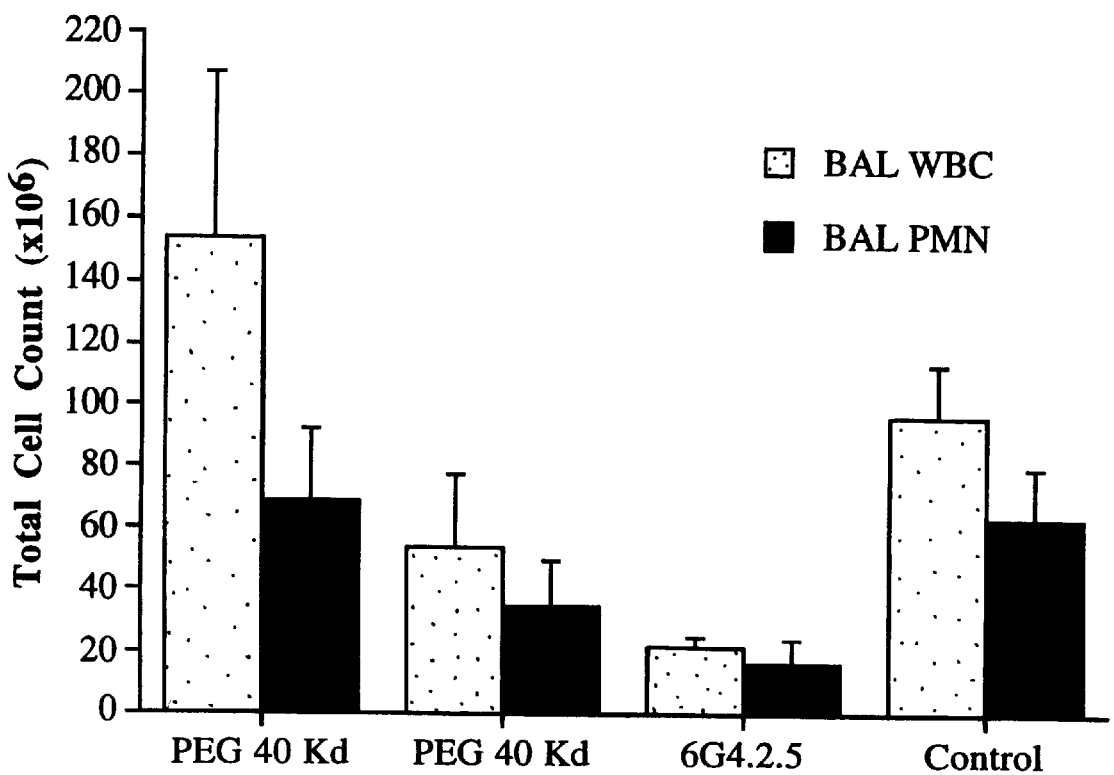
FIG. 68 is a graph depicting the effect of 6G4V11N35A Fab' coupled to one branched 40 kD PEG-maleimide molecule (denoted as "PEG 40 Kd") and murine anti-rabbit IL-8 monoclonal antibody 6G4.2.5 (full length IgG2a) (denoted as "6G4.2.5") on BAL total leukocyte (light columns) and polymorphonuclear cell (dark columns) counts in an ARDS rabbit model. Untreated (no therapeutics) control animal data is denoted as "Control".
Figure 69:
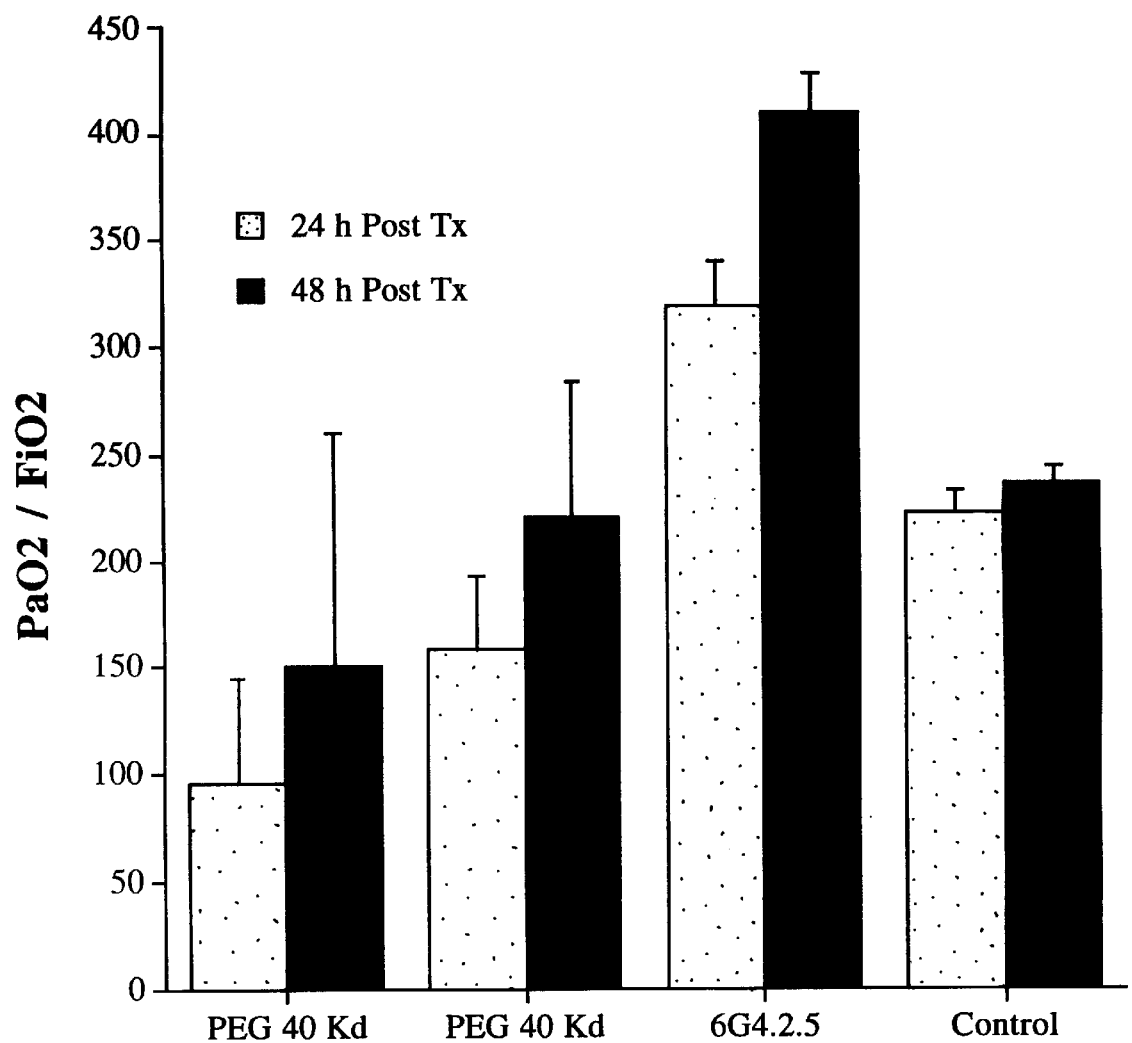
FIG. 69 is a graph depicting the effect of 6G4V11N35A Fab' coupled to one branched 40 kD PEG-maleimide molecule (denoted as "PEG 40 Kd") and murine anti-rabbit IL-8 monoclonal antibody 6G4.2.5 (full length IgG2a) (denoted as "6G4.2.5") on PaO2/FiO2 ratio at 24 hours-post treatment (light columns) and 48 hours post-treatment (dark columns) in an ARDS rabbit model. Untreated (no therapeutics) control animal data is denoted as "Control".

The gross lung weight, total leukocyte and polymorphonuclear cell counts in BAL, and PaO2/FiO2 data obtained are depicted in FIGS. 67, 68 and 69, respectively. Treatment with 40 kD branched PEG-6G4V11N35A Fab' exhibited no effect on the biological parameters measured in the model as compared to the "Control" group. However, the data do not contradict the pharmacokinetic analysis or the in vitro activity analysis for the 40 kD branched PEG-6G4V11N35A Fab' presented in Sections (V) and (X) above. In addition, these data do not contradict the ability of the 40 kD branched PEG-6G4V11N35A Fab' to reach and act on disease effector targets in circulation or other tissues.

The following biological materials have been deposited with the American Type Culture Collection, 12301 Parklawn Drive, Rockville, Md., USA (ATCC):

| Material | ATCC Accession No. | Deposit Date |
| --- | --- | --- |
| hybridoma cell line 5.12.14 | HB 11553 | February 15, 1993 |
| hybridoma cell line 6G4.2.5 | HB 11722 | September 28, 1994 |
| pantiIL-8.2, *E. coli* strain 294 mm | 97056 | February 10, 1995 |
| p6G425chim2, *E. coli* strain 294 mm | 97055 | February 10, 1995 |
| p6G4V11N35A.F(ab')$_2$ | 97890 | February 20, 1997 |
| *E. coli* strain 49D6(p6G4V11N35A.F(ab')$_2$) | 98332 | February 20, 1997 |
| p6G425V11N35A.choSD | 209552 | December 16, 1997 |
| clone#1933 aIL8.92 NB 28605/12 | CRL-12444 | December 11, 1997 |
| clone#1934 aIL8.42 NB 28605/14 | CRL-12445 | December 11, 1997 |

These deposits were made under the provisions of the Budapest Treaty on the International Recognition of the Deposit of Microorganisms for the Purpose of Patent Procedure and the Regulations thereunder (Budapest Treaty). This assures maintenance of a viable deposit for 30 years from the date of deposit. These cell lines will be made available by ATCC under the terms of the Budapest Treaty, and subject to an agreement between Genentech, Inc. and ATCC, which assures permanent and unrestricted availability of the cell lines to the public upon issuance of the pertinent U.S. patent or upon laying open to the public of any U.S. or foreign patent application, whichever comes first, and assures availability of the cell lines to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if the deposited cell lines should be lost or destroyed when cultivated under suitable conditions, they will be promptly replaced on notification with a specimen of the same cell line. Availability of the deposited cell lines is not to be construed as a license to practice the invention in contravention of the rights granted under the authority of any government in accordance with its patent laws.

```

We claim:

1. A polypeptide selected from the group consisting of: (1) a polypeptide that is a humanized anti-IL-8 monoclonal antibody or antibody fragment comprising a light chain amino acid sequence comprising the complementarity determining regions of the light chain polypeptide amino acid sequence of SEQ ID NO:56; (2) a polypeptide that is a humanized anti-IL-8 monoclonal antibody or antibody fragment comprising a light chain amino acid sequence comprising the complementarity determining regions of the light chain polypeptide amino acid sequence of SEQ ID NO:62; and (3) a polypeptide that is a humanized anti-IL-8 monoclonal antibody or antibody fragment comprising a heavy chain amino acid sequence comprising amino acids 24–253 of the heavy chain polypeptide amino acid sequence of SEQ ID NO:60.

2. The polypeptide of claim 1 that comprises a light chain amino acid sequence selected from the group consisting of: (1) a light chain amino acid sequence comprising the complementarity determining regions of the light chain polypeptide amino acid sequence of (SEQ ID NO:56; and (2) a light chain amino acid sequence comprising the complementarity determining regions of the light chain polypeptide amino acid sequence of (SEQ ID NO:62).

3. The polypeptide of claim 2, wherein the light chain amino acid sequence comprises the complementarity determining regions of the light chain polypeptide amino acid sequence of (SEQ ID NO:62).

4. The polypeptide of claim 2 that further comprises a heavy chain amino acid sequence comprising the complementarity determining regions of the heavy chain polypeptide amino acid sequence of (SEQ ID NO:60).

5. The polypeptide of claim 2, wherein the light chain amino acid sequence is selected from the group consisting of: (1) a light chain amino acid sequence comprising amino acids 24–242 of the light chain polypeptide amino acid sequence of (SEQ ID NO:56); and (2) a light chain amino acid sequence comprising amino acids 24–242 of the light chain polypeptide amino acid sequence of (SEQ ID NO:62).

6. The polypeptide of claim 5, wherein the light chain amino acid sequence comprises amino acids 24–242 of the light chain polypeptide amino acid sequence of (SEQ ID NO:62).

7. The polypeptide of claim 5 that further comprises a heavy chain amino acid sequence comprising amino acids 24–253 of the heavy chain polypeptide amino acid sequence of (SEQ ID NO: 60).

8. The polypeptide of claim 7 that is an antibody fragment, wherein the heavy chain amino acid sequence is fused at its C-terminus to a leucine zipper amino acid sequence.

9. The antibody fragment of claim 8, wherein the leucine zipper sequence comprises amino acids 254–298 of the heavy chain polypeptide amino acid sequence of (SEQ ID NO:60).

10. The polypeptide of claim 1 that comprises a heavy chain amino acid sequence comprising amino acids 24–253 of the heavy chain polypeptide amino acid sequence of (SEQ ID NO:60).

11. The polypeptide of claim 10 that further comprises a light chain amino acid sequence comprising amino acids 24–242 of the light chain polypeptide amino acid sequence of (SEQ ID NO:51).

12. The polypeptide of claim 1 that is an antibody fragment selected from the group consisting of Fab, Fab', Fab'-SH, Fv, scFv and F(ab')$_2$.

13. The polypeptide of claim 5 that is a F(ab')$_2$ antibody fragment, wherein the antibody fragment comprises a first heavy chain amino acid sequence and a second heavy chain amino acid sequence each comprising amino acids 24–261 of the heavy chain polypeptide amino acid sequence of (SEQ ID NO:60), and wherein each of the Cys residues at positions 254 and 257 in the first heavy chain amino acid sequence is in a disulfide linkage with the identical Cys residue in the second heavy chain amino acid sequence.

14. The polypeptide of claim 5 that is a Fab' or Fab'-SH antibody fragment, wherein the antibody fragment comprises a heavy chain amino acid sequence comprising amino acids 24–256 of the heavy chain polypeptide amino acid sequence of (SEQ ID NO:70).

15. The polypeptide of claim 1 that is an antibody.

16. A composition comprising the polypeptide of claim 1 and a carrier.

17. The composition of claim 16 that is sterile.

* * * * *

                         SEQUENCE LISTING (1) GENERAL INFORMATION:

(iii) NUMBER OF SEQUENCES: 72

(2) INFORMATION FOR SEQ ID NO:1:

(i) SEQUENCE CHARACTERISTICS:
         (A) LENGTH: 22 base pairs
         (B) TYPE: Nucleic Acid
         (C) STRANDEDNESS: Single
         (D) TOPOLOGY: Linear (xi) SEQUENCE DESCRIPTION: SEQ ID NO:1:

CAGTCCAACT GTTCAGGACG CC                                             22

(2) INFORMATION FOR SEQ ID NO:2:

(i) SEQUENCE CHARACTERISTICS:
         (A) LENGTH: 22 base pairs
         (B) TYPE: Nucleic Acid
         (C) STRANDEDNESS: Single
         (D) TOPOLOGY: Linear (xi) SEQUENCE DESCRIPTION: SEQ ID NO:2:

GTGCTGCTCA TGCTGTAGGT GC                                             22

(2) INFORMATION FOR SEQ ID NO:3:

(i) SEQUENCE CHARACTERISTICS:
         (A) LENGTH: 23 base pairs
         (B) TYPE: Nucleic Acid
         (C) STRANDEDNESS: Single
         (D) TOPOLOGY: Linear (xi) SEQUENCE DESCRIPTION: SEQ ID NO:3:

GAAGTTGATG TCTTGTGAGT GGC                                            23

(2) INFORMATION FOR SEQ ID NO:4:

(i) SEQUENCE CHARACTERISTICS:
         (A) LENGTH: 24 base pairs
         (B) TYPE: Nucleic Acid
         (C) STRANDEDNESS: Single
         (D) TOPOLOGY: Linear (xi) SEQUENCE DESCRIPTION: SEQ ID NO:4:

GCATCCTAGA GTCACCGAGG AGCC                                           24

(2) INFORMATION FOR SEQ ID NO:5:
```

(i) SEQUENCE CHARACTERISTICS:
        (A) LENGTH: 22 base pairs
        (B) TYPE: Nucleic Acid
        (C) STRANDEDNESS: Single
        (D) TOPOLOGY: Linear (xi) SEQUENCE DESCRIPTION: SEQ ID NO:5:

CACTGGCTCA GGGAAATAAC CC                                                    22

(2) INFORMATION FOR SEQ ID NO:6:

(i) SEQUENCE CHARACTERISTICS:
        (A) LENGTH: 22 base pairs
        (B) TYPE: Nucleic Acid
        (C) STRANDEDNESS: Single
        (D) TOPOLOGY: Linear (xi) SEQUENCE DESCRIPTION: SEQ ID NO:6:

GGAGAGCTGG GAAGGTGTGC AC                                                    22

(2) INFORMATION FOR SEQ ID NO:7:

(i) SEQUENCE CHARACTERISTICS:
        (A) LENGTH: 35 base pairs
        (B) TYPE: Nucleic Acid
        (C) STRANDEDNESS: Single
        (D) TOPOLOGY: Linear (xi) SEQUENCE DESCRIPTION: SEQ ID NO:7:

ACAAACGCGT ACGCTGACAT CGTCATGACC CAGTC                                      35

(2) INFORMATION FOR SEQ ID NO:8:

(i) SEQUENCE CHARACTERISTICS:
        (A) LENGTH: 35 base pairs
        (B) TYPE: Nucleic Acid
        (C) STRANDEDNESS: Single
        (D) TOPOLOGY: Linear (xi) SEQUENCE DESCRIPTION: SEQ ID NO:8:

ACAAACGCGT ACGCTGATAT TGTCATGACT CAGTC                                      35

(2) INFORMATION FOR SEQ ID NO:9:

(i) SEQUENCE CHARACTERISTICS:
        (A) LENGTH: 35 base pairs
        (B) TYPE: Nucleic Acid
        (C) STRANDEDNESS: Single
        (D) TOPOLOGY: Linear (xi) SEQUENCE DESCRIPTION: SEQ ID NO:9:

ACAAACGCGT ACGCTGACAT CGTCATGACA CAGTC                                      35

(2) INFORMATION FOR SEQ ID NO:10:

(i) SEQUENCE CHARACTERISTICS:
        (A) LENGTH: 37 base pairs
        (B) TYPE: Nucleic Acid
        (C) STRANDEDNESS: Single
        (D) TOPOLOGY: Linear (xi) SEQUENCE DESCRIPTION: SEQ ID NO:10:

GCTCTTCGAA TGGTGGGAAG ATGGATACAG TTGGTGC                                    37

(2) INFORMATION FOR SEQ ID NO:11:

(i) SEQUENCE CHARACTERISTICS:

```
        (A) LENGTH: 39 base pairs
        (B) TYPE: Nucleic Acid
        (C) STRANDEDNESS: Single
        (D) TOPOLOGY: Linear (xi) SEQUENCE DESCRIPTION: SEQ ID NO:11:

CGATGGGCCC GGATAGACCG ATGGGGCTGT TGTTTTGGC                      39

(2) INFORMATION FOR SEQ ID NO:12:

(i) SEQUENCE CHARACTERISTICS:
        (A) LENGTH: 39 base pairs
        (B) TYPE: Nucleic Acid
        (C) STRANDEDNESS: Single
        (D) TOPOLOGY: Linear (xi) SEQUENCE DESCRIPTION: SEQ ID NO:12:

CGATGGGCCC GGATAGACTG ATGGGGCTGT CGTTTTGGC                      39

(2) INFORMATION FOR SEQ ID NO:13:

(i) SEQUENCE CHARACTERISTICS:
        (A) LENGTH: 39 base pairs
        (B) TYPE: Nucleic Acid
        (C) STRANDEDNESS: Single
        (D) TOPOLOGY: Linear (xi) SEQUENCE DESCRIPTION: SEQ ID NO:13:

CGATGGGCCC GGATAGACGG ATGGGGCTGT TGTTTTGGC                      39

(2) INFORMATION FOR SEQ ID NO:14:

(i) SEQUENCE CHARACTERISTICS:
        (A) LENGTH: 39 base pairs
        (B) TYPE: Nucleic Acid
        (C) STRANDEDNESS: Single
        (D) TOPOLOGY: Linear (xi) SEQUENCE DESCRIPTION: SEQ ID NO:14:

CGATGGGCCC GGATAGACAG ATGGGGCTGT TGTTTTGGC                      39

(2) INFORMATION FOR SEQ ID NO:15:

(i) SEQUENCE CHARACTERISTICS:
        (A) LENGTH: 39 base pairs
        (B) TYPE: Nucleic Acid
        (C) STRANDEDNESS: Single
        (D) TOPOLOGY: Linear (xi) SEQUENCE DESCRIPTION: SEQ ID NO:15:

CGATGGGCCC GGATAGACTG ATGGGGCTGT TGTTTTGGC                      39

(2) INFORMATION FOR SEQ ID NO:16:

(i) SEQUENCE CHARACTERISTICS:
        (A) LENGTH: 369 base pairs
        (B) TYPE: Nucleic Acid
        (C) STRANDEDNESS: Double
        (D) TOPOLOGY: Linear (xi) SEQUENCE DESCRIPTION: SEQ ID NO:16:

GACATTGTCA TGACACAGTC TCAAAAATTC ATGTCCACAT CAGTAGGAGA          50

CAGGGTCAGC GTCACCTGCA AGGCCAGTCA GAATGTGGGT ACTAATGTAG         100

CCTGGTATCA ACAGAAACCA GGGCAATCTC CTAAAGCACT GATTTACTCG         150

TCATCCTACC GGTACAGTGG AGTCCCTGAT CGCTTCACAG GCAGTGGATC         200
```

```
TGGGACAGAT TTCACTCTCA CCATCAGCCA TGTGCAGTCT GAAGACTTGG              250

CAGACTATTT CTGTCAGCAA TATAACATCT ATCCTCTCAC GTTCGGTCCT              300

GGGACCAAGC TGGAGTTGAA ACGGGCTGAT GCTGCACCAC CAACTGTATC              350

CATCTTCCCA CCATTCGAA                                                369
```

(2) INFORMATION FOR SEQ ID NO:17:

(i) SEQUENCE CHARACTERISTICS:
        (A) LENGTH: 123 amino acids
        (B) TYPE: Amino Acid
        (D) TOPOLOGY: Linear (xi) SEQUENCE DESCRIPTION: SEQ ID NO:17:

```
Asp Ile Val Met Thr Gln Ser Gln Lys Phe Met Ser Thr Ser Val
 1               5                  10                  15

Gly Asp Arg Val Ser Val Thr Cys Lys Ala Ser Gln Asn Val Gly
                20                  25                  30

Thr Asn Val Ala Trp Tyr Gln Gln Lys Pro Gly Gln Ser Pro Lys
                35                  40                  45

Ala Leu Ile Tyr Ser Ser Ser Tyr Arg Tyr Ser Gly Val Pro Asp
                50                  55                  60

Arg Phe Thr Gly Ser Gly Ser Gly Thr Asp Phe Thr Leu Thr Ile
                65                  70                  75

Ser His Val Gln Ser Glu Asp Leu Ala Asp Tyr Phe Cys Gln Gln
                80                  85                  90

Tyr Asn Ile Tyr Pro Leu Thr Phe Gly Pro Gly Thr Lys Leu Glu
                95                 100                 105

Leu Lys Arg Ala Asp Ala Ala Pro Pro Thr Val Ser Ile Phe Pro
               110                 115                 120

Pro Phe Glu
       123
```

(2) INFORMATION FOR SEQ ID NO:18:

(i) SEQUENCE CHARACTERISTICS:
        (A) LENGTH: 417 base pairs
        (B) TYPE: Nucleic Acid
        (C) STRANDEDNESS: Double
        (D) TOPOLOGY: Linear (xi) SEQUENCE DESCRIPTION: SEQ ID NO:18:

```
TTCTATTGCT ACAAACGCGT ACGCTGAGGT GCAGCTGGTG GAGTCTGGGG               50

GAGGCTTAGT GCCGCCTGGA GGGTCCCTGA AACTCTCCTG TGCAGCCTCT              100

GGATTCATAT TCAGTAGTTA TGGCATGTCT TGGGTTCGCC AGACTCCAGG              150

CAAGAGCCTG GAGTTGGTCG CAACCATTAA TAATAATGGT GATAGCACCT              200

ATTATCCAGA CAGTGTGAAG GGCCGATTCA CCATCTCCCG AGACAATGCC              250

AAGAACACCC TGTACCTGCA AATGAGCAGT CTGAAGTCTG AGGACACAGC              300

CATGTTTTAC TGTGCAAGAG CCCTCATTAG TTCGGCTACT TGGTTTGGTT              350

ACTGGGGCCA AGGGACTCTG GTCACTGTCT CTGCAGCCAA AACAACAGCC              400

CCATCTGTCT ATCCGGG                                                  417
```

(2) INFORMATION FOR SEQ ID NO:19:

(i) SEQUENCE CHARACTERISTICS:

(A) LENGTH: 130 amino acids
                    (B) TYPE: Amino Acid
                    (D) TOPOLOGY: Linear (xi) SEQUENCE DESCRIPTION: SEQ ID NO:19:

Glu Val Gln Leu Val Glu Ser Gly Gly Gly Leu Val Pro Pro Gly
 1               5                  10                  15

Gly Ser Leu Lys Leu Ser Cys Ala Ala Ser Gly Phe Ile Phe Ser
                20                  25                  30

Ser Tyr Gly Met Ser Trp Val Arg Gln Thr Pro Gly Lys Ser Leu
            35                  40                  45

Glu Leu Val Ala Thr Ile Asn Asn Asn Gly Asp Ser Thr Tyr Tyr
        50                  55                  60

Pro Asp Ser Val Lys Gly Arg Phe Thr Ile Ser Arg Asp Asn Ala
65                  70                  75

Lys Asn Thr Leu Tyr Leu Gln Met Ser Ser Leu Lys Ser Glu Asp
                80                  85                  90

Thr Ala Met Phe Tyr Cys Ala Arg Ala Leu Ile Ser Ser Ala Thr
            95                 100                 105

Trp Phe Gly Tyr Trp Gly Gln Gly Thr Leu Val Thr Val Ser Ala
        110                 115                 120

Ala Lys Thr Thr Ala Pro Ser Val Tyr Pro
    125                 130

(2) INFORMATION FOR SEQ ID NO:20:

(i) SEQUENCE CHARACTERISTICS:
            (A) LENGTH: 31 base pairs
            (B) TYPE: Nucleic Acid
            (C) STRANDEDNESS: Single
            (D) TOPOLOGY: Linear (xi) SEQUENCE DESCRIPTION: SEQ ID NO:20:

ACAAACGCGT ACGCTGATAT CGTCATGACA G                                31

(2) INFORMATION FOR SEQ ID NO:21:

(i) SEQUENCE CHARACTERISTICS:
            (A) LENGTH: 31 base pairs
            (B) TYPE: Nucleic Acid
            (C) STRANDEDNESS: Single
            (D) TOPOLOGY: Linear (xi) SEQUENCE DESCRIPTION: SEQ ID NO:21:

GCAGCATCAG CTCTTCGAAG CTCCAGCTTG G                                31

(2) INFORMATION FOR SEQ ID NO:22:

(i) SEQUENCE CHARACTERISTICS:
            (A) LENGTH: 21 base pairs
            (B) TYPE: Nucleic Acid
            (C) STRANDEDNESS: Single
            (D) TOPOLOGY: Linear (xi) SEQUENCE DESCRIPTION: SEQ ID NO:22:

CCACTAGTAC GCAAGTTCAC G                                           21

(2) INFORMATION FOR SEQ ID NO:23:

(i) SEQUENCE CHARACTERISTICS:
            (A) LENGTH: 33 base pairs
            (B) TYPE: Nucleic Acid
            (C) STRANDEDNESS: Single (D) TOPOLOGY: Linear (xi) SEQUENCE DESCRIPTION: SEQ ID NO:23:

GATGGGCCCT TGGTGGAGGC TGCAGAGACA GTG                                    33

(2) INFORMATION FOR SEQ ID NO:24:

(i) SEQUENCE CHARACTERISTICS:
        (A) LENGTH: 714 base pairs
        (B) TYPE: Nucleic Acid
        (C) STRANDEDNESS: Double
        (D) TOPOLOGY: Linear (xi) SEQUENCE DESCRIPTION: SEQ ID NO:24:

ATGAAGAAGA ATATCGCATT TCTTCTTGCA TCTATGTTCG TTTTTTCTAT                  50

TGCTACAAAC GCGTACGCTG ATATCGTCAT GACACAGTCT CAAAAATTCA                  100

TGTCCACATC AGTAGGAGAC AGGGTCAGCG TCACCTGCAA GGCCAGTCAG                  150

AATGTGGGTA CTAATGTAGC CTGGTATCAA CAGAAACCAG GGCAATCTCC                  200

TAAAGCACTG ATTTACTCGT CATCCTACCG GTACAGTGGA GTCCCTGATC                  250

GCTTCACAGG CAGTGGATCT GGGACAGATT TCACTCTCAC CATCAGCCAT                  300

GTGCAGTCTG AAGACTTGGC AGACTATTTC TGTCAGCAAT ATAACATCTA                  350

TCCTCTCACG TTCGGTCCTG GGACCAAGCT GGAGCTTCGA AGAGCTGTGG                  400

CTGCACCATC TGTCTTCATC TTCCCGCCAT CTGATGAGCA GTTGAAATCT                  450

GGAACTGCTT CTGTTGTGTG CCTGCTGAAT AACTTCTATC CCAGAGAGGC                  500

CAAAGTACAG TGGAAGGTGG ATAACGCCCT CCAATCGGGT AACTCCCAGG                  550

AGAGTGTCAC AGAGCAGGAC AGCAAGGACA GCACCTACAG CCTCAGCAGC                  600

ACCCTGACGC TGAGCAAAGC AGACTACGAG AAACACAAAG TCTACGCCTG                  650

CGAAGTCACC CATCAGGGCC TGAGCTCGCC CGTCACAAAG AGCTTCAACA                  700

GGGGAGAGTG TTAA                                                         714

(2) INFORMATION FOR SEQ ID NO:25:

(i) SEQUENCE CHARACTERISTICS:
        (A) LENGTH: 237 amino acids
        (B) TYPE: Amino Acid
        (D) TOPOLOGY: Linear (xi) SEQUENCE DESCRIPTION: SEQ ID NO:25:

Met Lys Lys Asn Ile Ala Phe Leu Leu Ala Ser Met Phe Val Phe
  1               5                  10                  15

Ser Ile Ala Thr Asn Ala Tyr Ala Asp Ile Val Met Thr Gln Ser
                 20                  25                  30

Gln Lys Phe Met Ser Thr Ser Val Gly Asp Arg Val Ser Val Thr
                 35                  40                  45

Cys Lys Ala Ser Gln Asn Val Gly Thr Asn Val Ala Trp Tyr Gln
                 50                  55                  60

Gln Lys Pro Gly Gln Ser Pro Lys Ala Leu Ile Tyr Ser Ser Ser
                 65                  70                  75

Tyr Arg Tyr Ser Gly Val Pro Asp Arg Phe Thr Gly Ser Gly Ser
                 80                  85                  90

Gly Thr Asp Phe Thr Leu Thr Ile Ser His Val Gln Ser Glu Asp
                 95                 100                 105

Leu Ala Asp Tyr Phe Cys Gln Gln Tyr Asn Ile Tyr Pro Leu Thr

```
                110                 115                 120
Phe Gly Pro Gly Thr Lys Leu Glu Leu Arg Arg Ala Val Ala Ala
                125                 130                 135
Pro Ser Val Phe Ile Phe Pro Pro Ser Asp Glu Gln Leu Lys Ser
                140                 145                 150
Gly Thr Ala Ser Val Val Cys Leu Leu Asn Asn Phe Tyr Pro Arg
                155                 160                 165
Glu Ala Lys Val Gln Trp Lys Val Asp Asn Ala Leu Gln Ser Gly
                170                 175                 180
Asn Ser Gln Glu Ser Val Thr Glu Gln Asp Ser Lys Asp Ser Thr
                185                 190                 195
Tyr Ser Leu Ser Ser Thr Leu Thr Leu Ser Lys Ala Asp Tyr Glu
                200                 205                 210
Lys His Lys Val Tyr Ala Cys Glu Val Thr His Gln Gly Leu Ser
                215                 220                 225
Ser Pro Val Thr Lys Ser Phe Asn Arg Gly Glu Cys
                230                 235     237

(2) INFORMATION FOR SEQ ID NO:26:

(i) SEQUENCE CHARACTERISTICS:
        (A) LENGTH: 756 base pairs
        (B) TYPE: Nucleic Acid
        (C) STRANDEDNESS: Double
        (D) TOPOLOGY: Linear (xi) SEQUENCE DESCRIPTION: SEQ ID NO:26:

ATGAAAAAGA ATATCGCATT TCTTCTTGCA TCTATGTTCG TTTTTTCTAT             50

TGCTACAAAC GCGTACGCTG AGGTGCAGCT GGTGGAGTCT GGGGGAGGCT            100

TAGTGCCGCC TGGAGGGTCC CTGAAACTCT CCTGTGCAGC CTCTGGATTC            150

ATATTCAGTA GTTATGGCAT GTCTTGGGTT CGCCAGACTC CAGGCAAGAG            200

CCTGGAGTTG GTCGCAACCA TTAATAATAA TGGTGATAGC ACCTATTATC            250

CAGACAGTGT GAAGGGCCGA TTCACCATCT CCCGAGACAA TGCCAAGAAC            300

ACCCTGTACC TGCAAATGAG CAGTCTGAAG TCTGAGGACA CAGCCATGTT            350

TTACTGTGCA AGAGCCCTCA TTAGTTCGGC TACTTGGTTT GGTTACTGGG            400

GCCAAGGGAC TCTGGTCACT GTCTCTGCAG CCTCCACCAA GGGCCCATCG            450

GTCTTCCCCC TGGCACCCTC CTCCAAGAGC ACCTCTGGGG CACAGCGGC             500

CCTGGGCTGC CTGGTCAAGG ACTACTTCCC CGAACCGGTG ACGGTGTCGT            550

GGAACTCAGG CGCCCTGACC AGCGGCGTGC ACACCTTCCC GGCTGTCCTA            600

CAGTCCTCAG GACTCTACTC CCTCAGCAGC GTGGTGACCG TGCCCTCCAG            650

CAGCTTGGGC ACCCAGACCT ACATCTGCAA CGTGAATCAC AAGCCCAGCA            700

ACACCAAGGT GGACAAGAAA GTTGAGCCCA AATCTTGTGA CAAAACTCAC            750

ACATGA                                                           756

(2) INFORMATION FOR SEQ ID NO:27:

(i) SEQUENCE CHARACTERISTICS:
        (A) LENGTH: 251 amino acids
        (B) TYPE: Amino Acid
        (D) TOPOLOGY: Linear (xi) SEQUENCE DESCRIPTION: SEQ ID NO:27:
```

```
Met Lys Lys Asn Ile Ala Phe Leu Leu Ala Ser Met Phe Val Phe
  1               5                  10                  15

Ser Ile Ala Thr Asn Ala Tyr Ala Glu Val Gln Leu Val Glu Ser
                 20                  25                  30

Gly Gly Gly Leu Val Pro Pro Gly Gly Ser Leu Lys Leu Ser Cys
                 35                  40                  45

Ala Ala Ser Gly Phe Ile Phe Ser Ser Tyr Gly Met Ser Trp Val
                 50                  55                  60

Arg Gln Thr Pro Gly Lys Ser Leu Glu Leu Val Ala Thr Ile Asn
                 65                  70                  75

Asn Asn Gly Asp Ser Thr Tyr Tyr Pro Asp Ser Val Lys Gly Arg
                 80                  85                  90

Phe Thr Ile Ser Arg Asp Asn Ala Lys Asn Thr Leu Tyr Leu Gln
                 95                 100                 105

Met Ser Ser Leu Lys Ser Glu Asp Thr Ala Met Phe Tyr Cys Ala
                110                 115                 120

Arg Ala Leu Ile Ser Ser Ala Thr Trp Phe Gly Tyr Trp Gly Gln
                125                 130                 135

Gly Thr Leu Val Thr Val Ser Ala Ala Ser Thr Lys Gly Pro Ser
                140                 145                 150

Val Phe Pro Leu Ala Pro Ser Ser Lys Ser Thr Ser Gly Gly Thr
                155                 160                 165

Ala Ala Leu Gly Cys Leu Val Lys Asp Tyr Phe Pro Glu Pro Val
                170                 175                 180

Thr Val Ser Trp Asn Ser Gly Ala Leu Thr Ser Gly Val His Thr
                185                 190                 195

Phe Pro Ala Val Leu Gln Ser Ser Gly Leu Tyr Ser Leu Ser Ser
                200                 205                 210

Val Val Thr Val Pro Ser Ser Ser Leu Gly Thr Gln Thr Tyr Ile
                215                 220                 225

Cys Asn Val Asn His Lys Pro Ser Asn Thr Lys Val Asp Lys Lys
                230                 235                 240

Val Glu Pro Lys Ser Cys Asp Lys Thr His Thr
                245                 250 251
```

(2) INFORMATION FOR SEQ ID NO:28:

(i) SEQUENCE CHARACTERISTICS:
        (A) LENGTH: 37 base pairs
        (B) TYPE: Nucleic Acid
        (C) STRANDEDNESS: Single
        (D) TOPOLOGY: Linear (xi) SEQUENCE DESCRIPTION: SEQ ID NO:28:

CCAATGCATA CGCTGACATC GTGATGACCC AGACCCC                      37

(2) INFORMATION FOR SEQ ID NO:29:

(i) SEQUENCE CHARACTERISTICS:
        (A) LENGTH: 37 base pairs
        (B) TYPE: Nucleic Acid
        (C) STRANDEDNESS: Single
        (D) TOPOLOGY: Linear (xi) SEQUENCE DESCRIPTION: SEQ ID NO:29:

CCAATGCATA CGCTGATATT GTGATGACTC AGACTCC                      37

(2) INFORMATION FOR SEQ ID NO:30:

(i) SEQUENCE CHARACTERISTICS:
    (A) LENGTH: 37 base pairs
    (B) TYPE: Nucleic Acid
    (C) STRANDEDNESS: Single
    (D) TOPOLOGY: Linear (xi) SEQUENCE DESCRIPTION: SEQ ID NO:30:

CCAATGCATA CGCTGACATC GTGATGACAC AGACACC                              37

(2) INFORMATION FOR SEQ ID NO:31:

(i) SEQUENCE CHARACTERISTICS:
        (A) LENGTH: 35 base pairs
        (B) TYPE: Nucleic Acid
        (C) STRANDEDNESS: Single
        (D) TOPOLOGY: Linear (xi) SEQUENCE DESCRIPTION: SEQ ID NO:31:

AGATGTCAAT TGCTCACTGG ATGGTGGGAA GATGG                                35

(2) INFORMATION FOR SEQ ID NO:32:

(i) SEQUENCE CHARACTERISTICS:
        (A) LENGTH: 32 base pairs
        (B) TYPE: Nucleic Acid
        (C) STRANDEDNESS: Single
        (D) TOPOLOGY: Linear (xi) SEQUENCE DESCRIPTION: SEQ ID NO:32:

CAAACGCGTA CGCTGAGATC CAGCTGCAGC AG                                   32

(2) INFORMATION FOR SEQ ID NO:33:

(i) SEQUENCE CHARACTERISTICS:
        (A) LENGTH: 32 base pairs
        (B) TYPE: Nucleic Acid
        (C) STRANDEDNESS: Single
        (D) TOPOLOGY: Linear (xi) SEQUENCE DESCRIPTION: SEQ ID NO:33:

CAAACGCGTA CGCTGAGATT CAGCTCCAGC AG                                   32

(2) INFORMATION FOR SEQ ID NO:34:

(i) SEQUENCE CHARACTERISTICS:
        (A) LENGTH: 391 base pairs
        (B) TYPE: Nucleic Acid
        (C) STRANDEDNESS: Double
        (D) TOPOLOGY: Linear (xi) SEQUENCE DESCRIPTION: SEQ ID NO:34:

GATATCGTGA TGACACAGAC ACCACTCTCC CTGCCTGTCA GTCTTGGAGA                50

TCAGGCCTCC ATCTCTTGCA GATCTAGTCA GAGCCTTGTA CACGGTATTG               100

GAAACACCTA TTTACATTGG TACCTGCAGA AGCCAGGCCA GTCTCCAAAG               150

CTCCTGATCT ACAAAGTTTC CAACCGATTT TCTGGGGTCC CAGACAGGTT               200

CAGTGGCAGT GGATCAGGGA CAGATTTCAC ACTCAGGATC AGCAGAGTGG               250

AGGCTGAGGA TCTGGGACTT TATTTCTGCT CTCAAAGTAC ACATGTTCCG               300

CTCACGTTCG GTGCTGGGAC CAAGCTGGAG CTGAAACGGG CTGATGCTGC               350

ACCAACTGTA TCCATCTTCC CACCATCCAG TGAGCAATTG A                        391

(2) INFORMATION FOR SEQ ID NO:35:

(i) SEQUENCE CHARACTERISTICS:
    (A) LENGTH: 131 amino acids
    (B) TYPE: Amino Acid
    (D) TOPOLOGY: Linear (xi) SEQUENCE DESCRIPTION: SEQ ID NO:35:

```
Asp Ile Val Met Thr Gln Thr Pro Leu Ser Leu Pro Val Ser Leu
1               5                   10                  15

Gly Asp Gln Ala Ser Ile Ser Cys Arg Ser Ser Gln Ser Leu Val
            20                  25                  30

His Gly Ile Gly Asn Thr Tyr Leu His Trp Tyr Leu Gln Lys Pro
            35                  40                  45

Gly Gln Ser Pro Lys Leu Leu Ile Tyr Lys Val Ser Asn Arg Phe
            50                  55                  60

Ser Gly Val Pro Asp Arg Phe Ser Gly Ser Gly Ser Gly Thr Asp
            65                  70                  75

Phe Thr Leu Arg Ile Ser Arg Val Glu Ala Glu Asp Leu Gly Leu
            80                  85                  90

Tyr Phe Cys Ser Gln Ser Thr His Val Pro Leu Thr Phe Gly Ala
            95                  100                 105

Gly Thr Lys Leu Glu Leu Lys Arg Ala Asp Ala Ala Pro Thr Val
            110                 115                 120

Ser Ile Phe Pro Pro Ser Ser Glu Gln Leu Lys
            125                 130 131
```

(2) INFORMATION FOR SEQ ID NO:36:

(i) SEQUENCE CHARACTERISTICS:
        (A) LENGTH: 405 base pairs
        (B) TYPE: Nucleic Acid
        (C) STRANDEDNESS: Single
        (D) TOPOLOGY: Linear (xi) SEQUENCE DESCRIPTION: SEQ ID NO:36:

```
GAGATTCAGC TGCAGCAGTC TGGACCTGAG CTGATGAAGC CTGGGGCTTC         50

AGTGAAGATA TCCTGCAAGG CTTCTGGTTA TTCATTCAGT AGCCACTACA        100

TGCACTGGGT GAAGCAGAGC CATGGAAAGA GCCTTGAGTG GATTGGCTAC        150

ATTGATCCTT CCAATGGTGA AACTACTTAC AACCAGAAAT TCAAGGGCAA        200

GGCCACATTG ACTGTAGACA CATCTTCCAG CACAGCCAAC GTGCATCTCA        250

GCAGCCTGAC ATCTGATGAC TCTGCAGTCT ATTTCTGTGC AAGAGGGGAC        300

TATAGATACA ACGGCGACTG GTTTTTCGAT GTCTGGGGCG CAGGGACCAC        350

GGTCACCGTC TCCTCCGCCA AAACCGACAG CCCCATCGGT CTATCCGGGC        400

CCATC                                                        405
```

(2) INFORMATION FOR SEQ ID NO:37:

(i) SEQUENCE CHARACTERISTICS:
        (A) LENGTH: 135 amino acids
        (B) TYPE: Amino Acid
        (D) TOPOLOGY: Linear (xi) SEQUENCE DESCRIPTION: SEQ ID NO:37:

```
Glu Ile Gln Leu Gln Gln Ser Gly Pro Glu Leu Met Lys Pro Gly
1               5                   10                  15

Ala Ser Val Lys Ile Ser Cys Lys Ala Ser Gly Tyr Ser Phe Ser
            20                  25                  30
```

-continued

```
Ser His Tyr Met His Trp Val Lys Gln Ser His Gly Lys Ser Leu
            35                  40                  45

Glu Trp Ile Gly Tyr Ile Asp Pro Ser Asn Gly Glu Thr Thr Tyr
        50                  55                  60

Asn Gln Lys Phe Lys Gly Lys Ala Thr Leu Thr Val Asp Thr Ser
        65                  70                  75

Ser Ser Thr Ala Asn Val His Leu Ser Ser Leu Thr Ser Asp Asp
        80                  85                  90

Ser Ala Val Tyr Phe Cys Ala Arg Gly Asp Tyr Arg Tyr Asn Gly
        95                  100                 105

Asp Trp Phe Phe Asp Val Trp Gly Ala Gly Thr Thr Val Thr Val
            110                 115                 120

Ser Ser Ala Lys Thr Asp Ser Pro Ile Gly Leu Ser Gly Pro Ile
            125                 130                 135
```

(2) INFORMATION FOR SEQ ID NO:38:

(i) SEQUENCE CHARACTERISTICS:
        (A) LENGTH: 22 base pairs
        (B) TYPE: Nucleic Acid
        (C) STRANDEDNESS: Single
        (D) TOPOLOGY: Linear (xi) SEQUENCE DESCRIPTION: SEQ ID NO:38:

CTTGGTGGAG GCGGAGGAGA CG                                  22

(2) INFORMATION FOR SEQ ID NO:39:

(i) SEQUENCE CHARACTERISTICS:
        (A) LENGTH: 38 base pairs
        (B) TYPE: Nucleic Acid
        (C) STRANDEDNESS: Single
        (D) TOPOLOGY: Linear (xi) SEQUENCE DESCRIPTION: SEQ ID NO:39:

GAAACGGGCT GTTGCTGCAC CAACTGTATT CATCTTCC                  38

(2) INFORMATION FOR SEQ ID NO:40:

(i) SEQUENCE CHARACTERISTICS:
        (A) LENGTH: 31 base pairs
        (B) TYPE: Nucleic Acid
        (C) STRANDEDNESS: Single
        (D) TOPOLOGY: Linear (xi) SEQUENCE DESCRIPTION: SEQ ID NO:40:

GTCACCGTCT CCTCCGCCTC CACCAAGGGC C                           31

(2) INFORMATION FOR SEQ ID NO:41:

(i) SEQUENCE CHARACTERISTICS:
        (A) LENGTH: 729 base pairs
        (B) TYPE: Nucleic Acid
        (C) STRANDEDNESS: Double
        (D) TOPOLOGY: Linear (xi) SEQUENCE DESCRIPTION: SEQ ID NO:41:

ATGAAGAAGA ATATCGCATT TCTTCTTGCA TCTATGTTCG TTTTTTCTAT      50

TGCTACAAAT GCATACGCTG ATATCGTGAT GACACAGACA CCACTCTCCC     100

TGCCTGTCAG TCTTGGAGAT CAGGCCTCCA TCTCTTGCAG ATCTAGTCAG     150

AGCCTTGTAC ACGGTATTGG AAACACCTAT TTACATTGGT ACCTGCAGAA     200

```
GCCAGGCCAG TCTCCAAAGC TCCTGATCTA CAAAGTTTCC AACCGATTTT         250

CTGGGGTCCC AGACAGGTTC AGTGGCAGTG GATCAGGGAC AGATTTCACA         300

CTCAGGATCA GCAGAGTGGA GGCTGAGGAT CTGGGACTTT ATTTCTGCTC         350

TCAAAGTACA CATGTTCCGC TCACGTTCGG TGCTGGGACC AAGCTGGAGC         400

TGAAACGGGC TGTTGCTGCA CCAACTGTAT TCATCTTCCC ACCATCCAGT         450

GAGCAATTGA AATCTGGAAC TGCCTCTGTT GTGTGCCTGC TGAATAACTT         500

CTATCCCAGA GAGGCCAAAG TACAGTGGAA GGTGGATAAC GCCCTCCAAT         550

CGGGTAACTC CCAGGAGAGT GTCACAGAGC AGGACAGCAA GGACAGCACC         600

TACAGCCTCA GCAGCACCCT GACGCTGAGC AAAGCAGACT ACGAGAAACA         650

CAAAGTCTAC GCCTGCGAAG TCACCCATCA GGGCCTGAGC TCGCCCGTCA         700

CAAAGAGCTT CAACAGGGGA GAGTGTTAA                                 729
```

(2) INFORMATION FOR SEQ ID NO:42:

(i) SEQUENCE CHARACTERISTICS:
        (A) LENGTH: 242 amino acids
        (B) TYPE: Amino Acid
        (D) TOPOLOGY: Linear (xi) SEQUENCE DESCRIPTION: SEQ ID NO:42:

```
Met Lys Lys Asn Ile Ala Phe Leu Leu Ala Ser Met Phe Val Phe
 1               5                  10                  15

Ser Ile Ala Thr Asn Ala Tyr Ala Asp Ile Val Met Thr Gln Thr
                20                  25                  30

Pro Leu Ser Leu Pro Val Ser Leu Gly Asp Gln Ala Ser Ile Ser
                35                  40                  45

Cys Arg Ser Ser Gln Ser Leu Val His Gly Ile Gly Asn Thr Tyr
                50                  55                  60

Leu His Trp Tyr Leu Gln Lys Pro Gly Gln Ser Pro Lys Leu Leu
                65                  70                  75

Ile Tyr Lys Val Ser Asn Arg Phe Ser Gly Val Pro Asp Arg Phe
                80                  85                  90

Ser Gly Ser Gly Ser Gly Thr Asp Phe Thr Leu Arg Ile Ser Arg
                95                 100                 105

Val Glu Ala Glu Asp Leu Gly Leu Tyr Phe Cys Ser Gln Ser Thr
               110                 115                 120

His Val Pro Leu Thr Phe Gly Ala Gly Thr Lys Leu Glu Leu Lys
               125                 130                 135

Arg Ala Val Ala Ala Pro Thr Val Phe Ile Phe Pro Pro Ser Ser
               140                 145                 150

Glu Gln Leu Lys Ser Gly Thr Ala Ser Val Val Cys Leu Leu Asn
               155                 160                 165

Asn Phe Tyr Pro Arg Glu Ala Lys Val Gln Trp Lys Val Asp Asn
               170                 175                 180

Ala Leu Gln Ser Gly Asn Ser Gln Glu Ser Val Thr Glu Gln Asp
               185                 190                 195

Ser Lys Asp Ser Thr Tyr Ser Leu Ser Ser Thr Leu Thr Leu Ser
               200                 205                 210

Lys Ala Asp Tyr Glu Lys His Lys Val Tyr Ala Cys Glu Val Thr
               215                 220                 225

His Gln Gly Leu Ser Ser Pro Val Thr Lys Ser Phe Asn Arg Gly
```

```
                    230             235             240
Glu Cys
    242

(2) INFORMATION FOR SEQ ID NO:43:

(i) SEQUENCE CHARACTERISTICS:
        (A) LENGTH: 762 base pairs
        (B) TYPE: Nucleic Acid
        (C) STRANDEDNESS: Double
        (D) TOPOLOGY: Linear (xi) SEQUENCE DESCRIPTION: SEQ ID NO:43:

ATGAAAAAGA ATATCGCATT TCTTCTTGCA TCTATGTTCG TTTTTTCTAT              50

TGCTACAAAC GCGTACGCTG AGATTCAGCT GCAGCAGTCT GGACCTGAGC             100

TGATGAAGCC TGGGGCTTCA GTGAAGATAT CCTGCAAGGC TTCTGGTTAT             150

TCATTCAGTA GCCACTACAT GCACTGGGTG AAGCAGAGCC ATGGAAAGAG             200

CCTTGAGTGG ATTGGCTACA TTGATCCTTC CAATGGTGAA ACTACTTACA             250

ACCAGAAATT CAAGGGCAAG GCCACATTGA CTGTAGACAC ATCTTCCAGC             300

ACAGCCAACG TGCATCTCAG CAGCCTGACA TCTGATGACT CTGCAGTCTA             350

TTTCTGTGCA AGAGGGGACT ATAGATACAA CGGCGACTGG TTTTTCGATG             400

TCTGGGGCGC AGGGACCACG GTCACCGTCT CCTCCGCCTC CACCAAGGGC             450

CCATCGGTCT TCCCCCTGGC ACCCTCCTCC AAGAGCACCT CTGGGGGCAC             500

AGCGGCCCTG GGCTGCCTGG TCAAGGACTA CTTCCCCGAA CCGGTGACGG             550

TGTCGTGGAA CTCAGGCGCC CTGACCAGCG GCGTGCACAC CTTCCCGGCT             600

GTCCTACAGT CCTCAGGACT CTACTCCCTC AGCAGCGTGG TGACCGTGCC             650

CTCCAGCAGC TTGGGCACCC AGACCTACAT CTGCAACGTG AATCACAAGC             700

CCAGCAACAC CAAGGTGGAC AAGAAAGTTG AGCCCAAATC TTGTGACAAA             750

ACTCACACAT GA                                                     762

(2) INFORMATION FOR SEQ ID NO:44:

(i) SEQUENCE CHARACTERISTICS:
        (A) LENGTH: 253 amino acids
        (B) TYPE: Amino Acid
        (D) TOPOLOGY: Linear (xi) SEQUENCE DESCRIPTION: SEQ ID NO:44:

Met Lys Lys Asn Ile Ala Phe Leu Leu Ala Ser Met Phe Val Phe
  1               5                  10                  15

Ser Ile Ala Thr Asn Ala Tyr Ala Glu Ile Gln Leu Gln Gln Ser
                 20                  25                  30

Gly Pro Glu Leu Met Lys Pro Gly Ala Ser Val Lys Ile Ser Cys
                 35                  40                  45

Lys Ala Ser Gly Tyr Ser Phe Ser Ser His Tyr Met His Trp Val
                 50                  55                  60

Lys Gln Ser His Gly Lys Ser Leu Glu Trp Ile Gly Tyr Ile Asp
                 65                  70                  75

Pro Ser Asn Gly Glu Thr Thr Tyr Asn Gln Lys Phe Lys Gly Lys
                 80                  85                  90

Ala Thr Leu Thr Val Asp Thr Ser Ser Thr Ala Asn Val His
                 95                 100                 105
```

```
Leu Ser Ser Leu Thr Ser Asp Asp Ser Ala Val Tyr Phe Cys Ala
                110                 115                 120

Arg Gly Asp Tyr Arg Tyr Asn Gly Asp Trp Phe Phe Asp Val Trp
                125                 130                 135

Gly Ala Gly Thr Thr Val Thr Val Ser Ala Ser Thr Lys Gly
                140                 145                 150

Pro Ser Val Phe Pro Leu Ala Pro Ser Ser Lys Ser Thr Ser Gly
                155                 160                 165

Gly Thr Ala Ala Leu Gly Cys Leu Val Lys Asp Tyr Phe Pro Glu
                170                 175                 180

Pro Val Thr Val Ser Trp Asn Ser Gly Ala Leu Thr Ser Gly Val
                185                 190                 195

His Thr Phe Pro Ala Val Leu Gln Ser Ser Gly Leu Tyr Ser Leu
                200                 205                 210

Ser Ser Val Val Thr Val Pro Ser Ser Ser Leu Gly Thr Gln Thr
                215                 220                 225

Tyr Ile Cys Asn Val Asn His Lys Pro Ser Asn Thr Lys Val Asp
                230                 235                 240

Lys Lys Val Glu Pro Lys Ser Cys Asp Lys Thr His Thr
                245                 250                 253

(2) INFORMATION FOR SEQ ID NO:45:

(i) SEQUENCE CHARACTERISTICS:
        (A) LENGTH: 114 amino acids
        (B) TYPE: Amino Acid
        (D) TOPOLOGY: Linear (xi) SEQUENCE DESCRIPTION: SEQ ID NO:45:

Asp Ile Val Met Thr Gln Thr Pro Leu Ser Leu Pro Val Ser Leu
  1              5                  10                  15

Gly Asp Gln Ala Ser Ile Ser Cys Arg Ser Ser Gln Ser Leu Val
                 20                 25                  30

His Gly Ile Gly Asn Thr Tyr Leu His Trp Tyr Leu Gln Lys Pro
                 35                 40                  45

Gly Gln Ser Pro Lys Leu Leu Ile Tyr Tyr Lys Val Ser Asn Arg
                 50                 55                  60

Phe Ser Gly Val Pro Asp Arg Phe Ser Asp Ser Gly Ser Gly Thr
                 65                 70                  75

Asp Phe Thr Leu Arg Ile Ser Arg Val Glu Ala Glu Asp Leu Gly
                 80                 85                  90

Leu Tyr Phe Cys Ser Gln Ser Thr His Val Pro Leu Thr Phe Gly
                 95                 100                 105

Ala Gly Thr Lys Leu Glu Leu Lys Arg
                 110                114

(2) INFORMATION FOR SEQ ID NO:46:

(i) SEQUENCE CHARACTERISTICS:
        (A) LENGTH: 114 amino acids
        (B) TYPE: Amino Acid
        (D) TOPOLOGY: Linear (xi) SEQUENCE DESCRIPTION: SEQ ID NO:46:

Asp Ile Gln Met Thr Gln Ser Pro Ser Ser Leu Ser Ala Ser Val
  1              5                  10                  15

Gly Asp Arg Val Thr Ile Thr Cys Arg Ser Ser Gln Ser Leu Val
                 20                 25                  30
```

His Gly Ile Gly Asn Thr Tyr Leu His Trp Tyr Gln Gln Lys Pro
            35                  40                  45

Gly Lys Ala Pro Lys Leu Leu Ile Tyr Tyr Lys Val Ser Asn Arg
            50                  55                  60

Phe Ser Gly Val Pro Ser Arg Phe Ser Gly Ser Gly Ser Gly Thr
            65                  70                  75

Asp Phe Thr Leu Thr Ile Ser Ser Leu Gln Pro Glu Asp Phe Ala
            80                  85                  90

Thr Tyr Tyr Cys Ser Gln Ser Thr His Val Pro Leu Thr Phe Gly
            95                 100                 105

Gln Gly Thr Lys Val Glu Ile Lys Arg
            110             114

(2) INFORMATION FOR SEQ ID NO:47:

(i) SEQUENCE CHARACTERISTICS:
        (A) LENGTH: 109 amino acids
        (B) TYPE: Amino Acid
        (D) TOPOLOGY: Linear (xi) SEQUENCE DESCRIPTION: SEQ ID NO:47:

Asp Ile Gln Met Thr Gln Ser Pro Ser Ser Leu Ser Ala Ser Val
 1               5                  10                  15

Gly Asp Arg Val Thr Ile Thr Cys Arg Ala Ser Lys Thr Ile Ser
            20                  25                  30

Lys Tyr Leu Ala Trp Tyr Gln Gln Lys Pro Gly Lys Ala Pro Lys
            35                  40                  45

Leu Leu Ile Tyr Tyr Ser Gly Ser Thr Leu Glu Ser Gly Val Pro
            50                  55                  60

Ser Arg Phe Ser Gly Ser Gly Ser Gly Thr Asp Phe Thr Leu Thr
            65                  70                  75

Ile Ser Ser Leu Gln Pro Glu Asp Phe Ala Thr Tyr Tyr Cys Gln
            80                  85                  90

Gln His Asn Glu Tyr Pro Leu Thr Phe Gly Gln Gly Thr Lys Val
            95                 100                 105

Glu Ile Lys Arg
          109

(2) INFORMATION FOR SEQ ID NO:48:

(i) SEQUENCE CHARACTERISTICS:
        (A) LENGTH: 117 amino acids
        (B) TYPE: Amino Acid
        (D) TOPOLOGY: Linear (xi) SEQUENCE DESCRIPTION: SEQ ID NO:48:

Glu Ile Gln Leu Gln Gln Ser Gly Pro Glu Leu Met Lys Pro Gly
 1               5                  10                  15

Ala Ser Val Lys Ile Ser Cys Lys Ala Ser Gly Tyr Ser Phe Ser
            20                  25                  30

Ser His Tyr Met His Trp Val Lys Gln Ser His Gly Lys Ser Leu
            35                  40                  45

Glu Trp Ile Gly Tyr Ile Asp Pro Ser Asn Gly Glu Thr Thr Tyr
            50                  55                  60

Asn Gln Lys Phe Lys Gly Lys Ala Thr Leu Thr Val Asp Thr Ser
            65                  70                  75

Ser Ser Thr Ala Asn Val His Leu Ser Ser Leu Thr Ser Asp Asp

-continued

```
                 80                  85                  90

Ser Ala Val Tyr Phe Cys Ala Ala Arg Gly Asp Tyr Arg Tyr Asn
                 95                 100                 105

Gly Asp Trp Phe Phe Asp Val Trp Gly Ala Gly Thr
                110                 115     117
```

(2) INFORMATION FOR SEQ ID NO:49:

(i) SEQUENCE CHARACTERISTICS:
        (A) LENGTH: 117 amino acids
        (B) TYPE: Amino Acid
        (D) TOPOLOGY: Linear (xi) SEQUENCE DESCRIPTION: SEQ ID NO:49:

```
Glu Val Gln Leu Val Glu Ser Gly Gly Gly Leu Val Gln Pro Gly
 1                   5                  10                  15

Gly Ser Leu Arg Leu Ser Cys Ala Ala Ser Gly Tyr Ser Phe Ser
                 20                  25                  30

Ser His Tyr Met His Trp Val Arg Gln Ala Pro Gly Lys Gly Leu
                 35                  40                  45

Glu Trp Val Gly Tyr Ile Asp Pro Ser Asn Gly Glu Thr Thr Tyr
                 50                  55                  60

Asn Gln Lys Phe Lys Gly Arg Phe Thr Ile Ser Arg Asp Asn Ser
                 65                  70                  75

Lys Asn Thr Leu Tyr Leu Gln Met Asn Ser Leu Arg Ala Glu Asp
                 80                  85                  90

Thr Ala Val Tyr Tyr Cys Ala Ala Arg Gly Asp Tyr Arg Tyr Asn
                 95                 100                 105

Gly Asp Trp Phe Phe Asp Val Trp Gly Gln Gly Thr
                110                 115     117
```

(2) INFORMATION FOR SEQ ID NO:50:

(i) SEQUENCE CHARACTERISTICS:
        (A) LENGTH: 116 amino acids
        (B) TYPE: Amino Acid
        (D) TOPOLOGY: Linear (xi) SEQUENCE DESCRIPTION: SEQ ID NO:50:

```
Glu Val Gln Leu Val Glu Ser Gly Gly Gly Leu Val Gln Pro Gly
 1                   5                  10                  15

Gly Ser Leu Arg Leu Ser Cys Ala Ala Ser Gly Phe Ser Phe Thr
                 20                  25                  30

Gly His Trp Met Asn Trp Val Arg Gln Ala Pro Gly Lys Gly Leu
                 35                  40                  45

Glu Trp Val Gly Met Ile His Pro Ser Asp Ser Glu Thr Arg Tyr
                 50                  55                  60

Ala Asp Ser Val Lys Gly Arg Phe Thr Ile Ser Arg Asp Asn Ser
                 65                  70                  75

Lys Asn Thr Leu Tyr Leu Gln Met Asn Ser Leu Arg Ala Glu Asp
                 80                  85                  90

Thr Ala Val Tyr Tyr Cys Ala Ala Arg Gly Ile Tyr Phe Tyr Gly
                 95                 100                 105

Thr Thr Tyr Phe Asp Tyr Trp Gly Gln Gly Thr
                110                 115 116
```

(2) INFORMATION FOR SEQ ID NO:51:

(i) SEQUENCE CHARACTERISTICS:
        (A) LENGTH: 242 amino acids
        (B) TYPE: Amino Acid
        (D) TOPOLOGY: Linear (xi) SEQUENCE DESCRIPTION: SEQ ID NO:51:

Met Lys Lys Asn Ile Ala Phe Leu Leu Ala Ser Met Phe Val Phe
 1               5                  10                  15

Ser Ile Ala Thr Asn Ala Tyr Ala Asp Ile Gln Met Thr Gln Ser
                20                  25                  30

Pro Ser Ser Leu Ser Ala Ser Val Gly Asp Arg Val Thr Ile Thr
                35                  40                  45

Cys Arg Ser Ser Gln Ser Leu Val His Gly Ile Gly Asn Thr Tyr
                50                  55                  60

Leu His Trp Tyr Gln Gln Lys Pro Gly Lys Ala Pro Lys Leu Leu
                65                  70                  75

Ile Tyr Lys Val Ser Asn Arg Phe Ser Gly Val Pro Ser Arg Phe
                80                  85                  90

Ser Gly Ser Gly Ser Gly Thr Asp Phe Thr Leu Thr Ile Ser Ser
                95                 100                 105

Leu Gln Pro Glu Asp Phe Ala Thr Tyr Tyr Cys Ser Gln Ser Thr
               110                 115                 120

His Val Pro Leu Thr Phe Gly Gln Gly Thr Lys Val Glu Ile Lys
               125                 130                 135

Arg Thr Val Ala Ala Pro Ser Val Phe Ile Phe Pro Pro Ser Asp
               140                 145                 150

Glu Gln Leu Lys Ser Gly Thr Ala Ser Val Val Cys Leu Leu Asn
               155                 160                 165

Asn Phe Tyr Pro Arg Glu Ala Lys Val Gln Trp Lys Val Asp Asn
               170                 175                 180

Ala Leu Gln Ser Gly Asn Ser Gln Glu Ser Val Thr Glu Gln Asp
               185                 190                 195

Ser Lys Asp Ser Thr Tyr Ser Leu Ser Ser Thr Leu Thr Leu Ser
               200                 205                 210

Lys Ala Asp Tyr Glu Lys His Lys Val Tyr Ala Cys Glu Val Thr
               215                 220                 225

His Gln Gly Leu Ser Ser Pro Val Thr Lys Ser Phe Asn Arg Gly
               230                 235                 240

Glu Cys
   242

(2) INFORMATION FOR SEQ ID NO:52:

(i) SEQUENCE CHARACTERISTICS:
        (A) LENGTH: 253 amino acids
        (B) TYPE: Amino Acid
        (D) TOPOLOGY: Linear (xi) SEQUENCE DESCRIPTION: SEQ ID NO:52:

Met Lys Lys Asn Ile Ala Phe Leu Leu Ala Ser Met Phe Val Phe
 1               5                  10                  15

Ser Ile Ala Thr Asn Ala Tyr Ala Glu Val Gln Leu Val Gln Ser
                20                  25                  30

Gly Gly Gly Leu Val Gln Pro Gly Gly Ser Leu Arg Leu Ser Cys
                35                  40                  45

Ala Ala Ser Gly Tyr Ser Phe Ser Ser His Tyr Met His Trp Val
                50                  55                  60

```
Arg Gln Ala Pro Gly Lys Gly Leu Glu Trp Val Gly Tyr Ile Asp
                65                  70                  75

Pro Ser Asn Gly Glu Thr Thr Tyr Asn Gln Lys Phe Lys Gly Arg
                80                  85                  90

Phe Thr Leu Ser Arg Asp Asn Ser Lys Asn Thr Ala Tyr Leu Gln
                95                  100                 105

Met Asn Ser Leu Arg Ala Glu Asp Thr Ala Val Tyr Tyr Cys Ala
                110                 115                 120

Arg Gly Asp Tyr Arg Tyr Asn Gly Asp Trp Phe Phe Asp Val Trp
                125                 130                 135

Gly Gln Gly Thr Leu Val Thr Val Ser Ala Ser Thr Lys Gly
                140                 145                 150

Pro Ser Val Phe Pro Leu Ala Pro Ser Ser Lys Ser Thr Ser Gly
                155                 160                 165

Gly Thr Ala Ala Leu Gly Cys Leu Val Lys Asp Tyr Phe Pro Glu
                170                 175                 180

Pro Val Thr Val Ser Trp Asn Ser Gly Ala Leu Thr Ser Gly Val
                185                 190                 195

His Thr Phe Pro Ala Val Leu Gln Ser Ser Gly Leu Tyr Ser Leu
                200                 205                 210

Ser Ser Val Val Thr Val Pro Ser Ser Ser Leu Gly Thr Gln Thr
                215                 220                 225

Tyr Ile Cys Asn Val Asn His Lys Pro Ser Asn Thr Lys Val Asp
                230                 235                 240

Lys Lys Val Glu Pro Lys Ser Cys Asp Lys Thr His Thr
                245                 250         253

(2) INFORMATION FOR SEQ ID NO:53:

(i) SEQUENCE CHARACTERISTICS:
        (A) LENGTH: 159 amino acids
        (B) TYPE: Amino Acid
        (D) TOPOLOGY: Linear (xi) SEQUENCE DESCRIPTION: SEQ ID NO:53:

Ser Gly Gly Gly Ser Gly Ser Gly Asp Phe Asp Tyr Glu Lys Met
 1               5                  10                  15

Ala Asn Ala Asn Lys Gly Ala Met Thr Glu Asn Ala Asp Glu Asn
                20                  25                  30

Ala Leu Gln Ser Asp Ala Lys Gly Lys Leu Asp Ser Val Ala Thr
                35                  40                  45

Asp Tyr Gly Ala Ala Ile Asp Gly Phe Ile Gly Asp Val Ser Gly
                50                  55                  60

Leu Ala Asn Gly Asn Gly Ala Thr Gly Asp Phe Ala Gly Ser Ser
                65                  70                  75

Asn Ser Gln Met Ala Gln Val Gly Asp Gly Asp Asn Ser Pro Leu
                80                  85                  90

Met Asn Asn Phe Arg Gln Tyr Leu Pro Ser Leu Pro Gln Ser Val
                95                  100                 105

Glu Cys Arg Pro Phe Val Phe Ser Ala Gly Lys Pro Tyr Glu Phe
                110                 115                 120

Ser Ile Asp Cys Asp Lys Ile Asn Leu Phe Arg Gly Val Phe Ala
                125                 130                 135

Phe Leu Leu Tyr Val Ala Thr Phe Met Tyr Val Phe Ser Thr Phe
                140                 145                 150
```

Ala Asn Ile Leu Arg Asn Lys Glu Ser
          155               159

(2) INFORMATION FOR SEQ ID NO:54:

(i) SEQUENCE CHARACTERISTICS:
        (A) LENGTH: 780 base pairs
        (B) TYPE: Nucleic Acid
        (C) STRANDEDNESS: Single
        (D) TOPOLOGY: Linear (xi) SEQUENCE DESCRIPTION: SEQ ID NO:54:

| | | | | | |
|---|---|---|---|---|---|
| ATGAAAAAGA | ATATCGCATT | TCTTCTTGCA | TCTATGTTCG | TTTTTTCTAT | 50 |
| TGCTACAAAC | GCATACGCTG | ATATCCAGAT | GACCCAGTCC | CCGAGCTCCC | 100 |
| TGTCCGCCTC | TGTGGGCGAT | AGGGTCACCA | TCACCTGCAG | GTCAAGTCAA | 150 |
| AGCTTAGTAC | ATGGTATAGG | TAACACGTAT | TTACACTGGT | ATCAACAGAA | 200 |
| ACCAGGAAAA | GCTCCGAAAC | TACTGATTTA | CAAAGTATCC | AATCGATTCT | 250 |
| CTGGAGTCCC | TTCTCGCTTC | TCTGGATCCG | GTTCTGGGAC | GGATTTCACT | 300 |
| CTGACCATCA | GCAGTCTGCA | GCCAGAAGAC | TTCGCAACTT | ATTACTGTTC | 350 |
| ACAGAGTACT | CATGTCCCGC | TCACGTTTGG | ACAGGGTACC | AAGGTGGAGA | 400 |
| TCAAACGAAC | TGTGGCTGCA | CCATCTGTCT | TCATCTTCCC | GCCATCTGAT | 450 |
| GAGCAGTTGA | AATCTGGAAC | TGCTTCTGTT | GTGTGCCTGC | TGAATAACTT | 500 |
| CTATCCCAGA | GAGGCCAAAG | TACAGTGGAA | GGTGGATAAC | GCCCTCCAAT | 550 |
| CGGGTAACTC | CCAGGAGAGT | GTCACAGAGC | AGGACAGCAA | GGACAGCACC | 600 |
| TACAGCCTCA | GCAGCACCCT | GACGCTGAGC | AAAGCAGACT | ACGAGAAACA | 650 |
| CAAAGTCTAC | GCCTGCGAAG | TCACCCATCA | GGGCCTGAGC | TCGCCCGTCA | 700 |
| CAAAGAGCTT | CAACAGGGGA | GAGTGTTAAG | CTGATCCTCT | ACGCCGGACG | 750 |
| CATCGTGGCC | CTAGTACGCA | ACTAGTCGTA | | | 780 |

(2) INFORMATION FOR SEQ ID NO:55:

(i) SEQUENCE CHARACTERISTICS:
        (A) LENGTH: 253 amino acids
        (B) TYPE: Amino Acid
        (D) TOPOLOGY: Linear (xi) SEQUENCE DESCRIPTION: SEQ ID NO:55:

Met Lys Lys Asn Ile Ala Phe Leu Leu Ala Ser Met Phe Val Phe
 1             5                10             15

Ser Ile Ala Thr Asn Ala Tyr Ala Glu Val Gln Leu Val Glu Ser
           20             25             30

Gly Gly Gly Leu Val Gln Pro Gly Gly Ser Leu Arg Leu Ser Cys
           35             40             45

Ala Ala Ser Gly Tyr Ser Phe Ser Ser His Tyr Met His Trp Val
           50             55             60

Lys Gln Ala Pro Gly Lys Gly Leu Glu Trp Val Gly Tyr Ile Asp
           65             70             75

Pro Ser Asn Gly Glu Thr Thr Tyr Asn Gln Lys Phe Lys Gly Arg
           80             85             90

Phe Thr Leu Ser Arg Asp Asn Ser Lys Asn Thr Ala Tyr Leu Gln
           95            100           105

Met Asn Ser Leu Arg Ala Glu Asp Thr Ala Val Tyr Tyr Cys Ala

-continued

```
                        110                 115                 120
Arg Gly Asp Tyr Arg Tyr Asn Gly Asp Trp Phe Phe Asp Val Trp
                    125                 130                 135
Gly Gln Gly Thr Leu Val Thr Val Ser Ser Ala Ser Thr Lys Gly
                    140                 145                 150
Pro Ser Val Phe Pro Leu Ala Pro Ser Ser Lys Ser Thr Ser Gly
                    155                 160                 165
Gly Thr Ala Ala Leu Gly Cys Leu Val Lys Asp Tyr Phe Pro Glu
                    170                 175                 180
Pro Val Thr Val Ser Trp Asn Ser Gly Ala Leu Thr Ser Gly Val
                    185                 190                 195
His Thr Phe Pro Ala Val Leu Gln Ser Ser Gly Leu Tyr Ser Leu
                    200                 205                 210
Ser Ser Val Val Thr Val Pro Ser Ser Ser Leu Gly Thr Gln Thr
                    215                 220                 225
Tyr Ile Cys Asn Val Asn His Lys Pro Ser Asn Thr Lys Val Asp
                    230                 235                 240
Lys Lys Val Glu Pro Lys Ser Cys Asp Lys Thr His Thr
                    245                 250         253

(2) INFORMATION FOR SEQ ID NO:56:

(i) SEQUENCE CHARACTERISTICS:
        (A) LENGTH: 242 amino acids
        (B) TYPE: Amino Acid
        (D) TOPOLOGY: Linear (xi) SEQUENCE DESCRIPTION: SEQ ID NO:56:

Met Lys Lys Asn Ile Ala Phe Leu Leu Ala Ser Met Phe Val Phe
 1               5                  10                  15
Ser Ile Ala Thr Asn Ala Tyr Ala Asp Ile Gln Met Thr Gln Ser
                20                  25                  30
Pro Ser Ser Leu Ser Ala Ser Val Gly Asp Arg Val Thr Ile Thr
                35                  40                  45
Cys Arg Ser Ser Gln Ser Leu Val His Gly Ile Gly Ala Thr Tyr
                50                  55                  60
Leu His Trp Tyr Gln Gln Lys Pro Gly Lys Ala Pro Lys Leu Leu
                65                  70                  75
Ile Tyr Lys Val Ser Asn Arg Phe Ser Gly Val Pro Ser Arg Phe
                80                  85                  90
Ser Gly Ser Gly Ser Gly Thr Asp Phe Thr Leu Thr Ile Ser Ser
                95                  100                 105
Leu Gln Pro Glu Asp Phe Ala Thr Tyr Tyr Cys Ser Gln Ser Thr
                110                 115                 120
His Val Pro Leu Thr Phe Gly Gln Gly Thr Lys Val Glu Ile Lys
                125                 130                 135
Arg Thr Val Ala Ala Pro Ser Val Phe Ile Phe Pro Pro Ser Asp
                140                 145                 150
Glu Gln Leu Lys Ser Gly Thr Ala Ser Val Val Cys Leu Leu Asn
                155                 160                 165
Asn Phe Tyr Pro Arg Glu Ala Lys Val Gln Trp Lys Val Asp Asn
                170                 175                 180
Ala Leu Gln Ser Gly Asn Ser Gln Glu Ser Val Thr Glu Gln Asp
                185                 190                 195
Ser Lys Asp Ser Thr Tyr Ser Leu Ser Ser Thr Leu Thr Leu Ser
```

```
                200              205              210
Lys Ala Asp Tyr Glu Lys His Lys Val Tyr Ala Cys Glu Val Thr
                215              220              225
His Gln Gly Leu Ser Ser Pro Val Thr Lys Ser Phe Asn Arg Gly
                230              235              240
Glu Cys
    242
```

(2) INFORMATION FOR SEQ ID NO:57:

(i) SEQUENCE CHARACTERISTICS:
        (A) LENGTH: 45 amino acids
        (B) TYPE: Amino Acid
        (D) TOPOLOGY: Linear (xi) SEQUENCE DESCRIPTION: SEQ ID NO:57:

```
Cys Pro Pro Cys Pro Ala Pro Glu Leu Leu Gly Gly Arg Met Lys
  1              5               10               15
Gln Leu Glu Asp Lys Val Glu Glu Leu Leu Ser Lys Asn Tyr His
                20               25               30
Leu Glu Asn Glu Val Ala Arg Leu Lys Lys Leu Val Gly Glu Arg
                35               40               45
```

(2) INFORMATION FOR SEQ ID NO:58:

(i) SEQUENCE CHARACTERISTICS:
        (A) LENGTH: 780 base pairs
        (B) TYPE: Nucleic Acid
        (C) STRANDEDNESS: Single
        (D) TOPOLOGY: Linear (xi) SEQUENCE DESCRIPTION: SEQ ID NO:58:

| | |
|---|---:|
| ATGAAAAAGA ATATCGCATT TCTTCTTGCA TCTATGTTCG TTTTTTCTAT | 50 |
| TGCTACAAAC GCATACGCTG ATATCCAGAT GACCCAGTCC CCGAGCTCCC | 100 |
| TGTCCGCCTC TGTGGGCGAT AGGGTCACCA TCACCTGCAG GTCAAGTCAA | 150 |
| AGCTTAGTAC ATGGTATAGG TGCTACGTAT TTACACTGGT ATCAACAGAA | 200 |
| ACCAGGAAAA GCTCCGAAAC TACTGATTTA CAAAGTATCC AATCGATTCT | 250 |
| CTGGAGTCCC TTCTCGCTTC TCTGGATCCG GTTCTGGGAC GGATTTCACT | 300 |
| CTGACCATCA GCAGTCTGCA GCCAGAAGAC TTCGCAACTT ATTACTGTTC | 350 |
| ACAGAGTACT CATGTCCCGC TCACGTTTGG ACAGGGTACC AAGGTGGAGA | 400 |
| TCAAACGAAC TGTGGCTGCA CCATCTGTCT TCATCTTCCC GCCATCTGAT | 450 |
| GAGCAGTTGA AATCTGGAAC TGCTTCTGTT GTGTGCCTGC TGAATAACTT | 500 |
| CTATCCCAGA GAGGCCAAAG TACAGTGGAA GGTGGATAAC GCCCTCCAAT | 550 |
| CGGGTAACTC CCAGGAGAGT GTCACAGAGC AGGACAGCAA GGACAGCACC | 600 |
| TACAGCCTCA GCAGCACCCT GACGCTGAGC AAAGCAGACT ACGAGAAACA | 650 |
| CAAAGTCTAC GCCTGCGAAG TCACCCATCA GGGCCTGAGC TCGCCCGTCA | 700 |
| CAAAGAGCTT CAACAGGGGA GAGTGTTAAG CTGATCCTCT ACGCCGGACG | 750 |
| CATCGTGGCC CTAGTACGCA ACTAGTCGTA | 780 |

(2) INFORMATION FOR SEQ ID NO:59:

(i) SEQUENCE CHARACTERISTICS:
        (A) LENGTH: 927 base pairs
        (B) TYPE: Nucleic Acid (C) STRANDEDNESS: Single
        (D) TOPOLOGY: Linear (xi) SEQUENCE DESCRIPTION: SEQ ID NO:59:

| | | | | | |
|---|---|---|---|---|---|
| AAAAGGGTAT | CTAGAGGTTG | AGGTGATTTT | ATGAAAAAGA | ATATCGCATT | 50 |
| TCTTCTTGCA | TCTATGTTCG | TTTTTTCTAT | TGCTACAAAC | GCGTACGCTG | 100 |
| AGGTTCAGCT | AGTGCAGTCT | GGCGGTGGCC | TGGTGCAGCC | AGGGGGCTCA | 150 |
| CTCCGTTTGT | CCTGTGCAGC | TTCTGGCTAC | TCCTTCTCGA | GTCACTATAT | 200 |
| GCACTGGGTC | CGTCAGGCCC | CGGGTAAGGG | CCTGGAATGG | GTTGGATATA | 250 |
| TTGATCCTTC | CAATGGTGAA | ACTACGTATA | ATCAAAAGTT | CAAGGGCCGT | 300 |
| TTCACTTTAT | CTCGCGACAA | CTCCAAAAAC | ACAGCATACC | TGCAGATGAA | 350 |
| CAGCCTGCGT | GCTGAGGACA | CTGCCGTCTA | TTACTGTGCA | AGAGGGGATT | 400 |
| ATCGCTACAA | TGGTGACTGG | TTCTTCGACG | TCTGGGGTCA | AGGAACCCTG | 450 |
| GTCACCGTCT | CCTCGGCCTC | CACCAAGGGC | CCATCGGTCT | TCCCCCTGGC | 500 |
| ACCCTCCTCC | AAGAGCACCT | CTGGGGGCAC | AGCGGCCCTG | GGCTGCCTGG | 550 |
| TCAAGGACTA | CTTCCCCGAA | CCGGTGACGG | TGTCGTGGAA | CTCAGGCGCC | 600 |
| CTGACCAGCG | GCGTGCACAC | CTTCCCGGCT | GTCCTACAGT | CCTCAGGACT | 650 |
| CTACTCCCTC | AGCAGCGTGG | TGACCGTGCC | CTCCAGCAGC | TTGGGCACCC | 700 |
| AGACCTACAT | CTGCAACGTG | AATCACAAGC | CCAGCAACAC | CAAGGTCGAC | 750 |
| AAGAAAGTTG | AGCCCAAATC | TTGTGACAAA | ACTCACACAT | GCCCGCCGTG | 800 |
| CCCAGCACCA | GAACTGCTGG | GCGGCCGCAT | GAAACAGCTA | GAGGACAAGG | 850 |
| TCGAAGAGCT | ACTCTCCAAG | AACTACCACC | TAGAGAATGA | AGTGGCAAGA | 900 |
| CTCAAAAAGC | TTGTCGGGGA | GCGCTAA | | | 927 |

(2) INFORMATION FOR SEQ ID NO:60:

(i) SEQUENCE CHARACTERISTICS:
        (A) LENGTH: 298 amino acids
        (B) TYPE: Amino Acid
        (D) TOPOLOGY: Linear (xi) SEQUENCE DESCRIPTION: SEQ ID NO:60:

Met Lys Lys Asn Ile Ala Phe Leu Leu Ala Ser Met Phe Val Phe
  1               5                  10                  15

Ser Ile Ala Thr Asn Ala Tyr Ala Glu Val Gln Leu Val Gln Ser
                 20                  25                  30

Gly Gly Gly Leu Val Gln Pro Gly Gly Ser Leu Arg Leu Ser Cys
                 35                  40                  45

Ala Ala Ser Gly Tyr Ser Phe Ser Ser His Tyr Met His Trp Val
                 50                  55                  60

Arg Gln Ala Pro Gly Lys Gly Leu Glu Trp Val Gly Tyr Ile Asp
                 65                  70                  75

Pro Ser Asn Gly Glu Thr Thr Tyr Asn Gln Lys Phe Lys Gly Arg
                 80                  85                  90

Phe Thr Leu Ser Arg Asp Asn Ser Lys Asn Thr Ala Tyr Leu Gln
                 95                 100                 105

Met Asn Ser Leu Arg Ala Glu Asp Thr Ala Val Tyr Tyr Cys Ala
                110                 115                 120

Arg Gly Asp Tyr Arg Tyr Asn Gly Asp Trp Phe Phe Asp Val Trp
                125                 130                 135

```
Gly Gln Gly Thr Leu Val Thr Val Ser Ser Ala Ser Thr Lys Gly
                140                 145                 150

Pro Ser Val Phe Pro Leu Ala Pro Ser Ser Lys Ser Thr Ser Gly
                155                 160                 165

Gly Thr Ala Ala Leu Gly Cys Leu Val Lys Asp Tyr Phe Pro Glu
                170                 175                 180

Pro Val Thr Val Ser Trp Asn Ser Gly Ala Leu Thr Ser Gly Val
                185                 190                 195

His Thr Phe Pro Ala Val Leu Gln Ser Ser Gly Leu Tyr Ser Leu
                200                 205                 210

Ser Ser Val Val Thr Val Pro Ser Ser Ser Leu Gly Thr Gln Thr
                215                 220                 225

Tyr Ile Cys Asn Val Asn His Lys Pro Ser Asn Thr Lys Val Asp
                230                 235                 240

Lys Lys Val Glu Pro Lys Ser Cys Asp Lys Thr His Thr Cys Pro
                245                 250                 255

Pro Cys Pro Ala Pro Glu Leu Leu Gly Gly Arg Met Lys Gln Leu
                260                 265                 270

Glu Asp Lys Val Glu Glu Leu Leu Ser Lys Asn Tyr His Leu Glu
                275                 280                 285

Asn Glu Val Ala Arg Leu Lys Lys Leu Val Gly Glu Arg
                290                 295         298

(2) INFORMATION FOR SEQ ID NO:61:

(i) SEQUENCE CHARACTERISTICS:
        (A) LENGTH: 6563 base pairs
        (B) TYPE: Nucleic Acid
        (C) STRANDEDNESS: Single
        (D) TOPOLOGY: Linear (xi) SEQUENCE DESCRIPTION: SEQ ID NO:61:

GAATTCAACT TCTCCATACT TTGGATAAGG AAATACAGAC ATGAAAAATC            50

TCATTGCTGA GTTGTTATTT AAGCTTGCCC AAAAAGAAGA AGAGTCGAAT           100

GAACTGTGTG CGCAGGTAGA AGCTTTGGAG ATTATCGTCA CTGCAATGCT           150

TCGCAATATG GCGCAAAATG ACCAACAGCG GTTGATTGAT CAGGTAGAGG           200

GGGCGCTGTA CGAGGTAAAG CCCGATGCCA GCATTCCTGA CGACGATACG           250

GAGCTGCTGC GCGATTACGT AAAGAAGTTA TTGAAGCATC CTCGTCAGTA           300

AAAAGTTAAT CTTTTCAACA GCTGTCATAA AGTTGTCACG GCCGAGACTT           350

ATAGTCGCTT TGTTTTTATT TTTTAATGTA TTTGTAACTA GAATTCGAGC           400

TCGGTACCCG GGGATCCTCT CGAGGTTGAG GTGATTTTAT GAAAAAGAAT           450

ATCGCATTTC TTCTTGCATC TATGTTCGTT TTTTCTATTG CTACAAACGC           500

ATACGCTGAT ATCCAGATGA CCCAGTCCCC GAGCTCCCTG TCCGCCTCTG           550

TGGGCGATAG GGTCACCATC ACCTGCAGGT CAAGTCAAAG CTTAGTACAT           600

GGTATAGGTG CTACGTATTT ACACTGGTAT CAACAGAAAC CAGGAAAAGC           650

TCCGAAACTA CTGATTTACA AGTATCCAA TCGATTCTCT GGAGTCCCTT           700

CTCGCTTCTC TGGATCCGGT TCTGGGACGG ATTTCACTCT GACCATCAGC           750

AGTCTGCAGC CAGAAGACTT CGCAACTTAT TACTGTTCAC AGAGTACTCA           800

TGTCCCGCTC ACGTTTGGAC AGGGTACCAA GGTGGAGATC AAACGAACTG           850
```

| | |
|---|---|
| TGGCTGCACC ATCTGTCTTC ATCTTCCCGC CATCTGATGA GCAGTTGAAA | 900 |
| TCTGGAACTG CTTCTGTTGT GTGCCTGCTG AATAACTTCT ATCCCAGAGA | 950 |
| GGCCAAAGTA CAGTGGAAGG TGGATAACGC CCTCCAATCG GGTAACTCCC | 1000 |
| AGGAGAGTGT CACAGAGCAG GACAGCAAGG ACAGCACCTA CAGCCTCAGC | 1050 |
| AGCACCCTGA CGCTGAGCAA AGCAGACTAC GAGAAACACA AAGTCTACGC | 1100 |
| CTGCGAAGTC ACCCATCAGG GCCTGAGCTC GCCCGTCACA AAGAGCTTCA | 1150 |
| ACAGGGGAGA GTGTTAAGCT GATCCTCTAC GCCGGACGCA TCGTGGCCCT | 1200 |
| AGTACGCAAC TAGTCGTAAA AAGGGTATCT AGAGGTTGAG GTGATTTTAT | 1250 |
| GAAAAAGAAT ATCGCATTTC TTCTTGCATC TATGTTCGTT TTTTCTATTG | 1300 |
| CTACAAACGC GTACGCTGAG GTTCAGCTAG TGCAGTCTGG CGGTGGCCTG | 1350 |
| GTGCAGCCAG GGGGCTCACT CCGTTTGTCC TGTGCAGCTT CTGGCTACTC | 1400 |
| CTTCTCGAGT CACTATATGC ACTGGGTCCG TCAGGCCCCG GGTAAGGGCC | 1450 |
| TGGAATGGGT TGGATATATT GATCCTTCCA ATGGTGAAAC TACGTATAAT | 1500 |
| CAAAAGTTCA AGGGCCGTTT CACTTTATCT CGCGACAACT CCAAAAACAC | 1550 |
| AGCATACCTG CAGATGAACA GCCTGCGTGC TGAGGACACT GCCGTCTATT | 1600 |
| ACTGTGCAAG AGGGGATTAT CGCTACAATG GTGACTGGTT CTTCGACGTC | 1650 |
| TGGGGTCAAG GAACCCTGGT CACCGTCTCC TCGGCCTCCA CCAAGGGCCC | 1700 |
| ATCGGTCTTC CCCCTGGCAC CCTCCTCCAA GAGCACCTCT GGGGGCACAG | 1750 |
| CGGCCCTGGG CTGCCTGGTC AAGGACTACT TCCCCGAACC GGTGACGGTG | 1800 |
| TCGTGGAACT CAGGCGCCCT GACCAGCGGC GTGCACACCT TCCCGGCTGT | 1850 |
| CCTACAGTCC TCAGGACTCT ACTCCCTCAG CAGCGTGGTG ACCGTGCCCT | 1900 |
| CCAGCAGCTT GGGCACCCAG ACCTACATCT GCAACGTGAA TCACAAGCCC | 1950 |
| AGCAACACCA AGGTCGACAA GAAAGTTGAG CCCAAATCTT GTGACAAAAC | 2000 |
| TCACACATGC CCGCCGTGCC CAGCACCAGA ACTGCTGGGC GGCCGCATGA | 2050 |
| AACAGCTAGA GGACAAGGTC GAAGAGCTAC TCTCCAAGAA CTACCACCTA | 2100 |
| GAGAATGAAG TGGCAAGACT CAAAAAGCTT GTCGGGAGC GCTAAGCATG | 2150 |
| CGACGGCCCT AGAGTCCCTA ACGCTCGGTT GCCGCCGGGC GTTTTTTATT | 2200 |
| GTTAACTCAT GTTTGACAGC TTATCATCGA TAAGCTTTAA TGCGGTAGTT | 2250 |
| TATCACAGTT AAATTGCTAA CGCAGTCAGG CACCGTGTAT GAAATCTAAC | 2300 |
| AATGCGCTCA TCGTCATCCT CGGCACCGTC ACCCTGGATG CTGTAGGCAT | 2350 |
| AGGCTTGGTT ATGCCGGTAC TGCCGGGCCT CTTGCGGGAT ATCGTCCATT | 2400 |
| CCGACAGCAT CGCCAGTCAC TATGGCGTGC TGCTAGCGCT ATATGCGTTG | 2450 |
| ATGCAATTTC TATGCGCACC CGTTCTCGGA GCACTGTCCG ACCGCTTTGG | 2500 |
| CCGCCGCCCA GTCCTGCTCG CTTCGCTACT TGGAGCCACT ATCGACTACG | 2550 |
| CGATCATGGC GACCACACCC GTCCTGTGGA TCCTCTACGC CGGACGCATC | 2600 |
| GTGGCCGGCA TCACCGGCGC CACAGGTGCG GTTGCTGGCG CCTATATCGC | 2650 |
| CGACATCACC GATGGGGAAG ATCGGGCTCG CCACTTCGGG CTCATGAGCG | 2700 |
| CTTGTTTCGG CGTGGGTATG GTGGCAGGCC CCGTGGCCGG GGGACTGTTG | 2750 |
| GGCGCCATCT CCTTGCACGC ACCATTCCTT GCGGCGGCGG TGCTCAACGG | 2800 |
| CCTCAACCTA CTACTGGGCT GCTTCCTAAT GCAGGAGTCG CATAAGGGAG | 2850 |

```
AGCGTCGTCC GATGCCCTTG AGAGCCTTCA ACCCAGTCAG CTCCTTCCGG      2900
TGGGCGCGGG GCATGACTAT CGTCGCCGCA CTTATGACTG TCTTCTTTAT      2950
CATGCAACTC GTAGGACAGG TGCCGGCAGC GCTCTGGGTC ATTTTCGGCG      3000
AGGACCGCTT TCGCTGGAGC GCGACGATGA TCGGCCTGTC GCTTGCGGTA      3050
TTCGGAATCT TGCACGCCCT CGCTCAAGCC TTCGTCACTG GTCCCGCCAC      3100
CAAACGTTTC GGCGAGAAGC AGGCCATTAT CGCCGGCATG GCGGCCGACG      3150
CGCTGGGCTA CGTCTTGCTG GCGTTCGCGA CGCGAGGCTG GATGGCCTTC      3200
CCCATTATGA TTCTTCTCGC TTCCGGCGGC ATCGGGATGC CCGCGTTGCA      3250
GGCCATGCTG TCCAGGCAGG TAGATGACGA CCATCAGGGA CAGCTTCAAG      3300
GATCGCTCGC GGCTCTTACC AGCCTAACTT CGATCACTGG ACCGCTGATC      3350
GTCACGGCGA TTTATGCCGC CTCGGCGAGC ACATGGAACG GGTTGGCATG      3400
GATTGTAGGC GCCGCCCTAT ACCTTGTCTG CCTCCCCGCG TTGCGTCGCG      3450
GTGCATGGAG CCGGGCCACC TCGACCTGAA TGGAAGCCGG CGGCACCTCG      3500
CTAACGGATT CACCACTCCA AGAATTGGAG CCAATCAATT CTTGCGGAGA      3550
ACTGTGAATG CGCAAACCAA CCCTTGGCAG AACATATCCA TCGCGTCCGC      3600
CATCTCCAGC AGCCGCACGC GGCGCATCTC GGGCAGCGTT GGGTCCTGGC      3650
CACGGGTGCG CATGATCGTG CTCCTGTCGT TGAGGACCCG GCTAGGCTGG      3700
CGGGGTTGCC TTACTGGTTA GCAGAATGAA TCACCGATAC GCGAGCGAAC      3750
GTGAAGCGAC TGCTGCTGCA AAACGTCTGC GACCTGAGCA CAACATGAA       3800
TGGTCTTCGG TTTCCGTGTT TCGTAAAGTC TGGAAACGCG GAAGTCAGCG      3850
CCCTGCACCA TTATGTTCCG GATCTGCATC GCAGGATGCT GCTGGCTACC      3900
CTGTGGAACA CCTACATCTG TATTAACGAA GCGCTGGCAT TGACCCTGAG      3950
TGATTTTTCT CTGGTCCCGC CGCATCCATA CCGCCAGTTG TTTACCCTCA      4000
CAACGTTCCA GTAACCGGGC ATGTTCATCA TCAGTAACCC GTATCGTGAG      4050
CATCCTCTCT CGTTTCATCG GTATCATTAC CCCCATGAAC AGAAATTCCC      4100
CCTTACACGG AGGCATCAAG TGACCAAACA GGAAAAAACC GCCCTTAACA      4150
TGGCCCGCTT TATCAGAAGC CAGACATTAA CGCTTCTGGA GAAACTCAAC      4200
GAGCTGGACG CGGATGAACA GGCAGACATC TGTGAATCGC TTCACGACCA      4250
CGCTGATGAG CTTTACCGCA GCTGCCTCGC GCGTTTCGGT GATGACGGTG      4300
AAAACCTCTG ACACATGCAG CTCCCGGAGA CGGTCACAGC TTGTCTGTAA      4350
GCGGATGCCG GGAGCAGACA AGCCCGTCAG GGCGCGTCAG CGGGTGTTGG      4400
CGGGTGTCGG GGCGCAGCCA TGACCCAGTC ACGTAGCGAT AGCGGAGTGT      4450
ATACTGGCTT AACTATGCGG CATCAGAGCA GATTGTACTG AGAGTGCACC      4500
ATATGCGGTG TGAAATACCG CACAGATGCG TAAGGAGAAA ATACCGCATC      4550
AGGCGCTCTT CCGCTTCCTC GCTCACTGAC TCGCTGCGCT CGGTCGTTCG      4600
GCTGCGGCGA GCGGTATCAG CTCACTCAAA GGCGGTAATA CGGTTATCCA      4650
CAGAATCAGG GGATAACGCA GGAAAGAACA TGTGAGCAAA AGGCCAGCAA      4700
AAGGCCAGGA ACCGTAAAAA GGCCGCGTTG CTGGCGTTTT TCCATAGGCT      4750
CCGCCCCCCT GACGAGCATC ACAAAAATCG ACGCTCAAGT CAGAGGTGGC      4800
```

| | |
|---|---|
| GAAACCCGAC AGGACTATAA AGATACCAGG CGTTTCCCCC TGGAAGCTCC | 4850 |
| CTCGTGCGCT CTCCTGTTCC GACCCTGCCG CTTACCGGAT ACCTGTCCGC | 4900 |
| CTTTCTCCCT TCGGGAAGCG TGGCGCTTTC TCATAGCTCA CGCTGTAGGT | 4950 |
| ATCTCAGTTC GGTGTAGGTC GTTCGCTCCA AGCTGGGCTG TGTGCACGAA | 5000 |
| CCCCCCGTTC AGCCCGACCG CTGCGCCTTA TCCGGTAACT ATCGTCTTGA | 5050 |
| GTCCAACCCG GTAAGACACG ACTTATCGCC ACTGGCAGCA GCCACTGGTA | 5100 |
| ACAGGATTAG CAGAGCGAGG TATGTAGGCG GTGCTACAGA GTTCTTGAAG | 5150 |
| TGGTGGCCTA ACTACGGCTA CACTAGAAGG ACAGTATTTG GTATCTGCGC | 5200 |
| TCTGCTGAAG CCAGTTACCT TCGGAAAAAG AGTTGGTAGC TCTTGATCCG | 5250 |
| GCAAACAAAC CACCGCTGGT AGCGGTGGTT TTTTTGTTTG CAAGCAGCAG | 5300 |
| ATTACGCGCA GAAAAAAAGG ATCTCAAGAA GATCCTTTGA TCTTTTCTAC | 5350 |
| GGGGTCTGAC GCTCAGTGGA ACGAAAACTC ACGTTAAGGG ATTTTGGTCA | 5400 |
| TGAGATTATC AAAAAGGATC TTCACCTAGA TCCTTTTAAA TTAAAAATGA | 5450 |
| AGTTTTAAAT CAATCTAAAG TATATATGAG TAAACTTGGT CTGACAGTTA | 5500 |
| CCAATGCTTA ATCAGTGAGG CACCTATCTC AGCGATCTGT CTATTTCGTT | 5550 |
| CATCCATAGT TGCCTGACTC CCCGTCGTGT AGATAACTAC GATACGGGAG | 5600 |
| GGCTTACCAT CTGGCCCCAG TGCTGCAATG ATACCGCGAG ACCCACGCTC | 5650 |
| ACCGGCTCCA GATTTATCAG CAATAAACCA GCCAGCCGGA AGGGCCGAGC | 5700 |
| GCAGAAGTGG TCCTGCAACT TTATCCGCCT CCATCCAGTC TATTAATTGT | 5750 |
| TGCCGGGAAG CTAGAGTAAG TAGTTCGCCA GTTAATAGTT TGCGCAACGT | 5800 |
| TGTTGCCATT GCTGCAGGCA TCGTGGTGTC ACGCTCGTCG TTTGGTATGG | 5850 |
| CTTCATTCAG CTCCGGTTCC CAACGATCAA GGCGAGTTAC ATGATCCCCC | 5900 |
| ATGTTGTGCA AAAAAGCGGT TAGCTCCTTC GGTCCTCCGA TCGTTGTCAG | 5950 |
| AAGTAAGTTG GCCGCAGTGT TATCACTCAT GGTTATGGCA GCACTGCATA | 6000 |
| ATTCTCTTAC TGTCATGCCA TCCGTAAGAT GCTTTTCTGT GACTGGTGAG | 6050 |
| TACTCAACCA AGTCATTCTG AGAATAGTGT ATGCGGCGAC CGAGTTGCTC | 6100 |
| TTGCCCGGCG TCAACACGGG ATAATACCGC GCCACATAGC AGAACTTTAA | 6150 |
| AAGTGCTCAT CATTGGAAAA CGTTCTTCGG GGCGAAAACT CTCAAGGATC | 6200 |
| TTACCGCTGT TGAGATCCAG TTCGATGTAA CCCACTCGTG CACCCAACTG | 6250 |
| ATCTTCAGCA TCTTTTACTT TCACCAGCGT TTCTGGGTGA GCAAAAACAG | 6300 |
| GAAGGCAAAA TGCCGCAAAA AAGGGAATAA GGGCGACACG GAAATGTTGA | 6350 |
| ATACTCATAC TCTTCCTTTT TCAATATTAT TGAAGCATTT ATCAGGGTTA | 6400 |
| TTGTCTCATG AGCGGATACA TATTTGAATG TATTTAGAAA AATAAACAAA | 6450 |
| TAGGGGTTCC GCGCACATTT CCCCGAAAAG TGCCACCTGA CGTCTAAGAA | 6500 |
| ACCATTATTA TCATGACATT AACCTATAAA AATAGGCGTA TCACGAGGCC | 6550 |
| CTTTCGTCTT CAA | 6563 |

(2) INFORMATION FOR SEQ ID NO:62:

(i) SEQUENCE CHARACTERISTICS:
        (A) LENGTH: 242 amino acids
        (B) TYPE: Amino Acid
        (D) TOPOLOGY: Linear (xi) SEQUENCE DESCRIPTION: SEQ ID NO:62:

Met Lys Lys Asn Ile Ala Phe Leu Leu Ala Ser Met Phe Val Phe
  1               5                  10                  15

Ser Ile Ala Thr Asn Ala Tyr Ala Asp Ile Gln Met Thr Gln Ser
                 20                  25                  30

Pro Ser Ser Leu Ser Ala Ser Val Gly Asp Arg Val Thr Ile Thr
                 35                  40                  45

Cys Arg Ser Ser Gln Ser Leu Val His Gly Ile Gly Glu Thr Tyr
                 50                  55                  60

Leu His Trp Tyr Gln Gln Lys Pro Gly Lys Ala Pro Lys Leu Leu
                 65                  70                  75

Ile Tyr Lys Val Ser Asn Arg Phe Ser Gly Val Pro Ser Arg Phe
                 80                  85                  90

Ser Gly Ser Gly Ser Gly Thr Asp Phe Thr Leu Thr Ile Ser Ser
                 95                 100                 105

Leu Gln Pro Glu Asp Phe Ala Thr Tyr Tyr Cys Ser Gln Ser Thr
                110                 115                 120

His Val Pro Leu Thr Phe Gly Gln Gly Thr Lys Val Glu Ile Lys
                125                 130                 135

Arg Thr Val Ala Ala Pro Ser Val Phe Ile Phe Pro Pro Ser Asp
                140                 145                 150

Glu Gln Leu Lys Ser Gly Thr Ala Ser Val Val Cys Leu Leu Asn
                155                 160                 165

Asn Phe Tyr Pro Arg Glu Ala Lys Val Gln Trp Lys Val Asp Asn
                170                 175                 180

Ala Leu Gln Ser Gly Asn Ser Gln Glu Ser Val Thr Glu Gln Asp
                185                 190                 195

Ser Lys Asp Ser Thr Tyr Ser Leu Ser Ser Thr Leu Thr Leu Ser
                200                 205                 210

Lys Ala Asp Tyr Glu Lys His Lys Val Tyr Ala Cys Glu Val Thr
                215                 220                 225

His Gln Gly Leu Ser Ser Pro Val Thr Lys Ser Phe Asn Arg Gly
                230                 235                 240

Glu Cys
242

(2) INFORMATION FOR SEQ ID NO:63:

(i) SEQUENCE CHARACTERISTICS:
        (A) LENGTH: 27 base pairs
        (B) TYPE: Nucleic Acid
        (C) STRANDEDNESS: Single
        (D) TOPOLOGY: Linear (xi) SEQUENCE DESCRIPTION: SEQ ID NO:63:

CATGGTATAG GTTAAACTTA TTTACAC                                27

(2) INFORMATION FOR SEQ ID NO:64:

(i) SEQUENCE CHARACTERISTICS:
        (A) LENGTH: 27 base pairs
        (B) TYPE: Nucleic Acid
        (C) STRANDEDNESS: Single
        (D) TOPOLOGY: Linear (xi) SEQUENCE DESCRIPTION: SEQ ID NO:64:

CATGGTATAG GTNNSACTTA TTTACAC                                27

(2) INFORMATION FOR SEQ ID NO:65:

(i) SEQUENCE CHARACTERISTICS:
        (A) LENGTH: 780 base pairs
        (B) TYPE: Nucleic Acid
        (C) STRANDEDNESS: Single
        (D) TOPOLOGY: Linear (xi) SEQUENCE DESCRIPTION: SEQ ID NO:65:

```
ATGAAAAAGA ATATCGCATT TCTTCTTGCA TCTATGTTCG TTTTTTCTAT          50
TGCTACAAAC GCATACGCTG ATATCCAGAT GACCCAGTCC CCGAGCTCCC         100
TGTCCGCCTC TGTGGGCGAT AGGGTCACCA TCACCTGCAG GTCAAGTCAA         150
AGCTTAGTAC ATGGTATAGG TGAGACGTAT TTACACTGGT ATCAACAGAA         200
ACCAGGAAAA GCTCCGAAAC TACTGATTTA CAAAGTATCC AATCGATTCT         250
CTGGAGTCCC TTCTCGCTTC TCTGGATCCG GTTCTGGGAC GGATTTCACT         300
CTGACCATCA GCAGTCTGCA GCCAGAAGAC TTCGCAACTT ATTACTGTTC         350
ACAGAGTACT CATGTCCCGC TCACGTTTGG ACAGGGTACC AAGGTGGAGA         400
TCAAACGAAC TGTGGCTGCA CCATCTGTCT TCATCTTCCC GCCATCTGAT         450
GAGCAGTTGA AATCTGGAAC TGCTTCTGTT GTGTGCCTGC TGAATAACTT         500
CTATCCCAGA GAGGCCAAAG TACAGTGGAA GGTGGATAAC GCCCTCCAAT         550
CGGGTAACTC CCAGGAGAGT GTCACAGAGC AGGACAGCAA GGACAGCACC         600
TACAGCCTCA GCAGCACCCT GACGCTGAGC AAAGCAGACT ACGAGAAACA         650
CAAAGTCTAC GCCTGCGAAG TCACCCATCA GGGCCTGAGC TCGCCCGTCA         700
CAAAGAGCTT CAACAGGGGA GAGTGTTAAG CTGATCCTCT ACGCCGGACG         750
CATCGTGGCC CTAGTACGCA ACTAGTCGTA                               780
```

(2) INFORMATION FOR SEQ ID NO:66:

(i) SEQUENCE CHARACTERISTICS:
        (A) LENGTH: 78 base pairs
        (B) TYPE: Nucleic Acid
        (C) STRANDEDNESS: Single
        (D) TOPOLOGY: Linear (xi) SEQUENCE DESCRIPTION: SEQ ID NO:66:

```
CTAGTGCAGT CTGGCGGTGG CCTGGTGCAG CCAGGGGGCT CACTCCGTTT          50
GTCCTGTGCA GCTTCTGGCT ACTCCTTC                                  78
```

(2) INFORMATION FOR SEQ ID NO:67:

(i) SEQUENCE CHARACTERISTICS:
        (A) LENGTH: 82 base pairs
        (B) TYPE: Nucleic Acid
        (C) STRANDEDNESS: Single
        (D) TOPOLOGY: Linear (xi) SEQUENCE DESCRIPTION: SEQ ID NO:67:

```
TCGAGAAGGA GTAGCCAGAA GCTGCACAGG ACAAACGGAG TGAGCCCCCT          50
GGCTGCACCA GGCCACCGCC AGACTGCACT AG                             82
```

(2) INFORMATION FOR SEQ ID NO:68:

(i) SEQUENCE CHARACTERISTICS:
        (A) LENGTH: 8120 base pairs

```
        (B) TYPE: Nucleic Acid
        (C) STRANDEDNESS: Single
        (D) TOPOLOGY: Linear (xi) SEQUENCE DESCRIPTION: SEQ ID NO:68:

TTCGAGCTCG CCCGACATTG ATTATTGACT AGAGTCGATC GACAGCTGTG            50

GAATGTGTGT CAGTTAGGGT GTGGAAAGTC CCCAGGCTCC CCAGCAGGCA           100

GAAGTATGCA AAGCATGCAT CTCAATTAGT CAGCAACCAG GTGTGGAAAG           150

TCCCCAGGCT CCCCAGCAGG CAGAAGTATG CAAAGCATGC ATCTCAATTA           200

GTCAGCAACC ATAGTCCCGC CCCTAACTCC GCCCATCCCG CCCCTAACTC           250

CGCCCAGTTC CGCCCATTCT CCGCCCCATG GCTGACTAAT TTTTTTTATT           300

TATGCAGAGG CCGAGGCCGC CTCGGCCTCT GAGCTATTCC AGAAGTAGTG           350

AGGAGGCTTT TTTGGAGGCC TAGGCTTTTG CAAAAAGCTA GCTTATCCGG           400

CCGGGAACGG TGCATTGGAA CGCGGATTCC CCGTGCCAAG AGTGACGTAA           450

GTACCGCCTA TAGAGCGATA AGAGGATTTT ATCCCCGCTG CCATCATGGT           500

TCGACCATTG AACTGCATCG TCGCCGTGTC CCAAAATATG GGGATTGGCA           550

AGAACGGAGA CCTACCCTGG CCTCCGCTCA GGAACGAGTT CAAGTACTTC           600

CAAAGAATGA CCACAACCTC TTCAGTGGAA GGTAAACAGA ATCTGGTGAT           650

TATGGGTAGG AAAACCTGGT TCTCCATTCC TGAGAAGAAT CGACCTTTAA           700

AGGACAGAAT TAATATAGTT CTCAGTAGAG AACTCAAAGA ACCACCACGA           750

GGAGCTCATT TTCTTGCCAA AAGTTTGGAT GATGCCTTAA GACTTATTGA           800

ACAACCGGAA TTGGCAAGTA AAGTAGACAT GGTTTGGATA GTCGGAGGCA           850

GTTCTGTTTA CCAGGAAGCC ATGAATCAAC CAGGCCACCT TAGACTCTTT           900

GTGACAAGGA TCATGCAGGA ATTTGAAAGT GACACGTTTT TCCCAGAAAT           950

TGATTTGGGG AAATATAAAC CTCTCCCAGA ATACCCAGGC GTCCTCTCTG          1000

AGGTCCAGGA GGAAAAAGGC ATCAAGTATA AGTTTGAAGT CTACGAGAAG          1050

AAAGACTAAC AGGAAGATGC TTTCAAGTTC TCTGCTCCCC TCCTAAAGCT          1100

ATGCATTTTT ATAAGACCAT GGGACTTTTG CTGGCTTTAG ATCCCCTTGG          1150

CTTCGTTAGA ACGCAGCTAC AATTAATACA TAACCTTATG TATCATACAC          1200

ATACGATTTA GGTGACACTA TAGATAACAT CCACTTTGCC TTTCTCTCCA          1250

CAGGTGTCCA CTCCCAGGTC CAACTGCACC TCGGTTCTAT CGATTGAATT          1300

CCACCATGGG ATGGTCATGT ATCATCCTTT TTCTAGTAGC AACTGCAACT          1350

GGAGTACATT CAGAAGTTCA GCTAGTGCAG TCTGGCGGTG GCCTGGTGCA          1400

GCCAGGGGGC TCACTCCGTT TGTCCTGTGC AGCTTCTGGC TACTCCTTCT          1450

CGAGTCACTA TATGCACTGG GTCCGTCAGG CCCCGGGTAA GGGCCTGGAA          1500

TGGGTTGGAT ATATTGATCC TTCCAATGGT GAAACTACGT ATAATCAAAA          1550

GTTCAAGGGC CGTTTCACTT TATCTCGCGA CAACTCCAAA AACACAGCAT          1600

ACCTGCAGAT GAACAGCCTG CGTGCTGAGG ACACTGCCGT CTATTACTGT          1650

GCAAGAGGGG ATTATCGCTA CAATGGTGAC TGGTTCTTCG ACGTCTGGGG          1700

TCAAGGAACC CTGGTCACCG TCTCCTCGGC CTCCACCAAG GGCCCATCGG          1750

TCTTCCCCCT GGCACCCTCC TCCAAGAGCA CCTCTGGGGG CACAGCGGCC          1800

CTGGGCTGCC TGGTCAAGGA CTACTTCCCC GAACCGGTGA CGGTGTCGTG          1850
```

```
GAACTCAGGC GCCCTGACCA GCGGCGTGCA CACCTTCCCG GCTGTCCTAC        1900

AGTCCTCAGG ACTCTACTCC CTCAGCAGCG TGGTGACTGT GCCCTCTAGC        1950

AGCTTGGGCA CCCAGACCTA CATCTGCAAC GTGAATCACA AGCCCAGCAA        2000

CACCAAGGTG GACAAGAAAG TTGAGCCCAA ATCTTGTGAC AAAACTCACA        2050

CATGCCCACC GTGCCCAGCA CCTGAACTCC TGGGGGGACC GTCAGTCTTC        2100

CTCTTCCCCC CAAAACCCAA GGACACCCTC ATGATCTCCC GGACCCCTGA        2150

GGTCACATGC GTGGTGGTGG ACGTGAGCCA CGAAGACCCT GAGGTCAAGT        2200

TCAACTGGTA CGTGGACGGC GTGGAGGTGC ATAATGCCAA GACAAAGCCG        2250

CGGGAGGAGC AGTACAACAG CACGTACCGT GTGGTCAGCG TCCTCACCGT        2300

CCTGCACCAG GACTGGCTGA ATGGCAAGGA GTACAAGTGC AAGGTCTCCA        2350

ACAAAGCCCT CCCAGCCCCC ATCGAGAAAA CCATCTCCAA AGCCAAAGGG        2400

CAGCCCCGAG AACCACAGGT GTACACCCTG CCCCCATCCC GGGAAGAGAT        2450

GACCAAGAAC CAGGTCAGCC TGACCTGCCT GGTCAAAGGC TTCTATCCCA        2500

GCGACATCGC CGTGGAGTGG GAGAGCAATG GGCAGCCGGA GAACAACTAC        2550

AAGACCACGC CTCCCGTGCT GGACTCCGAC GGCTCCTTCT TCCTCTACAG        2600

CAAGCTCACC GTGGACAAGA GCAGGTGGCA GCAGGGGAAC GTCTTCTCAT        2650

GCTCCGTGAT GCATGAGGCT CTGCACAACC ACTACACGCA GAAGAGCCTC        2700

TCCCTGTCTC CGGGTAAATG AGTGCGACGG CCCTAGAGTC GACCTGCAGA        2750

AGCTTGGCCG CCATGGCCCA ACTTGTTTAT TGCAGCTTAT AATGGTTACA        2800

AATAAAGCAA TAGCATCACA AATTTCACAA ATAAAGCATT TTTTTCACTG        2850

CATTCTAGTT GTGGTTTGTC CAAACTCATC AATGTATCTT ATCATGTCTG        2900

GATCGATCGG GAATTAATTC GGCGCAGCAC CATGGCCTGA ATAACCTCT         2950

GAAAGAGGAA CTTGGTTAGG TACCTTCTGA GGCGGAAAGA ACCATCTGTG        3000

GAATGTGTGT CAGTTAGGGT GTGGAAAGTC CCCAGGCTCC CCAGCAGGCA        3050

GAAGTATGCA AAGCATGCAT CTCAATTAGT CAGCAACCAG GTGTGGAAAG        3100

TCCCCAGGCT CCCCAGCAGG CAGAAGTATG CAAAGCATGC ATCTCAATTA        3150

GTCAGCAACC ATAGTCCCGC CCCTAACTCC GCCCATCCCG CCCCTAACTC        3200

CGCCCAGTTC CGCCCATTCT CCGCCCCATG GCTGACTAAT TTTTTTTATT        3250

TATGCAGAGG CCGAGGCCGC CTCGGCCTCT GAGCTATTCC AGAAGTAGTG        3300

AGGAGGCTTT TTTGGAGGCC TAGGCTTTTG CAAAAAGCTA GCTTATCCGG        3350

CCGGGAACGG TGCATTGGAA CGCGGATTCC CCGTGCCAAG AGTCAGGTAA        3400

GTACCGCCTA TAGAGTCTAT AGGCCCACCC CCTTGGCTTC GTTAGAACGC        3450

GGCTACAATT AATACATAAC CTTTTGGATC GATCCTACTG ACACTGACAT        3500

CCACTTTTTC TTTTTCTCCA CAGGTGTCCA CTCCCAGGTC CAACTGCACC        3550

TCGGTTCGCG AAGCTAGCTT GGGCTGCATC GATTGAATTC CACCATGGGA        3600

TGGTCATGTA TCATCCTTTT TCTAGTAGCA ACTGCAACTG GAGTACATTC        3650

AGATATCCAG ATGACCCAGT CCCCGAGCTC CCTGTCCGCC TCTGTGGGCG        3700

ATAGGGTCAC CATCACCTGC AGGTCAAGTC AAAGCTTAGT ACATGGTATA        3750

GGTGCTACGT ATTTACACTG GTATCAACAG AAACCAGGAA AAGCTCCGAA        3800
```

```
ACTACTGATT TACAAAGTAT CCAATCGATT CTCTGGAGTC CCTTCTCGCT      3850

TCTCTGGATC CGGTTCTGGG ACGGATTTCA CTCTGACCAT CAGCAGTCTG      3900

CAGCCAGAAG ACTTCGCAAC TTATTACTGT TCACAGAGTA CTCATGTCCC      3950

GCTCACGTTT GGACAGGGTA CCAAGGTGGA GATCAAACGA ACTGTGGCTG      4000

CACCATCTGT CTTCATCTTC CCGCCATCTG ATGAGCAGTT GAAATCTGGA      4050

ACTGCTTCTG TTGTGTGCCT GCTGAATAAC TTCTATCCCA GAGAGGCCAA      4100

AGTACAGTGG AAGGTGGATA ACGCCCTCCA ATCGGGTAAC TCCCAGGAGA      4150

GTGTCACAGA GCAGGACAGC AAGGACAGCA CCTACAGCCT CAGCAGCACC      4200

CTGACGCTGA GCAAAGCAGA CTACGAGAAA CACAAAGTCT ACGCCTGCGA      4250

AGTCACCCAT CAGGGCCTGA GCTCGCCCGT CACAAAGAGC TTCAACAGGG      4300

GAGAGTGTTA AGCTTGGCCG CCATGGCCCA ACTTGTTTAT TGCAGCTTAT      4350

AATGGTTACA AATAAAGCAA TAGCATCACA AATTTCACAA ATAAAGCATT      4400

TTTTTCACTG CATTCTAGTT GTGGTTTGTC CAAACTCATC AATGTATCTT      4450

ATCATGTCTG GATCGATCGG GAATTAATTC GGCGCAGCAC CATGGCCTGA      4500

AATAACCTCT GAAAGAGGAA CTTGGTTAGG TACCTTCTGA GGCGGAAAGA      4550

ACCAGCTGTG GAATGTGTGT CAGTTAGGGT GTGGAAAGTC CCCAGGCTCC      4600

CCAGCAGGCA GAAGTATGCA AAGCATGCAT CTCAATTAGT CAGCAACCAG      4650

GTGTGGAAAG TCCCCAGGCT CCCCAGCAGG CAGAAGTATG CAAAGCATGC      4700

ATCTCAATTA GTCAGCAACC ATAGTCCCGC CCCTAACTCC GCCCATCCCG      4750

CCCCTAACTC CGCCCAGTTC CGCCCATTCT CCGCCCCATG GCTGACTAAT      4800

TTTTTTTATT TATGCAGAGG CCGAGGCCGC CTCGGCCTCT GAGCTATTCC      4850

AGAAGTAGTG AGGAGGCTTT TTTGGAGGCC TAGGCTTTTG CAAAAAGCTG      4900

TTACCTCGAG CGGCCGCTTA ATTAAGGCGC GCCATTTAAA TCCTGCAGGT      4950

AACAGCTTGG CACTGGCCGT CGTTTTACAA CGTCGTGACT GGGAAAACCC      5000

TGGCGTTACC CAACTTAATC GCCTTGCAGC ACATCCCCCC TTCGCCAGCT      5050

GGCGTAATAG CGAAGAGGCC CGCACCGATC GCCCTTCCCA ACAGTTGCGT      5100

AGCCTGAATG GCGAATGGCG CCTGATGCGG TATTTTCTCC TTACGCATCT      5150

GTGCGGTATT TCACACCGCA TACGTCAAAG CAACCATAGT ACGCGCCCTG      5200

TAGCGGCGCA TTAAGCGCGG CGGGTGTGGT GGTTACGCGC AGCGTGACCG      5250

CTACACTTGC CAGCGCCCTA GCGCCCGCTC CTTTCGCTTT CTTCCCTTCC      5300

TTTCTCGCCA CGTTCGCCGG CTTTCCCCGT CAAGCTCTAA ATCGGGGCT      5350

CCCTTTAGGG TTCCGATTTA GTGCTTTACG GCACCTCGAC CCCAAAAAAC      5400

TTGATTTGGG TGATGGTTCA CGTAGTGGGC CATCGCCCTG ATAGACGGTT      5450

TTTCGCCCTT TGACGTTGGA GTCCACGTTC TTTAATAGTG GACTCTTGTT      5500

CCAAACTGGA ACAACACTCA ACCCTATCTC GGGCTATTCT TTTGATTTAT      5550

AAGGGATTTT GCCGATTTCG GCCTATTGGT TAAAAAATGA GCTGATTTAA      5600

CAAAAATTTA ACGCGAATTT TAACAAAATA TTAACGTTTA CAATTTTATG      5650

GTGCACTCTC AGTACAATCT GCTCTGATGC CGCATAGTTA AGCCAACTCC      5700

GCTATCGCTA CGTGACTGGG TCATGGCTGC GCCCCGACAC CCGCCAACAC      5750

CCGCTGACGC GCCCTGACGG GCTTGTCTGC TCCCGGCATC CGCTTACAGA      5800
```

```
CAAGCTGTGA CCGTCTCCGG GAGCTGCATG TGTCAGAGGT TTTCACCGTC          5850

ATCACCGAAA CGCGCGAGGC AGTATTCTTG AAGACGAAAG GGCCTCGTGA          5900

TACGCCTATT TTTATAGGTT AATGTCATGA TAATAATGGT TTCTTAGACG          5950

TCAGGTGGCA CTTTTCGGGG AAATGTGCGC GGAACCCCTA TTTGTTTATT          6000

TTTCTAAATA CATTCAAATA TGTATCCGCT CATGAGACAA TAACCCTGAT          6050

AAATGCTTCA ATAATATTGA AAAGGAAGA GTATGAGTAT TCAACATTTC           6100

CGTGTCGCCC TTATTCCCTT TTTTGCGGCA TTTTGCCTTC CTGTTTTTGC          6150

TCACCCAGAA ACGCTGGTGA AAGTAAAAGA TGCTGAAGAT CAGTTGGGTG          6200

CACGAGTGGG TTACATCGAA CTGGATCTCA ACAGCGGTAA GATCCTTGAG          6250

AGTTTTCGCC CCGAAGAACG TTTTCCAATG ATGAGCACTT TTAAAGTTCT          6300

GCTATGTGGC GCGGTATTAT CCCGTGATGA CGCCGGGCAA GAGCAACTCG          6350

GTCGCCGCAT ACACTATTCT CAGAATGACT TGGTTGAGTA CTCACCAGTC          6400

ACAGAAAAGC ATCTTACGGA TGGCATGACA GTAAGAGAAT TATGCAGTGC          6450

TGCCATAACC ATGAGTGATA ACACTGCGGC CAACTTACTT CTGACAACGA          6500

TCGGAGGACC GAAGGAGCTA ACCGCTTTTT GCACAACAT GGGGGATCAT          6550

GTAACTCGCC TTGATCGTTG GGAACCGGAG CTGAATGAAG CCATACCAAA          6600

CGACGAGCGT GACACCACGA TGCCAGCAGC AATGGCAACA ACGTTGCGCA          6650

AACTATTAAC TGGCGAACTA CTTACTCTAG CTTCCCGGCA ACAATTAATA          6700

GACTGGATGG AGGCGGATAA AGTTGCAGGA CCACTTCTGC GCTCGGCCCT          6750

TCCGGCTGGC TGGTTTATTG CTGATAAATC TGGAGCCGGT GAGCGTGGGT          6800

CTCGCGGTAT CATTGCAGCA CTGGGGCCAG ATGGTAAGCC CTCCCGTATC          6850

GTAGTTATCT ACACGACGGG GAGTCAGGCA ACTATGGATG AACGAAATAG          6900

ACAGATCGCT GAGATAGGTG CCTCACTGAT TAAGCATTGG TAACTGTCAG          6950

ACCAAGTTTA CTCATATATA CTTTAGATTG ATTTAAAACT TCATTTTTAA          7000

TTTAAAAGGA TCTAGGTGAA GATCCTTTTT GATAATCTCA TGACCAAAAT          7050

CCCTTAACGT GAGTTTTCGT TCCACTGAGC GTCAGACCCC GTAGAAAAGA          7100

TCAAAGGATC TTCTTGAGAT CCTTTTTTTC TGCGCGTAAT CTGCTGCTTG          7150

CAAACAAAAA AACCACCGCT ACCAGCGGTG GTTTGTTTGC CGGATCAAGA          7200

GCTACCAACT CTTTTTCCGA AGGTAACTGG CTTCAGCAGA GCGCAGATAC          7250

CAAATACTGT CCTTCTAGTG TAGCCGTAGT TAGGCCACCA CTTCAAGAAC          7300

TCTGTAGCAC CGCCTACATA CCTCGCTCTG CTAATCCTGT TACCAGTGGC          7350

TGCTGCCAGT GGCGATAAGT CGTGTCTTAC CGGGTTGGAC TCAAGACGAT          7400

AGTTACCGGA TAAGGCGCAG CGGTCGGGCT GAACGGGGGG TTCGTGCACA          7450

CAGCCCAGCT TGGAGCGAAC GACCTACACC GAACTGAGAT ACCTACAGCG          7500

TGAGCATTGA GAAAGCGCCA CGCTTCCCGA AGGGAGAAAG GCGGACAGGT          7550

ATCCGGTAAG CGGCAGGGTC GGAACAGGAG AGCGCACGAG GGAGCTTCCA          7600

GGGGGAAACG CCTGGTATCT TTATAGTCCT GTCGGGTTTC GCCACCTCTG          7650

ACTTGAGCGT CGATTTTTGT GATGCTCGTC AGGGGGGCGG AGCCTATGGA          7700

AAAACGCCAG CAACGCGGCC TTTTTACGGT TCCTGGCCTT TTGCTGGCCT          7750
```

-continued

| | |
|---|---|
| TTTGCTCACA TGTTCTTTCC TGCGTTATCC CCTGATTCTG TGGATAACCG | 7800 |
| TATTACCGCC TTTGAGTGAG CTGATACCGC TCGCCGCAGC CGAACGACCG | 7850 |
| AGCGCAGCGA GTCAGTGAGC GAGGAAGCGG AAGAGCGCCC AATACGCAAA | 7900 |
| CCGCCTCTCC CCGCGCGTTG GCCGATTCAT TAATCCAGCT GGCACGACAG | 7950 |
| GTTTCCCGAC TGGAAAGCGG GCAGTGAGCG CAACGCAATT AATGTGAGTT | 8000 |
| ACCTCACTCA TTAGGCACCC CAGGCTTTAC ACTTTATGCT TCCGGCTCGT | 8050 |
| ATGTTGTGTG GAATTGTGAG CGGATAACAA TTTCACACAG GAAACAGCTA | 8100 |
| TGACCATGAT TACGAATTAA | 8120 |

(2) INFORMATION FOR SEQ ID NO:69:

(i) SEQUENCE CHARACTERISTICS:
        (A) LENGTH: 800 base pairs
        (B) TYPE: Nucleic Acid
        (C) STRANDEDNESS: Single
        (D) TOPOLOGY: Linear (xi) SEQUENCE DESCRIPTION: SEQ ID NO:69:

| | |
|---|---|
| AAAAGGGTAT CTAGAGGTTG AGGTGATTTT ATGAAAAAGA ATATCGCATT | 50 |
| TCTTCTTGCA TCTATGTTCG TTTTTTCTAT TGCTACAAAC GCGTACGCTG | 100 |
| AGGTTCAGCT AGTGCAGTCT GGCGGTGGCC TGGTGCAGCC AGGGGGCTCA | 150 |
| CTCCGTTTGT CCTGTGCAGC TTCTGGCTAC TCCTTCTCGA GTCACTATAT | 200 |
| GCACTGGGTC CGTCAGGCCC CGGGTAAGGG CCTGGAATGG GTTGGATATA | 250 |
| TTGATCCTTC CAATGGTGAA ACTACGTATA ATCAAAAGTT CAAGGGCCGT | 300 |
| TTCACTTTAT CTCGCGACAA CTCCAAAAAC ACAGCATACC TGCAGATGAA | 350 |
| CAGCCTGCGT GCTGAGGACA CTGCCGTCTA TTACTGTGCA AGAGGGGATT | 400 |
| ATCGCTACAA TGGTGACTGG TTCTTCGACG TCTGGGGTCA AGGAACCCTG | 450 |
| GTCACCGTCT CCTCGGCCTC CACCAAGGGC CCATCGGTCT TCCCCCTGGC | 500 |
| ACCCTCCTCC AAGAGCACCT CTGGGGGCAC AGCGGCCCTG GGCTGCCTGG | 550 |
| TCAAGGACTA CTTCCCCGAA CCGGTGACGG TGTCGTGGAA CTCAGGCGCC | 600 |
| CTGACCAGCG GCGTGCACAC CTTCCCGGCT GTCCTACAGT CCTCAGGACT | 650 |
| CTACTCCCTC AGCAGCGTGG TGACCGTGCC CTCCAGCAGC TTGGGCACCC | 700 |
| AGACCTACAT CTGCAACGTG AATCACAAGC CCAGCAACAC CAAGGTCGAC | 750 |
| AAGAAAGTTG AGCCCAAATC TTGTGACAAA ACTCACACAT GCCCGCCTGA | 800 |

(2) INFORMATION FOR SEQ ID NO:70:

(i) SEQUENCE CHARACTERISTICS:
        (A) LENGTH: 256 amino acids
        (B) TYPE: Amino Acid
        (D) TOPOLOGY: Linear (xi) SEQUENCE DESCRIPTION: SEQ ID NO:70:

Met Lys Lys Asn Ile Ala Phe Leu Leu Ala Ser Met Phe Val Phe
 1            5                    10                    15

Ser Ile Ala Thr Asn Ala Tyr Ala Glu Val Gln Leu Val Gln Ser
                20                    25                    30

Gly Gly Gly Leu Val Gln Pro Gly Gly Ser Leu Arg Leu Ser Cys
                35                    40                    45

Ala Ala Ser Gly Tyr Ser Phe Ser Ser His Tyr Met His Trp Val

-continued

```
                  50                  55                  60
Arg Gln Ala Pro Gly Lys Gly Leu Glu Trp Val Gly Tyr Ile Asp
                65                  70                  75
Pro Ser Asn Gly Glu Thr Thr Tyr Asn Gln Lys Phe Lys Gly Arg
                80                  85                  90
Phe Thr Leu Ser Arg Asp Asn Ser Lys Asn Thr Ala Tyr Leu Gln
                95                 100                 105
Met Asn Ser Leu Arg Ala Glu Asp Thr Ala Val Tyr Tyr Cys Ala
               110                 115                 120
Arg Gly Asp Tyr Arg Tyr Asn Gly Asp Trp Phe Phe Asp Val Trp
               125                 130                 135
Gly Gln Gly Thr Leu Val Thr Val Ser Ser Ala Ser Thr Lys Gly
               140                 145                 150
Pro Ser Val Phe Pro Leu Ala Pro Ser Ser Lys Ser Thr Ser Gly
               155                 160                 165
Gly Thr Ala Ala Leu Gly Cys Leu Val Lys Asp Tyr Phe Pro Glu
               170                 175                 180
Pro Val Thr Val Ser Trp Asn Ser Gly Ala Leu Thr Ser Gly Val
               185                 190                 195
His Thr Phe Pro Ala Val Leu Gln Ser Ser Gly Leu Tyr Ser Leu
               200                 205                 210
Ser Ser Val Val Thr Val Pro Ser Ser Ser Leu Gly Thr Gln Thr
               215                 220                 225
Tyr Ile Cys Asn Val Asn His Lys Pro Ser Asn Thr Lys Val Asp
               230                 235                 240
Lys Lys Val Glu Pro Lys Ser Cys Asp Lys Thr His Thr Cys Pro
               245                 250                 255
Pro
256
```

(2) INFORMATION FOR SEQ ID NO:71:

(i) SEQUENCE CHARACTERISTICS:
        (A) LENGTH: 452 amino acids
        (B) TYPE: Amino Acid
        (D) TOPOLOGY: Linear (xi) SEQUENCE DESCRIPTION: SEQ ID NO:71:

```
Glu Val Gln Leu Val Gln Ser Gly Gly Gly Leu Val Gln Pro Gly
 1               5                  10                  15
Gly Ser Leu Arg Leu Ser Cys Ala Ala Ser Gly Tyr Ser Phe Ser
                20                  25                  30
Ser His Tyr Met His Trp Val Arg Gln Ala Pro Gly Lys Gly Leu
                35                  40                  45
Glu Trp Val Gly Tyr Ile Asp Pro Ser Asn Gly Glu Thr Thr Tyr
                50                  55                  60
Asn Gln Lys Phe Lys Gly Arg Phe Thr Leu Ser Arg Asp Asn Ser
                65                  70                  75
Lys Asn Thr Ala Tyr Leu Gln Met Asn Ser Leu Arg Ala Glu Asp
                80                  85                  90
Thr Ala Val Tyr Tyr Cys Ala Arg Gly Asp Tyr Arg Tyr Asn Gly
                95                 100                 105
Asp Trp Phe Phe Asp Val Trp Gly Gln Gly Thr Leu Val Thr Val
               110                 115                 120
Ser Ser Ala Ser Thr Lys Gly Pro Ser Val Phe Pro Leu Ala Pro
```

```
                       125                 130                 135

Ser Ser Lys Ser Thr Ser Gly Gly Thr Ala Ala Leu Gly Cys Leu
                140                 145                 150

Val Lys Asp Tyr Phe Pro Glu Pro Val Thr Val Ser Trp Asn Ser
                155                 160                 165

Gly Ala Leu Thr Ser Gly Val His Thr Phe Pro Ala Val Leu Gln
                170                 175                 180

Ser Ser Gly Leu Tyr Ser Leu Ser Ser Val Thr Val Pro Ser
                185                 190                 195

Ser Ser Leu Gly Thr Gln Thr Tyr Ile Cys Asn Val Asn His Lys
                200                 205                 210

Pro Ser Asn Thr Lys Val Asp Lys Lys Val Glu Pro Lys Ser Cys
                215                 220                 225

Asp Lys Thr His Thr Cys Pro Pro Cys Pro Ala Pro Glu Leu Leu
                230                 235                 240

Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp
                275                 280                 285

Gly Val Glu Val His Asn Ala Lys Thr Lys Pro Arg Glu Glu Gln
                290                 295                 300

Tyr Asn Ser Thr Tyr Arg Val Val Ser Val Leu Thr Val Leu His
                305                 310                 315

Gln Asp Trp Leu Asn Gly Lys Glu Tyr Lys Cys Lys Val Ser Asn
                320                 325                 330

Lys Ala Leu Pro Ala Pro Ile Glu Lys Thr Ile Ser Lys Ala Lys
                335                 340                 345

Gly Gln Pro Arg Glu Pro Gln Val Tyr Thr Leu Pro Pro Ser Arg
                350                 355                 360

Glu Glu Met Thr Lys Asn Gln Val Ser Leu Thr Cys Leu Val Lys
                365                 370                 375

Gly Phe Tyr Pro Ser Asp Ile Ala Val Glu Trp Glu Ser Asn Gly
                380                 385                 390

Gln Pro Glu Asn Asn Tyr Lys Thr Thr Pro Pro Val Leu Asp Ser
                395                 400                 405

Asp Gly Ser Phe Phe Leu Tyr Ser Lys Leu Thr Val Asp Lys Ser
                410                 415                 420

Arg Trp Gln Gln Gly Asn Val Phe Ser Cys Ser Val Met His Glu
                425                 430                 435

Ala Leu His Asn His Tyr Thr Gln Lys Ser Leu Ser Leu Ser Pro
                440                 445                 450

Gly Lys
452

(2) INFORMATION FOR SEQ ID NO:72:

(i) SEQUENCE CHARACTERISTICS:
        (A) LENGTH: 219 amino acids
        (B) TYPE: Amino Acid
        (D) TOPOLOGY: Linear (xi) SEQUENCE DESCRIPTION: SEQ ID NO:72:

Asp Ile Gln Met Thr Gln Ser Pro Ser Ser Leu Ser Ala Ser Val
```

-continued

```
  1              5              10              15

Gly Asp Arg Val Thr Ile Thr Cys Arg Ser Ser Gln Ser Leu Val
                 20                  25                  30

His Gly Ile Gly Ala Thr Tyr Leu His Trp Tyr Gln Gln Lys Pro
                 35                  40                  45

Gly Lys Ala Pro Lys Leu Leu Ile Tyr Lys Val Ser Asn Arg Phe
                 50                  55                  60

Ser Gly Val Pro Ser Arg Phe Ser Gly Ser Gly Ser Gly Thr Asp
                 65                  70                  75

Phe Thr Leu Thr Ile Ser Ser Leu Gln Pro Glu Asp Phe Ala Thr
                 80                  85                  90

Tyr Tyr Cys Ser Gln Ser Thr His Val Pro Leu Thr Phe Gly Gln
                 95                 100                 105

Gly Thr Lys Val Glu Ile Lys Arg Thr Val Ala Ala Pro Ser Val
                110                 115                 120

Phe Ile Phe Pro Pro Ser Asp Glu Gln Leu Lys Ser Gly Thr Ala
                125                 130                 135

Ser Val Val Cys Leu Leu Asn Asn Phe Tyr Pro Arg Glu Ala Lys
                140                 145                 150

Val Gln Trp Lys Val Asp Asn Ala Leu Gln Ser Gly Asn Ser Gln
                155                 160                 165

Glu Ser Val Thr Glu Gln Asp Ser Lys Asp Ser Thr Tyr Ser Leu
                170                 175                 180

Ser Ser Thr Leu Thr Leu Ser Lys Ala Asp Tyr Glu Lys His Lys
                185                 190                 195

Val Tyr Ala Cys Glu Val Thr His Gln Gly Leu Ser Ser Pro Val
                200                 205                 210

Thr Lys Ser Phe Asn Arg Gly Glu Cys
                215                 219
```